US011248248B2

(12) United States Patent
Houghton-Larsen

(10) Patent No.: US 11,248,248 B2
(45) Date of Patent: Feb. 15, 2022

(54) PRODUCTION OF MOGROSIDE COMPOUNDS IN RECOMBINANT HOSTS

(71) Applicant: EVOLVA SA, Reinach (CH)

(72) Inventor: Jens Houghton-Larsen, Reinach (CH)

(73) Assignee: EVOLVA SA, Reinach (CH)

( * ) Notice: Subject to any disclaimer, the term of this patent is extended or adjusted under 35 U.S.C. 154(b) by 0 days.

(21) Appl. No.: 16/618,880

(22) PCT Filed: Jun. 15, 2018

(86) PCT No.: PCT/EP2018/066027
§ 371 (c)(1),
(2) Date: Dec. 3, 2019

(87) PCT Pub. No.: WO2018/229283
PCT Pub. Date: Dec. 20, 2018

(65) Prior Publication Data
US 2020/0165652 A1 May 28, 2020

Related U.S. Application Data

(60) Provisional application No. 62/520,395, filed on Jun. 15, 2017.

(51) Int. Cl.
| C12P 33/20 | (2006.01) |
| A23L 27/30 | (2016.01) |
| A23L 2/385 | (2006.01) |
| A23L 2/60 | (2006.01) |
| B01D 9/00 | (2006.01) |
| B01D 11/04 | (2006.01) |
| B01D 15/32 | (2006.01) |
| B01D 15/36 | (2006.01) |
| C12N 1/16 | (2006.01) |
| C12N 9/42 | (2006.01) |
| C12N 15/81 | (2006.01) |
| C12N 9/24 | (2006.01) |
| C12P 19/56 | (2006.01) |

(52) U.S. Cl.
CPC .............. C12P 33/20 (2013.01); A23L 2/385 (2013.01); A23L 2/60 (2013.01); A23L 27/36 (2016.08); B01D 9/00 (2013.01); B01D 11/04 (2013.01); B01D 15/325 (2013.01); B01D 15/361 (2013.01); C12N 1/16 (2013.01); C12N 9/244 (2013.01); C12N 9/2405 (2013.01); C12N 15/81 (2013.01); C12P 19/56 (2013.01); C12Y 302/01006 (2013.01); A23V 2002/00 (2013.01); C12Y 302/01058 (2013.01)

(58) Field of Classification Search
None
See application file for complete search history.

(56) References Cited

U.S. PATENT DOCUMENTS

| 8,257,948 | B1 | 9/2012 | Markosyan |
| 9,932,619 | B2 | 4/2018 | Liu et al. |
| 10,011,859 | B2 | 7/2018 | Liu et al. |
| 2006/0014264 | A1 | 1/2006 | Sauer et al. |
| 2007/0039067 | A1 | 2/2007 | Feldmann et al. |
| 2007/0118916 | A1 | 5/2007 | Puzio et al. |
| 2015/0322473 | A1 | 11/2015 | Liu et al. |
| 2016/0177360 | A1* | 6/2016 | Boer .................. A23L 2/60 435/78 |
| 2018/0010160 | A1* | 1/2018 | Ochiai .................. C12P 19/44 |

FOREIGN PATENT DOCUMENTS

| EP | 1510573 | 3/2005 |
| EP | 1897951 | 12/2010 |
| EP | 3249044 | 11/2017 |
| RU | 2008123244 | 12/2009 |
| WO | WO 0112845 | 2/2001 |
| WO | WO 2007/061753 | 5/2007 |
| WO | WO 2008/062165 | 5/2008 |
| WO | WO 2008/065370 | 5/2008 |
| WO | WO 2010/106318 | 9/2010 |
| WO | WO 2011/153378 | 12/2011 |
| WO | WO 2013/076577 | 5/2013 |
| WO | WO 2014/086842 | 6/2014 |
| WO | WO 2016/050890 | 4/2016 |
| WO | WO-2016050890 A2 * | 4/2016 ........... C12N 9/1051 |
| WO | WO 2016/117549 | 7/2016 |

OTHER PUBLICATIONS

Uniprot, Accession No. P23776, 2016, www.uniport.org. (Year: 2016).*
Van Rensburg et al., Over-expression of the Saccharomyces cerevisiae exo-beta-1,3-glucanase gene, J. Biotechnol. 55, 1997, 43-53. (Year: 1997).*
Wang et al., Hyperproduction of β-Glucanase Exg1 Promotes the Bioconversion of Mogrosides in Saccharomyces cerevisiae Mutants Defective in Mannoprotein Deposition, J. Agric. Food Chem. 63, 2015, 10271-79. (Year: 2015).*
UniProt Accession No. A7VJN1 (pp. 1-5), dated Oct. 23, 2007.
UniProt Accession No. B5AID3, dated Sep. 23, 2008.
UniProt Accession No. B5AID4 (pp. 1-4), dated Sep. 23, 2008.
UniProt Accession No. B5AID5 (pp. 1-4), dated Sep. 23, 2008.
UniProt Accession No. B9R6V0 (pp. 1-5), dated Mar. 24, 2009.
UniProt Accession No. B9RHC3 (pp. 1-6), dated Mar. 24, 2009.
UniProt Accession No. B9S6Y2 (pp. 1-5), dated Mar. 24, 2009.
UniProt Accession No. B9S7T0 (pp. 1-5), dated Mar. 24, 2009.
UniProt Accession No. B9S7W5 (pp. 1-5), dated Mar. 24, 2009.

(Continued)

Primary Examiner — Robert B Mondesi
Assistant Examiner — Todd M Epstein
(74) Attorney, Agent, or Firm — McDonnell Boehnen Hulbert & Berghoff LLP

(57) ABSTRACT

The invention relates to recombinant microorganisms and methods for producing mogroside compounds and mogroside precursors.

24 Claims, 8 Drawing Sheets
Specification includes a Sequence Listing.

(56) References Cited

OTHER PUBLICATIONS

UniProt Accession No. B9SX91 (pp. 1-6), dated Mar. 24, 2009.
UniProt Accession No. B9T0Y3 (pp. 1-5), dated Mar. 24, 2009.
UniProt Accession No. B9WZW7 (pp. 1-5), dated Apr. 14, 2009.
UniProt Accession No. C4P9M2 (pp. 1-5), dated Jul. 7, 2009 (pp. 1-5).
UniProt Accession No. C4P9M3, dated Jul. 7, 2009 (pp. 1-5).
UniProt Accession No. C6KE07, dated Sep. 1, 2009 (pp. 1-5).
UniProt Accession No. C6KE08, dated Sep. 1, 2009 (pp. 1-5).
UniProt Accession No. C7EDC9, dated Sep. 22, 2009 (pp. 1-5).
UniProt Accession No. C7EDD0, dated Sep. 22, 2009 (pp. 1-5).
UniProt Accession No. D6QX35, dated Jul. 13, 2010 (pp. 1-5).
UniProt Accession No. D6QX37, dated Jul. 13, 2010 (pp. 1-5).
UniProt Accession No. D6QX38, dated Jul. 13, 2010 (pp. 1-5).
UniProt Accession No. D6QX39, dated Jul. 13, 2010 (pp. 1-5).
UniProt Accession No. D6QX40, dated Jul. 13, 2010 (pp. 1-5).
UniProt Accession No. D6QX41, dated Jul. 13, 2010 (pp. 1-5).
UniProt Accession No. D6QX42, dated Jul. 13, 2010 (pp. 1-5).
UniProt Accession No. D6QX43, dated Jul. 13, 2010 (pp. 1-5).
UniProt Accession No. D6QX44, dated Jul. 13, 2010 (pp. 1-5).
UniProt Accession No. D6QX45, dated Jul. 13, 2010 (pp. 1-5).
UniProt Accession No. D6QX47, dated Jul. 13, 2010 (pp. 1-5).
UniProt Accession No. D6QX53, dated Jul. 13, 2010 (pp. 1-5).
UniProt Accession No. D6QX55, dated Jul. 13, 2010 (pp. 1-5).
UniProt Accession No. O65402, dated Aug. 1, 1998 (pp. 1-9).
UniProt Accession No. O65403, dated Aug. 1, 1998 (pp. 1-10).
UniProt Accession No. O65404, dated May 30, 2000 (pp. 1-10).
UniProt Accession No. O65726, dated May 30, 2000 (pp. 1-7).
UniProt Accession No. O65727, dated Aug. 1, 1998 (pp. 1-7).
UniProt Accession No. O81000, dated Nov. 1, 1998 (pp. 1-9).
UniProt Accession No. Q42760, dated Nov. 1, 1996 (pp. 1-5).
UniProt Accession No. Q42761, dated Nov. 1, 1996 (pp. 1-5).
UniProt Accession No. Q84LE3, dated Jun. 1, 2003 (pp. 1-5).
UniProt Accession No. Q8GSL6, dated Mar. 1, 2003 (pp. 1-6).
UniProt Accession No. Q8GSM8, dated Mar. 1, 2003 (pp. 1-5).
UniProt Accession No. Q8GSM9, dated Mar. 1, 2003 (pp. 1-5).
UniProt Accession No. Q9SM02, dated May 1, 2000 (pp. 1-11).
UniProt Accession No. Q9T064 (Q8VYH2), dated Mar. 1, 2002 (pp. 1-10).
International Search Report issued by the International Searching Authority for International Application No. PCT/IB2012/002857, dated May 14, 2013 (pp. 1-6).
Written Opinion of the International Searching Authority for International Application No. PCT/IB2012/002857, dated May 14, 2013 (pp. 1-7).
International Preliminary Report on Patentability issued by the International Preliminary Examining Authority for International Application No. PCT/IB2012/002857, dated Jan. 9, 2014 (pp. 1-13).
Non-Final Office Action for U.S. Appl. No. 14/356,782, dated Oct. 30, 2015 (pp. 1-12).
Final Office Action for U.S. Appl. No. 14/356,782, dated Jul. 18, 2016, pp. 1-16.
Response to Non-Final Office Action for U.S. Appl. No. 14/356,782, filed Mar. 22, 2016 (pp. 1-10).
UniProt Database Accession No. AT223684, "Stevia rebaudiana protein SEQ ID No. 10008," Feb. 3, 2011 (1 page).
GenBank Accession No. XP_008442743; last accessed Apr. 28, 2016 (pp. 1-2).
GenBank Accession No. XP_008450117; last accessed Apr. 28, 2016 (p. 1-2).
GenBank Accession No. XP_008454322; last accessed Apr. 21, 2016 (pp. 1-2).
UniProt Accession No. F6GXH0; last accessed Apr. 21, 2016 (pp. 1-2).
UniProt Accession No. F6HIX7; last accessed Apr. 28, 2016 (pp. 1-2).
UniProt Accession No. K7NBR2; last accessed Apr. 29, 2016 (p. 1).
UniProt Accession No. K7NBZ9; last accessed Apr. 21, 2016 (p. 1).
UniProt Accession No. W7PH03; last accessed Apr. 28, 2016 (p. 1).
UniProt Accession No. W9SCC7; last accessed Apr. 21, 2016 (p. 1).

UniProt Accession No. K7NBX0; last accessed Nov. 29, 2016 (pp. 1-4).
Bateman et al., "Pfam 3.1: 1313 multiple alignments and profile HMMs match the majority of proteins," Nucl Acids Res. 27(1):260-2 (1999).
Bowles et al., "Glycosyltransferases: manages of small molecules," Curr Opin Plant Biol. 8(3):254-63 (2005).
Brochado et al., "Improved vanillin production in baker's yeast through in silico design," Microb Cell Fact. 9:84 (2010).
Chatuvedula & Prakash, "Cucurbitane glycosides from Siraitia grosvenorii," J Carbohydrate Chem. 30(1):16-26 (2011).
Chiu et al., "Biotransformation of mogrosides from Siraitia grosvenorii Swingle by *Saccharomyces cerevisiae*," J Agric Food Chem. 61(29):7127-34 (2013).
Donald et al., "Effects of overproduction of the catalytic domain of 3-hydroxy-3-methylglutaryl coenzyme A reductase on squalene synthesis in *Saccharomyces cerevisiae*," Appl Environ Microbiol. 63(9):3341-4 (1997).
Guo et al., "Protein tolerance to random amino acid change," Proc Natl Acad Sci U 22;101(25):9205-10 (2004).
Hamberger & Bak, "Plant P450s as versatile drivers for evolution of species-specific chemical diversity," Philos Trans R Soc Lond B Biol Sci. 368(1612):20120426 (2013).
Jia & Yang, "A minor, sweet cucurbitane glycoside from Siraitia grosvenorii," Nat Prod Commun. 4(6):769-72 (2009).
Kasai et al., "Sweet cucurbitane glycosides from fruits of Siraitia siamensis (chi-zi luo-han-guo), a Chinese folk medicine," Agric Biol Chem. 53(12):3347-9 (1989).
Kirby et al., "Engineering triterpene production in *Saccharomyces cerevisiae*-beta-amyrin synthase from Artemisia annua," FEBS J. 275(8):1852-9 (2008).
Li et al. "Cucurbitane glycosides from unripe fruits of Lo Han Kuo (Siraiitia grosvenori)," Chem Pharm Bull (Tokyo) 54(10):1425-8 (2006).
Matsumoto, "Minor cucurbitane-glycosides from fruits of Siraitia grosvenorii (Cucurbitaceae)," Chem Pharm Bull. 38(7):2030-2 (1990).
Nilsson et al., "Chemical synthesis of proteins," Annu Rev Biophys Biomol Struct. 34: 91-118 (2005).
Poppenberger et al., "Heterologous expression of Arabidopsis UDP-glucosyltransferases in *Saccharomyces cerevisiae* for production of zearalenone-4-O-glucoside," Appl Environ Microbiol. 72(6):4404-10 (Jun. 2006).
Richman, Functional genomics uncovers three glucosyltransferases involved in the synthesis of the major sweet glucosides of Stevia rebaudiana, Plant J. 41(1):56-67 (2005).
Seki, Licorice beta-amyrin 11-oxidase, a cytochrome P450 with a key role in the biosynthesis of the triterpene sweetener glycyrrhizin. Proc Natl Acad Sci U S A. 105(37):14204-9 (2008).
Shao et al., "Crysal structures of a multifunctional triterpene/flavonoid glycosyltransferase from Medicago truncatula," Plant Cell. 17(11):3141-54 (Nov. 2005).
Shibuya et al., "Cucurbitadienol synthase, the first committed enzyme for cucurbitacin biosynthesis, is a distinct enzyme from cycloartenol synthase for phytosterol biosynthesis," Tetrahedron 60(33):6995-7003 (2004).
Sonnhammer et al., "Pfam: a comprehensive database of protein domain families based on seed alignments," Proteins 28(3):405-20 (1997).
Sonnhammer et al., "Pfam: multiple sequence alignments and HMM-profiles of protein domains," Nucl Acids Res. 26(1):320-2 (1998).
Takemoto et al., "Studies on the constituents of Fructus Momordicae. I. On the sweet principle," Yakugaku Zasshi 103(11):1151-4 (1983).
Takemoto et al., "Studies on the constituents of Fructus Momordicae. II. Structure of sapogenin," Yakugaku Zasshi 103(11):1155-66 (1983).
Takemoto et al., "Studies on the constituents of Fructus Momordicae. III. Structures of mogrosides," Yakugaku Zasshi 103(11):1167-73 (1983).
Tang et al., "An efficient approach to finding Siraitia grosvenorii triterpene biosynthetic genes by RNA-seq and digital gene expression analysis," BMC Genomics 12:343, p. 1-13 (2011).

(56) References Cited

OTHER PUBLICATIONS

Thompson et al., "CLUSTAL W: improving the sensitivity of progressive multiple sequence alignment through sequence weighting, position-specific gap penalties and weight matrix choice," Nucleic Acids Res. 22(22):4673-80 (1994).
Ukiya et al., "Inhibitory effects of cucurbitane glycosides and other triterpenoids from the fruit of Momordica grosvenori on epstein-barr virus early antigen induced by tumor promoter 12-O-tetradecanoylphorbol-13-acetate," J Agric Food Chem. 50(23):6710-5 (2002).
Xiong Mian-jing et al., "Biosynthesis of triterpene glycoside in Lo Han Kuo," Guangdong Pharmaceutical University 27(5):544-5 (2011). English abstract provided.
Wikipedia: "Mogroside," Internet Archive Wayback Machine Jan. 9, 2014 (Jan. 9, 2014), retrieved from the Internet: URL:https://web.archive.org/web/20140109130110/http://en.wikipedia.org/wiki/Mogroside [retrieved on Apr. 14, 2016] (pp. 1-2).
GenBank Accession No. AAS01524, dated Jul. 6, 2009 (pp. 1-2).
GenBank Accession No. ADC84219, dated Mar. 21, 2011 (pp. 1-2).
GenBank Accession No. BAA33460, dated Oct. 3, 1998 (pp. 1-2).
GenBank Accession No. BAA76902, dated Dec. 14, 2001 (pp. 1-2).
GenBank Accession No. BAB83085, dated Aug. 15, 2009 (pp. 1-2).
GenBank Accession No. BAB83086, dated Aug. 15, 2009 (pp. 1-2).
GenBank Accession No. BAD34645.1, dated Mar. 11, 2010 (pp. 1-2).
GenBank Accession No. BAE53431, dated Apr. 20, 2006 (pp. 1-2).
GenBank Accession No. XP_002264289, dated Dec. 10, 2014 (pp. 1-2).
GenBank Accession No. XP_002310905, dated Dec. 31, 2013 (pp. 1-2).
International Search Report issued by the International Searching Authority for International Application No. PCT/EP2013/075510, dated May 4, 2015 (pp. 1-7).
Written Opinion of the International Searching Authority for International Application No. PCT/EP2013/075510, dated Apr. 23, 2014 (pp. 1-14).
Written Opinion of the International Preliminary Examining Authority for International Application No. PCT/EP2013/075510, dated Feb. 4, 2015 (pp. 1-14).
Written Opinion of the International Preliminary Examining Authority for International Application No. PCT/EP2013/075510, dated May 5, 2015 (pp. 1-15).
International Search Report and Written Opinion of the International Searching Authority for International Application No. PCT/EP2015/072645, dated May 20, 2016 (pp. 1-39).
Non-Final Office Action for U.S. Appl. No. 14/356,782, dated Jun. 1, 2017 (pp. 1-15).
International Preliminary Report on Patentability issued by the International Preliminary Examining Authority for International Application No. PCT/EP2013/075510, dated Jul. 23, 2015 (pp. 1-15).
International Preliminary Report on Patentability issued by the International Preliminary Examining Authority for International Application No. PCT/EP2015/072645, dated Apr. 4, 2017 (pp. 1-28).
Non-Final Office Action for U.S. Appl. No. 14/442,694, dated May 16, 2017, pp. 1-13.
Frankel et al., "Characterization of diphtheria fusion proteins targeted to the human interleukin-3 receptor", Protein Eng., v.13, No. 8, p. 575-581 abstract, p. 579-580 (2000).
Pakula et al., "Genetic analysis of protein stability and function," Anna. Rev. Genet., v.23, 289-310 (p. 305-306) (1989).
Poppenberger et al., "Detoxification of the Fusarium mycotoxin deoxynivalenol by a UDP-glucosyltransferase from *Arabidopsis thaliana*," J Biol Chem. 278(48):47905-14 (Epub 2003).
Non-Final Office Action for U.S. Appl. No. 14/504,109, dated Jun. 29, 2016, pp. 1-13.
Final Office Action for U.S. Appl. No. 14/504,109, dated Sep. 8, 2016, pp. 1-18.
Non-Final Office Action for U.S. Appl. No. 14/504,109, dated Aug. 31, 2017 pp. 1-22.
Qiao et al., "Identification of a Novel Specific Cucurbitadienol Synthase Allele in Siraitia grosvenorii Correlates with High Catalytic Efficiency," Molecules. 24(3) (2019).
Wang et al., "Hyperproduction of β-Glucanase Exg1 Promotes the Bioconversion of Mogrosides in *Saccharomyces cerevisiae* Mutants Defective in Mannoprotein Deposition," J Agric Food Chem. 63(47):10271-9 (2015).
International Search Report issued by the International Searching Authority for International Application No. PCT/EP2018/066027, dated Aug. 10, 2018 (pp. 1-3).
Written Opinion of the International Searching Authority for International Application No. PCT/EP2018/066027, dated Aug. 10, 2018 (pp. 1-7).
Non-Final Office Action for U.S. Appl. No. 15/900,557, dated Aug. 30, 2019, pp. 1-15.
Non-Final Office Action for U.S. Appl. No. 15/511,565, dated Aug. 6, 2019, pp. 1-14.
Non-Final Office Action for U.S. Appl. No. 15/974,429, dated Dec. 26, 2018, pp. 1-8.
Ageitos et al., "Oily yeasts as oleaginous cell factories," Appl Microbiol Biotechnol. 90(4):1219-27 (May 2011).
Bankar et al., "Environmental and industrial applications of Yarrowia lipolytica," Appl Microbiol Biotechnol. 84(5):847-65 (Oct. 2009).
Beopoulos et al., "Yarrowia lipolytica: A model and a tool to understand the mechanisms implicated in lipid accumulation," Biochimie 91(6):692-6 (Jun. 2009).
Carmichael , "Geotrichum candidum," Mycologica, 49(6):820-830 (1957).
Chenna et al., "Multiple sequence alignment with the Clustal series of programs," Nucleic Acids Res. 31(13):3497-500 (2003).
Giaever & Nislow, "The yeast deletion collection: a decade of functional genomics," Genetics 197(2):451-65 (Jun. 2014).
Gossen & Bujard, "Studying gene function in eukaryotes by conditional gene inactivation," Ann Rev Genet. 36:153-73 (2002).
Hoffman et al., "An Ancient Yeast for Young Geneticists: A primer on the Schizosaccharomyces pombe Model System", Genetics, 201(2):403-23 (Oct. 2015).
Khoury et al., "Computational design of Candida boidinii xylose reductase for altered cofactor specificity," Protein Sci. 18(10):2125-38 (Oct. 2009).
Li et al., "High-density cultivation of oleaginous yeast Rhodosporidium toruloides Y4 in fed-batch culture," Enzyme and Microbial Technology 41(3):312-7 (Aug. 2007).
Mastromarino et al., "Bacterial vaginosis: a review on clinical trials with probiotics," New Microbiologica, 36:229-239 (Jul. 2013); Epub (Jun. 2013).
Mattanovich et al., "Recombinant protein production in yeasts," Methods Mol Biol. 824:329-58 (2012).
Nicaud, "Yarrowia lipolytica," Yeast 29(10):409-18 (Oct. 2012).
Nour-Eldin et al., "USER cloning and USER fusion: the ideal cloning techniques for small and big laboratories," Methods Mol Biol. 643:185-200 (2010).
Ooyen et al., "Heterologous protein production in the yeast Kluyveromyces lactis," FEMS Yeast Res. 6(3):381-92 (May 2006).
Osmani et al., "Substrate specificity of plant UDP-dependent glycosyltransferases predicted from crystal structures and homology modeling," Phytochemistry 70(3):325-47 (2009).
Papini et al., "Scheffersomyces stipitis: a comparative systems biology study with the Crabtree positive yeast *Saccharomyces cerevisae*", Micobial Cell Factories, 11:136 (Oct. 2012).
Piirainen et al., "Glycoengineering of yeasts from the perspective of glycosylation efficiency," N Biotechnol. 31(6):532-7 (Dec. 2014).
Prelich, "Gene overexpression: uses, mechanisms, and interpretation," Genetics 190(3):841-54 (Mar. 2012).
Saenge et al., "Potential use of oleaginous red yeast Rhodotorula glutinis for the bioconversion of crude glycerol from biodiesel plant to lipids and carotenoids," Process Biochemistry 46(1):210-8 (Jan. 2011).
Xu et al., "Generation of hepatitis B virus PreS2-S antigen in Hansenula polymorpha," Virol Sin. 29(6):403-9 (Dec. 2014).

(56) References Cited

OTHER PUBLICATIONS

Zhu et al., "A multi-omic map of the lipid-producing yeast Rhodosporidium toruloides," Nature Commun. 3:1112 (Oct. 2012).
International Preliminary Report on Patentability issued by the International Preliminary Examining Authority for International Application No. PCT/EP2018/066027, dated Dec. 17, 2019 (pp. 1-8).

* cited by examiner

Figure 4

PRODUCTION OF MOGROSIDE COMPOUNDS IN RECOMBINANT HOSTS

This application is a U.S. national phase of International Application No. PCT/EP2018/066027 filed on Jun. 15, 2018, which claims priority to and benefit of the U.S. Provisional Application Ser. No. 62/520,395, filed on Jun. 15, 2017. The entire disclosure contents of these applications are herewith incorporated by reference in their entirety into the present application.

REFERENCE TO AN ELECTRONIC SEQUENCE LISTING

A computer readable form of the Sequence Listing as an ASCII text file format is filed with this application by electronic submission and is incorporated into this application by reference in its entirety. The Sequence Listing is contained in the text file created on Jun. 15, 2018, having the file name "17_102_WO_ST25.txt" and is 389 kb in size.

BACKGROUND OF THE INVENTION

Field of the Invention

This disclosure relates to recombinant production of mogrol precursors, mogrol, and/or mogroside compounds in recombinant hosts. In particular, this disclosure relates to production of mogroside compounds comprising mono-glycosylated, di-glycosylated, tri-glycosylated, tetra-glycosylated, penta-glycosylated, and hexa-glycosylated mogrol in recombinant hosts.

Mogrosides are a family of triterpene glycosides isolated from fruit of Siraitia grosvenorii (S. grosvenorii, Swingle), also known as Momordica grosvenori. Fruit extracts are commercially used as natural sweeteners. Four major compounds, mogroside V, mogroside IV, siamenoside I, and 11-oxomogroside V (see FIG. 1) have been identified from S. grosvenorii as being responsible for the fruit's sweetness. Mogroside V is the most abundant of these four compounds, at approximately 0.57% (w/w) of the dry fruit, followed by mogroside IV and siamenoside I, each of which contains four glucose moieties. 11-oxomogroside V has a ketone group instead of a hydroxyl at C11. See, e.g., Takemoto et al., 1983, *Yakugaku Zasshi* 103: 1151-4; 1155-66; 1167-73; Kasai et al., 1989, *Agric. Biol. Chem.* 53:3347-9; Matsumoto *Chem. Pharm. Bull.*, 1990, 38:2030-2; and Prakash et al., 2011, *J. Carbohydrate Chem.* 30:16-26.

All mogrosides share the same mogrol triterpene core. The aglycone mogrol is glycosylated with different numbers of glucose moieties to form various mogroside compounds. Mogrosides can be synthesized in the following manner: synthesis of cucurbitadienol from the common triterpene precursor oxidosqualene, oxidation of cucurbitadienol to produce mogrol, and glycosylation of mogrol to produce various mogrosides. See, Tang et al., BMC Genomics 12: 343 (2011). Tang et al., 2011, BMC Genomics 12:343 describes seven cytochrome P450s and five UGTs as potential candidates involved in mogroside biosynthesis.

Chemical structures for several mogroside compounds are shown in FIG. 1. Extracts of S. grosvenorii generally comprise mogrosides that contribute to the sweet flavor, although the amount of each mogroside often varies, inter alia, among different production batches. Moreover, several mogroside compounds other than the four major compounds listed above are produced in relatively minor amounts.

As recovery and purification of mogrosides from S. grosvenorii have proven to be labor intensive and inefficient, there remains a need for a recombinant production system that can accumulate high yields of desired mogroside compounds, such as mogroside IIIE (MG-IIIE). There also remains a need for improved production of mogroside compounds in recombinant hosts for commercial uses.

SUMMARY OF THE INVENTION

It is against the above background that the present invention provides certain advantages and advancements over the prior art.

Although this invention as disclosed herein is not limited to specific advantages or functionalities, (such for example, the ability to scale up production of a one or more mogroside compounds, purify the one or more mogroside compounds, and produce mogroside compositions where the different proportions of the various mogroside compounds provide the advantage of having a reduced level of S. grosvenorii plant-derived components relative to a plant-derived S. grosvenorii extract), the invention provides a recombinant host cell capable of producing one or more mogroside compounds in a cell culture, the host cell comprising a recombinant gene encoding a heterologous or an endogenous polypeptide capable of deglycosylating a mogroside precursor; wherein the one or more mogroside compounds are a deglycosylation product of the mogroside precursor; and wherein expression of the gene increases production of the one or more mogroside compounds.

In some aspects of the recombinant host cells disclosed herein, the heterologous or the endogenous polypeptide is free of a domain facilitating secretion of the heterologous or the endogenous polypeptide from the host cell, preferably selected from a signal peptide or a transmembrane domain.

In some aspects of the recombinant host cells disclosed herein, the host cell is capable of retaining at least about 50% of an expressed heterologous or endogenous polypeptide capable of deglycosylating the mogroside precursor in a cytosol of the host cell.

In some aspects of the recombinant host cells disclosed herein, expression of the gene increases a cytosolic mogroside precursor deglycosylation activity of the host cell relative to a corresponding host cell lacking the gene.

In some aspects of the recombinant host cells disclosed herein, expression of the gene increases the cytosolic mogroside precursor deglycosylation activity of the host cell by at least about 10% relative to the corresponding host cell lacking the gene.

In some aspects of the recombinant host cells disclosed herein, expression of the gene increases the cytosolic mogroside precursor deglycosylation activity of the heterologous or the endogenous polypeptide comprising the host cell relative to the corresponding host cell lacking the gene.

In some aspects of the recombinant host cells disclosed herein, expression of the gene increases the cytosolic mogroside precursor deglycosylation activity of the heterologous or the endogenous polypeptide comprising the recombinant host cell by at least about 10%, relative to the corresponding host cell lacking the recombinant gene.

In some aspects of the recombinant host cells disclosed herein, the mogroside precursor is a tri-glycosylated, a tetra-glycosylated, a penta-glycosylated, a hexa-glycosylated mogrol, or an isomer thereof.

In some aspects of the recombinant host cells disclosed herein:
(a) the tri-glycosylated mogrol is mogroside III (MG-III), mogroside III A1 (MG-IIIA1), mogroside III A2 (MG-IIIA2), or mogroside III E (MG-IIIE);
(b) the tetra-glycosylated mogrol is mogroside IV (MG-IV), mogroside IV A (MG-IVA), or siamenoside I (SM-I); and
(c) the penta-glycosylated mogrol is mogroside V (MG-V) or 11-oxo-mogroside V (11-O-MG-V).

In some aspects of the recombinant host cells disclosed herein, the mogroside precursor is MG-V.

In some aspects of the recombinant host cells disclosed herein, the one or more mogroside compounds are a di-glycosylated, a tri-glycosylated, a tetra-glycosylated, a penta-glycosylated mogroside compound, or an isomer thereof.

In some aspects of the recombinant host cells disclosed herein:
(a) the di-glycosylated mogroside compound is mogroside II A (MG-IIA), mogroside II A1 (MG-IIA1), mogroside II A2 (MG-IIA2), or mogroside II E (MG-IIE),
(b) the tri-glycosylated mogroside compound is MG-III, MG-IIIA1, MG-IIIA2, or MG-IIIE;
(c) the tetra-glycosylated mogroside compound is MG-IV, MG-IVA, or SM-I; and
(d) the penta-glycosylated mogroside compound is MG-V or 11-O-MG-V.

In some aspects of the recombinant host cells disclosed herein, the mogroside compound is MG-IIIE.

In some aspects of the recombinant host cells disclosed herein, the heterologous or the endogenous polypeptide is a glucosidase polypeptide or a glucanase polypeptide.

In some aspects of the recombinant host cells disclosed herein, the polypeptide comprises a catalytically active portion of an endogenous glucosidase polypeptide or an endogenous glucanase polypeptide; and wherein the polypeptide does not comprise a signal peptide or a transmembrane domain that is comprised by the endogenous glucoside polypeptide.

In some aspects of the recombinant host cells disclosed herein, the heterologous or the endogenous polypeptide comprises a polypeptide having at least 50% sequence identity to the amino acid sequence set forth in SEQ ID NO:2.

In some aspect, the recombinant host cells disclosed herein further comprise:
(a) a gene encoding a polypeptide capable of synthesizing oxidosqualene from squalene; wherein the polypeptide comprises a polypeptide having at least 45% sequence identity to the amino acid sequence set forth in SEQ ID NO:3, or at least 50% sequence identity to the amino acid sequence set forth in any one of SEQ ID NOs:6-8, 11-12, or 20, or at least 55% sequence identity to the amino acid sequence set forth in SEQ ID NO:21, or at least 60% sequence identity to the amino acid sequence set forth in any one of SEQ ID NOs:10, 13-14, or 16-19, or at least 65% sequence identity to the amino acid sequence set forth in any one of SEQ ID NOs:4-5, 9, or 15,
(b) a gene encoding a polypeptide capable of synthesizing cucurbitadienol from oxidosqualene, or 24,25-epoxy-cucurbitadienol from dioxidosqualene; wherein the polypeptide comprises a polypeptide having at least 70% sequence identity to the amino acid sequence set forth in SEQ ID NO:24, or at least 75% sequence identity to the amino acid sequence set forth in SEQ ID NO:25, or at least 80% sequence identity to the amino acid sequence set forth in SEQ ID NO:26;
(c) a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol; wherein the polypeptide comprises a polypeptide having at least 70% sequence identity to the amino acid sequence set forth in SEQ ID NO:29;
(d) a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol; wherein the polypeptide comprises a polypeptide having at least 50% sequence identity to the amino acid sequence set forth in SEQ ID NO:31;
(e) a gene encoding a polypeptide capable of reducing a cytochrome P450 complex; wherein the polypeptide comprises a polypeptide having at least 50% sequence identity to the amino acid sequence set forth in SEQ ID NO:34;
(f) a gene encoding a polypeptide capable of synthesizing mogrol from 11-hydroxy-24,25-epoxy-cucurbitadienol; wherein the polypeptide comprises a polypeptide having at least 75% sequence identity to the amino acid sequence set forth in SEQ ID NO:36, or at least 65% sequence identity to the amino acid sequence set forth in SEQ ID NO:39; (g) a gene encoding a polypeptide capable of synthesizing mogrol from 11-hydroxy-cucurbitadienol; wherein the polypeptide comprises a polypeptide having at least 50% sequence identity to the amino acid sequence set forth in any one of SEQ ID NOs:41, 43, 47, 49, 51, 53, 55, 57, 59, 61, 65, 67, 69, 71, 73, or 75;
(h) a gene encoding a polypeptide capable of glycosylating mogrol or a mogroside compound at its C3 hydroxyl group, C11 hydroxyl group, C24 hydroxyl group, and/or C25 hydroxyl group thereof; wherein the polypeptide comprises a polypeptide having at least 50% sequence identity to the amino acid sequence set forth in any one of SEQ ID NOs:76-80, or at least 45% sequence identity to the amino acid sequence set forth in any one of SEQ ID NOs:83 or 86, or at least 60% sequence identity to the amino acid sequence set forth in SEQ ID NO:89; and/or
(i) a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound; wherein the polypeptide comprises a polypeptide having at least 70% sequence identity to the amino acid sequence set forth in any one of SEQ ID NOs:93 or 95, or at least 50% sequence identity to the amino acid sequence set forth in any one of SEQ ID NOs:99, 101, 103, 105, 107, 109, 115, or 117;
wherein at least one of the genes is a recombinant gene.

In some aspects, the recombinant host cells disclosed herein further comprise a gene encoding a polypeptide capable of synthesizing squalene from farnesyl pyrophosphate (FPP); wherein the polypeptide comprises a polypeptide having at least 55% sequence identity to the amino acid sequence set forth in SEQ ID NO:119.

In some aspects of the recombinant host cells disclosed herein, the recombinant host cell has reduced expression of at least one endogenous gene encoding a glucanase polypeptide or glucosidase polypeptide or at least one endogenous transcription factor gene that regulates expression of the at least one endogenous gene encoding the glucanase polypeptide or the glucosidase polypeptide.

In some aspects of the recombinant host cells disclosed herein, the endogenous gene encodes an exo-1,3-β-glucanase polypeptide having at least 50% sequence identity to the amino acid sequence set forth in SEQ ID NO:115 or 117.

In some aspects of the recombinant host cells disclosed herein, the recombinant host cell has reduced expression of at least one endogenous gene encoding a lanosterol synthase polypeptide.

In some aspects of the recombinant host cells disclosed herein, the lanosterol synthase polypeptide comprises an ERG7 polypeptide having an amino acid sequence set forth in SEQ ID NO:118.

The invention also provides a recombinant host cell capable of producing one or more mogroside compounds in a cell culture, comprising a recombinant gene encoding a polypeptide capable of deglycosylating a mogroside precursor having at least 50% sequence identity to the amino acid sequence set forth in SEQ ID NO:2, wherein the one or more mogroside compounds are a deglycosylation product of the mogroside precursor; and further comprising:
  (a) one or more genes encoding one or more polypeptides capable of glycosylating mogrol or a mogroside compound at its C3 hydroxyl group, C11 hydroxyl group, C24 hydroxyl group, and/or C25 hydroxyl group thereof; wherein the one or more polypeptides comprise a polypeptide having at least 45% sequence identity to the amino acid sequence set forth in any one of SEQ ID NOs:83 or 86, or at least 60% sequence identity to the amino acid sequence set forth in SEQ ID NO:89; and
  (b) one or more genes encoding one or more polypeptides capable of beta-1,2-glycosylation of the C2' position of the 24-O-glucose and/or beta-1,6-glycosylation of the C6' position of the 3-O-glucose and/or the 24-O-glucose of a mogroside compound; wherein the one or more polypeptides comprise a polypeptide having at least 70% sequence identity to the amino acid sequence set forth in SEQ ID NO:93 or at least 50% sequence identity to the amino acid sequence set forth in SEQ ID NO:99.

In some aspects, the recombinant host cells disclosed herein further comprise:
  (c) a gene encoding a polypeptide capable of synthesizing cucurbitadienol from oxidosqualene, or 24,25-epoxy-cucurbitadienol from dioxidosqualene having at least 70% sequence identity to the amino acid sequence set forth in SEQ ID NO:24;
  (d) a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol having at least 70% sequence identity to the amino acid sequence set forth in SEQ ID NO:29;
  (e) a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol having at least 50% sequence identity to the amino acid sequence set forth in SEQ ID NO:31;
  (f) a gene encoding a polypeptide capable of reducing cytochrome P450 complex having at least 50% sequence identity to the amino acid sequence set forth in SEQ ID NO:34; and
  (g) a gene encoding a polypeptide capable of synthesizing mogrol from 11-hydroxy-24,25-epoxy-cucurbitadienol having at least 65% sequence identity to the amino acid sequence set forth in SEQ ID NO:39;
wherein at least one of the genes is a recombinant gene.

In some aspects of the recombinant host cells disclosed herein, the recombinant host cell comprises a plant cell, a mammalian cell, an insect cell, a fungal cell from *Aspergillus* genus, or a yeast cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* species, an algal cell, or a bacterial cell from *Escherichia coli* species or *Bacillus* genus.

In some aspects of the recombinant host cells disclosed herein, the recombinant host cell is a *Saccharomyces cerevisiae* cell.

In some aspects of the recombinant host cells disclosed herein, the recombinant host cell is a *Yarrowia lipolytica* cell.

The invention also provides a method of producing one or more mogroside compounds in a cell culture, comprising culturing the recombinant host cells disclosed herein in the cell culture, under conditions in which the genes are expressed; wherein the one or more mogroside compounds are produced by the recombinant host cells; and wherein the one or more mogroside compounds are a deglycosylation product of the mogroside precursor.

In some aspects of the methods disclosed herein, the genes are constitutively expressed.

In some aspects of the methods disclosed herein, the expression of the genes is induced.

In some aspects of the methods disclosed herein, the mogroside precursor is produced by the recombinant host cell.

The invention also provides a method of producing one or more mogroside compounds, comprising whole cell bioconversion of one or more plant-derived or synthetic mogroside precursors in a cell culture medium of a recombinant host cell using a polypeptide capable of deglycosylating a mogroside precursor; and, optionally:
  (a) a polypeptide capable of glycosylating mogrol or a mogroside compound at its C3 hydroxyl group, C11 hydroxyl group, C24 hydroxyl group, and/or C25 hydroxyl group thereof; and/or
  (b) a polypeptide capable of beta-1,2-glycosylation of the C2' position of the 24-O-glucose and/or beta-1,6-glycosylation of the C6' position of the 3-O-glucose and/or the 24-O-glucose of a mogroside compound;
wherein at least one of the polypeptides is a recombinant polypeptide expressed in the recombinant host cell; wherein the one or more mogroside compounds are a deglycosylation product of the mogroside precursor; and producing the one or more mogroside compounds thereby.

In some aspects, the methods disclosed herein further comprise whole cell bioconversion of one or more plant-derived or synthetic mogrol precursors in a cell culture medium of a recombinant host cell further using:
  (c) a polypeptide capable of synthesizing oxidosqualene from squalene;
  (d) a polypeptide capable of synthesizing cucurbitadienol from oxidosqualene, or 24,25-epoxy-cucurbitadienol from dioxidosqualene;
  (e) a polypeptide capable of synthesizing 24,25-epoxy-cucurbitadienol from cucurbitadienol, or 11-hydroxy-24,25-epoxy-cucurbitadienol from 11-hydroxy-cucurbitadienol;

(f) a polypeptide capable of synthesizing 11-hydroxy-cucurbitadienol from cucurbitadienol, or 11-hydroxy-24,25-epoxy-cucurbitadienol from 24,25-epoxy-cucurbitadienol;
(g) a polypeptide capable of reducing cytochrome P450 complex;
(h) a polypeptide capable of synthesizing mogrol from 11-hydroxy-24,25-epoxy-cucurbitadienol; and/or
(i) a polypeptide capable of synthesizing mogrol from 11-hydroxy-cucurbitadienol;
wherein at least one of the polypeptides is a recombinant polypeptide expressed in the recombinant host cell.

In some aspects of the methods disclosed herein, the polypeptide capable of deglycosylating a mogroside precursor comprises a polypeptide having at least 50% sequence identity to the amino acid sequence set forth in SEQ ID NO:2, and wherein:
(a) the polypeptide capable of glycosylating mogrol or a mogroside compound at its C3 hydroxyl group, C11 hydroxyl group, C24 hydroxyl group, and/or C25 hydroxyl group thereof comprises a polypeptide having at least 50% sequence identity to the amino acid sequence set forth in any one of SEQ ID NOs:76-80, or at least 45% sequence identity to the amino acid sequence set forth in SEQ ID NOs:83 or 86, or at least 60% sequence identity to the amino acid sequence set forth in SEQ ID NO:89;
(b) the polypeptide capable of beta-1,2-glycosylation of the C2' position of the 24-O-glucose and/or beta-1,6-glycosylation of the C6' position of the 3-O-glucose and/or the 24-O-glucose of a mogroside compound comprises a polypeptide having at least 70% sequence identity to the amino acid sequence set forth in SEQ ID NOs:93 or 95, or at least 50% sequence identity to the amino acid sequence set forth in any one of SEQ ID NOs:99, 101, 103, 105, 107, 109, 115, or 117;
(c) the polypeptide capable of synthesizing oxidosqualene from squalene comprises a polypeptide having at least 45% sequence identity to the amino acid sequence set forth in SEQ ID NO:3, or at least 50% sequence identity to the amino acid sequence set forth in any one of SEQ ID NOs:6-8, 11-12, or 20, or at least 55% sequence identity to the amino acid sequence set forth in SEQ ID NO:21, or at least 60% sequence identity to the amino acid sequence set forth in any one of SEQ ID NOs:10, 13-14, or 16-19, or at least 65% sequence identity to the amino acid sequence set forth in any one of SEQ ID NOs:4-5, 9, or 15;
(d) the polypeptide capable of synthesizing cucurbitadienol from oxidosqualene, or 24,25-epoxy-cucurbitadienol from dioxidosqualene or cucurbitadienol comprises a polypeptide having at least 70% sequence identity to the amino acid sequence set forth in SEQ ID NO:24, or at least 75% sequence identity to the amino acid sequence set forth in SEQ ID NO:25, or at least 80% sequence identity to the amino acid sequence set forth in SEQ ID NO:26;
(e) the polypeptide capable of synthesizing 24,25-epoxy-cucurbitadienol from cucurbitadienol, or 11-hydroxy-24,25-epoxy-cucurbitadienol from 11-hydroxy-cucurbitadienol comprises a polypeptide having at least 70% sequence identity to the amino acid sequence set forth in SEQ ID NO:29;
(f) the polypeptide capable of synthesizing 11-hydroxy-cucurbitadienol from cucurbitadienol, or 11-hydroxy-24,25-epoxy-cucurbitadienol from 24,25-epoxy-cucurbitadienol comprises a polypeptide having at least 50% sequence identity to the amino acid sequence set forth in SEQ ID NO:31;
(g) the polypeptide capable of reducing cytochrome P450 complex comprises a polypeptide having at least 50% sequence identity to the amino acid sequence set forth in SEQ ID NO:34;
(h) the polypeptide capable of synthesizing mogrol from 11-hydroxy-24,25-epoxy-cucurbitadienol comprises a polypeptide having at least 75% sequence identity to the amino acid sequence set forth in SEQ ID NO:36, or at least 65% sequence identity to the amino acid sequence set forth in SEQ ID NO:39; and/or
(i) the polypeptide capable of synthesizing mogrol from 11-hydroxy-cucurbitadienol comprises a polypeptide having at least 50% sequence identity to the amino acid sequence set forth in any one of SEQ ID NOs:41, 43, 47, 49, 51, 53, 55, 57, 59, 61, 65, 67, 69, 71, 73, or 75.

In some aspects of the methods disclosed herein, the recombinant host cell is cultured in a fermentor at a temperature for a period of time, wherein the temperature and period of time facilitate the production of the one or more mogroside compounds.

In some aspects of the methods disclosed herein, the recombinant host cell comprises a plant cell, a mammalian cell, an insect cell, a fungal cell from *Aspergillus* genus, or a yeast cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* species, an algal cell, or a bacterial cell from *Escherichia coli* species or *Bacillus* genus.

In some aspects of the methods disclosed herein, the recombinant host cell is a *Saccharomyces cerevisiae* cell.

In some aspects of the methods disclosed herein, the recombinant host cell is a *Yarrowia lipolytica* cell.

The invention also provides an in vitro method of producing one or more mogroside compounds, comprising adding a polypeptide capable of deglycosylating a mogroside precursor; and, optionally:
(a) a polypeptide capable of glycosylating mogrol or a mogroside compound at its C3 hydroxyl group, C11 hydroxyl group, C24 hydroxyl group, and/or C25 hydroxyl group thereof; and/or
(b) a polypeptide capable of beta-1,2-glycosylation of the C2' position of the 24-O-glucose and/or beta-1,6-glycosylation of the C6' position of the 3-O-glucose and/or the 24-O-glucose of a mogroside compound; and
one or more plant-derived or synthetic mogroside precursors to a reaction mixture;
wherein at least one of the polypeptides is a recombinant polypeptide;
wherein the one or more mogroside compounds are a deglycosylation product of the mogroside precursor; and producing the one or more mogroside compounds thereby.

In some aspects, the methods disclosed herein further comprise adding:
(c) a polypeptide capable of synthesizing oxidosqualene from squalene;
(d) a polypeptide capable of synthesizing cucurbitadienol from oxidosqualene, or 24,25-epoxy-cucurbitadienol from dioxidosqualene;

(e) a polypeptide capable of synthesizing 24,25-epoxy-cucurbitadienol from cucurbitadienol, or 11-hydroxy-24,25-epoxy-cucurbitadienol from 11-hydroxy-cucurbitadienol;
(f) a polypeptide capable of synthesizing 11-hydroxy-cucurbitadienol from cucurbitadienol, or 11-hydroxy-24,25-epoxy-cucurbitadienol from 24,25-epoxy-cucurbitadienol;
(g) a polypeptide capable of reducing cytochrome P450 complex;
(h) a polypeptide capable of synthesizing mogrol from 11-hydroxy-24,25-epoxy-cucurbitadienol; and/or
(i) a polypeptide capable of synthesizing mogrol from 11-hydroxy-cucurbitadienol; and one or more plant-derived or synthetic mogrol precursors to a reaction mixture; and producing the one or more mogroside compounds thereby.

In some aspects of the methods disclosed herein, the polypeptide capable of deglycosylating a mogroside precursor comprises polypeptide having at least 50% sequence identity to the amino acid sequence set forth in SEQ ID NO:2, and wherein:
(a) the polypeptide capable of glycosylating mogrol or a mogroside compound at its C3 hydroxyl group, C11 hydroxyl group, C24 hydroxyl group, and/or C25 hydroxyl group thereof comprises a polypeptide having at least 50% sequence identity to the amino acid sequence set forth in any one of SEQ ID NOs:76-80, or at least 45% sequence identity to the amino acid sequence set forth in any one of SEQ ID NOs:83 or 86, or at least 60% sequence identity to the amino acid sequence set forth in SEQ ID NO:89;
(b) the polypeptide capable of beta-1,2-glycosylation of the C2' position of the 24-O-glucose and/or beta-1,6-glycosylation of the C6' position of the 3-O-glucose and/or the 24-O-glucose of a mogroside compound comprises a polypeptide having at least 70% sequence identity to the amino acid sequence set forth in any one of SEQ ID NOs:93 or 95, or at least 50% sequence identity to the amino acid sequence set forth in any one of SEQ ID NOs:99, 101, 103, 105, 107, 109, 115, or 117;
(c) the polypeptide capable of synthesizing oxidosqualene from squalene comprises a polypeptide having at least 45% sequence identity to the amino acid sequence set forth in SEQ ID NO:3, or at least 50% sequence identity to the amino acid sequence set forth in any one of SEQ ID NOs:6-8, 11-12, or 20, or at least 55% sequence identity to the amino acid sequence set forth in SEQ ID NO:21, or at least 60% sequence identity to the amino acid sequence set forth in any one of SEQ ID NOs:10, 13-14, or 16-19, or at least 65% sequence identity to the amino acid sequence set forth in any one of SEQ ID NOs:4-5, 9, or 15;
(d) the polypeptide capable of synthesizing cucurbitadienol from oxidosqualene, or 24,25-epoxy-cucurbitadienol from dioxidosqualene or cucurbitadienol comprises a polypeptide having at least 70% sequence identity to the amino acid sequence set forth in SEQ ID NO:24, or at least 75% sequence identity to the amino acid sequence set forth in SEQ ID NO:25, or at least 80% sequence identity to the amino acid sequence set forth in SEQ ID NO:26;
(e) the polypeptide capable of synthesizing 24,25-epoxy-cucurbitadienol from cucurbitadienol, or 11-hydroxy-24,25-epoxy-cucurbitadienol from 11-hydroxy-cucurbitadienol comprises a polypeptide having at least 70% sequence identity to the amino acid sequence set forth in SEQ ID NO:29;
(f) the polypeptide capable of synthesizing 11-hydroxy-cucurbitadienol from cucurbitadienol, or 11-hydroxy-24,25-epoxy-cucurbitadienol from 24,25-epoxy-cucurbitadienol comprises a polypeptide having at least 50% sequence identity to the amino acid sequence set forth in SEQ ID NO:31;
(g) the polypeptide capable of reducing cytochrome P450 complex comprises a polypeptide having at least 50% sequence identity to the amino acid sequence set forth in SEQ ID NO:34; (h) the polypeptide capable of synthesizing mogrol from 11-hydroxy-24,25-epoxy-cucurbitadienol comprises a polypeptide having at least 75% sequence identity to the amino acid sequence set forth in SEQ ID NO:36, or at least 65% sequence identity to the amino acid sequence set forth in SEQ ID NO:39; and/or
(i) the polypeptide capable of synthesizing mogrol from 11-hydroxy-cucurbitadienol comprises a polypeptide having at least 50% sequence identity to the amino acid sequence set forth in any one of SEQ ID NOs:41, 43, 47, 49, 51, 53, 55, 57, 59, 61, 65, 67, 69, 71, 73, or 75.

In some aspects, the methods disclosed herein further comprise isolating the produced one or more mogroside compounds.

In some aspects of the methods disclosed herein, the isolating step comprises separating a liquid phase of the cell culture or the reaction mixture from a solid phase of the cell culture or the reaction mixture to obtain a supernatant comprising the produced one or more mogroside compounds, and:
(a) contacting the supernatant with one or more adsorbent resins in order to obtain at least a portion of the produced one or more mogroside compounds; or
(b) contacting the supernatant with one or more ion exchange or reversed-phase chromatography columns in order to obtain at least a portion of the produced one or more mogroside compounds; or
(c) crystallizing or extracting the produced one or more mogroside compounds;
thereby isolating the produced one or more mogroside compounds.

In some aspects, the methods disclosed herein further comprise recovering a mogroside composition comprising the one or more mogroside compounds from the cell culture or the reaction mixture.

In some aspects of the methods disclosed herein, the recovered mogroside composition is enriched for the one or more mogroside compounds relative to a mogroside composition from a S. grosvenorii plant and has a reduced level of S. grosvenorii plant-derived components relative to a plant-derived S. grosvenorii extract.

In some aspects of the methods disclosed herein, the recovered mogroside composition comprises MG-IIA, MG-IIA1, MG-IIA2, MG-III, MG-IIIA1, MG-IIIA2, MG-IIIE, MG-IV, MG-IVA, SM-I, 11-O-MG-V, and/or MG-V.

In some aspects of the methods disclosed herein, rein the mogroside precursor is a tri-glycosylated, a tetra-glycosylated, a penta-glycosylated, or a hexa-glycosylated mogrol.

In some aspects of the methods disclosed herein:
(a) the tri-glycosylated mogrol is MG-III, MG-IIIA1, MG-IIIA2, or MG-IIIE;
(b) the tetra-glycosylated mogrol is MG-IV, MG-IVA, or SM-I; and
(c) the penta-glycosylated mogrol is MG-V or 11-O-MG-V.

In some aspects of the methods disclosed herein, the mogroside precursor is MG-V.

In some aspects of the methods disclosed herein, the one or more mogroside compounds are a di-glycosylated, a tri-glycosylated, a tetra-glycosylated, a penta-glycosylated mogroside compound, or an isomer thereof.

In some aspects of the methods disclosed herein:
(a) di-glycosylated mogroside compound is MG-IIA, MG-IIA1, MG-IIA2, or MG-IIE,
(b) the tri-glycosylated mogroside compound is MG-III, MG-IIIA1, MG-IIIA2, or MG-IIIE;
(c) the tetra-glycosylated mogroside compound is MG-IV, MG-IVA, or SM-I; and
(d) the penta-glycosylated mogroside compound is MG-V or 11-O-MG-V.

In some aspects of the methods disclosed herein, the mogroside compound is MG-IIIE.

The invention also provides a method of converting a mogroside precursor into a mogroside compound, the method comprising contacting the mogroside precursor with the recombinant host cell disclosed herein, a cell free extract derived from the recombinant host cell, or a polypeptide capable of deglycosylating a mogroside precursor; a polypeptide capable of synthesizing oxidosqualene from squalene; a polypeptide capable of synthesizing cucurbitadienol from oxidosqualene, or 24,25-epoxy-cucurbitadienol from dioxidosqualene; a polypeptide capable of synthesizing 24,25-epoxy-cucurbitadienol from cucurbitadienol, or 11-hydroxy-24,25-epoxy-cucurbitadienol from 11-hydroxy-cucurbitadienol; a polypeptide capable of synthesizing 11-hydroxy-cucurbitadienol from cucurbitadienol, or 11-hydroxy-24,25-epoxy-cucurbitadienol from 24,25-epoxy-cucurbitadienol; a polypeptide capable of reducing cytochrome P450 complex; a polypeptide capable of synthesizing mogrol from 11-hydroxy-24,25-epoxy-cucurbitadienol; a polypeptide capable of synthesizing mogrol from 11-hydroxy-cucurbitadienol; a polypeptide capable of glycosylating mogrol or a mogroside compound at its C3 hydroxyl group, C11 hydroxyl group, C24 hydroxyl group, and/or C25 hydroxyl group thereof; and/or a polypeptide capable of beta-1,2-glycosylation of the C2' position of the 24-O-glucose and/or beta-1,6-glycosylation of the C6' position of the 3-O-glucose and/or the 24-O-glucose of a mogroside compound; or a mixture of the polypeptides derived from the recombinant host cell or the cell free extract derived from the recombinant host cell to convert the mogroside precursor into the mogroside compound; wherein the mogroside compound is a deglycosylation product of the mogroside precursor.

In some aspects of the methods disclosed herein, the polypeptide capable of synthesizing oxidosqualene from squalene comprises a polypeptide having at least 45% sequence identity to the amino acid sequence set forth in SEQ ID NO:3, or at least 50% sequence identity to the amino acid sequence set forth in any one of SEQ ID NOs:6-8, 11-12, or 20, or at least 55% sequence identity to the amino acid sequence set forth in SEQ ID NO:21, or at least 60% sequence identity to the amino acid sequence set forth in any one of SEQ ID NOs:10, 13-14, or 16-19, or at least 65% sequence identity to the amino acid sequence set forth in any one of SEQ ID NOs:4-5, 9, or 15; the polypeptide capable of synthesizing cucurbitadienol from oxidosqualene, or 24,25-epoxy-cucurbitadienol from dioxidosqualene or cucurbitadienol comprises a polypeptide having at least 70% sequence identity to the amino acid sequence set forth in SEQ ID NO:24, or at least 75% sequence identity to the amino acid sequence set forth in SEQ ID NO:25, or at least 80% sequence identity to the amino acid sequence set forth in SEQ ID NO:26; the polypeptide capable of synthesizing 24,25-epoxy-cucurbitadienol from cucurbitadienol, or 11-hydroxy-24,25-epoxy-cucurbitadienol from 11-hydroxy-cucurbitadienol comprises a polypeptide having at least 70% sequence identity to the amino acid sequence set forth in SEQ ID NO:29; the polypeptide capable of synthesizing 11-hydroxy-cucurbitadienol from cucurbitadienol, or 11-hydroxy-24,25-epoxy-cucurbitadienol from 24,25-epoxy-cucurbitadienol comprises a polypeptide having at least 50% sequence identity to the amino acid sequence set forth in SEQ ID NO:31; the polypeptide capable of reducing cytochrome P450 complex comprises a polypeptide having at least 50% sequence identity to the amino acid sequence set forth in SEQ ID NO:34; the polypeptide capable of synthesizing mogrol from 11-hydroxy-24,25-epoxy-cucurbitadienol comprises a polypeptide having at least 75% sequence identity to the amino acid sequence set forth in SEQ ID NO:36, or at least 65% sequence identity to the amino acid sequence set forth in SEQ ID NO:39; the polypeptide capable of synthesizing mogrol from 11-hydroxy-cucurbitadienol comprises a polypeptide having at least 50% sequence identity to the amino acid sequence set forth in any one of SEQ ID NOs:41, 43, 47, 49, 51, 53, 55, 57, 59, 61, 65, 67, 69, 71, 73, or 75; the polypeptide capable of deglycosylating a mogroside precursor comprises polypeptide having at least 50% sequence identity to the amino acid sequence set forth in SEQ ID NO:2; the polypeptide capable of glycosylating mogrol or a mogroside compound at its C3 hydroxyl group, C11 hydroxyl group, C24 hydroxyl group, and/or C25 hydroxyl group thereof comprises a polypeptide having at least 50% sequence identity to the amino acid sequence set forth in any one of SEQ ID NOs:76-80, or at least 45% sequence identity to the amino acid sequence set forth in any one of SEQ ID NOs:83 or 86, or at least 60% sequence identity to the amino acid sequence set forth in SEQ ID NO:89; and the polypeptide capable of beta-1,2-glycosylation of the C2' position of the 24-O-glucose and/or beta-1,6-glycosylation of the C6' position of the 3-O-glucose and/or the 24-O-glucose of a mogroside compound comprises a polypeptide having at least 70% sequence identity to the amino acid sequence set forth in any one of SEQ ID NOs:93 or 95, or at least 50% sequence identity to the amino acid sequence set forth in any one of SEQ ID NOs:99, 101, 103, 105, 107, 109, 115, or 117.

The invention also provides a method of producing one or more mogroside compounds, comprising:
(a) transferring a glucose moiety from a mogroside precursor, comprising contacting the mogroside precursor with a polypeptide capable of deglycosylating the mogroside precursor under suitable reaction conditions for the transfer of the glucose moiety from the mogroside precursor; and further comprising:
(b) transferring the glucose moiety to the C3 hydroxyl group, the C11 hydroxyl group, the C24 hydroxyl group, the C25 hydroxyl group, the C2' position of the 24-O-glucose, the C6' position of the 3-O-glucose and/or the 24-O-glucose of the mogroside precursor; comprising contacting the mogroside precursor with the polypeptide capable of glycosylating the mogroside precursor compound at its C3 hydroxyl group, C11 hydroxyl group, C24 hydroxyl group, and/or C25 hydroxyl group thereof and/or the polypeptide capable of beta-1,2-glycosylation of the C2' position of the 24-O-glucose and/or beta-1,6-glycosylation of the C6' position of the 3-O-glucose and/or the 24-O-glucose of the mogroside precursor and a one or more UDP-glucose under suitable reaction conditions for the transfer of the glucose moiety to the mogroside precursor;

wherein the mogroside precursor is a tri-glycosylated, a tetra-glycosylated, a penta-glycosylated, or a hexa-glycosylated mogrol;

wherein at least one of the polypeptides is a recombinant polypeptide; and producing the one or more mogroside compounds thereby; and wherein the one or more mogroside compounds are a deglycosylation product of the mogroside precursor.

In some aspects of the methods disclosed herein, the polypeptide capable of deglycosylating a mogroside precursor comprises polypeptide having at least 50% sequence identity to the amino acid sequence set forth in SEQ ID NO:2; the polypeptide capable of glycosylating mogrol or a mogroside compound at its C3 hydroxyl group, C11 hydroxyl group, C24 hydroxyl group, and/or C25 hydroxyl group thereof comprises a polypeptide having at least 50% sequence identity to the amino acid sequence set forth in any one of SEQ ID NOs:76-80, or at least 45% sequence identity to the amino acid sequence set forth in any one of SEQ ID NOs:83 or 86, or at least 60% sequence identity to the amino acid sequence set forth in SEQ ID NO:89; and the polypeptide capable of beta-1,2-glycosylation of the C2' position of the 24-O-glucose and/or beta-1,6-glycosylation of the C6' position of the 3-O-glucose and/or the 24-O-glucose of a mogroside compound comprises a polypeptide having at least 70% sequence identity to the amino acid sequence set forth in any one of SEQ ID NOs:93 or 95, or at least 50% sequence identity to the amino acid sequence set forth in any one of SEQ ID NOs:99, 101, 103, 105, 107, 109, 115, or 117.

In some aspects, the method disclosed herein is an in vitro method, further comprising supplying the one or more UDP-glucose or a cell-free system for regeneration of the one or more UDP-glucose.

In some aspects of the methods disclosed herein, the in vitro method is an enzymatic in vitro method or a whole cell in vitro method.

The invention also provides a cell culture, comprising the recombinant host cells disclosed herein, the cell culture further comprising:
(a) the one or more mogroside compounds produced by the recombinant host cells;
(b) glucose, fructose, sucrose, xylose, rhamnose, uridine diphosphate (UDP)-glucose, UDP-rhamnose, UDP-xylose, and/or N-acetyl-glucosamine; and
(c) supplemental nutrients comprising trace metals, vitamins, salts, YNB, and/or amino acids;

wherein the one or more mogroside compounds is present at a concentration of at least 1 mg/liter of the cell culture;

wherein the cell culture is enriched for the one or more mogroside compounds relative to a mogroside composition from a *S. grosvenorii* plant; and wherein the cell culture has a reduced level of *S. grosvenorii* plant-derived components relative to a plant-derived *S. grosvenorii* extract.

The invention also provides a cell lysate from the recombinant host cells disclosed herein grown in the cell culture, wherein the cell lysate comprises:
(a) the one or more mogroside compounds produced by the recombinant host cells;
(b) glucose, fructose, sucrose, xylose, rhamnose, uridine diphosphate (UDP)-glucose, UDP-rhamnose, UDP-xylose, and/or N-acetyl-glucosamine; and
(c) supplemental nutrients comprising trace metals, vitamins, salts, YNB, and/or amino acids;

wherein the one or more mogroside compounds is present at a concentration of at least 1 mg/liter of the cell culture.

The invention also provides a mogroside composition, comprising the one or more mogroside compounds produced by the recombinant host cells or the methods disclosed herein;

wherein the one or more mogroside compounds in the mogroside composition are present in relative amounts that are different from a mogroside composition from a *S. grosvenorii* plant; and wherein the cell culture has a reduced level of *S. grosvenorii* plant-derived components relative to a plant-derived *S. grosvenorii* extract.

The invention also provides a sweetener composition, comprising the mogroside composition disclosed herein.

The invention also provides a food product comprising the sweetener composition disclosed herein.

The invention also provides a beverage or a beverage concentrate, comprising the sweetener composition disclosed herein.

The invention also provides a nucleic acid molecule encoding a polypeptide or a catalytically active portion thereof capable of deglycosylating a mogroside precursor, wherein the encoded polypeptide or the catalytically active portion thereof comprises a polypeptide having at least 50% sequence identity to the amino acid sequence set forth in SEQ ID NO:2.

In some aspects of the nucleic acids disclosed herein, the nucleic acid is an isolated nucleic acid.

In some aspects of the nucleic acids disclosed herein, the nucleic acid is cDNA.

The invention also provides a polypeptide or a catalytically active portion thereof capable of deglycosylating a mogroside precursor, wherein the polypeptide or the catalytically active portion thereof comprises a polypeptide having at least 50% sequence identity to the amino acid sequence set forth in SEQ ID NO:2.

In some aspects of the polypeptide or the catalytically active portion thereof disclosed herein, the polypeptide or the catalytically active portion thereof is a purified polypeptide or a catalytically active portion thereof.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 2 shows production of cucurbitadienol from oxidosqualene using a cucurbitadienol synthase (step A), production of 24,25 epoxy cucurbitadienol from dioxidosqualene using a cucurbitadienol synthase (step B), production of 11-hydroxy-cucurbitadienol from cucurbitadienol using a cytochrome P450 (step C), production of 11-hydroxy 24,25 epoxy cucurbitadienol from 24,25 epoxy cucurbitadienol using a cytochrome P450 (step D), production of 24,25 epoxy cucurbitadienol from cucurbitadienol using a cytochrome P450 (step E), production of 11-hydroxy 24,25 epoxy cucurbitadienol from 11-hydroxy-cucurbitadienol using a cytochrome P450 (step F), production of mogrol from 11-hydroxy 24,25 epoxy cucurbitadienol from using an epoxide hydrolase (step G), production of mogrol from 11-hydroxy-cucurbitadienol using a cytochrome P450 and an epoxide hydrolase (steps F and G), and production of one or more mogroside compounds using one or more UGTs (step H).

FIG. 4 shows the area-under-the-curve (AUC) values of MG-V excretion and total MG-V production, provided via LC-MS, of an *S. cerevisiae* strain comprising and expressing a recombinant gene encoding a UGT430 polypeptide, a recombinant gene encoding a UGT98 polypeptide, a recombinant gene encoding a UGT1576 polypeptide, and a recombinant gene encoding a UGT11789 polypeptide further engineered to disrupt expression of native exo-1,3-β-glucanase polypeptide (EXG1; SEQ ID NO:115), as described in more detail in Example 2, below.

Figure 1:
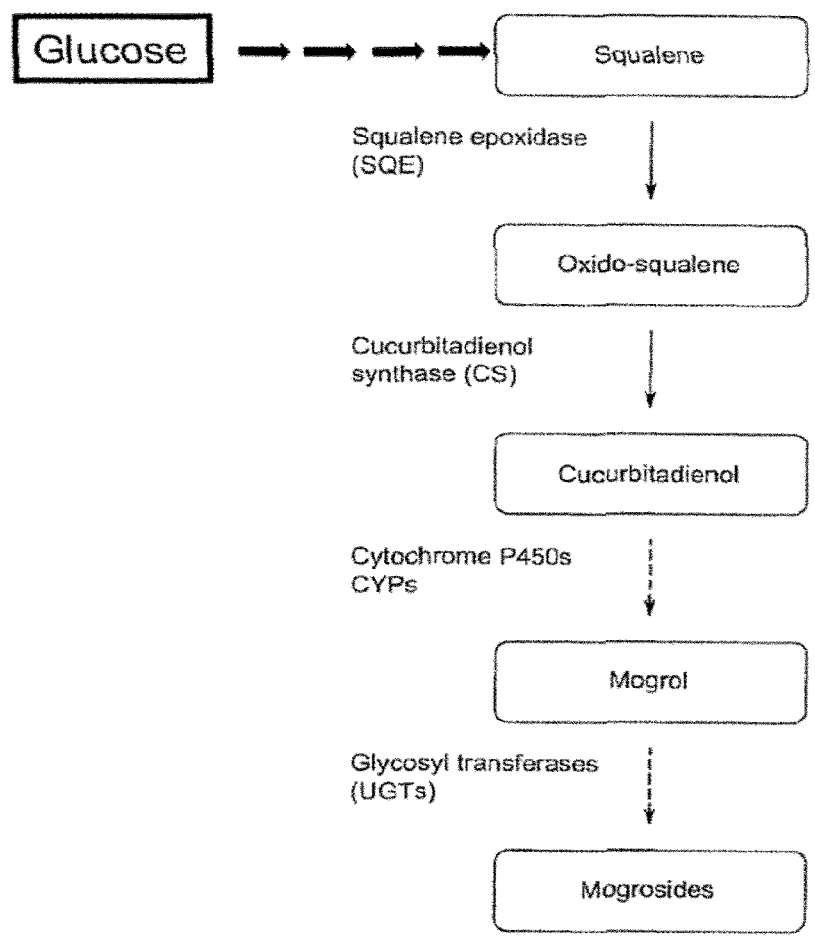
FIG. 1 is a schematic diagram of a pathway for producing mogrosides from glucose.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide," "nucleotide," "oligonucleotide," and "nucleic acid" can be used interchangeably to refer to nucleic acid comprising DNA, RNA, derivatives thereof, or combinations thereof, in either single-stranded or double-stranded embodiments depending on context as understood by the skilled worker.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In some aspects, said recombinant genes are encoded by cDNA. In other embodiments, recombinant genes are synthetic and/or codon-optimized for expression in *S. cerevisiae*.

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to *S. cerevisiae*, including, but not limited to *S. cerevisiae* strain S288C. In some embodiments, an endogenous yeast gene is overexpressed. As used herein, the term "overexpress" is used to refer to the expression of a gene in an organism at levels higher than the level of gene expression in a wild type organism. See, e.g., Prelich, 2012, *Genetics* 190:841-54. See, e.g., Giaever & Nislow, 2014, *Genetics* 197(2):451-65. In some aspects, overexpression can be performed by integration using the USER cloning system; see, e.g., Nour-Eldin et al., 2010, Methods Mol Biol. 643:185-200. As used herein, the terms "deletion," "deleted," "knockout," and "knocked out" can be used interchangeably to refer to an endogenous gene that has been manipulated to no longer be expressed in an organism, including, but not limited to, *S. cerevisiae*.

As used herein, the terms "heterologous sequence" and "heterologous coding sequence" are used to describe a sequence derived from a species other than the recombinant host. In some embodiments, the recombinant host is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

As used herein, the term "heterologous polypeptide" is used to describe a form of an endogenous polypeptide that has been genetically engineered to lack a signal peptide or a transmembrane domain present in the endogenous polypeptide.

As used herein, the term "endogenous polypeptide" is used to describe a full-length endogenous polypeptide or a modified, for example but not limited to, a truncated endogenous polypeptide.

As used herein, the term "heterologous or endogenous polypeptide" is used to describe a form of an endogenous polypeptide that has been genetically engineered to lack a signal peptide or a transmembrane domain present in the endogenous polypeptide or a full-length endogenous polypeptide or a modified, for example but not limited to, a truncated endogenous polypeptide.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, *Ann. Rev. Genetics* 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

Figure 2:
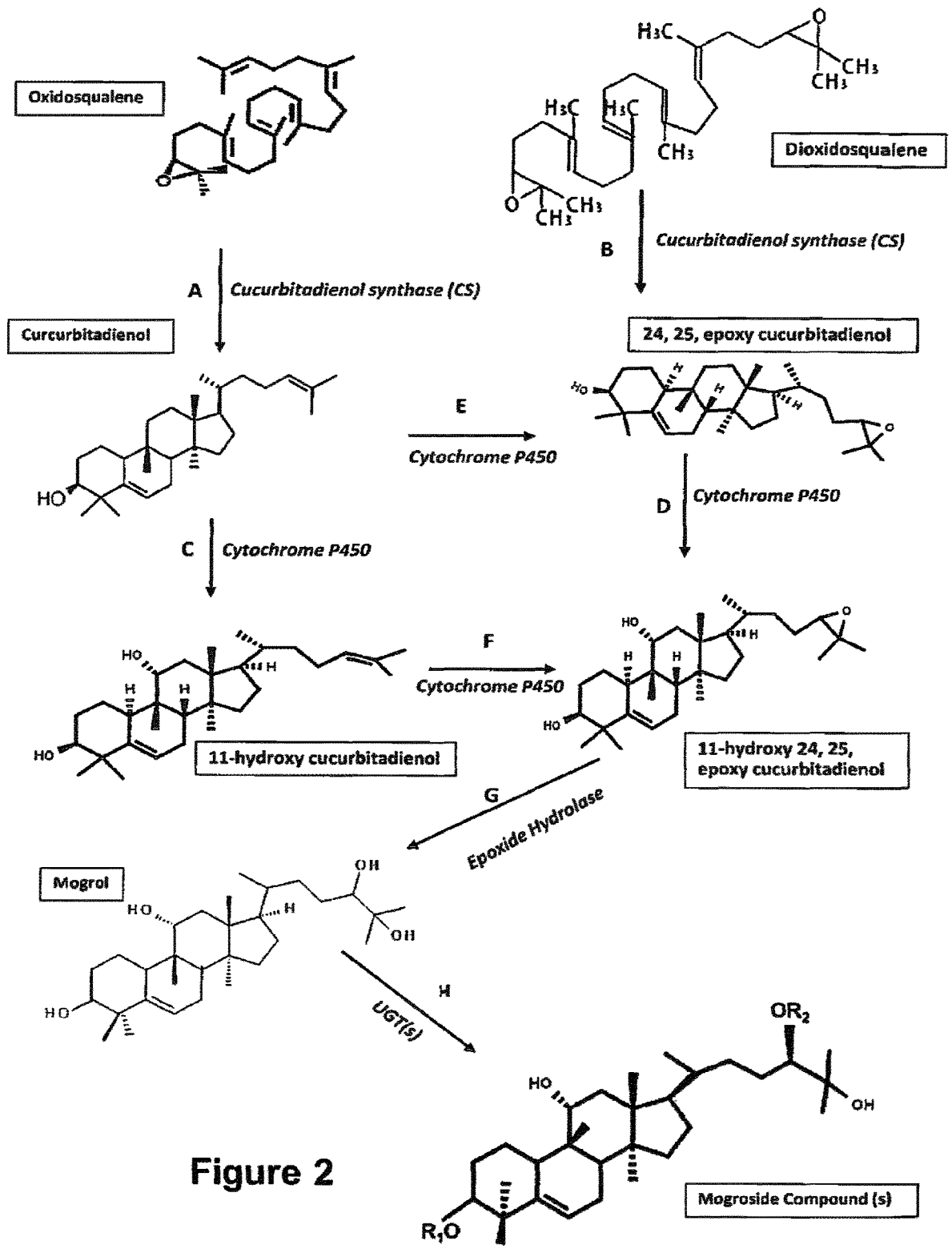
FIG. 2 shows a pathway for production of mogrol precursors, mogrol, and mogroside compounds.

As used herein, the terms "mogrol precursor" and "mogrol precursor compound" are used interchangeably to refer to intermediate compounds in the mogrol biosynthetic pathway. Mogrol precursors include, but are not limited to, squalene, oxidosqualene, dioxidosqualene, cucurbitadienol, 24,25-epoxy-cucurbitadienol, 11-oxo-cucurbitadienol, 11-oxo-24,25-epoxy-cucurbitabienol, 11-hydroxy-cucurbitadienol, and 11-hydroxy-24,25-epoxy-cucurbitabienol. See FIG. 2.

As used herein, the terms "mogroside," "mogroside compound," "glycosylated mogrol," and "glycosylated mogrol compound" are used interchangeably to describe mogrol glycosylated at one or more positions. In particular, a mogroside compound can be mogrol glycosylated with one or more glucose moieties at the C-1, C-3, C-11, C-24, and C-25 positions of Formula I, as noted below. The person of ordinary skill in the art will appreciate that the mogrol moiety of a mogroside compound may be further modified—e.g., the C-11 position of a mogroside compound may be an oxo-group.

Formula I

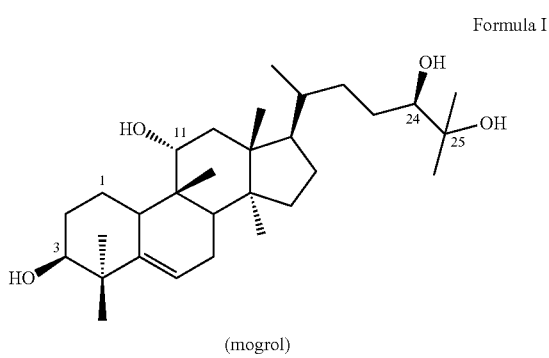

(mogrol)

Figure 3A:
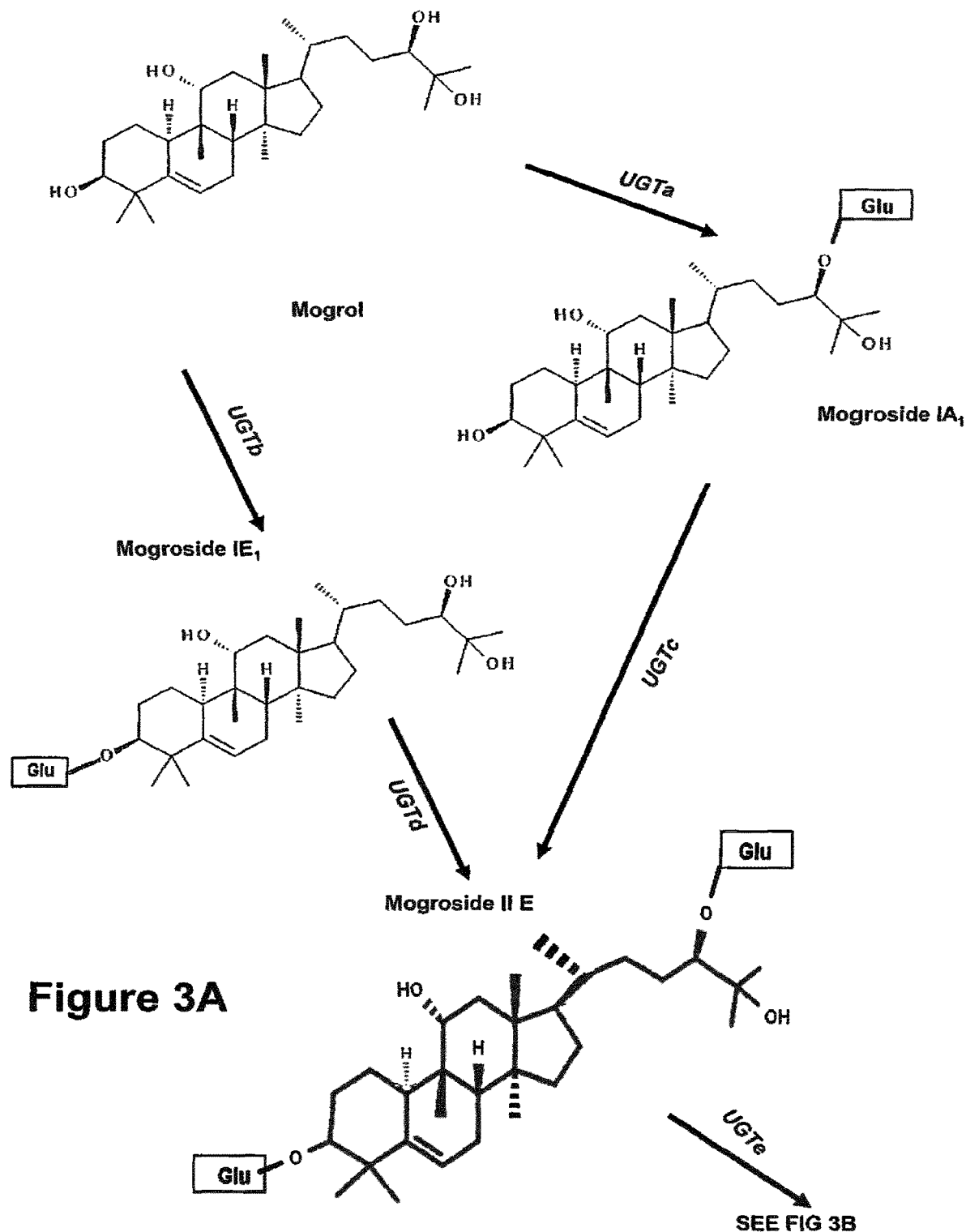
FIGS. 3A-3B shows schematic diagram of pathways for the biosynthesis of mogroside I E1, mogroside I A1, mogroside II E, mogroside III A2, mogroside III, mogroside IV, mogroside V, and Mogroside III E from mogrol using UGTs and/or glucanases or glucosidases. UGTa of FIG. 3A can be, for example, UGT1576 (SEQ ID NO:89) or UGT1697 (SEQ ID NO:86). UGTb of FIG. 3A can be, for example, UGT430 (SEQ ID NO:83) or UGT1697 (SEQ ID NO:86). UGTc of FIG. 3A can be, for example, UGT430 (SEQ ID NO:83) or UGT1697 (SEQ ID NO:86). UGTd of FIG. 3A can be, for example, UGT1576 (SEQ ID NO:89) or UGT1697 (SEQ ID NO:86). UGTe of FIGS. 3A-3B can be, for example, UGT98 (SEQ ID NO:93) or UGT11789 (SEQ ID NO:99). UGTf of FIG. 3B can be, for example, UGT98 (SEQ ID NO:93) or UGT11789 (SEQ ID NO:99). UGTg of FIG. 3B can be, for example, UGT98 (SEQ ID NO:93) or UGT11789 (SEQ ID NO:99). X of FIG. 3B can be, for example, tEXG1 (SEQ ID NO:2).
Figure 3B:
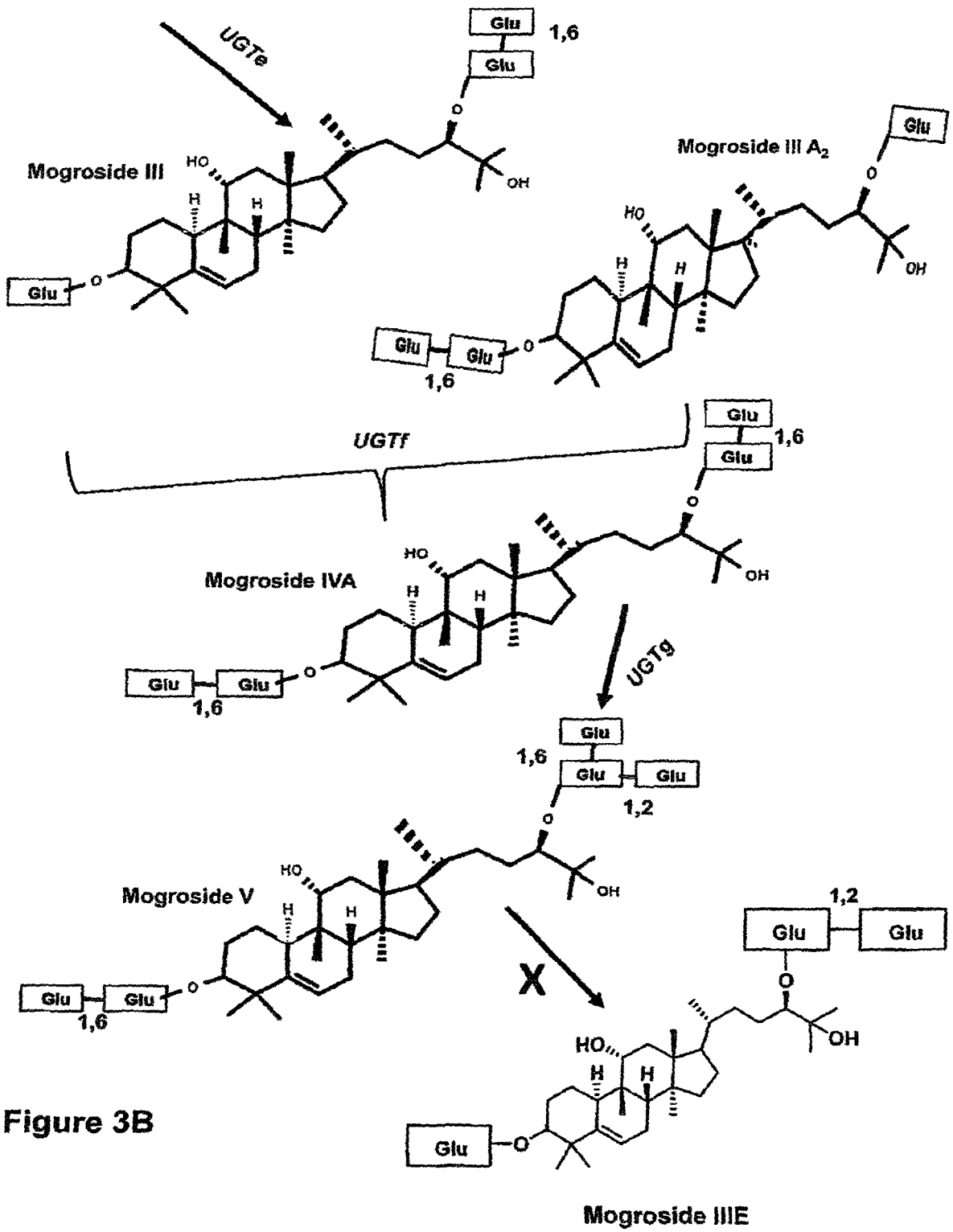

As used herein, the terms "mogroside compound," "glycosylated mogrol," and "glycosylated mogrol compound" are used interchangeably to refer to, for example but not limited to, mogroside V (MG-V) (CAS #88901-36-4), 11-oxo-mogroside V (11-O-MG-V) (CAS #126105-11-1), siamenoside I (SM-I) (CAS #126105-12-2), mogroside IV (MG-IV) (CAS #89590-95-4), mogroside IV A (MG-IVA) (CAS #88901-41-1), mogroside III (MG-III) (CAS # 130567-83-8), mogroside III A1 (MG-IIIA1) (CAS #88901-42-2), mogroside III A2 (MG-IIIA2) (CAS #88901-43-3), mogroside III E (MG-IIIE) (CAS #88901-37-5), mogroside II A (MG-IIA), mogroside II A1 (MG-IIA1) (CAS #88901-44-4), mogroside II A2 (MG-IIA2) (CAS #88901-45-5), mogroside II E (MG-IIE) (CAS #88901-38-6), mogroside I A1 (MG-IA1) (CAS #88901-46-6) (also referred to as mogroside 1b), mogroside I E1 (MG-IE1) (CAS #88901-39-7) (also referred to as mogroside Ia), a tri-glycosylated mogroside compound, a tetra-glycosylated mogroside compound, a penta-glycosylated mogroside compound, a hexa-glycosylated mogroside compound, a hepta-glycosylated mogroside compound, and isomers thereof. See FIGS. 3A-3B.

In some embodiments, the mogroside compound (i.e., that is a deglycosylation product of the mogroside precursor) is a di-glycosylated mogroside compound (e.g., MG-IIA, MG-IIA1, MG-IIA2, or MG-IIE), a tri-glycosylated mogroside compound (e.g., MG-III, MG-IIIA1, MG-IIIA2, or MG-IIIE), a tetra-glycosylated mogroside compound (e.g., MG-IV, MG-IVA, or SM-I), a penta-glycosylated mogroside compound (e.g., MG-V or 11-O-MG-V), or an isomer thereof.

As used herein, the terms "mogroside precursor" and "mogroside precursor compound" are used interchangeably to refer to intermediate compounds in the mogroside biosynthetic pathway. See FIGS. 3A-3B. In some embodiments, mogroside precursors are themselves mogroside compounds or glycosylated mogrol compounds, for example but not limited to, a tri-glycosylated (e.g., MG-III, MG-IIIA1, MG-IIIA2, or MG-IIIE), a tetra-glycosylated (e.g., MG-IV, MG-IVA, or SM-I), a penta-glycosylated (e.g., MG-V or 11-O-MG-V), or a hexa-glycosylated mogroside compounds or glycosylated mogrol compounds, or isomers thereof. In some embodiments, the mogroside precursor is MG-V.

In certain such embodiments, the mogroside compound is a glycosylation product of a mogroside precursor that is itself a mogroside compound or a glycosylated mogrol compound. For example, MG-IIA, MG-IIIA1, and SM-I are precursors of MG-V. In other such embodiments, the mogroside compound is a deglycosylation product of a mogroside precursor that is itself a mogroside compound. For example, MG-V is a precursor of MG-IIIE.

Mogroside compounds and/or mogroside precursors can be produced in vivo (i.e., in a recombinant host), in vitro (i.e., enzymatically), or by whole cell bioconversion. As used herein, the terms "produce" and "accumulate" can be used interchangeably to describe synthesis of mogroside compounds and mogroside precursors in vivo, in vitro, or by whole cell bioconversion.

As used herein, the terms "culture broth," "culture medium," and "growth medium" can be used interchangeably to refer to a liquid or solid that supports growth of a cell. A culture broth can comprise glucose, fructose, sucrose, trace metals, vitamins, salts, yeast nitrogen base (YNB), and/or amino acids. The trace metals can be divalent cations, including, but not limited to, $Mn^{2+}$ and/or $Mg^{2+}$. In some embodiments, $Mn^{2+}$ can be in the form of $MnCl_2$ dihydrate and range from approximately 0.01 g/L to 100 g/L. In some embodiments, $Mg^{2+}$ can be in the form of $MgSO_4$ heptahydrate and range from approximately 0.01 g/L to 100 g/L. For example, a culture broth can comprise i) approximately 0.02-0.03 g/L $MnCl_2$ dihydrate and approximately 0.5-3.8 g/L $MgSO_4$ heptahydrate, ii) approximately 0.03-0.06 g/L $MnCl_2$ dihydrate and approximately 0.5-3.8 g/L $MgSO_4$ heptahydrate, and/or iii) approximately 0.03-0.17 g/L $MnCl_2$ dihydrate and approximately 0.5-7.3 g/L $MgSO_4$ heptahydrate. Additionally, a culture broth can comprise one or more mogroside precursors or mogroside compounds produced by a recombinant host, as described herein.

Recombinant mogroside-producing *Saccharomyces cerevisiae* (*S. cerevisiae*) strains are described in WO 2014/086842 and WO 2016/050890, each of which is incorporated by reference in their entirety. Methods of producing mogroside compounds in recombinant hosts, by whole cell bioconversion, and in vitro are also described in WO 2013/076577, which is incorporated by reference in its entirety, as well as WO 2014/086842 and WO 2016/050890.

In some embodiments, mogroside compounds and/or mogroside precursors are produced in vivo through expression of one or more enzymes involved in the mogroside biosynthetic pathway in a recombinant host.

In some embodiments, a recombinant host comprising a gene encoding a polypeptide capable of synthesizing oxidosqualene or dioxidosqualene from squalene (e.g., squalene epoxidase or squalene monooxygenase); a gene encoding a polypeptide capable of synthesizing cucurbitadienol from oxidosqualene, or 24,25-epoxy-cucurbitadienol from dioxidosqualene (e.g., a cucurbitadienol synthase (CS)); a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol (e.g., a cytochrome P450 (CYP)); a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol (e.g., a CYP); a gene encoding a polypeptide capable of reducing cytochrome P450 complex (e.g., a cytochrome P450 reductase (CPR); for example, but not limited to a polypeptide capable of electron transfer from NADPH to cytochrome P450 complex during conversion of NADPH to $NADP^+$, which is utilized as a cofactor for terpene biosynthesis); a gene encoding a polypeptide capable of synthesizing mogrol from 11-hydroxy-24,25-epoxy-cucurbitadienol (e.g., a CYP); and/or a gene encoding a polypeptide capable of synthesizing mogrol from 11-hydroxy-24,25-epoxy-cucurbitadienol (e.g., an epoxide hydrolase) can produce mogrol in vivo. See, e.g., FIG. 2. The skilled worker will appreciate that one or more of these genes can be endogenous to the host provided that at least one (and in some embodiments, all) of these genes is a recombinant gene introduced into the recombinant host.

In some embodiments, a mogrol-producing recombinant host further comprises a gene encoding a polypeptide capable of synthesizing squalene from farnesyl pyrophosphate (FPP) (e.g., squalene synthase).

In some embodiments, a recombinant host comprising a gene encoding a polypeptide capable of glycosylating mogrol or a mogroside compound at its C3 hydroxyl group, C11 hydroxyl group, C24 hydroxyl group, and/or C25 hydroxyl group thereof (e.g., a UDP-glucuronosyltransferase (UGT)); and/or a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound (e.g., a UGT) can produce a mogroside compound in vivo. In some embodiments, the recombinant host is a mogrol-producing recombinant host. The skilled worker will appreciate that one or more of these genes can be endogenous to the host provided that at least one (and in some embodiments, all) of these genes is a recombinant gene introduced into the recombinant host.

In some embodiments, mogroside compounds and/or mogroside precursors are produced in vivo through expression of one or more enzymes involved in the mogroside biosynthetic pathway in a recombinant host. For example, a recombinant host comprising a gene encoding a polypeptide capable of synthesizing oxidosqualene or dioxidosqualene from squalene; a gene encoding a polypeptide capable of synthesizing cucurbitadienol from oxidosqualene, or 24,25-epoxy-cucurbitadienol from dioxidosqualene; a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol; a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol; a gene encoding a polypeptide capable of reducing cytochrome P450 complex; a gene encoding a polypeptide capable of synthesizing mogrol from 11-hydroxy-24,25-epoxy-cucurbitadienol; a gene encoding a polypeptide capable of synthesizing mogrol from 11-hydroxy-24,25-epoxy-cucurbitadienol; a gene encoding a polypeptide capable of glycosylating mogrol or a mogroside compound at its C3 hydroxyl group, C11 hydroxyl group, C24 hydroxyl group, and/or C25 hydroxyl group thereof; and/or a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound can produce a mogroside and/or a mogroside precursor in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

In some embodiments, one or more of the recombinant genes encoding one or more polypeptides involved in the mogroside biosynthetic pathway comprises a nucleotide sequence that originated from or is present in the same species as the recombinant host. In some aspects, expression of a recombinant gene encoding a mogroside biosynthetic pathway polypeptide results in a total expression level of genes encoding a mogroside biosynthetic pathway polypeptide, i.e., an overexpression of a mogroside biosynthetic pathway polypeptide.

For example, in some embodiments, a recombinant host comprises a recombinant gene comprising a nucleotide sequence native to the host, encoding a polypeptide capable of synthesizing oxidosqualene or dioxidosqualene from squalene, resulting in overexpression of a polypeptide capable of synthesizing oxidosqualene or dioxidosqualene from squalene.

In some embodiments, one or more of the genes encoding one or more polypeptides involved in the mogroside biosynthetic pathway is a gene present in the same species as the recombinant host, i.e., an endogenous gene. In some embodiments, the wild-type promoter of an endogenous gene encoding the mogroside biosynthetic pathway polypeptide can be exchanged for a strong promoter. In some aspects, the strong promoter drives high expression of the endogenous gene (i.e., overexpression of the gene). In other embodiments, the wild-type enhancer of an endogenous gene encoding a mogroside biosynthetic pathway polypeptide can be exchanged for a strong enhancer. In some embodiments, the strong enhancer drivers high expression of the endogenous gene (i.e., overexpression of the gene). In some embodiments, both the wild-type enhancer (i.e., operably linked to the promoter) and the wild-type promoter (i.e., operably linked to the endogenous gene) of the endogenous gene can be exchanged for a strong enhancer and strong promoter, respectively, resulting in overexpression of a mogroside biosynthetic pathway polypeptide (i.e., relative to the expression level of endogenous genes operably linked to wild-type enhancer and/or promoters). The endogenous gene operably linked to the strong enhancer and/or promoter may be located at the native loci, or may be located elsewhere in the genome.

For example, in some embodiments, a recombinant host comprises an endogenous gene encoding a polypeptide capable of synthesizing oxidosqualene or dioxidosqualene from squalene, operably linked to a strong promoter (e.g., a strong promoter native to the host, or a heterologous strong promoter), resulting in overexpression of a polypeptide capable of synthesizing oxidosqualene or dioxidosqualene from squalene.

The person of ordinary skill in the art will appreciate that, e.g., expression of a recombinant gene encoding a mogroside biosynthetic pathway polypeptide; expression of a recombinant gene and a native gene encoding a mogroside biosynthetic pathway polypeptide; and expression of a native gene encoding a mogroside biosynthetic pathway polypeptide, wherein the wild-type promoter and/or enhancer of the native gene are exchanged for a strong promoter and/or enhancer, each result in overexpression of the mogroside biosynthetic pathway polypeptide relative to a corresponding host not expressing a recombinant gene encoding a mogroside biosynthetic pathway polypeptide and/or a corresponding host expressing only a native gene encoding a mogroside biosynthetic pathway polypeptide, operably linked to the wild-type promoter and enhancer—i.e., as used herein, the term "expression" may include "overexpression".

In some embodiments, a recombinant host expressing one or more enzymes involved in the mogroside biosynthetic pathway in a recombinant host comprises reduced expression (or repressed expression) of one or more endogenous genes. For example, in some embodiments, a recombinant host comprises reduced expression of an endogenous gene encoding a lanosterol synthase polypeptide (e.g., a polypeptide having the amino acid sequence set forth in SEQ ID NO:118) (i.e., to increase oxidosqualene accumulation, see WO 2016/050890). In another example, in some embodiments, a recombinant host comprises reduced expression of an endogenous gene encoding an exo-1,3-β-glucanase polypeptide (e.g., a polypeptide having the amino acid sequence set forth in SEQ ID NO:115 or SEQ ID NO:117) (i.e., to reduce deglycosylation of mogroside compounds, see WO 2016/050890).

Expression of an endogenous gene is typically reduced by disrupting expression of the endogenous gene itself, e.g., by exchanging the wild-type promoter of an endogenous gene with a weak promoter or inducible promoter, by disrupting expression of a transcription factor gene that regulates expression of the endogenous gene, or by deleting the endogenous gene and/or a transcription factor gene that regulates expression of the endogenous gene. Reduced expression may also comprise inactivation of a gene, e.g., by introducing a mutation to an endogenous gene to reduce or even completely eliminate the activity of the polypeptide encoded by the endogenous gene.

In some aspects, a recombinant host expressing a recombinant gene encoding a polypeptide capable of deglycosylating a mogroside precursor is capable of producing, in vivo, one or more mogroside compounds that are a deglycosylation product of the mogroside precursor. In some embodiments, the mogroside precursor is a tri-glycosylated mogroside compound (e.g., MG-III, MG-IIIA1, MG-IIIA2, or MG-IIIE), a tetra-glycosylated mogroside compound (e.g., MG-IV, MG-IVA, or SM-I), a penta-glycosylated mogroside compound (e.g., MG-V or 11-O-MG-V), a hexa-glycosylated mogroside compound, or an isomer thereof. In some embodiments, the mogroside precursor is MG-V. In some embodiments, the mogroside compound (i.e., that is a deglycosylation product of the mogroside precursor) is a di-glycosylated mogroside compound (e.g., MG-IIA, MG-IIA1, MG-IIA2, or MG-IIE), a tri-glycosylated mogroside compound (e.g., MG-III, MG-IIIA1, MG-IIIA2, or MG-IIIE), a tetra-glycosylated mogroside compound (e.g., MG-IV, MG-IVA, or SM-I), a penta-glycosylated mogroside compound (e.g., MG-V or 11-O-MG-V), or an isomer thereof. In some embodiments, the mogroside compound is MG-IIIE. For example, in some embodiments, a recombinant host expressing a recombinant gene encoding a polypeptide capable of deglycosylating a mogroside precursor is capable of producing MG-IIIE, a deglycosylation product of MG-V, in vivo.

In some embodiments, the polypeptide capable of deglycosylating a mogroside precursor does not comprise a signal peptide or a transmembrane domain. As used herein, the term "signal peptide" describes any polypeptide domain that facilitates excretion of the polypeptide comprising the signal peptide from a host cell. Also as used herein, the term "transmembrane domain" describes any polypeptide domain that facilitates translocation of the polypeptide comprising the transmembrane domain into the membrane of a host cell. In some embodiments, the polypeptide capable of deglycosylating a mogroside precursor is a glucosidase polypeptide or a glucanase polypeptide. In some embodiments, the heterologous or endogenous polypeptide comprising the recombinant host cell and capable of deglycosylating the mogroside precursor does not comprise a signal peptide or a transmembrane domain. In some embodiments, less than about 50% of the expressed heterologous or endogenous polypeptide capable of deglycosylating the mogroside precursor, in total, is excreted from the recombinant host cell or translocated into the recombinant host cell membrane.

The person of ordinary skill in the art will appreciate that a polypeptide lacking a signal peptide or a transmembrane domain, expressed in a recombinant host, will be retained in the cytosol of the recombinant host in a level higher than that of a corresponding polypeptide comprising a signal peptide or transmembrane domain. For example, in some embodiments, the polypeptide capable of deglycosylating a mogroside precursor is an exo-1,3-β-glucanase polypeptide. For example, in some embodiments, the polypeptide capable of deglycosylating a mogroside precursor is a truncated exo-1,3-β-glucanase polypeptide lacking an N-terminal signal peptide. In some embodiments, at least about 60%, e.g., at least about 65%, at least about 70%, at least about 75%, at least about 80%, at least about 85%, at least about 90%, or at least about 95% of a polypeptide capable of deglycosylating a mogroside precursor, expressed in a recombinant host, is localized in the cytosol of the recombinant host.

In some embodiments, the polypeptide capable of deglycosylating a mogroside precursor comprises a polypeptide having the amino acid sequence set forth in SEQ ID NO:2 (which can be encoded by the nucleotide sequence set forth in SEQ ID NO:1). In some embodiments, a polypeptide having the amino acid sequence set forth in SEQ ID NO:2 is capable of deglycosylating MG-V to provide MG-IIIE.

In some embodiments, expression of a recombinant gene increases the cytosolic mogroside precursor glycosylation activity of the recombinant host cell by at least about 10%, or about 25%, or about 50%, or at about 75%, or about 100%, relative to a corresponding host cell lacking the recombinant gene.

In some embodiments, expression of a recombinant gene encoding a polypeptide capable of deglycosylating a mogroside precursor in a mogroside-producing recombinant host results in increase the amount of one or more mogroside compounds that are a deglycosylation product of the mogroside precursor by at least about 5%, e.g. at least about 7.5%, or at least about 10%, or at least about 12.5%, or at least about 15%, or at least about 17.5%, or at least about 20%, or at least about 25%, or at least about 27.5%, or at least about 30%, or at least about 35%, or at least about 40%, or at least about 45%, or at least about 50%, or at least about 60%, or at least about 70%, or at least about 80%, or at least about 90%, or at least about 100%, or at least about 110%, or at least about 120%, or at least about 130%, or at least about 140%, or at least about 150%, or at least about 160%, or at least about 170%, or at least about 180%, or at least about 190%, or at least about 200%, relative to a corresponding host lacking the recombinant gene encoding a polypeptide capable of deglycosylating a mogroside precursor. For example, in some embodiments, expression of a recombinant gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2) in a recombinant host capable of producing mogroside V increases the amount of MG-IIIE produced by the host by at least about 5%, e.g. at least about 7.5%, or at least about 10%, or at least about 12.5%, or at least about 15%, or at least about 17.5%, or at least about 20%, or at least about 25%, or at least about 27.5%, or at least about 30%, or at least about 35%, or at least about 40%, or at least about 45%, or at least about 50%, or at least about 60%, or at least about 70%, or at least about 80%, or at least about 90%, or at least about 100%, or at least about 110%, or at least about 120%, or at least about 130%, or at least about 140%, or at least about 150%, or at least about 160%, or at least about 170%, or at least about 180%, or at least about 190%, or at least about 200%, calculated as an increase in intracellular MG-IIIE concentration relative to a corresponding mogroside-producing host lacking the recombinant gene encoding a polypeptide capable of deglycosylating a mogroside precursor.

In some aspects, mogroside compounds are produced in vivo through expression of a recombinant gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2) and one or more enzymes involved in the mogroside biosynthetic pathway in a recombinant host. For example, in some embodiments, a recombinant host comprising a recombinant gene encoding a polypeptide capable of deglycosylating a mogroside precursor (e.g., a glucanase polypeptide or glucosidase polypeptide; e.g., an exo-1,3-β-glucanase polypeptide; e.g., a polypeptide having the amino acid sequence set forth in SEQ ID NO:2), a gene encoding a polypeptide capable of synthesizing oxidosqualene or dioxidosqualene from squalene; a gene encoding a polypeptide capable of synthesizing cucurbitadienol from oxidosqualene, or 24,25-epoxy-cucurbitadienol from dioxidosqualene; a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol; a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol; a gene encoding a polypeptide capable of reducing cytochrome P450 complex; a gene encoding a polypeptide capable of synthesizing mogrol from 11-hydroxy-epoxy-cucurbitadienol; a gene encoding a polypeptide capable of synthesizing mogrol from 11-hydroxy-24,25-epoxy-cucurbitadienol; a gene encoding a polypeptide capable of glycosylating mogrol or a mogroside compound at its C3 hydroxyl group, C11 hydroxyl group, C24 hydroxyl group, and/or C25 hydroxyl group thereof; and/or a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound can produce a mogroside compound in vivo. In some embodiments, the recombinant host further comprises a gene encoding a polypeptide capable of synthesizing squalene from FPP. The skilled worker will appreciate that one or more of these genes can be endogenous to the host provided that at least one (and in some embodiments, all) of these genes is a recombinant gene introduced into the recombinant host. In some embodiments, the recombinant host cell comprises reduced expression of at least one endogenous gene encoding a glucanase polypeptide or a glucosidase polypeptide, or a transcription factor gene that regulates expression of at least one endogenous gene encoding a glucanase polypeptide or a glucosidase polypeptide. In some embodiments, the recombinant host cell comprises reduced expression of at least one endogenous gene encoding a lanosterol synthase polypeptide.

In some embodiments, the polypeptide capable of synthesizing squalene from FPP comprises a polypeptide having the amino acid sequence set forth in SEQ ID NO:119. In some embodiments, a recombinant host comprising a gene encoding a polypeptide capable of synthesizing squalene from FPP further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of synthesizing oxidosqualene from squalene comprises a polypeptide having the amino acid sequence set forth in any one of SEQ ID NOs:3-21. In some embodiments, a recombinant host comprising a gene encoding a polypeptide capable of synthesizing oxidosqualene from squalene further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of synthesizing cucurbitadienol from oxidosqualene, or 24,25-epoxy-cucurbitadienol from dioxidosqualene comprises a polypeptide having the amino acid sequence set forth in SEQ ID NO:24 (which can be encoded by the nucleotide sequence set forth in SEQ ID NO:22 or SEQ ID NO:23), SEQ ID NO:25, or SEQ ID NO:26. In some embodiments, a recombinant host comprising a gene encoding a polypeptide capable of synthesizing cucurbitadienol from oxidosqualene, or 24,25-epoxy-cucurbitadienol from dioxidosqualene further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of synthesizing 24,25-epoxy-cucurbitadienol from cucurbitadienol, or 11-hydroxy-24,25-epoxy-cucurbitadienol from 11-hydroxy-cucurbitadienol comprises a polypeptide having the amino acid sequence set forth in SEQ ID NO:29 (which can be encoded by the nucleotide sequence set forth in SEQ ID NO:27 or SEQ ID NO:28). In some embodiments, a recombinant host comprising a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of synthesizing 11-hydroxy-cucurbitadienol from cucurbitadienol, or 11-hydroxy-24,25-epoxy-cucurbitadienol 24,25-epoxy-cucurbitadienol comprises a polypeptide having the amino acid sequence set forth in SEQ ID NO:31 (which can be encoded by the nucleotide sequence set forth in SEQ ID NO:30). In some embodiments, a recombinant host comprising a gene encoding a polypeptide capable of synthesizing 11-hydroxy-cucurbitadienol from cucurbitadienol, or 11-hydroxy-24,25-epoxy-cucurbitadienol 24,25-epoxy-cucurbitadienol further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of reducing cytochrome P450 complex comprises a polypeptide having the amino acid sequence set forth in SEQ ID NO:34 (which can be encoded by the nucleotide sequence set forth in SEQ ID NO:33). In some embodiments, a recombinant host comprising a gene encoding a polypeptide capable of reducing cytochrome P450 complex further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of synthesizing mogrol from 11-hydroxy-24,25-epoxy-cucurbitadienol comprises a polypeptide having the amino acid sequence set forth in SEQ ID NO:36 (which can be encoded by the nucleotide sequence set forth in SEQ ID NO:35) or SEQ ID NO:39 (encoded by the nucleotide sequence set forth in SEQ ID NO:37 or SEQ ID NO:38). In some embodiments, a recombinant host comprising a gene encoding a polypeptide capable of synthesizing mogrol from 11-hydroxy-24,25-epoxy-cucurbitadienol further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of synthesizing mogrol from 11-hydroxy-cucurbitadienol comprises a polypeptide having the amino acid sequence set forth in SEQ ID NO:41 (which can be encoded by the nucleotide sequence set forth in SEQ ID NO:40), SEQ ID NO:43 (encoded by the nucleotide sequence set forth in SEQ ID NO:42), SEQ ID NO:47 (encoded by the nucleotide sequence set forth in SEQ ID NO:46), SEQ ID NO:49 (encoded by the nucleotide sequence set forth in SEQ ID NO:48), SEQ ID NO:51 (encoded by the nucleotide sequence set forth in SEQ ID NO:50), SEQ ID NO:53 (encoded by the nucleotide sequence set forth in SEQ ID NO:52), SEQ ID NO:55 (encoded by the nucleotide sequence set forth in SEQ ID NO:54), SEQ ID NO:57 (encoded by the nucleotide sequence set forth in SEQ ID NO:56), SEQ ID NO:59 (encoded by the nucleotide sequence set forth in SEQ ID NO:58), SEQ ID NO:61 (encoded by the nucleotide sequence set forth in SEQ ID NO:60), SEQ ID NO:65 (encoded by the nucleotide sequence set forth in SEQ ID NO:64), SEQ ID NO:67 (encoded by the nucleotide sequence set forth in SEQ ID NO:66), SEQ ID NO:69 (encoded by the nucleotide sequence set forth in SEQ ID NO:68), SEQ ID NO:71 (encoded by the nucleotide sequence set forth in SEQ ID NO:70), SEQ ID NO:73 (encoded by the nucleotide sequence set forth in SEQ ID NO:72), or SEQ ID NO:75 (encoded by the nucleotide sequence set forth in SEQ ID NO:74). In some embodiments, a recombinant host comprising a gene encoding a polypeptide capable of synthesizing mogrol from 11-hydroxy-epoxy-cucurbitadienol further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of glycosylating mogrol or a mogroside compound at its C3 hydroxyl group, C11 hydroxyl group, C24 hydroxyl group, and/or C25 hydroxyl group thereof comprises a polypeptide having the amino acid sequence set forth in SEQ ID NO:76, SEQ ID NO:77, SEQ ID NO:78, SEQ ID NO:79, or SEQ ID NO:80, SEQ ID NO:83 (which can be encoded by the nucleotide sequence set forth in SEQ ID NO:81 or SEQ ID NO:82), SEQ ID NO:86 (encoded by the nucleotide sequence set forth in SEQ ID NO:84 or SEQ ID NO:85), or SEQ ID NO:89 (encoded by the nucleotide sequence set forth in SEQ ID NO:87 or SEQ ID NO:88). In some embodiments, a recombinant host comprising a gene encoding a polypeptide capable of glycosylating mogrol or a mogroside compound at its C3 hydroxyl group, C11 hydroxyl group, C24 hydroxyl group, and/or C25 hydroxyl group thereof further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of glycosylating mogrol or a mogroside compound at its C3 hydroxyl group, C11 hydroxyl group, C24 hydroxyl group, and/or C25 hydroxyl group thereof are capable of synthesizing, e.g., MG-IE1, MG-IA1, MG-IIE, SM-I, from, e.g., mogrol, MG-IE1, MG-IA1, and MG-IIIA1.

In some embodiments, the polypeptide capable of glycosylating mogrol or a mogroside compound (e.g., a polypeptide having the amino acid sequence set forth in SEQ ID NO:76, SEQ ID NO:78, SEQ ID NO:80, SEQ ID NO:79, SEQ ID NO:77, SEQ ID NO:89 (which can be encoded by the nucleotide sequence set forth in SEQ ID NO:87 or SEQ ID NO:88), or SEQ ID NO:86 (encoded by the nucleotide sequence set forth in SEQ ID NO:85 or SEQ ID NO:84)) is capable of glycosylating mogrol or a mogroside compound at its C-24 hydroxyl group thereof. For example, in some embodiments, a polypeptide having the amino acid sequence set forth in SEQ ID NO:76, SEQ ID NO:78, SEQ ID NO:80, SEQ ID NO:79, SEQ ID NO:77, SEQ ID NO:89 (encoded by the nucleotide sequence set forth in SEQ ID NO:87 or SEQ ID NO:88), or SEQ ID NO:86 (encoded by the nucleotide sequence set forth in SEQ ID NO:85 or SEQ ID NO:84) is capable of synthesizing MG-IA1 from mogrol. In another example, in some embodiments, a polypeptide having the amino acid sequence set forth in SEQ ID NO:77, SEQ ID NO:89 (encoded by the nucleotide sequence set forth in SEQ ID NO:87 or SEQ ID NO:88), or SEQ ID NO:86 (encoded by the nucleotide sequence set forth in SEQ ID NO:85 or SEQ ID NO:84) is capable of synthesizing MG-IIE from MG-IE1. In some embodiments, the polypeptide capable of glycosylating mogrol or a mogroside compound (e.g., a polypeptide having the amino acid sequence set forth in SEQ ID NO:77, SEQ ID NO:83 (encoded by the nucleotide sequence set forth in SEQ ID NO:82 or SEQ ID NO:81), or SEQ ID NO:86 (encoded by the nucleotide sequence set forth in SEQ ID NO:85 or SEQ ID NO:84)) is capable of glycosylating mogrol or a mogroside compound at its C-3 hydroxyl group thereof. For example, in some embodiments, a polypeptide having the amino acid sequence set forth in SEQ ID NO:77, or SEQ ID NO:83 (encoded by the nucleotide sequence set forth in SEQ ID NO:82 or SEQ ID NO:81) is capable of synthesizing MG-IE1 from mogrol. In another example, in some embodiments, a polypeptide having the amino acid sequence set forth in SEQ ID NO:86 (encoded by the nucleotide sequence set forth in SEQ ID NO:85 or SEQ ID NO:84), or SEQ ID NO:83 (encoded by the nucleotide sequence set forth in SEQ ID NO:82 or SEQ ID NO:81) is capable of synthesizing MG-IIE from MG-IA1. In yet another example, in some embodiments, a polypeptide having the amino acid sequence set forth in SEQ ID NO:77 is capable of synthesizing SM-I from MG-IIIA1.

In some embodiments, the polypeptide capable of beta-1,2-glycosylation of the C2' position of the 24-O-glucose and/or beta-1,6-glycosylation of the C6' position of the 3-O-glucose and/or the 24-O-glucose of a mogroside compound comprises a polypeptide having the amino acid sequence set forth in SEQ ID NO:93 (which can be encoded by the nucleotide sequence set forth in SEQ ID NO:91 or 92), SEQ ID NO:95 (encoded by the nucleotide sequence set forth in SEQ ID NO:94), SEQ ID NO:99 (encoded by the nucleotide sequence set forth in SEQ ID NO:96, SEQ ID NO:97, or SEQ ID NO:98), SEQ ID NO:101 (encoded by the nucleotide sequence set forth in SEQ ID NO:100), SEQ ID NO:103 (encoded by the nucleotide sequence set forth in SEQ ID NO:102), SEQ ID NO:105 (encoded by the nucleotide sequence set forth in SEQ ID NO:104), SEQ ID NO:107 (encoded by the nucleotide sequence set forth in SEQ ID NO:106), or SEQ ID NO:109 (encoded by the nucleotide sequence set forth in SEQ ID NO:108). In some embodiments, a recombinant host comprising a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound further comprises a gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2).

In some embodiments, the polypeptide capable of beta-1,2-glycosylation of the C2' position of the 24-O-glucose and/or beta-1,6-glycosylation of the C6' position of the 3-O-glucose and/or the 24-O-glucose of a mogroside compound are capable of synthesizing, e.g., MG-IIA, MG-IIA1, MG-IIA2, MG-IIIA1, MG-IIIA2, MG-III, MG-IV, MG-IVA, SM-I, or MG-V from, e.g., MG-IE1, MG-IA1, MG-IIA, MG-IIE, MG-IIIA2, MG-III, MG-IIIE, MG-IV, or SM-I.

In some embodiments, the polypeptide capable of glycosylation of a mogroside compound (e.g., a polypeptide having the amino acid sequence set forth in SEQ ID NO:99 (which can be encoded by the nucleotide sequence set forth in SEQ ID NO:98, SEQ ID NO:97, or SEQ ID NO:96), SEQ ID NO:93 (encoded by the nucleotide sequence set forth in SEQ ID NO:92, SEQ ID NO:91, or SEQ ID NO:90), or SEQ ID NO:95 (encoded by the nucleotide sequence set forth in SEQ ID NO:94)) is capable of beta-1,2-glycosylation of the C2' position of the 24-O-glucose of a mogroside compound. For example, in some embodiments, a polypeptide having the amino acid sequence set forth in SEQ ID NO:93 (encoded by the nucleotide sequence set forth in SEQ ID NO:92, SEQ ID NO:91, or SEQ ID NO:90), SEQ ID NO:95 (encoded by the nucleotide sequence set forth in SEQ ID NO:94), or SEQ ID NO:99 (encoded by the nucleotide sequence set forth in SEQ ID NO:98, SEQ ID NO:97, or SEQ ID NO:96) is capable of synthesizing MG-IIA from MG-IA1. In another example, in some embodiments, a polypeptide having the amino acid sequence set forth in SEQ ID NO:99 (encoded by the nucleotide sequence set forth in SEQ ID NO:98, SEQ ID NO:97, or SEQ ID NO:96)) is capable of synthesizing MG-IV from MG-IIIA2. In some embodiments, the polypeptide capable of glycosylation of a mogroside compound (e.g., a polypeptide having the amino acid sequence set forth in SEQ ID NO:99 (encoded by the nucleotide sequence set forth in SEQ ID NO:98, SEQ ID NO:97, or SEQ ID NO:96), or SEQ ID NO:93 (encoded by the nucleotide sequence set forth in SEQ ID NO:92, SEQ ID NO:91, or SEQ ID NO:90)) is capable of beta-1,6-glycosylation of the C6' position of the 3-O-glucose of a mogroside compound. For example, in some embodiments, a polypeptide having the amino acid sequence set forth in SEQ ID NO:99 (encoded by the nucleotide sequence set forth in SEQ ID NO:98, SEQ ID NO:97, or SEQ ID NO:96) is capable of synthesizing MG-IV from MG-III. In another example, in some embodiments, a polypeptide having the amino acid sequence set forth in SEQ ID NO:93 (encoded by the nucleotide sequence set forth in SEQ ID NO:92, SEQ ID NO:91, or SEQ ID NO:90), or SEQ ID NO:99 (encoded by the nucleotide sequence set forth in SEQ ID NO:98, SEQ ID NO:97, or SEQ ID NO:96) is capable of synthesizing MG-V from SM-I. In yet another example, in some embodiments, a polypeptide having the amino acid sequence set forth SEQ ID NO:99 (encoded by the nucleotide sequence set forth in SEQ ID NO:98, SEQ ID NO:97, or SEQ ID NO:96) is capable of synthesizing MG-IIA1 from MG-IE1. In yet another example, in some embodiments, a polypeptide having the amino acid sequence set forth in SEQ ID NO:93 (encoded by the nucleotide sequence set forth in SEQ ID NO:92, SEQ ID NO:91, or SEQ ID NO:90), or SEQ ID NO:99 (encoded by the nucleotide sequence set forth in SEQ ID NO:98, SEQ ID NO:97, or SEQ ID NO:96) is capable of synthesizing MG-IIIA2 from MG-IIE. In some embodiments, the polypeptide capable of glycosylation of a mogroside compound (e.g., a polypeptide having the amino acid sequence set forth in SEQ ID NO:93 (encoded by the nucleotide sequence set forth in SEQ ID NO:92, SEQ ID NO:91, or SEQ ID NO:90), or SEQ ID NO:99 (encoded by the nucleotide sequence set forth in SEQ ID NO:98, SEQ ID NO:97, or SEQ ID NO:96)) is capable of beta-1,6-glycosylation of the C6' position of the 24-O-glucose of a mogroside compound. For example, in some embodiments, a polypeptide having the amino acid sequence set forth in SEQ ID NO:99 (encoded by the nucleotide sequence set forth in SEQ ID NO:98, SEQ ID NO:97, or SEQ ID NO:96) is capable of synthesizing MG-IIA2 from MG-IA1. In another example, in some embodiments, a polypeptide having the amino acid sequence set forth in SEQ ID NO:93 (encoded by the nucleotide sequence set forth in SEQ ID NO:92, SEQ ID NO:91, or SEQ ID NO:90), or SEQ ID NO:99 (encoded by the nucleotide sequence set forth in SEQ ID NO:98, SEQ ID NO:97, or SEQ ID NO:96) is capable of synthesizing MG-IIIA1 from MG-IIA. In yet another example, in some embodiments, a polypeptide having the amino acid sequence set forth SEQ ID NO:93 (encoded by the nucleotide sequence set forth in SEQ ID NO:92, SEQ ID NO:91, or SEQ ID NO:90), or SEQ ID NO:99 (encoded by the nucleotide sequence set forth in SEQ ID NO:98, SEQ ID NO:97, or SEQ ID NO:96) is capable of synthesizing MG-III from MG-IIE.

In some embodiments, a recombinant host comprising a recombinant gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2) further comprises one or more genes encoding one or more polypeptides capable of glycosylating mogrol or a mogroside compound at its C3 hydroxyl group, C11 hydroxyl group, C24 hydroxyl group, and/or C25 hydroxyl group thereof (e.g. one or more polypeptides having the amino acid sequence set forth in SEQ ID NO:83, SEQ ID NO:86, and/or SEQ ID NO:89); and/or one or more genes encoding one or more polypeptides capable of beta-1,2-glycosylation of the C2' position of the 24-O-glucose and/or beta-1,6-glycosylation of the C6' position of the 3-O-glucose and/or the 24-0-glucose of a mogroside compound (e.g. one or more polypeptides having the amino acid sequence set forth in SEQ ID NO:93 and/or SEQ ID NO:99).

In some embodiments, a recombinant host comprising a recombinant gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2) further comprises one or more genes encoding one or more polypeptides capable of glycosylating mogrol or a mogroside compound at its C3 hydroxyl group, C11 hydroxyl group, C24 hydroxyl group, and/or C25 hydroxyl group thereof (e.g. one or more polypeptides having the amino acid sequence set forth in SEQ ID NO:83, SEQ ID NO:86, and/or SEQ ID NO:89); and/or one or more genes encoding one or more polypeptides capable of beta-1,2-glycosylation of the C2' position of the 24-O-glucose and/or beta-1,6-glycosylation of the C6' position of the 3-O-glucose and/or the 24-0-glucose of a mogroside compound (e.g. one or more polypeptides having the amino acid sequence set forth in SEQ ID NO:93 and/or SEQ ID NO:99), and also comprises reduced expression of an endogenous gene encoding a glucanase polypeptide (e.g., a polypeptide having the amino acid sequence set forth in SEQ ID NO:115).

In some embodiments, a recombinant host comprising a recombinant gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2) further comprises a gene encoding a polypeptide capable of synthesizing squalene from FPP (e.g., a polypeptide having the amino acid sequence set forth in SEQ ID NO:119), a gene encoding a polypeptide capable of synthesizing oxidosqualene or dioxidosqualene from squalene (e.g. a polypeptide having the amino acid sequence set forth in SEQ ID NO:3); a gene encoding a polypeptide capable of synthesizing cucurbitadienol from oxidosqualene, or 24,25-epoxy-cucurbitadienol from dioxidosqualene (e.g. a polypeptide having the amino acid sequence set forth in SEQ ID NO:24); a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol (e.g. a polypeptide having the amino acid sequence set forth in SEQ ID NO:29); a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol (e.g. a polypeptide having the amino acid sequence set forth in SEQ ID NO:31); a gene encoding a polypeptide capable of reducing cytochrome P450 complex (e.g. a polypeptide having the amino acid sequence set forth in SEQ ID NO:34); a gene encoding a polypeptide capable of synthesizing mogrol from 11-hydroxy-24,25-epoxy-cucurbitadienol (e.g. a polypeptide having the amino acid sequence set forth in SEQ ID NO:39); one or more genes encoding one or more polypeptides capable of glycosylating mogrol or a mogroside compound at its C3 hydroxyl group, C11 hydroxyl group, C24 hydroxyl group, and/or C25 hydroxyl group thereof (e.g. one or more polypeptides having the amino acid sequence set forth in SEQ ID NO:83, SEQ ID NO:86, and/or SEQ ID NO:89); and/or one or more genes encoding one or more polypeptides capable of beta-1,2-glycosylation of the C2' position of the 24-O-glucose and/or beta-1,6-glycosylation of the C6' position of the 3-O-glucose and/or the 24-0-glucose of a mogroside compound (e.g. one or more polypeptides having the amino acid sequence set forth in SEQ ID NO:93 and/or SEQ ID NO:99).

In some embodiments, a recombinant host comprising a recombinant gene encoding a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2) further comprises a gene encoding a polypeptide capable of synthesizing squalene from FPP (e.g., a polypeptide having the amino acid sequence set forth in SEQ ID NO:119), a gene encoding a polypeptide capable of synthesizing oxidosqualene or dioxidosqualene from squalene (e.g. a polypeptide having the amino acid sequence set forth in SEQ ID NO:3); a gene encoding a polypeptide capable of synthesizing cucurbitadienol from oxidosqualene, or 24,25-epoxy-cucurbitadienol from dioxidosqualene (e.g. a polypeptide having the amino acid sequence set forth in SEQ ID NO:24); a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol (e.g. a polypeptide having the amino acid sequence set forth in SEQ ID NO:29); a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol (e.g. a polypeptide having the amino acid sequence set forth in SEQ ID NO:31); a gene encoding a polypeptide capable of reducing cytochrome P450 complex (e.g. a polypeptide having the amino acid sequence set forth in SEQ ID NO:34); a gene encoding a polypeptide capable of synthesizing mogrol from 11-hydroxy-24,25-epoxy-cucurbitadienol (e.g. a polypeptide having the amino acid sequence set forth in SEQ ID NO:39); one or more genes encoding one or more polypeptides capable of glycosylating mogrol or a mogroside compound at its C3 hydroxyl group, C11 hydroxyl group, C24 hydroxyl group, and/or C25 hydroxyl group thereof (e.g. one or more polypeptides having the amino acid sequence set forth in SEQ ID NO:83, SEQ ID NO:86, and/or SEQ ID NO:89); and/or one or more genes encoding one or more polypeptides capable of beta-1,2-glycosylation of the C2' position of the 24-O-glucose and/or beta-1,6-glycosylation of the C6' position of the 3-O-glucose and/or the 24-O-glucose of a mogroside compound (e.g. one or more polypeptides having the amino acid sequence set forth in SEQ ID NO:93 and/or SEQ ID NO:99), and also comprises reduced expression of an endogenous gene encoding a glucanase polypeptide (e.g., a polypeptide having the amino acid sequence set forth in SEQ ID NO:115).

In some embodiments, mogroside compounds and/or mogroside precursors are produced through contact of a mogroside precursor with one or more enzymes involved in the mogroside biosynthetic pathway in vitro. For example, contacting a mogroside precursor with a polypeptide capable of deglycosylating a mogroside precursor, a polypeptide capable of glycosylating mogrol or a mogroside compound at its C3 hydroxyl group, C11 hydroxyl group, C24 hydroxyl group, and/or C25 hydroxyl group thereof, and/or a polypeptide capable of beta-1,2-glycosylation of the C2' position of the 24-O-glucose and/or beta-1,6-glycosylation of the C6' position of the 3-O-glucose and/or the 24-O-glucose of a mogroside compound can result in production of a mogroside compound in vitro. In some embodiments, a mogroside precursor is produced through contact of a mogrol precursor with one or more enzymes involved in the mogroside biosynthetic pathway in vitro. For example, contacting a mogrol precursor with a polypeptide capable of deglycosylating a mogroside precursor, a polypeptide capable of glycosylating mogrol or a mogroside compound at its C3 hydroxyl group, C11 hydroxyl group, C24 hydroxyl group, and/or C25 hydroxyl group thereof, and/or a polypeptide capable of beta-1,2-glycosylation of the C2' position of the 24-O-glucose and/or beta-1,6-glycosylation of the C6' position of the 3-O-glucose and/or the 24-O-glucose; and a polypeptide capable of synthesizing squalene from FPP, a polypeptide capable of synthesizing oxidosqualene or dioxidosqualene from squalene; a polypeptide capable of synthesizing cucurbitadienol from oxidosqualene, or 24,25-epoxy-cucurbitadienol from dioxidosqualene; a polypeptide capable of synthesizing 24,25-epoxy-cucurbitadienol from cucurbitadienol, or 11-hydroxy-24,25-epoxy-cucurbitadienol from 11-hydroxy-cucurbitadienol; a polypeptide capable of synthesizing 11-hydroxy-cucurbitadienol from cucurbitadienol, or 11-hydroxy-24,25-epoxy-cucurbitadienol from 24,25-epoxy-cucurbitadienol; a polypeptide capable of reducing cytochrome P450 complex; a polypeptide capable of synthesizing mogrol from 11-hydroxy-24,25-epoxy-cucurbitadienol; and/or a polypeptide capable of synthesizing mogrol from 11-hydroxy-24,25-epoxy-cucurbitadienol can result in production of a mogroside compound in vitro.

In some embodiments, the method of producing one or more mogroside compounds in vitro comprises adding a polypeptide capable of deglycosylating a mogroside precursor; and, optionally, a polypeptide capable of glycosylating mogrol or a mogroside compound at its C3 hydroxyl group, C11 hydroxyl group, C24 hydroxyl group, and/or C25 hydroxyl group thereof; and/or a polypeptide capable of beta-1,2-glycosylation of the C2' position of the 24-O-glucose and/or beta-1,6-glycosylation of the C6' position of the 3-O-glucose and/or the 24-O-glucose of a mogroside compound; and one or more plant-derived or synthetic mogroside precursors to a reaction mixture; wherein at least one of the polypeptides is a recombinant polypeptide; wherein the one or more mogroside compounds are a deglycosylation product of the mogroside precursor; and producing the one or more mogroside compounds thereby.

In some embodiments, the method of producing one or more mogroside compounds in vitro comprises adding a polypeptide capable of deglycosylating a mogroside precursor, the polypeptide having an amino acid sequence set forth in SEQ ID NO:2; and, optionally, a polypeptide capable of glycosylating mogrol or a mogroside compound at its C3 hydroxyl group, C11 hydroxyl group, C24 hydroxyl group, and/or C25 hydroxyl group thereof, the polypeptide having an amino acid sequence set forth in SEQ ID NO:76, SEQ ID NO:77, SEQ ID NO:78, SEQ ID NO:79, or SEQ ID NO:80, SEQ ID NO:83, SEQ ID NO:86, or SEQ ID NO:89; and/or a polypeptide capable of beta-1,2-glycosylation of the C2' position of the 24-O-glucose and/or beta-1,6-glycosylation of the C6' position of the 3-O-glucose and/or the 24-O-glucose of a mogroside compound, the polypeptide having an amino acid sequence set forth in SEQ ID NO:93, SEQ ID NO:95, SEQ ID NO:99, SEQ ID NO:101, SEQ ID NO:103, SEQ ID NO:105, SEQ ID NO:107, or SEQ ID NO:109; and one or more plant-derived or synthetic mogroside precursors to a reaction mixture; wherein at least one of the polypeptides is a recombinant polypeptide; wherein the one or more mogroside compounds are a deglycosylation product of the mogroside precursor; and producing the one or more mogroside compounds thereby.

For example, in some embodiments, contacting, MG-V with a polypeptide capable of deglycosylating a mogroside precursor (e.g., a glucanase polypeptide or glucosidase polypeptide; e.g., a glucanase polypeptide or glucosidase polypeptide lacking a signal peptide or a transmembrane domain; e.g., a truncated exo-1,3-β-glucanase polypeptide; e.g., a polypeptide having the amino acid sequence set forth in SEQ ID NO:2) in vitro can produce MG-IIIE.

In some embodiments, a mogroside compound or mogroside precursor is produced by whole cell bioconversion. For whole cell bioconversion to occur, a host cell expressing one or more enzymes involved in the mogroside biosynthetic pathway takes up and modifies a mogroside precursor in the cell; following modification in vivo, a mogroside compound remains in the cell and/or is excreted into the culture medium. For example, a host cell expressing a gene encoding a polypeptide capable of deglycosylating a mogroside precursor; and, optionally, a gene encoding a polypeptide capable of glycosylating mogrol or a mogroside compound at its C3 hydroxyl group, C11 hydroxyl group, C24 hydroxyl group, and/or C25 hydroxyl group thereof, and/or a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound can take up a mogroside precursor and glycosylate the mogroside precursor in the cell; following modification in vivo, a mogroside compound can be excreted into the culture medium. In some embodiments, the mogroside compound is a deglycosylation product of the mogroside precursor. In some embodiments, the host cell may further express a gene encoding a polypeptide capable of synthesizing squalene from FPP, a gene encoding a polypeptide capable of synthesizing oxidosqualene or dioxidosqualene from squalene; a gene encoding a polypeptide capable of synthesizing cucurbitadienol from oxidosqualene, or 24,25-epoxy-cucurbitadienol from dioxidosqualene; a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol; a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol; a gene encoding a polypeptide capable of reducing cytochrome P450 complex; a gene encoding a polypeptide capable of synthesizing mogrol from 11-hydroxy-24,25-epoxy-cucurbitadienol; and/or a gene encoding a polypeptide capable of synthesizing mogrol from 11-hydroxy-24,25-epoxy-cucurbitadienol, and, accordingly, can take up a mogrol precursor and, following modification in vivo, a mogroside precursor compound can be excreted into the cell culture medium, or can remain in the cell.

In some embodiments, the method of producing one or more mogroside compounds comprises whole cell bioconversion of one or more plant-derived or synthetic mogroside precursors in a cell culture medium or a recombinant host cell using a polypeptide capable of deglycosylating a mogroside precursor; and, optionally, a gene encoding a polypeptide capable of glycosylating mogrol or a mogroside compound at its C3 hydroxyl group, C11 hydroxyl group, C24 hydroxyl group, and/or C25 hydroxyl group thereof, and/or a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound; wherein at least one of the polypeptides is a recombinant polypeptide expressed in the recombinant host cell; wherein the one or more mogroside compounds are a deglycosylation product of the mogroside precursor; and producing the one or more mogroside compounds thereby.

In some embodiments, the method of producing one or more mogroside compounds comprises whole cell bioconversion of one or more plant-derived or synthetic mogroside precursors in a cell culture medium or a recombinant host cell using a polypeptide capable of deglycosylating a mogroside precursor, the polypeptide having an amino acid sequence set forth in SEQ ID NO:2; and, optionally, a gene encoding a polypeptide capable of glycosylating mogrol or a mogroside compound at its C3 hydroxyl group, C11 hydroxyl group, C24 hydroxyl group, and/or C25 hydroxyl group thereof, the polypeptide having an amino acid sequence set forth in SEQ ID NO:76, SEQ ID NO:77, SEQ ID NO:78, SEQ ID NO:79, or SEQ ID NO:80, SEQ ID NO:83, SEQ ID NO:86, or SEQ ID NO:89, and/or a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound, the polypeptide having an amino acid sequence set forth in SEQ ID NO:93, SEQ ID NO:95, SEQ ID NO:99, SEQ ID NO:101, SEQ ID NO:103, SEQ ID NO:105, SEQ ID NO:107, or SEQ ID NO:109; wherein at least one of the polypeptides is a recombinant polypeptide expressed in the recombinant host cell; wherein the one or more mogroside compounds are a deglycosylation product of the mogroside precursor; and producing the one or more mogroside compounds thereby.

In some embodiments, a cell is permeabilized to take up a substrate to be modified or to excrete a modified product. In some embodiments, a permeabilizing agent can be added to aid the feedstock entering into the host and product getting out. In some embodiments, the cells are permeabilized with a solvent such as toluene, or with a detergent such as Triton-X or Tween. In some embodiments, the cells are permeabilized with a surfactant, for example a cationic surfactant such as cetyltrimethylammonium bromide (CTAB). In some embodiments, the cells are permeabilized with periodic mechanical shock such as electroporation or a slight osmotic shock. For example, a crude lysate of the cultured microorganism can be centrifuged to obtain a supernatant. The resulting supernatant can then be applied to a chromatography column, e.g., a C18 column, and washed with water to remove hydrophilic compounds, followed by elution of the compound(s) of interest with a solvent such as methanol. The compound(s) can then be further purified by preparative HPLC.

In some embodiments, mogrol, one or more mogroside precursors, and/or one or more mogroside compounds are produced by co-culturing of two or more hosts. In some embodiments, one or more hosts, each expressing one or more enzymes involved in the mogroside biosynthetic pathway, produce mogrol, one or more mogroside precursors, and/or one or more mogroside compounds. For example, a host expressing a gene encoding a gene encoding a polypeptide capable of synthesizing squalene from FPP, a gene encoding a polypeptide capable of synthesizing oxidosqualene or dioxidosqualene from squalene; a gene encoding a polypeptide capable of synthesizing cucurbitadienol from oxidosqualene, or 24,25-epoxy-cucurbitadienol from dioxidosqualene; a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol; a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol; a gene encoding a polypeptide capable of reducing cytochrome P450 complex; a gene encoding a polypeptide capable of synthesizing mogrol from 11-hydroxy-24,25-epoxy-cucurbitadienol; and/or a gene encoding a polypeptide capable of synthesizing mogrol from 11-hydroxy-24,25-epoxy-cucurbitadienol and a host expressing a polypeptide capable of deglycosylating a mogroside precursor; and a gene encoding a polypeptide capable of glycosylating mogrol or a mogroside compound at its C3 hydroxyl group, C11 hydroxyl group, C24 hydroxyl group, and/or C25 hydroxyl group thereof; and/or a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound, can produce one or more mogroside compounds. In certain such embodiments, the one or more mogroside compounds are a deglycosylation product of the mogroside precursor.

In some embodiments, one or more mogroside compounds comprise, e.g., MG-V, 11-O-MG-V, SM-I, MG-IV, MG-IVA, MG-III, MG-IIIA1, MG-IIIA2, MG-IIIE, MG-IIA, MG-IIA1, MG-IIA2, MG-IIE, MG-IA1, MG-IE1, MG-I, a tri-glycosylated mogroside compound, a tetra-glycosylated mogroside compound, a penta-glycosylated mogroside compound, a hexa-glycosylated mogroside compound, a hepta-glycosylated mogroside compound, or isomers thereof.

In some embodiments, a mogroside composition (i.e., comprising one or more mogroside compounds) produced in vivo, in vivo, or by whole cell bioconversion does not comprise or comprises a reduced amount of plant-derived components than an extract of *E. grosvenorii*. Plant-derived components can contribute to off-flavors and include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α- and β-amyrin, lupeol, β-amryin acetate, pentacyclic triterpenes, centauredin, quercitin, epi-alpha-cadinol, carophyllenes and derivatives, beta-pinene, beta-sitosterol, and gibberellin. In some embodiments, the plant-derived components referred to herein are non-mogroside compounds.

In some embodiments a mogroside compound is produced using a method of converting a mogroside precursor into the mogroside compound, the method comprising contacting the mogroside precursor with the recombinant host cell disclosed herein, a cell free extract derived from the recombinant host cell, or a polypeptide capable of deglycosylating a mogroside precursor; a polypeptide capable of synthesizing oxidosqualene from squalene; a polypeptide capable of synthesizing cucurbitadienol from oxidosqualene, or 24,25-epoxy-cucurbitadienol from dioxidosqualene; a polypeptide capable of synthesizing 24,25-epoxy-cucurbitadienol from cucurbitadienol, or 11-hydroxy-24,25-epoxy-cucurbitadienol from 11-hydroxy-cucurbitadienol; a polypeptide capable of synthesizing 11-hydroxy-cucurbitadienol from cucurbitadienol, or 11-hydroxy-24,25-epoxy-cucurbitadienol from 24,25-epoxy-cucurbitadienol; a polypeptide capable of reducing cytochrome P450 complex; a polypeptide capable of synthesizing mogrol from 11-hydroxy-24,25-epoxy-cucurbitadienol; a polypeptide capable of synthesizing mogrol from 11-hydroxy-cucurbitadienol; a polypeptide capable of glycosylating mogrol or a mogroside compound at its C3 hydroxyl group, C11 hydroxyl group, C24 hydroxyl group, and/or C25 hydroxyl group thereof; and/or a polypeptide capable of beta-1,2-glycosylation of the C2' position of the 24-O-glucose and/or beta-1,6-glycosylation of the C6' position of the 3-O-glucose and/or the 24-O-glucose of a mogroside compound; or a mixture of the polypeptides derived from the recombinant host cell or the cell free extract derived from the recombinant host cell to convert the mogroside precursor into the mogroside compound; wherein the mogroside compound is a deglycosylation product of the mogroside precursor.

In some aspects of the method discussed above, the polypeptide capable of synthesizing oxidosqualene from squalene comprises a polypeptide having at least 45% sequence identity to the amino acid sequence set forth in SEQ ID NO:3, or at least 50% sequence identity to the amino acid sequence set forth in any one of SEQ ID NOs:6-8, 11-12, or 20, or at least 55% sequence identity to the amino acid sequence set forth in SEQ ID NO:21, or at least 60% sequence identity to the amino acid sequence set forth in any one of SEQ ID NOs:10, 13-14, or 16-19, or at least 65% sequence identity to the amino acid sequence set forth in any one of SEQ ID NOs:4-5, 9, or 15; the polypeptide capable of synthesizing cucurbitadienol from oxidosqualene, or 24,25-epoxy-cucurbitadienol from dioxidosqualene or cucurbitadienol comprises a polypeptide having at least 70% sequence identity to the amino acid sequence set forth in SEQ ID NO:24, or at least 75% sequence identity to the amino acid sequence set forth in SEQ ID NO:25, or at least 80% sequence identity to the amino acid sequence set forth in SEQ ID NO:26; the polypeptide capable of synthesizing 24,25-epoxy-cucurbitadienol from cucurbitadienol, or 11-hydroxy-24,25-epoxy-cucurbitadienol from 11-hydroxy-cucurbitadienol comprises a polypeptide having at least 70% sequence identity to the amino acid sequence set forth in SEQ ID NO:29; the polypeptide capable of synthesizing 11-hydroxy-cucurbitadienol from cucurbitadienol, or 11-hydroxy-24,25-epoxy-cucurbitadienol from 24,25-epoxy-cucurbitadienol comprises a polypeptide having at least 50% sequence identity to the amino acid sequence set forth in SEQ ID NO:31; the polypeptide capable of reducing cytochrome P450 complex comprises a polypeptide having at least 50% sequence identity to the amino acid sequence set forth in SEQ ID NO:34; the polypeptide capable of synthesizing mogrol from 11-hydroxy-24,25-epoxy-cucurbitadienol comprises a polypeptide having at least 75% sequence identity to the amino acid sequence set forth in SEQ ID NO:36, or at least 65% sequence identity to the amino acid sequence set forth in SEQ ID NO:39; the polypeptide capable of synthesizing mogrol from 11-hydroxy-cucurbitadienol comprises a polypeptide having at least 50% sequence identity to the amino acid sequence set forth in any one of SEQ ID NOs:41, 43, 47, 49, 51, 53, 55, 57, 59, 61, 65, 67, 69, 71, 73, or 75; the polypeptide capable of deglycosylating a mogroside precursor comprises polypeptide having at least 50% sequence identity to the amino acid sequence set forth in SEQ ID NO:2; the polypeptide capable of glycosylating mogrol or a mogroside compound at its C3 hydroxyl group, C11 hydroxyl group, C24 hydroxyl group, and/or C25 hydroxyl group thereof comprises a polypeptide having at least 50% sequence identity to the amino acid sequence set forth in any one of SEQ ID NOs:76-80, or at least 45% sequence identity to the amino acid sequence set forth in any one of SEQ ID NOs:83 or 86, or at least 60% sequence identity to the amino acid sequence set forth in SEQ ID NO:89; and the polypeptide capable of beta-1,2-glycosylation of the C2' position of the 24-O-glucose and/or beta-1,6-glycosylation of the C6' position of the 3-O-glucose and/or the 24-O-glucose of a mogroside compound comprises a polypeptide having at least 70% sequence identity to the amino acid sequence set forth in any one of SEQ ID NOs:93 or 95, or at least 50% sequence identity to the amino acid sequence set forth in any one of SEQ ID NOs:99, 101, 103, 105, 107, 109, 115, or 117.

In some embodiments one or more mogroside compounds are produced using a method, comprising transferring a glucose moiety from a mogroside precursor, comprising contacting the mogroside precursor with a polypeptide capable of deglycosylating the mogroside precursor under suitable reaction conditions for the transfer of the glucose moiety from the mogroside precursor; and further comprising transferring the glucose moiety to the C3 hydroxyl group, the C11 hydroxyl group, the C24 hydroxyl group, the C25 hydroxyl group, the C2' position of the 24-O-glucose, the C6' position of the 3-O-glucose and/or the 24-O-glucose of the mogroside precursor; comprising contacting the mogroside precursor with the polypeptide capable of glycosylating the mogroside precursor compound at its C3 hydroxyl group, C11 hydroxyl group, C24 hydroxyl group, and/or C25 hydroxyl group thereof and/or the polypeptide capable of beta-1,2-glycosylation of the C2' position of the 24-O-glucose and/or beta-1,6-glycosylation of the C6' position of the 3-O-glucose and/or the 24-O-glucose of the mogroside precursor and a one or more UDP-glucose under suitable reaction conditions for the transfer of the glucose moiety to the mogroside precursor; wherein the mogroside precursor is a tri-glycosylated, a tetra-glycosylated, a penta-glycosylated, or a hexa-glycosylated mogrol; wherein at least one of the polypeptides is a recombinant polypeptide; and producing the one or more mogroside compounds thereby; and wherein the one or more mogroside compounds are a deglycosylation product of the mogroside precursor.

In some aspects of the method discussed above, the polypeptide capable of deglycosylating a mogroside precursor comprises polypeptide having at least 50% sequence identity to the amino acid sequence set forth in SEQ ID NO:2; the polypeptide capable of glycosylating mogrol or a mogroside compound at its C3 hydroxyl group, C11 hydroxyl group, C24 hydroxyl group, and/or C25 hydroxyl group thereof comprises a polypeptide having at least 50% sequence identity to the amino acid sequence set forth in any one of SEQ ID NOs:76-80, or at least 45% sequence identity to the amino acid sequence set forth in any one of SEQ ID NOs:83 or 86, or at least 60% sequence identity to the amino acid sequence set forth in SEQ ID NO:89; and the polypeptide capable of beta-1,2-glycosylation of the C2' position of the 24-O-glucose and/or beta-1,6-glycosylation of the C6' position of the 3-O-glucose and/or the 24-O-glucose of a mogroside compound comprises a polypeptide having at least 70% sequence identity to the amino acid sequence set forth in any one of SEQ ID NOs:93 or 95, or at least 50% sequence identity to the amino acid sequence set forth in any one of SEQ ID NOs:99, 101, 103, 105, 107, 109, 115, or 117.

In some aspects of the method discussed above, the method is an in vitro method, further comprising supplying the one or more UDP-glucose or a cell-free system for regeneration of the one or more UDP-glucose.

In some aspects of the method discussed above, the in vitro method is an enzymatic in vitro method or a whole cell in vitro method.

As used herein, the terms "detectable amount," "detectable concentration," "measurable amount," and "measurable concentration" refer to a level of mogroside precursors or mogroside compounds measured in AUC, $\mu M/OD_{600}$, mg/L, $\mu M$, or mM. Mogroside precursor or mogroside compound production (i.e., total, supernatant, and/or intracellular mogroside precursor or mogroside compound levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vis), mass spectrometry (MS), and nuclear magnetic resonance spectroscopy (NMR).

As used herein, the term "undetectable concentration" refers to a level of a compound that is too low to be measured and/or analyzed by techniques such as TLC, HPLC, UV-Vis, MS, or NMR. In some embodiments, a compound of an "undetectable concentration" is not present in a mogroside composition.

After the recombinant microorganism has been grown in culture for the period of time, wherein the temperature and period of time facilitate the production of mogrol, a mogroside precursor, or a mogroside compound can then be recovered from the culture using various techniques known in the art. Mogroside precursors and mogroside compounds can be isolated using a method described herein. For example, following fermentation, a culture broth can be centrifuged for 30 min at 7000 rpm at 4° C. to remove cells, or cells can be removed by filtration. The cell-free lysate can be obtained, for example, by mechanical disruption or enzymatic disruption of the host cells and additional centrifugation to remove cell debris. Mechanical disruption of the dried broth materials can also be performed, such as by sonication. The dissolved or suspended broth materials can be filtered using a micron or sub-micron prior to further purification, such as by preparative chromatography. The fermentation media or cell-free lysate can optionally be treated to remove low molecular weight compounds such as salt; and can optionally be dried prior to purification and re-dissolved in a mixture of water and solvent.

The supernatant or cell-free lysate can be purified as follows: a column can be filled with, for example, HP20 Diaion resin (aromatic type Synthetic Adsorbent; Supelco) or other suitable non-polar adsorbent or reversed-phase chromatography resin, and an aliquot of supernatant or cell-free lysate can be loaded on to the column and washed with water to remove the hydrophilic components. The mogroside precursor or mogroside compound product can be eluted by stepwise incremental increases in the solvent concentration in water or a gradient from, e.g., 0%→100% methanol). The levels of mogroside precursors and/or mogroside compounds in each fraction, including the flow-through, can then be analyzed by LC-MS. Fractions can then be combined and reduced in volume using a vacuum evaporator. Additional purification steps can be utilized, if desired, such as additional chromatography steps and crystallization. For example, mogroside compounds can be isolated by methods not limited to ion exchange chromatography, reversed-phase chromatography (i.e., using a C18 column), extraction, crystallization, and carbon columns and/or decoloring steps.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of mogroside compounds and/or mogroside precursors. In some embodiments, "and/or" is used to refer to production of mogroside compounds, wherein one or more mogroside compounds are produced. In some embodiments, "and/or" is used to refer to production of mogroside compounds, wherein one or more mogroside compounds are produced through one or more of the following steps: culturing a recombinant microorganism, synthesizing one or more mogroside compounds in a recombinant microorganism, and/or isolating one or more mogroside compounds.

The recombinant host cells capable of producing one or more mogroside compounds (for example, a di-glycosylated mogroside compound such as mogroside II A (MG-IIA), mogroside II A1 (MG-IIA1), mogroside II A2 (MG-IIA2), or mogroside II E (MG-IIE); a tri-glycosylated mogroside compound such as mogroside III (MG-III), mogroside III A1 (MG-IIIA1), mogroside III A2 (MG-IIIA2), or mogroside III E (MG-IIIE); a tetra-glycosylated mogroside compound such as mogroside IV (MG-IV), mogroside IV A (MG-IVA), or siamenoside I (SM-I); or a penta-glycosylated mogroside compound such as mogroside V (MG-V) or 11-oxo-mogroside V (11-O-MG-V)) in a cell culture disclosed herein comprise a recombinant gene encoding a heterologous or an endogenous polypeptide (such as, for example, a polypeptide having at least 50% sequence identity to the amino acid sequence set forth in SEQ ID NO:2) capable of deglycosylating a mogroside precursor (for example, a tri-glycosylated mogrol such as MG-III, MG-IIIA1, MG-IIIA2, or MG-IIIE; a tetra-glycosylated mogrol such as MG-IV, MG-IVA, or SM-I; a penta-glycosylated mogrol such as MG-V or 11-O-MG-V; or a hexa-glycosylated mogrol), wherein the one or more mogroside compounds are a deglycosylation product of the mogroside precursor, and wherein expression of the gene increases production of the one or more mogroside compounds. The heterologous or the endogenous polypeptide comprising the recombinant host cells disclosed herein, can be free of a domain facilitating secretion of the heterologous or the endogenous polypeptide from the host cell, preferably selected from a signal peptide or a transmembrane domain, and the recombinant host cells are capable of retaining at least about 50% of an expressed heterologous or endogenous polypeptide capable of deglycosylating the mogroside precursor in a cytosol of the host cell. In particular, expression of the recombinant gene comprising the recombinant host cells and encoding the heterologous or the endogenous polypeptide capable of deglycosylating the mogroside precursor increases a cytosolic mogroside precursor deglycosylation activity of the recombinant host cell by at least about 10% relative to a corresponding host cell lacking the gene. Furthermore, the expression of the recombinant gene comprising the recombinant host cells and encoding the heterologous or the endogenous polypeptide capable of deglycosylating the mogroside precursor increases the cytosolic mogroside precursor deglycosylation activity of the heterologous or the endogenous polypeptide by at least about 10% relative to the corresponding host cell lacking the gene. The heterologous or the endogenous polypeptide (such as, for example, a glucosidase polypeptide or a glucanase polypeptide) comprising the recombinant host cells disclosed herein can comprise a catalytically active portion of an endogenous glucosidase polypeptide or an endogenous glucanase polypeptide and does not comprise a signal peptide or a transmembrane domain that is comprised by the endogenous glucoside polypeptide.

Furthermore, the recombinant host cells disclosed herein and capable of producing one or more mogroside compounds, as discussed above, can further comprise a gene encoding a polypeptide capable of synthesizing oxidosqualene from squalene, wherein the polypeptide comprises a polypeptide having at least 45% sequence identity to the amino acid sequence set forth in SEQ ID NO:3, or at least 50% sequence identity to the amino acid sequence set forth in any one of SEQ ID NOs:6-8, 11-12, or 20, or at least 55% sequence identity to the amino acid sequence set forth in SEQ ID NO:21, or at least 60% sequence identity to the amino acid sequence set forth in any one of SEQ ID NOs:10, 13-14, or 16-19, or at least 65% sequence identity to the amino acid sequence set forth in any one of SEQ ID NOs:4-5, 9, or 15; a gene encoding a polypeptide capable of synthesizing cucurbitadienol from oxidosqualene, or 24,25-epoxy-cucurbitadienol from dioxidosqualene, wherein the polypeptide comprises a polypeptide having at least 70% sequence identity to the amino acid sequence set forth in SEQ ID NO:24, or at least 75% sequence identity to the amino acid sequence set forth in SEQ ID NO:25, or at least 80% sequence identity to the amino acid sequence set forth in SEQ ID NO:26; a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol, wherein the polypeptide comprises a polypeptide having at least 70% sequence identity to the amino acid sequence set forth in SEQ ID NO:29, a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol, wherein the polypeptide comprises a polypeptide having at least 50% sequence identity to the amino acid sequence set forth in SEQ ID NO:31; a gene encoding a polypeptide capable of reducing a cytochrome P450 complex, wherein the polypeptide comprises a polypeptide having at least 50% sequence identity to the amino acid sequence set forth in SEQ ID NO:34; a gene encoding a polypeptide capable of synthesizing mogrol from 11-hydroxy-24,25-epoxy-cucurbitadienol, wherein the polypeptide comprises a polypeptide having at least 75% sequence identity to the amino acid sequence set forth in SEQ ID NO:36, or at least 65% sequence identity to the amino acid sequence set forth in SEQ ID NO:39; a gene encoding a polypeptide capable of synthesizing mogrol from 11-hydroxy-cucurbitadienol, wherein the polypeptide comprises a polypeptide having at least 50% sequence identity to the amino acid sequence set forth in any one of SEQ ID NOs:41, 43, 47, 49, 51, 53, 55, 57, 59, 61, 65, 67, 69, 71, 73, or 75; a gene encoding a polypeptide capable of glycosylating mogrol or a mogroside compound at its C3 hydroxyl group, C11 hydroxyl group, C24 hydroxyl group, and/or C25 hydroxyl group thereof, wherein the polypeptide comprises a polypeptide having at least 50% sequence identity to the amino acid sequence set forth in any one of SEQ ID NOs:76-80, or at least 45% sequence identity to the amino acid sequence set forth in any one of SEQ ID NOs:83 or 86, or at least 60% sequence identity to the amino acid sequence set forth in SEQ ID NO:89; and/or a gene encoding a polypeptide capable of beta-1,2-glycosylation of the C2' position of the 24-O-glucose and/or beta-1,6-glycosylation of the C6' position of the 3-O-glucose and/or the 24-O-glucose of a mogroside compound, wherein the polypeptide comprises a polypeptide having at least 70% sequence identity to the amino acid sequence set forth in any one of SEQ ID NOs:93 or 95, or at least 50% sequence identity to the amino acid sequence set forth in any one of SEQ ID NOs:99, 101, 103, 105, 107, 109, 115, or 117; wherein at least one of the genes is a recombinant gene. In addition, the recombinant host cells disclosed herein and capable of producing one or more mogroside compounds as discussed above can further comprise a gene encoding a polypeptide capable of synthesizing squalene from farnesyl pyrophosphate (FPP); wherein the polypeptide comprises a polypeptide having at least 55% sequence identity to the amino acid sequence set forth in SEQ ID NO:119. Furthermore, the recombinant host cells disclosed herein and capable of producing one or more mogroside compounds as discussed above can have reduced expression of at least one endogenous gene encoding a glucanase polypeptide (such as, for example, an exo-1,3-β-glucanase polypeptide having at least 50% sequence identity to the amino acid sequence set forth in SEQ ID NO:115 or 117) or glucosidase polypeptide or at least one endogenous transcription factor gene that regulates expression of the at least one endogenous gene encoding the glucanase polypeptide or the glucosidase polypeptide. In addition, the recombinant host cells disclosed herein and capable of producing one or more mogroside compounds as discussed above can have reduced expression of at least one endogenous gene encoding a lanosterol synthase polypeptide (such as, for example, ERG7 polypeptide having an amino acid sequence set forth in SEQ ID NO:118).

The recombinant host cells capable of producing one or more mogroside compounds (for example, a di-glycosylated mogroside compound such as mogroside II A (MG-IIA), mogroside II A1 (MG-IIA1), mogroside II A2 (MG-IIA2), or mogroside II E (MG-IIE); a tri-glycosylated mogroside compound such as mogroside III (MG-III), mogroside III A1 (MG-IIIA1), mogroside III A2 (MG-IIIA2), or mogroside III E (MG-IIIE); a tetra-glycosylated mogroside compound such as mogroside IV (MG-IV), mogroside IV A (MG-IVA), or siamenoside I (SM-I); or a penta-glycosylated mogroside compound such as mogroside V (MG-V) or 11-oxo-mogroside V (11-O-MG-V)) in a cell culture disclosed herein comprise a recombinant gene encoding a polypeptide capable of deglycosylating a mogroside precursor having at least 50% sequence identity to the amino acid sequence set forth in SEQ ID NO:2, wherein the one or more mogroside compounds are a deglycosylation product of the mogroside precursor (for example, a tri-glycosylated mogrol such as MG-III, MG-IIIA1, MG-IIIA2, or MG-IIIE; a tetra-glycosylated mogrol such as MG-IV, MG-IVA, or SM-I; a penta-glycosylated mogrol such as MG-V or 11-O-MG-V; or a hexa-glycosylated mogrol); and further comprise one or more genes encoding one or more polypeptides capable of glycosylating mogrol or a mogroside compound at its C3 hydroxyl group, C11 hydroxyl group, C24 hydroxyl group, and/or C25 hydroxyl group thereof, wherein the one or more polypeptides comprise a polypeptide having at least 45% sequence identity to the amino acid sequence set forth in any one of SEQ ID NOs:83 or 86, or at least 60% sequence identity to the amino acid sequence set forth in SEQ ID NO:89; and one or more genes encoding one or more polypeptides capable of beta-1,2-glycosylation of the C2' position of the 24-O-glucose and/or beta-1,6-glycosylation of the C6' position of the 3-O-glucose and/or the 24-O-glucose of a mogroside compound, wherein the one or more polypeptides comprise a polypeptide having at least 70% sequence identity to the amino acid sequence set forth in SEQ ID NO:93 or at least 50% sequence identity to the amino acid sequence set forth in SEQ ID NO:99. The recombinant host cells disclosed herein and capable of producing one or more mogroside compounds as discussed above can further comprise a gene encoding a polypeptide capable of synthesizing cucurbitadienol from oxidosqualene, or 24,25-epoxy-cucurbitadienol from dioxidosqualene having at least 70% sequence identity to the amino acid sequence set forth in SEQ ID NO:24; a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol having at least 70% sequence identity to the amino acid sequence set forth in SEQ ID NO:29; a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol having at least 50% sequence identity to the amino acid sequence set forth in SEQ ID NO:31; a gene encoding a polypeptide capable of reducing cytochrome P450 complex having at least 50% sequence identity to the amino acid sequence set forth in SEQ ID NO:34; and a gene encoding a polypeptide capable of synthesizing mogrol from 11-hydroxy-24,25-epoxy-cucurbitadienol having at least 65% sequence identity to the amino acid sequence set forth in SEQ ID NO:39; wherein at least one of the genes is a recombinant gene.

The recombinant host cells disclosed herein and capable of producing one or more mogroside compounds as discussed above comprise a plant cell, a mammalian cell, an insect cell, a fungal cell from *Aspergillus* genus, or a yeast cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous,* or *Candida albicans* species, an algal cell, or a bacterial cell from *Escherichia coli* species or *Bacillus* genus, wherein the recombinant host cell can be, for example a *Saccharomyces cerevisiae* cell or a *Yarrowia lipolytica* cell.

The methods of producing one or more mogroside compounds (for example, a di-glycosylated mogroside compound such as mogroside II A (MG-IIA), mogroside II A1 (MG-IIA1), mogroside II A2 (MG-IIA2), or mogroside II E (MG-IIE); a tri-glycosylated mogroside compound such as mogroside III (MG-III), mogroside III A1 (MG-IIIA1), mogroside III A2 (MG-IIIA2), or mogroside III E (MG-IIIE); a tetra-glycosylated mogroside compound such as mogroside IV (MG-IV), mogroside IV A (MG-IVA), or siamenoside I (SM-I); or a penta-glycosylated mogroside compound such as mogroside V (MG-V) or 11-oxo-mogroside V (11-O-MG-V)) in a cell culture disclosed herein, comprise culturing (such as, for example, in a fermentor at a temperature for a period of time, wherein the temperature and period of time facilitate the production of the one or more mogroside compounds) the recombinant host cells disclosed herein and capable of producing one or more mogroside compounds, as discussed above, in the cell culture, under conditions in which the genes comprising the recombinant host cells are expressed (such as, for example, the genes are constitutively expressed or the expression of the genes is induced), wherein the one or more mogroside compounds are produced by the recombinant host cell, and wherein the one or more mogroside compounds are a deglycosylation product of the mogroside precursor (for example, a tri-glycosylated mogrol such as MG-III, MG-IIIA1, MG-IIIA2, or MG-IIIE; a tetra-glycosylated mogrol such as MG-IV, MG-IVA, or SM-I; a penta-glycosylated mogrol such as MG-V or 11-O-MG-V; or a hexa-glycosylated mogrol). Furthermore, in the methods of producing one or more mogroside compounds disclosed herein and described above, the mogroside precursor can be produced by the recombinant host cell.

The methods of producing one or more mogroside compounds (for example, a di-glycosylated mogroside compound such as mogroside II A (MG-IIA), mogroside II A1 (MG-IIA1), mogroside II A2 (MG-IIA2), or mogroside II E (MG-IIE); a tri-glycosylated mogroside compound such as mogroside III (MG-III), mogroside III A1 (MG-IIIA1), mogroside III A2 (MG-IIIA2), or mogroside III E (MG-IIIE); a tetra-glycosylated mogroside compound such as mogroside IV (MG-IV), mogroside IV A (MG-IVA), or siamenoside I (SM-I); or a penta-glycosylated mogroside compound such as mogroside V (MG-V) or 11-oxo-mogroside V (11-O-MG-V)) disclosed herein comprise whole cell bioconversion of one or more plant-derived or synthetic mogroside precursors in a cell culture medium of a recombinant host cell using a polypeptide capable of deglycosylating a mogroside precursor, comprising a polypeptide having at least 50% sequence identity to the amino acid sequence set forth in SEQ ID NO:2 and, optionally, a polypeptide capable of glycosylating mogrol or a mogroside compound at its C3 hydroxyl group, C11 hydroxyl group, C24 hydroxyl group, and/or C25 hydroxyl group thereof, comprising a polypeptide having at least 50% sequence identity to the amino acid sequence set forth in any one of SEQ ID NOs:76-80, or at least 45% sequence identity to the amino acid sequence set forth in SEQ ID NOs:83 or 86, or at least 60% sequence identity to the amino acid sequence set forth in SEQ ID NO:89; and/or a polypeptide capable of beta-1,2-glycosylation of the C2' position of the 24-O-glucose and/or beta-1,6-glycosylation of the C6' position of the 3-O-glucose and/or the 24-O-glucose of a mogroside compound, comprising a polypeptide having at least 70% sequence identity to the amino acid sequence set forth in SEQ ID NOs:93 or 95, or at least 50% sequence identity to the amino acid sequence set forth in any one of SEQ ID NOs:99, 101, 103, 105, 107, 109, 115, or 117, wherein at least one of the polypeptides is a recombinant polypeptide expressed in the recombinant host cell, wherein the one or more mogroside compounds are a deglycosylation product of the mogroside precursor, and producing the one or more mogroside compounds thereby. The whole cell bioconversion methods of producing one or more mogroside compounds disclosed herein and described above, can further use a polypeptide capable of synthesizing oxidosqualene from squalene, comprising a polypeptide having at least 45% sequence identity to the amino acid sequence set forth in SEQ ID NO:3, or at least 50% sequence identity to the amino acid sequence set forth in any one of SEQ ID NOs:6-8, 11-12, or 20, or at least 55% sequence identity to the amino acid sequence set forth in SEQ ID NO:21, or at least 60% sequence identity to the amino acid sequence set forth in any one of SEQ ID NOs:10, 13-14, or 16-19, or at least 65% sequence identity to the amino acid sequence set forth in any one of SEQ ID NOs:4-5, 9, or 15; a polypeptide capable of synthesizing cucurbitadienol from oxidosqualene, or 24,25-epoxy-cucurbitadienol from dioxidosqualene, comprising a polypeptide having at least 70% sequence identity to the amino acid sequence set forth in SEQ ID NO:24, or at least 75% sequence identity to the amino acid sequence set forth in SEQ ID NO:25, or at least 80% sequence identity to the amino acid sequence set forth in SEQ ID NO:26; a polypeptide capable of synthesizing 24,25-epoxy-cucurbitadienol from cucurbitadienol, or 11-hydroxy-24,25-epoxy-cucurbitadienol from 11-hydroxy-cucurbitadienol, comprising a polypeptide having at least 70% sequence identity to the amino acid sequence set forth in SEQ ID NO:29; a polypeptide capable of synthesizing 11-hydroxy-cucurbitadienol from cucurbitadienol, or 11-hydroxy-24,25-epoxy-cucurbitadienol from 24,25-epoxy-cucurbitadienol, comprising a polypeptide having at least 50% sequence identity to the amino acid sequence set forth in SEQ ID NO:31; a polypeptide capable of reducing cytochrome P450 complex, comprising a polypeptide having at least 50% sequence identity to the amino acid sequence set forth in SEQ ID NO:34; a polypeptide capable of synthesizing mogrol from 11-hydroxy-24,25-epoxy-cucurbitadienol, comprising a polypeptide having at least 75% sequence identity to the amino acid sequence set forth in SEQ ID NO:36, or at least 65% sequence identity to the amino acid sequence set forth in SEQ ID NO:39; and/or a polypeptide capable of synthesizing mogrol from 11-hydroxy-cucurbitadienol, comprising a polypeptide having at least 50% sequence identity to the amino acid sequence set forth in any one of SEQ ID NOs:41, 43, 47, 49, 51, 53, 55, 57, 59, 61, 65, 67, 69, 71, 73, or 75, wherein at least one of the polypeptides is a recombinant polypeptide expressed in the recombinant host cell.

The recombinant host cells used in the methods of producing one or more mogroside compounds disclosed herein and described above comprise a plant cell, a mammalian cell, an insect cell, a fungal cell from *Aspergillus* genus, or a yeast cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* species, an algal cell, or a bacterial cell from *Escherichia coli* species or *Bacillus* genus, wherein the recombinant host cell can be, for example a *Saccharomyces cerevisiae* cell or a *Yarrowia lipolytica* cell.

The in vitro methods of producing one or more mogroside compounds (for example, a di-glycosylated mogroside compound such as mogroside II A (MG-IIA), mogroside II A1 (MG-IIA1), mogroside II A2 (MG-IIA2), or mogroside II E (MG-IIE); a tri-glycosylated mogroside compound such as mogroside III (MG-III), mogroside III A1 (MG-IIIA1), mogroside III A2 (MG-IIIA2), or mogroside III E (MG-IIIE); a tetra-glycosylated mogroside compound such as mogroside IV (MG-IV), mogroside IV A (MG-IVA), or siamenoside I (SM-I); or a penta-glycosylated mogroside compound such as mogroside V (MG-V) or 11-oxo-mogroside V (11-O-MG-V)) disclosed herein comprise adding a polypeptide capable of deglycosylating a mogroside precursor, comprising a polypeptide having at least 50% sequence identity to the amino acid sequence set forth in SEQ ID NO:2 and, optionally, a polypeptide capable of glycosylating mogrol or a mogroside compound at its C3 hydroxyl group, C11 hydroxyl group, C24 hydroxyl group, and/or C25 hydroxyl group thereof, comprising a polypeptide having at least 50% sequence identity to the amino acid sequence set forth in any one of SEQ ID NOs:76-80, or at least 45% sequence identity to the amino acid sequence set forth in SEQ ID NOs:83 or 86, or at least 60% sequence identity to the amino acid sequence set forth in SEQ ID NO:89; and/or a polypeptide capable of beta-1,2-glycosylation of the C2' position of the 24-O-glucose and/or beta-1,6-glycosylation of the C6' position of the 3-O-glucose and/or the 24-O-glucose of a mogroside compound, comprising a polypeptide having at least 70% sequence identity to the amino acid sequence set forth in SEQ ID NOs:93 or 95, or at least 50% sequence identity to the amino acid sequence set forth in any one of SEQ ID NOs:99, 101, 103, 105, 107, 109, 115, or 117 and one or more plant-derived or synthetic mogroside precursors to a reaction mixture, wherein at least one of the polypeptides is a recombinant polypeptide, wherein the one or more mogroside compounds are a deglycosylation product of the mogroside precursor, and producing the one or more mogroside compounds thereby. The in vitro methods of producing one or more mogroside compounds disclosed herein and described above, can further use a polypeptide capable of synthesizing oxidosqualene from squalene, comprising a polypeptide having at least 45% sequence identity to the amino acid sequence set forth in SEQ ID NO:3, or at least 50% sequence identity to the amino acid sequence set forth in any one of SEQ ID NOs:6-8, 11-12, or 20, or at least 55% sequence identity to the amino acid sequence set forth in SEQ ID NO:21, or at least 60% sequence identity to the amino acid sequence set forth in any one of SEQ ID NOs:10, 13-14, or 16-19, or at least 65% sequence identity to the amino acid sequence set forth in any one of SEQ ID NOs:4-5, 9, or 15; a polypeptide capable of synthesizing cucurbitadienol from oxidosqualene, or 24,25-epoxy-cucurbitadienol from dioxidosqualene, comprising a polypeptide having at least 70% sequence identity to the amino acid sequence set forth in SEQ ID NO:24, or at least 75% sequence identity to the amino acid sequence set forth in SEQ ID NO:25, or at least 80% sequence identity to the amino acid sequence set forth in SEQ ID NO:26; a polypeptide capable of synthesizing 24,25-epoxy-cucurbitadienol from cucurbitadienol, or 11-hydroxy-24,25-epoxy-cucurbitadienol from 11-hydroxy-cucurbitadienol, comprising a polypeptide having at least 70% sequence identity to the amino acid sequence set forth in SEQ ID NO:29; a polypeptide capable of synthesizing 11-hydroxy-cucurbitadienol from cucurbitadienol, or 11-hydroxy-24,25-epoxy-cucurbitadienol from 24,25-epoxy-cucurbitadienol, comprising a polypeptide having at least 50% sequence identity to the amino acid sequence set forth in SEQ ID NO:31; a polypeptide capable of reducing cytochrome P450 complex, comprising a polypeptide having at least 50% sequence identity to the amino acid sequence set forth in SEQ ID NO:34; a polypeptide capable of synthesizing mogrol from 11-hydroxy-24,25-epoxy-cucurbitadienol, comprising a polypeptide having at least 75% sequence identity to the amino acid sequence set forth in SEQ ID NO:36, or at least 65% sequence identity to the amino acid sequence set forth in SEQ ID NO:39; and/or a polypeptide capable of synthesizing mogrol from 11-hydroxy-cucurbitadienol, comprising a polypeptide having at least 50% sequence identity to the amino acid sequence set forth in any one of SEQ ID NOs:41, 43, 47, 49, 51, 53, 55, 57, 59, 61, 65, 67, 69, 71, 73, or 75. The in vitro methods of producing one or more mogroside compounds disclosed herein and described above are (such as, for example, enzymatic in vitro methods or whole cell in vitro methods), can further comprise supplying the one or more UDP-glucose or a cell-free system for regeneration of the one or more UDP-glucose.

The methods of producing one or more mogroside compounds disclosed herein and described above, comprising recombinant production methods, whole cell bioconversion methods, and in vitro production methods, can further comprise isolating the produced one or more mogroside compounds, wherein the isolating step can comprise separating a liquid phase of the cell culture or the reaction mixture from a solid phase of the cell culture or the reaction mixture to obtain a supernatant comprising the produced one or more mogroside compounds, and contacting the supernatant with one or more adsorbent resins in order to obtain at least a portion of the produced one or more mogroside compounds; or contacting the supernatant with one or more ion exchange or reversed-phase chromatography columns in order to obtain at least a portion of the produced one or more mogroside compounds; or crystallizing or extracting the produced one or more mogroside compounds; thereby isolating the produced one or more mogroside compounds. The methods of producing one or more mogroside compounds disclosed herein and described above, comprising recombinant production methods, whole cell bioconversion methods, and in vitro production methods, can further comprise recovering a mogroside composition comprising the one or more mogroside compounds from the cell culture or the reaction mixture, wherein the recovered mogroside composition, comprising comprises MG-IIA, MG-IIA1, MG-IIA2, MG-III, MG-IIIA1, MG-IIIA2, MG-IIIE, MG-IV, MG-IVA, SM-I, 11-O-MG-V, and/or MG-V, is enriched for the one or more mogroside compounds relative to a mogroside composition from a S. grosvenorii plant and has a reduced level of S. grosvenorii plant-derived components relative to a plant-derived S. grosvenorii extract.

The methods of converting a mogroside precursor (for example, a tri-glycosylated mogrol such as mogroside III (MG-III), mogroside III A1 (MG-IIIA1), mogroside III A2 (MG-IIIA2), or mogroside III E (MG-IIIE); a tetra-glycosylated mogrol such as mogroside IV (MG-IV), mogroside IV A (MG-IVA), or siamenoside I (SM-I); a penta-glycosylated mogrol such as mogroside V (MG-V) or 11-oxo-mogroside V (11-O-MG-V); or a hexa-glycosylated mogrol) into a mogroside compound (for example, a di-glycosylated mogroside compound such as MG-IIA, MG-IIA1, MG-IIA2, or MG-IIE; a tri-glycosylated mogroside compound such as MG-III, MG-IIIA1, MG-IIIA2, or MG-IIIE; a tetra-glycosylated mogroside compound such as MG-IV, MG-IVA, or SM-I; or a penta-glycosylated mogroside compound such as MG-V or 11-O-MG-V) disclosed herein comprise contacting the mogroside precursor with the recombinant host cells disclosed herein and capable of producing one or more mogroside compounds, as discussed above, a cell free extract derived from the recombinant host cell, or a polypeptide capable of deglycosylating a mogroside precursor, comprising a polypeptide having at least 50% sequence identity to the amino acid sequence set forth in SEQ ID NO:2; a polypeptide capable of synthesizing oxidosqualene from squalene, comprising a polypeptide having at least 45% sequence identity to the amino acid sequence set forth in SEQ ID NO:3, or at least 50% sequence identity to the amino acid sequence set forth in any one of SEQ ID NOs:6-8, 11-12, or 20, or at least 55% sequence identity to the amino acid sequence set forth in SEQ ID NO:21, or at least 60% sequence identity to the amino acid sequence set forth in any one of SEQ ID NOs:10, 13-14, or 16-19, or at least 65% sequence identity to the amino acid sequence set forth in any one of SEQ ID NOs:4-5, 9, or 15; a polypeptide capable of synthesizing cucurbitadienol from oxidosqualene, or 24,25-epoxy-cucurbitadienol from dioxidosqualene, comprising a polypeptide having at least 70% sequence identity to the amino acid sequence set forth in SEQ ID NO:24, or at least 75% sequence identity to the amino acid sequence set forth in SEQ ID NO:25, or at least 80% sequence identity to the amino acid sequence set forth in SEQ ID NO:26; a polypeptide capable of synthesizing 24,25-epoxy-cucurbitadienol from cucurbitadienol, or 11-hydroxy-24,25-epoxy-cucurbitadienol from 11-hydroxy-cucurbitadienol, comprising a polypeptide having at least 70% sequence identity to the amino acid sequence set forth in SEQ ID NO:29; a polypeptide capable of synthesizing 11-hydroxy-cucurbitadienol from cucurbitadienol, or 11-hydroxy-24,25-epoxy-cucurbitadienol from 24,25-epoxy-cucurbitadienol, comprising a polypeptide having at least 50% sequence identity to the amino acid sequence set forth in SEQ ID NO:31; a polypeptide capable of reducing cytochrome P450 complex, comprising a polypeptide having at least 50% sequence identity to the amino acid sequence set forth in SEQ ID NO:34; a polypeptide capable of synthesizing mogrol from 11-hydroxy-24,25-epoxy-cucurbitadienol, comprising a polypeptide having at least 75% sequence identity to the amino acid sequence set forth in SEQ ID NO:36, or at least 65% sequence identity to the amino acid sequence set forth in SEQ ID NO:39; a polypeptide capable of synthesizing mogrol from 11-hydroxy-cucurbitadienol, comprising a polypeptide having at least 50% sequence identity to the amino acid sequence set forth in any one of SEQ ID NOs:41, 43, 47, 49, 51, 53, 55, 57, 59, 61, 65, 67, 69, 71, 73, or 75; a polypeptide capable of glycosylating mogrol or a mogroside compound at its C3 hydroxyl group, C11 hydroxyl group, C24 hydroxyl group, and/or C25 hydroxyl group thereof, comprising a polypeptide having at least 50% sequence identity to the amino acid sequence set forth in any one of SEQ ID NOs:76-80, or at least 45% sequence identity to the amino acid sequence set forth in SEQ ID NOs:83 or 86, or at least 60% sequence identity to the amino acid sequence set forth in SEQ ID NO:89; and/or a polypeptide capable of beta-1,2-glycosylation of the C2' position of the 24-O-glucose and/or beta-1,6-glycosylation of the C6' position of the 3-O-glucose and/or the 24-O-glucose of a mogroside compound, comprising a polypeptide having at least 70% sequence identity to the amino acid sequence set forth in SEQ ID NOs:93 or 95, or at least 50% sequence identity to the amino acid sequence set forth in any one of SEQ ID NOs:99, 101, 103, 105, 107, 109, 115, or 117; or a mixture of the polypeptides derived from the recombinant host cell or the cell free extract derived from the recombinant host cell to convert the mogroside precursor into the mogroside compound; wherein the mogroside compound is a deglycosylation product of the mogroside precursor.

The methods of producing one or more mogroside compounds (for example, a di-glycosylated mogroside compound such as mogroside II A (MG-IIA), mogroside II A1 (MG-IIA1), mogroside II A2 (MG-IIA2), or mogroside II E (MG-IIE); a tri-glycosylated mogroside compound such as mogroside III (MG-III), mogroside III A1 (MG-IIIA1), mogroside III A2 (MG-IIIA2), or mogroside III E (MG-IIIE); a tetra-glycosylated mogroside compound such as mogroside IV (MG-IV), mogroside IV A (MG-IVA), or siamenoside I (SM-I); or a penta-glycosylated mogroside compound such as mogroside V (MG-V) or 11-oxo-mogroside V (11-O-MG-V)) disclosed herein comprise transferring a glucose moiety from a mogroside precursor (for example, a tri-glycosylated mogrol such as MG-III, MG- IIIA1, MG-IIIA2, or MG-IIIE; a tetra-glycosylated mogrol such as MG-IV, MG-IVA, or SM-I; a penta-glycosylated mogrol such as MG-V or 11-O-MG-V; or a hexa-glycosylated mogrol), comprising contacting the mogroside precursor with a polypeptide capable of deglycosylating the mogroside precursor under suitable reaction conditions for the transfer of the glucose moiety from the mogroside precursor; and further comprising transferring the glucose moiety to the C3 hydroxyl group, the C11 hydroxyl group, the C24 hydroxyl group, the C25 hydroxyl group, the C2' position of the 24-O-glucose, the C6' position of the 3-O-glucose and/or the 24-O-glucose of the mogroside precursor; comprising contacting the mogroside precursor with the polypeptide capable of glycosylating the mogroside precursor compound at its C3 hydroxyl group, C11 hydroxyl group, C24 hydroxyl group, and/or C25 hydroxyl group thereof and/or the polypeptide capable of beta-1,2-glycosylation of the C2' position of the 24-O-glucose and/or beta-1,6-glycosylation of the C6' position of the 3-O-glucose and/or the 24-O-glucose of the mogroside precursor and a one or more UDP-glucose under suitable reaction conditions for the transfer of the glucose moiety to the mogroside precursor, wherein the mogroside precursor is a tri-glycosylated, a tetra-glycosylated, a penta-glycosylated, or a hexa-glycosylated mogrol, wherein at least one of the polypeptides is a recombinant polypeptide; and producing the one or more mogroside compounds thereby, wherein the one or more mogroside compounds are a deglycosylation product of the mogroside precursor, and wherein the polypeptide capable of deglycosylating a mogroside precursor comprises polypeptide having at least 50% sequence identity to the amino acid sequence set forth in SEQ ID NO:2; the polypeptide capable of glycosylating mogrol or a mogroside compound at its C3 hydroxyl group, C11 hydroxyl group, C24 hydroxyl group, and/or C25 hydroxyl group thereof comprises a polypeptide having at least 50% sequence identity to the amino acid sequence set forth in any one of SEQ ID NOs:76-80, or at least 45% sequence identity to the amino acid sequence set forth in any one of SEQ ID NOs:83 or 86, or at least 60% sequence identity to the amino acid sequence set forth in SEQ ID NO:89; and the polypeptide capable of beta-1,2-glycosylation of the C2' position of the 24-O-glucose and/or beta-1,6-glycosylation of the C6' position of the 3-O-glucose and/or the 24-O-glucose of a mogroside compound comprises a polypeptide having at least 70% sequence identity to the amino acid sequence set forth in any one of SEQ ID NOs:93 or 95, or at least 50% sequence identity to the amino acid sequence set forth in any one of SEQ ID NOs:99, 101, 103, 105, 107, 109, 115, or 117.

A cell culture disclosed herein comprises recombinant host cells disclosed herein and capable of producing one or more mogroside compounds, as discussed above, and can further comprise the one or more mogroside compounds produced by the recombinant host cell; glucose, fructose, sucrose, xylose, rhamnose, uridine diphosphate (UDP)-glucose, UDP-rhamnose, UDP-xylose, and/or N-acetyl-glucosamine; and supplemental nutrients comprising trace metals, vitamins, salts, YNB, and/or amino acids, wherein the one or more mogroside compounds is present at a concentration of at least 1 mg/liter of the cell culture, wherein the cell culture is enriched for the one or more mogroside compounds relative to a mogroside composition from a S. grosvenorii plant; and wherein the cell culture has a reduced level of S. grosvenorii plant-derived components relative to a plant-derived S. grosvenorii extract. A cell lysate from recombinant host cells disclosed herein and capable of producing one or more mogroside compounds, as discussed above, grown in the cell culture, comprises the one or more mogroside compounds produced by the recombinant host cell; glucose, fructose, sucrose, xylose, rhamnose, uridine diphosphate (UDP)-glucose, UDP-rhamnose, UDP-xylose, and/or N-acetyl-glucosamine; and supplemental nutrients comprising trace metals, vitamins, salts, YNB, and/or amino acids, wherein the one or more mogroside compounds is present at a concentration of at least 1 mg/liter of the cell culture.

Nucleic acid molecules disclosed herein encode polypeptides or catalytically active portions thereof capable of deglycosylating a mogroside precursor, comprise polypeptide having at least 50% sequence identity to the amino acid sequence set forth in SEQ ID NO:2, can further be isolated nucleic acids, and can further be cDNAs.

Polypeptide or catalytically active portions thereof disclosed herein that capable of deglycosylating a mogroside precursor and having at least 50% sequence identity to the amino acid sequence set forth in SEQ ID NO:2 can further be purified polypeptides or catalytically active portions thereof.

Functional Homologs

Functional homologs of the polypeptides described above are also suitable for use in producing mogroside precursors or mogroside compounds in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of mogroside biosynthesis polypeptides. Sequence analysis can involve BLAST, Reciprocal BLAST, or PSI-BLAST analysis of non-redundant databases using a UGT amino acid sequence as the reference sequence. Amino acid sequence is, in some instances, deduced from the nucleotide sequence. Those polypeptides in the database that have greater than 40% sequence identity are candidates for further evaluation for suitability as a mogroside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in mogroside biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of a mogroside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.*, 26:320-322 (1998); Sonnhammer et al., Proteins, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing a mogroside precursor or mogroside compound in a recombinant host include functional homologs of UGTs.

Methods to modify the substrate specificity of, for example, a UGT, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, *Phytochemistry* 70: 325-347.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program Clustal Omega (version 1.2.1, default parameters), which allows alignments of nucleic acid or polypeptide sequences to be carried out across their entire length (global alignment). Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method:% age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine a % identity of a candidate nucleic acid or amino acid sequence to a reference sequence, the sequences are aligned using Clustal Omega, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional UGT proteins (e.g., a polypeptide capable of glycosylating mogrol or a mogroside compound at its C3 hydroxyl group, C11 hydroxyl group, C24 hydroxyl group, and/or C25 hydroxyl group thereof) can include additional amino acids that are not involved in the enzymatic activities carried out by the enzymes. In some embodiments, UGT proteins are fusion proteins. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins. In some embodiments, a nucleic acid sequence encoding a UGT polypeptide (e.g., a polypeptide capable of glycosylating mogrol or a mogroside compound at its C3 hydroxyl group, C11 hydroxyl group, C24 hydroxyl group, and/or C25 hydroxyl group thereof) can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), and Flag™ tag (Kodak, New Haven, Conn.). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein.

In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a UGT polypeptide (e.g., a polypeptide capable of glycosylating mogrol or a mogroside compound at its C3 hydroxyl group, C11 hydroxyl group, C24 hydroxyl group, and/or C25 hydroxyl group thereof) is altered by domain swapping.

In some embodiments, a fusion protein is a protein altered by circular permutation, which consists in the covalent attachment of the ends of a protein that would be opened elsewhere afterwards. Thus, the order of the sequence is altered without causing changes in the amino acids of the protein. In some embodiments, a targeted circular permutation can be produced, for example but not limited to, by designing a spacer to join the ends of the original protein. Once the spacer has been defined, there are several possibilities to generate permutations through generally accepted molecular biology techniques, for example but not limited to, by producing concatemers by means of PCR and subsequent amplification of specific permutations inside the concatemer or by amplifying discrete fragments of the protein to exchange to join them in a different order. The step of generating permutations can be followed by creating a circular gene by binding the fragment ends and cutting back at random, thus forming collections of permutations from a unique construct. In some embodiments, a polypeptide capable of deglycosylating a mogroside precursor is altered by circular permutation.

Mogroside Biosynthesis Genes

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of mogrol and/or mogroside compound production. Combining a plurality of genes in a module, particularly a polycistronic module, facilitates the use of the module in a variety of species. For example, a mogrol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for mogrol or mogroside compound production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards mogrol or mogroside compound biosynthesis. For example, it may be desirable to downregulate synthesis of sterols in a yeast strain in order to further increase mogrol or mogroside compound production, e.g., by downregulating lanosterol synthase. As another example, it may be desirable to inhibit degradative functions of certain endogenous gene products, e.g., glucanases or glucosidases that remove glucose moieties from secondary metabolites or phosphatases as discussed herein. In such cases, a nucleic acid that overexpresses the polypeptide or gene product may be included in a recombinant construct that is transformed into the strain. Alternatively, mutagenesis can be used to generate mutants in genes for which it is desired to increase or enhance function.

One aspect of the disclosure is a nucleic acid molecule encoding a polypeptide capable of deglycosylating a mogroside precursor, or a catalytically active portion thereof. In some embodiments, the nucleic acid is an isolated nucleic acid. In some embodiments, the nucleic acid is cDNA. In some embodiments, the encoded polypeptide is a glucosidase polypeptide or a glucanase polypeptide. In some embodiments, the encoded polypeptide does not comprise a signal peptide or a transmembrane domain. In some embodiments, the encoded polypeptide comprises a polypeptide having the amino acid sequence set forth in SEQ ID NO:2.

One aspect of the disclosure is a polypeptide capable of deglycosylating a mogroside precursor, or a catalytically active portion thereof. In some embodiments, the polypeptide is a purified polypeptide. In some embodiments, the polypeptide is a glucosidase polypeptide or a glucanase polypeptide. In some embodiments, the encoded polypeptide does not comprise a signal peptide or a transmembrane domain. In some embodiments, the encoded polypeptide comprises a polypeptide having the amino acid sequence set forth in SEQ ID NO:2.

Host Microorganisms

Recombinant hosts can be used to express polypeptides for producing mogroside precursors or mogroside compounds, including, but not limited to, a plant cell, comprising a plant cell that is grown in a plant, a mammalian cell, an insect cell, a fungal cell, an algal cell, or a bacterial cell.

A number of prokaryotes and eukaryotes are also suitable for use in constructing the recombinant microorganisms described herein, e.g., gram-negative bacteria, yeast, and fungi. A species and strain selected for use as a mogroside production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function (s).

Typically, the recombinant microorganism is grown in a fermenter at a temperature(s) for a period of time, wherein the temperature and period of time facilitate the production of a mogroside compound. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, GGPP, ent-kaurene and ent-kaurenoic acid, can be determined by extracting samples from culture media for analysis according to published methods.

Carbon sources of use in the instant method include any molecule that can be metabolized by the recombinant host cell to facilitate growth and/or production of the mogroside compound. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

It will be appreciated that the various genes and modules discussed herein can be present in two or more recombinant hosts rather than a single host. When a plurality of recombinant hosts is used, they can be grown in a mixed culture to accumulate mogrol and/or a mogroside compound.

Alternatively, the two or more hosts each can be grown in a separate culture medium and the product of the first culture medium, e.g., mogrol, can be introduced into second culture medium to be converted into a subsequent intermediate, or into an end product such as, for example, MG-V. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia* (formally known as *Hansuela*), *Scheffersomyces, Physcomitrella, Rhodoturula, Saccharomyces, Schizosaccharomyces, Sphaceloma, Xanthophyllomyces, Humicola, Issatchenkia, Brettanomyces, Yamadazyma, Lachancea, Zygosaccharomyces, Komagataella, Kazachstania, Xanthophyllomyces, Geotrichum, Blakeslea, Dunaliella, Haematococcus, Chlorella, Undaria, Sargassum, Laminaria, Scenedesmus, Pachysolen, Trichosporon, Acremonium, Aureobasidium, Cryptococcus, Corynascus, Chrysosporium, Filibasidium, Fusarium, Magnaporthe, Monascus, Mucor, Myceliophthora, Mortierella, Neocallimastix, Neurospora, Paecilomyces, Penicillium, Piromyces, Pachysolen, Phanerochaete, Podospora, Pycnoporus, Rhizopus, Schizophyllum, Sordaria, Talaromyces, Rasmsonia, Thermoascus, Thielavia, Tolypocladium, Kloeckera, Pachysolen, Schwanniomyces, Trametes, Trichoderma, Acinetobacter, Nocardia, Xanthobacter, Streptomyces, Erwinia, Klebsiella, Serratia, Pseudomonas, Salmonella, Choroflexus, Chloronema, Chlorobium, Pelodictyon, Chromatium, Rhode-spirillum, Rhodobacter, Rhodomicrobium,* or *Yarrowia*.

Exemplary species from such genera include *Lentinus tigrinus, Laetiporus sulphureus, Phanerochaete chrysosporium, Pichia pastoris, Pichia kudriavzevii, Cyberlindnera jadinii, Physcomitrella patens, Rhodoturula glutinis, Rhodoturula mucilaginosa, Phaffia rhodozyma, Xanthophyllomyces dendrorhous, Issatchenkia orientalis, Saccharomyces cerevisiae, Saccharomyces bayanus, Saccharomyces pastorianus, Saccharomyces carlsbergensis, Hansuela polymorpha, Brettanomyces anomalus, Yamadazyma philogaea,*

*Fusarium fujikuroilGibberella fujikuroi, Candida utilis, Candida glabrata, Candida krusei, Candida revkaufi, Candida pulcherrima, Candida tropicalis, Aspergillus niger, Aspergillus oryzae, Aspergillus fumigatus, Penicillium chrysogenum, Penicillium citrinum, Acremonium* chrysogenum, *Trichoderma reesei, Rasamsonia emersonii* (formerly known as *Talaromyces emersonii*), *Aspergillus sojae, Chrysosporium lucknowense, Myceliophtora thermophyla, Candida albicans, Bacillus subtilis, Bacillus amyloliquefaciens, Bacillius licheniformis, Bacillus puntis, Bacillius megaterium, Bacillius halofurans, Baciilius punilus, Serratia marcessans, Pseudomonas aeruginosa, Salmonella typhimurium, Blakeslea trispora, Dunaliella salina, Haematococcus pluvialis, Chlorella* sp., *Undaria pinnatifida, Sargassum, Laminaria japonica, Scenedesmus almeriensis, Salmonella typhi, Choroflexus* aurantiacus, *Chloronema* gigateum, *Chlorobium limicola, Pelodictyon luteolum, Chromatium okenii, Rhode-spirillum rubrum, Rhodobacter spaeroides, Rhodobacter capsulatus, Rhodomicrobium vanellii, Pachysolen tannophilus, Trichosporon beigelii*, and *Yarrowia lipolytica*.

In some embodiments, a microorganism can be a prokaryote such as *Escherichia* bacteria cells, for example, *Escherichia coli* cells; *Lactobacillus* bacteria cells; *Lactococcus* bacteria cells; *Comebacterium* bacteria cells; *Acetobacter* bacteria cells; *Acinetobacter* bacteria cells; or *Pseudomonas* bacterial cells.

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii*, or *S. cerevisiae*.

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be a fungi from the genera including but not limited to *Acremonium, Arxula, Agaricus, Aspergillus, Agaricus, Aureobasidium, Brettanomyces, Candida, Cryptococcus, Corynascus, Chrysosporium, Debaromyces, Filibasidium, Fusarium, Gibberella, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Schizosaccharomyces, Sordaria, Scheffersomyces, Talaromyces, Rhodotorula, Rhodosporidium, Rasmsonia, Zygosaccharomyces, Thermoascus, Thielavia, Trichosporon, Tolypocladium, Trametes*, and *Trichoderma*. Fungal species include, but are not limited to, *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*.

In some embodiments, a microorganism can be a cyanobacterial cell such as *Blakeslea trispora, Dunaliella salina, Haematococcus pluvialis, Chlorella* sp., *Undaria pinnatifida, Sargassum, Laminaria japonica, Scenedesmus almeriensis*.

*Agaricus, Gibberella*, and *Phanerochaete* spp.

*Agaricus, Gibberella*, and *Phanerochaete* spp. can be useful because they are known to produce large amounts of isoprenoids in culture. Thus, the terpene precursors for producing large amounts of mogrosides are already produced by endogenous genes. Thus, modules comprising recombinant genes for mogroside biosynthesis polypeptides can be introduced into species from such genera without the necessity of introducing mevalonate or MEP pathway genes.

*Arxula Adeninivorans* (Blastobotrys Adeninivorans)

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Schizosaccharomyces* spp.

*Schizosaccharomyces* is a genus of fission yeasts. Similar to *S. cerevisiae*, *Schizosaccharomyces* is a model organism in the study of eukaryotic cell biology. It provides an evolutionary distant comparison to *S. cerevisiae*. Species include but are not limited to *S. cryophilius* and *S. pombe*. (See Hoffman et al., 2015, Genetics. 201(2):403-23).

*Humicola* spp.

*Humicola* is a genus of filamentous fungi. Species include but are not limited to *H. alopallonella* and *H. siamensis*.

*Brettanomyces* spp.

*Brettanomyces* is a non-spore forming genus of yeast. It is from the Saccharomycetaceae family and commonly used in the brewing and wine industries. *Brettanomyces* produces several sensory compounds that contribute to the complexity of wine, specifically red wine. *Brettanomyces* species include but are not limited to *B. bruxellensis* and *B. claussenii*. See, e.g., Fugelsang et al., 1997, *Wine Microbiology*.

*Trichosporon* spp.

*Trichosporon* is a genus of the fungi family. *Trichosporon* species are yeast commonly isolated from the soil, but can also be found in the skin microbiota of humans and animals. Species include, for example but are not limited to, *T. aquatile, T. beigelii*, and *T. dermatis*.

*Debaromyces* spp.

*Debaromyces* is a genus of the ascomycetous yeast family, in which species are characterized as a salt-tolerant marine species. Species include but are not limited to *D. hansenii* and *D. hansenius*.

*Physcomitrella* spp.

*Physcomitrella* mosses, when grown in suspension culture, have characteristics similar to yeast or other fungal cultures. This genera can be used for producing plant secondary metabolites, which can be difficult to produce in other types of cells.

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms. Examples of *Saccharomyces* species include *S. castellii*, also known as *Naumovozyma castelli*.

*Zygosaccharomyces* spp.

*Zygosaccharomyces* is a genus of yeast. Originally classified under the *Saccharomyces* genus it has since been reclassified. It is widely known in the food industry because several species are extremely resistant to commercially used food preservation techniques. Species include but are not limited to *Z. bisporus* and *Z. cidri*. (See Barnett et al, Yeasts: Charactertistics and Identification, 1983).

*Geotrichum* spp.

*Geotrichum* is a fungi commonly found in soil, water and sewage worldwide. It's often identified in plants, cereal and diary products. Species include, for example but are not limited to, *G. candidum* and *G. klebahnii* (see Carmichael et al., Mycologica, 1957, 49(6):820-830.)

*Kazachstania* sp

*Kazachstania* is a yeast genus in the family Sacchromycetaceae.

*Torulaspora* spp.

*Torulaspora* is a genus of yeasts and species include but are not limited to *T. franciscae* and *T. globosa*.

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for producing mogrosides.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g., alkanes, fatty acids, and oils) and can grow on sugars. It has a high potential for industrial applications and is an oleaginous microorgamism. *Yarrowia lipolyptica* can accumulate lipid content to approximately 40% of its dry cell weight and is a model organism for lipid accumulation and remobilization. See e.g., Nicaud, 2012, *Yeast* 29(10):409-18; Beopoulos et al., 2009, *Biochimie* 91(6):692-6; Bankar et al., 2009, *Appl Microbiol Biotechnol.* 84(5):847-65.

*Rhodosporidium toruloides*

*Rhodosporidium toruloides* is oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

*Hansenula polymorpha* (*Pichia angusta*)

*Hansenula polymorpha* is methylotrophic yeast (see *Candida boidinii*). It can furthermore grow on a wide range of other substrates; it is thermo-tolerant and can assimilate nitrate (see also, *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Candida krusei* (*Issatchenkia orientalis*)

*Candida krusei*, scientific name *Issatchenkia orientalis*, is widely used in chocolate production. *C. krusei* is used to remove the bitter taste of and break down cacao beans. In addition to this species involvement in chocolate production, *C. krusei* is commonly found in the immunocompromised as a fungal nosocomial pathogen (see Mastromarino et al., New Microbiolgica, 36:229-238; 2013)

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

*Pichia pastoris*

*Pichia pastoris* is methylotrophic yeast (see *Candida boidinii* and *Hansenula polymorpha*). It is also commonly referred to as *Komagataella pastoris*. It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

*Scheffersomyces stipitis*

*Scheffersomyces stipitis* also known as *Pichia stipitis* is homothallic yeast found in haploid form. Commonly used instead of *S. cerevisiae* due to its enhanced respiratory capacity that results from and alternative respiratory system. (See Papini et al., Microbial Cell Factories, 11:136 (2012)).

In some embodiments, a microorganism can be an insect cell such as *Drosophilia*, specifically, *Drosophilia melanogaster*.

In some embodiments, a microorganism can be an algal cell such as, for example but not limited to, *Blakeslea trispora, Dunaliella salina, Haematococcus pluvialis, Chlorella* sp.

In some embodiments, a microorganism can be a cyanobacterial cell such as, for example but not limited to, *Blakeslea trispora, Dunaliella salina, Haematococcus pluvialis, Chlorella* sp., *Undaria pinnatifida, Sargassum, Laminaria japonica*, and *Scenedesmus almeriensis*.

In some embodiments, a microorganism can be a bacterial cell. Examples of bacteria include, but are not limited to, the genenera *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli*), *Streptomyces, Erwinia, Klebsiella, Serratia* (e.g., *S. marcessans*), *Pseudomonas* (e.g., *P. aeruginosa*), *Salmonella* (e.g., *S. typhimurium*, and *S. typhi*). Bacterial cells may also include, but are not limited to, photosynthetic bacteria (e.g., green non-sulfur bacteria (e.g.,

*Choroflexus* bacteria (e.g., *C. aurantiacus*), *Chloronema* (e.g., *C. gigateum*), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., Rhode-spirillum (e.g., *R. rubrum*), *Rhodobacter* (e.g., *R. sphaeroides, R. capsulatus*), and Rhodomicrobium bacteria (e.g., *R. vanellii*)).

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

It can be appreciated that the recombinant host cell disclosed herein can comprise a plant cell, comprising a plant cell that is grown in a plant, a mammalian cell, an insect cell, a fungal cell from *Aspergillus* genus; a yeast cell from *Saccharomyces* (e.g., *S. cerevisiae, S. bayanus, S. pastorianus*, and *S. carlsbergensis*), *Schizosaccharomyces* (e.g., *S. pombe*), *Yarrowia* (e.g., *Y. lipolytica*), *Candida* (e.g., *C. glabrata, C. albicans, C. krusei, C. revkaufi, C. pulcherrima, Candida tropicalis, C. utilis*, and *C. boidinii*), *Ashbya* (e.g., *A. gossypii*), *Cyberlindnera* (e.g., *C. jadinii*), *Pichia* (e.g., *P. pastoris* and *P. kudriavzevii*), *Kluyveromyces* (e.g., *K. lactis*), Hansenual (e.g., *H. polymorpha*), *Arxula* (e.g., *A. adeninivorans*), *Xanthophyllomyces* (e.g., *X. dendrorhous*), *Issatchenkia* (e.g., *I. orientali*), *Torulaspora* (e.g., *T. franciscae* and *T. globosa*), *Geotrichum* (e.g., *G. candidum* and *G. klebahni*), *Zygosaccharomyces* (e.g., *Z. bisporus* and *Z. cidri*), *Yamadazyma* (e.g., *Y. philogaea*), *Lanchancea* (e.g., *L. kluyven*), *Kodamaea* (e.g., *K. ohmen*), *Brettanomyces* (e.g., *B. anomalus*), *Trichosporon* (e.g., *T. aquatile, T. beigelii*, and *T. dermatis*), *Debaromyces* (e.g., *D. hansenuis* and *D. hansenii*), *Scheffersomyces* (e.g., *S. stipis*), *Rhodosporidium* (e.g., *R. toruloides*), *Pachysolen* (e.g., *P. tannophilus*), and *Physcomitrella, Rhodotorula, Kazachstania, Gibberella, Agaricus*, and *Phanerochaete* genera; an insect cell including, but not limited to, *Drosophilia melanogaster*, an algal cell including, but not limited to, *Blakeslea trispora, Dunaliella salina, Haematococcus pluvialis, Chlorella* sp., *Undaria pinnatifida, Sargassum, Laminaria japonica*, and *Scenedesmus almeriensis* species; or a bacterial cell from *Bacillus* genus (e.g., *B. subtilis, B. amyloliquefaciens, B. licheniformis, B. puntis, B. megaterium, B. halodurans*, and *B. pumilus*) *Acinetobacter, Nocardia, Xanthobacter* genera, *Escherichia* (e.g., *E. coli*), *Streptomyces, Erwinia, Klebsiella, Serratia* (e.g., *S. marcessans*), *Pseudomonas* (e.g., *P. aeruginosa*), *Salmonella* (e.g., *S. typhimurium* and *S. typhi*), and further including, *Choroflexus* bacteria (e.g., *C. aurantiacus*), *Chlonema* (e.g., *C. gigateum*), green sulfur bacteria (e.g., *Chlorobium* bacteria (e.g., *C. limicola*), *Pelodictyon* (e.g., *P. luteolum*)), purple sulfur bacteria (e.g., *Chromatium* (e.g., *C. okenii*)), and purple non-sulfur bacteria (e.g., Rhode-spirillum (e.g., *R. rubrum*), *Rhodobacter* (e.g., *R. sphaeroides* and *R. capsulatus*), and *Rhodomicrobium* bacteria (e.g., *R. vanellii*).

The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1. LC-MS Analytical Procedures

LC-MS analyses were performed using a Waters Acquity I-Class UPLC (Waters Corporation, Milford, Mass.) with Waters Acquity UPLC®BEH C18 column (2.1×50 mm, 1.7 µm particles, 130 Å pore size) coupled to a Waters Xevo TQD triple quadropole mass spectrometer with electrospray ionization (ESI) in negative mode. Compound separation was achieved by a gradient of the two mobile phases: A (water with 0.1% formic acid) and B (MeCN with 0.1% formic acid), by increasing linearly from 20% to 40% B between 0.3 to 3.5 min, increasing linearly to 100% B within 1.0 min, holding 100% B for 1.0 min and re-equilibrating. The flow rate was 0.6 ml/min and the column temperature 55° C.

Example 2. MG-V Production/Excretion Analysis

Figure 4:
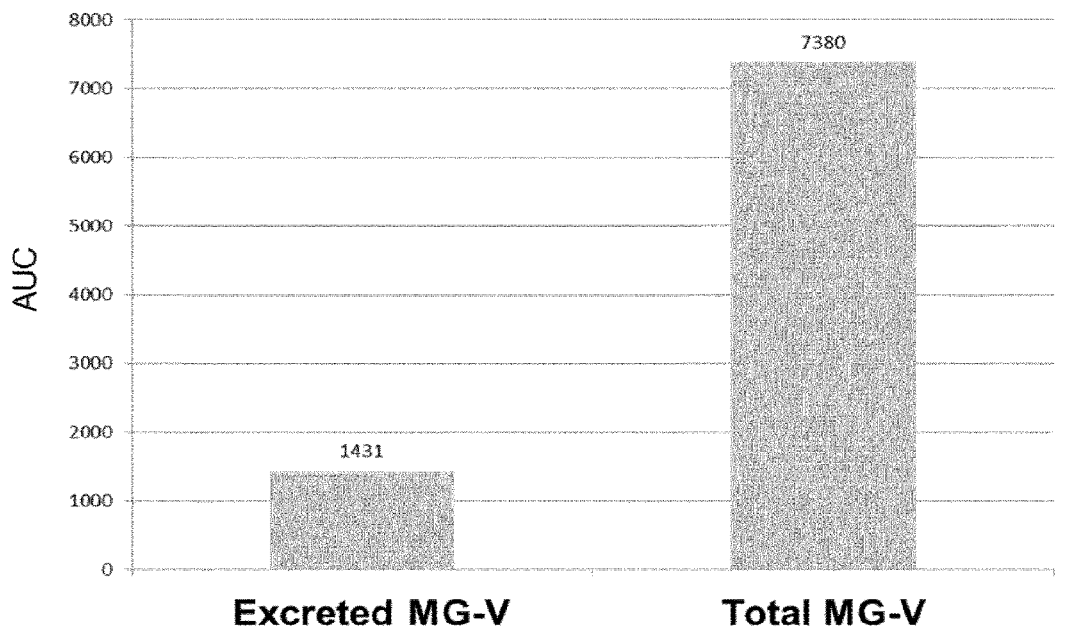

An *S. cerevisiae* strain comprising and expressing a recombinant gene encoding a UGT430 polypeptide, a recombinant gene encoding a UGT98 polypeptide, a recombinant gene encoding a UGT1576 polypeptide, and a recombinant gene encoding a UGT11789 polypeptide was further engineered to disrupt expression of native exo-1,3-β-glucanase polypeptide (EXG1; SEQ ID NO:115). The strain was incubated in synthetic complete (SC) uracil dropout media containing 25 µM mogrol at 30° C. for two days, with shaking. To determine the total amount of MG-V produced, culture samples were mixed 1:1 with ethanol, heated to 80° C. for 10 minutes, and centrifuged to provide a supernatant for LC-MS analysis, carried out according to Example 1. To determine the amount of MG-V excreted, culture samples were centrifuged, and samples of the resultant supernatant were mixed 1:1 with ethanol for LC-MS analysis, carried out according to Example 1. FIG. 4 shows the area-under-the-curve (AUC) values of MG-V excretion and total MG-V production provided via LC-MS.

Example 3. Strain Engineering

Mogroside compound-producing *S. cerevisiae* strains were constructed as described in WO 2016/050890, which is incorporated by reference in its entirety. For example, yeast strains comprising one or more copies of: a recombinant gene encoding a cucurbitadienol synthase (CS) polypeptide (SEQ ID NO:23, SEQ ID NO:24), a recombinant gene encoding a CYP5491 polypeptide (SEQ ID NO:30, SEQ ID NO:31), a recombinant gene encoding a CYP1798 polypeptide (SEQ ID NO:44/SEQ ID NO:28, SEQ ID NO:29), a recombinant gene encoding a CYP4497 polypeptide (SEQ ID NO:32/SEQ ID NO:33, SEQ ID NO:34), a recombinant gene encoding an epoxide hydroxylase 1 polypeptide (SEQ ID NO:35, SEQ ID NO:36), a recombinant gene encoding an epoxide hydroxylase 2 polypeptide (SEQ ID NO:38, SEQ ID NO:39), a recombinant gene encoding a UGT1576 polypeptide (SEQ ID NO:88, SEQ ID NO:89), a recombinant gene encoding a UGT430 polypeptide (SEQ ID NO:82, SEQ ID NO:83), a recombinant gene encoding a UGT1697 polypeptide (SEQ ID NO:85, SEQ ID NO:86), a recombinant gene encoding a UGT98 polypeptide (SEQ ID NO:92, SEQ ID NO:93), and a recombinant gene encoding a UGT11789 polypeptide (SEQ ID NO:89, SEQ ID NO:99) were engineered to accumulate mogroside compounds.

Example 4. Truncated Glucanase Expression

A mogroside compound-producing *S. cerevisiae* strain as described in Example 3, further engineered to disrupt expression of native exo-1,3-β-glucanase polypeptide (EXG1; SEQ ID NO:115) was transformed with a vector comprising a gene encoding an exo-1,3-β-glucanase polypeptide, truncated to remove the N-terminal signal peptide of the wild-type polypeptide (tEXG1; SEQ ID NO:1, SEQ ID NO:2). The strain was incubated in SC uracil dropout media at 30° C. for five days, with shaking. Cell cultures were mixed 1:1 with ethanol, heated to 80° C. for 10 minutes, and centrifuged to provide a supernatant for LC-MS analysis, carried out according to Example 1.

Mogrol and mogrosides were monitored using SIR (Single Ion Recording) and compared with a commercial available mogroside mixture from plant extract (3W botanical extract. Inc.). The SIR traces are the following: mogrol (m/z 521.4; [M+FA–H]$^-$), mogrol+1Glucose (m/z 683.5; [M+FA–H]$^-$), mogrol+2Glucose (m/z 799.5; [M-H]$^-$), mogrol+3Glucose (m/z 961.6; [M-H]$^-$), mogrol+4Glucose (m/z 1123.6; [M-H]$^-$) and mogrol+5Glucose (m/z 1285.66; [M-H]$^-$).

Figure 5A:
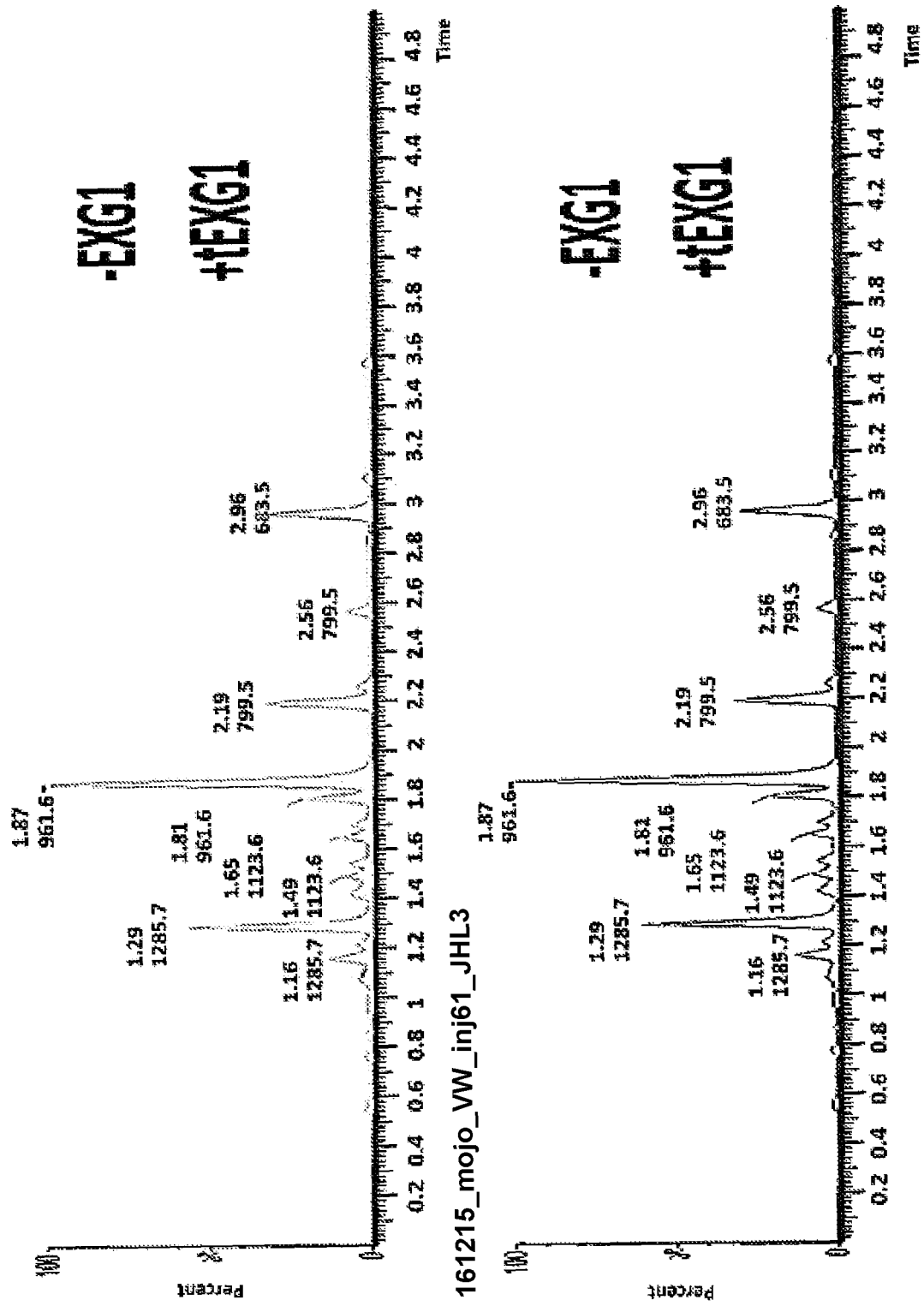
FIG. 5A shows the total ion chromatogram (TIC) of a mogroside compound-producing *S. cerevisiae* strain comprising and expressing tEXG1, in comparison to a control *S. cerevisiae* strain (FIG. 5B), and MG-V and MG-IIIE reference standards (FIG. 5C), as described in more detail in Example 4, below.
Figure 5B:
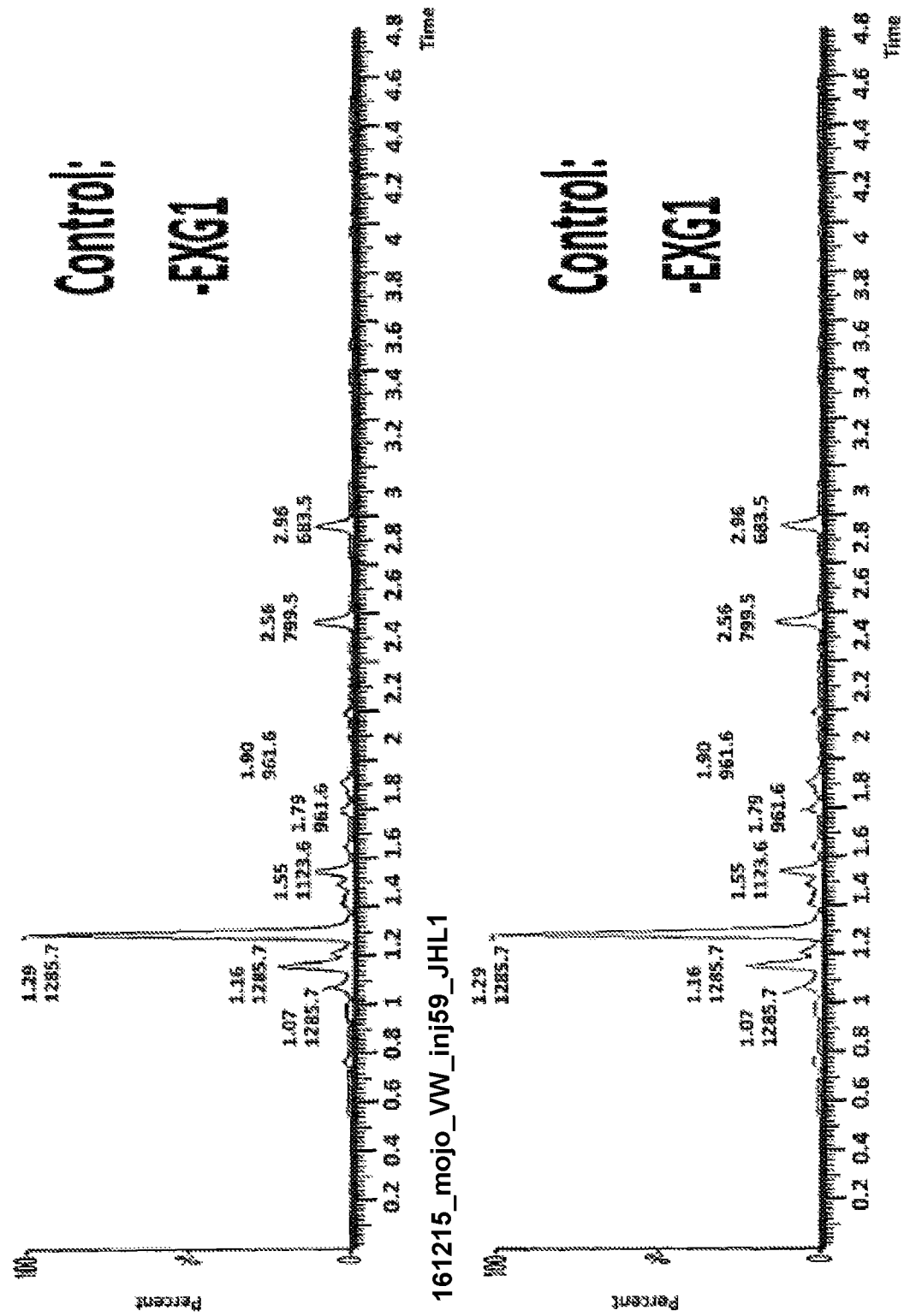
Figure 5C:
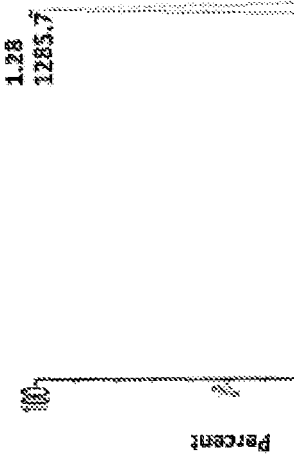

FIG. 5A shows the total ion chromatogram (TIC) of an *S. cerevisiae* strain comprising and expressing tEXG1, in comparison to a control *S. cerevisiae* strain (as described in Example 3; FIG. 5B), and MG-V and MG-IIIE reference standards (FIG. 5C). The results demonstrate that expression of tEXG1 in an MG-V-producing host increases MG-IIIE production.

Without being bound by theory, the results suggest that tEXG1, retained in the host cell cytosol because it lacks an N-terminal signal peptide, deglycosylates MG-V produced by the host cell to form MG-IIIE.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

TABLE 1

Sequences disclosed herein.

SEQ ID NO: 1
Artificial Sequence

| | | | | | |
|---|---|---|---|---|---|
| atgacccccag | tccctgcaag | agacccttct | tccattcaat | ttgttcatga | ggagaacaag | 60 |
| aaaagatact | acgattatga | ccacggttcc | ctcggagaac | caatccgtgg | tgtcaacatt | 120 |
| ggtggttggt | tacttcttga | accatacatt | actccatctt | tgttcgaggc | tttccgtaca | 180 |
| aatgatgaca | acgacgaagg | aattcctgtc | gacgaatatc | acttctgtca | atatttaggt | 240 |
| aaggatttgg | ctaaaagccg | tttacagagc | cattggtcta | ctttctacca | agaacaagat | 300 |
| ttcgctaata | ttgcttccca | aggtttcaac | cttgtcagaa | ttcctatcgg | ttactgggct | 360 |
| ttccaaactt | tggacgatga | tccttatgtt | agcggcctac | aggaatctta | cctagaccaa | 420 |
| gccatcggtt | gggctagaaa | caacagcttg | aaagtttggg | ttgatttgca | tggtgccgct | 480 |
| ggttcgcaga | acgggtttga | taactctggt | ttgagagatt | catacaagtt | tttggaagac | 540 |
| agcaatttgg | ccgttactac | aaatgtcttg | aactacatat | tgaaaaaata | ctctgcggag | 600 |
| gaatacttgg | acactgttat | tggtatcgaa | ttgattaatg | agccattggg | tcctgttcta | 660 |
| gacatggata | aaatgaagaa | tgactacttg | gcacctgctt | acgaatactt | gagaaacaac | 720 |
| atcaagagtg | accaagttat | catcatccat | gacgctttcc | aaccatacaa | ttattgggat | 780 |
| gacttcatga | ctgaaaacga | tggctactgg | ggtgtcacta | tcgaccatca | tcactaccaa | 840 |
| gtctttgctt | ctgatcaatt | ggaaagatcc | attgatgaac | atattaaagt | agcttgtgaa | 900 |
| tggggtaccg | gagttttgaa | tgaatcccac | tggactgttt | gtggtgagtt | tgctgccgct | 960 |
| ttgactgatt | gtacaaaatg | gttgaatagt | gttggcttcg | gcgctagata | cgacggttct | 1020 |
| tgggtcaatg | gtgaccaaac | atcttcttac | attggctctt | gtgctaacaa | cgatgatata | 1080 |
| gcttactggt | ctgacgaaag | aaaggaaaac | acaagacgtt | atgtggaggc | acaactagat | 1140 |
| gcctttgaaa | tgagaggggg | ttggattatc | tggtgttaca | agacagaatc | tagtttggaa | 1200 |
| tgggatgctc | aaagattgat | gttcaatggt | ttattccctc | aaccattgac | tgacagaaag | 1260 |
| tatccaaacc | aatgtggcac | aatttctaac | taa | | | 1293 |

SEQ ID NO: 2
Artificial Sequence

| | | | | | |
|---|---|---|---|---|---|
| MTPVPARDPS | SIQFVHEENK | KRYYDYDHGS | LGEPIRGVNI | GGWLLLEPYI | TPSLFEAFRT | 60 |

TABLE 1-continued

Sequences disclosed herein.

```
NDDNDEGIPV DEYHFCQYLG KDLAKSRLQS HWSTFYQEQD FANIASQGFN LVRIPIGYWA    120

FQTLDDDPYV SGLQESYLDQ AIGWARNNSL KVWVDLHGAA GSQNGFDNSG LRDSYKFLED    180

SNLAVTTNVL NYILKKYSAE EYLDTVIGIE LINEPLGPVL DMDKMKNDYL APAYEYLRNN    240

IKSDQVIIIH DAFQPYNYWD DFMTENDGYW GVTIDHHHYQ VFASDQLERS IDEHIKVACE    300

WGTGVLNESH WTVCGEFAAA LTDCTKWLNS VGFGARYDGS WVNGDQTSSY IGSCANNDDI    360

AYWSDERKEN TRRYVEAQLD AFEMRGGWII WCYKTESSLE WDAQRLMFNG LFPQPLTDRK    420

YPNQCGTISN                                                          430

SEQ ID NO: 3
Saccharomyces cerevisiae
MSAVNVAPEL INADNTITYD AIVIGAGVIG PCVATGLARK GKKVLIVERD WAMPDRIVGE     60

LMQPGGVRAL RSLGMIQSIN NIEAYPVTGY TVFFNGEQVD IPYPYKADIP KVEKLKDLVK    120

DGNDKVLEDS TIHIKDYEDD ERERGVAFVH GRFLNNLRNI TAQEPNVTRV QGNCIEILKD    180

EKNEVVGAKV DIDGRGKVEF KAHLTFICDG IFSRFRKELH PDHVPTVGSS FVGMSLFNAK    240

NPAPMHGHVI LGSDHMPILV YQISPEETRI LCAYNSPKVP ADIKSWMIKD VQPFIPKSLR    300

PSFDEAVSQG KFRAMPNSYL PARQNDVTGM CVIGDALNMR HPLTGGGMTV GLHDVVLLIK    360

KIGDLDFSDR EKVLDELLDY HFERKSYDSV INVLSVALYS LFAADSDNLK ALQKGCFKYF    420

QRGGDCVNKP VEFLSGVLPK PLQLTRVFFA VAFYTIYLNM EERGFLGLPM ALLEGIMILI    480

TAIRVFTPFL FGELIG                                                   496

SEQ ID NO: 4
Gynostemma pentaphyllum
MVDQFSLAFI FASVLGAVAF YYLFLRNRIF RVSREPRRES LKNIATTNGE CKSSYSDGDI     60

IIVGAGVAGS ALAYTLGKDG RRVHVIERDL TEPDRTVGEL LQPGGYLKLT ELGLEDCVNE    120

IDAQRVYGYA LFKDGKDTKL SYPLEKFHSD VSGRSFHNGR FIQRMREKAA TLPNVRLEQG    180

TVTSLLEENG IIKGVQYKSK TGQEMTAYAP LTIVCDGCFS NLRRSLCNPK VDVPSCFVAL    240

VLENCELPHA NYGHVILADP SPILFYPISS TEVRCLVDVP GQKVPSISNG EMANYLKSVV    300

APQIPPQIYD ALRSCYDKGN IRTMPNRSMP ADPYPTPGAL LMGDAFNMRH PLTGGGMTVA    360

LSDIVVLRDL LKPLRDLHDA PILSNYLEAF YTLRKPVAST INTLAGALYK VFCASPDQAR    420

REMRQACFDY LSLGGVFSNG PVSLLSGLNP RPLSLVLHFF AVAIYGVGRL LIPFPSPRRV    480

WIGARLISGA SGIIFPIIKA EGVRQIFFPA TLPAYYRAPP LVRGR                    525

SEQ ID NO: 5
Arabidopsis thaliana
MESQLWNWIL PLLISSLLIS FVAFYGFFVK PKRNGLRHDR KTVSTVTSDV GSVNITGDTV     60

ADVIVVGAGV AGSALAYTLG KDKRRVHVIE RDLSEPDRIV GELLQPGGYL KLLELGIEDC    120

VEEIDAQRVY GYALFKNGKR IRLAYPLEKF HEDVSGRSFH NGRFIQRMRE KAASLPNVQL    180

EQGTVLSLLE ENGTIKGVRY KNKAGEEQTA FAALTIVCDG CFSNLRRSLC NPQVEVPSCF    240

VGLVLENCNL PYANHGHVVL ADPSPILMYP ISSTEVRCLV DVPGQKVPSI ANGEMKNYLK    300

TVVAPQMPHE VYDSFIAAVD KGNIKSMPNR SMPASPYPTP GALLMGDAFN MRHPLTGGGM    360

TVALADIVVL RNLLRPLRDL SDGASLCKYL ESFYTLRKPV AATINTLANA LYQVFCSSEN    420

EARNEMREAC FDYLGLGGMC TSGPVSLLSG LNPRPLTLVC HFFAVAVYGV IRLLIPFPSP    480

KRIWLGAKLI SGASGIIFPI IKAEGVRQMF FPATVPAYYY KAPTVGETKC S             531

SEQ ID NO: 6
Arabidopsis thaliana
MTYAWLWTLL AFVLTWMVFH LIKMKKAATG DLEAEAEARR DGATDVIIVG AGVAGASLAY     60
```

TABLE 1-continued

Sequences disclosed herein.

```
ALAKDGRRVH VIERDLKEPQ RFMGELMQAG GRFMLAQLGL EDCLEDIDAQ EAKSLAIYKD      120

GKHATLPFPD DKSFPHEPVG RLLRNGRLVQ RLRQKAASLS NVQLEEGTVK SLIEEEGVVK      180

GVTYKNSAGE EITAFAPLTV VCDGCYSNLR RSLVDNTEEV LSYMVGYVTK NSRLEDPHSL      240

HLIFSKPLVC VIYQITSDEV RCVAEVPADS IPSISNGEMS TFLKKSMAPQ IPETGNLREI      300

FLKGIEEGLP EIKSTATKSM SSRLCDKRGV IVLGDAFNMR HPIIASGMMV ALSDICILRN      360

LLKPLPNLSN TKKVSDLVKS FYIIRKPMSA TVNTLASIFS QVLVATTDEA REGMRQGCFN      420

YLARGDFKTR GLMTILGGMN PHPLTLVLHL VAITLTSMGH LLSPFPSPRR FWHSLRILAW      480

ALQMLGAHLV DEGFKEMLIP TNAAAYRRNY IATTTV                               516

SEQ ID NO: 7
Arabidopsis thaliana
MAFTHVCLWT LVAFVLTWTV FYLTNMKKKA TDLADTVAED QKDGAADVII VGAGVGGSAL       60

AYALAKDGRR VHVIERDMRE PERMMGEFMQ PGGRLMLSKL GLQDCLEDID AQKATGLAVY      120

KDGKEADAPF PVDNNNFSYE PSARSFHNGR FVQQLRRKAF SLSNVRLEEG TVKSLLEEKG     180

VVKGVTYKNK EGEETTALAP LTVVCDGCYS NLRRSLNDDN NAEIMSYIVG YISKNCRLEE     240

PEKLHLILSK PSFTMVYQIS STDVRCGFEV LPENFPSIAN GEMSTFMKNT IVPQVPPKLR     300

KIFLKGIDEG AHIKVVPAKR MTSTLSKKKG VIVLGDAFNM RHPVVASGMM VLLSDILILR     360

RLLQPLSNLG DANKVSEVIN SFYDIRKPMS ATVNTLGNAF SQVLIGSTDE AKEAMRQGVY    420

DYLCSGGFRT SGMMALLGGM NPRPLSLVYH LCAITLSSIG QLLSPFPSPL RIWHSLKLFG    480

LAMKMLVPNL KAEGVSQMLF PANAAAYHKS YMAATTL                              517

SEQ ID NO: 8
Arabidopsis thaliana
MAFTNVCLWT LLAFMLTWTV FYVTNRGKKA TQLADAVVEE REDGATDVII VGAGVGGSAL       60

AYALAKDGRR VHVIERDLRE PERIMGEFMQ PGGRLMLSKL GLEDCLEGID AQKATGMTVY      120

KDGKEAVASF PVDNNNFPFD PSARSFHNGR FVQRLRQKAS SLPNVRLEEG TVKSLIEEKG     180

VIKGVTYKNS AGEETTALAP LTVVCDGCYS NLRRSLNDNN AEVLSYQVGF ISKNCQLEEP     240

EKLKLIMSKP SFTMLYQISS TDVRCVFEVL PNNIPSISNG EMATFVKNTI APQVPLKLRK    300

IFLKGIDEGE HIKAMPTKKM TATLSEKKGV ILLGDAFNMR HPAIASGMMV LLSDILILRR    360

LLQPLSNLGN AQKISQVIKS FYDIRKPMSA TVNTLGNAFS QVLVASTDEA KEAMRQGCYD   420

YLSSGGFRTS GMMALLGGMN PRPISLIYHL CAITLSSIGH LLSPFPSPLR IWHSLRLFGL    480

AMKMLVPHLK AEGVSQMLFP VNAAAYSKSY MAATAL                               516

SEQ ID NO: 9
Arabidopsis thaliana
MKPFVIRNLP RFQSTLRSSL LYTNHRPSSR FSLSTRRFTT GATYIRRWKA TAAQTLKLSA       60

VNSTVMMKPA KIALDQFIAS LFTFLLLYIL RRSSNKNKKN RGLVVSQNDT VSKNLETEVD     120

SGTDVIIVGA GVAGSALAHT LGKEGRRVHV IERDFSEQDR IVGELLQPGG YLKLIELGLE     180

DCVKKIDAQR VLGYVLFKDG KHTKLAYPLE TFDSDVAGRS FHNGRFVQRM REKALTLSNV     240

RLEQGTVTSL LEEHGTIKGV RYRTKEGNEF RSFAPLTIVC DGCFSNLRRS LCKPKVDVPS    300

TFVGLVLENC ELPFANHGHV VLGDPSPILM YPISSSEVRC LVDVPGQKLP PIANGEMAKY    360

LKTRVAPQVP TKVREAFITA VEKGNIRTMP NRSMPADPIP TPGALLLGDA FNMRHPLTGG    420

GMTVALADIV VLRDLLRPIR NLNDKEALSK YIESFYTLRK PVASTINTLA DALYKVFLAS    480

SDEARTEMRE ACFDYLSLGG VFSSGPVALL SGLNPRPLSL VLHFFAVAIY AVCRLMLPFP    540

SIESFWLGAR IISSASSIIF PIIKAEGVRQ MFFPRTIPAI YRAPP                    585
```

TABLE 1-continued

Sequences disclosed herein.

SEQ ID NO: 10
*Arabidopsis thaliana*
```
MAPTIFVDHC ILTTTFVASL FAFLLLYVLR RRSKTIHGSV NVRNGTLTVK SGTDVDIIIV      60

GAGVAGAALA HTLGKEGRRV HVIERDLTEP DRIVGELLQP GGYLKLIELG LEDCVKDIDA     120

QRVLGYALFK DGKHTKLSYP LDQFDSDVAG RSFHNGRFVQ RMREKASLLP NVRMEQGTVT    180

SLVEENGIIK GVQYKTKDGQ ELKSFAPLTI VCDGCFSNLR RSLCKPKVEV PSNFVGLVLE    240

NCELPFPNHG HVVLGDPSPI LFYPISSSEV RCLVDVPGSK LPSVASGEMA HHLKTMVAPQ    300

VPPQIRDAFI SAVEKGNIRT MPNRSMPADP IHTPGALLLG DAFNMRHPLT GGGMTVALSD    360

IVILRDLLNP LVDLTNKESL SKYIESFYTL RKPVASTINT LAGALYKVFL ASPDDARSEM    420

RRACFDYLSL GGVCSSGPVA LLSGLNPRPM SLVLHFFAVA IFGVGRLLVP LPSVKRLWLG    480

ARLISSASGI IFPIIKAEGV RQMFFPRTIP AIYRAPPTPS SSSPQ                     525
```

SEQ ID NO: 11
*Brassica napus*
```
MDLAFPHVCL WTLLAFVLTW TVFYVNNRRK KVAKLPDAAT EVRRDGDADV IIVGAGVGGS     60

ALAYALAKDG RRVHVIERDM REPVRMMGEF MQPGGRLLLS KLGLEDCLEG IDEQIATGLA    120

VYKDGQKALV SFPEDNDFPY EPTGRAFYNG RFVQRLRQKA SSLPTVQLEE GTVKSLIEEK    180

GVIKGVTYKN SAGEETTAFA PLTVVCDGCY SNLRRSVNDN NAEVISYQVG YVSKNCQLED    240

PEKLKLIMSK PSFTMLYQIS STDVRCVMEI FPGNIPSISN GEMAVYLKNT MAPQVPPELR    300

KIFLKGIDEG AQIKAMPTKR MEATLSEKQG VIVLGDAFNM RHPAIASGMM VVLSDILILR    360

RLLQPLRNLS DANKVSEVIK SFYVIRKPMS ATVNTLGNAF SQVLIASTDE AKEAMRQGCF    420

DYLSSGGFRT SGMMALLGGM NPRPLSLIFH LCGITLSSIG QLLSPFPSPL GIWHSLRLFG    480

AEGVSQMLSP AYAAAYRKSY MTATAL                                          506
```

SEQ ID NO: 12
*Brassica napus*
```
MDMAFVEVCL RMLLVFVLSW TIFHVNNRKK KKATKLADLA TEERKEGGPD VIIVGAGVGG     60

SALAYALAKD GRRVHVIERD MREPVRMMGE FMQPGGRLML SKLGLQDCLE EIDAQKSTGI    120

RLFKDGKETV ACFPVDTNFP YEPSGRFFHN GRFVQRLRQK ASSLPNVRLE EGTVRSLIEE    180

KGVVKGVTYK NSSGEETTSF APLTVVCDGC HSNLRRSLND NNAEVTAYEI GYISRNCRLE    240

QPDKLHLIMA KPSFAMLYQV SSTDVRCNFE LLSKNLPSVS NGEMTSFVRN SIAPQVPLKL    300

RKTFLKGLDE GSHIKITQAK RIPATLSRKK GVIVLGDAFN MRHPVIASGM MVLLSDILIL    360

SRLLKPLGNL GDENKVSEVM KSFYALRKPM SATVNTLGNS FWQVLIASTD EAKEAMRQGC    420

FDYLSSGGFR TSGLMALIGG MNPRPLSLFY HLFVISLSSI GQLLSPFPTP LRVWHSLRLL    480

DLSLKMLVPH LKAEGIGQML SPTNAAAYRK SYMAATVV                             518
```

SEQ ID NO: 13
*Euphorbia tirucalli*
```
MEVIFDTYIF GTFFASLCAF LLLFILRPKV KKMGKIREIS SINTQNDTAI TPPKGSGTDV     60

IIVGAGVGA ALACTLGKDG RRVHVIERDL KEPDRIVGEL LQPGGYLKLV ELGLQDCVEE     120

IDAQRIVGYA LFMDGNNTKL SYPLEKFDAE VSGKSFHNGR FIQRMREKAA SLPNVQLEQG    180

TVTSLLEENG TIKGVQYKTK DGQEHKAYAP LTVVCDGCFS NLRRSLCKPK VDVPSHFVGL    240

VLENCDLPFA NHGHVILADP SPILFYPISS TEVRCLVDVP GQKLPSIASG EMAKYLKTMV    300

AKQIPPVLHD AFVSAIDKGN IRTMPNRSMP ADPLPTPGAL LMGDAFNMRH PLTGGGMTVA    360

LADIVLLRDL LKPLRDLNDA PALAKYLESF YTLRKPVAST INTLGALYK VFSASPDEAR    420

KEMRQACFDY LSLGGECAMG PVSLLSGLNP SPLTLVHFF GVAIYGVGRL LIPFPTPKGM    480
```

TABLE 1-continued

Sequences disclosed herein.

```
WIGARIISSA SGIIFPIIKA EGVRQVFFPA TVPAIYRNPP VNGKSVEVPK S           531

SEQ ID NO: 14
Medicago truncatula
MIDPYGFGWI TCTLITLAAL YNFLFSRKNH SDSTTTENIT TATGECRSFN PNGDVDIIIV  60
GAGVAGSALA YTLGKDGRRV LIIERDLNEP DRIVGELLQP GGYLKLIELG LDDCVEKIDA  120
QKVFGYALFK DGKHTRLSYP LEKFHSDIAG RSFHNGRFIL RMREKAASLP NVRLEQGTVT  180
SLLEENGTIK GVQYKTKDAQ EFSACAPLTI VCDGCFSNLR RSLCNPKVEV PSCFVGLVLE  240
NCELPCADHG HVILGDPSPV LFYPISSTEI RCLVDVPGQK VPSISNGEMA KYLKTVVAPQ  300
VPPELHAAFI AAVDKGHIRT MPNRSMPADP YPTPGALLMG DAFNMRHPLT GGGMTVALSD  360
IVVLRNLLKP LRDLNDASSL CKYLESFYTL RKPVASTINT LAGALYKVFC ASPDPARKEM  420
RQACFDYLSL GGLFSEGPVS LLSGLNPCPL SLVLHFFAVA IYGVGRLLLP FPSPKRLWIG  480
IRLIASASGI ILPIIKAEGI RQMFFPATVP AYYRAPPDA                        519

SEQ ID NO: 15
Medicago truncatula
MDLYNIGWIL SSVLSLFALY NLIFAGKKNY DVNEKVNQRE DSVTSTDAGE IKSDKLNGDA  60
DVIIVGAGIA GAALAHTLGK DGRRVHIIER DLSEPDRIVG ELLQPGGYLK LVELGLQDCV  120
DNIDAQRVFG YALFKDGKHT RLSYPLEKFH SDVSGRSFHN GRFIQRMREK AASLPNVNME  180
QGTVISLLEE KGTIKGVQYK NKDGQALTAY APLTIVCDGC FSNLRRSLCN PKVDNPSCFV  240
GLILENCELP CANHGHVILG DPSPILFYPI SSTEIRCLVD VPGTKVPSIS NGDMTKYLKT  300
TVAPQVPPEL YDAFIAAVDK GNIRTMPNRS MPADPRPTPG AVLMGDAFNM RHPLTGGGMT  360
VALSDIVVLR NLLKPMRDLN DAPTLCKYLE SFYTLRKPVA STINTLAGAL YKVFSASPDE  420
ARKEMRQACF DYLSLGGLFS EGPISLLSGL NPRPLSLVLH FFAVAVFGVG RLLLPFPSPK  480
RVWIGARLLS GASGIILPII KAEGIRQMFF PATVPAYYRA PPVNAF                526

SEQ ID NO: 16
Ricinus communis
MADNYLLGWI LCSIIGLFGL YYMVYLVVKR EEEDNNRKAL LQARSDSAKT MSAVSQNGEC  60
RSDNPADADI IIVGAGVAGS ALAHTLGKDG RRVHVIERDL TEPDRIVGEL LQPGGYLKLI  120
ELGLEDCVEE IDAQRVFGYA LFMDGKHTQL SYPLEKFHSD VAGRSFHNGR FIQRMREKAS  180
SIPNVRLEQG TVTSLIEEKG IIRGVVYKTK TGEELTAFAP LTIVCDGCFS NLRRSLCNPK  240
VDVPSCFVGL VLEDCKLPYQ YHGHVVLADP SPILFYQISS TEVRCLVDVP GQKVPSISNG  300
EMAKYLKNVV APQVPPEIYD SFVAAVDKGN IRTMPNRSMP ASPYPTPGAL LMGDAFNMRH  360
PLTGGGMTVA LSDIVVLREL LKPLRDLHDA PTLCRYLESF YTLRKPVAST INTLAGALYK  420
VFCASSDEAR NEMRQACFDY LSLGGVFSTG PISLLSGLNP RPLSLVVHFF AVAIYGVGRL  480
LLPFPSPKRV WVGARLISGA SGIIFPIIKA EGVRQMFFPA TVPAYYRAPP VECN        534

SEQ ID NO: 17
Ricinus communis
MEYKLAVAGI IASLWALFML CSLKRKKNIT RASFNNYTDE TLKSSSKEIC QPEIVASPDI  60
IIVGAGVAGA ALAYALGEDG RQVHVIERDL SEPDRIVGEL LQPGGYLKLI ELGLEDCVEK  120
IDAQQVFGYA IFKDGKSTKL SYPLDGFQTN VSGRSFHNGR FIQRMREKAT SLPNLILQQG  180
TVTSLVEKKG TVKGVNYRTR NGQEMTAYAP LTIVCDGCFS NLRRSLCNPK VEIPSCFVAL  240
VLENCDLPYA NHGHVILADP SPILFYPISS TEVRCLVDIP GQKVPSISNG ELAQYLKSTV  300
AKQIPSELHD AFISAIEKGN IRTMPNRSMP ASPHPTPGAL LVGDAFNMRH PLTGGGMTVA  360
LSDIVLLRNL LRPLENLNDA SVLCKYLESF YILRKPMAST INTLAGALYK VFSASTDRAR  420
```

TABLE 1-continued

Sequences disclosed herein.

```
SEMRQACFDY LSLGGVFSNG PIALLSGLNP RPLNLVLHFF AVAVYGVGRL ILPFPSPKSI      480

WDGVKLISGA SSVIFPIMKA EGIGQIFFPI TKPPNHKSQT W                          521

SEQ ID NO: 18
Ricinus communis
MGVSREENAR DEKCHYYENG ISLSEKSMST DIIIVGAGVA GSALAYTLGK DGRRVHVIER       60

DLSLQDRIVG ELLQPGGYLK LIELGLEDCV EEIDAQQVFG YALYKNGRST KLSYPLESFD      120

SDVSGRSFHN GRFIQRMREK AASLPNVRLE EGTVTSLLEV KGTIKGVQYK TKNGEELTAS      180

APLTIVCDGC FSNLRRSLCN PKVDIPSCFV ALILENSGQK LPSISNGDMA NYLKSVVAPQ      240

IPPVLSEAFI SAIEKGKIRT MPNRSMPAAP HPTPGALLLG DAFNMRHPLT GGGMTVALSD      300

IVVLRNLLKP LHDLTDASAL CEYLKSFYSL RKPVASTINT LAGALYKVFS ASHDPARNEM      360

RQACFDYLSL GGVFSNGPIA LLSGLNPRPL SLVAHFFAVA IYGVGRLIFP LPSAKGMWMG      420

ARMIKVASGI IFPIIRAEGV QHMFFSKTLS AFSRSQTS                              458

SEQ ID NO: 19
Ricinus communis
MEYQYFVGGI IASALLFVLV CRLAGKRQRR ALRDTVDRDE ISQNSENGIS QSEKNMNTDI       60

IIVGAGVAGS TLAYTLGKDG RRVRVIERDL SLQDRIVGEL LQPGGYLKLI ELGLEDCVEE      120

IDALQVFGYA LYKNGRSTKL SYPLDSFDSD VSGRSFHNGR FIQRMREKAA SLPNVRMEGG      180

TVTSLLEVKG TIKGVQYKNK NGEELIACAP LTIVCDGCFS NLRRSLCNSK VDIPFCFVAL      240

ILENCELPYP NHGHVILADP SPILFYRISI SEIRCLVDIP AGQKLPSISN GEMANYLKSV      300

VAPQIPPELS NAFLSAIEKG KIRTMPKRSM PAAPHPTPGA LLLGDAFNMR HPLTGGVMTV      360

ALSDIVVLRS LLRPLHDLTD ASALCEYLKS FYSLRKPMVS TINTLAGALY RVFSASQDPA      420

RDEMRQACFD YLSLGGVFSN GPIALLSGLN PRPLSLIVHF FAVAVYGVGR LIFPLPSAKR      480

MWMQE                                                                   485

SEQ ID NO: 20
Ricinus communis
MEYQYLMGGG IMTLLFVLSY RLKRETRASV ENARDEVLQN SENGISQSEK AMNTDIKLLL       60

EQIVQKIAML NSIRLEEGTV TSLLEVKRDI KGVQYKTKNG EELTACAPLT IVSHGCFSNL      120

RLHVTPSTSK FKSFIGLEVD IPSSFAALIL GNCELPFPNH GHVILADPSS ILFYRISSSE      180

ICCLVDVPAG QKLPSISNGE MANYLKSVVA HQAFKVGLAY                            220

SEQ ID NO: 21
Ricinus communis
MSPISIQLPP RPQLYRSLIS SLSLSTYKQP PSPPSFSLTI ANSPPQPQPQ ATVSSKTRTI       60

TRLSNSSNRV NLLQAEQHPQ EPSSDLSYSS SPPHCVSGGY NIKLMEVGTD NYAVIIILGT      120

FFASLFAFVF LSILRYNFKN KNKAKIHDET TLKTQNDNVR LPDNGSGNDV IIVGAGVAGA      180

ALAYTLGKDG RRVHVIERDL TEPDRIVGEL LQPGGYLKLI ELGLEDCVQE IDAQRVLGYA      240

LFKDGKNTRL SYPLEKFHAD VAGRSFHNGR FIQRMREKAA SLPNVKLEQG TVTSLLEENG      300

TIKGVQYKTK DGQEIRAYAP LTIVCDGCFS NLRRSLCNPK VDVPSCFVGL VLENCQLPFA      360

NHGHVVLADP SPILFYPISS TEVRCLVDVP GQKVPSIANG EMAKYLKNVV APQIPPVLHD      420

AFISAIDKGN IRTMPNRSMP ADPHPTPGAL LMGDAFNMRH PLTGGGMTVA LSDIVVLRDL      480

LKPLRDLNDA TSLTKYLESF YTLRKPVAST INTLAGALYK VFSASPDQAR KEMRQACFDY      540

LSLGGIFSSG PVALLSGLNP RPLSLVMHFF AVAIYGVGRL LLPFPSPKSV WIGARLISSA      600

SGIIFPIIKA EGVRQMFFPA TIPAIYRPPP VKDTSDDEQK SR                         642

SEQ ID NO: 22
```

TABLE 1-continued

Sequences disclosed herein.

*Siraitia grosvenorii*

| | |
|---|---:|
| atgtggaggt taaaggtcgg agcagaaagc gttggggaga atgatgagaa atggttgaag | 60 |
| agcataagca atcacttggg acgccaggtg tgggagttct gtccggatgc cggcacccaa | 120 |
| caacagctct tgcaagtcca caaagctcgt aaagctttcc acgatgaccg tttccaccga | 180 |
| aagcaatctt ccgatctctt tatcactatt cagtatggaa aggaagtaga aaatggtgga | 240 |
| aagacagcgg gagtgaaatt gaaagaaggg gaagaggtga ggaaagaggc agtagagagt | 300 |
| agcttagaga gggcattaag tttctactca agcatccaga caagcgatgg gaactgggct | 360 |
| tcggatcttg gggggcccat gttttactt ccgggtctgg tgattgccct ctacgttaca | 420 |
| ggcgtcttga attctgtttt atccaagcac caccggcaag agatgtgcag atatgtttac | 480 |
| aatcaccaga atgaagatgg ggggtgggt ctccacatcg agggcccaag caccatgttt | 540 |
| ggttccgcac tgaattatgt tgcactcagg ctgcttggag aagacgccaa cgccggggca | 600 |
| atgccaaaag cacgtgcttg gatcttggac acggtggcg ccaccggaat cacttcctgg | 660 |
| ggcaaattgt ggcttctgt acttggagtc tacgaatgga gtggcaataa tcctcttcca | 720 |
| cccgaatttt ggttatttcc ttacttccta ccatttcatc caggaagaat gtggtgccat | 780 |
| tgtcgaatgg tttatctacc aatgtcatac ttatatggaa agagatttgt tgggccaatc | 840 |
| acacccatag ttctgtctct cagaaaagaa ctctacgcag ttccatatca tgaaatagac | 900 |
| tggaataaat ctcgcaatac atgtgcaaag gaggatctgt actatccaca tcccaagatg | 960 |
| caagatattc tgtggggatc tctccaccac gtgtatgagc ccttgtttac tcgttggcct | 1020 |
| gccaaacgcc tgagagaaaa ggctttgcag actgcaatgc aacatattca ctatgaagat | 1080 |
| gagaataccc gatatatatg ccttggcccct gtcaacaagg tactcaatct gctttgttgt | 1140 |
| tgggttgaag atccctactc cgacgccttc aaacttcatc ttcaacgagt ccatgactat | 1200 |
| ctctggtttg ctgaagatgg catgaaaatg cagggttata tgggagcca gttgtgggac | 1260 |
| actgctttct ccatccaagc aatcgtatcc accaaacttg tagacaacta tggcccaacc | 1320 |
| ttaagaaagg cacacgactt cgttaaaagt tctcagattc agcaggactg tcctggggat | 1380 |
| cctaatgttt ggtaccgtca cattcataaa ggtgcatggc cattttcaac tcgagatcat | 1440 |
| ggatggctca tctctgactg tacagcagag ggattaaagg ctgctttgat gttatccaaa | 1500 |
| cttccatccg aaacagttgg ggaatcatta gaacggaatc gcctttgcga tgctgtaaac | 1560 |
| gttctcctt ctttgcaaaa cgataatggt ggctttgcat catatgagtt gacaagatca | 1620 |
| taccctttggt tggagttgat caaccccgca gaaacgtttg gagatattgt cattgattat | 1680 |
| ccgtatgtgg agtgcacctc agccacaatg gaagcactga cgttgtttaa gaaattacat | 1740 |
| cccggccata ggaccaaaga aattgatact gctattgtca gggcggccaa cttccttgaa | 1800 |
| aatatgcaaa ggacggatgg ctcttggtat ggatgttggg gggtttgctt cacgtatgcg | 1860 |
| gggtggtttg gcataaaggg attggtggct gcaggaagga catataataa ttgccttgcc | 1920 |
| attcgcaagg cttgcgattt tttactatct aaagagctgc ccggcggtgg atggggagag | 1980 |
| agttaccttt catgtcagaa taaggtatac acaaatcttg aaggaaacag accgcacctg | 2040 |
| gttaacacgg cctgggtttt aatggccctc atagaagctg gccaggctga gagagaccca | 2100 |
| acaccattgc atcgtgcagc aaggttgtta atcaattccc agttggagaa tggtgatttc | 2160 |
| ccccaacagg agatcatggg agtctttaat aaaaattgca tgatcacata tgctgcatac | 2220 |
| cgaaacattt ttcccatttg ggctcttgga gagtattgcc atcgggttt gactgaataa | 2280 |

SEQ ID NO: 23

TABLE 1-continued

Sequences disclosed herein.

Artificial Sequence

| | |
|---|---|
| atgtggagat tgaaagtagg tgctgaatcc gtaggtgaaa acgacgaaaa gtggttgaaa | 60 |
| agtataagta atcatttggg tagacaagtc tgggaatttt gtccagatgc aggtacacaa | 120 |
| caacaattgt tgcaagtaca taaggctaga aaggcatttc atgatgacag attccacaga | 180 |
| aagcaatctt cagatttgtt catcaccatc caatacggca aggaagtaga aaacggtggc | 240 |
| aagactgctg gtgttaaatt gaaggaaggt gaagaagtta gaaaagaagc agttgaatcc | 300 |
| agtttggaaa gagccttgtc tttctactct tcaatccaaa cctctgatgg taattgggca | 360 |
| tcagacttgg gtggtccaat gttcttgtta cctggtttgg tcattgcctt gtacgtaact | 420 |
| ggtgttttga actctgtatt gtcaaagcat cacagacaag aaatgtgtag atacgtttac | 480 |
| aaccatcaaa acgaagatgg tggttggggt ttgcacattg aaggtccatc cactatgttt | 540 |
| ggtagtgcat tgaattatgt cgccttaaga ttgttaggtg aagatgcaaa cgccggtgct | 600 |
| atgcctaagg caagagcctg gatattagac atggtggtg ctactggtat cacatcctgg | 660 |
| ggtaaattgt ggttaagtgt cttaggtgta tatgaatggt ctggtaataa cccattgcca | 720 |
| cctgaatttt ggttgttccc ttacttttta ccattccatc ctggtagaat gtggtgtcac | 780 |
| tgcagaatgg tttacttgcc aatgtcttac ttgtacggca agagattcgt tggtccaata | 840 |
| acacctatcg tcttgtcatt gagaaaggaa ttgtacgcag ttccttacca tgaaatcgat | 900 |
| tggaacaagt ccagaaacac ctgtgctaag aagatttgt attacccaca ccctaaaatg | 960 |
| caagacattt tgtggggtag tttacatcac gtttacgaac cattatttac tagatggcct | 1020 |
| gctaaaagat tgagagaaaa ggcattacaa acagccatgc aacatatcca ctacgaagat | 1080 |
| gaaaacacca gatacatctg cttgggtcca gttaacaagg tcttgaactt gttgtgttgc | 1140 |
| tgggttgaag atccttattc tgacgctttc aagttgcatt tgcaaagagt acacgattac | 1200 |
| ttgtgggttg cagaagacgg tatgaaaatg caaggttaca atggttcaca attgtgggat | 1260 |
| acagcttttt ccattcaagc aatagtcagt actaagttgg tagataacta cggtccaaca | 1320 |
| ttaagaaaag ctcatgactt cgtaaagtcc agtcaaatac aacaagattg tccaggtgac | 1380 |
| cctaatgttt ggtatagaca tatccacaaa ggtgcatggc catttttctac cagagatcat | 1440 |
| ggttggttga tttcagactg tactgctgaa ggtttgaagg ctgcattgat gttgtctaag | 1500 |
| ttgccatcag aaactgttgg tgaatccttg gaaagaaata gattatgcga tgccgttaac | 1560 |
| gtcttgttga gtttgcaaaa cgacaacggt ggtttcgctt cttacgaatt gactagatca | 1620 |
| tacccatggt tggaattaat taatcctgct gaaacattcg gtgatatcgt cattgactat | 1680 |
| ccatacgtag aatgtacctc cgctactatg gaagcattga ccttgttcaa gaagttgcat | 1740 |
| cctggtcaca gaacaaagga aatcgatacc gcaattgtta gagccgctaa tttcttggaa | 1800 |
| aacatgcaaa gaacagacgg ttcttggtat ggttgttggg gtgtttgctt tacctacgct | 1860 |
| ggttggttcg gtattaaagg tttagtcgca gccggtagaa catacaataa ctgtttggcc | 1920 |
| ataagaaaag cttgcgattt cttgttatct aaggaattac aggtggtgg ttggggtgaa | 1980 |
| tcctacttga gttgtcaaaa caaggtttac actaatttgg aaggcaacag acctcattta | 2040 |
| gttaacacag cctgggtctt gatggctttta atcgaagccg gtcaagctga aagagatcca | 2100 |
| actcctttgc atagagctgc aagattgttg atcaactcac aattggaaaa cggtgatttt | 2160 |
| ccacaacaag aaatcatggg tgttttcaac aagaactgca tgataacata tgccgcttac | 2220 |
| agaaacattt ttcctatatg ggctttgggt gaatactgcc acagagtctt gaccgaataa | 2280 |

SEQ ID NO: 24

TABLE 1-continued

Sequences disclosed herein.

*Siraitia grosvenorii*
```
MWRLKVGAES VGENDEKWLK SISNHLGRQV WEFCPDAGTQ QQLLQVHKAR KAFHDDRFHR    60
KQSSDLFITI QYGKEVENGG KTAGVKLKEG EEVRKEAVES SLERALSFYS SIQTSDGNWA   120
SDLGGPMFLL PGLVIALYVT GVLNSVLSKH HRQEMCRYVY NHQNEDGGWG LHIEGPSTMF   180
GSALNYVALR LLGEDANAGA MPKARAWILD HGGATGITSW GKLWLSVLGV YEWSGNNPLP   240
PEFWLFPYFL PFHPGRMWCH CRMVYLPMSY LYGKRFVGPI TPIVLSLRKE LYAVPYHEID   300
WNKSRNTCAK EDLYYPHPKM QDILWGSLHH VYEPLFTRWP AKRLREKALQ TAMQHIHYED   360
ENTRYICLGP VNKVLNLLCC WVEDPYSDAF KLHLQRVHDY LWVAEDGMKM QGYNGSQLWD   420
TAFSIQAIVS TKLVDNYGPT LRKAHDFVKS SQIQQDCPGD PNVWYRHIHK GAWPFSTRDH   480
GWLISDCTAE GLKAALMLSK LPSETVGESL ERNRLCDAVN VLLSLQNDNG GFASYELTRS   540
YPWLELINPA ETFGDIVIDY PYVECTSATM EALTLFKKLH PGHRTKEIDT AIVRAANFLE   600
NMQRTDGSWY GCWGVCFTYA GWFGIKGLVA AGRTYNNCLA IRKACDFLLS KELPGGGWGE   660
SYLSCQNKVY TNLEGNRPHL VNTAWVLMAL IEAGQAERDP TPLHRAARLL INSQLENGDF   720
PQQEIMGVFN KNCMITYAAY RNIFPIWALG EYCHRVLTE                         759
```

SEQ ID NO: 25
*Cucurbita pepo*
```
MWRLKVGAES VGEEDKWVK SVSNHLGRQV WEFCADAAAD TPHQLLQIQN ARNHFHHNRF    60
HRKQSSDLFL AIQYEKEIAK GAKGGAVKVK EGEEVGKEAV KSTLERALGF YSAVQTRDGN   120
WASDLGGPLF LLPGLVIALH VTGVLNSVLS KHHRVEMCRY LYNHQNEDGG WGLHIEGTST   180
MFGSALNYVA LRLLGEDADG GDGGAMTKAR AWILERGGAT AITSWGKLWL SVLGVYEWSG   240
NNPLPPEFWL LPYSLPFHPG RMWCHCRMVY LPMSYLYGKR FVGPITPKVL SLRQELYTIP   300
YHEIDWNKSR NTCAKEDLYY PHPKMQDILW GSIYHVYEPL FTRWPGKRLR EKALQAAMKH   360
IHYEDENSRY ICLGPVNKVL NMLCCWVEDP YSDAFKLHLQ RVHDYLWVAE DGMRMQGYNG   420
SQLWDTAFSI QAIVATKLVD SYAPTLRKAH DFVKDSQIQE DCPGDPNVWF RHIHKGAWPL   480
STRDHGWLIS DCTAEGLKAS LMLSKLPSTM VGEPLEKNRL CDAVNVLLSL QNDNGGFASY   540
ELTRSYPWLE LINPAETFGD IVIDYPYVEC TAATMEALTL FKKLHPGHRT KEIDTAIGKA   600
ANFLEKMQRA DGSWYGCWGV CFTYAGWFGI KGLVAAGRTY NSCLAIRKAC EFLLSKELPG   660
GGWGESYLSC QNKVYTNLEG NKPHLVNTAW VLMALIEAGQ GERDPAPLHR AARLLMNSQL   720
ENGDFVQQEI MGVFNKNCMI TYAAYRNIFP IWALGEYCHR VLTE                   764
```

SEQ ID NO: 26
Artificial Sequence
```
LERNRLCDAV NVLLSLQNDN GGFASYELTR SYPWLELINP AETFGDIVID YPYVECTSAT    60
MEALTLFKKL HPGHRTKEID TAIVRAANFL ENMQRTDGSW YGCWGVCFTY AGWFGIKGLV   120
AAGRTYNNCL AIRKACDFLL SKELPGGGWG ESYLSCQNKV YTNLEGNRPH LVNTAWVLMA   180
LIEAGQAERD PTPLHRAARL LINSQLENGD FPQQEIMGVF NKNCMITYAA YRNIFPIWAL   240
GEYCHRVLTE                                                         250
```

SEQ ID NO: 27
*Siraitia grosvenorii*
```
atggaaatgt cgtcgtctgt tgcagctacg atttcaatat ggatggttgt ggtgtgcata    60
gtgggagtgg gatggagagt tgtgaactgg gtttggttga ggccgaagaa gcttgagaag   120
cggctgagag agcaaggcct cgccggaaac tcttaccggc ttctgttcgg agacttgaag   180
gagagggcgg cgatggagga gcaggccaac tccaagccca tcaacttctc ccatgatatc   240
ggaccacgtg tcttcccctc catgtacaaa accatccaga attatggtaa gaattcgtac   300
```

TABLE 1-continued

Sequences disclosed herein.

| | |
|---|---|
| atgtggcttg gcccatatcc aagagtgcac atcatggacc ctcagcaact taaaactgtt | 360 |
| tttactctag tctatgatat ccaaaagcca aatttgaacc cccttatcaa gtttcttttg | 420 |
| gatggaatag taactcatga aggagaaaaa tgggctaaac acagaaagat aatcaaccct | 480 |
| gcatttcatt tggaaaagtt gaaggatatg ataccagcat tctttcatag ttgtaatgag | 540 |
| atagttaacg aatgggaaag attaatctcg aaagagggtt cgtgtgagtt ggatgttatg | 600 |
| ccatatctgc aaaatttggc agctgatgcc atttctcgaa ctgcatttgg gagtagctat | 660 |
| gaagaaggaa aaatgatctt ccaacttta aaagaactaa ctgatttggt ggttaaagtt | 720 |
| gcatttggag tttatattcc cggatggagg tttctaccaa ctaagtcaaa caataaaatg | 780 |
| aaagaaataa atagaaaaat taaagtttg cttttgggta ttataaacaa aaggcaaaag | 840 |
| gctatggaag aaggtgaagc tggacaaagt gatttattag gcattctcat ggaatccaat | 900 |
| tcaaacgaaa ttcaaggaga aggaaacaat aaagaagatg gaatgagcat agaagatgtt | 960 |
| attgaagaat gcaaggtttt ctatattggt ggccaagaaa ccacagccag attactgatt | 1020 |
| tggaccatga ttttgttgag ttcacacacg gaatggcaag agcgagcaag aactgaggta | 1080 |
| ttaaaagtat ttggtaacaa gaagccagat tttgatggtt tgagtcgact aaaagttgta | 1140 |
| actatgattt tgaacgaggt tctcaggtta tacccaccag caagtatgct tactcgtatt | 1200 |
| attcaaaagg aaacaagagt tggaaaattg actctaccag ctggtgtgat attgatcatg | 1260 |
| ccaattattc ttatccatcg tgatcatgac ctatggggtg aagatgcaaa cgaatttaaa | 1320 |
| ccagaaagat tttctaaggg agtctctaaa gcagcaaaag ttcaacccgc tttcttccca | 1380 |
| tttggatggg gtcctcgaat atgcatgggg cagaactttg cgatgattga agcaaaaatg | 1440 |
| gcattatcat taattctaca acgcttctca tttgagcttt cttcgtcgta tgttcatgct | 1500 |
| cctaccgtcg ttttcactac tcaacctcaa catggagctc atatcgtcct gcgcaaactg | 1560 |
| tag | 1563 |
| SEQ ID NO: 28 Artificial Sequence | |
| atggaaatgt cctcttctgt tgctgccacc atttctattt ggatggttgt tgtatgtatc | 60 |
| gttggtgttg gttggagagt tgttaattgg gtttggttaa gaccaaagaa gttggaaaag | 120 |
| agattgagag aacaaggttt ggctggtaac tcttacagat tgttgttcgg tgacttgaaa | 180 |
| gaaagagctg ctatggaaga acaagctaac tctaagccaa tcaacttctc ccatgatatt | 240 |
| ggtccaagag ttttcccatc tatgtacaag accattcaaa actacggtaa gaactcctat | 300 |
| atgtggttgg gtccataccc aagagttcat attatggatc cacaacaatt gaaaaccgtc | 360 |
| tttaccttgg tttacgacat ccaaaagcca aacttgaacc cattgatcaa gttcttgttg | 420 |
| gatggtattg tcacccatga aggtgaaaaa tgggctaaac atagaaagat tatcaaccca | 480 |
| gccttccact tggaaaagtt gaaagatatg attccagcct tcttccactc ttgcaacgaa | 540 |
| atagttaatg aatgggaaag attgatctcc aaagaaggtt cttgcgaatt ggatgttatg | 600 |
| ccatacttgc aaaatttggc tgctgatgct atttctagaa ctgcttttgg ttcctcttac | 660 |
| gaagaaggta agatgatctt ccaattattg aaagaattga ccgacttggt tgttaaggtt | 720 |
| gctttcggtg tttacattcc aggttggaga ttttgccaa ctaagtccaa caacaagatg | 780 |
| aaggaaatca acagaaagat caagtctttg ttgttaggta tcatcaacaa gagacaaaag | 840 |
| gccatggaag aaggtgaagc tggtcaatct gatttgttgg gtattttgat ggaatccaac | 900 |
| tccaacgaaa ttcaaggtga aggtaacaac aaagaagatg gtatgtccat cgaagatgtt | 960 |

| | |
|---|---:|
| atcgaagaat gcaaggtttt ctacatcggt ggtcaagaaa ctaccgccag attattgatt | 1020 |
| tggaccatga tcttgttgag ttcccatact gaatggcaag aaagagcaag aactgaagtc | 1080 |
| ttgaaggttt tcggtaacaa aaagccagat ttcgacggtt tgtctagatt gaaggttgtc | 1140 |
| accatgattt tgaacgaagt tttgagatta tacccaccag cttctatgtt gaccagaatc | 1200 |
| attcaaaaag aaaccagagt cggtaagttg actttgccag ctggtgttat tttgatcatg | 1260 |
| ccaatcatct tgatccacag agatcatgat tgtggggtg aagatgctaa tgaattcaag | 1320 |
| ccagaaagat tctccaaggg tgtttctaaa gctgctaaag ttcaaccagc tttcttttcca | 1380 |
| tttggttggg gtccaagaat atgtatgggt caaaatttcg ctatgatcga agctaagatg | 1440 |
| gccttgtctt tgatcttgca aagattttcc ttcgaattgt cctcctcata tgttcatgct | 1500 |
| ccaactgttg ttttcaccac tcaaccacaa catggtgctc atatcgtttt gagaaagttg | 1560 |
| taa | 1563 |

SEQ ID NO: 29
Siraitia grosvenorii

| | |
|---|---:|
| MEMSSSVAAT ISIWMVVVCI VGVGWRVVNW VWLRPKKLEK RLREQGLAGN SYRLLFGDLK | 60 |
| ERAAMEEQAN SKPINFSHDI GPRVFPSMYK TIQNYGKNSY MWLGPYPRVH IMDPQQLKTV | 120 |
| FTLVYDIQKP NLNPLIKFLL DGIVTHEGEK WAKHRKIINP AFHLEKLKDM IPAFFHSCNE | 180 |
| IVNEWERLIS KEGSCELDVM PYLQNLAADA ISRTAFGSSY EEGKMIFQLL KELTDLVVKV | 240 |
| AFGVYIPGWR FLPTKSNNKM KEINRKIKSL LLGIINKRQK AMEEGEAGQS DLLGILMESN | 300 |
| SNEIQGEGNN KEDGMSIEDV IEECKVFYIG GQETTARLLI WTMILLSSHT EWQERARTEV | 360 |
| LKVFGNKKPD FDGLSRLKVV TMILNEVLRL YPPASMLTRI IQKETRVGKL TLPAGVILIM | 420 |
| PIILIHRDHD LWGEDANEFK PERFSKGVSK AAKVQPAFFP FGWGPRICMG QNFAMIEAKM | 480 |
| ALSLILQRFS FELSSSYVHA PTVVFTTQPQ HGAHIVLRKL | 520 |

SEQ ID NO: 30
Artificial Sequence

| | |
|---|---:|
| atgtggactg ttgttttggg tttggctact tgtttgttg cctactacat tcactggatc | 60 |
| aacaagtgga gagactctaa gtttaatggt gttttgccac caggtactat gggttttgcca | 120 |
| ttgattggtg aaaccatcca attgtcaaga ccatccgatt ctttggatgt tcatccattc | 180 |
| atccaaaaaa aggtcgaaag atacggtcca atcttcaaga cttgtttggc tggtagacca | 240 |
| gttgttgttt ctgctgatgc tgaatttaac aactacatca tgttgcaaga aggtagagct | 300 |
| gttgaaatgt ggtacttgga tactttgtct aagttcttcg gtttggatac cgaatggttg | 360 |
| aaggctttgg gtttaatcca taagtacatc agatccatca ccttgaatca ttttggtgct | 420 |
| gaagccttga gagaaagatt cttgcctttt attgaagcct cttctatgga agccttgcat | 480 |
| tcttggtcta ctcaaccatc tgttgaagtt aagaatgctt ccgctttgat ggttttcaga | 540 |
| acctctgtta acaagatgtt tggtgaagat gccaagaagt tgtctggtaa tattccaggt | 600 |
| aagttcacca gttgttggg tggtttttg tctttgcctt tgaatttccc aggtacaacc | 660 |
| taccataagt gcttgaaaga tatgaaggaa atccaaaaga agttgagaga agtcgttgat | 720 |
| gatagattgg ctaatgttgg tccagatgtc gaagattttt tgggtcaagc cttgaaggac | 780 |
| aaagaatccg aaaagttcat ctccgaagaa tttatcattc aattgttgtt ctctatctcc | 840 |
| ttcgcctcct tcgaatctat ttctactact ttgaccttga tcttgaagtt gttagacgaa | 900 |
| catccagaag tcgtcaaaga attggaagct gaacatgaag ctattagaaa ggctagagct | 960 |
| gatccagatg gtccaattac ttgggaagaa tacaagtcta tgaccttcac cttgcaagtt | 1020 |

TABLE 1-continued

Sequences disclosed herein.

```
atcaacgaaa ctttgagatt gggttctgtt actccagctt tgttgagaaa aactgtcaag    1080
gacttacaag tcaagggtta cattattcct gaaggttgga ccattatgtt ggttactgct    1140
tcaagacata gagatccaaa ggtttacaaa gacccacata ttttcaatcc ttggagatgg    1200
aaggatttgg actccattac tattcaaaag aacttcatgc cattcggtgg tggtttgaga    1260
cattgtgctg gtgcagaata ctctaaggtt tacttgtgta ctttcttgca catcttgtgc    1320
actaagtaca gatggacaaa attgggtggt ggtagaattg ctagagccca tattttgtca    1380
ttcgaagatg gtttacatgt caagttcacc ccaaaagaat ga                       1422
```

SEQ ID NO: 31
*Siraitia grosvenorii*

```
MWTVVLGLAT LFVAYYIHWI NKWRDSKFNG VLPPGTMGLP LIGETIQLSR PSDSLDVHPF      60

IQKKVERYGP IFKTCLAGRP VVVSADAEFN NYIMLQEGRA VEMWYLDTLS KFFGLDTEWL     120

KALGLIHKYI RSITLNHFGA EALRERFLPF IEASSMEALH SWSTQPSVEV KNASALMVFR     180

TSVNKMFGED AKKLSGNIPG KFTKLLGGFL SLPLNFPGTT YHKCLKDMKE IQKKLREVVD     240

DRLANVGPDV EDFLGQALKD KESEKFISEE FIIQLLFSIS FASFESISTT LTLILKLLDE     300

HPEVVKELEA EHEAIRKARA DPDGPITWEE YKSMTFTLQV INETLRLGSV TPALLRKTVK     360

DLQVKGYIIP EGWTIMLVTA SRHRDPKVYK DPHIFNPWRW KDLDSITIQK NFMPFGGGLR     420

HCAGAEYSKV YLCTFLHILC TKYRWTKLGG GRIARAHILS FEDGLHVKFT PKE            473
```

SEQ ID NO: 32
*Siraitia grosvenorii*

```
atgaaggtct ctccatttga gttcatgtcg gcaataatta agggcaggat ggacccgtcc      60
aattcttcat ttgagtcgac tggcgaggtt gcctcagtta ttttcgagaa ccgtgagctg     120
gttgcgatct taaccacctc gatcgccgtc atgattggct gcttcgttgt tctcatgtgg     180
cgaagagccg gcagtcggaa agttaagaac gtggagctac ctaagccgtt gattgtgcac     240
gagccggagc ccgaagttga agacggcaag aagaaggttt caatcttctt cggtacacag     300
acaggcaccg ccgaaggatt tgcaaaggct ctagctgacg aggcgaaagc acgatacgag     360
aaggccacat ttagagttgt tgatttggat gattatgcag ctgatgacga tcagtatgaa     420
gagaagttga agaacgagtc tttcgctgtc ttcttattgg caacgtatgg cgatggagag     480
cccactgata atgccgcaag attctataaa tggttcgcgg aggggaaaga gagagggggag    540 tggcttcaga accttcatta tgcggtctttt ggccttggca accgacagta cgagcattt     600 aataagattg caaaggtggc agatgagctg cttgaggcac agggaggcaa ccgccttgtt    660
aaagttggtc ttggagatga cgatcagtgc atagaggatg acttcagtgc ctggagagaa    720
tcattgtggc ctgagttgga tatgttgctt cgagatgagg atgatgcaac aacagtgacc    780
accccttaca cagctgccgt attagaatat cgagttgtat ccatgattc tgcagatgta    840 gctgctgagg acaagagctg gatcaatgca acggtcatg ctgtacatga tgctcagcat    900
cccttcagat ctaatgtggt tgtgaggaag gagctccata cgtccgcatc tgatcgctcc    960
tgtagtcatc tagaatttaa tatttctggg tctgcactca attatgaaac aggggatcat   1020
gtcggtgttt actgtgaaaa cttaactgag actgtggacg aggcactaaa cttattgggt   1080
ttgtctcctg aaacgtattt ctccatatat actgataacg aggatggcac tccacttggt   1140
ggaagctctt taccacctcc ttttccatcc tgcaccctca gaacagcatt gactcgatat   1200
gcagatctct tgaattcacc caagaagtca gctttgcttg cattagcagc acatgcttca   1260
aatccagtag aggctgaccg attaagatat cttgcatcac ctgccgggaa ggatgaatac   1320
```

TABLE 1-continued

Sequences disclosed herein.

```
gcccagtctg tgattggtag ccagaaaagc cttcttgagg tcatggctga atttccttct    1380
gccaagcccc cacttggtgt cttcttcgca gctgttgcac cgcgcttgca gcctcgattc    1440
tactccatat catcatctcc aaggatggct ccatctagaa ttcatgttac ttgtgcttta    1500
gtctatgaca aaatgccaac aggacgtatt cataaaggag tgtgctcaac ttggatgaag    1560
aattctgtgc ccatggagaa aagccatgaa tgcagttggg ctccaatttt cgtgagacaa    1620
tcaaacttca agcttcctgc agagagtaaa gtgcccatta tcatggttgg tcctggaact    1680
ggattggctc ctttcagagg tttcttacag gaaagattag ctttgaagga atctggagta    1740
gaattggggc cttccatatt gttctttgga tgcagaaacc gtaggatgga ttacatatac    1800
gaggatgagc tgaacaactt tgttgagact ggtgctctct ctgagttggt tattgccttc    1860
tcacgcgaag ggccaactaa ggaatatgtg cagcataaaa tggcagagaa ggcttcggat    1920
atctggaatt tgatatcaga aggggcttac ttatatgtat gtggtgatgc aaagggcatg    1980
gctaaggatg tccaccgaac tctccatact atcatgcaag agcagggatc tcttgacagc    2040
tcaaaagctg agagcatggt gaagaatctg caaatgaatg aaggtatctg cgtgatgtc    2100
tggtga                                                               2106
```

SEQ ID NO: 33
Artificial Sequence

```
atgaaggtca gtccattcga attcatgtcc gctattatca agggtagaat ggacccatct      60
aactcctcat ttgaatctac tggtgaagtt gcctccgtta tctttgaaaa cagagaattg     120
gttgccatct tgaccacttc tattgctgtt atgattggtt gcttcgttgt cttgatgtgg     180
agaagagctg gttctagaaa ggttaagaat gtcgaattgc caaagccatt gattgtccat     240
gaaccagaac ctgaagttga agatggtaag aagaaggttt ccatcttctt cggtactcaa     300
actggtactg ctgaaggttt tgctaaggct ttggctgatg aagctaaagc tagatacgaa     360
aaggctacct tcagagttgt tgatttggat gattatgctg ccgatgatga ccaatacgaa     420
gaaaaattga gaacgaatc cttcgccgtt ttccttgttgg ctacttatgg tgatggtgaa     480
cctactgata atgctgctag atttttacaag tggttcgccg aaggtaaaga agaggtgaa     540
tggttgcaaa acttgcacta tgctgttttt ggtttgggta acagacaata cgaacacttc     600
aacaagattg ctaaggttgc cgacgaatta ttggaagctc aaggtggtaa tagattggtt     660
aaggttggtt taggtgatga cgatcaatgc atcgaagatg attttctgc ttggagagaa     720
tctttgtggc cagaattgga tatgttgttg agagatgaag atgatgctac tactgttact     780
actccatata ctgctgctgt cttggaatac agagttgtct ttcatgattc tgctgatgtt     840
gctgctgaag ataagtcttg gattaacgct aatggtcatg ctgttcatga tgctcaacat     900
ccattcagat ctaacgttgt cgtcagaaaa gaattgcata cttctgcctc tgatagatcc     960
tgttctcatt tggaattcaa catttccggt tccgctttga attacgaaac tggtgatcat    1020
gttggtgtct actgtgaaaa cttgactgaa actgttgatg aagccttgaa cttgttgggt    1080
ttgtctccag aaacttactt ctctatctac accgataacg aagatggtac tccattgggt    1140
ggttcttcat tgccaccacc atttccatca tgtactttga aactgctttt gaccagatac    1200
gctgattgt tgaactctcc aaaaaagtct gctttgttgg ctttagctgc tcatgcttct    1260
aatccagttg aagctgatag attgagatac ttggcttctc cagctggtaa agatgaatat    1320
gcccaatctg ttatcggttc ccaaaagtct ttgttggaag ttatggctga attcccatct    1380
gctaaaccac cattaggtgt ttttttgct gctgttgctc caagattgca acctagattc    1440
```

TABLE 1-continued

Sequences disclosed herein.

```
tactccattt catcctctcc aagaatggct ccatctagaa tccatgttac ttgtgctttg    1500
gtttacgata agatgccaac tggtagaatt cataagggtg tttgttctac ctggatgaag    1560
aattctgttc caatggaaaa gtcccatgaa tgttcttggg ctccaatttt cgttagacaa    1620
tccaatttta agttgccagc cgaatccaag gttccaatta tcatggttgg tccaggtact    1680
ggtttggctc cttttagagg ttttttacaa gaaagattgg ccttgaaaga atccggtgtt    1740
gaattgggtc catccatttt gttttttcggt tgcagaaaca aagaatgga ttacatctac     1800 gaagatgaat tgaacaactt cgttgaaacc ggtgctttgt ccgaattggt tattgctttt    1860
tctagagaag gtcctaccaa agaatacgtc caacataaga tggctgaaaa ggcttctgat    1920
atctggaact tgatttctga aggtgcttac ttgtacgttt gtggtgatgc taaaggtatg    1980
gctaaggatg ttcatagaac cttgcatacc atcatgcaag aacaaggttc tttggattct    2040
tccaaagctg aatccatggt caagaacttg caaatgaatg gtagatactt aagagatgtt    2100
tggtaa                                                              2106
```

SEQ ID NO: 34
*Siraitia grosvenorii*

```
MKVSPFEFMS AIIKGRMDPS NSSFESTGEV ASVIFENREL VAILTTSIAV MIGCFVVLMW     60

RRAGSRKVKN VELPKPLIVH EPEPEVEDGK KKVSIFFGTQ TGTAEGFAKA LADEAKARYE    120

KATFRVVDLD DYAADDDQYE EKLKNESFAV FLLATYGDGE PTDNAARFYK WFAEGKERGE    180

WLQNLHYAVF GLGNRQYEHF NKIAKVADEL LEAQGGNRLV KVGLGDDDQC IEDDFSAWRE    240

SLWPELDMLL RDEDDATTVT TPYTAAVLEY RVVFHDSADV AAEDKSWINA NGHAVHDAQH    300

PFRSNVVVRK ELHTSASDRS CSHLEFNISG SALNYETGDH VGVYCENLTE TVDEALNLLG    360

LSPETYFSIY TDNEDGTPLG GSSLPPPFPS CTLRTALTRY ADLLNSPKKS ALLALAAHAS    420

NPVEADRLRY LASPAGKDEY AQSVIGSQKS LLEVMAEFPS AKPPLGVFFA AVAPRLQPRF    480

YSISSSPRMA PSRIHVTCAL VYDKMPTGRI HKGVCSTWMK NSVPMEKSHE CSWAPIFVRQ    540

SNFKLPAESK VPIIMVGPGT GLAPFRGFLQ ERLALKESGV ELGPSILFFG CRNRRMDYIY    600

EDELNNFVET GALSELVIAF SREGPTKEYV QHKMAEKASD IWNLISEGAY LYVCGDAKGM    660

AKDVHRTLHT IMQEQGSLDS SKAESMVKNL QMNGRYLRDV W                       701
```

SEQ ID NO: 35
Artificial Sequence

```
atggacgcga ttgaacatag aaccgtaagt gttaatggta tcaatatgca tgtggcagaa     60
aagggagagg gacctgtcgt gttgttgctt catggtttcc cagaattgtg gtacagttgg    120
agacatcaaa tattggctct ttcctctttta ggttacagag ctgtcgcacc agacttacga    180
ggctacgggg atacagatgc cccagggtca atttcatcat acacatgctt tcacatcgta    240
ggagatctcg tggctctagt tgagtctctg ggtatggaca gggttttttgt tgtagcccac    300 gattggggtg ccatgatcgc ttggtgtttg tgtctgttta gacctgaaat ggttaaagct    360
tttgtttgtc tctccgtccc attcagacag agaaaccta agatgaaacc agttcaaagt    420
atgagagcct ttttcggcga tgattactat atttgcagat tcaaaatcc tggggaaatc     480 gaagaggaga tggctcaagt gggtgcaagg gaagtcttaa gaggaattct aacatctcgt    540
cgtcctggac accaatcttt accaaaaggg caagctttta gagcaagacc aggagcatcc    600
actgcattgc catcttggct atctgaaaaa gatctgtcat ttttcgcttc taagtatgat    660
caaaagggct ttacaggccc actaaactac tacagagcca tggatcttaa ttgggaattg    720
actgcgtcat ggactggtgt ccaagttaaa gtacctgtca aatacatcgt gggtgacgtt    780
```

TABLE 1-continued

Sequences disclosed herein.

```
gacatggttt ttacgactcc tggtgtaaag gaatatgtca acggcggtgg tttcaaaaag      840
gacgttccat ttttacagga agtggtaatc atggaaggcg ttggtcattt cattaatcag      900
gaaaaacctg aggagatttc atctcatata cacgatttca taagcaaatt ctaa           954
```

SEQ ID NO: 36
*Siraitia grosvenorii*
```
MDAIEHRTVS VNGINMHVAE KGEGPVVLLL HGFPELWYSW RHQILALSSL GYRAVAPDLR     60

GYGDTDAPGS ISSYTCFHIV GDLVALVESL GMDRVFVVAH DWGAMIAWCL CLFRPEMVKA    120

FVCLSVPFRQ RNPKMKPVQS MRAFFGDDYY ICRFQNPGEI EEEMAQVGAR EVLRGILTSR    180

RPGPPILPKG QAFRARPGAS TALPSWLSEK DLSFFASKYD QKGFTGPLNY YRAMDLNWEL    240

TASWTGVQVK VPVKYIVGDV DMVFTTPGVK EYVNGGGFKK DVPFLQEVVI MEGVGHFINQ    300

EKPEEISSHI HDFISKF                                                   317
```

SEQ ID NO: 37
*Siraitia grosvenorii*
```
atggacgaga ttgagcatat caccatcaac accaatggca tcaaaatgca cattgcctct      60
gtagggacgg gcccagtagt tcttcttctc catggcttcc cggagctctg gtactcatgg     120
cgccaccagc ttctgtatct ttcttccgta ggatatcgag ctattgcgcc ggacctccgc     180
ggctatggcg acacggactc gccggcgtct cctacctcct acaccgcgct ccacatcgtc     240
ggcgatttgg ttggggctct ggacgagctt gggatcgaga aggtgttcct ggtcggacat     300
gactgggggg cgatcatcgc ctggtacttt tgcttgttca ggcccgatag aatcaaggcg     360
ctggtgaatc tgagcgtcca gttcataccc agaaacccag cgattccttt catcgagggt     420
ttcagaactg cgttcggtga tgacttctat atttgcaggt tcaggttcc aggagaggca     480 gaagaagatt ttgcctccat cgacacagct cagctgttca agacatcatt atgtaataga     540
agttctgcac ctccatgctt gcctaaagaa attggatttc gtgcgatccc acctccagag     600
aaccttcctt cttggctgac agaagaagat atcaacttttt atgctgccaa atttaagcag     660
acaggcttca ccggagcgtt gaactactat cgagcttttg acctaacttg ggagctcacg     720
gcgccatgga cgggagcaca gattcaggta ccggtgaagt tcatcgtcgg ggattcggat     780
ctaacttacc attttccggg agccaaggaa tatatccata atggcggatt caaaagggac     840
gtgccgttgc tggaggaagt agttgtagta aaagatgctt gtcacttcat caaccaagaa     900
aggccacaag aaatcaatgc tcacatccat gacttcatca taaaattctg a             951
```

SEQ ID NO: 38
Artificial Sequence
```
atggatgaaa tcgaacatat taccatcaat acaaatggaa tcaaaatgca tattgcgtca      60
gtcggcacag gaccagttgt tctcttgcta cacggctttc cagaattatg gtactcttgg    120
agacaccaac tactttacct gtcctccgtt gggtacagag caatagctcc agatttgaga    180
ggctatggcg atactgacag tccagctagt cctacctctt atactgctct tcatattgta    240
ggtgacctgg tcggcgcatt agacgaattg gaatagaaa aggtcttttt agtgggtcat     300
gactggggtg ctattatcgc atggtacttt tgtttgttta ccagatag aattaaagca      360 cttgtgaatt tgtctgtcca gtttatccca cgtaacccag caatacctt tatagaaggt     420 ttcagaacag cttttggtga tgacttctac atttgtagat tcaagtacc tggggaagct    480 gaagaggatt tcgcgtctat cgatactgct caattgttta aacttcatt atgcaataga    540 agctcagccc ctccttgttt gcctaaagag attggtttta gggctatccc accaccagaa    600
aatctgccat cttggctcac agaggaagat atcaacttct acgcagccaa gtttaaacaa    660
```

TABLE 1-continued

Sequences disclosed herein.

| | |
|---|---|
| actggtttta ctggtgccct taactattat agagcattcg acttgacatg ggaattaaca | 720 |
| gccccatgga caggagccca gatccaagtt cctgtaaagt tcatagttgg tgattcagat | 780 |
| ctcacgtacc atttccctgg tgctaaggaa tacatccaca acggagggtt taaaagagat | 840 |
| gtgccactat tagaggaagt tgttgtggta aaagatgcct gccacttcat taaccaagag | 900 |
| cgaccacaag agattaatgc tcatattcat gacttcatca ataagttcta a | 951 |

SEQ ID NO: 39
*Siraitia grosvenorii*

| | |
|---|---|
| MDEIEHITIN TNGIKMHIAS VGTGPVVLLL HGFPELWYSW RHQLLYLSSV GYRAIAPDLR | 60 |
| GYGDTDSPAS PTSYTALHIV GDLVGALDEL GIEKVFLVGH DWGAIIAWYF CLFRPDRIKA | 120 |
| LVNLSVQFIP RNPAIPFIEG FRTAFGDDFY ICRFQVPGEA EEDFASIDTA QLFKTSLCNR | 180 |
| SSAPPCLPKE IGFRAIPPPE NLPSWLTEED INFYAAKFKQ TGFTGALNYY RAFDLTWELT | 240 |
| APWTGAQIQV PVKFIVGDSD LTYHFPGAKE YIHNGGFKRD VPLLEEVVVV KDACHFINQE | 300 |
| RPQEINAHIH DFINKF | 316 |

SEQ ID NO: 40
*Siraitia grosvenorii*

| | |
|---|---|
| atggaactct tctctaccaa aactgcagcc gagatcatcg ctgttgtctt gttttctac | 60 |
| gctctcatcc ggctattatc tggaagattc agctctcaac agaagagact gccacctgaa | 120 |
| gccggtggcg cctggccact gatcggccat ctccatctcc taggtgggtc ggaacctgca | 180 |
| cataaaacct tggcgaacat ggcggacgcc tacggaccag tttttacgtt gaaactgggc | 240 |
| atgcatacag ctttggttat gagcagttgg gaaatagcga gagagtgctt tactaaaaac | 300 |
| gacagaatct ttgcctcccg ccccatagtc actgcctcaa agcttctcac ctataaccat | 360 |
| accatgtttg ggttcagcca atatggtcca ttctggcgcc atatgcgcaa aatagccacg | 420 |
| cttcaactcc tctcaaacca ccgcctcgag cagctccaac acatcagaat atcggaggtc | 480 |
| cagacttcga ttaagaaact gtacgagttg tgggtcaaca gcagaaataa tggaggcgag | 540 |
| aaagtgttgg tggagatgaa gacgtggttc ggaggcataa ccttgaacac catattcagg | 600 |
| atggtggtcg gaaagcgatt ctcgactgct ttcgaaggca gtggtggcga acggtatcgg | 660 |
| aaggcgttga gggattctct tgaatggttt ggggcattcg ttccgtcaga ttcattcccg | 720 |
| tttttaagat ggttggattt gggaggatat gagaaggcga tgaagaagac ggcgagtgtg | 780 |
| ctggacgagg tgcttgataa atggctcaaa gagcatcagc agaggagaaa ctccggtgaa | 840 |
| ctggagacgg aggagcacga cttcatgcac gtgatgctgt ctattgttaa ggatgatgaa | 900 |
| gaactatccg gctacgatgc cgatacagtc acaaaagcta catgtttgaa tttaatagtt | 960 |
| ggtggattcg acactacaca agtaactatg acatgggctc tttctttgct tctcaacaat | 1020 |
| gaagaggtat taaaaaaggc ccaacttgaa ctagacgaac aagttggaag agagaggttt | 1080 |
| gtggaagagt ccgatgttaa aaatctgtta tatctccagg ccatcgtgaa ggaaactttg | 1140 |
| cgtttgtacc cttcagcgcc aatctcgaca tttcatgagg ccatggaaga ttgcactgtt | 1200 |
| tctggctacc acatcttttc agggacgcgt ttgatggtga atcttcaaaa gcttcaaaga | 1260 |
| gatccacttg catgggagga tccatgtgac tttcgaccgg agagatttct gacaactcat | 1320 |
| aaggatttcg atcttagagg acatagtcct caattgatac catttgggag tggtcgaaga | 1380 |
| atatgccctg gcatctcgtt tgccattcaa gttttgcatc ttacgcttgc aaatctactt | 1440 |
| catgggtttg acattggaag gccatctcat gaaccaatcg atatgcagga gagtaaagga | 1500 |
| ctaacgagta ttaaaacaac tccacttgag gttgttttag ctccacgcct tgctgctcaa | 1560 |

TABLE 1-continued

Sequences disclosed herein.

```
gtttatgagt ga                                                        1572
SEQ ID NO: 41
Siraitia grosvenorii
MELFSTKTAA EIIAVVLFFY ALIRLLSGRF SSQQKRLPPE AGGAWPLIGH LHLLGGSEPA      60

HKTLANMADA YGPVFTLKLG MHTALVMSSW EIARECFTKN DRIFASRPIV TASKLLTYNH     120

TMFGFSQYGP FWRHMRKIAT LQLLSNHRLE QLQHIRISEV QTSIKKLYEL WVNSRNNGGE     180

KVLVEMKTWF GGITLNTIFR MVVGKRFSTA FEGSGGERYR KALRDSLEWF GAFVPSDSFP     240

FLRWLDLGGY EKAMKKTASV LDEVLDKWLK EHQQRRNSGE LETEEHDFMH VMLSIVKDDE     300

ELSGYDADTV TKATCLNLIV GGFDTTQVTM TWALSLLLNN EEVLKKAQLE LDEQVGRERF     360

VEESDVKNLL YLQAIVKETL RLYPSAPIST FHEAMEDCTV SGYHIFSGTR LMVNLQKLQR     420

DPLAWEDPCD FRPERFLTTH KDFDLRGHSP QLIPFGSGRR ICPGISFAIQ VLHLTLANLL     480

HGFDIGRPSH EPIDMQESKG LTSIKTTPLE VVLAPRLAAQ VYE                       523

SEQ ID NO: 42
Siraitia grosvenorii
atgccgatcg cagaaggtgc agtctctgat ttgtttggtc gcccactctt ctttgcacta     60
tatgattggt tcttagagca tggatctgtt tataaacttg cctttggacc aaaagccttt    120
gttgttgtat cagatcccat tgtggcaaga tatattcttc gagaaaatgc atttggttat    180
gacaagggag tgcttgctga tattttagaa ccgataatgg gtaaaggact aataccagct    240
gaccttggca cttggaagca gaggagacga gttattgctc caggattcca tgccttgtac    300
ttggaagcta tgaccaaagt atttgccaat tgttcagaac gatcaatatt gaaattggag    360
aagcttctag gagaaggtga actacaggag aataaaacca ttgagttgga tatggaagca    420
gagttttcaa gtttggctct tgatatcatt ggactcggtg ttttcaacta tgattttggt    480
tctgtaacca agaatctcc ggtgattaag gctgtatatg gactctttt tgaagcagag     540 catagatcga ctttctatat cccatattgg aaagtacctt tggcaaggtg atagtccca    600 aggcagcgta aattccatgg tgaccttaag gttattaatg agtgtcttga tggcctaata    660
cgcaacgcaa gagaaacccg agacgaaacg gatgttgaga aattgcagca aagggactac    720
ttaaatctca aggatgccag tcttttgcgt ttcttagttg atatgcgggg agctgatgtt    780
gatgatcgcc agcttaggga cgatctgatg acgatgctta ttgctggcca tgaaacaact    840
gctgctgtgc ttacatgggc tgtttttttg cttgcacaaa atccttcaaa aatgaaaaaa    900
gcgcaagcag agattgattt ggttcttggc atggggaggc aacttttga atcatttaaa    960 gcattgaagt acatcagact tatcgttgca gagactcttc gtttgtttcc tcagcctcca   1020
ttgctgataa gacgagctct caaatcagat atattaccag gaggatacaa tggtgacaaa   1080
actggatatg caattcctgc agggactgac atcttcatct ctgtttacaa tctccacaga   1140
tctccctact tctgggataa tcctcaagaa tttgaaccag agagatttca agtaaagagg   1200
gcaagcgagg gaattgaagg atgggatggt ttcgacccat ctagaagccc tggagctcta   1260
tacccgaatg agattgtagc agacttttcc ttccttaccat ttggtggagg ccctagaaaa   1320
tgtgtgggag atcaatttgc tctaatggag tcaactatag cattggccat gttactgcag   1380
aagtttgatg tggagctaaa aggaagtcca gaatctgtag aactagttac tggagccaca   1440
atacatacca aaagtgggtt gtggtgcaaa ctgagaagaa gatcacaagt aaactga      1497

SEQ ID NO: 43
Siraitia grosvenorii
MPIAEGAVSD LFGRPLFFAL YDWFLEHGSV YKLAFGPKAF VVVSDPIVAR YILRENAFGY     60
```

TABLE 1-continued

Sequences disclosed herein.

```
DKGVLADILE PIMGKGLIPA DLGTWKQRRR VIAPGFHALY LEAMTKVFAN CSERSILKLE       120

KLLGEGELQE NKTIELDMEA EFSSLALDII GLGVFNYDFG SVTKESPVIK AVYGTLFEAE       180

HRSTFYIPYW KVPLARWIVP RQRKFHGDLK VINECLDGLI RNARETRDET DVEKLQQRDY       240

LNLKDASLLR FLVDMRGADV DDRQLRDDLM TMLIAGHETT AAVLTWAVFL LAQNPSKMKK       300

AQAEIDLVLG MGRPTFESFK ALKYIRLIVA ETLRLFPQPP LLIRRALKSD ILPGGYNGDK       360

TGYAIPAGTD IFISVYNLHR SPYFWDNPQE FEPERFQVKR ASEGIEGWDG FDPSRSPGAL       420

YPNEIVADFS FLPFGGGPRK CVGDQFALME STIALAMLLQ KFDVELKGSP ESVELVTGAT       480

IHTKSGLWCK LRRRSQVN                                                    498

SEQ ID NO: 44
Artificial Sequence
atggaaatgt cctcaagtgt cgcagccaca atcagtatct ggatggtcgt cgtatgtatc        60
gtaggtgtag gttggagagt cgtaaattgg gtttggttga gaccaaagaa attggaaaag       120
agattgagag aacaaggttt ggccggtaat tcttacagat tgttgttcgg tgacttgaag       180
gaaagagctg caatggaaga acaagcaaat tcaaagccta taaacttctc ccatgacatc       240
ggtccaagag ttttcccttc aatgtacaag accatccaaa actacggtaa aaactcctac       300
atgtggttag tccataccc tagagtccac atcatggatc cacaacaatt gaagaccgtt        360
tttactttgg tctacgacat tcaaaagcca aatttgaacc ctttgattaa attcttgtta       420
gatggtatcg ttacacatga aggtgaaaag tgggctaagc acagaaagat tattaaccca       480
gcattccatt tggaaaagtt gaaggatatg atacctgctt tctttcactc atgtaatgaa       540
atcgtcaacg aatgggaaag attgatttca aaagaaggtt cctgcgaatt ggatgtaatg       600
ccttatttgc aaaatttggc cgctgacgcc atttcaagaa ccgcttttgg ttcttcatac       660
gaagaaggta aatgatcttc caattgttg aaggaattga ctgatttggt tgtcaaggta        720
gcttttggtg tttatattcc aggttggaga ttcttgccta caaagagtaa caacaaaatg       780
aaggaaatta atagaaaaat caagtctttg ttgttgggta tcattaacaa gagacaaaag       840
gcaatggaag aaggtgaagc cggtcaatct gatttgttgg gtatattaat ggaaagtaat       900
tctaacgaaa tccaaggtga aggtaataac aaggaagatg gcatgtctat tgaagacgtc       960
atcgaagagt gtaaggtatt ttatataggt ggtcaagaaa ctacagcaag attattgatc      1020
tggactatga tattgttgtc cagtcataca gaatggcaag aaagagccag aaccgaagtc      1080
ttgaaggtat ttggtaataa gaaaccagat ttcgacggtt tgtcaagatt gaaggtagtt      1140
actatgatct tgaacgaagt tttaagattg tacccacctg cttccatgtt gacaagaatc      1200
atccaaaagg aaacaagagt tggtaaatta accttgccag caggtgttat cttgataatg      1260
cctatcatct tgatacatag agatcacgac ttgtggggtg aagatgctaa cgagtttaaa      1320
ccagaaagat tcagtaaagg tgtttctaag gcagccaaag tccaaccagc cttttttccct     1380 tttggttggg gtcctagaat ttgcatgggt caaaacttcg ctatgatcga agctaagatg      1440
gcattgagtt tgatcttgca agatttttct ttcgaattgt cttcatccta cgttcatgca      1500
ccaactgtcg tcttcactac acaaccacaa cacggtgccc acatcgttt gagaaagtta        1560 tga                                                                   1563

SEQ ID NO: 46
Siraitia grosvenorii
atggaaccac aaccaagtgc ggaattcaac tggaatcaca gcctaagcac cgtcgctatc        60
ggtgtcattg ccattatttt cttccgtttt ctcgtcaaaa gagtcaccgg cgccggtgag       120
```

TABLE 1-continued

Sequences disclosed herein.

```
cgaaagggtc cgaagccgcc aaaagtagcc ggagggtggc ctctaattgg ccacctccct      180
ctcctcggag gacctgaact gccccatgtc aaactgggtg gtttggctga taaatatggt      240
ccaatcttct cgatccggct gggtgtccac tccgccgtcg tgataaacag ttgggaggcg      300
gcgaaacagt tattaaccaa ccatgacgtc gccgtctctt cccgccccca aatgctcggc      360
ggaaaactcc tgggctacaa ctacgccgtg tttggtttcg gaccctacgg ctcttactgg      420
cgcaacatgc gcaagataac cacgcaagag cttctatcca atagcagaat ccagctccta      480
agagacgttc gagcgtcaga agtgaaccaa ggcataaaag agctctacca gcactggaaa      540
gaaagaagag acggtcacga ccaagccttg gtggaactgc agcagtgggt cggggacttg      600
actatgaatc tgattctcgg agtcatcgcc gggaaaaggt tctttggagc tgcagcaacg      660
gtagacgagg aagaggcgcg acggagccat aaagcattga aggagttgtt acattatatg      720 gggcttttc tactgggtga tgctgttcca tatctaggat ggttggacgt cggcggccat      780
gtgaaggcga tgaagaaaac ttcaaaagaa ttggaccgta tgttaacaca gtggttggag      840
gagcacaaga aggaaggacc caagaaagat cataaagact tcatggacgt gatgctttca      900
gttctcaatg aaacatccga tgttctttca gataagaccc atggcttcga tgctgatacc      960
atcatcaaag ctacatgtat gacgatggtt ttaggaggga gtgatacgac ggcggtggtt     1020
gtgatatggg caatctcgct gctgctgaat aatcgccctg cgttgagaaa agtgcaagaa     1080
gaactggaag cccatatcgg ccgagacaga gaactggagg aatcggatct cggtaagcta     1140
gtgtatttgc aggcagtcgt gaaggagaca ttgcggctgt acggagccgg aggccttttc     1200
tttcgtgaaa ccacagagga tgtcaccatc gacggattcc atgtcgagaa agggacatgg     1260
ctgttcgtga acgtggggaa gatccacaga gatgggaagg tgtggccgga gccaacggag     1320
ttcaaaccgg agaggtttct gacgacccac aaagattttg atctgaaggg ccagcggttt     1380
gagctcatcc cttttcgggg aggaagaaga tcgtgccctg gaatgtcttt tgggctccaa     1440
atgctacagc ttatttttggg taaactgctt caggcttttg atatatcgac gccgggggac     1500
gccgccgttg atatgaccgg atccattgga ctgacgaaca tgaaagccac tccattggaa     1560
gtgctcatca ccccgcgctt gcctctttcg ctttacgatt ga                        1602
```

SEQ ID NO: 47
*Siraitia grosvenorii*

```
MEPQPSAEFN WNHSLSTVAI GVIAIIFFRF LVKRVTGAGE RKGPKPPKVA GGWPLIGHLP       60

LLGGPELPHV KLGGLADKYG PIFSIRLGVH SAVVINSWEA AKQLLTNHDV AVSSRPQMLG      120

GKLLGYNYAV FGFGPYGSYW RNMRKITTQE LLSNSRIQLL RDVRASEVNQ GIKELYQHWK      180

ERRDGHDQAL VELQQWVGDL TMNLILGVIA GKRFFGAAAT VDEEEARRSH KALKELLHYM      240

GLFLLGDAVP YLGWLDVGGH VKAMKKTSKE LDRMLTQWLE EHKKEGPKKD HKDFMDVMLS      300

VLNETSDVLS DKTHGFDADT IIKATCMTMV LGGSDTTAVV VIWAISLLLN NRPALRKVQE     360

ELEAHIGRDR ELEESDLGKL VYLQAVVKET LRLYGAGGLF FRETTEDVTI DGFHVEKGTW      420

LFVNVGKIHR DGKVWPEPTE FKPERFLTTH KDFDLKGQRF ELIPFGGGRR SCPGMSFGLQ      480

MLQLILGKLL QAFDISTPGD AAVDMTGSIG LTNMKATPLE VLITPRLPLS LYD             533
```

SEQ ID NO: 48
*Siraitia grosvenorii*

```
atggagactc ttcttcttca tcttcaatcg ttatttcatc caatttcctt cactggtttc       60
gttgtcctct ttagcttcct gttcctgctc cagaaatggt tactgacacg tccaaaactct      120 tcatcagaag cctcaccccc ttctccacca aagcttccca tcttcggaca ccttctaaac      180
```

TABLE 1-continued

Sequences disclosed herein.

```
ctgggtctgc atccccacat caccctcgga gcctacgctc gccgctatgg ccctctcttc    240
ctcctccact tcggcagcaa gcccaccatc gtcgtctctt ctgccgaaat cgctcgcgat    300
atcatgaaga cccacgacct cgtcttcgcc aaccgtccta aatcaagcat cagcgaaaag    360
attctttacg gctccaaaga tttagccgca tctccttacg gcgaatactg gaggcagatg    420
aaaagcgttg gcgtgcttca tcttttgagc aacaaaaggg ttcaatcctt tcgctctgtc    480
agagaagaag aagtcgaact gatgatccag aagatccaac agaacccct atcagttaat     540 ttaagcgaaa tattctctgg actgacgaac gacatagttt gcagggtggc tttagggaga    600
aagtatggcg tgggagaaga cggaaagaag ttccggtctc ttctgctgga gtttggggaa    660
gtattgggaa gtttcagtac gagagacttc atcccgtggc tgggttggat tgatcgtatc    720
agtgggctgg acgccaaagc cgagagggta gccaaagagc tcgatgcttt ctttgacaga    780
gtgatcgaag atcacatcca tctaaacaag agagagaata tcccgatga gcagaaggac     840 ttggtggatg tgctgctttg tgtacagaga gaagactcca tcgggtttcc ccttgagatg    900
gatagcataa aagctttaat cttggacatg tttgctgcag gcacagacac gacatacacg    960
gtgttggagt gggcaatgtc ccaactgttg agacacccag aagcgatgaa gaaactgcag   1020
agggaggtca gagaaatagc aggtgagaaa gaacacgtaa gtgaggatga tttagaaaag   1080
atgcattact tgaaggcagt aatcaaagaa acgctgcggc tacacccacc aatcccactc   1140
ctcgtcccca gagaatcaac ccaagacatc aggttgaggg ggtacgatat cagaggcggc   1200
acccgggtta tgatcaatgc atgggccatc ggaaga                              1236
```

SEQ ID NO: 49
*Siraitia grosvenorii*

```
METLLLLHLQS LFHPISFTGF VVLFSFLFLL QKWLLTRPNS SSEASPPSPP KLPIFGHLLN    60

LGLHPHITLG AYARRYGPLF LLHFGSKPTI VVSSAEIARD IMKTHDLVFA NRPKSSISEK   120

ILYGSKDLAA SPYGEYWRQM KSVGVLHLLS NKRVQSFRSV REEEVELMIQ KIQQNPLSVN   180

LSEIFSGLTN DIVCRVALGR KYGVGEDGKK FRSLLLEFGE VLGSFSTRDF IPWLGWIDRI   240

SGLDAKAERV AKELDAFFDR VIEDHIHLNK RENNPDEQKD LVDVLLCVQR EDSIGFPLEM   300

DSIKALILDM FAAGTDTTYT VLEWAMSQLL RHPEAMKKLQ REVREIAGEK EHVSEDDLEK   360

MHYLKAVIKE TLRLHPPIPL LVPRESTQDI RLRGYDIRGG TRVMINAWAI GR           412
```

SEQ ID NO: 50
*Siraitia grosvenorii*

```
atgtcgatga gtagtgaaat tgaaagcctc tgggttttcg cgctggcttc taaatgctct     60
gctttaacta agaaaaacat cctctggtct ttactcttct ttttcctaat ctgggtttct    120
gtttccattc tccactgggc ccatccgggc ggcccggctt ggggccgcta ctggtggcgc    180
cgccgccgca gcaattccac cgccgctgct attcccggcc cgagaggcct cccctcgtc    240 ggcagcatgg gcttgatggc cgacttggcc caccaccgga ttgccgccgt ggctgactcc    300
ttaaacgcca cccgcctcat ggccttttcg ctcggcgaca ctcgcgtgat cgtcacatgc    360
aaccccgacg tcgccaaaga gattctcaac agctccctct tcgccgaccg cccgttaag    420 gagtccgctt actccttgat gttcaaccgc gccattgggt cgcccccta tggccttac     480 tggcggaccc tccgccgcat cgcttcccac cacctcttct gccccaagca aatcaagtcc    540
tcccagtccc agcgccgcca aatcgcttcc caaatggtcg caatgttcgc aaaccgcgat    600
gccacacaga gcctctgcgt tcgcgactct ctcaagcggg cttctctcaa caacatgatg    660
ggctctgttt tcggccgagt ttacgacctc tctgactcgg ctaacaatga cgtccaagaa    720
```

TABLE 1-continued

Sequences disclosed herein.

```
ctccagagcc tcgtcgacga aggctacgac ttgctgggcc tcctcaactg gtccgaccat    780
ctcccatggc tcgccgactt cgactctcag aaaatccggt tcagatgctc ccgactcgtc    840
cccaaggtga accacttcgt cggccggatc atcgccgaac accgcgccaa atccgacaac    900
caagtcctag atttcgtcga cgttttgctc tctctccaag aagccgacaa actctctgac    960
tccgatatga tcgccgttct ttgggaaatg atttttcgtg ggacggacac ggtggcagtt   1020
ttaatcgagt ggatactggc caggatggta cttcacaacg atatccaaag gaaagttcaa   1080
gaggagctag ataacgtggt tgggagtaca cgcgccgtcg cggaatccga cattccgtcg   1140
ctggtgtatc taacgctgtg ggttaaggaa gttctgaggt tacatccgcc gggcccactc   1200
ctgtcgtggg cccgcctagc catcactgat acaatcatcg atgggcatca cgtgccccgg   1260
gggaccaccg ctatggttaa catgtggtcg atagcgcggg acccacaggt ctggtcggac   1320
ccactcgaat ttatgccccca gaggtttgtg tccgaccccg gtgacgtgga gttctcggtc   1380
atgggttcgg atctccggct ggctccgttc gggtcgggca gaaggacctg ccccgggaag   1440
gccttcgcct ggacaactgt caccttctgg gtggccacgc ttttacacga cttcaaatgg   1500
tcgccgtccg atcaaaacga cgccgtcgac ttgtcggagg tcctcaagct ctcctgcgag   1560
atggccaatc ccctcaccgt taaagtacac ccaaggcgca gtttaagctt ttaa          1614
```

SEQ ID NO: 51
*Siraitia grosvenorii*
```
MSMSSEIESL WVFALASKCS ALTKENILWS LLFFFLIWVS VSILHWAHPG GPAWGRYWWR     60

RRRSNSTAAA IPGPRGLPLV GSMGLMADLA HHRIAAVADS LNATRLMAFS LGDTRVIVTC   120

NPDVAKEILN SSLFADRPVK ESAYSLMFNR AIGFAPYGLY WRTLRRIASH HLFCPKQIKS   180

SQSQRRQIAS QMVAMFANRD ATQSLCVRDS LKRASLNNMM GSVFGRVYDL SDSANNDVQE   240

LQSLVDEGYD LLGLLNWSDH LPWLADFDSQ KIRFRCSRLV PKVNHFVGRI IAEHRAKSDN   300

QVLDFVDVLL SLQEADKLSD SDMIAVLWEM IFRGTDTVAV LIEWILARMV LHNDIQRKVQ   360

EELDNVVGST RAVAESDIPS LVYLTAVVKE VLRLHPPGPL LSWARLAITD TIIDGHHVPR   420

GTTAMVNMWS IARDPQVWSD PLEFMPQRFV SDPGDVEFSV MGSDLRLAPF GSGRRTCPGK   480

AFAWTTVTFW VATLLHDFKW SPSDQNDAVD LSEVLKLSCE MANPLTVKVH PRRSLSF     537
```

SEQ ID NO: 52
*Siraitia grosvenorii*
```
atggatggtt ttcttccaac agtggcggcg agcgtgcctg tgggagtggg tgcaatattg     60
ttcacggcgt tgtgcgtcgt cgtgggaggg gttttggttt atttctatgg accttactgg    120
ggagtgagaa gggtgcctgg tccaccagct attccactgg tcggacatct tcccttgctg    180
gctaagtacg gcccagacgt tttctctgtc cttgccaccc aatatggccc tatcttcagg    240
ttccatatgg gtaggcagcc attgataatt atagcagacc ctgagctttg taaagaagct    300
ggtattaaga aattcaagga catcccaaat agaagtgtcc cttctccaat atcagcttcc    360
cctcttcatc agaagggtct tttcttcaca agggatgcaa gatggtcgac aatgcggaac    420
acgatattat cggtctatca gtcctcccat ctagcgagac taatacctac tatgcaatca    480
atcattgaaa ctgcaactca aaatctccat tcctctgtcc aggaagacat ccctttctcc    540
aatctctccc tcaaattgac caccgatgtg attggaacag cagccttcgg tgtcaacttt    600
gggctctcta atccacaggc aaccaaaact tgtgctacca acggccaaga caacaaaaat    660
gacgaagttt cagacttcat caatcaacac atctactcca caacgcagct caagatggat    720
ttatcaggtt ccttctcaat catacttgga ctgcttgtcc ctatactcca agaaccattt    780
```

TABLE 1-continued

Sequences disclosed herein.

```
agacaagtcc taaagagaat accattcacc atggactgga agtggaccg gacaaatcag      840 aaattaagtg gtcggcttaa tgagattgtg gagaagagaa tgaagtgtaa cgatcaaggt      900
tcaaaagact tcttatcgct cattttgaga gcaagagagt cagagacagt atcaaggaat      960
gtcttcactc cagactacat cagtgcagtt acgtatgaac acctacttgc tgggtcggct     1020
accacggcgt ttacgttgtc ttctattgta tatttagttg ctgggcatcc agaagtcgag     1080
aagaagttgc tagaagagat tgacaacttt ggtccatccg atcagatacc aacagctaat     1140
gatcttcatc agaagtttcc atatcttgat caggtgatta agaggctat gaggttctac      1200 actgtttccc ctctagtagc cagagaaaca gctaaagatg tggagattgg tggatatctt     1260
cttccaaagg ggacatgggt ttggttagca cttggagttc ttgccaagga tccaaagaac     1320
tttccagaac cagataaatt caaaccagag aggtttgatc caaatgaaga agaggagaaa     1380
caaaggcatc cttatgcttt aatcccctt ggaattggtc ctcgagcatg cattggtaaa     1440
aaattcgccc ttcaggagtt gaagctctcg ttgattcatt tgtacaggaa gtttgtattt     1500
cggcat                                                              1506
```

SEQ ID NO: 53
Siraitia grosvenorii
```
MDGFLPTVAA SVPVGVGAIL FTALCVVVGG VLVYFYGPYW GVRRVPGPPA IPLVGHLPLL      60

AKYGPDVFSV LATQYGPIFR FHMGRQPLII IADPELCKEA GIKKFKDIPN RSVPSPISAS     120

PLHQKGLFFT RDARWSTMRN TILSVYQSSH LARLIPTMQS IIETATQNLH SSVQEDIPFS     180

NLSLKLTTDV IGTAAFGVNF GLSNPQATKT CATNGQDNKN DEVSDFINQH IYSTTQLKMD     240

LSGSFSIILG LLVPILQEPF RQVLKRIPFT MDWKVDRTNQ KLSGRLNEIV EKRMKCNDQG     300

SKDFLSLILR ARESETVSRN VFTPDYISAV TYEHLLAGSA TTAFTLSSIV YLVAGHPEVE     360

KKLLEEIDNF GPSDQIPTAN DLHQKFPYLD QVIKEAMRFY TVSPLVARET AKDVEIGGYL     420

LPKGTWVWLA LGVLAKDPKN FPEPDKFKPE RFDPNEEEEK QRHPYALIPF GIGPRACIGK     480

KFALQELKLS LIHLYRKFVF RH                                           502
```

SEQ ID NO: 54
Siraitia grosvenorii
```
atggaaatca ttttatcata tctcaacagc tccatagctg gactcttcct cttgcttctc       60
ttctcgtttt ttgttttgaa aaaggctaga acctgtaaac gcagacagcc tcctgaagca      120
gccggcggat ggccgatcat cggccacctg agactgctcg ggggttcgca acttccccat      180
gaaaccttgg gagccatggc cgacaagtat ggaccaatct tcagcatccg agttggtgtc      240
cacccatctc ttgttataag cagttgggaa gtggctaaag agtgctacac caccctcgac      300
tcagttgtct cctctcgtcc caagagtttg ggtggaaagt tgttgggcta caacttcgcc      360
gcttttgggt tcaggcctta tgattccttt taccggagta ccgcaaaaac catagcctcc      420
gaggtgctgt cgaaccgccg tctggagttg cagagacaca ttcgagtttc tgaggtgaag      480
agatcggtga aggagcttta caatctgtgg acgcagagag aggaaggctc agaccacata      540
cttattgatg cggatgaatg gattggtaat attaatttga acgtgattct gatgatggtt      600
tgtgggaagc ggtttcttgg cggttctgcc agcgatgaga aggagatgag gcggtgtctc      660
aaagtctcga gagatttctt cgatttgaca gggcagttta cggtgggaga tgccattcct     720
ttcctgcgat ggctggattt gggtggatat gcgaaggcga tgaagaaaac tgcaaaagaa     780
atggactgtc tcgttgagga atggctggaa gaacaccgcc ggaagagaga ctccggcgcc     840
accgacggtg aacgtgactt catggatgtg atgctttcga ttcttgaaga gatggacctt     900
```

TABLE 1-continued

Sequences disclosed herein.

| | |
|---|---|
| gctggctacg acgctgacac agtcaacaaa gccacatgcc tgagcattat ttctgggga | 960 |
| atcgatacta taacgctaac tctgacatgg gcgatctcgt tattgctgaa caatcgagag | 1020 |
| gcactgcgaa gggttcaaga ggaggtggac atccatgtcg gaaacaaaag gcttgtggat | 1080 |
| gaatcagact tgagcaagct ggtgtatctc caagccgtcg tgaaagagac attaaggttg | 1140 |
| tacccagcag ggccgctgtc gggagctcga gagttcagtc gggactgcac ggtcggaggg | 1200 |
| tatgacgtgg ccgccggcac acggctcatc acaaaccttt ggaagataca gacggaccct | 1260 |
| cgggtgtggc cggagccact tgagttcagg ccggagaggt ttctgagcag ccaccagcag | 1320 |
| ttggatgtga agggccagaa ctttgaactg gccccatttg gttgtggaag aagagtgtgc | 1380 |
| cctggggcgg ggcttggggt tcagatgacg cagttggtgc tggcgagtct gattcattcg | 1440 |
| gtggaacttg gaactcgctc cgatgaagcg gtggacatgg ctgctaagtt tggactcaca | 1500 |
| atgtacagag ccaccccct  tcaggctctc gtcaagccac gcctccaagc cggtgcttat | 1560 |
| tcatga | 1566 |

SEQ ID NO: 55
*Siraitia grosvenorii*

| | |
|---|---|
| MEIILSYLNS SIAGLFLLLL FSFFVLKKAR TCKRRQPPEA AGGWPIIGHL RLLGGSQLPH | 60 |
| ETLGAMADKY GPIFSIRVGV HPSLVISSWE VAKECYTTLD SVVSSRPKSL GGKLLGYNFA | 120 |
| AFGFRPYDSF YRSIRKTIAS EVLSNRRLEL QRHIRVSEVK RSVKELYNLW TQREEGSDHI | 180 |
| LIDADEWIGN INLNVILMMV CGKRFLGGSA SDEKEMRRCL KVSRDFFDLT GQFTVGDAIP | 240 |
| FLRWLDLGGY AKAMKKTAKE MDCLVEEWLE EHRRKRDSGA TDGERDFMDV MLSILEEMDL | 300 |
| AGYDADTVNK ATCLSIISGG IDTITLTLTW AISLLLNNRE ALRRVQEEVD IHVGNKRLVD | 360 |
| ESDLSKLVYL QAVVKETLRL YPAGPLSGAR EFSRDCTVGG YDVAAGTRLI TNLWKIQTDP | 420 |
| RVWPEPLEFR PERFLSSHQQ LDVKGQNFEL APFGCGRRVC PGAGLGVQMT QLVLASLIHS | 480 |
| VELGTRSDEA VDMAAKFGLT MYRATPLQAL VKPRLQAGAY S | 521 |

SEQ ID NO: 56
*Siraitia grosvenorii*

| | |
|---|---|
| atgggtgtat tgtccatttt attattcaga tattccgtca agaagaagcc attaagatgc | 60 |
| ggtcacgatc aaagaagtac cacagatagt ccacctggtt caagaggttt gccattgata | 120 |
| ggtgaaactt tgcaattcat ggctgctatt aattctttga acggtgtata cgatttcgtt | 180 |
| agaataagat gtttgagata cggtagatgc tttaagacaa gaatcttcgg tgaaacccat | 240 |
| gttttttgtct caactacaga atccgctaag ttgatcttga aggatggtgg tgaaaaattc | 300 |
| accaaaaagt acatcagatc aatcgctgaa ttggttggtg acagaagttt gttatgtgca | 360 |
| tctcatttgc aacacaagag attgagaggt ttgttgacta atttgttttc tgccacattc | 420 |
| ttggcttctt tcgtaactca attcgatgaa caaatcgttg aagcttttag atcatgggaa | 480 |
| tccggtagta ccataatcgt tttgaacgaa gcattgaaga tcacttgtaa ggccatgtgc | 540 |
| aaaatggtca tgtccttaga aagagaaaac gaattggaag ctttgcaaaa ggaattgggt | 600 |
| catgtttgtg aagctatgtt ggcatttcca tgcagattcc ctggtacaag atttcacaat | 660 |
| ggtttgaagg caagaagaag aatcattaaa gttgtcgaaa tggccattag agaaagaaga | 720 |
| agatctgaag ctcctagaga agatttcttg caaagattgt tgcagaagaa aaggaagaa  | 780 |
| gaagacggtg gtggtgtttt aagtgatgcc gaaattggtg acaacatatt gacaatgatg | 840 |
| atcgcaggtc aagataccac tgcctctgct attacctgga tggtcaagtt tttgaagaa  | 900 |
| aaccaagatg tattgcaaaa cttaagagac gaacaattcg aaatcatggg taaacaagaa | 960 |

TABLE 1-continued

Sequences disclosed herein.

```
ggttgtggtt catgcttctt gacattagaa gatttgggta atatgtccta tggtgcaaaa      1020
gtagttaagg aatcattgag attagcctcc gtcgtaccat ggtttcctag attggtttta      1080
caagattctt tgatccaagg ttacaaaatt aaaaagggtt ggaacgtcaa catagacgta      1140
agatctttac attcagatcc atccttgtat aatgacccaa caaagtttaa ccctagtaga      1200
ttcgatgacg aagctaaacc ttactcattt ttggcattcg gtatgggtgg tagacaatgt      1260
ttgggtatga acatggcaaa ggccatgatg ttggttttct tgcacagatt ggtcacctca      1320
ttcagatgga aggttataga ttccgactct tcaatcgaaa aatgggcttt gttctctaag      1380
ttgaagtcag gttgccctat cgtagttacc cacatcggtt cctaa                      1425
```

SEQ ID NO: 57
Siraitia grosvenorii

```
MGVLSILLFR YSVKKKPLRC GHDQRSTTDS PPGSRGLPLI GETLQFMAAI NSLNGVYDFV       60

RIRCLRYGRC FKTRIFGETH VFVSTTESAK LILKDGGEKF TKKYIRSIAE LVGDRSLLCA      120

SHLQHKRLRG LLTNLFSATF LASFVTQFDE QIVEAFRSWE SGSTIIVLNE ALKITCKAMC      180

KMVMSLEREN ELEALQKELG HVCEAMLAFP CRFPGTRFHN GLKARRRIIK VVEMAIRERR      240

RSEAPREDFL QRLLTEEKEE EDGGGVLSDA EIGDNILTMM IAGQDTTASA ITWMVKFLEE      300

NQDVLQNLRD EQFEIMGKQE GCGSCFLTLE DLGNMSYGAK VVKESLRLAS VVPWFPRLVL      360

QDSLIQGYKI KKGWNVNIDV RSLHSDPSLY NDPTKFNPSR FDDEAKPYSF LAFGMGGRQC      420

LGMNMAKAMM LVFLHRLVTS FRWKVIDSDS SIEKWALFSK LKSGCPIVVT HIGS            474
```

SEQ ID NO: 58
Siraitia grosvenorii

```
atggatttct actggatctg tgttcttctg cttttgcttcg catggttttc cattttatcc       60
cttcactcga gaacaaacag cagcggcact tccaaacttc ctcccggacc gaaaccttg       120 ccgatcatcg gaagcctttt ggctctcggc cacgagcccc acaagtcttt ggctaatctc      180
gctaaatctc atggccctct tatgaccta aagctcggcc aaatcaccac cgtcgtagtt      240
tcctccgctg ccatggctaa gcaagttctc caaacgcacg accagtttct gtccagcagg      300
accgttccag acgcaatgac ctctcacaac cacgatgctt cgcactccc atggattccg       360 gtttcacccc tctggcgaaa ccttcgacga atatgcaaca accagttgtt tgccggcaag      420
attctcgacg ccaacgagaa tctccggcga accaaagtgg ccgagctcgt atccgatatc      480
tcgagaagtg cattgaaagg tgagatggtg gattttggaa acgtggtgtt cgtcacttcg      540
ctcaatctgc tttccaatac gattttctcg gtggatttct tcgacccaaa ttctgaaatt      600
gggaaagagt tcaggcacgc agtacgaggc ctcatggaag aagctgccaa accaaatttg      660
ggggattatt tccctctgct gaagaagata gatcttcaag gaataaagag gagacagacc      720
acttacttcg atcgggtttt taatgttttg gagcacatga tcgaccagcg tcttcagcag      780
cagaagacga cgtctggttc tacctccaac aacaacaacg acttactgca ctaccttctc      840
aacctcagca acgaaaatag cgacatgaaa ttggggaaac ttgagctgaa acacttctta      900
ttggtgctat tcgtcgctgg gactgaaacg agttctgcaa cactgcaatg ggcaatggca      960
gaactactaa gaaacccaga aaagttagca aaagctcaag cggagaccag gcgggtgatt      1020
gggaaaggga acccaattga agaatcagac atttcgaggc tgccttatct gcaagcagtg      1080
gtgaaagaaa ctttcagatt gcacacacca gcgccatttc tactgccgcg caaagcacta      1140
caggacgtga aaattgcagg tttcacagtc ccaaaggacg ctcaggtact ggtaaattta      1200
tgggctatga gcagagattc aagcatctgg gagaacccag agtggttcga gccagaaagg      1260
```

TABLE 1-continued

Sequences disclosed herein.

```
tttttggagt cggagctgga cgttagaggg agagattttg agctgatccc gttcggcggt      1320
gggcggagga tttgcccgg tctgccgttg gcgatgagaa tgttgcattt gattttgggt       1380
tctctcatcc acttctttga ttggaagctt gaagatgggt gtcggccgga agacgtgaaa      1440
atggacgaaa agcttggcct cactctggag ttggcttttc ccctcacagc cttgcctgtc      1500
cttgtctaa                                                              1509
```

SEQ ID NO: 59
*Siraitia grosvenorii*
```
MDFYWICVLL LCFAWFSILS LHSRTNSSGT SKLPPGPKPL PIIGSLLALG HEPHKSLANL       60

AKSHGPLMTL KLGQITTVVV SSAAMAKQVL QTHDQFLSSR TVPDAMTSHN HDAFALPWIP      120

VSPLWRNLRR ICNNQLFAGK ILDANENLRR TKVAELVSDI SRSALKGEMV DFGNVVFVTS      180

LNLLSNTIFS VDFFDPNSEI GKEFRHAVRG LMEEAAKPNL GDYFPLLKKI DLQGIKRRQT      240

TYFDRVFNVL EHMIDQRLQQ QKTTSGSTSN NNNDLLHYLL NLSNENSDMK LGKLELKHFL      300

LVLFVAGTET SSATLQWAMA ELLRNPEKLA KAQAETRRVI GKGNPIEESD ISRLPYLQAV      360

VKETFRLHTP APFLLPRKAL QDVEIAGFTV PKDAQVLVNL WAMSRDSSIW ENPEWFEPER      420

FLESELDVRG RDFELIPFGG GRRICPGLPL AMRMLHLILG SLIHFFDWKL EDGCRPEDVK      480

MDEKLGLTLE LAFPLTALPV LV                                              502
```

SEQ ID NO: 60
*Siraitia grosvenorii*
```
atgtcctcct gcggtggtcc aactcctttg aatgttatcg gtatcttatt acaatcagaa      60
tcctccagag cctgcaactc agacgaaaac tcaagaattt tgagagattt cgtaacaaga      120
gaagttaacg ctttcttatg gttgtccttg atcactatca cagcagtttt gatcagtaaa      180
gttgtcggtt tgtttagatt gtggtctaag gcaaagcaat tgagaggtcc accttgtcca      240
tcattctacg gtcattctaa gatcatctca agacaaaatt tgactgattt gttatatgac      300
tcccacaaaa agtacggtcc agtagttaaa ttgtggttag gtcctatgca attgttagtc      360
tccgtaaagg aaccaagttt gttgaaggaa atattggtta agctgaggga taagttgcct      420
ttaacaggta gagcctttag attggctttc ggtagatctt cattatttgc atccagtttc      480
gaaaaggttc aaaacagaag acaaagattg gccgaaaagt tgaataagat cgcattccaa      540
agagccaaca tcattccaga aaaggccgta gcttgtttca tgggtagagt tcaagatttg      600
atgatagaag aatctgtcga ctgtaataag gtttctcaac atttggcttt tactttgtta      660
ggttgcacat tgtttggtga cgccttctta ggttggtcta aggctacaat ctatgaagaa      720
ttgttgatga tgatcgctaa ggacgcatcc ttttgggcta gttatagagt taccccaatc      780
tggaagcaag gtttctggag ataccaaaga ttgtgtatga agttgaagtg cttgactcaa      840
gatatcgttc aacaatacag aaagcattac aagttgtttt ctcactcaca aaaccaaaac      900
ttacacaacg aaaccaagtc aactggtgtt gaagtcgctt ttgatattcc accttgtcct      960
gctgcagacg ttagaaattc ttgctttttc tacggtttga cgatcatgt taacccaaac       1020 gaagaacctt gtggtaatat tatgggtgtc atgtttcacg gttgcttgac tacaacctct      1080
ttgatcgcat caatcttgga agattggcc actaacccag aaatccaaga aaagattaat       1140
tctgaattga acttagttca aaagggtcca gtcaaggatc atagaaagaa tgttgacaac      1200
atgcctttgt tattggcaac aatctatgaa tcagctagat tattgccagc aggtcctta       1260 ttgcaaagat gtccttttgaa gcaagatttg gttttgaaaa caggtatcac cattccagct      1320
ggtaccttgg tcgtagttcc tattaaattg gttcaaatgg atgactcttc atggggttca      1380
```

TABLE 1-continued

Sequences disclosed herein.

| | |
|---|---|
| gatgccaatg agtttaatcc atacagattc ttgtccatgg cttgtaatgg tattgacatg | 1440 |
| atacaaagaa cccctttagc tggtgaaaac attggtgacc aaggtgaagg ttcatttgtc | 1500 |
| ttgaatgacc caattggtaa cgtaggtttc ttacctttg gtttcggtgc aagagcctgc | 1560 |
| gttggtcaaa agtttataat ccaaggtgtc gctactttgt tcgcaagttt gttggcccat | 1620 |
| tacgaaatta aattgcaatc cgagagtaag aatgattcta aaccatccag taacacctct | 1680 |
| gccagtcaaa tcgtcccaaa ctcaaaaatc gtattcgtaa aagaaactc ataa | 1734 |

SEQ ID NO: 61
*Siraitia grosvenorii*

| | |
|---|---|
| MSSCGGPTPL NVIGILLQSE SSRACNSDEN SRILRDFVTR EVNAFLWLSL ITITAVLISK | 60 |
| VVGLFRLWSK AKQLRGPPCP SFYGHSKIIS RQNLTDLLYD SHKKYGPVVK LWLGPMQLLV | 120 |
| SVKEPSLLKE ILVKAEDKLP LTGRAFRLAF GRSSLFASSF EKVQNRRQRL AEKLNKIAFQ | 180 |
| RANIIPEKAV ACFMGRVQDL MIEESVDCNK VSQHLAFTLL GCTLFGDAFL GWSKATIYEE | 240 |
| LLMMIAKDAS FWASYRVTPI WKQGFWRYQR LCMKLKCLTQ DIVQQYRKHY KLFSHSQNQN | 300 |
| LHNETKSTGV EVAFDIPPCP AADVRNSCFF YGLNDHVNPN EEPCGNIMGV MFHGCLTTTS | 360 |
| LIASILERLA TNPEIQEKIN SELNLVQKGP VKDHRKNVDN MPLLLATIYE SARLLPAGPL | 420 |
| LQRCPLKQDL VLKTGITIPA GTLVVVPIKL VQMDDSSWGS DANEFNPYRF LSMACNGIDM | 480 |
| IQRTPLAGEN IGDQGEGSFV LNDPIGNVGF LPFGFGARAC VGQKFIIQGV ATLFASLLAH | 540 |
| YEIKLQSESK NDSKPSSNTS ASQIVPNSKI VFVRRNS | 577 |

SEQ ID NO: 62
*Siraitia grosvenorii*

| | |
|---|---|
| atgtggactg tcgtgctcgg tttggcgacg ctgtttgtcg cctactacat ccattggatt | 60 |
| aacaaatgga gagattccaa gttcaacgga gttctgccgc cgggcaccat gggtttgccg | 120 |
| ctcatcggag agacgattca actgagtcga cccagtgact ccctcgacgt tcacccttc | 180 |
| atccagaaaa aagttgaaag atacgggccg atcttcaaaa catgtctggc cggaaggccg | 240 |
| gtggtggtgt cggcggacgc agagttcaac aactacataa tgctgcagga aggaagagca | 300 |
| gtggaaatgt ggtatttgga tacgctctcc aaattttcg gcctcgacac cgagtggctc | 360 |
| aaagctctgg gcctcatcca caagtacatc agaagcatta ctctcaatca cttcggcgcc | 420 |
| gaggccctgc gggagagatt tcttcctttt attgaagcat cctccatgga agcccttcac | 480 |
| tcctggtcta ctcaacctag cgtcgaagtc aaaaatgcct ccgctctcat ggttttagg | 540 |
| acctcggtga ataagatgtt cggtgaggat gcgaagaagc tatcgggaaa tatccctggg | 600 |
| aagttcacga agcttctagg aggatttctc agtttaccac tgaattttcc cggcaccacc | 660 |
| taccacaaat gcttgaagga tatgaaggaa atccagaaga agctaagaga ggttgtagac | 720 |
| gatagattgg ctaatgtggg ccctgatgtg aagatttct tggggcaagc ccttaaagat | 780 |
| aaggaatcag agaagttcat ttcagaggag ttcatcatcc aactgttgtt ttctatcagt | 840 |
| tttgctagct ttgagtccat ctccaccact cttactttga ttctcaagct ccttgatgaa | 900 |
| cacccagaag tagtgaaaga gttggaagct gaacacgagg cgattcgaaa agctagagca | 960 |
| gatccagatg gaccaattac ttgggaagaa tacaaatcca tgactttac attacaagtc | 1020 |
| atcaatgaaa ccctaaggtt ggggagtgtc acacctgcct tgttgaggaa aacagttaaa | 1080 |
| gatcttcaag taaaaggata cataatcccg gaaggatgga caataatgct tgtcaccgct | 1140 |
| tcacgtcaca gagacccaaa agtctataag gaccctcata tcttcaatcc atggcgttgg | 1200 |
| aaggacttgg actcaattac catccaaaag aacttcatgc cttttggggg aggcttaagg | 1260 |

TABLE 1-continued

Sequences disclosed herein.

```
cattgtgctg gtgctgagta ctctaaagtc tacttgtgca ccttcttgca catcctctgt     1320
accaaatacc gatggaccaa acttggggga ggaaggattg caagagctca tatattgagt     1380
tttgaagatg ggttacatgt gaagttcaca cccaaggaat ga                        1422
```

SEQ ID NO: 64
*Siraitia grosvenorii*
```
atgaagatga agatggaatc catgcgcacc tccctggata tctccgacca tgacatactt     60
ccaagggttt atcctcatgt tcacctatgg atcaacaaat atgggaaaaa cttcattcag     120
tggaatggca acgtagctca gttgattgtt tcggatcctg acacgatcaa ggagatactc     180
caaaaccgag aacaagctgt tcccaaaata gatctcagcg gagatgcacg gaggatattc     240
gggaatgggc tttcgacttc tgacggtgaa aaatgggcta aggctcgaag aatcgctgat     300
tacgctttcc acggggatct cctaagaaat atggggccaa ccatggtttc ctgtgctgag     360
gcaatggtgg aaaagtggaa gcatcatcaa ggcaaagagc ttgatttgtt cgaagagttt     420
aaggtgctca cttcagatat cattgcacat acagcctttg gaagcagtta tttggaaggg     480
aaagttattt ttcagactct aagtaagctg agcatgatat tatttaagaa tcagttcaaa     540
cgaaggattc ctgttatcag caagttcttc agatcaaagg atgcgaggga gggagaggag     600
ctggaaagaa ggttgaaaaa ttccataatt tcaataatgg aaaagagaga agagaaggtg     660
ataagtggtg aagcagataa ctatggtaat gattttcttg gattactttt gaaggcaaag     720
aatgagcctg accagaggca gaggatttct gttgatgatg tagtggatga atgcaaaaca     780
gtttacttcg ctgggcaaga aactacaagt gttttgcttg cttggaccgc ttttcttta     840 gcaactcatg agcattggca agaagaagca agaaaggaag tgctgaatat gtttggcaac     900
aagaatccaa ctttagaagg catcacaaaa ttaagatta tgagcatgat catcaaggaa     960
tctctaagat tatatcctcc agccccgccc atgtcaagga aggttaaaaa ggaagtcaga     1020
ttggggaagc tggttctccc ccccaacatt caagtaagca tctcaactat tgcagttcat     1080
catgatactg caatatgggg tgaagatgcc catgtattca accagaaaag attttctgaa     1140
ggaacagcta agatatccc atcagctgca tacatcccat ttggctttgg tcctcgaaac     1200
tgcatcggca atatcttggc catcaacgaa actaagattg cactgtcgat gattctacaa     1260
cgattttctt tcaccatctc cccggcctac gtccacgcac ctttccagtt cctcactatc     1320
tgcccccaac acggggttca ggtaaagctt cagtccctat taagtgaaag gtga          1374
```

SEQ ID NO: 65
*Siraitia grosvenorii*
```
MKMKMESMRT SLDISDHDIL PRVYPHVHLW INKYGKNFIQ WNGNVAQLIV SDPDTIKEIL     60

QNREQAVPKI DLSGDARRIF GNGLSTSDGE KWAKARRIAD YAFHGDLLRN MGPTMVSCAE     120

AMVEKWKHHQ GKELDLFEEF KVLTSDIIAH TAFGSSYLEG KVIFQTLSKL SMILFKNQFK     180

RRIPVISKFF RSKDAREGEE LERRLKNSII SIMEKREEKV ISGEADNYGN DFLGLLLKAK     240

NEPDQRQRIS VDDVVDECKT VYFAGQETTS VLLAWTAFLL ATHEHWQEEA RKEVLNMFGN     300

KNPTLEGITK LKIMSMIIKE SLRLYPPAPP MSRKVKKEVR LGKLVLPPNI QVSISTIAVH     360

HDTAIWGEDA HVFKPERFSE GTAKDIPSAA YIPFGFGPRN CIGNILAINE TKIALSMILQ     420

RFSFTISPAY VHAPFQFLTI CPQHGVQVKL QSLLSER                             457
```

SEQ ID NO: 66
*Siraitia grosvenorii*
```
atggaagctg aatttggtgc cggtgctact atggtattat ccgttgtcgc aatcgtcttc     60
tttttcacat tttacactt gtttgaatct ttcttttga agccagatag attgagatct     120
```

TABLE 1-continued

Sequences disclosed herein.

```
aagttgagaa agcaaggtat tggtggtcca tctccttcat ttttgttggg taatttgtca      180
gaaattaaat ccatcagagc tttgtcttca caagctaaga acgcagaaga tgcctctgct      240
ggtggtggtg gtggttccgc cagtatagct catggttgga cttcaaattt gtttcctcac      300
ttagaacaat ggagaaacag atatggtcca attttcgtat actccagtgg tacaatccaa      360
atcttgtgta tcacagaaat ggaaaccgtt aaggaaatct ctttgtcaac ctccttgagt      420
ttaggtaaac ctgctcattt gtctaaggat agaggtccat tgttaggttt gggtatctta      480
gcctcttcag gtcctatttg ggttcaccaa agaaagatca tcgctccaca attgtatttg      540
gataaagtaa agggtatgac ctcattgatg gttgaaagtg caaattctat gttaagatcc      600
tgggaaacta aagttgaaaa tcatggtggt caagccgaaa ttaacgtcga tggtgacttg      660
agagcattaa gtgccgatat catttctaag gcttgctttg gttcaaacta ttccgaaggt      720
gaagaaattt tcttgaagtt gagagcattg caagttgtca tgagtaaggg ttctattggt      780
atacctggtt ttagatacat accaactaaa aataacagag aaatgtggaa gttggaaaag      840
gaaatcgaat caatgatctt gaaggttgcc aacgaaagaa cacaacattc cagtcacgaa      900
caagatttgt tgcaaatgat tttggaaggt gcaaagtctt gggtgaaga caataagagt      960 atgaacatat caagagacaa gtttattgtt gacaattgta agaacatcta tttcgctggt     1020
catgaaacta cagctataac cgcatcttgg tgcttgatgt tgttagctgc acaccctgat     1080
tggcaagcaa gagccagatc tgaagtttta caatgttgcg atgacagacc aatcgatgca     1140
gacacagtca aaaatatgaa gaccttgact atggtaattc aagaaacttt gagattgtac     1200
ccacctgctg tattcgttac aagacaagca ttagaagata tcagattcaa aaacatcaca     1260
ataccaaagg gtatgaactt tcatatacca atccctatgt tgcaacaaga cttccactta     1320
tggggtcctg atgcttgttc atttgaccca caaagattct ccaatggtgt cttaggtgca     1380
tgcaaaaacc cacaagccta tgccttttt ggtgttggtc caagagtctg tgccggtcaa     1440
catttcgcta tgatcgaatt gaaagtcatc gtatcattgg ttttgtccag attcgaattt     1500
tctttgtcac cttcctacaa gcattcacca gccttcagat tagttgtcga accagaaaac     1560
ggtgtcatat tgcatgtcag aaagttgtga                                      1590
```

SEQ ID NO: 67  
Siraitia grosvenorii

```
MEAEFGAGAT MVLSVVAIVF FFTFLHLFES FFLKPDRLRS KLRKQGIGGP SPSFLLGNLS       60

EIKSIRALSS QAKNAEDASA GGGGGSASIA HGWTSNLFPH LEQWRNRYGP IFVYSSGTIQ      120

ILCITEMETV KEISLSTSLS LGKPAHLSKD RGPLLGLGIL ASSGPIWVHQ RKIIAPQLYL      180

DKVKGMTSLM VESANSMLRS WETKVENHGG QAEINVDGDL RALSADIISK ACFGSNYSEG      240

EEIFLKLRAL QVVMSKGSIG IPGFRYIPTK NNREMWKLEK EIESMILKVA NERTQHSSHE      300

QDLLQMILEG AKSLGEDNKS MNISRDKFIV DNCKNIYFAG HETTAITASW CLMLLAAHPD      360

WQARARSEVL QCCDDRPIDA DTVKNMKTLT MVIQETLRLY PPAVFVTRQA LEDIRFKNIT      420

IPKGMNFHIP IPMLQQDFHL WGPDACSFDP QRFSNGVLGA CKNPQAYMPF GVGPRVCAGQ      480

HFAMIELKVI VSLVLSRFEF SLSPSYKHSP AFRLVVEPEN GVILHVRKL                 529
```

SEQ ID NO: 68  
Siraitia grosvenorii

```
atggaagtgg atatcaatat cttcaccgtc ttttccttcg tattatgcac agtcttcctc       60
ttctttctat ccttcttgat cctcctcctc tcccgaacgc tcgccggaaa atccataacg      120
agctccgagt acacgccagt gtacggcacc gtctacggtc aggctttcta tttcaacaac      180
```

TABLE 1-continued

Sequences disclosed herein.

```
ctgtacgatc atctaacgga ggtggccaag agacatcgaa ccttccggct gcttgcgccg      240
gcatacagcg agatatacac gaccgatccg agaaacatcg agcatatgtt gaagacgaaa      300
ttcgataagt attcgaaagg aagcaaggat caagaaatcg ttggggatct gtttggagag      360
gggatatttg cagtcgatgg agataagtgg aagcagcaga ggaagctggc tagctatgaa      420
ttctcgacga ggattcttag ggattttagc tgctcggttt tcagacgaag tgctgctaaa      480
cttgttggag ttgtttcgga gttttccagc atgggtcggg ttttttgatat ccaggatttg      540 ctaatgcggt gcgctttgga ctccattttc aaagtggggt tcggggttga tttgaattgc      600
ttggaggaat caagcaaaga agggagcgat ttcatgaaag ccttcgatga ttctagcgct      660
cagatttttt ggcgctatat cgatcccttc tggaaattga agagattgct taacatcggt      720
tccgaagctt cgtttaggaa caacataaaa accatagatg cttttgtgca ccagttgatc      780
agagacaaga gaaaattgct tcagcaaccg aatcacaaga atgacaaaga ggacatactt      840
tggaggtttc tgatggaaag tgagaaggat ccaacaagaa tgaatgatca atatctaagg      900
gatatagtcc tcaatttcat gttggctggc aaagattcaa gtggaggaac tctgtcctgg      960
ttcttctaca tgctatgcaa gaacccttta atacaggaaa aagttgcaga agaagtgagg     1020
caaattgttg cgtttgaagg ggaagaagtt gacatcaatt tgttcataca aaacttaact     1080
gattcagctc ttgacaaaat gcattatctt catgcagcat tgaccgagac tctgaggcta     1140
tatcctgcag tccctttgga tggaaggact gcagaaatag atgacattct tcctgatggc     1200
tataaactaa gaaaagggga tggagtatac tacatggcct attccatggg caggatgtcc     1260
tcccttgggg agaagatgc tgaagatttt aaacccgaaa gatggcttga agtggaact      1320 tttcaacccg aatcaccttt caaattcatc gcttttcatg cgggtcctcg aatgtgtttg     1380
ggaaaagagt ttgcttatcg acaaatgaag atagtatctg ctgctttgct tcaatttttt     1440
cgattcaaag tagctgatac aacgaggaat gtgacttata ggatcatgct taccttcac      1500 attgatggag gtctccctct tcttgcaatt ccgagaatta gaaaatttac ctaa           1554
```

SEQ ID NO: 69
*Siraitia grosvenorii*
```
MEVDINIFTV FSFVLCTVFL FFLSFLILLL LRTLAGKSIT SSEYTPVYGT VYGQAFYFNN       60

LYDHLTEVAK RHRTFRLLAP AYSEIYTTDP RNIEHMLKTK FDKYSKGSKD QEIVGDLFGE      120

GIFAVDGDKW KQQRKLASYE FSTRILRDFS CSVFRRSAAK LVGVVSEFSS MGRVFDIQDL      180

LMRCALDSIF KVGFGVDLNC LEESSKEGSD FMKAFDDSSA QIFWRYIDPF WKLKRLLNIG      240

SEASFRNNIK TIDAFVHQLI RDKRKLLQQP NHKNDKEDIL WRFLMESEKD PTRMNDQYLR      300

DIVLNFMLAG KDSSGGTLSW FFYMLCKNPL IQEKVAEEVR QIVAFEGEEV DINLFIQNLT      360

DSALDKMHYL HAALTETLRL YPAVPLDGRT AEIDDILPDG YKLRKGDGVY YMAYSMGRMS      420

SLWGEDAEDF KPERWLESGT FQPESPFKFI AFHAGPRMCL GKEFAYRQMK IVSAALLQFF      480

RFKVADTTRN VTYRIMLTLH IDGGLPLLAI PRIRKFT                               517
```

SEQ ID NO: 70
*Siraitia grosvenorii*
```
ttggatagtg gagttaaaag agtgaaacgg ctagttgaag agaaacggcg agcagaattg       60
tctgcccgga ttgcctctgg agaattcaca gtcgaaaaag ctggttttcc atctgtattg      120
aggagtggct tatcaaagat gggtgttccc agtgagattc tggacatatt atttggtttc      180
gttgatgctc aagaagaata tcccaagatt cccgaagcaa aggatcagt aaatgcaatt      240 cgtagtgagg ccttcttcat acctctctat gagctttatc tcacatatgg tggaatattt      300
```

TABLE 1-continued

Sequences disclosed herein.

```
aggttgactt tgggccaaa gtcattcttg atagtttctg atccttccat tgctaaacat    360
atactgaagg ataatccgag gaattattct aagggtatct tagctgaaat tctagagttt    420
gtcatgggga agggacttat accagctgac gagaagatat ggcgtgtacg aaggcgggct    480
atagtcccat ctttgcatct gaagtatgta ggtgctatga ttaatctttt ggagaagct     540 gcagataggc tttgcaagaa gctagatgct gcagcatctg atggggttga tgtggaaatg    600
gagtccctgt tctcccgttt gactttagat atcattggca aggcagtttt taactatgac    660
tttgattcac ttacaaatga cactggcata gttgaggctg tttacactgt gctaagagaa    720
gcagaggatc gcagtgttgc accaattcca gtatgggaaa ttccaatttg gaaggatatt    780
tcaccacggc aaaaaaaggt ctctaaagcc ctcaaattga tcaacgacac cctcgatcaa    840
ctaattgcta tatgcaagag gatggttgat gaggaggagc tgcagtttca tgaggaatac    900
atgaatgagc aagatccaag catccttcat ttccttttgg catcaggaga tgatgtttca    960
agcaagcagc ttcgtgatga cttgatgact atgcttatag ctgggcatga aacatctgct   1020
gcagttttaa catggacctt ttatcttctt tccaaggagc cgaggatcat gtccaagctc   1080
caggaggagg ttgattcagt ccttggggat cggtttccaa ctattgaaga tatgaagaac   1140
ctcaaatatg ccacacgaat aattaacgaa tccttgaggc tttacccaca gccaccagtt   1200
ttaatacgtc gatctcttga caatgatatg ctcgggaagt accccattaa aaagggtgag   1260
gacatattca tttctgtttg gaacttgcat cgcagtccaa aactctggga tgatgcggat   1320
aaatttaatc ctgaaaggtg gcctctggat ggacccaatc caaatgagac aaatcaaaat   1380
ttcagatatt tacctttgg tggcggacca cggaaatgtg tgggagacat gttttgcttcg  1440 tacgagactg ttgtagcact tgcaatgctt gttcggcgat ttgacttcca aatggcactt   1500
ggagcacctc ctgtaaaaat gacaactgga gctacaattc acacaacaga tggattgaaa   1560
atgacagtta cacgaagaat gagacctcca atcatacccca cattagagat gcctgcagtg   1620
gtcgttgact cgtctgtcgt ggactcgtcc gtcgccattt tgaaagaaga aacacaaatt   1680
ggttag                                                             1686
```

SEQ ID NO: 71
Siraitia grosvenorii

```
MGVPSEILDI LFGFVDAQEE YPKIPEAKGS VNAIRSEAFF IPLYELYLTY GGIFRLTFGP     60

KSFLIVSDPS IAKHILKDNP RNYSKGILAE ILEFVMGKGL IPADEKIWRV RRRAIVPSLH    120

LKYVGAMINL FGEAADRLCK KLDAAASDGV DVEMESLFSR LTLDIIGKAV FNYDFDSLTN   180

DTGIVEAVYT VLREAEDRSV APIPVWEIPI WKDISPRQKK VSKALKLIND TLDQLIAICK   240

RMVDEEELQF HEEYMNEQDP SILHFLLASG DDVSSKQLRD DLMTMLIAGH ETSAAVLTWT   300

FYLLSKEPRI MSKLQEEVDS VLGDRFPTIE DMKNLKYATR IINESLRLYP QPPVLIRRSL   360

DNDMLGKYPI KKGEDIFISV WNLHRSPKLW DDADKFNPER WPLDGPNPNE TNQNFRYLPF   420

GGGPRKCVGD MFASYETVVA LAMLVRRFDF QMALGAPPVK MTTGATIHTT DGLKMTVTRR   480

MRPPIIPTLE MPAVVVDSSV VDSSVAILKE ETQIG                             515
```

SEQ ID NO: 72
Siraitia grosvenorii

```
cagttcctct cctggtcctc ccagtttggc aagaggttca tcttctggaa tgggatcgag     60
cccagaatgt gcctcaccga gaccgatttg atcaaagagc ttctctctaa gtacagcgcc    120
gtctccggta agtcatggct tcagcaacag ggctccaagc acttcatcgg ccgcggtctc    180
ttaatggcca acggccaaaa ctggtaccac cagcgtcaca tcgtcgcgcc ggccttcatg    240
```

TABLE 1-continued

Sequences disclosed herein.

| | |
|---|---|
| ggagacagac tcaagagtta cgccgggtac atggtggaat gcacaaagga gatgcttcag | 300 |
| tcaattgaaa acgaggtcaa ctcggggcga tccgagttcg aaatcggtga gtatatgacc | 360 |
| agactcaccg ccgatataat atcacgaacc gagttcgaaa gcagctacga aaagggaaag | 420 |
| caaattttcc atttgctcac cgttttacag catctctgcg ctcaggcgag ccgccacctc | 480 |
| tgccttcctg gaagccggtt ttttccgagt aaatacaaca gagagataaa ggcattgaag | 540 |
| acgaaggtgg aggggttgtt aatggagata atacagagca gaagagactg tgtggaggtg | 600 |
| gggaggagca gttcgtatgg aaatgatctg ttgggaatgt tgctgaatga gatgcagaag | 660 |
| aagaaagatg ggaatgggtt gagcttgaat ttgcagatta taatggatga atgcaagacc | 720 |
| ttcttcttcg ccggccatga aaccactgct ctttgctca cttggactgt aatgttattg | 780 |
| gccagcaacc cttcttggca acacaaggtt cgagccgaag ttatggccgt ctgcaatgga | 840 |
| ggaactctct ctcttgaaca tctctccaag ctctctctgt tgagtatggt gataaatgaa | 900 |
| tcgttgaggc tataccgcc agcaagtatt cttccaagaa tggcatttga agatataaag | 960 |
| ctgggagatc ttgagatccc aaaagggctg tcgatatgga tcccagtgct tgcaattcac | 1020 |
| cacagtgaag agctatgggg caaagatgca aatgagttca acccagaaag atttgcaaat | 1080 |
| tcaaaagcct tcacttcggg gagattcatt ccctttgctt ctggccctcg caactgcgtt | 1140 |
| ggccaatcat ttgctctcat ggaaaccaag atcattttgg ctatgctcat ctccaagttt | 1200 |
| tccttcacca tctctgacaa ttatcgccat gcacccgtgg tcgtcctcac tataaaaccc | 1260 |
| aaatacggag tccaagtttg cttgaagcct ttcaattaa | 1299 |

SEQ ID NO: 73
*Siraitia grosvenorii*

| | |
|---|---|
| MCLTETDLIK ELLSKYSAVS GKSWLQQQGS KHFIGRGLLM ANGQNWYHQR HIVAPAFMGD | 60 |
| RLKSYAGYMV ECTKEMLQSI ENEVNSGRSE FEIGEYMTRL TADIISRTEF ESSYEKGKQI | 120 |
| FHLLTVLQHL CAQASRHLCL PGSRFFPSKY NREIKALKTK VEGLLMEIIQ SRRDCVEVGR | 180 |
| SSSYGNDLLG MLLNEMQKKK DGNGLSLNLQ IIMDECKTFF FAGHETTALL LTWTVMLLAS | 240 |
| NPSWQHKVRA EVMAVCNGGT LSLEHLSKLS LLSMVINESL RLYPPASILP RMAFEDIKLG | 300 |
| DLEIPKGLSI WIPVLAIHHS EELWGKDANE FNPERFANSK AFTSGRFIPF ASGPRNCVGQ | 360 |
| SFALMETKII LAMLISKFSF TISDNYRHAP VVVLTIKPKY GVQVCLKPFN | 410 |

SEQ ID NO: 74
*Siraitia grosvenorii*

| | |
|---|---|
| atggaagaca ccttcctact ctatccttcc ctctctcttc tctttcttct ttttgctttc | 60 |
| aagctcatcc gtcgatccgg aggagttcgc aggaacttac cgccgagtcc gccctctctt | 120 |
| ccggttatcg gccacctcca tctcttgaaa aagccactcc accggacttt ccagaaactt | 180 |
| tccgccaaat atggtcctgt tatgtccctc cgcctcgggt ctcgcctcgc agtcattgta | 240 |
| tcgtcgtcgt cggcggtgga cgagtgtttc actaaaaacg acgtcgtgct cgccaaccgt | 300 |
| cctcgttttgc taattggcaa acacctcggc tacaactaca ctaccatggt tggggctccc | 360 |
| tacgcgacc actggcgtag cctccgccgc atcggtgccc tcgaaatctt ctcttcatct | 420 |
| cgcctcaaca aattcgccga catccgaagg gatgaagtag agggattgct tcgcaaactc | 480 |
| tcacgcaatt cgctccatca attctcgaaa gtggaagttc aatcggcctt gtcggagctg | 540 |
| acgttcaaca tctcgatgag aatggcggca gggaacggt attacggaga tgacgtgacg | 600 |
| gacgaggaag aggcgagaaa gttcagagag ttaattaaac agatagtggc gctgggcgga | 660 |
| gtatcaaatc caggggattt cgtcccgatt ctgaattgga ttccgaacgg tttcgagagg | 720 |

TABLE 1-continued

Sequences disclosed herein.

```
aagttgatcg agtgtgggaa gaagacggat gcgttcttgc aggggctgat cgaggaccac    780
cggagaaaga aggaagaggg taggaacacg atgatcgatc acctgctctc tctgcaagaa    840
tcggagcctg ctcactacgg agaccaaata atcaaaggat ttatactggt gttactgacg    900
gcggggaccg atacatcggc cgtgacaatg gagtgggcgc tatctcatct cctgaacaat    960
cctgaagtgc taaagaaggc aagagatgag gtcgacactg aaattggaca agaacgactt   1020
gtcgaagaat cagacgtagt atctaagtta ccctatcttc aagggatcat ctccgagact   1080
ctccggctga atcccgccgc tccgatgttg ttgccccatt acgcctcgga cgactgcacg   1140
atatgtggat acgacgtgcc acgtgacaca atcgtaatgg tcaatgcatg gccatacat    1200 agggatccaa acgaatggga ggagcccacg tgtttcagac agaacgata tgaaaagtcg    1260 tcgtcggaag cggaggtaca caagtcggtg agtttcgggg tgggaaggcg agcttgtcct   1320
gggtctggca tggcgcagag ggtgatgggc ttgactttgg cggcactggt tcagtgcttc   1380
gagtgggaga gagttggaga agaagaagtg gacatgaacg aaggctcagg tgccacaatg   1440
cccaagatgg tgccattgga ggccatgtgc agagctcgtc ccatcgtcca aaccttctt   1500 tactga                                                              1506
```

SEQ ID NO: 75
*Siraitia grosvenorii*

```
MEDTFLLYPS LSLLFLLFAF KLIRRSGGVR RNLPPSPPSL PVIGHLHLLK KPLHRTFQKL     60

SAKYGPVMSL RLGSRLAVIV SSSSAVDECF TKNDVVLANR PRLLIGKHLG YNYTTMVGAP   120

YGDHWRSLRR IGALEIFSSS RLNKFADIRR DEVEGLLRKL SRNSLHQFSK VEVQSALSEL   180

TFNISMRMAA GKRYYGDDVT DEEEARKFRE LIKQIVALGG VSNPGDFVPI LNWIPNGFER   240

KLIECGKKTD AFLQGLIEDH RRKKEEGRNT MIDHLLSLQE SEPAHYGDQI IKGFILVLLT   300

AGTDTSAVTM EWALSHLLNN PEVLKKARDE VDTEIGQERL VEESDVVSKL PYLQGIISET   360

LRLNPAAPML LPHYASDDCT ICGYDVPRDT IVMVNAWAIH RDPNEWEEPT CFRPERYEKS   420

SSEAEVHKSV SFGVGRRACP GSGMAQRVMG LTLAALVQCF EWERVGEEEV DMNEGSGATM   480

PKMVPLEAMC RARPIVHNLL Y                                             501
```

SEQ ID NO: 76
*Arabidopsis thaliana*

```
MATEKTHQFH PSLHFVLFPF MAQGHMIPMI DIARLLAQRG VTITIVTTPH NAARFKNVLN    60

RAIESGLAIN ILHVKFPYQE FGLPEGKENI DSLDSTELMV PFFKAVNLLE DPVMKLMEEM   120

KPRPSCLISD WCLPYTSIIA KNFNIPKIVF HGMGCFNLLC MHVLRRNLEI LENVKSDEEY   180

FLVPSFPDRV EFTKLQLPVK ANASGDWKEI MDEMVKAEYT SYGVIVNTFQ ELEPPYVKDY   240

KEAMDGKVWS IGPVSLCNKA GADKAERGSK AAIDQDECLQ WLDSKEEGSV LYVCLGSICN   300

LPLSQLKELG LGLEESRRSF IWVIRGSEKY KELFEWMLES GFEERIKERG LLIKGWAPQV   360

LILSHPSVGG FLTHCGWNST LEGITSGIPL ITWPLFGDQF CNQKLVVQVL KAGVSAGVEE   420

VMKWGEEDKI GVLVDKEGVK KAVEELMGDS DDAKERRRRV KELGELAHKA VEKGGSSHSN   480

ITLLLQDIMQ LAQFKN                                                   496
```

SEQ ID NO: 77
*Arabidopsis thaliana*

```
MVSETTKSSP LHFVLFPFMA QGHMIPMVDI ARLLAQRGVI ITIVTTPHNA ARFKNVLNRA    60

IESGLPINLV QVKFPYLEAG LQEGQENIDS LDTMERMIPF FKAVNFLEEP VQKLIEEMNP   120

RPSCLISDFC LPYTSKIAKK FNIPKILFHG MGCFCLLCMH VLRKNREILD NLKSDKELFT   180

VPDFPDRVEF TRTQVPVETY VPAGDWKDIF DGMVEANETS YGVIVNSFQE LEPAYAKDYK   240
```

TABLE 1-continued

Sequences disclosed herein.

```
EVRSGKAWTI GPVSLCNKVG ADKAERGNKS DIDQDECLKW LDSKKHGSVL YVCLGSICNL    300

PLSQLKELGL GLEESQRPFI WVIRGWEKYK ELVEWFSESG FEDRIQDRGL LIKGWSPQML    360

ILSHPSVGGF LTHCGWNSTL EGITAGLPLL TWPLFADQFC NEKLVVEVLK AGVRSGVEQP    420

MKWGEEEKIG VLVDKEGVKK AVEELMGESD DAKERRRRAK ELGDSAHKAV EEGGSSHSNI    480

SFLLQDIMEL AEPNN                                                   495
```

SEQ ID NO: 78
*Arabidopsis thaliana*
```
MAFEKNNEPF PLHFVLFPFM AQGHMIPMVD IARLLAQRGV LITIVTTPHN AARFKNVLNR    60

AIESGLPINL VQVKFPYQEA GLQEGQENMD LLTTMEQITS FFKAVNLLKE PVQNLIEEMS   120

PRPSCLISDM CLSYTSEIAK KFKIPKILFH GMGCFCLLCV NVLRKNREIL DNLKSDKEYF   180

IVPYFPDRVE FTRPQVPVET YVPAGWKEIL EDMVEADKTS YGVIVNSFQE LEPAYAKDFK   240

EARSGKAWTI GPVSLCNKVG VDKAERGNKS DIDQDECLEW LDSKEPGSVL YVCLGSICNL   300

PLSQLLELGL GLEESQRPFI WVIRGWEKYK ELVEWFSESG FEDRIQDRGL LIKGWSPQML   360

ILSHPSVGGF LTHCGWNSTL EGITAGLPML TWPLFADQFC NEKLVVQILK VGVSAEVKEV   420

MKWGEEEKIG VLVDKEGVKK AVEELMGESD DAKERRRRAK ELGESAHKAV EEGGSSHSNI   480

TFLLQDIMQL AQSNN                                                   495
```

SEQ ID NO: 79
*Arabidopsis thaliana*
```
MSPKMVAPPT NLHFVLFPLM AQGHLVPMVD IARILAQRGA TVTIITTPYH ANRVRPVISR    60

AIATNLKIQL LELQLRSTEA GLPEGCESFD QLPSFEYWKN ISTAIDLLQQ PAEDLLRELS   120

PPPDCIISDF LFPWTTDVAR RLNIPRLVFN GPGCFYLLCI HVAITSNILG ENEPVSSNTE   180

RVVLPGLPDR IEVTKLQIVG SSRPANVDEM GSWLRAVEAE KASFGIVVNT FEELEPEYVE   240

EYKTVKDKKM WCIGPVSLCN KTGPDLAERG NKAAITEHNC LKWLDERKLG SVLYVCLGSL   300

ARISAAQAIE LGLGLESINR PFIWCVRNET DELKTWFLDG FEERVRDRGL IVHGWAPQVL   360

ILSHPTIGGF LTHCGWNSTI ESITAGVPMI TWPFFADQFL NEAFIVEVLK IGVRIGVERA   420

CLFGEEDKVG VLVKKEDVKK AVECLMDEDE DGDQRRKRVI ELAKMAKIAM AEGGSSYENV   480

SSLIRDVTET VRAPH                                                   495
```

SEQ ID NO: 80
*Arabidopsis thaliana*
```
MDAMATTEKK PHVIFIPFPA QSHIKAMLKL AQLLHHKGLQ ITFVNTDFIH NQFLESSGPH    60

CLDGAPGFRF ETIPDGVSHS PEASIPIRES LLRSIETNFL DRFIDLVTKL PDPPTCIISD   120

GFLSVFTIDA AKKLGIPVMM YWTLAACGFM GFYHIHSLIE KGFAPLKDAS YLTNGYLDTV   180

IDWVPGMEGI RLKDFPLDWS TDLNDKVLMF TTEAPQRSHK VSHHIFHTFD ELEPSIIKTL   240

SLRYNHIYTI GPLQLLLDQI PEEKKQTGIT SLHGYSLVKE EPECFQWLQS KEPNSVVYVN   300

FGSTTVMSLE DMTEFGWGLA NSNHYFLWII RSNLVIGENA VLPPELEEHI KKRGFIASWC   360

SQEKVLKHPS VGGFLTHCGW GSTIESLSAG VPMICWPYSW DQLTNCRYIC KEWEVGLEMG   420

TKVKRDEVKR LVQELMGEGG HKMRNKAKDW KEKARIAIAP NGSSSLNIDK MVKEITVLAR   480

N                                                                  481
```

SEQ ID NO: 81
*Siraitia grosvenorii*
```
atggagcaag ctcatgatct tcttcacgtc ctccttttc cgtatccggc gaagggccac     60
atcaagccct tcctctgcct cgccgagctc tctgcaacg ccggtctcaa cgtcaccttc    120
ctcaacaccg actacaacca ccgccgcctc cacaatctcc atctcctcgc cgcctgcttt   180
```

TABLE 1-continued

Sequences disclosed herein.

```
ccctctcttc atttcgagtc catttccgac ggcctccagc ccgatcagcc tcgagatata      240
ctggacccca agttttatat atccatctgt caagtcacta aaccccttttt ccgggagctc     300 ctcctttcct acaaacgaac ttccagtgtc cagaccggcc gcccgccaat aacttgcgtt     360
attacagatg tgattttttcg ttttccgatc gacgtagctg aagaactgga tattcctgtg   420 tttagttttct gtactttcag tgcccgtttc atgtttcttt acttctggat tcccaagctc    480
attgaagatg gccagcttcc atacccaaac ggcaatatca accagaaaact ctacggtgtt   540 gctcctgagg cggaaggcct tttaagatgt aaagatttgc cgggacattg ggctttcgca   600
gacgaactaa aagatgatca acttaacttt gtggaccaga caacggcgtc acttcgatcc   660
tccggtctca ttctcaacac attcgacgac ctcgaagctc catttctggg gcgtctctcc   720
accatcttta agaaaatcta cgccgttgga cccatccacg ctctgttgaa ctccccaccac  780 tgtggtctttt ggaaagaaga tcacagttgc ctggcgtggc tcgactcccg ggcggcgaga   840
tccgtcgtgt tcgtcagctt cgggagcttg gtgaagataa caagtaggca gctgatggag    900
ttttggcatg gcttgctcaa cagtggaacg tcgttcctct tcgtgttgag atctgacgta    960
gttgagggcg atggtgaaaa acaagtcgtc aaagaaattt acgagacgaa ggcagagggg  1020
aaatggttgg ttgtggggtg ggctccgcaa gagaaggtgt tagcccatga agctgttggt   1080
ggatttctga cccattcggg ctggaactcc atttagaga gcattgctgc tggggttcct     1140
atgatctcct gccccaaaat tggagaccag tccagtaact gtacgtggat cagtaaagta   1200
tggaaaattg ggctcgaaat ggaggaccaa tacgaccggg ccacggtcga ggcaatggtt  1260
aggtctataa tgaaacatga aggagaaaaa attcaaaaga caattgcaga gttagcaaaa   1320
cgagccaagt ataaagttag taaagatggg acatcgtatc gaaatttaga aattttaatt   1380
gaggatatta aaaaaattaa accaaattaa                                                                             1410
```

SEQ ID NO: 82  
Artificial Sequence

```
atggaacaag cccacgattt gctgcatgtt ttactttttc catatccagc taaagggcat       60 attaagcect ttttgtgtct tgcggaactt ttatgcaacg caggtcttaa tgttacgttt    120
ttgaataccg attataatca cagaagatta cacaatctgc acctattagc ggcttgtttt   180
cctagtttgc attttgaaag tatcagtgat ggtttgcagc cagatcaacc tagagatatc   240
ttggacccaa agttttacat ctctatttgc caagttacca agccattatt cagagaattg   300
ttattatcct ataaaaggac atcctcagta caaaccggca ggccgccaat aacttgtgtt   360
ataacagatg ttatatttcg ttttccaatc gatgtagccg aggaattaga tatccctgtt    420
ttttctttct gtacttttag cgcgcgtttt atgtttcttt acttctggat cccaaagctt    480
atcgaggatg ggcaattgcc ttacccaaac ggtaacataa atcagaaaact gtatggtgtt  540 gcacctgaag cagaaggatt attaaggtgt aaggatttac cgggacactg gctttcgct   600 gatgagttaa aagacgatca gttgaacttt gttgatcaaa ctaccgccag tttgagatca   660
tctggtttga tcttaaacac tttcgacgat ttggaagctc cattcctggg acgtttgtca   720
acaatattta agaagatcta cgctgttggg ccaatacatg cgttgctaaa cagtcaccat    780 tgcggttttat ggaaagaaga ccacagctgt ttggcctggt tagatagtag agcggcacgt  840
tctgtcgtgt tcgtcagttt cggttcttttg gttaagatca cttctaggca attgatggaa   900
ttctggcatg gattgttgaa tagcgggaca agctttttgt ttgtcttgag aagtgatgtt    960
gtagaaggtg atggggaaaa gcaagttgtc aaagaaatct acgaaacgaa agcagagggt   1020
```

TABLE 1-continued

Sequences disclosed herein.

```
aaatggttag ttgttggttg ggctccacaa gaaaaagtat tggcacatga agccgttgga    1080
ggtttcttaa ctcattccgg ttggaactca atcttagagt ctatagccgc aggtgtacct    1140
atgataagtt gcccaaaaat aggagaccaa tcttctaatt gtacctggat tagtaaagtt    1200
tggaagattg gtttagaaat ggaagaccag tatgacagag caactgtgga agctatggtg    1260
agatcaatta tgaaacacga aggtgagaag atacaaaaga ctattgcgga acttgcaaaa    1320
agagcaaaat ataaagtttc caaggacggc acttcatata gaaatctgga aattttgatc    1380
gaagatatca agaagatcaa gccgaattag                                     1410
```

SEQ ID NO: 83
*Siraitia grosvenorii*

```
MEQAHDLLHV LLFPYPAKGH IKPFLCLAEL LCNAGLNVTF LNTDYNHRRL HNLHLLAACF     60

PSLHFESISD GLQPDQPRDI LDPKFYISIC QVTKPLFREL LLSYKRTSSV QTGRPPITCV    120

ITDVIFRFPI DVAEELDIPV FSFCTFSARF MFLYFWIPKL IEDGQLPYPN GNINQKLYGV    180

APEAEGLLRC KDLPGHWAFA DELKDDQLNF VDQTTASLRS SGLILNTFDD LEAPFLGRLS    240

TIFKKIYAVG PIHALLNSHH CGLWKEDHSC LAWLDSRAAR SVVEVSEGSL VKITSRQLME    300

FWHGLLNSGT SFLFVLRSDV VEGDGEKQVV KEIYETKAEG KWLVVGWAPQ EKVLAHEAVG    360

GFLTHSGWNS ILESIAAGVP MISCPKIGDQ SSNCTWISKV WKIGLEMEDQ YDRATVEAMV    420

RSIMKHEGEK IQKTIAELAK RAKYKVSKDG TSYRNLEILI EDIKKIKPN                469
```

SEQ ID NO: 84
*Siraitia grosvenorii*

```
atggtgcaac ctcgggtact gctgtttcct ttcccggcac tgggccacgt gaagcccttc     60
ttatcactgg cggagctgct ttccgacgcc ggcatagacg tcgtcttcct cagcaccgag    120
tataaccacc gtcggatctc caacactgaa gccctagcct cccgcttccc gacgcttcat    180
ttcgaaacta taccggatgg cctgccgcct aatgagtcgc gcgctcttgc cgacggccca    240
ctgtatttct ccatgcgtga gggaactaaa ccgagattcc ggcaactgat tcaatctctt    300
aacgacggtc gttggcccat cacctgcatt atcactgaca tcatgttatc ttctccgatt    360
gaagtagcgg aagaatttgg gattccagta attgccttct gccctgcag tgctcgctac     420 ttatcgattc acttttttat accgaagctc gttgaggaag gtcaaattcc atacgcagat    480
gacgatccga ttggagagat ccaggggtg cccttgttcg aaggtctttt gcgacggaat    540
catttgcctg gttcttggtc tgataaatct gcagatatat ctttctcgca tggcttgatt    600
aatcagaccc ttgcagctgg tcgagcctcg gctcttatac tcaacacctt cgacgagctc    660
gaagctccat ttctgaccca tctctcttcc attttcaaca aaatctacac cattggaccc    720
ctccatgctc tgtccaaatc aaggctcggc gactcctcct cctccgcttc tgccctctcc    780
ggattctgga agaggatag agcctgcatg tcctggctcg actgtcagcc gccgagatct    840
gtggttttcg tcagtttcgg gagtacgatg aagatgaaag ccgatgaatt gagagagttc    900
tggtatgggt tggtgagcag cgggaaaccg ttcctctgcg tgttgagatc cgacgttgtt    960
tccggcggag aagcggcgga attgatcgaa cagatggcgg aggaggaggg agctggaggg   1020
aagctgggaa tggtagtgga gtgggcagcg caagagaagg tcctgagcca ccctgccgtc   1080
ggtgggtttt tgacgcactg cgggtggaac tcaacggtgg aaagcattgc cgcgggagtt   1140
ccgatgatgt gctggccgat tctcggcgac caacccagca acgccacttg gatcgacaga   1200
gtgtggaaaa ttgggggttga aaggaacaat cgtgaatggg acaggttgac ggtggagaag   1260
atggtgagag cattgatgga aggccaaaag agagtggaga ttcagagatc aatggagaag   1320
```

TABLE 1-continued

Sequences disclosed herein.

| | | | | | |
|---|---|---|---|---|---|
| ctttcaaagt | tggcaaatga | gaaggttgtc | aggggtgggt | tgtcttttga | taacttggaa | 1380 |
| gttctcgttg | aagacatcaa | aaaattgaaa | ccatataaat | tttaa | | 1425 |

SEQ ID NO: 85
Artificial Sequence

| | | | | | |
|---|---|---|---|---|---|
| atggttcaac | ctagggtctt | attgtttccc | ttccctgctt | tgggacatgt | caaacccttt | 60 |
| ctgtcactgg | cagaattact | ttccgatgct | gggatagacg | ttgtatttct | tagtacagaa | 120 |
| tacaatcata | ggaggattag | taacacggag | gctctggcct | caagatttcc | aaccttgcat | 180 |
| tttgaaacaa | taccagatgg | tcttccacct | aacgagagca | gggctttggc | agacggccct | 240 |
| ttgtactttta | gcatgcgtga | ggggacaaaa | cccagattca | gacagctgat | acagagcctg | 300 |
| aacgatggca | gatggcctat | cacgtgtatc | attaccgata | tcatgttgag | tagccccatc | 360 |
| gaagtagctg | aggagtttgg | aattccagta | attgcctttt | gtccctgctc | cgctagatac | 420 |
| ttgtctattc | atttttttcat | acccaagttg | gttgaagagg | tcagatccc | ttatgcagat | 480 |
| gatgatccaa | tcggtgaaat | tcaaggtgtg | ccacttttcg | aagggcttct | gaggagaaat | 540 |
| catttgccag | gcagctggag | tgataagtct | gcagacatct | cattttccca | tggtttgatc | 600 |
| aaccaaacat | tagcagccgg | tagagcttct | gcattaatct | gaatacgtt | tgatgagttg | 660 |
| gaagctccat | ttctgactca | tcttttctagt | attttttaata | agatttatac | aattggtcct | 720 |
| ttgcatgcct | tatctaagtc | aaggttagga | gactcctcat | ctagtgctag | tgcacttagt | 780 |
| ggattctgga | aggaagatag | ggcttgtatg | tcttggttgg | attgtcaacc | tcctagatct | 840 |
| gttgttttcg | tctcttttgg | cagtactatg | aaaatgaagg | cggacgaact | aagagaattt | 900 |
| tggtatggat | tagtatcttc | aggaaaacca | tttttatgcg | ttttaagatc | cgatgtagtc | 960 |
| tcaggcggag | aagctgcgga | gttaattgaa | caaatggcag | aagaggaagg | tgccggggt | 1020 |
| aagtggggca | tggttgttga | atgggcagct | caggagaagg | tacttagcca | tccagcggtt | 1080 |
| ggtggatttt | tgacgcattg | cgggtggaat | agcactgtgg | aaagtatagc | agcagggggc | 1140 |
| ccgatgatgt | gttggccaat | cttgggagat | caaccatcca | acgcgacctg | gatcgataga | 1200 |
| gtttggaaaa | tcggtgtaga | agaaataat | agagaatggg | atagattaac | tgttgaaaaa | 1260 |
| atggttagag | ccttgatgga | aggacagaaa | agagttgaaa | ttcagcgttc | aatggaaaag | 1320 |
| ctatcaaagt | tggccaatga | aaaagtagtt | aggggggggtc | tttcatttga | taatcttgaa | 1380 |
| gttcttgtcg | aagatattaa | aaagttaaag | ccgtacaagt | tttaa | | 1425 |

SEQ ID NO: 86
Siraitia grosvenorii

| | | | | | |
|---|---|---|---|---|---|
| MVQPRVLLFP | FPALGHVKPF | LSLAELLSDA | GIDVVFLSTE | YNHRRISNTE | ALASRFPTLH | 60 |
| FETIPDGLPP | NESRALADGP | LYFSMREGTK | PRFRQLIQSL | NDGRWPITCI | ITDIMLSSPI | 120 |
| EVAEEFGIPV | IAFCPCSARY | LSIHFFIPKL | VEEGQIPYAD | DDPIGEIQGV | PLFEGLLRRN | 180 |
| HLPGSWSDKS | ADISFSHGLI | NQTLAAGRAS | ALILNTFDEL | EAPFLTHLSS | IFNKIYTIGP | 240 |
| LHALSKSRLG | DSSSSASALS | GFWKEDRACM | SWLDCQPPRS | VVFVSFGSTM | KMKADELREF | 300 |
| WYGLVSSGKP | FLCVLRSDVV | SGGEAAELIE | QMAEEEGAGG | KLGMVVEWAA | QEKVLSHPAV | 360 |
| GGFLTHCGWN | STVESIAAGV | PMMCWPILGD | QPSNATWIDR | VWKIGVERNN | REWDRLTVEK | 420 |
| MVRALMEGQK | RVEIQRSMEK | LSKLANEKVV | RGGLSFDNLE | VLVEDIKKLK | PYKF | 474 |

SEQ ID NO: 87
Siraitia grosvenorii

| | | | | | |
|---|---|---|---|---|---|
| atggcttctc | ctcgccacac | tcctcacttt | ctgctcttcc | ctttcatggc | tcaaggccac | 60 |
| atgatcccca | tgattgacct | tgccaggctt | ctggctcagc | gaggagttat | catcactatt | 120 |

TABLE 1-continued

Sequences disclosed herein.

| | |
|---|---|
| atcaccacgc cccacaatgc tgctcgctac cactctgttc ttgctcgcgc catcgattct | 180 |
| gggttacaca tccatgtcct ccaactgcag tttccatgta aggaaggtgg gctgccagaa | 240 |
| gggtgcgaga atgtggactt gctaccttca cttgcttcca tacccagatt ctacagagca | 300 |
| gcaagtgatc tcctttacga accatctgaa aaactgtttg aggaactcat cccccggccg | 360 |
| acctgcataa tctccgatat gtgcctgccc tggaccatgc gaattgctct gaaatatcac | 420 |
| gtcccaaggc tcgttttcta cagtttgagc tgcttctttc ttctctgtat gcggagttta | 480 |
| aaaaacaatc tagcgcttat aagctccaag tctgattctg agttcgtaac tttctctgac | 540 |
| ttgcctgatc cagtcgagtt tctcaagtcg gagctaccta aatccaccga tgaagacttg | 600 |
| gtgaagttta gttatgaaat gggggaggcc gatcggcagt catacggcgt tattttaaat | 660 |
| ctatttgagg agatggaacc aaagtatctt gcagaatatg aaaaggaaag agaatcgccg | 720 |
| gaaagagtct ggtgcgtcgg cccagtttcg ctttgcaacg acaacaaact cgacaaagct | 780 |
| gaaagaggca acaaagcctc catcgacgaa tacaaatgca tcaggtggct cgacgggcag | 840 |
| cagccatctt cggtggttta cgtctcttta ggaagcttgt gcaatctggt gacggcgcag | 900 |
| atcatagagc tgggtttggg tttggaggca tcaaagaaac ccttcatttg ggtcataaga | 960 |
| agaggaaaca taacagagga gttacagaaa tggcttgtgg agtacgattt cgaggagaaa | 1020 |
| attaaaggga gagggctggt gattcttggc tgggctcccc aagttctgat actgtcacac | 1080 |
| cctgcaatcg gatgcttttt gacgcactgc ggttggaact caagcatcga agggatatcg | 1140 |
| gccggcgtgc caatggtcac ctggccgctt tttgcggatc aagtcttcaa cgagaagcta | 1200 |
| attgtacaaa tactcagaat cggcgtaagt gtaggcacgg aaactactat gaactgggga | 1260 |
| gaggaagagg agaaaggggt ggttgtgaag agagagaaag tgagggaagc catagaaata | 1320 |
| gtgatggatg gagatgagag agaagagagg agagagagat gcaaagagct tgctgaaacg | 1380 |
| gcgaagagag ctatagaaga aggggctcg tctcaccgga acctcacgat gttgattgaa | 1440 |
| gatataattc atggaggagg tttgagttat gagaaaggaa gttgtcgctga | 1491 |

SEQ ID NO: 88
Artificial Sequence

| | |
|---|---|
| atggcgtcac ctagacatac tcctcatttc ttgttatttc catttatggc tcaaggacat | 60 |
| atgataccta tgattgatct ggctaggcta ctagcacaaa gaggtgttat tatcactatt | 120 |
| attactactc cacataatgc agctcgttat catagtgttt tagctcgtgc cattgactct | 180 |
| ggtttacata tccacgtttt acaactacaa ttcccttgca agaaggcgg actaccggaa | 240 |
| ggttgtgaga acgtagactt acttccatcc ttagcgagca ttccaagatt ttacagagct | 300 |
| gcctctgatc tactatatga acctagcgaa aaacttttcg aagagttgat accgagacca | 360 |
| acttgtatca tttctgatat gtgtttacca tggactatga gaattgcctt aaagtatcat | 420 |
| gtgcccagac ttgttttcta ctctttgtct tgcttttttc tgctgtgcat gagaagctta | 480 |
| aagaacaatt tagcattaat ttctagcaag tcagattccg agttcgtaac tttctctgat | 540 |
| ttacccgatc cagttgaatt tttgaagtct gagcttccta agtccacaga cgaagacttg | 600 |
| gttaaatttt catatgaaat gggtgaggca gacagacaat catatggcgt tatactaaac | 660 |
| ttgtttgaag aaatggagcc caaatatttg gcagagtatg aaaagaaag agaaagtccc | 720 |
| gaaagagttt ggtgtgttgg tccagtatct ttgtgcaacg ataacaaatt agataaagca | 780 |
| gagaggggta acaaagcatc aattgacgaa tataagtgta ttagatggtt agatgggcaa | 840 |
| caacctagca gtgttgttta tgttagtctt ggatcattat gcaacttggt tactgctcaa | 900 |

TABLE 1-continued

Sequences disclosed herein.

```
attattgaat tggggttggg gttggaagct tctaaaaagc cattcatttg ggttattagg    960 agggcaaca taacagaaga actacaaaaa tggctggttg aatatgactt tgaggagaag   1020
attaagggac gtggattagt catattaggg tgggcgcccc aagtacttat tctatctcat   1080
ccagctattg gttgcttctt aactcattgc ggttggaatt cctctatcga aggtatttcc   1140
gccggtgttc ctatggttac ctggcctcta tttgcagatc aggttttcaa cgaaaaatta   1200
atagttcaaa tcttgagaat cggagttagc gttggtacag aaacaaccat gaactgggt    1260 gaggaagaag aaaaaggtgt ggtggtcaaa agggagaaag tgagagaggc gatagagatc   1320
gtaatggatg gcgacgaaag agaagaaaga agagaaaggt gtaaagaact agcagaaact   1380
gccaaacgtg ctatcgagga aggtggtagc agtcatagaa atttgaccat gctaattgaa   1440
gatattatcc acgtggtggg cttatcttac gagaaagggt cctgcaggta g            1491
```

SEQ ID NO: 89
*Siraitia grosvenorii*

```
MASPRHTPHF LLFPFMAQGH MIPMIDLARL LAQRGVIITI ITTPHNAARY HSVLARAIDS    60

GLHIHVLQLQ FPCKEGGLPE GCENVDLLPS LASIPRFYRA ASDLLYEPSE KLFEELIPRP   120

TCIISDMCLP WTMRIALKYH VPRLVFYSLS CFFLLCMRSL KNNLALISSK SDSEFVTFSD   180

LPDPVEFLKS ELPKSTDEDL VKFSYEMGEA DRQSYGVILN LFEEMEPKYL AEYEKERESP   240

ERVWCVGPVS LCNDNKLDKA ERGNKASIDE YKCIRWLDGQ QPSSVVYVSL GSLCNLVTAQ   300

IIELGLGLEA SKKPFIWVIR RGNITEELQK WLVEYDFEEK IKGRGLVILG WAPQVLILSH   360

PAIGCFLTHC GWNSSIEGIS AGVPMVTWPL FADQVFNEKL IVQILRIGVS VGTETTMNWG   420

EEEEKGVVVK REKVREAIEI VMDGDEREER RERCKELAET AKRAIEEGGS SHRNLTMLIE   480

DIIHGGGLSY EKGSCR                                                    496
```

SEQ ID NO: 90
*Siraitia grosvenorii*

```
atggatgccc agcgaggtca caccaccacc attttgatgc ttccatgggt cggctacggc    60
catctcttgc ctttcctcga gctggccaaa agcctctcca ggaggaaatt attccacatc   120
tacttctgtt caacgtctgt tagcctcgac gccattaaac caaagcttcc tccttctatc   180
tcttctgatg attccatcca acttgtggaa cttcgtctcc cttcttctcc tgagttacct   240
cctcatcttc acacaaccaa cggccttccc tctcacctca tgcccgctct ccaccaagcc   300 tcgtcatgg ccgcccaaca ctttcaggtc attttacaaa cacttgcccc gcatctcctc    360
atttatgaca ttctccaacc ttgggctcct caagtggctt catccctcaa cattccagcc   420
atcaacttca gtactaccgg agcttcaatg ctttctcgaa cgcttcaccc tactcactac   480
ccaagttcta aattcccaat ctcagagttt gttcttcaca atcactggag agccatgtac   540
accaccgccg atgggctct acagaagaa ggccacaaaa ttgaagaaac acttgcgaat    600
tgcttgcata cttcttgcgg ggtagttttg gtcaatagtt tcagagagct tgagacgaaa   660
tatatcgatt atctctctgt tctcttgaac aagaaagttg ttccggtcgg tcctttggtt   720
tacgaaccga atcaagaagg ggaagatgaa ggttattcaa gcatcaaaaa ttggcttgac   780
aaaaaggaac cgtcctcaac cgtcttcgtt tcatttggaa ccgaatactt cccgtcaaag   840
gaagaaatgg aagagatagc gtatgggtta gagctgagcg aggttaattt catctgggtc   900
cttagatttc tcaaggaga cagcaccagc accattgaag acgccttgcc gaaggggttt    960
ctggagagag cggagagag ggcgatggtg gtgaagggtt gggctcctca ggcgaagata   1020
ctgaagcatt ggagcacagg ggggcttgtg agtcactgtg gatggaactc gatgatggag   1080
```

TABLE 1-continued

Sequences disclosed herein.

| | |
|---|---|
| ggcatgatgt ttggcgtacc cataatagcg gtcccgatgc atctggacca gcccttaac | 1140 |
| gccggactct tggaagaagc tggcgtcggc gtggaagcca agcgaggttc ggacggcaaa | 1200 |
| attcaaagag aagaagttgc aaagtcgatc aaagaagtgg tgattgagaa aaccagggaa | 1260 |
| gacgtgagga agaaagcaag agaaatgggt gagattttga ggagtaaagg agatgagaaa | 1320 |
| attgatgagt tggtggctga aatttctctt ttgcgcaaaa aggctccatg ttcaatttaa | 1380 |

SEQ ID NO: 91
*Siraitia grosvenorii*

| | |
|---|---|
| atggatgccc agcgaggtca caccacaacc attttgatgt ttccatggct cggctatggc | 60 |
| catctttcgg ctttcctaga gttggccaaa agcctctcaa ggaggaactt ccatatctac | 120 |
| ttctgttcaa cctctgttaa cctcgacgcc attaaaccaa agcttccttc ttcttcctct | 180 |
| tctgattcca tccaacttgt ggaactttgt cttccatctt ctcctgatca gctccctcct | 240 |
| catcttcaca caaccaacgc cctccccct cacctcatgc ccactctcca ccaagccttc | 300 |
| tccatggctg cccaacactt tgctgccatt ttacacacac ttgctccgca tctcctcatt | 360 |
| tacgactctt tccaaccttg ggctcctcaa ctagcttcat ccctcaacat tccagccatc | 420 |
| aacttcaata ctacgggagc ttcagtcctg acccgaatgc ttcacgctac tcactaccca | 480 |
| agttctaaat tcccaatttc agagtttgtt ctccacgatt attggaaagc catgtacagc | 540 |
| gccgccggtg gggctgttac aaaaaaagac cacaaaattg gagaaacact tgcgaattgc | 600 |
| ttgcatgctt cttgtagtgt aattctaatc aatagtttca gagagctcga ggagaaatat | 660 |
| atggattatc tctccgttct cttgaacaag aaagttgttc cggttggtcc tttggtttac | 720 |
| gaaccgaatc aagacgggga agatgaaggt tattcaagca tcaaaaattg gcttgacaaa | 780 |
| aaggaaccgt cctccaccgt cttcgtttca tttggaagcg aatacttccc gtcaaaggaa | 840 |
| gaaatggaag agatagccca tgggttagag gcgagcgagg ttcatttcat ctgggtcgtt | 900 |
| aggtttcctc aaggagacaa caccagcgcc attgaagatg ccttgccgaa ggggtttctg | 960 |
| gagagggtgg gagagagagg gatggtggtg aagggttggg ctcctcaggc gaagatactg | 1020 |
| aagcattgga gcacaggggg attcgtgagc cactgtggat ggaactcggt gatggaaagc | 1080 |
| atgatgtttg gcgttcccat aatagggggtt ccgatgcatc tggaccagcc ctttaacgcc | 1140 |
| ggactcgcgg aagaagctgg cgtcggcgtg gaagccaagc gagattcgga cggcaaaatt | 1200 |
| caaagagaag aagttgcaaa gtcgatcaaa gaagtggtga ttgagaaaac cagggaagac | 1260 |
| gtgaggaaga aagcaagaga aatgggtgag attttgagga gtaaaggaga tgagaaaatt | 1320 |
| gatgagttgg tggctgaaat ttctcttttg cgcaaaaagg ctccatgttc aatttaa | 1377 |

SEQ ID NO: 92
Artificial Sequence

| | |
|---|---|
| atggatgccc agcgaggtca caccacaacc attttgatgt ttccatggct cggctatggc | 60 |
| catctttcgg ctttcctaga gttggccaaa agcctctcaa ggaggaactt ccatatctac | 120 |
| ttctgttcaa cctctgttaa cctcgacgcc attaaaccaa agcttccttc ttcttcctct | 180 |
| tctgattcca tccaacttgt ggaactttgt cttccatctt ctcctgatca gctccctcct | 240 |
| catcttcaca caaccaacgc cctccccct cacctcatgc ccactctcca ccaagccttc | 300 |
| tccatggctg cccaacactt tgctgccatt ttacacacac ttgctccgca tctcctcatt | 360 |
| tacgactctt tccaaccttg ggctcctcaa ctagcttcat ccctcaacat tccagccatc | 420 |
| aacttcaata ctacgggagc ttcagtcctg acccgaatgc ttcacgctac tcactaccca | 480 |
| agttctaaat tcccaatttc agagtttgtt ctccacgatt attggaaagc catgtacagc | 540 |

TABLE 1-continued

Sequences disclosed herein.

```
gccgccggtg gggctgttac aaaaaaagac cacaaaattg gagaaacact tgcgaattgc    600
ttgcatgctt cttgtagtgt aattctaatc aatagtttca gagagctcga ggagaaatat    660
atggattatc tctccgttct cttgaacaag aaagttgttc cggttggtcc tttggtttac    720
gaaccgaatc aagacgggga agatgaaggt tattcaagca tcaaaaattg gcttgacaaa    780
aaggaaccgt cctccaccgt cttcgtttca tttggaagcg aatacttccc gtcaaaggaa    840
gaaatggaag agatagccca tgggttagag gcgagcgagg ttcatttcat ctgggtcgtt    900
aggtttcctc aaggagacaa caccagcgcc attgaagatg ccttgccgaa ggggtttctg    960
gagagggtgg agagagagg gatggtggtg aaggggttggg ctcctcaggc gaagatactg   1020
aagcattgga gcacaggggg attcgtgagc cactgtggat ggaactcggt gatggaaagc   1080
atgatgtttg gcgttcccat aatagggggtt ccgatgcatc tggaccagcc ctttaacgcc   1140
ggactcgcgg aagaagctgg cgtcggcgtg aagccaagc gagattcgga cggcaaaatt    1200
caaagagaag aagttgcaaa gtcgatcaaa gaagtggtga ttgagaaaac cagggaagac    1260
gtgaggaaga aagcaagaga aatgggtgag attttgagga gtaaaggaga tgagaaaatt    1320
gatgagttgg tggctgaaat ttctctttg cgcaaaaagg ctccatgttc aatttaa       1377
```

SEQ ID NO: 93
*Siraitia grosvenorii*

```
MDAQRGHTTT ILMFPWLGYG HLSAFLELAK SLSRRNFHIY FCSTSVNLDA IKPKLPSSSS     60

SDSIQLVELC LPSSPDQLPP HLHTTNALPP HLMPTLHQAF SMAAQHFAAI LHTLAPHLLI    120

YDSFQPWAPQ LASSLNIPAI NFNTTGASVL TRMLHATHYP SSKFPISEFV LHDYWKAMYS    180

AAGGAVTKKD HKIGETLANC LHASCSVILI NSFRELEEKY MDYLSVLLNK KVVPVGPLVY    240

EPNQDGEDEG YSSIKNWLDK KEPSSTVFVS FGSEYFPSKE EMEEIAHGLE ASEVHFIWVV    300

RFPQGDNTSA IEDALPKGFL ERVGERGMVV KGWAPQAKIL KHWSTGGFVS HCGWNSVMES    360

MMFGVPIIGV PMHLDQPFNA GLAEEAGVGV EAKRDSDGKI QREEVAKSIK EVVIEKTRED    420

VRKKAREMGE ILRSKGDEKI DELVAEISLL RKKAPCSI                            458
```

SEQ ID NO: 94
*Siraitia grosvenorii*

```
atggatgccc agcgaggtca caccaccacc attttgatgc ttccatgggt cggctacggc     60
catctcttgc ctttcctcga gctggccaaa agcctctcca ggaggaaatt attccacatc    120
tacttctgtt caacgtctgt tagcctcgac gccattaaac caaagcttcc tccttctatc    180
tcttctgatg attccatcca acttgtggaa cttcgtctcc cttcttctcc tgagttacct    240
cctcatcttc acacaaccaa cggccttccc tctcacctca tgcccgctct ccaccaagcc    300
ttcgtcatgg ccgcccaaca ctttcaggtc attttacaaa cacttgcccc gcatctcctc    360
atttatgaca ttctccaacc ttgggctcct caagtggctt catccctcaa cattccagcc    420
atcaacttca gtactaccgg agcttcaatg ctttctcgaa cgcttcaccc tactcactac    480
ccaagttcta aattcccaat ctcagagttt gttcttcaca atcactggag agccatgtac    540
accaccgccg atggggctct tacagaagaa ggccacaaaa ttgaagaaac acttgcgaat    600
tgcttgcata cttcttgcgg ggtagttttg tcaatagtt tcagagagct gagacgaaa     660 tatatcgatt atctctctgt tctccttgaac aagaaagttg ttccggtcgg tcctttggtt    720
tacgaaccga atcaagaagg ggaagatgaa ggttattcaa gcatcaaaaa ttggcttgac    780
aaaaaggaac cgtcctcaac cgtcttcgtt tcatttggaa ccgaatactt cccgtcaaag    840
gaagaaatgg aagagatagc gtatgggtta gagctgagcg aggttaattt catctgggtc    900
```

TABLE 1-continued

Sequences disclosed herein.

```
cttagatttc tcaaggaga cagcaccagc accattgaag acgccttgcc gaagggtttt     960
ctggagagag cggagagag ggcgatggtg gtgaagggtt gggctcctca ggcgaagata    1020
ctgaagcatt ggagcacagg ggggcttgtg agtcactgtg gatggaactc gatgatggag   1080
ggcatgatgt ttggcgtacc cataatagcg gtcccgatgc atctggacca gcccctttaac  1140 gccggactct tggaagaagc tggcgtcggc gtggaagcca agcgaggttc ggacggcaaa   1200
attcaaagag aagaagttgc aaagtcgatc aaagaagtgg tgattgagaa aaccagggaa   1260
gacgtgagga agaaagcaag agaaatgggt gagattttga ggagtaaagg agatgagaaa   1320
attgatgagt tggtggctga aatttctctt ttgcgcaaaa aggctccatg ttcaatttaa   1380
```

SEQ ID NO: 95
*Siraitia grosvenorii*

```
MDAQRGHTTT ILMLPWVGYG HLLPFLELAK SLSRRKLFHI YFCSTSVSLD AIKPKLPPSI     60

SSDDSIQLVE LRLPSSPELP PHLHTTNGLP SHLMPALHQA FVMAAQHFQV ILQTLAPHLL   120

IYDILQPWAP QVASSLNIPA INFSTTGASM LSRTLHPTHY PSSKFPISEF VLHNHWRAMY   180

TTADGALTEE GHKIEETLAN CLHTSCGVVL VNSFRELETK YIDYLSVLLN KKVVPVGPLV   240

YEPNQEGEDE GYSSIKNWLD KKEPSSTVFV SFGTEYFPSK EEMEEIAYGL ELSEVNFIWV   300

LRFPQGDSTS TIEDALPKGF LERAGERAMV VKGWAPQAKI LKHWSTGGLV SHCGWNSMME   360

GMMFGVPIIA VPMHLDQPFN AGLLEEAGVG VEAKRGSDGK IQREEVAKSI KEVVIEKTRE   420

DVRKKAREMG EILRSKGDEK IDELVAEISL LRKKAPCSI                          459
```

SEQ ID NO: 96
*Siraitia grosvenorii*

```
atggatgcaa aagaagaaag cttgaaagtt tttatgcttc catggttggc ccatggtcat     60
atatcgccct acctagagct agccaagagg cttgcaaaga gaaaatttct tgtttatttc   120
tgctccacgc ctgtaaattt ggaagccatt aaaccaaagc tttccaaaag ctactctgat   180
tcgatccaac taatggaggt tcctctcgaa tcgacgccgg agcttcctcc tcactatcat   240
acagccaaag gccttccgcc gcatttaatg cccaaactca tgaatgcctt taaaatggtt   300
gctcccaatc tcgaatcgat cctaaaaacc ctaaacccag atctgctcat cgtcgacatt   360
ctccttccat ggatgcttcc actcgcttca tcgctcaaaa ttccgatggt tttcttcact   420
attttcggtg ccatggccat ctcctttatg atttataatc gaaccgtctc gaacgagctt   480
ccatttccag aatttgaact tcacgagtgc tggaaatcga agtgccccta tttgttcaag   540
gaccaagcgg aaagtcaatc gttcttagaa tacttggatc aatcttcagg cgtaattttg   600
atcaaaactt ccagagagat tgaggctaag tatgtagact ttctcacttc gtcgtttacg   660
aagaaggttg tgaccaccgg tccctggtt cagcaaccct cttccggcga agacgagaag   720
cagtactccg atatcatcga atggctagac aagaaggagc cgttatcgac ggtgctcgtt   780
tcgtttggga gcgagtatta tctgtcaaag gaagagatgg aagaaatcgc ctacgggctg   840
gagagcgcca gcgaggtgaa tttcatctgg attgttaggt ttccgatggg acaggaaacg   900
gaggtcgagg cggcgctgcc ggagggttc atccagaggg caggagagag agggaaagtg   960
gtcgagggct gggctccgca ggcgaaaata ttggcgcatc cgagcaccgg cggccatgtg  1020
agccacaacg ggtggagctc gattgtggag tgcttgatgt ccggtgtacc ggtgatcggc  1080
gcgccgatgc aacttgacgg gccaatcgtc gcaaggctgg tggaggagat cggcgtgggt  1140
ttggaaatca agagagatga ggaagggaga atcacgaggg gcgaagttgc cgatgcaatc  1200
aagacggtgg cggtgggcaa aaccggggaa gattttagaa ggaaagcaaa aaaaatcagc  1260
```

TABLE 1-continued

Sequences disclosed herein.

| | |
|---|---|
| agcattttga agatgaaaga tgaagaagag gttgacactt tggcaatgga attagtgagg | 1320 |
| ttatgccaaa tgaaaagagg gcaggagtct caggactaa | 1359 |

SEQ ID NO: 97
Artificial Sequence

| | |
|---|---|
| atggacgcca aagaagaatc cttgaaggtt tttatgttgc catggttggc tcatggtcat | 60 |
| atttctccat atttggaatt ggctaagaga ttggccaaga gaaagttctt ggtttacttc | 120 |
| tgttctaccc cagttaactt ggaagctatt aagccaaagt tgtccaagtc ctactccgat | 180 |
| tctattcaat tgatggaagt cccattggaa tccactccag aattgccacc acattatcat | 240 |
| actgctaaag gtttgccacc tcatttgatg ccaaaattga tgaacgcttt caagatggtt | 300 |
| gctccaaact tggaatcaat cttgaaaacc ttgaacccag acttgttgat cgttgatatt | 360 |
| ttgttgcctt ggatgttgcc tttggcctcc tctttgaaaa ttcctatggt tttcttcacc | 420 |
| atcttcggtg ctatggctat ttcttcatg atctacaaca gaaccgtttc caacgaattg | 480 |
| ccatttccag aatttgaatt gcacgaatgc tggaagtcta agtgtccata cttgtttaag | 540 |
| gatcaagccg aatcccaatc cttcttggaa tatttggatc aatcctccgg tgtcattttg | 600 |
| atcaagacct ctagagaaat tgaagccaag tacgttgatt tcttgacctc ttcattcacc | 660 |
| aagaaggttg ttactactgg tccattggtt caacaaccat catctggtga agatgaaaag | 720 |
| caatactccg atatcattga atggttggac aagaaagaac cattgtccac tgttttggtt | 780 |
| tctttcggtt ccgaatatta cttgtctaaa gaagaaatgg aagaaatcgc ctacggtttg | 840 |
| gaatctgctt ctgaagttaa tttcatctgg atcgtcagat tcccaatggg tcaagaaact | 900 |
| gaagttgaag ctgctttgcc agaaggtttt attcaaagag ctggtgaaag aggtaaagtt | 960 |
| gttgaaggtt gggctccaca agctaagatt ttggctcatc catctactgg tggtcacgtt | 1020 |
| tctcataatg gttggtcatc tatcgttgaa tgcttgatgt ctggtgttcc agttattggt | 1080 |
| gctccaatgc aattggatgg tccaatagtt gctagattgg tcgaagaaat tggtgttggt | 1140 |
| ttggaaatca agagagatga agaaggtaga atcaccagag gtgaagttgc tgatgctatt | 1200 |
| aagactgttg ctgttggtaa accggtgaa gatttagaa gaaaggccaa gaagatctcc | 1260 |
| tccattttaa agatgaagga cgaagaagaa gttgacacct tggctatgga attggttaga | 1320 |
| ttgtgtcaaa tgaagagagg tcaagaatcc caagactga | 1359 |

SEQ ID NO: 98
Artificial Sequence

| | |
|---|---|
| atggatgcta aggaagaatc tttgaaagtc tttatgctgc cttggttggc tcacggtcat | 60 |
| atttccccgt atttggaatt ggcaaaaaga ctggccaaga gaaaattctt agtgtatttc | 120 |
| tgttcaactc cagtgaattt ggaagccatc aaaccaaaat tgtctaagtc atattctgac | 180 |
| tctatacaac tgatggaagt tccttttggaa agtacaccgg aactgccacc ccattatcat | 240 |
| acagctaaag ggttacccc acacttgatg cccaagctaa tgaatgcatt taagatggtc | 300 |
| gcaccaaatc tggaaagtat acttaagacg ctaaaccctg atttattaat tgtagatatc | 360 |
| cttctaccat ggatgttgcc cttagcttca tcttttaaaaa ttccgatggt ttttttcact | 420 |
| atctttggag ccatggcaat ttcctttatg atttacaata gaacagtctc aaatgagtta | 480 |
| cctttcccag agtttgaatt acatgaatgc tggaaatcta agtgtccata tttgttcaaa | 540 |
| gaccaagcag aatcccaatc tttcttagaa tacttagatc agagttccgg agttatcttg | 600 |
| atcaagacat ctagggaaat tgaagcaaag tatgtggact ttttgacctc cagtttttact | 660 |
| aagaaagtcg taacaacggg tcctctagtc caacaaccta gttcaggaga ggatgagaaa | 720 |

TABLE 1-continued

Sequences disclosed herein.

```
caatatagcg atataatcga atggttagat aaaaaagagc cattgagtac cgttctagtg      780
tcctttggtt cagaatatta tttgtctaaa gaagagatgg aagagattgc ctacggctta      840
gaatcagctt ccgaagtaaa ctttatatgg attgtcagat ttcccatggg acaagaaacc      900
gaggtcgaag cagcttttgcc cgaaggtttt attcaacgtg ccggcgaaag aggaaaagta    960
gtggaaggtt gggctccaca agccaaaatt ctagctcacc cgtccactgg tggtcatgtc    1020
tctcataacg gatggagttc aattgttgaa tgtttgatga gtggtgttcc agtgatagga    1080
gctcctatgc agctggacgg tccaatagtc gccaggttag tcgaagaaat tggtgttggt    1140
ttagaaataa agagagacga agaaggtaga attactagag gtgaagtagc agatgcaatt    1200
aaaactgttg ctgtcggcaa gactggagag gattttcgta gaaaagccaa aaaaatatca    1260
tctatactaa aaatgaaaga cgaagaggag gttgatacgc tggcgatgga actagttaga    1320
ttgtgtcaga tgaagcgtgg tcaggaaagt caagactaa                            1359
```

SEQ ID NO: 99
*Siraitia grosvenorii*
```
MDAKEESLKV FMLPWLAHGH ISPYLELAKR LAKRKFLVYF CSTPVNLEAI KPKLSKSYSD     60

SIQLMEVPLE STPELPPHYH TAKGLPPHLM PKLMNAFKMV APNLESILKT LNPDLLIVDI    120

LLPWMLPLAS SLKIPMVFFT IFGAMAISFM IYNRTVSNEL PFPEFELHEC WKSKCPYLFK    180

DQAESQSFLE YLDQSSGVIL IKTSREIEAK YVDFLTSSFT KKVVTTGPLV QQPSSGEDEK    240

QYSDIIEWLD KKEPLSTVLV SFGSEYYLSK EEMEEIAYGL ESASEVNFIW IVRFPMGQET    300

EVEAALPEGF IQRAGERGKV VEGWAPQAKI LAHPSTGGHV SHNGWSSIVE CLMSGVPVIG    360

APMQLDGPIV ARLVEEIGVG LEIKRDEEGR ITRGEVADAI KTAVGKTGE DFRRKAKKIS     420

SILKMKDEEE VDTLAMELVR LCQMKRGQES QD                                  452
```

SEQ ID NO: 100
*Siraitia grosvenorii*
```
atgcttccat ggctggctca cggccatgtc tcccctttct tcgagctcgc caagttgctc      60
gccgctagaa acttccacat attcttctgc tccaccgccg taaacctccg ctccgtcgaa    120
ccaaaactct ctcagaagct ctcctcccac gtggagctgg tggagctcaa cctaccgccc    180
tcgccggagc tccctccgca ccgccacacc accgccggcc ttccaccgca cctcatgttc    240
tcgctcaagc gagctttcga catggccgct cccgccttcg ccgccatcct ccgcgacctg    300
aacccggact gctcatcta cgacttcctg cagccgtggg cggcggcgga ggctctgtcg    360
gcggatattc cggccgtgat gttcaaaagc acgggtgcgc tcatggcggc catggtcgcg    420
tacgagctga cgtttccgaa ctctgatttt ttctcgcttt ccctgagat tcgtctctcc    480 gagtgcgaga ttaaacagct gaagaacttg tttcaatgtt ctgtgaatga tgcgaaagac    540
aagcaaagga ttaagggatg ttatgagaga tcttgcggca tgattttggt gaaatctttc    600
agagaaatcg aaggcaaata tattgatttt ctctctactc tgctgggcaa gaaggttgtt    660
ccagttggtc cacttgttca acaaacagaa gacgacgtcg tatcaggaag tttttgacgaa    720 tggctaaatg gaaaagatag atcgtcttcc atactcgtgt ctttcggaag cgagttctac    780
ctgtccagag aagacatgga agagatcgcg catggcttag agctgagcca ggtgaacttc    840
atatgggtcg tcaggtttcc ggcgggagga gagagaaaca cgacaaaggt ggaagaagaa    900
ctgccaaaag ggtttctaga gagagttaga gagagaggga tggtggtgga gggctgggcg    960
ccgcaggctc agatcttgaa acatccaagc gtcggcggat tcctcagcca ctgcgggtgg   1020
agctccgtcg tggagagcat gaaattcggc gttccgatca tcgccatgcc gatgcacctc   1080
```

TABLE 1-continued

Sequences disclosed herein.

| | |
|---|---|
| gaccagccgc tgaattcccg gctggtcgag cggctcggcg tcggcgtagt ggtggagaga | 1140 |
| gacggccgcc tccggggaga ggtggagaga gttgtcagag aggtggtggt ggagaaaagt | 1200 |
| ggagagagag tgaggaagaa ggtggaggag tttgcagaga tcatgaagaa gaaaaaagac | 1260 |
| aatgaagaga tggacgtagt cgtggaagag ttggtgacgc tctgcaggaa gaagaagaag | 1320 |
| gaggaggatt tacagagtaa ttattggtgc agaaccgcca ttgatgacca ttgttctgaa | 1380 |
| gtcgtgaaga ttgaagatgc tgcagcagcc gacgaggagc ctctttgcaa ataa | 1434 |

SEQ ID NO: 101
*Siraitia grosvenorii*

| | |
|---|---|
| MLPWLAHGHV SPFFELAKLL AARNFHIFFC STAVNLRSVE PKLSQKLSSH VELVELNLPP | 60 |
| SPELPPHRHT TAGLPPHLMF SLKRAFDMAA PAFAAILRDL NPDLLIYDFL QPWAAAEALS | 120 |
| ADIPAVMFKS TGALMAAMVA YELTFPNSDF FSLFPEIRLS ECEIKQLKNL FQCSVNDAKD | 180 |
| KQRIKGCYER SCGMILVKSF REIEGKYIDF LSTLLGKKVV PVGPLVQQTE DDVVSGSFDE | 240 |
| WLNGKDRSSS ILVSFGSEFY LSREDMEEIA HGLELSQVNF IWVVREPAGG ERNTTKVEEE | 300 |
| LPKGFLERVR ERGMVVEGWA PQAQILKHPS VGGFLSHCGW SSVVESMKFG VPIIAMPMHL | 360 |
| DQPLNSRLVE RLGVGVVVER DGRLRGEVER VVREVVVEKS GERVRKKVEE FAEIMKKKKD | 420 |
| NEEMDVVVEE LVTLCRKKKK EEDLQSNYWC RTAIDDHCSE VVKIEDAAAA DEEPLCK | 477 |

SEQ ID NO: 102
*Siraitia grosvenorii*

| | |
|---|---|
| atggctgtca cttacagcct gcacatagca atgtaccctt ggtttgcttt cggccacttg | 60 |
| actccatttc tccaagtctc caacaagctt gccaaggaag ccacaaaat ctccttcttc | 120 |
| atcccaacga aaacgctaac caaattgcag cctttcaatc tctttccaga tctcattacc | 180 |
| tttgtcccca tcactgttcc tcatgttgat ggtctccctc ttggagctga actactgct | 240 |
| gatgtttctc acccttcaca gctcagtctc atcatgactg ctatggattg cacccaaccc | 300 |
| gaaatcgagt gtcttcttcg agacataaaa cctgatgcca tcttcttcga tttcgcgcac | 360 |
| tgggtgccaa aattggcatg tggattgggc attaagtcga ttgattacag tgtctgttct | 420 |
| gcagtatcaa ttggttatgt tttgccccta ttaaggaaag tttgtggaca agatttatta | 480 |
| actgaagatg attttatgca gccatctcct ggctacccga gttccaccat caatcttcaa | 540 |
| gctcatgagg ctcgatattt tgcatctctg agccgctgga ggtttggcag tgatgtccct | 600 |
| ttctttagtc gccatcttac tgcacttaat gaatgcaatg ctttagcatt caggtcatgt | 660 |
| agggagattg aagggccttt tatagactat ccagaaagtg aattaaaaaa gcctgtgttg | 720 |
| ctttccggag cagtggatct acaaccgcca ccacaactg tagaagaaag atgggcaaaa | 780 |
| tggctatcag ggttcaacac cgactcggtc gtatattgtg catttggaag tgagtgtacc | 840 |
| ttagcaaaag accaattcca agaactgctg tgggttttg agctttcaaa tatgccattc | 900 |
| tttgctgcac ttaaaccacc ttttggtgtt gactcggttg aagcagcctt gcctgaaggt | 960 |
| tttgaacaga gagttcaggg aagaggggtg gtctatgggg gatgggtcca acagcagctc | 1020 |
| attttggagc acccatcaat tggatgcttt gttacacatt gtggatcagg ctccttatca | 1080 |
| gaggcgttag tgaagaagtg tcaattagtg ttgttacctc gtatcggtga ccactttttc | 1140 |
| cgagcaagaa tgttgagcaa ttatttgaaa gttggtgtgg aggtagagaa aggagaagga | 1200 |
| gatggatctt ttacaaagga aagtgtgtgg aaggcagtga agacagtgat ggatgaagag | 1260 |
| aatgaaactg ggaaagagtt cagagcgaac cgtgccaaga taagagagct attgctcgac | 1320 |
| gaagatctcg aggagtctta tatcaacaat ttcatccaca gcctgcatac tttgaatgca | 1380 |

TABLE 1-continued

Sequences disclosed herein.

| | |
|---|---|
| tga | 1383 |

SEQ ID NO: 103
*Siraitia grosvenorii*

| | |
|---|---|
| MAVTYSLHIA MYPWFAFGHL TPFLQVSNKL AKEGHKISFF IPTKTLTKLQ PFNLFPDLIT | 60 |
| FVPITVPHVD GLPLGAETTA DVSHPSQLSL IMTAMDCTQP EIECLLRDIK PDAIFFDFAH | 120 |
| WVPKLACGLG IKSIDYSVCS AVSIGYVLPL LRKVCGQDLL TEDDFMQPSP GYPSSTINLQ | 180 |
| AHEARYFASL SRWRFGSDVP FFSRHLTALN ECNALAFRSC REIEGPFIDY PESELKKPVL | 240 |
| LSGAVDLQPP TTTVEERWAK WLSGFNTDSV VYCAFGSECT LAKDQFQELL LGFELSNMPF | 300 |
| FAALKPPFGV DSVEAALPEG FEQRVQGRGV VYGGWVQQQL ILEHPSIGCF VTHCGSGSLS | 360 |
| EALVKKCQLV LLPRIGDHFF RARMLSNYLK VGVEVEKGEG DGSFTKESVW KAVKTVMDEE | 420 |
| NETGKEFRAN RAKIRELLLD EDLEESYINN FIHSLHTLNA | 460 |

SEQ ID NO: 104
*Siraitia grosvenorii*

| | |
|---|---|
| atggaagcta agaactgcaa aaaggttctg atgttcccat ggctggcgca tggtcacata | 60 |
| tcaccatttg tagagctggc caagaagctc acagacaaca acttcgccgt ttttctatgt | 120 |
| tcttcccctg caaatcttca aaacgtcaag ccaaaactcc cccatcacta ctctgattcc | 180 |
| attgaactcg tggagctcaa ccttccatcg tcgccggagc ttcccccctca tatgcacacc | 240 |
| accaatggcc tcctttgca tttagttccc accctcgttg acgccttgga catggccgct | 300 |
| ccgcacttct ccgccatttt acaggaactg aatccagatt ttctcatatt cgacatcttc | 360 |
| caaccctggg cggctgaaat cgcttcctcc ttcggcgttc ctgctatttt gttgcttatc | 420 |
| gttggatctg ctataaccgc tttaggggtt cattttgtcc ggagctccgg tacggaattc | 480 |
| ccctttcccg agcttactaa atcattcaag aaggaggacg accgaaaacc tccaggagat | 540 |
| tccggcaacg atagaggaaa acggctattc aaatgtctgc tggacctgga acattcttca | 600 |
| gagactattt tggtgaacag ttttacagag atagagggca aatatatgga ctatctctcg | 660 |
| gtcttactga agaagaagat ccttccgatt ggtcctttgg ttcagaaaat tggctccgat | 720 |
| gacgatgaat cgggaatcct ccggtggctt gacaagaaga aaccgaattc aactgtgtac | 780 |
| gtttcgttcg ggagtgagta ctatttgagc aaagaagaca tagcagagct tgcgcatggt | 840 |
| ctggaaatca gcggcgtcaa tttcatctgg attgttcggt ttccaaaggg agagaaaatc | 900 |
| gccattgaag aggcattacc agatgaattt cttgaaagag tcggagagag aggcgtcgtc | 960 |
| gttgatggat gggcgccgca gatgaaaata ttagggcatt cgagcgtcgg cgggtttctg | 1020 |
| tctcactgcg gatggaactc tgtgctggag agtctggtgc tcggcgtgcc gatcatatcc | 1080 |
| ctgccgatac acctcgaaca gccgtggaac gccttggtag cggagcacgt cggcgtttgt | 1140 |
| gtgagggcga agagagacga cggaggaaat cttcaaagag agttggtggc ggaggccatt | 1200 |
| aaagaagtgg tggttgagga acaggagcg gaactgagaa gcaaagcaag agtaattagt | 1260 |
| gaaatcttga aaataaaga agctgaaaca atacaagatt tggtggctga gcttcaccgg | 1320 |
| ctttctgacg caagaagagc ttgttga | 1347 |

SEQ ID NO: 105
*Siraitia grosvenorii*

| | |
|---|---|
| MEAKNCKKVL MFPWLAHGHI SPFVELAKKL TDNNFAVFLC SSPANLQNVK PKLPHHYSDS | 60 |
| IELVELNLPS SPELPPHMHT TNGLPLHLVP TLVDALDMAA PHFSAILQEL NPDFLIFDIF | 120 |
| QPWAAEIASS FGVPAILLLI VGSAITALGV HFVRSSGTEF PFPELTKSFK KEDDRKPPGD | 180 |
| SGNDRGKRLF KCLLDLEHSS ETILVNSFTE IEGKYMDYLS VLLKKKILPI GPLVQKIGSD | 240 |

TABLE 1-continued

Sequences disclosed herein.

```
DDESGILRWL DKKKPNSTVY VSFGSEYYLS KEDIAELAHG LEISGVNFIW IVRFPKGEKI       300

AIEEALPDEF LERVGERGVV VDGWAPQMKI LGHSSVGGFL SHCGWNSVLE SLVLGVPIIS       360

LPIHLEQPWN ALVAEHVGVC VRAKRDDGGN LQRELVAEAI KEVVVEETGA ELRSKARVIS       420

EILKNKEAET IQDLVAELHR LSDARRAC                                          448

SEQ ID NO: 106
Siraitia grosvenorii
atggaaaaaa atcttcacat agtgatgctt ccatggtcgg cgttcggcca tctcatacca        60 tttttttcacc tctccatagc cttagccaaa gccaaagttt atatctcctt cgtctccact      120
ccaagaaata ttcagagact yccccaaatc ccgccggact tagcttcttt catagatttg      180
gtggccattc ccttgccgag actcgacgac gatctgttgc tagaatctgc agaggccact      240
tctgatattc cgatcgacaa gattcagtat ttgaagcgag ccgtcgacct cctccgccac      300
cccttcaaga gtttgtcgc cgaacaatcg ccggactggg tcgtcgttga ttttcatgct       360
tattgggccg gcgagatcta ccaggagttt caagttcccg tcgcctactt ctgtattttc      420
tcggccatct gtttgcttta tcttggacct ccagacgtgt attcgaagga tcctcagatc      480
atggcacgaa tatctcccgt taccatgacg gtgccgccgg agtgggtcgg ttttccgtcc      540
gccgtagcct acaacttgca tgaggcgacg gtcatgtact ctgctctcta tgaaacaaat      600
gggtctggaa taagcgactg cgagaggatt cgccggctcg tcctttcctg tcaagccgtg      660
gccattcgaa gctgcgagga gattgaaggc gaataccta ggttatgtaa gaaactgatt      720
ccaccgcagg ggattgccgt cggcttgctt ccgccggaaa agccaccaaa atcagatcac      780
gagctcatca aatggcttga cgagcaaaag ctccgattcg tcgtgtacgt gacattcggc      840
agcgaatgca acctgacgaa ggaccaagtt cacgagatag cccacgggct ggaactgtcg      900
gagctgccat ttatggggc actgaggaaa cccagctggg cagctgagga agacgatggg      960
ctgccgtctg ggtttcgtga gaacgtcc gggagagggg tggtgagcat ggagtgggtg     1020
ccgcagttgg agattctggc gcaccaggcc atcggcgtct ctttagttca cgggggctgg     1080
ggctctatta tcgagtcgct acaagctggg cactgtctgg ttgtgctgcc gtttatcatc     1140
gaccagccgc tgaactcaaa gcttttggtg gagaaaggga tggcgcttga atcagaagg      1200 aacggttctg atggatggtt tagtagagaa gacatcgccg gaactttgag agaagctatg     1260
cggtcgtctg aggaaggcgg gcagctgagg agccgtgcaa agaggcggc ggccatcgtt     1320 ggagatgaga agctgcagtg ggaacaatac ttcggcgcgt tcgtacagtt tctgagggac     1380
aagtcttga                                                              1389

SEQ ID NO: 107
Siraitia grosvenorii
MEKNLHIVML PWSAFGHLIP FFHLSIALAK AKVYISFVST PRNIQRXPQI PPDLASFIDL        60

VAIPLPRLDD DLLLESAEAT SDIPIDKIQY LKRAVDLLRH PFKKFVAEQS PDWVVVDFHA      120

YWAGEIYQEF QVPVAYFCIF SAICLLYLGP PDVYSKDPQI MARISPVTMT VPPEWVGFPS      180

AVAYNLHEAT VMYSALYETN GSGISDCERI RRLVLSCQAV AIRSCEEIEG EYLRLCKKLI      240

PPQGIAVGLL PPEKPPKSDH ELIKWLDEQK LRFVVYVTFG SECNLTKDQV HEIAHGLELS      300

ELPFLWALRK PSWAAEEDDG LPSGFRERTS GRGVVSMEWV PQLEILAHQA IGVSLVHGGW      360

GSIIESLQAG HCLVVLPFII DQPLNSKLLV EKGMALEIRR NGSDGWFSRE DIAGTLREAM      420

RSSEEGGQLR SRAKEAAAIV GDEKLQWEQY FGAFVQFLRD KS                         462

SEQ ID NO: 108
```

TABLE 1-continued

Sequences disclosed herein.

*Siraitia grosvenorii*

| | |
|---|---|
| atgtccgagg agaaaggcag agggcacagc tcgtcgacgg agagacacac tgctgccgcc | 60 |
| atgaacgccg agaaacgaag caccaaaatc ttgatgctcc catggctggc tcacggccac | 120 |
| atatctccat acttcgagct cgccaagagg ctcaccaaga aaaactgcca cgtttacttg | 180 |
| tgttcttcgc ctgtaaatct ccaaggcatc aagccgaaac tctctgaaaa ttactcttcc | 240 |
| tccattgaac ttgtggagct tcatcttcca tctctcccg accttcctcc ccatatgcac | 300 |
| acgaccaaag gcatccctct acatctacaa tccacccctca tcaaagcctt cgacatggcc | 360 |
| gcccctgatt tttccgacct gttgcagaaa ctcgagccgg atctcgtcat ttccgatctc | 420 |
| ttccagccat gggcagttca attagcgtcg tctcggaaca ttcccgtcgt caatttcgtt | 480 |
| gtcaccggag tcgctgttct tagtcgtttg gctcacgtgt tttgcaactc cgttaaggaa | 540 |
| ttccctttcc cggaactcga tctaaccgac cattggatct ccaagagccg ccgcaaaacg | 600 |
| tccgacgaat taggtcgcga gtgcgcgatg cgattttca actgcatgaa acaatcttca | 660 |
| aacatcactc tagccaacac tttccccgag ttcgaagaaa aatacatcga ttatctctct | 720 |
| tcctcgttta agaaaaagat tcttccggtt gctcctctag ttcctgaaat cgacgcagac | 780 |
| gacgagaaat cggaaattat cgagtggctt gacaagaaga accgaaatc gactgtttac | 840 |
| gtttcgtttg ggagtgagta ttatctgacg aaagaagaca gggaagagct cgcccatggc | 900 |
| ttagaaaaga gcggcgtgaa tttcatctgg gttattaggt tccaaagggg cgagaagatc | 960 |
| accattgaag gcttttacc agaaggattt ctcgagagag taggggacag gggagtgatt | 1020 |
| atcgacgggt gggcgccgca gttgaaaata ttgaggcatt caagcgtggg cgggttcgtg | 1080 |
| tgccactgcg gtggaactc tgtggtggag agcgtggtgt ttggggtgcc gatcatagcc | 1140 |
| ttgccgatgc agctcgatca gccatggcat gcgaaggtgg cggaggacgg cggcgtctgt | 1200 |
| gcggaggcga agagagacgt tgaagggagc gttcagagag aagaggtggc gaaggccatt | 1260 |
| aaagaggtgg tgtttgagaa gaaggggggg gttctgagtg gaaaagcaag agagatcagc | 1320 |
| gaggccttga gaagagggaa aggggaaatc atagaggaat tggttgctga gtttcaccag | 1380 |
| ctctgtgaag cttga | 1395 |

SEQ ID NO: 109
*Siraitia grosvenorii*

| | |
|---|---|
| MSEEKGRGHS SSTERHTAAA MNAEKRSTKI LMLPWLAHGH ISPYFELAKR LTKKNCHVYL | 60 |
| CSSPVNLQGI KPKLSENYSS SIELVELHLP SLPDLPPHMH TTKGIPLHLQ STLIKAFDMA | 120 |
| APDFSDLLQK LEPDLVISDL FQPWAVQLAS SRNIPVVNFV VTGVAVLSRL AHVFCNSVKE | 180 |
| FPFPELDLTD HWISKSRRKT SDELGRECAM RFFNCMKQSS NITLANTFPE FEEKYIDYLS | 240 |
| SSFKKKILPV APLVPEIDAD DEKSEIIEWL DKKKPKSTVY VSFGSEYYLT KEDREELAHG | 300 |
| LEKSGVNFIW VIRFPKGEKI TIEEALPEGF LERVGDRGVI IDGWAPQLKI LRHSSVGGFV | 360 |
| CHCGWNSVVE SVVFGVPIIA LPMQLDQPWH AKVAEDGGVC AEAKRDVEGS VQREEVAKAI | 420 |
| KEVVFEKKGG VLSGKAREIS EALRKREGEI IEELVAEFHQ LCEA | 464 |

SEQ ID NO: 114
*Saccharomyces cerevisiae*

| | |
|---|---|
| atgctttcgc ttaaaacgtt actgtgtacg ttgttgactg tgtcatcagt actcgctacc | 60 |
| ccagtccctg caagagaccc ttcttccatt caatttgttc atgaggagaa caagaaaaga | 120 |
| tactacgatt atgaccacgg ttccctcgga gaaccaatcc gtggtgtcaa cattggtggt | 180 |
| tggttacttc ttgaaccata cattactcca tctttgttcg aggctttccg tacaaatgat | 240 |
| gacaacgacg aaggaattcc tgtcgacgaa tatcacttct gtcaatattt aggtaaggat | 300 |

TABLE 1-continued

Sequences disclosed herein.

```
ttggctaaaa gccgtttaca gagccattgg tctactttct accaagaaca agatttcgct      360
aatattgctt cccaaggttt caaccttgtc agaattccta tcggttactg ggcttttccaa     420 actttggacg atgatcctta tgttagcggc ctacaggaat cttacctaga ccaagccatc     480
ggttgggcta gaaacaacag cttgaaagtt tgggttgatt tgcatggtgc cgctggttcg     540
cagaacgggt ttgataactc tggtttgaga gattcataca gttttttgga agacagcaat     600
ttggccgtta ctacaaatgt cttgaactac atattgaaaa atactctgcg gaggaatac      660 ttggacactg ttattggtat cgaattgatt aatgagccat gggtcctgt tctagacatg      720 gataaaatga agaatgacta cttggcaccct gcttacgaat acttgagaaa caacatcaag    780
agtgaccaag ttatcatcat ccatgacgct ttccaaccat acaattattg ggatgacttc     840
atgactgaaa acgatggcta ctggggtgtc actatcgacc atcatcacta ccaagtcttt     900
gcttctgatc aattggaaag atccattgat gaacatatta agtagcttg tgaatggggt      960 accggagttt tgaatgaatc ccactggact gtttgtggtg agtttgctgc cgctttgact    1020
gattgtacaa aatggttgaa tagtgttggc ttcggcgcta gatacgacgg ttcttgggtc   1080
aatggtgacc aaacatcttc ttacattggc tcttgtgcta acaacgatga tatagcttac   1140
tggtctgacg aaagaaagga aaacacaaga cgttatgtgg aggcacaact agatgccttt   1200
gaaatgagag ggggttggat tatctggtgt tacaagacag aatctagttt ggaatgggat   1260
gctcaaagat tgatgttcaa tggtttattc cctcaaccat tgactgacag aaagtatcca   1320
aaccaatgtg gcacaatttc taactaa                                         1347
```

SEQ ID NO: 115
*Saccharomyces cerevisiae*

```
MLSLKTLLCT LLTVSSVLAT PVPARDPSSI QFVHEENKKR YYDYDHGSLG EPIRGVNIGG      60

WLLLEPYITP SLFEAFRTND DNDEGIPVDE YHFCQYLGKD LAKSRLQSHW STFYQEQDFA    120

NIASQGFNLV RIPIGYWAFQ TLDDDPYVSG LQESYLDQAI GWARNNSLKV WVDLHGAAGS    180

QNGFDNSGLR DSYKFLEDSN LAVTTNVLNY ILKKYSAEEY LDTVIGIELI NEPLGPVLDM   240

DKMKNDYLAP AYEYLRNNIK SDQVIIIHDA FQPYNYWDDF MTENDGYWGV TIDHHHYQVF    300

ASDQLERSID EHIKVACEWG TGVLNESHWT VCGEFAAALT DCTKWLNSVG FGARYDGSWV    360

NGDQTSSYIG SCANNDDIAY WSDERKENTR RYVEAQLDAF EMRGGWIIWC YKTESSLEWD    420

AQRLMFNGLF PQPLTDRKYP NQCGTISN                                        448
```

SEQ ID NO: 116
*Saccharomyces cerevisiae*

```
atgcctttga agtcgttttt tttttcagca tttctagttt tatgcctgtc taaattcacg       60
caaggcgttg gcaccacaga gaaggaagaa tcgttatcgc ctttggaact aaatatttta    120
caaaacaaat tcgcctccta ctatgcaaac gacactatca ccgtgaaagg tattactatt    180
ggcggctggc tagtaacaga accttatatc acgccatcat tatatcgtaa tgctacgtca    240
ctggcaaaac agcaaaactc ttccagcaat atctccattg tcgacgaatt tactctttgt   300
aaaaccttag gatataacac ctctctaact ttattggata tcacttcaa aacttggatt    360 acagaggatg attttgaaca aatcaaaacc aacggtttca atttagttag gatccccatc   420
ggatattggg cgtggaaaca aaatactgat aaaaacttgt acatcgataa cataactttc   480
aatgatccat acgtaagtga tggattacaa ctgaaatatt taaataatgc tctcgaatgg   540
gcgcaaaagt acgaactaaa tgtatggtta gatctacatg gtgctcctgg atcccagaat   600
ggattcgata attccggtga aagaatactc tatggcgatt taggctggtt aaggttgaat   660
```

TABLE 1-continued

Sequences disclosed herein.

```
aatactaaag aactgactct ggctatttgg agagatatgt tccagacatt tttaaataaa        720
ggtgacaaaa gtcctgtggt gggtattcaa atcgtcaacg aaccgcttgg tggcaaaatc        780
gatgtttcag acataacgga gatgtattac gaagcatttg acttgctcaa gaaaaatcag        840
aattcgagtg acaacactac gtttgttatt catgacggtt ttcaaggaat cggtcactgg        900
aacttggagc taaacccaac ctaccagaat gtatcgcatc attatttcaa tttgactggt        960
gcaaattaca gctctcaaga tatattggtc gaccatcatc attatgaagt gtttactgat       1020
gcgcaattgg ccgaaactca gtttgcacgt attgaaaaca ttatcaatta tgggactct        1080 atccacaaag aactttcttt tcacccagca gtagtcggag aatggtcagg cgctattact       1140
gattgtgcaa cctggctaaa tggtgttggg gtgggtgcac gttacgatgg atcatactac       1200
aatacaacgt tgtttaccac caacgacaag ccagttggaa catgtatatc ccaaaatagc       1260
ttagctgatt ggacgcaaga ttaccgtgac cgtgtgagca aattcattga ggcacagcta       1320
gccacttatt cgtcaaaaac aacgggatgg attttttgga attggaagac cgaagacgcc       1380
gtagaatggg attatttgaa gctaaaagaa gctaacctttt cccttccccc tttcgacaac       1440
tacacgtact tcaaagcaga tggatctatc gaagaaaaat tctcatcctc tttatcagca       1500
caggcatttc caagaacaac gtcatcggtt ttgtcctcca ctacgacttc caggaagagt       1560
aagaatgctg caatttctaa taaactaaca acttcgcagc tattaccaat caaaaatatg       1620
agtttgacct ggaaagcgag cgtatgcgca ctcgctatca ccattgccgc tctttgcgct       1680
tctctttaa                                                               1689
```

SEQ ID NO: 117
*Saccharomyces cerevisiae*

```
MPLKSFFFSA FLVLCLSKFT QGVGTTEKEE SLSPLELNIL QNKFASYYAN DTITVKGITI        60

GGWLVTEPYI TPSLYRNATS LAKQQNSSSN ISIVDEFTLC KTLGYNTSLT LLDNHFKTWI       120

TEDDFEQIKT NGFNLVRIPI GYWAWKQNTD KNLYIDNITF NDPYVSDGLQ LKYLNNALEW      180

AQKYELNVWL DLHGAPGSQN GFDNSGERIL YGDLGWLRLN NTKELTLAIW RDMFQTFLNK      240

GDKSPVVGIQ IVNEPLGGKI DVSDITEMYY EAFDLLKKNQ NSSDNTTFVI HDGFQGIGHW      300

NLELNPTYQN VSHHYFNLTG ANYSSQDILV DHHHYEVFTD AQLAETQFAR IENIINYGDS      360

IHKELSFHPA VVGEWSGAIT DCATWLNGVG VGARYDGSYY NTTLFTTNDK PVGTCISQNS      420

LADWTQDYRD RVRQFIEAQL ATYSSKTTGW IFWNWKTEDA VEWDYLKLKE ANLFPSPFDN      480

YTYFKADGSI EEKFSSSLSA QAFPRTTSSV LSSTTTSRKS KNAAISNKLT TSQLLPIKNM      540

SLTWKASVCA LAITIAALCA SL                                              562
```

SEQ ID NO: 118
*Saccharomyces cerevisiae*

```
MTEFYSDTIG LPKTDPRLWR LRTDELGRES WEYLTPQQAA NDPPSTFTQW LLQDPKFPQP        60

HPERNKHSPD FSAFDACHNG ASFFKLLQEP DSGIFPCQYK GPMFMTIGYV AVNYIAGIEI       120

PEHERIELIR YIVNTAHPVD GGWGLHSVDK STVFGTVLNY VILRLLGLPK DHPVCAKARS      180

TLLRLGGAIG SPHWGKIWLS ALNLYKWEGV NPAPPETWLL PYSLPMHPGR WWVHTRGVYI      240

PVSYLSLVKF SCPMTPLLEE LRNEIYTKPF DKINFSKNRN TVCGVDLYYP HSTTLNIANS      300

LVVFYEKYLR NRFIYSLSKK KVYDLIKTEL QNTDSLCIAP VNQAFCALVT LIEEGVDSEA      360

FQRLQYRFKD ALFHGPQGMT IMGTNGVQTW DCAFAIQYFF VAGLAERPEF YNTIVSAYKF      420

LCHAQFDTEC VPGSYRDKRK GAWGFSTKTQ GYTVADCTAE AIKAIIMVKN SPVFSEVHHM      480

ISSERLFEGI DVLLNLQNIG SFEYGSFATY EKIKAPLAME TLNPAEVFGN IMVEYPYVEC      540
```

TABLE 1-continued

Sequences disclosed herein.

```
TDSSVLGLTY FHKYFDYRKE EIRTRIRIAI EFIKKSQLPD GSWYGSWGIC FTYAGMFALE    600

ALHTVGETYE NSSTVRKGCD FLVSKQMKDG GWGESMKSSE LHSYVDSEKS LVVQTAWALI    660

ALLFAEYPNK EVIDRGIDLL KNRQEESGEW KFESVEGVFN HSCAIEYPSY RFLFPIKALG    720

MYSRAYETHT L                                                          731
```

SEQ ID NO: 119
*Saccharomyces cerevisiae*
```
MGKLLQLALH PVEMKAALKL KFCRTPLFSI YDQSTSPYLL HCFELLNLTS RSFAAVIREL     60

HPELRNCVTL FYLILRALDT IEDDMSIEHD LKIDLLRHFH EKLLLTKWSF DGNAPDVKDR    120

AVLTDFESIL IEFHKLKPEY QEVIKEITEK MGNGMADYIL DENYNLNGLQ TVHDYDVYCH    180

YVAGLVGDGL TRLIVIAKFA NESLYSNEQL YESMGLFLQK TNIIRDYNED LVDGRSFWPK    240

EIWSQYAPQL KDFMKPENEQ LGLDCINHLV LNALSHVIDV LTYLAGIHEQ STFQFCAIPQ    300

VMAIATLALV FNNREVLHGN VKIRKGTTCY LILKSRTLRG CVEIFDYYLR DIKSKLAVQD    360

PNFLKLNIQI SKIEQFMEEM YQDKLPPNVK PNETPIFLKV KERSRYDDEL VPTQQEEEYK    420

FNMVLSIILS VLLGFYYIYT LHRA                                            444
```

SEQ ID NO: 120
*Saccharomyces cerevisiae*
```
atgtctgtta ttaatttcac aggtagttct ggtccattgg tgaaagtttg cggcttgcag     60
agcacagagg ccgcagaatg tgctctagat tccgatgctg acttgctggg tattatatgt    120
gtgcccaata gaaagagaac aattgacccg gttattgcaa ggaaaatttc aagtcttgta    180
aaagcatata aaaatagttc aggcactccg aaatacttgg ttggcgtgtt cgtaatcaa     240 cctaaggagg atgttttggc tctggtcaat gattacggca ttgatatcgt ccaactgcat    300
ggagatgagt cgtggcaaga ataccaagag ttcctcggtt tgccagttat taaaagactc    360
gtatttccaa aagactgcaa catactactc agtgcagctt cacagaaacc tcattcgttt    420
attcccttgt ttgattcaga agcaggtggg acaggtgaac ttttggattg aactcgatt     480 tctgactggg ttggaaggca agagagcccc gaaagcttac attttatgtt agctggtgga    540
ctgacgccag aaaatgttgg tgatgcgctt agattaaatg gcgttattgg tgttgatgta    600
agcggaggtg tggagacaaa tggtgtaaaa gactctaaca aaatagcaaa tttcgtcaaa    660
aatgctaaga aatag                                                      675
```

SEQ ID NO: 121
*Saccharomyces cerevisiae*
```
MSVINFTGSS GPLVKVCGLQ STEAAECALD SDADLLGIIC VPNRKRTIDP VIARKISSLV     60

KAYKNSSGTP KYLVGVFRNQ PKEDVLALVN DYGIDIVQLH GDESWQEYQE FLGLPVIKRL    120

VFPKDCNILL SAASQKPHSF IPLFDSEAGG TGELLDWNSI SDWVGRQESP ESLHFMLAGG    180

LTPENVGDAL RLNGVIGVDV SGGVETNGVK DSNKIANFVK NAKK                      224
```

SEQ ID NO: 122
*Saccharomyces cerevisiae*
```
atggcagctg accaattggt gaaaactgaa gtcaccaaga agtcttttac tgctcctgta     60
caaaaggctt ctacaccagt tttaaccaat aaaacagtca tttctggatc gaaagtcaaa    120
agtttatcat ctgcgcaatc gagctcatca ggaccttcat catctagtga ggaagatgat    180
tcccgcgata ttgaaagctt ggataagaaa atacgtcctt tagaagaatt agaagcatta    240
ttaagtagtg gaaatacaaa acaattgaag aacaaagagg tcgctgcctt ggttattcac    300
ggtaagttac ctttgtacgc tttggagaaa aaattaggtg atactacgag agcggttgcg    360
gtacgtagga aggctctttc aattttggca gaagctcctg tattagcatc tgatcgttta    420
```

TABLE 1-continued

Sequences disclosed herein.

```
ccatataaaa attatgacta cgaccgcgta tttggcgctt gttgtgaaaa tgttataggt    480
tacatgcctt tgcccgttgg tgttataggc cccttggtta tcgatggtac atcttatcat    540
ataccaatgg caactacaga gggttgtttg gtagcttctg ccatgcgtgg ctgtaaggca    600
atcaatgctg gcggtggtgc aacaactgtt ttaactaagg atggtatgac aagaggccca    660
gtagtccgtt tcccaacttt gaaaagatct ggtgcctgta agatatggtt agactcagaa    720
gagggacaaa acgcaattaa aaaagctttt aactctacat caagatttgc acgtctgcaa    780
catattcaaa cttgtctagc aggagattta ctcttcatga gatttagaac aactactggt    840
gacgcaatgg gtatgaatat gatttctaaa ggtgtcgaat actcattaaa gcaaatggta    900
gaagagtatg gctgggaaga tatggaggtt gtctccgttt ctggtaacta ctgtaccgac    960
aaaaaaccag ctgccatcaa ctggatcgaa ggtcgtggta agagtgtcgt cgcagaagct   1020
actattcctg gtgatgttgt cagaaaagtg ttaaaaagtg atgtttccgc attggttgag   1080
ttgaacattg ctaagaattt ggttggatct gcaatggctg gtctgttgg tggatttaac   1140 gcacatgcag ctaatttagt gacagctgtt ttcttggcat taggacaaga tcctgcacaa   1200
aatgttgaaa gttccaactg tataacattg atgaaagaag tggacggtga tttgagaatt   1260
tccgtatcca tgccatccat cgaagtaggg accatcggtg gtgtactgt tctagaacca   1320 caaggtgcca tgttggactt attaggtgta agaggcccgc atgctaccgc tcctggtacc   1380
aacgcacgtc aattagcaag aatagttgcc tgtgccgtct tggcaggtga attatcctta   1440
tgtgctgccc tagcagccgg ccatttggtt caaagtcata tgacccacaa caggaaacct   1500
gctgaaccaa caaaacctaa caatttggac gccactgata taaatcgttt gaaagatggg   1560
tccgtcacct gcattaaatc ctaa                                          1584
```

SEQ ID NO: 123
*Saccharomyces cerevisiae*

```
MAADQLVKTE VTKKSFTAPV QKASTPVLTN KTVISGSKVK SLSSAQSSSS GPSSSSEEDD    60

SRDIESLDKK IRPLEELEAL LSSGNTKQLK NKEVAALVIH GKLPLYALEK KLGDTTRAVA   120

VRRKALSILA EAPVLASDRL PYKNYDYDRV FGACCENVIG YMPLPVGVIG PLVIDGTSYH   180

IPMATTEGCL VASAMRGCKA INAGGGATTV LTKDGMTRGP VVRFPTLKRS GACKIWLDSE   240

EGQNAIKKAF NSTSRFARLQ HIQTCLAGDL LFMRFRTTTG DAMGMNMISK GVEYSLKQMV   300

EEYGWEDMEV VSVSGNYCTD KKPAAINWIE GRGKSVVAEA TIPGDVVRKV LKSDVSALVE   360

LNIAKNLVGS AMAGSVGGFN AHAANLVTAV FLALGQDPAQ NVESSNCITL MKEVDGDLRI   420

SVSMPSIEVG TIGGGTVLEP QGAMLDLLGV RGPHATAPGT NARQLARIVA CAVLAGELSL   480

CAALAAGHLV QSHMTHNRKP AEPTKPNNLD ATDINRLKDG SVTCIKS                527
```

What is claimed is:

1. A recombinant host cell capable of producing one or more mogroside compounds in a cell culture, the host cell comprising a recombinant gene encoding a polypeptide capable of deglycosylating a mogroside precursor and having at least 90% sequence identity to the amino acid sequence set forth in SEQ ID NO:2;
   wherein the polypeptide:
   (a) comprises a catalytically active portion of an endogenous glucosidase polypeptide or an endogenous glucanase polypeptide;
   (b) does not comprise a signal peptide or a transmembrane domain that is comprised by the endogenous glucoside polypeptide; and
   (c) is free of a domain facilitating secretion of the polypeptide from the host cell;
   wherein the host cell is capable of retaining at least about 50% of the expressed polypeptide capable of deglycosylating the mogroside precursor in a cytosol of the host cell;
   wherein the one or more mogroside compounds are a deglycosylation product of the mogroside precursor; and
   wherein expression of the gene increases production of the one or more mogroside compounds.

2. The recombinant host cell of claim 1, wherein expression of the gene increases a cytosolic mogroside precursor deglycosylation activity of the host cell by at least about 10% relative to a corresponding host cell lacking the gene.

3. The recombinant host cell of claim 1, wherein expression of the gene increases a cytosolic mogroside precursor deglycosylation activity of the polypeptide capable of deglycosylating the mogroside precursor comprising the host cell by at least about 10% relative to a corresponding host cell lacking the gene.

4. The recombinant host cell of claim 1, wherein the mogroside precursor is a tri-glycosylated mogrol, comprising mogroside III (MG-III), mogroside III A1 (MG-IIIA1), mogroside III A2 (MG-IIIA2), or mogroside III E (MG-IIIE), a tetra-glycosylated mogrol, comprising mogroside IV (MG-IV), mogroside IV A (MG-IVA), or siamenoside I (SM-I), a penta-glycosylated mogrol, comprising mogroside V (MG-V) or 11-oxo-mogroside V (11-O-MG-V), a hexa-glycosylated mogrol, or an isomer thereof.

5. The recombinant host cell of claim 1, wherein the one or more mogroside compounds are a di-glycosylated mogroside compound, comprising mogroside II A (MG-IIA), mogroside II A1 (MG-IIA1), mogroside II A2 (MG-IIA2), or mogroside II E (MG-IIE), a tri-glycosylated mogroside compound, comprising MG-Ill, MG-IIIA1, MG-IIIA2, or MG-IIIE, a tetra-glycosylated mogroside compound, comprising MG-IV, MG-IVA, or SM-I, a penta-glycosylated mogroside compound, comprising MG-V or 11-O-MG-V, or an isomer thereof.

6. The recombinant host cell of claim 1, further comprising:
   (a) a gene encoding a polypeptide capable of synthesizing squalene from farnesyl pyrophosphate (FPP);
      wherein the polypeptide capable of synthesizing squalene from FPP comprises a polypeptide having at least 90% sequence identity to the amino acid sequence set forth in SEQ ID NO:119;
   (b) a gene encoding a polypeptide capable of synthesizing oxidosqualene from squalene;
      wherein the polypeptide capable of synthesizing oxidosqualene from squalene comprises a polypeptide having at least 90% sequence identity to the amino acid sequence set forth in any one of SEQ ID NOs:3-21,
   (c) a gene encoding a polypeptide capable of synthesizing cucurbitadienol from oxidosqualene, or 24,25-epoxy-cucurbitadienol from dioxidosqualene;
      wherein the polypeptide capable of synthesizing cucurbitadienol from oxidosqualene, or 24,25-epoxy-cucurbitadienol from dioxidosqualene comprises a polypeptide having at least 90% sequence identity to the amino acid sequence set forth in any one of SEQ ID NOs:24-26;
   (d) a gene encoding a polypeptide capable of synthesizing 24,25-epoxy-cucurbitadienol from cucurbitadienol, or 11-hydroxy-24,25-epoxy-cucurbitadienol from 11-hydroxy-cucurbitadienol;
      wherein the polypeptide capable of synthesizing 24,25-epoxy-cucurbitadienol from cucurbitadienol, or 11-hydroxy-24,25-epoxy-cucurbitadienol from 11-hydroxy-cucurbitadienol comprises a polypeptide having at least 90% sequence identity to the amino acid sequence set forth in SEQ ID NO:29;
   (e) a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol;
      wherein the polypeptide capable of synthesizing 11-hydroxy-cucurbitadienol from cucurbitadienol, or 11-hydroxy-24,25-epoxy-cucurbitadienol from 24,25-epoxy-cucurbitadienol comprises a polypeptide having at least 90% sequence identity to the amino acid sequence set forth in SEQ ID NO:31;
   (f) a gene encoding a polypeptide capable of reducing a cytochrome P450 complex;
      wherein the polypeptide capable of reducing a cytochrome P450 complex comprises a polypeptide having at least 90% sequence identity to the amino acid sequence set forth in SEQ ID NO:34; and
   (g) a gene encoding a polypeptide capable of synthesizing mogrol from 11-hydroxy-cucurbitadienol or 11-hydroxy-24,25-epoxy-cucurbitadienol;
      wherein the polypeptide capable of synthesizing mogrol from 11-hydroxy-cucurbitadienol or 11-hydroxy-24,25-epoxy-cucurbitadienol comprises a polypeptide having at least 90% sequence identity to the amino acid sequence set forth in any one of SEQ ID NO:36, 39, 41, 43, 47, 49, 51, 53, 55, 57, 59, 61, 65, 67, 69, 71, 73, or 75; and further comprising:
   (h) a gene encoding a polypeptide capable of glycosylating mogrol or a mogroside compound at its C3 hydroxyl group, C11 hydroxyl group, C24 hydroxyl group, and/or C25 hydroxyl group thereof;
      wherein the polypeptide capable of glycosylating mogrol or a mogroside compound at its C3 hydroxyl group, C11 hydroxyl group, C24 hydroxyl group, and/or C25 hydroxyl group thereof comprises a polypeptide having at least 90% sequence identity to the amino acid sequence set forth in any one of SEQ ID NOs:76-80, 83, 86, or 89; and/or
   (i) a gene encoding a polypeptide capable of beta-1,2-glycosylation of the C2' position of a 24-O-glucose and/or beta-1,6-glycosylation of the C6' position of a 3-O-glucose and/or the 24-O-glucose of a mogroside compound;
      wherein the polypeptide comprises a polypeptide having at least 70% sequence identity to the amino acid sequence set forth in any one of SEQ ID NOs:93, 95, 99, 101, 103, 105, 107, or 109;
wherein at least one of the genes is a recombinant gene.

7. The recombinant host cell of claim 1, wherein the recombinant host cell further has reduced expression of an endogenous gene encoding a polypeptide having at least 90% sequence identity to the amino acid sequence set forth in any one of SEQ ID NOs:115, 117, or 118.

8. The recombinant host cell of claim 1, wherein the recombinant host cell comprises a plant cell, a mammalian cell, an insect cell, a fungal cell from *Aspergillus* genus, or a yeast cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous,* or *Candida albicans* species, an algal cell, or a bacterial cell from *Escherichia coli* species or *Bacillus* genus.

9. A cell culture, comprising the recombinant host cell of claim 1, the cell culture further comprising:
(a) the one or more mogroside compounds produced by the recombinant host cell;
(b) glucose, fructose, sucrose, xylose, rhamnose, uridine diphosphate (UDP)-glucose, UDP-rhamnose, UDP-xylose, and/or N-acetyl-glucosamine; and
(c) supplemental nutrients comprising trace metals, vitamins, salts, YNB, and/or amino acids;
wherein the one or more mogroside compounds is present at a concentration of at least 1 mg/liter of the cell culture.

10. A cell lysate from the recombinant host cell of claim 1 grown in the cell culture, wherein the cell lysate comprises:
(a) the one or more mogroside compounds produced by the recombinant host cell;
(b) glucose, fructose, sucrose, xylose, rhamnose, uridine diphosphate (UDP)-glucose, UDP-rhamnose, UDP-xylose, and/or N-acetyl-glucosamine; and
(c) supplemental nutrients comprising trace metals, vitamins, salts, YNB, and/or amino acids;
wherein the one or more mogroside compounds is present at a concentration of at least 1 mg/liter of the cell culture.

11. A method of producing one or more mogroside compounds, comprising whole cell bioconversion of one or more plant-derived or synthetic mogroside precursors in a cell culture medium of the recombinant host cell of claim 1 using a polypeptide capable of deglycosylating a mogroside precursor and having at least 90% sequence identity to the amino acid sequence set forth in SEQ ID NO:2;
wherein the polypeptide is expressed in the recombinant host cell; and
wherein the one or more mogroside compounds are a deglycosylation product of the mogroside precursor;
and producing the one or more mogroside compounds thereby.

12. The method of claim 11, further comprising whole cell bioconversion of one or more plant-derived or synthetic mogrol precursors in a cell culture medium of the recombinant host cell, further using:
(a) a polypeptide capable of synthesizing squalene from farnesyl pyrophosphate (FPP) having at least 90% sequence identity to the amino acid sequence set forth in SEQ ID NO:119;
(b) a polypeptide capable of synthesizing oxidosqualene from squalene having at least 90% sequence identity to the amino acid sequence set forth in any one of SEQ ID NOs:3-21;
(c) a polypeptide capable of synthesizing cucurbitadienol from oxidosqualene, or 24,25-epoxy-cucurbitadienol from dioxidosqualene having at least 90% sequence identity to the amino acid sequence set forth in any one of SEQ ID NOs:24-26;
(d) a polypeptide capable of synthesizing 24,25-epoxy-cucurbitadienol from cucurbitadienol, or 11-hydroxy-24,25-epoxy-cucurbitadienol from 11-hydroxy-cucurbitadienol having at least 90% sequence identity to the amino acid sequence set forth in SEQ ID NO:29;
(e) a polypeptide capable of synthesizing 11-hydroxy-cucurbitadienol from cucurbitadienol, or 11-hydroxy-24,25-epoxy-cucurbitadienol from 24,25-epoxy-cucurbitadienol having at least 90% sequence identity to the amino acid sequence set forth in SEQ ID NO:31;
(f) a polypeptide capable of reducing a cytochrome P450 complex having at least 90% sequence identity to the amino acid sequence set forth in SEQ ID NO:34; and/or
(g) a polypeptide capable of synthesizing mogrol from 11-hydroxy-cucurbitadienol or 11-hydroxy-24,25-epoxy-cucurbitadienol having at least 90% sequence identity to the amino acid sequence set forth in any one of SEQ ID NO:36, 39, 41, 43, 47, 49, 51, 53, 55, 57, 59, 61, 65, 67, 69, 71, 73, or 75; and further using:
(h) a polypeptide capable of glycosylating mogrol or a mogroside compound at its C3 hydroxyl group, C11 hydroxyl group, C24 hydroxyl group, and/or C25 hydroxyl group thereof having at least 90% sequence identity to the amino acid sequence set forth in any one of SEQ ID NOs:76-80, 83, 86, or 89; and/or
(i) a polypeptide capable of beta-1,2-glycosylation of the C2' position of a 24-O-glucose and/or beta-1,6-glycosylation of the C6' position of a 3-O-glucose and/or a 24-O-glucose of a mogroside compound having at least 90% sequence identity to the amino acid sequence set forth in any one of SEQ ID NOs:93, 95, 99, 101, 103, 105, 107, or 109;
wherein at least one of the polypeptides is a recombinant polypeptide expressed in the recombinant host cell.

13. A method of producing one or more mogroside compounds in a cell culture, comprising culturing a recombinant host cell capable of producing the one or more mogroside compounds in the cell culture, the host cell comprising a recombinant gene encoding a polypeptide capable of deglycosylating a mogroside precursor and having at least 90% sequence identity to the amino acid sequence set forth in SEQ ID NO:2 in the cell culture, under conditions in which the genes are expressed;
wherein the polypeptide:
(a) comprises a catalytically active portion of an endogenous glucosidase polypeptide or an endogenous glucanase polypeptide;
(b) does not comprise a signal peptide or a transmembrane domain that is comprised by the endogenous glucoside polypeptide; and
(c) is free of a domain facilitating secretion of the polypeptide from the host cell;
wherein the host cell is capable of retaining at least about 50% of the expressed polypeptide capable of deglycosylating the mogroside precursor in a cytosol of the host cell;
wherein expression of the gene increases production of the one or more mogroside compounds;

wherein the one or more mogroside compounds are produced by the recombinant host cell; and wherein the one or more mogroside compounds are a deglycosylation product of the mogroside precursor.

14. The method of claim 13, wherein the genes are constitutively expressed.

15. The method of claim 13, wherein the expression of the genes is induced.

16. The method of claim 13, further comprising isolating the produced one or more mogroside compounds.

17. The method of claim 16, wherein the isolating step comprises separating a liquid phase of the cell culture from a solid phase of the cell culture to obtain a supernatant comprising the produced one or more mogroside compounds, and:
 (a) contacting the supernatant with one or more adsorbent resins in order to obtain at least a portion of the produced one or more mogroside compounds; or
 (b) contacting the supernatant with one or more ion exchange or reversed-phase chromatography columns in order to obtain at least a portion of the produced one or more mogroside compounds; or
 (c) crystallizing or extracting the produced one or more mogroside compounds;
 thereby isolating the produced one or more mogroside compounds.

18. The method of claim 13, further comprising recovering a mogroside composition comprising the one or more mogroside compounds from the cell culture.

19. The method of claim 18, wherein the recovered mogroside composition comprises mogroside II A (MG-IIA), mogroside II A1 (MG-IIA1), mogroside II A2 (MG-IIA2), mogroside III (MG-III), mogroside III A1 (MG-IIIA1), mogroside III A2 (MG-IIIA2), mogroside III E (MG-IIIE), mogroside IV (MG-IV), mogroside IV A (MG-IVA), siamenoside I (SM-I), 11-oxo-mogroside V (11-O-MG-V), and/or mogroside V (MG V).

20. The method of claim 13, wherein the mogroside precursor is a tri-glycosylated mogrol, comprising mogroside III (MG-III), mogroside III A1 (MG-IIIA1), mogroside III A2 (MG-IIIA2), or mogroside III E (MG-IIIE), a tetra-glycosylated mogrol, comprising mogroside IV (MG-IV), mogroside IV A (MG-IVA), or siamenoside I (SM-I), a penta-glycosylated mogrol is mogroside V (MG-V) or 11-oxo-mogroside V (11-O-MG-V), a hexa-glycosylated mogrol, or an isomer thereof.

21. The method of claim 13, wherein the one or more mogroside compounds are a di-glycosylated mogroside compound, comprising mogroside II A (MG-IIA), mogroside II A1 (MG-IIA1), mogroside II A2 (MG-IIA2), or mogroside II E (MG-IIE), a tri-glycosylated mogroside compound, comprising MG-III, MG-IIIA1, MG-IIIA2, or MG-IIIE, a tetra-glycosylated mogroside compound, comprising MG-IV, MG-IVA, or SM-I, a penta-glycosylated mogroside compound, comprising MG-V or 11-O-MG-V, or an isomer thereof.

22. The method of claim 13, wherein expression of the gene increases a cytosolic mogroside precursor deglycosylation activity of the host cell by at least about 10% relative to a corresponding host cell lacking the gene.

23. The method of claim 13, wherein expression of the gene increases a cytosolic mogroside precursor deglycosylation activity of the polypeptide capable of deglycosylating the mogroside precursor comprising the host cell by at least about 10% relative to a corresponding host cell lacking the gene.

24. The method of claim 13, wherein the recombinant host cell comprises a plant cell, a mammalian cell, an insect cell, a fungal cell from *Aspergillus* genus, or a yeast cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous,* or *Candida albicans* species, an algal cell, or a bacterial cell from *Escherichia coli* species or *Bacillus* genus.

* * * * *

SEQUENCE LISTING

<160> NUMBER OF SEQ ID NOS: 123

<210> SEQ ID NO 1
<211> LENGTH: 1293
<212> TYPE: DNA
<213> ORGANISM: Artificial Sequence
<220> FEATURE:
<223> OTHER INFORMATION: Truncated S. cerevisiae EXG1 nucleotide sequence

<400> SEQUENCE: 1

```
atgacccag tccctgcaag agacccttct tccattcaat ttgttcatga ggagaacaag      60
aaaagatact acgattatga ccacggttcc ctcggagaac caatccgtgg tgtcaacatt     120
ggtggttggt tacttcttga accatacatt actccatctt tgttcgaggc tttccgtaca     180
aatgatgaca acgacgaagg aattcctgtc gacgaatatc acttctgtca atatttaggt     240
aaggatttgg ctaaaagccg tttacagagc cattggtcta ctttctacca agaacaagat     300
ttcgctaata ttgcttccca aggtttcaac cttgtcagaa ttcctatcgg ttactgggct     360
ttccaaactt tggacgatga tccttatgtt agcggcctac aggaatctta cctagaccaa     420
gccatcggtt gggctagaaa caacagcttg aaagtttggg ttgatttgca tggtgccgct     480
ggttcgcaga acgggtttga taactctggt ttgagagatt catacaagtt tttggaagac     540
agcaatttgg ccgttactac aaatgtcttg aactacatat tgaaaaaata ctctgcggag     600
gaatacttgg acactgttat tggtatcgaa ttgattaatg agccattggg tcctgttcta     660
gacatggata aaatgaagaa tgactacttg gcacctgctt acgaatactt gagaaacaac     720
atcaagagtg accaagttat catcatccat gacgctttcc aaccatacaa ttattgggat     780
gacttcatga ctgaaaacga tggctactgg ggtgtcacta tcgaccatca tcactaccaa     840
gtctttgctt ctgatcaatt ggaaagatcc attgatgaac atattaaagt agcttgtgaa     900
tggggtaccg agtttttgaa tgaatcccac tggactgttt tgtgtgagtt tgctgccgct     960
ttgactgatt gtacaaaatg gttgaatagt gttggcttcg gcgctagata cgacggttct    1020
tgggtcaatg gtgaccaaac atcttcttac attggctctt gtgctaacaa cgatgatata    1080
gcttactggt ctgacgaaag aaaggaaaac acaagacgtt atgtggaggc acaactagat    1140
gcctttgaaa tgagagggg ttggattatc tggtgttaca agacagaatc tagtttggaa    1200
tgggatgctc aaagattgat gttcaatggt ttattccctc aaccattgac tgacagaaag    1260
tatccaaacc aatgtggcac aatttctaac taa                                 1293
```

<210> SEQ ID NO 2
<211> LENGTH: 430
<212> TYPE: PRT
<213> ORGANISM: Artificial Sequence
<220> FEATURE:
<223> OTHER INFORMATION: Exo-1,3-beta-glucanase polypeptide encoded by
      truncated S. cerevisiae EXG1 nucleotide sequence

<400> SEQUENCE: 2

```
Met Thr Pro Val Pro Ala Arg Asp Pro Ser Ser Ile Gln Phe Val His
1               5                   10                  15

Glu Glu Asn Lys Lys Arg Tyr Tyr Asp Tyr Asp His Gly Ser Leu Gly
            20                  25                  30

Glu Pro Ile Arg Gly Val Asn Ile Gly Gly Trp Leu Leu Leu Glu Pro
        35                  40                  45

Tyr Ile Thr Pro Ser Leu Phe Glu Ala Phe Arg Thr Asn Asp Asp Asn
    50                  55                  60

Asp Glu Gly Ile Pro Val Asp Glu Tyr His Phe Cys Gln Tyr Leu Gly
65                  70                  75                  80

Lys Asp Leu Ala Lys Ser Arg Leu Gln Ser His Trp Ser Thr Phe Tyr
                85                  90                  95

Gln Glu Gln Asp Phe Ala Asn Ile Ala Ser Gln Gly Phe Asn Leu Val
            100                 105                 110

Arg Ile Pro Ile Gly Tyr Trp Ala Phe Gln Thr Leu Asp Asp Asp Pro
```

```
            115                 120                 125
Tyr Val Ser Gly Leu Gln Glu Ser Tyr Leu Asp Gln Ala Ile Gly Trp
    130                 135                 140

Ala Arg Asn Asn Ser Leu Lys Val Trp Val Asp Leu His Gly Ala Ala
145                 150                 155                 160

Gly Ser Gln Asn Gly Phe Asp Asn Ser Gly Leu Arg Asp Ser Tyr Lys
                165                 170                 175

Phe Leu Glu Asp Ser Asn Leu Ala Val Thr Thr Asn Val Leu Asn Tyr
            180                 185                 190

Ile Leu Lys Lys Tyr Ser Ala Glu Glu Tyr Leu Asp Thr Val Ile Gly
        195                 200                 205

Ile Glu Leu Ile Asn Glu Pro Leu Gly Pro Val Leu Asp Met Asp Lys
    210                 215                 220

Met Lys Asn Asp Tyr Leu Ala Pro Ala Tyr Glu Tyr Leu Arg Asn Asn
225                 230                 235                 240

Ile Lys Ser Asp Gln Val Ile Ile His Asp Ala Phe Gln Pro Tyr
                245                 250                 255

Asn Tyr Trp Asp Asp Phe Met Thr Glu Asn Asp Gly Tyr Trp Gly Val
            260                 265                 270

Thr Ile Asp His His Tyr Gln Val Phe Ala Ser Asp Gln Leu Glu
        275                 280                 285

Arg Ser Ile Asp Glu His Ile Lys Val Ala Cys Glu Trp Gly Thr Gly
    290                 295                 300

Val Leu Asn Glu Ser His Trp Thr Val Cys Gly Glu Phe Ala Ala Ala
305                 310                 315                 320

Leu Thr Asp Cys Thr Lys Trp Leu Asn Ser Val Gly Phe Gly Ala Arg
                325                 330                 335

Tyr Asp Gly Ser Trp Val Asn Gly Asp Gln Thr Ser Ser Tyr Ile Gly
            340                 345                 350

Ser Cys Ala Asn Asn Asp Asp Ile Ala Tyr Trp Ser Asp Glu Arg Lys
        355                 360                 365

Glu Asn Thr Arg Arg Tyr Val Glu Ala Gln Leu Asp Ala Phe Glu Met
    370                 375                 380

Arg Gly Gly Trp Ile Ile Trp Cys Tyr Lys Thr Glu Ser Ser Leu Glu
385                 390                 395                 400

Trp Asp Ala Gln Arg Leu Met Phe Asn Gly Leu Phe Pro Gln Pro Leu
                405                 410                 415

Thr Asp Arg Lys Tyr Pro Asn Gln Cys Gly Thr Ile Ser Asn
            420                 425                 430

<210> SEQ ID NO 3
<211> LENGTH: 496
<212> TYPE: PRT
<213> ORGANISM: Saccharomyces cerevisiae

<400> SEQUENCE: 3

Met Ser Ala Val Asn Val Ala Pro Glu Leu Ile Asn Ala Asp Asn Thr
1               5                   10                  15

Ile Thr Tyr Asp Ala Ile Val Ile Gly Ala Gly Val Ile Gly Pro Cys
            20                  25                  30

Val Ala Thr Gly Leu Ala Arg Lys Gly Lys Lys Val Leu Ile Val Glu
        35                  40                  45

Arg Asp Trp Ala Met Pro Asp Arg Ile Val Gly Glu Leu Met Gln Pro
    50                  55                  60
```

```
Gly Gly Val Arg Ala Leu Arg Ser Leu Gly Met Ile Gln Ser Ile Asn
 65                  70                  75                  80

Asn Ile Glu Ala Tyr Pro Val Thr Gly Tyr Thr Val Phe Phe Asn Gly
                 85                  90                  95

Glu Gln Val Asp Ile Pro Tyr Pro Tyr Lys Ala Asp Ile Pro Lys Val
                100                 105                 110

Glu Lys Leu Lys Asp Leu Val Lys Asp Gly Asn Asp Lys Val Leu Glu
            115                 120                 125

Asp Ser Thr Ile His Ile Lys Asp Tyr Glu Asp Glu Arg Glu Arg
130                 135                 140

Gly Val Ala Phe Val His Gly Arg Phe Leu Asn Asn Leu Arg Asn Ile
145                 150                 155                 160

Thr Ala Gln Glu Pro Asn Val Thr Arg Val Gln Gly Asn Cys Ile Glu
                165                 170                 175

Ile Leu Lys Asp Glu Lys Asn Glu Val Val Gly Ala Lys Val Asp Ile
            180                 185                 190

Asp Gly Arg Gly Lys Val Glu Phe Lys Ala His Leu Thr Phe Ile Cys
            195                 200                 205

Asp Gly Ile Phe Ser Arg Phe Arg Lys Glu Leu His Pro Asp His Val
210                 215                 220

Pro Thr Val Gly Ser Ser Phe Val Gly Met Ser Leu Phe Asn Ala Lys
225                 230                 235                 240

Asn Pro Ala Pro Met His Gly His Val Ile Leu Gly Ser Asp His Met
                245                 250                 255

Pro Ile Leu Val Tyr Gln Ile Ser Pro Glu Glu Thr Arg Ile Leu Cys
            260                 265                 270

Ala Tyr Asn Ser Pro Lys Val Pro Ala Asp Ile Lys Ser Trp Met Ile
            275                 280                 285

Lys Asp Val Gln Pro Phe Ile Pro Lys Ser Leu Arg Pro Ser Phe Asp
290                 295                 300

Glu Ala Val Ser Gln Gly Lys Phe Arg Ala Met Pro Asn Ser Tyr Leu
305                 310                 315                 320

Pro Ala Arg Gln Asn Asp Val Thr Gly Met Cys Val Ile Gly Asp Ala
                325                 330                 335

Leu Asn Met Arg His Pro Leu Thr Gly Gly Met Thr Val Gly Leu
            340                 345                 350

His Asp Val Val Leu Leu Ile Lys Lys Ile Gly Asp Leu Asp Phe Ser
            355                 360                 365

Asp Arg Glu Lys Val Leu Asp Glu Leu Leu Asp Tyr His Phe Glu Arg
370                 375                 380

Lys Ser Tyr Asp Ser Val Ile Asn Val Leu Ser Val Ala Leu Tyr Ser
385                 390                 395                 400

Leu Phe Ala Ala Asp Ser Asp Asn Leu Lys Ala Leu Gln Lys Gly Cys
                405                 410                 415

Phe Lys Tyr Phe Gln Arg Gly Gly Asp Cys Val Asn Lys Pro Val Glu
            420                 425                 430

Phe Leu Ser Gly Val Leu Pro Lys Pro Leu Gln Leu Thr Arg Val Phe
            435                 440                 445

Phe Ala Val Ala Phe Tyr Thr Ile Tyr Leu Asn Met Glu Glu Arg Gly
            450                 455                 460

Phe Leu Gly Leu Pro Met Ala Leu Leu Glu Gly Ile Met Ile Leu Ile
465                 470                 475                 480

Thr Ala Ile Arg Val Phe Thr Pro Phe Leu Phe Gly Glu Leu Ile Gly
```

```
                        485                 490                 495

<210> SEQ ID NO 4
<211> LENGTH: 525
<212> TYPE: PRT
<213> ORGANISM: Gynostemma pentaphyllum

<400> SEQUENCE: 4

Met Val Asp Gln Phe Ser Leu Ala Phe Ile Phe Ala Ser Val Leu Gly
1               5                   10                  15

Ala Val Ala Phe Tyr Tyr Leu Phe Leu Arg Asn Arg Ile Phe Arg Val
            20                  25                  30

Ser Arg Glu Pro Arg Arg Glu Ser Leu Lys Asn Ile Ala Thr Thr Asn
        35                  40                  45

Gly Glu Cys Lys Ser Ser Tyr Ser Asp Gly Asp Ile Ile Ile Val Gly
    50                  55                  60

Ala Gly Val Ala Gly Ser Ala Leu Ala Tyr Thr Leu Gly Lys Asp Gly
65                  70                  75                  80

Arg Arg Val His Val Ile Glu Arg Asp Leu Thr Glu Pro Asp Arg Thr
                85                  90                  95

Val Gly Glu Leu Leu Gln Pro Gly Gly Tyr Leu Lys Leu Thr Glu Leu
            100                 105                 110

Gly Leu Glu Asp Cys Val Asn Glu Ile Asp Ala Gln Arg Val Tyr Gly
        115                 120                 125

Tyr Ala Leu Phe Lys Asp Gly Lys Asp Thr Lys Leu Ser Tyr Pro Leu
    130                 135                 140

Glu Lys Phe His Ser Asp Val Ser Gly Arg Ser Phe His Asn Gly Arg
145                 150                 155                 160

Phe Ile Gln Arg Met Arg Glu Lys Ala Ala Thr Leu Pro Asn Val Arg
                165                 170                 175

Leu Glu Gln Gly Thr Val Thr Ser Leu Leu Glu Glu Asn Gly Ile Ile
            180                 185                 190

Lys Gly Val Gln Tyr Lys Ser Lys Thr Gly Gln Glu Met Thr Ala Tyr
        195                 200                 205

Ala Pro Leu Thr Ile Val Cys Asp Gly Cys Phe Ser Asn Leu Arg Arg
    210                 215                 220

Ser Leu Cys Asn Pro Lys Val Asp Val Pro Ser Cys Phe Val Ala Leu
225                 230                 235                 240

Val Leu Glu Asn Cys Glu Leu Pro His Ala Asn Tyr Gly His Val Ile
                245                 250                 255

Leu Ala Asp Pro Ser Pro Ile Leu Phe Tyr Pro Ile Ser Ser Thr Glu
            260                 265                 270

Val Arg Cys Leu Val Asp Val Pro Gly Gln Lys Val Pro Ser Ile Ser
        275                 280                 285

Asn Gly Glu Met Ala Asn Tyr Leu Lys Ser Val Val Ala Pro Gln Ile
    290                 295                 300

Pro Pro Gln Ile Tyr Asp Ala Leu Arg Ser Cys Tyr Asp Lys Gly Asn
305                 310                 315                 320

Ile Arg Thr Met Pro Asn Arg Ser Met Pro Ala Asp Pro Tyr Pro Thr
                325                 330                 335

Pro Gly Ala Leu Leu Met Gly Asp Ala Phe Asn Met Arg His Pro Leu
            340                 345                 350

Thr Gly Gly Gly Met Thr Val Ala Leu Ser Asp Ile Val Val Leu Arg
        355                 360                 365
```

-continued

Asp Leu Leu Lys Pro Leu Arg Asp Leu His Asp Ala Pro Ile Leu Ser
    370                 375                 380

Asn Tyr Leu Glu Ala Phe Tyr Thr Leu Arg Lys Pro Val Ala Ser Thr
385                 390                 395                 400

Ile Asn Thr Leu Ala Gly Ala Leu Tyr Lys Val Phe Cys Ala Ser Pro
                405                 410                 415

Asp Gln Ala Arg Arg Glu Met Arg Gln Ala Cys Phe Asp Tyr Leu Ser
            420                 425                 430

Leu Gly Gly Val Phe Ser Asn Gly Pro Val Ser Leu Ser Gly Leu
        435                 440                 445

Asn Pro Arg Pro Leu Ser Leu Val Leu His Phe Phe Ala Val Ala Ile
    450                 455                 460

Tyr Gly Val Gly Arg Leu Leu Ile Pro Phe Pro Ser Pro Arg Arg Val
465                 470                 475                 480

Trp Ile Gly Ala Arg Leu Ile Ser Gly Ala Ser Gly Ile Ile Phe Pro
                485                 490                 495

Ile Ile Lys Ala Glu Gly Val Arg Gln Ile Phe Phe Pro Ala Thr Leu
            500                 505                 510

Pro Ala Tyr Tyr Arg Ala Pro Pro Leu Val Arg Gly Arg
        515                 520                 525

<210> SEQ ID NO 5
<211> LENGTH: 531
<212> TYPE: PRT
<213> ORGANISM: Arabidopsis thaliana

<400> SEQUENCE: 5

Met Glu Ser Gln Leu Trp Asn Trp Ile Leu Pro Leu Leu Ile Ser Ser
1               5                   10                  15

Leu Leu Ile Ser Phe Val Ala Phe Tyr Gly Phe Val Lys Pro Lys
                20                  25                  30

Arg Asn Gly Leu Arg His Asp Arg Lys Thr Val Ser Thr Val Thr Ser
            35                  40                  45

Asp Val Gly Ser Val Asn Ile Thr Gly Asp Thr Val Ala Asp Val Ile
        50                  55                  60

Val Val Gly Ala Gly Val Ala Gly Ser Ala Leu Ala Tyr Thr Leu Gly
65                  70                  75                  80

Lys Asp Lys Arg Arg Val His Val Ile Glu Arg Asp Leu Ser Glu Pro
                85                  90                  95

Asp Arg Ile Val Gly Glu Leu Leu Gln Pro Gly Gly Tyr Leu Lys Leu
            100                 105                 110

Leu Glu Leu Gly Ile Glu Asp Cys Val Glu Glu Ile Asp Ala Gln Arg
        115                 120                 125

Val Tyr Gly Tyr Ala Leu Phe Lys Asn Gly Lys Arg Ile Arg Leu Ala
    130                 135                 140

Tyr Pro Leu Glu Lys Phe His Glu Asp Val Ser Gly Arg Ser Phe His
145                 150                 155                 160

Asn Gly Arg Phe Ile Gln Arg Met Arg Glu Lys Ala Ala Ser Leu Pro
                165                 170                 175

Asn Val Gln Leu Glu Gln Gly Thr Val Leu Ser Leu Glu Glu Asn
            180                 185                 190

Gly Thr Ile Lys Gly Val Arg Tyr Lys Asn Lys Ala Gly Glu Glu Gln
        195                 200                 205

Thr Ala Phe Ala Ala Leu Thr Ile Val Cys Asp Gly Cys Phe Ser Asn
    210                 215                 220

```
Leu Arg Arg Ser Leu Cys Asn Pro Gln Val Glu Val Pro Ser Cys Phe
225                 230                 235                 240

Val Gly Leu Val Leu Glu Asn Cys Asn Leu Pro Tyr Ala Asn His Gly
            245                 250                 255

His Val Val Leu Ala Asp Pro Ser Pro Ile Leu Met Tyr Pro Ile Ser
        260                 265                 270

Ser Thr Glu Val Arg Cys Leu Val Asp Val Pro Gly Gln Lys Val Pro
    275                 280                 285

Ser Ile Ala Asn Gly Glu Met Lys Asn Tyr Leu Lys Thr Val Val Ala
290                 295                 300

Pro Gln Met Pro His Glu Val Tyr Asp Ser Phe Ile Ala Ala Val Asp
305                 310                 315                 320

Lys Gly Asn Ile Lys Ser Met Pro Asn Arg Ser Met Pro Ala Ser Pro
            325                 330                 335

Tyr Pro Thr Pro Gly Ala Leu Leu Met Gly Asp Ala Phe Asn Met Arg
        340                 345                 350

His Pro Leu Thr Gly Gly Met Thr Val Ala Leu Ala Asp Ile Val
    355                 360                 365

Val Leu Arg Asn Leu Leu Arg Pro Leu Arg Asp Leu Ser Asp Gly Ala
370                 375                 380

Ser Leu Cys Lys Tyr Leu Glu Ser Phe Tyr Thr Leu Arg Lys Pro Val
385                 390                 395                 400

Ala Ala Thr Ile Asn Thr Leu Ala Asn Ala Leu Tyr Gln Val Phe Cys
            405                 410                 415

Ser Ser Glu Asn Glu Ala Arg Asn Glu Met Arg Glu Ala Cys Phe Asp
        420                 425                 430

Tyr Leu Gly Leu Gly Gly Met Cys Thr Ser Gly Pro Val Ser Leu Leu
    435                 440                 445

Ser Gly Leu Asn Pro Arg Pro Leu Thr Leu Val Cys His Phe Phe Ala
450                 455                 460

Val Ala Val Tyr Gly Val Ile Arg Leu Leu Ile Pro Phe Pro Ser Pro
465                 470                 475                 480

Lys Arg Ile Trp Leu Gly Ala Lys Leu Ile Ser Gly Ala Ser Gly Ile
            485                 490                 495

Ile Phe Pro Ile Ile Lys Ala Glu Gly Val Arg Gln Met Phe Phe Pro
        500                 505                 510

Ala Thr Val Pro Ala Tyr Tyr Tyr Lys Ala Pro Thr Val Gly Glu Thr
    515                 520                 525

Lys Cys Ser
530

<210> SEQ ID NO 6
<211> LENGTH: 516
<212> TYPE: PRT
<213> ORGANISM: Arabidopsis thaliana

<400> SEQUENCE: 6

Met Thr Tyr Ala Trp Leu Trp Thr Leu Leu Ala Phe Val Leu Thr Trp
1               5                   10                  15

Met Val Phe His Leu Ile Lys Met Lys Lys Ala Ala Thr Gly Asp Leu
            20                  25                  30

Glu Ala Glu Ala Glu Ala Arg Arg Asp Gly Ala Thr Asp Val Ile Ile
        35                  40                  45

Val Gly Ala Gly Val Ala Gly Ala Ser Leu Ala Tyr Ala Leu Ala Lys
```

-continued

```
                 50                  55                  60
Asp Gly Arg Arg Val His Val Ile Glu Arg Asp Leu Lys Glu Pro Gln
 65                  70                  75                  80

Arg Phe Met Gly Glu Leu Met Gln Ala Gly Gly Arg Phe Met Leu Ala
                 85                  90                  95

Gln Leu Gly Leu Glu Asp Cys Leu Glu Asp Ile Asp Ala Gln Glu Ala
                100                 105                 110

Lys Ser Leu Ala Ile Tyr Lys Asp Gly Lys His Ala Thr Leu Pro Phe
                115                 120                 125

Pro Asp Asp Lys Ser Phe Pro His Glu Pro Val Gly Arg Leu Leu Arg
                130                 135                 140

Asn Gly Arg Leu Val Gln Arg Leu Arg Gln Lys Ala Ala Ser Leu Ser
145                 150                 155                 160

Asn Val Gln Leu Glu Glu Gly Thr Val Lys Ser Leu Ile Glu Glu Glu
                165                 170                 175

Gly Val Val Lys Gly Val Thr Tyr Lys Asn Ser Ala Gly Glu Glu Ile
                180                 185                 190

Thr Ala Phe Ala Pro Leu Thr Val Val Cys Asp Gly Cys Tyr Ser Asn
                195                 200                 205

Leu Arg Arg Ser Leu Val Asp Asn Thr Glu Glu Val Leu Ser Tyr Met
                210                 215                 220

Val Gly Tyr Val Thr Lys Asn Ser Arg Leu Glu Asp Pro His Ser Leu
225                 230                 235                 240

His Leu Ile Phe Ser Lys Pro Leu Val Cys Val Ile Tyr Gln Ile Thr
                245                 250                 255

Ser Asp Glu Val Arg Cys Val Ala Glu Val Pro Ala Asp Ser Ile Pro
                260                 265                 270

Ser Ile Ser Asn Gly Glu Met Ser Thr Phe Leu Lys Lys Ser Met Ala
                275                 280                 285

Pro Gln Ile Pro Glu Thr Gly Asn Leu Arg Glu Ile Phe Leu Lys Gly
                290                 295                 300

Ile Glu Glu Gly Leu Pro Glu Ile Lys Ser Thr Ala Thr Lys Ser Met
305                 310                 315                 320

Ser Ser Arg Leu Cys Asp Lys Arg Gly Val Ile Val Leu Gly Asp Ala
                325                 330                 335

Phe Asn Met Arg His Pro Ile Ile Ala Ser Gly Met Met Val Ala Leu
                340                 345                 350

Ser Asp Ile Cys Ile Leu Arg Asn Leu Leu Lys Pro Leu Pro Asn Leu
                355                 360                 365

Ser Asn Thr Lys Lys Val Ser Asp Leu Val Lys Ser Phe Tyr Ile Ile
                370                 375                 380

Arg Lys Pro Met Ser Ala Thr Val Asn Thr Leu Ala Ser Ile Phe Ser
385                 390                 395                 400

Gln Val Leu Val Ala Thr Thr Asp Glu Ala Arg Glu Gly Met Arg Gln
                405                 410                 415

Gly Cys Phe Asn Tyr Leu Ala Arg Gly Asp Phe Lys Thr Arg Gly Leu
                420                 425                 430

Met Thr Ile Leu Gly Gly Met Asn Pro His Pro Leu Thr Leu Val Leu
                435                 440                 445

His Leu Val Ala Ile Thr Leu Thr Ser Met Gly His Leu Leu Ser Pro
                450                 455                 460

Phe Pro Ser Pro Arg Arg Phe Trp His Ser Leu Arg Ile Leu Ala Trp
465                 470                 475                 480
```

Ala Leu Gln Met Leu Gly Ala His Leu Val Asp Gly Phe Lys Glu
            485                 490                 495

Met Leu Ile Pro Thr Asn Ala Ala Tyr Arg Arg Asn Tyr Ile Ala
            500                 505                 510

Thr Thr Thr Val
        515

<210> SEQ ID NO 7
<211> LENGTH: 517
<212> TYPE: PRT
<213> ORGANISM: Arabidopsis thaliana

<400> SEQUENCE: 7

Met Ala Phe Thr His Val Cys Leu Trp Thr Leu Val Ala Phe Val Leu
1               5                   10                  15

Thr Trp Thr Val Phe Tyr Leu Thr Asn Met Lys Lys Lys Ala Thr Asp
                20                  25                  30

Leu Ala Asp Thr Val Ala Glu Asp Gln Lys Asp Gly Ala Ala Asp Val
            35                  40                  45

Ile Ile Val Gly Ala Gly Val Gly Gly Ser Ala Leu Ala Tyr Ala Leu
        50                  55                  60

Ala Lys Asp Gly Arg Arg Val His Val Ile Glu Arg Asp Met Arg Glu
65                  70                  75                  80

Pro Glu Arg Met Met Gly Glu Phe Met Gln Pro Gly Gly Arg Leu Met
                85                  90                  95

Leu Ser Lys Leu Gly Leu Gln Asp Cys Leu Glu Asp Ile Asp Ala Gln
            100                 105                 110

Lys Ala Thr Gly Leu Ala Val Tyr Lys Asp Gly Lys Glu Ala Asp Ala
        115                 120                 125

Pro Phe Pro Val Asp Asn Asn Phe Ser Tyr Glu Pro Ser Ala Arg
        130                 135                 140

Ser Phe His Asn Gly Arg Phe Val Gln Gln Leu Arg Arg Lys Ala Phe
145                 150                 155                 160

Ser Leu Ser Asn Val Arg Leu Glu Glu Gly Thr Val Lys Ser Leu Leu
                165                 170                 175

Glu Glu Lys Gly Val Val Lys Gly Val Thr Tyr Lys Asn Lys Glu Gly
            180                 185                 190

Glu Glu Thr Thr Ala Leu Ala Pro Leu Thr Val Val Cys Asp Gly Cys
        195                 200                 205

Tyr Ser Asn Leu Arg Arg Ser Leu Asn Asp Asn Asn Ala Glu Ile
        210                 215                 220

Met Ser Tyr Ile Val Gly Tyr Ile Ser Lys Asn Cys Arg Leu Glu Glu
225                 230                 235                 240

Pro Glu Lys Leu His Leu Ile Leu Ser Lys Pro Ser Phe Thr Met Val
                245                 250                 255

Tyr Gln Ile Ser Ser Thr Asp Val Arg Cys Gly Phe Glu Val Leu Pro
            260                 265                 270

Glu Asn Phe Pro Ser Ile Ala Asn Gly Glu Met Ser Thr Phe Met Lys
        275                 280                 285

Asn Thr Ile Val Pro Gln Val Pro Pro Lys Leu Arg Lys Ile Phe Leu
        290                 295                 300

Lys Gly Ile Asp Glu Gly Ala His Ile Lys Val Val Pro Ala Lys Arg
305                 310                 315                 320

Met Thr Ser Thr Leu Ser Lys Lys Lys Gly Val Ile Val Leu Gly Asp

```
                    325                 330                 335
Ala Phe Asn Met Arg His Pro Val Val Ala Ser Gly Met Met Val Leu
                340                 345                 350
Leu Ser Asp Ile Leu Ile Leu Arg Arg Leu Leu Gln Pro Leu Ser Asn
                355                 360                 365
Leu Gly Asp Ala Asn Lys Val Ser Glu Val Ile Asn Ser Phe Tyr Asp
                370                 375                 380
Ile Arg Lys Pro Met Ser Ala Thr Val Asn Thr Leu Gly Asn Ala Phe
385                 390                 395                 400
Ser Gln Val Leu Ile Gly Ser Thr Asp Glu Ala Lys Glu Ala Met Arg
                405                 410                 415
Gln Gly Val Tyr Asp Tyr Leu Cys Ser Gly Phe Arg Thr Ser Gly
                420                 425                 430
Met Met Ala Leu Leu Gly Gly Met Asn Pro Arg Pro Leu Ser Leu Val
                435                 440                 445
Tyr His Leu Cys Ala Ile Thr Leu Ser Ser Ile Gly Gln Leu Leu Ser
                450                 455                 460
Pro Phe Pro Ser Pro Leu Arg Ile Trp His Ser Leu Lys Leu Phe Gly
465                 470                 475                 480
Leu Ala Met Lys Met Leu Val Pro Asn Leu Lys Ala Glu Gly Val Ser
                485                 490                 495
Gln Met Leu Phe Pro Ala Asn Ala Ala Ala Tyr His Lys Ser Tyr Met
                500                 505                 510
Ala Ala Thr Thr Leu
                515

<210> SEQ ID NO 8
<211> LENGTH: 516
<212> TYPE: PRT
<213> ORGANISM: Arabidopsis thaliana

<400> SEQUENCE: 8

Met Ala Phe Thr Asn Val Cys Leu Trp Thr Leu Leu Ala Phe Met Leu
1               5                  10                  15
Thr Trp Thr Val Phe Tyr Val Thr Asn Arg Gly Lys Lys Ala Thr Gln
                20                  25                  30
Leu Ala Asp Ala Val Val Glu Glu Arg Glu Asp Gly Ala Thr Asp Val
                35                  40                  45
Ile Ile Val Gly Ala Gly Val Gly Gly Ser Ala Leu Ala Tyr Ala Leu
            50                  55                  60
Ala Lys Asp Gly Arg Arg Val His Val Ile Glu Arg Asp Leu Arg Glu
65                  70                  75                  80
Pro Glu Arg Ile Met Gly Glu Phe Met Gln Pro Gly Gly Arg Leu Met
                85                  90                  95
Leu Ser Lys Leu Gly Leu Glu Asp Cys Leu Glu Gly Ile Asp Ala Gln
                100                 105                 110
Lys Ala Thr Gly Met Thr Val Tyr Lys Asp Gly Lys Glu Ala Val Ala
                115                 120                 125
Ser Phe Pro Val Asp Asn Asn Phe Pro Phe Asp Pro Ser Ala Arg
                130                 135                 140
Ser Phe His Asn Gly Arg Phe Val Gln Arg Leu Arg Gln Lys Ala Ser
145                 150                 155                 160
Ser Leu Pro Asn Val Arg Leu Glu Glu Gly Thr Val Lys Ser Leu Ile
                165                 170                 175
```

Glu Glu Lys Gly Val Ile Lys Gly Val Thr Tyr Lys Asn Ser Ala Gly
            180                 185                 190

Glu Glu Thr Thr Ala Leu Ala Pro Leu Thr Val Val Cys Asp Gly Cys
            195                 200                 205

Tyr Ser Asn Leu Arg Arg Ser Leu Asn Asp Asn Asn Ala Glu Val Leu
        210                 215                 220

Ser Tyr Gln Val Gly Phe Ile Ser Lys Asn Cys Gln Leu Glu Glu Pro
225                 230                 235                 240

Glu Lys Leu Lys Leu Ile Met Ser Lys Pro Ser Phe Thr Met Leu Tyr
                245                 250                 255

Gln Ile Ser Ser Thr Asp Val Arg Cys Val Phe Glu Val Leu Pro Asn
            260                 265                 270

Asn Ile Pro Ser Ile Ser Asn Gly Glu Met Ala Thr Phe Val Lys Asn
        275                 280                 285

Thr Ile Ala Pro Gln Val Pro Leu Lys Leu Arg Lys Ile Phe Leu Lys
        290                 295                 300

Gly Ile Asp Glu Gly Glu His Ile Lys Ala Met Pro Thr Lys Lys Met
305                 310                 315                 320

Thr Ala Thr Leu Ser Glu Lys Lys Gly Val Ile Leu Leu Gly Asp Ala
                325                 330                 335

Phe Asn Met Arg His Pro Ala Ile Ala Ser Gly Met Met Val Leu Leu
            340                 345                 350

Ser Asp Ile Leu Ile Leu Arg Arg Leu Leu Gln Pro Leu Ser Asn Leu
        355                 360                 365

Gly Asn Ala Gln Lys Ile Ser Gln Val Ile Lys Ser Phe Tyr Asp Ile
        370                 375                 380

Arg Lys Pro Met Ser Ala Thr Val Asn Thr Leu Gly Asn Ala Phe Ser
385                 390                 395                 400

Gln Val Leu Val Ala Ser Thr Asp Glu Ala Lys Glu Ala Met Arg Gln
                405                 410                 415

Gly Cys Tyr Asp Tyr Leu Ser Ser Gly Phe Arg Thr Ser Gly Met
            420                 425                 430

Met Ala Leu Leu Gly Gly Met Asn Pro Arg Pro Ile Ser Leu Ile Tyr
        435                 440                 445

His Leu Cys Ala Ile Thr Leu Ser Ser Ile Gly His Leu Leu Ser Pro
        450                 455                 460

Phe Pro Ser Pro Leu Arg Ile Trp His Ser Leu Arg Leu Phe Gly Leu
465                 470                 475                 480

Ala Met Lys Met Leu Val Pro His Leu Lys Ala Glu Gly Val Ser Gln
                485                 490                 495

Met Leu Phe Pro Val Asn Ala Ala Ala Tyr Ser Lys Ser Tyr Met Ala
            500                 505                 510

Ala Thr Ala Leu
        515

<210> SEQ ID NO 9
<211> LENGTH: 585
<212> TYPE: PRT
<213> ORGANISM: Arabidopsis thaliana

<400> SEQUENCE: 9

Met Lys Pro Phe Val Ile Arg Asn Leu Pro Arg Phe Gln Ser Thr Leu
1               5                   10                  15

Arg Ser Ser Leu Leu Tyr Thr Asn His Arg Pro Ser Ser Arg Phe Ser
            20                  25                  30

-continued

Leu Ser Thr Arg Arg Phe Thr Thr Gly Ala Thr Tyr Ile Arg Arg Trp
         35                  40                  45

Lys Ala Thr Ala Ala Gln Thr Leu Lys Leu Ser Ala Val Asn Ser Thr
 50                  55                  60

Val Met Met Lys Pro Ala Lys Ile Ala Leu Asp Gln Phe Ile Ala Ser
 65                  70                  75                  80

Leu Phe Thr Phe Leu Leu Leu Tyr Ile Leu Arg Arg Ser Ser Asn Lys
                 85                  90                  95

Asn Lys Lys Asn Arg Gly Leu Val Val Ser Gln Asn Asp Thr Val Ser
                100                 105                 110

Lys Asn Leu Glu Thr Glu Val Asp Ser Gly Thr Asp Val Ile Ile Val
            115                 120                 125

Gly Ala Gly Val Ala Gly Ser Ala Leu Ala His Thr Leu Gly Lys Glu
        130                 135                 140

Gly Arg Arg Val His Val Ile Glu Arg Asp Phe Ser Glu Gln Asp Arg
145                 150                 155                 160

Ile Val Gly Glu Leu Leu Gln Pro Gly Gly Tyr Leu Lys Leu Ile Glu
                165                 170                 175

Leu Gly Leu Glu Asp Cys Val Lys Lys Ile Asp Ala Gln Arg Val Leu
            180                 185                 190

Gly Tyr Val Leu Phe Lys Asp Gly Lys His Thr Lys Leu Ala Tyr Pro
        195                 200                 205

Leu Glu Thr Phe Asp Ser Asp Val Ala Gly Arg Ser Phe His Asn Gly
    210                 215                 220

Arg Phe Val Gln Arg Met Arg Glu Lys Ala Leu Thr Leu Ser Asn Val
225                 230                 235                 240

Arg Leu Glu Gln Gly Thr Val Thr Ser Leu Leu Glu Glu His Gly Thr
                245                 250                 255

Ile Lys Gly Val Arg Tyr Arg Thr Lys Glu Gly Asn Glu Phe Arg Ser
            260                 265                 270

Phe Ala Pro Leu Thr Ile Val Cys Asp Gly Cys Phe Ser Asn Leu Arg
        275                 280                 285

Arg Ser Leu Cys Lys Pro Lys Val Asp Val Pro Ser Thr Phe Val Gly
    290                 295                 300

Leu Val Leu Glu Asn Cys Glu Leu Pro Phe Ala Asn His Gly His Val
305                 310                 315                 320

Val Leu Gly Asp Pro Ser Pro Ile Leu Met Tyr Pro Ile Ser Ser Ser
                325                 330                 335

Glu Val Arg Cys Leu Val Asp Val Pro Gly Gln Lys Leu Pro Pro Ile
            340                 345                 350

Ala Asn Gly Glu Met Ala Lys Tyr Leu Lys Thr Arg Val Ala Pro Gln
        355                 360                 365

Val Pro Thr Lys Val Arg Glu Ala Phe Ile Thr Ala Val Glu Lys Gly
    370                 375                 380

Asn Ile Arg Thr Met Pro Asn Arg Ser Met Pro Ala Asp Pro Ile Pro
385                 390                 395                 400

Thr Pro Gly Ala Leu Leu Leu Gly Asp Ala Phe Asn Met Arg His Pro
                405                 410                 415

Leu Thr Gly Gly Gly Met Thr Val Ala Leu Ala Asp Ile Val Val Leu
            420                 425                 430

Arg Asp Leu Leu Arg Pro Ile Arg Asn Leu Asn Asp Lys Glu Ala Leu
        435                 440                 445

-continued

```
Ser Lys Tyr Ile Glu Ser Phe Tyr Thr Leu Arg Lys Pro Val Ala Ser
    450                 455                 460

Thr Ile Asn Thr Leu Ala Asp Ala Leu Tyr Lys Val Phe Leu Ala Ser
465                 470                 475                 480

Ser Asp Glu Ala Arg Thr Glu Met Arg Glu Ala Cys Phe Asp Tyr Leu
                485                 490                 495

Ser Leu Gly Gly Val Phe Ser Ser Gly Pro Val Ala Leu Leu Ser Gly
            500                 505                 510

Leu Asn Pro Arg Pro Leu Ser Leu Val Leu His Phe Phe Ala Val Ala
            515                 520                 525

Ile Tyr Ala Val Cys Arg Leu Met Leu Pro Phe Pro Ser Ile Glu Ser
530                 535                 540

Phe Trp Leu Gly Ala Arg Ile Ile Ser Ser Ala Ser Ser Ile Ile Phe
545                 550                 555                 560

Pro Ile Ile Lys Ala Glu Gly Val Arg Gln Met Phe Phe Pro Arg Thr
                565                 570                 575

Ile Pro Ala Ile Tyr Arg Ala Pro Pro
                580                 585

<210> SEQ ID NO 10
<211> LENGTH: 525
<212> TYPE: PRT
<213> ORGANISM: Arabidopsis thaliana

<400> SEQUENCE: 10

Met Ala Pro Thr Ile Phe Val Asp His Cys Ile Leu Thr Thr Thr Phe
1               5                   10                  15

Val Ala Ser Leu Phe Ala Phe Leu Leu Leu Tyr Val Leu Arg Arg Arg
                20                  25                  30

Ser Lys Thr Ile His Gly Ser Val Asn Val Arg Asn Gly Thr Leu Thr
            35                  40                  45

Val Lys Ser Gly Thr Asp Val Asp Ile Ile Val Gly Ala Gly Val
        50                  55                  60

Ala Gly Ala Ala Leu Ala His Thr Leu Gly Lys Glu Gly Arg Val
65                  70                  75                  80

His Val Ile Glu Arg Asp Leu Thr Glu Pro Asp Arg Ile Val Gly Glu
                85                  90                  95

Leu Leu Gln Pro Gly Gly Tyr Leu Lys Leu Ile Glu Leu Gly Leu Glu
            100                 105                 110

Asp Cys Val Lys Asp Ile Asp Ala Gln Arg Val Leu Gly Tyr Ala Leu
        115                 120                 125

Phe Lys Asp Gly Lys His Thr Lys Leu Ser Tyr Pro Leu Asp Gln Phe
    130                 135                 140

Asp Ser Asp Val Ala Gly Arg Ser Phe His Asn Gly Arg Phe Val Gln
145                 150                 155                 160

Arg Met Arg Glu Lys Ala Ser Leu Leu Pro Asn Val Arg Met Glu Gln
                165                 170                 175

Gly Thr Val Thr Ser Leu Val Glu Glu Asn Gly Ile Ile Lys Gly Val
            180                 185                 190

Gln Tyr Lys Thr Lys Asp Gly Gln Glu Leu Lys Ser Phe Ala Pro Leu
        195                 200                 205

Thr Ile Val Cys Asp Gly Cys Phe Ser Asn Leu Arg Arg Ser Leu Cys
    210                 215                 220

Lys Pro Lys Val Glu Val Pro Ser Asn Phe Val Gly Leu Val Leu Glu
225                 230                 235                 240
```

-continued

Asn Cys Glu Leu Pro Phe Pro Asn His Gly His Val Val Leu Gly Asp
            245                 250                 255

Pro Ser Pro Ile Leu Phe Tyr Pro Ile Ser Ser Glu Val Arg Cys
        260                 265                 270

Leu Val Asp Val Pro Gly Ser Lys Leu Pro Ser Val Ala Ser Gly Glu
            275                 280                 285

Met Ala His His Leu Lys Thr Met Val Ala Pro Gln Val Pro Pro Gln
            290                 295                 300

Ile Arg Asp Ala Phe Ile Ser Ala Val Glu Lys Gly Asn Ile Arg Thr
305                 310                 315                 320

Met Pro Asn Arg Ser Met Pro Ala Asp Pro Ile His Thr Pro Gly Ala
                325                 330                 335

Leu Leu Leu Gly Asp Ala Phe Asn Met Arg His Pro Leu Thr Gly Gly
            340                 345                 350

Gly Met Thr Val Ala Leu Ser Asp Ile Val Ile Leu Arg Asp Leu Leu
        355                 360                 365

Asn Pro Leu Val Asp Leu Thr Asn Lys Glu Ser Leu Ser Lys Tyr Ile
    370                 375                 380

Glu Ser Phe Tyr Thr Leu Arg Lys Pro Val Ala Ser Thr Ile Asn Thr
385                 390                 395                 400

Leu Ala Gly Ala Leu Tyr Lys Val Phe Leu Ala Ser Pro Asp Asp Ala
                405                 410                 415

Arg Ser Glu Met Arg Arg Ala Cys Phe Asp Tyr Leu Ser Leu Gly Gly
            420                 425                 430

Val Cys Ser Ser Gly Pro Val Ala Leu Leu Ser Gly Leu Asn Pro Arg
        435                 440                 445

Pro Met Ser Leu Val Leu His Phe Phe Ala Val Ala Ile Phe Gly Val
    450                 455                 460

Gly Arg Leu Leu Val Pro Leu Pro Ser Val Lys Arg Leu Trp Leu Gly
465                 470                 475                 480

Ala Arg Leu Ile Ser Ser Ala Ser Gly Ile Ile Phe Pro Ile Ile Lys
                485                 490                 495

Ala Glu Gly Val Arg Gln Met Phe Phe Pro Arg Thr Ile Pro Ala Ile
            500                 505                 510

Tyr Arg Ala Pro Pro Thr Pro Ser Ser Ser Ser Pro Gln
            515                 520                 525

<210> SEQ ID NO 11
<211> LENGTH: 506
<212> TYPE: PRT
<213> ORGANISM: Brassica napus

<400> SEQUENCE: 11

Met Asp Leu Ala Phe Pro His Val Cys Leu Trp Thr Leu Leu Ala Phe
1               5                   10                  15

Val Leu Thr Trp Thr Val Phe Tyr Val Asn Asn Arg Arg Lys Lys Val
            20                  25                  30

Ala Lys Leu Pro Asp Ala Ala Thr Glu Val Arg Arg Asp Gly Asp Ala
        35                  40                  45

Asp Val Ile Ile Val Gly Ala Gly Val Gly Gly Ser Ala Leu Ala Tyr
    50                  55                  60

Ala Leu Ala Lys Asp Gly Arg Arg Val His Val Ile Glu Arg Asp Met
65                  70                  75                  80

Arg Glu Pro Val Arg Met Met Gly Glu Phe Met Gln Pro Gly Gly Arg

```
                    85                  90                  95
Leu Leu Leu Ser Lys Leu Gly Leu Glu Asp Cys Leu Glu Gly Ile Asp
                100                 105                 110
Glu Gln Ile Ala Thr Gly Leu Ala Val Tyr Lys Asp Gly Gln Lys Ala
                115                 120                 125
Leu Val Ser Phe Pro Glu Asp Asn Asp Phe Pro Tyr Glu Pro Thr Gly
                130                 135                 140
Arg Ala Phe Tyr Asn Gly Arg Phe Val Gln Arg Leu Arg Gln Lys Ala
145                 150                 155                 160
Ser Ser Leu Pro Thr Val Gln Leu Glu Glu Gly Thr Val Lys Ser Leu
                165                 170                 175
Ile Glu Glu Lys Gly Val Ile Lys Gly Val Thr Tyr Lys Asn Ser Ala
                180                 185                 190
Gly Glu Glu Thr Thr Ala Phe Ala Pro Leu Thr Val Val Cys Asp Gly
                195                 200                 205
Cys Tyr Ser Asn Leu Arg Arg Ser Val Asn Asp Asn Asn Ala Glu Val
                210                 215                 220
Ile Ser Tyr Gln Val Gly Tyr Val Ser Lys Asn Cys Gln Leu Glu Asp
225                 230                 235                 240
Pro Glu Lys Leu Lys Leu Ile Met Ser Lys Pro Ser Phe Thr Met Leu
                245                 250                 255
Tyr Gln Ile Ser Ser Thr Asp Val Arg Cys Val Met Glu Ile Phe Pro
                260                 265                 270
Gly Asn Ile Pro Ser Ile Ser Asn Gly Glu Met Ala Val Tyr Leu Lys
                275                 280                 285
Asn Thr Met Ala Pro Gln Val Pro Pro Glu Leu Arg Lys Ile Phe Leu
                290                 295                 300
Lys Gly Ile Asp Glu Gly Ala Gln Ile Lys Ala Met Pro Thr Lys Arg
305                 310                 315                 320
Met Glu Ala Thr Leu Ser Glu Lys Gln Gly Val Ile Val Leu Gly Asp
                325                 330                 335
Ala Phe Asn Met Arg His Pro Ala Ile Ala Ser Gly Met Met Val Val
                340                 345                 350
Leu Ser Asp Ile Leu Ile Leu Arg Arg Leu Leu Gln Pro Leu Arg Asn
                355                 360                 365
Leu Ser Asp Ala Asn Lys Val Ser Glu Val Ile Lys Ser Phe Tyr Val
                370                 375                 380
Ile Arg Lys Pro Met Ser Ala Thr Val Asn Thr Leu Gly Asn Ala Phe
385                 390                 395                 400
Ser Gln Val Leu Ile Ala Ser Thr Asp Glu Ala Lys Glu Ala Met Arg
                405                 410                 415
Gln Gly Cys Phe Asp Tyr Leu Ser Ser Gly Phe Arg Thr Ser Gly
                420                 425                 430
Met Met Ala Leu Leu Gly Gly Met Asn Pro Arg Pro Leu Ser Leu Ile
                435                 440                 445
Phe His Leu Cys Gly Ile Thr Leu Ser Ser Ile Gly Gln Leu Leu Ser
                450                 455                 460
Pro Phe Pro Ser Pro Leu Gly Ile Trp His Ser Leu Arg Leu Phe Gly
465                 470                 475                 480
Ala Glu Gly Val Ser Gln Met Leu Ser Pro Ala Tyr Ala Ala Tyr
                485                 490                 495
Arg Lys Ser Tyr Met Thr Ala Thr Ala Leu
                500                 505
```

<210> SEQ ID NO 12
<211> LENGTH: 518
<212> TYPE: PRT
<213> ORGANISM: Brassica napus

<400> SEQUENCE: 12

```
Met Asp Met Ala Phe Val Glu Val Cys Leu Arg Met Leu Leu Val Phe
1               5                   10                  15

Val Leu Ser Trp Thr Ile Phe His Val Asn Asn Arg Lys Lys Lys Lys
            20                  25                  30

Ala Thr Lys Leu Ala Asp Leu Ala Thr Glu Glu Arg Lys Glu Gly Gly
        35                  40                  45

Pro Asp Val Ile Ile Val Gly Ala Gly Val Gly Ser Ala Leu Ala
    50                  55                  60

Tyr Ala Leu Ala Lys Asp Gly Arg Arg Val His Val Ile Glu Arg Asp
65                  70                  75                  80

Met Arg Glu Pro Val Arg Met Met Gly Glu Phe Met Gln Pro Gly Gly
                85                  90                  95

Arg Leu Met Leu Ser Lys Leu Gly Leu Gln Asp Cys Leu Glu Glu Ile
            100                 105                 110

Asp Ala Gln Lys Ser Thr Gly Ile Arg Leu Phe Lys Asp Gly Lys Glu
        115                 120                 125

Thr Val Ala Cys Phe Pro Val Asp Thr Asn Phe Pro Tyr Glu Pro Ser
    130                 135                 140

Gly Arg Phe His Asn Gly Arg Phe Val Gln Arg Leu Arg Gln Lys
145                 150                 155                 160

Ala Ser Ser Leu Pro Asn Val Arg Leu Glu Glu Gly Thr Val Arg Ser
                165                 170                 175

Leu Ile Glu Glu Lys Gly Val Val Lys Gly Val Thr Tyr Lys Asn Ser
            180                 185                 190

Ser Gly Glu Glu Thr Thr Ser Phe Ala Pro Leu Thr Val Val Cys Asp
        195                 200                 205

Gly Cys His Ser Asn Leu Arg Arg Ser Leu Asn Asp Asn Asn Ala Glu
    210                 215                 220

Val Thr Ala Tyr Glu Ile Gly Tyr Ile Ser Arg Asn Cys Arg Leu Glu
225                 230                 235                 240

Gln Pro Asp Lys Leu His Leu Ile Met Ala Lys Pro Ser Phe Ala Met
                245                 250                 255

Leu Tyr Gln Val Ser Ser Thr Asp Val Arg Cys Asn Phe Glu Leu Leu
            260                 265                 270

Ser Lys Asn Leu Pro Ser Val Ser Asn Gly Glu Met Thr Ser Phe Val
        275                 280                 285

Arg Asn Ser Ile Ala Pro Gln Val Pro Leu Lys Leu Arg Lys Thr Phe
    290                 295                 300

Leu Lys Gly Leu Asp Glu Gly Ser His Ile Lys Ile Thr Gln Ala Lys
305                 310                 315                 320

Arg Ile Pro Ala Thr Leu Ser Arg Lys Lys Gly Val Ile Val Leu Gly
                325                 330                 335

Asp Ala Phe Asn Met Arg His Pro Val Ile Ala Ser Gly Met Met Val
            340                 345                 350

Leu Leu Ser Asp Ile Leu Ile Leu Ser Arg Leu Leu Lys Pro Leu Gly
        355                 360                 365

Asn Leu Gly Asp Glu Asn Lys Val Ser Glu Val Met Lys Ser Phe Tyr
```

```
        370                 375                 380
Ala Leu Arg Lys Pro Met Ser Ala Thr Val Asn Thr Leu Gly Asn Ser
385                 390                 395                 400

Phe Trp Gln Val Leu Ile Ala Ser Thr Asp Glu Ala Lys Glu Ala Met
                405                 410                 415

Arg Gln Gly Cys Phe Asp Tyr Leu Ser Ser Gly Gly Phe Arg Thr Ser
            420                 425                 430

Gly Leu Met Ala Leu Ile Gly Gly Met Asn Pro Arg Pro Leu Ser Leu
        435                 440                 445

Phe Tyr His Leu Phe Val Ile Ser Leu Ser Ser Ile Gly Gln Leu Leu
    450                 455                 460

Ser Pro Phe Pro Thr Pro Leu Arg Val Trp His Ser Leu Arg Leu Leu
465                 470                 475                 480

Asp Leu Ser Leu Lys Met Leu Val Pro His Leu Lys Ala Glu Gly Ile
                485                 490                 495

Gly Gln Met Leu Ser Pro Thr Asn Ala Ala Ala Tyr Arg Lys Ser Tyr
            500                 505                 510

Met Ala Ala Thr Val Val
        515
```

<210> SEQ ID NO 13
<211> LENGTH: 531
<212> TYPE: PRT
<213> ORGANISM: Euphorbia tirucalli

<400> SEQUENCE: 13

```
Met Glu Val Ile Phe Asp Thr Tyr Ile Phe Gly Thr Phe Phe Ala Ser
1               5                   10                  15

Leu Cys Ala Phe Leu Leu Leu Phe Ile Leu Arg Pro Lys Val Lys Lys
                20                  25                  30

Met Gly Lys Ile Arg Glu Ile Ser Ser Ile Asn Thr Gln Asn Asp Thr
            35                  40                  45

Ala Ile Thr Pro Pro Lys Gly Ser Gly Thr Asp Val Ile Ile Val Gly
        50                  55                  60

Ala Gly Val Ala Gly Ala Ala Leu Ala Cys Thr Leu Gly Lys Asp Gly
65                  70                  75                  80

Arg Arg Val His Val Ile Glu Arg Asp Leu Lys Glu Pro Asp Arg Ile
                85                  90                  95

Val Gly Glu Leu Leu Gln Pro Gly Gly Tyr Leu Lys Leu Val Glu Leu
            100                 105                 110

Gly Leu Gln Asp Cys Val Glu Glu Ile Asp Ala Gln Arg Ile Val Gly
        115                 120                 125

Tyr Ala Leu Phe Met Asp Gly Asn Asn Thr Lys Leu Ser Tyr Pro Leu
    130                 135                 140

Glu Lys Phe Asp Ala Glu Val Ser Gly Lys Ser Phe His Asn Gly Arg
145                 150                 155                 160

Phe Ile Gln Arg Met Arg Glu Lys Ala Ala Ser Leu Pro Asn Val Gln
                165                 170                 175

Leu Glu Gln Gly Thr Val Thr Ser Leu Leu Glu Glu Asn Gly Thr Ile
            180                 185                 190

Lys Gly Val Gln Tyr Lys Thr Lys Asp Gly Gln Glu His Lys Ala Tyr
        195                 200                 205

Ala Pro Leu Thr Val Val Cys Asp Gly Cys Phe Ser Asn Leu Arg Arg
    210                 215                 220
```

```
Ser Leu Cys Lys Pro Lys Val Asp Val Pro His Phe Val Gly Leu
225                 230                 235                 240

Val Leu Glu Asn Cys Asp Leu Pro Phe Ala Asn His Gly His Val Ile
                245                 250                 255

Leu Ala Asp Pro Ser Pro Ile Leu Phe Tyr Pro Ile Ser Ser Thr Glu
            260                 265                 270

Val Arg Cys Leu Val Asp Val Pro Gly Gln Lys Leu Pro Ser Ile Ala
        275                 280                 285

Ser Gly Glu Met Ala Lys Tyr Leu Lys Thr Met Val Ala Lys Gln Ile
    290                 295                 300

Pro Pro Val Leu His Asp Ala Phe Val Ser Ala Ile Asp Lys Gly Asn
305                 310                 315                 320

Ile Arg Thr Met Pro Asn Arg Ser Met Pro Ala Asp Pro Leu Pro Thr
                325                 330                 335

Pro Gly Ala Leu Leu Met Gly Asp Ala Phe Asn Met Arg His Pro Leu
            340                 345                 350

Thr Gly Gly Gly Met Thr Val Ala Leu Ala Asp Ile Val Leu Leu Arg
        355                 360                 365

Asp Leu Leu Lys Pro Leu Arg Asp Leu Asn Asp Ala Pro Ala Leu Ala
    370                 375                 380

Lys Tyr Leu Glu Ser Phe Tyr Thr Leu Arg Lys Pro Val Ala Ser Thr
385                 390                 395                 400

Ile Asn Thr Leu Ala Gly Ala Leu Tyr Lys Val Phe Ser Ala Ser Pro
                405                 410                 415

Asp Glu Ala Arg Lys Glu Met Arg Gln Ala Cys Phe Asp Tyr Leu Ser
            420                 425                 430

Leu Gly Gly Glu Cys Ala Met Gly Pro Val Ser Leu Leu Ser Gly Leu
        435                 440                 445

Asn Pro Ser Pro Leu Thr Leu Val Leu His Phe Phe Gly Val Ala Ile
    450                 455                 460

Tyr Gly Val Gly Arg Leu Leu Ile Pro Phe Pro Thr Pro Lys Gly Met
465                 470                 475                 480

Trp Ile Gly Ala Arg Ile Ile Ser Ser Ala Ser Gly Ile Ile Phe Pro
                485                 490                 495

Ile Ile Lys Ala Glu Gly Val Arg Gln Val Phe Phe Pro Ala Thr Val
            500                 505                 510

Pro Ala Ile Tyr Arg Asn Pro Val Asn Gly Lys Ser Val Glu Val
        515                 520                 525

Pro Lys Ser
    530

<210> SEQ ID NO 14
<211> LENGTH: 519
<212> TYPE: PRT
<213> ORGANISM: Medicago truncatula

<400> SEQUENCE: 14

Met Ile Asp Pro Tyr Gly Phe Gly Trp Ile Thr Cys Thr Leu Ile Thr
1               5                   10                  15

Leu Ala Ala Leu Tyr Asn Phe Leu Phe Ser Arg Lys Asn His Ser Asp
                20                  25                  30

Ser Thr Thr Thr Glu Asn Ile Thr Thr Ala Thr Gly Glu Cys Arg Ser
            35                  40                  45

Phe Asn Pro Asn Gly Asp Val Asp Ile Ile Ile Val Gly Ala Gly Val
        50                  55                  60
```

-continued

```
Ala Gly Ser Ala Leu Ala Tyr Thr Leu Gly Lys Asp Gly Arg Arg Val
 65                  70                  75                  80

Leu Ile Ile Glu Arg Asp Leu Asn Glu Pro Asp Arg Ile Val Gly Glu
                 85                  90                  95

Leu Leu Gln Pro Gly Gly Tyr Leu Lys Leu Ile Glu Leu Gly Leu Asp
                100                 105                 110

Asp Cys Val Glu Lys Ile Asp Ala Gln Lys Val Phe Gly Tyr Ala Leu
                115                 120                 125

Phe Lys Asp Gly Lys His Thr Arg Leu Ser Tyr Pro Leu Glu Lys Phe
            130                 135                 140

His Ser Asp Ile Ala Gly Arg Ser Phe His Asn Gly Arg Phe Ile Leu
145                 150                 155                 160

Arg Met Arg Glu Lys Ala Ala Ser Leu Pro Asn Val Arg Leu Glu Gln
                165                 170                 175

Gly Thr Val Thr Ser Leu Leu Glu Glu Asn Gly Thr Ile Lys Gly Val
                180                 185                 190

Gln Tyr Lys Thr Lys Asp Ala Gln Glu Phe Ser Ala Cys Ala Pro Leu
            195                 200                 205

Thr Ile Val Cys Asp Gly Cys Phe Ser Asn Leu Arg Arg Ser Leu Cys
            210                 215                 220

Asn Pro Lys Val Glu Val Pro Ser Cys Phe Val Gly Leu Val Leu Glu
225                 230                 235                 240

Asn Cys Glu Leu Pro Cys Ala Asp His Gly His Val Ile Leu Gly Asp
                245                 250                 255

Pro Ser Pro Val Leu Phe Tyr Pro Ile Ser Ser Thr Glu Ile Arg Cys
                260                 265                 270

Leu Val Asp Val Pro Gly Gln Lys Val Pro Ser Ile Ser Asn Gly Glu
            275                 280                 285

Met Ala Lys Tyr Leu Lys Thr Val Ala Pro Gln Val Pro Pro Glu
290                 295                 300

Leu His Ala Ala Phe Ile Ala Ala Val Asp Lys Gly His Ile Arg Thr
305                 310                 315                 320

Met Pro Asn Arg Ser Met Pro Ala Asp Pro Tyr Pro Thr Pro Gly Ala
                325                 330                 335

Leu Leu Met Gly Asp Ala Phe Asn Met Arg His Pro Leu Thr Gly Gly
                340                 345                 350

Gly Met Thr Val Ala Leu Ser Asp Ile Val Val Leu Arg Asn Leu Leu
            355                 360                 365

Lys Pro Leu Arg Asp Leu Asn Asp Ala Ser Ser Leu Cys Lys Tyr Leu
            370                 375                 380

Glu Ser Phe Tyr Thr Leu Arg Lys Pro Val Ala Ser Thr Ile Asn Thr
385                 390                 395                 400

Leu Ala Gly Ala Leu Tyr Lys Val Phe Cys Ala Ser Pro Asp Pro Ala
                405                 410                 415

Arg Lys Glu Met Arg Gln Ala Cys Phe Asp Tyr Leu Ser Leu Gly Gly
                420                 425                 430

Leu Phe Ser Glu Gly Pro Val Ser Leu Leu Ser Gly Leu Asn Pro Cys
            435                 440                 445

Pro Leu Ser Leu Val Leu His Phe Ala Val Ala Ile Tyr Gly Val
            450                 455                 460

Gly Arg Leu Leu Leu Pro Phe Pro Ser Pro Lys Arg Leu Trp Ile Gly
465                 470                 475                 480
```

```
Ile Arg Leu Ile Ala Ser Ala Ser Gly Ile Ile Leu Pro Ile Ile Lys
                485                 490                 495

Ala Glu Gly Ile Arg Gln Met Phe Phe Pro Ala Thr Val Pro Ala Tyr
            500                 505                 510

Tyr Arg Ala Pro Pro Asp Ala
        515

<210> SEQ ID NO 15
<211> LENGTH: 526
<212> TYPE: PRT
<213> ORGANISM: Medicago truncatula

<400> SEQUENCE: 15

Met Asp Leu Tyr Asn Ile Gly Trp Ile Leu Ser Ser Val Leu Ser Leu
1               5                   10                  15

Phe Ala Leu Tyr Asn Leu Ile Phe Ala Gly Lys Lys Asn Tyr Asp Val
                20                  25                  30

Asn Glu Lys Val Asn Gln Arg Glu Asp Ser Val Thr Ser Thr Asp Ala
            35                  40                  45

Gly Glu Ile Lys Ser Asp Lys Leu Asn Gly Asp Ala Asp Val Ile Ile
        50                  55                  60

Val Gly Ala Gly Ile Ala Gly Ala Ala Leu Ala His Thr Leu Gly Lys
65                  70                  75                  80

Asp Gly Arg Arg Val His Ile Ile Glu Arg Asp Leu Ser Glu Pro Asp
                85                  90                  95

Arg Ile Val Gly Glu Leu Leu Gln Pro Gly Gly Tyr Leu Lys Leu Val
                100                 105                 110

Glu Leu Gly Leu Gln Asp Cys Val Asp Asn Ile Asp Ala Gln Arg Val
            115                 120                 125

Phe Gly Tyr Ala Leu Phe Lys Asp Gly Lys His Thr Arg Leu Ser Tyr
        130                 135                 140

Pro Leu Glu Lys Phe His Ser Asp Val Ser Gly Arg Ser Phe His Asn
145                 150                 155                 160

Gly Arg Phe Ile Gln Arg Met Arg Glu Lys Ala Ala Ser Leu Pro Asn
                165                 170                 175

Val Asn Met Glu Gln Gly Thr Val Ile Ser Leu Leu Glu Glu Lys Gly
                180                 185                 190

Thr Ile Lys Gly Val Gln Tyr Lys Asn Lys Asp Gly Gln Ala Leu Thr
            195                 200                 205

Ala Tyr Ala Pro Leu Thr Ile Val Cys Asp Gly Cys Phe Ser Asn Leu
        210                 215                 220

Arg Arg Ser Leu Cys Asn Pro Lys Val Asp Asn Pro Ser Cys Phe Val
225                 230                 235                 240

Gly Leu Ile Leu Glu Asn Cys Glu Leu Pro Cys Ala Asn His Gly His
                245                 250                 255

Val Ile Leu Gly Asp Pro Ser Pro Ile Leu Phe Tyr Pro Ile Ser Ser
                260                 265                 270

Thr Glu Ile Arg Cys Leu Val Asp Val Pro Gly Thr Lys Val Pro Ser
            275                 280                 285

Ile Ser Asn Gly Asp Met Thr Lys Tyr Leu Lys Thr Thr Val Ala Pro
        290                 295                 300

Gln Val Pro Pro Glu Leu Tyr Asp Ala Phe Ile Ala Ala Val Asp Lys
305                 310                 315                 320

Gly Asn Ile Arg Thr Met Pro Asn Arg Ser Met Pro Ala Asp Pro Arg
                325                 330                 335
```

```
Pro Thr Pro Gly Ala Val Leu Met Gly Asp Ala Phe Asn Met Arg His
            340                 345                 350

Pro Leu Thr Gly Gly Gly Met Thr Val Ala Leu Ser Asp Ile Val Val
            355                 360                 365

Leu Arg Asn Leu Leu Lys Pro Met Arg Asp Leu Asn Asp Ala Pro Thr
370                 375                 380

Leu Cys Lys Tyr Leu Glu Ser Phe Tyr Thr Leu Arg Lys Pro Val Ala
385                 390                 395                 400

Ser Thr Ile Asn Thr Leu Ala Gly Ala Leu Tyr Lys Val Phe Ser Ala
                405                 410                 415

Ser Pro Asp Glu Ala Arg Lys Glu Met Arg Gln Ala Cys Phe Asp Tyr
            420                 425                 430

Leu Ser Leu Gly Gly Leu Phe Ser Glu Gly Pro Ile Ser Leu Leu Ser
            435                 440                 445

Gly Leu Asn Pro Arg Pro Leu Ser Leu Val Leu His Phe Phe Ala Val
            450                 455                 460

Ala Val Phe Gly Val Gly Arg Leu Leu Leu Pro Phe Pro Ser Pro Lys
465                 470                 475                 480

Arg Val Trp Ile Gly Ala Arg Leu Leu Ser Gly Ala Ser Gly Ile Ile
                485                 490                 495

Leu Pro Ile Ile Lys Ala Glu Gly Ile Arg Gln Met Phe Phe Pro Ala
            500                 505                 510

Thr Val Pro Ala Tyr Tyr Arg Ala Pro Pro Val Asn Ala Phe
            515                 520                 525

<210> SEQ ID NO 16
<211> LENGTH: 534
<212> TYPE: PRT
<213> ORGANISM: Ricinus communis

<400> SEQUENCE: 16

Met Ala Asp Asn Tyr Leu Leu Gly Trp Ile Leu Cys Ser Ile Ile Gly
1               5                   10                  15

Leu Phe Gly Leu Tyr Tyr Met Val Tyr Leu Val Val Lys Arg Glu Glu
            20                  25                  30

Glu Asp Asn Asn Arg Lys Ala Leu Leu Gln Ala Arg Ser Asp Ser Ala
            35                  40                  45

Lys Thr Met Ser Ala Val Ser Gln Asn Gly Glu Cys Arg Ser Asp Asn
50                  55                  60

Pro Ala Asp Ala Asp Ile Ile Ile Val Gly Ala Gly Val Ala Gly Ser
65                  70                  75                  80

Ala Leu Ala His Thr Leu Gly Lys Asp Gly Arg Arg Val His Val Ile
                85                  90                  95

Glu Arg Asp Leu Thr Glu Pro Asp Arg Ile Val Gly Glu Leu Leu Gln
            100                 105                 110

Pro Gly Gly Tyr Leu Lys Leu Ile Glu Leu Gly Leu Glu Asp Cys Val
            115                 120                 125

Glu Glu Ile Asp Ala Gln Arg Val Phe Gly Tyr Ala Leu Phe Met Asp
130                 135                 140

Gly Lys His Thr Gln Leu Ser Tyr Pro Leu Glu Lys Phe His Ser Asp
145                 150                 155                 160

Val Ala Gly Arg Ser Phe His Asn Gly Arg Phe Ile Gln Arg Met Arg
                165                 170                 175

Glu Lys Ala Ser Ser Ile Pro Asn Val Arg Leu Glu Gln Gly Thr Val
```

```
            180                 185                 190

Thr Ser Leu Ile Glu Glu Lys Gly Ile Ile Arg Gly Val Val Tyr Lys
        195                 200                 205

Thr Lys Thr Gly Glu Glu Leu Thr Ala Phe Ala Pro Leu Thr Ile Val
    210                 215                 220

Cys Asp Gly Cys Phe Ser Asn Leu Arg Arg Ser Leu Cys Asn Pro Lys
225                 230                 235                 240

Val Asp Val Pro Ser Cys Phe Val Gly Leu Val Leu Glu Asp Cys Lys
                245                 250                 255

Leu Pro Tyr Gln Tyr His Gly His Val Val Leu Ala Asp Pro Ser Pro
            260                 265                 270

Ile Leu Phe Tyr Gln Ile Ser Ser Thr Glu Val Arg Cys Leu Val Asp
        275                 280                 285

Val Pro Gly Gln Lys Val Pro Ser Ile Ser Asn Gly Glu Met Ala Lys
    290                 295                 300

Tyr Leu Lys Asn Val Val Ala Pro Gln Val Pro Pro Glu Ile Tyr Asp
305                 310                 315                 320

Ser Phe Val Ala Ala Val Asp Lys Gly Asn Ile Arg Thr Met Pro Asn
                325                 330                 335

Arg Ser Met Pro Ala Ser Pro Tyr Pro Thr Pro Gly Ala Leu Leu Met
            340                 345                 350

Gly Asp Ala Phe Asn Met Arg His Pro Leu Thr Gly Gly Gly Met Thr
        355                 360                 365

Val Ala Leu Ser Asp Ile Val Val Leu Arg Glu Leu Leu Lys Pro Leu
    370                 375                 380

Arg Asp Leu His Asp Ala Pro Thr Leu Cys Arg Tyr Leu Glu Ser Phe
385                 390                 395                 400

Tyr Thr Leu Arg Lys Pro Val Ala Ser Thr Ile Asn Thr Leu Ala Gly
                405                 410                 415

Ala Leu Tyr Lys Val Phe Cys Ala Ser Ser Asp Glu Ala Arg Asn Glu
            420                 425                 430

Met Arg Gln Ala Cys Phe Asp Tyr Leu Ser Leu Gly Gly Val Phe Ser
        435                 440                 445

Thr Gly Pro Ile Ser Leu Leu Ser Gly Leu Asn Pro Arg Pro Leu Ser
    450                 455                 460

Leu Val Val His Phe Phe Ala Val Ala Ile Tyr Gly Val Gly Arg Leu
465                 470                 475                 480

Leu Leu Pro Phe Pro Ser Pro Lys Arg Val Trp Val Gly Ala Arg Leu
                485                 490                 495

Ile Ser Gly Ala Ser Gly Ile Ile Phe Pro Ile Ile Lys Ala Glu Gly
            500                 505                 510

Val Arg Gln Met Phe Phe Pro Ala Thr Val Pro Ala Tyr Tyr Arg Ala
        515                 520                 525

Pro Pro Val Glu Cys Asn
    530

<210> SEQ ID NO 17
<211> LENGTH: 521
<212> TYPE: PRT
<213> ORGANISM: Ricinus communis

<400> SEQUENCE: 17

Met Glu Tyr Lys Leu Ala Val Ala Gly Ile Ile Ala Ser Leu Trp Ala
1               5                   10                  15
```

```
Leu Phe Met Leu Cys Ser Leu Lys Arg Lys Asn Ile Thr Arg Ala
         20                  25                  30

Ser Phe Asn Asn Tyr Thr Asp Glu Thr Leu Lys Ser Ser Lys Glu
         35                  40                  45

Ile Cys Gln Pro Glu Ile Val Ala Ser Pro Asp Ile Ile Val Gly
 50                  55                  60

Ala Gly Val Ala Gly Ala Ala Leu Ala Tyr Ala Leu Gly Glu Asp Gly
 65              70                  75                  80

Arg Gln Val His Val Ile Glu Arg Asp Leu Ser Glu Pro Asp Arg Ile
                 85                  90                  95

Val Gly Glu Leu Leu Gln Pro Gly Gly Tyr Leu Lys Leu Ile Glu Leu
                100                 105                 110

Gly Leu Glu Asp Cys Val Glu Lys Ile Asp Ala Gln Gln Val Phe Gly
            115                 120                 125

Tyr Ala Ile Phe Lys Asp Gly Lys Ser Thr Lys Leu Ser Tyr Pro Leu
        130                 135                 140

Asp Gly Phe Gln Thr Asn Val Ser Gly Arg Ser Phe His Asn Gly Arg
145                 150                 155                 160

Phe Ile Gln Arg Met Arg Glu Lys Ala Thr Ser Leu Pro Asn Leu Ile
                165                 170                 175

Leu Gln Gln Gly Thr Val Thr Ser Leu Val Glu Lys Lys Gly Thr Val
                180                 185                 190

Lys Gly Val Asn Tyr Arg Thr Arg Asn Gly Gln Glu Met Thr Ala Tyr
                195                 200                 205

Ala Pro Leu Thr Ile Val Cys Asp Gly Cys Phe Ser Asn Leu Arg Arg
210                 215                 220

Ser Leu Cys Asn Pro Lys Val Glu Ile Pro Ser Cys Phe Val Ala Leu
225                 230                 235                 240

Val Leu Glu Asn Cys Asp Leu Pro Tyr Ala Asn His Gly His Val Ile
                245                 250                 255

Leu Ala Asp Pro Ser Pro Ile Leu Phe Tyr Pro Ile Ser Ser Thr Glu
                260                 265                 270

Val Arg Cys Leu Val Asp Ile Pro Gly Gln Lys Val Pro Ser Ile Ser
                275                 280                 285

Asn Gly Glu Leu Ala Gln Tyr Leu Lys Ser Thr Val Ala Lys Gln Ile
290                 295                 300

Pro Ser Glu Leu His Asp Ala Phe Ile Ser Ala Ile Glu Lys Gly Asn
305                 310                 315                 320

Ile Arg Thr Met Pro Asn Arg Ser Met Pro Ala Ser Pro His Pro Thr
                325                 330                 335

Pro Gly Ala Leu Leu Val Gly Asp Ala Phe Asn Met Arg His Pro Leu
                340                 345                 350

Thr Gly Gly Gly Met Thr Val Ala Leu Ser Asp Ile Val Leu Leu Arg
        355                 360                 365

Asn Leu Leu Arg Pro Leu Glu Asn Leu Asn Asp Ala Ser Val Leu Cys
        370                 375                 380

Lys Tyr Leu Glu Ser Phe Tyr Ile Leu Arg Lys Pro Met Ala Ser Thr
385                 390                 395                 400

Ile Asn Thr Leu Ala Gly Ala Leu Tyr Lys Val Phe Ser Ala Ser Thr
                405                 410                 415

Asp Arg Ala Arg Ser Glu Met Arg Gln Ala Cys Phe Asp Tyr Leu Ser
                420                 425                 430

Leu Gly Gly Val Phe Ser Asn Gly Pro Ile Ala Leu Leu Ser Gly Leu
```

```
               435                 440                 445
Asn Pro Arg Pro Leu Asn Leu Val Leu His Phe Phe Ala Val Ala Val
    450                 455                 460

Tyr Gly Val Gly Arg Leu Ile Leu Pro Phe Pro Ser Pro Lys Ser Ile
465                 470                 475                 480

Trp Asp Gly Val Lys Leu Ile Ser Gly Ala Ser Ser Val Ile Phe Pro
                485                 490                 495

Ile Met Lys Ala Glu Gly Ile Gly Gln Ile Phe Phe Pro Ile Thr Lys
                500                 505                 510

Pro Pro Asn His Lys Ser Gln Thr Trp
                515                 520

<210> SEQ ID NO 18
<211> LENGTH: 458
<212> TYPE: PRT
<213> ORGANISM: Ricinus communis

<400> SEQUENCE: 18

Met Gly Val Ser Arg Glu Glu Asn Ala Arg Asp Glu Lys Cys His Tyr
1               5                   10                  15

Tyr Glu Asn Gly Ile Ser Leu Ser Glu Lys Ser Met Ser Thr Asp Ile
                20                  25                  30

Ile Ile Val Gly Ala Gly Val Ala Gly Ser Ala Leu Ala Tyr Thr Leu
            35                  40                  45

Gly Lys Asp Gly Arg Arg Val His Val Ile Glu Arg Asp Leu Ser Leu
    50                  55                  60

Gln Asp Arg Ile Val Gly Glu Leu Leu Gln Pro Gly Gly Tyr Leu Lys
65                  70                  75                  80

Leu Ile Glu Leu Gly Leu Glu Asp Cys Val Glu Glu Ile Asp Ala Gln
                85                  90                  95

Gln Val Phe Gly Tyr Ala Leu Tyr Lys Asn Gly Arg Ser Thr Lys Leu
                100                 105                 110

Ser Tyr Pro Leu Glu Ser Phe Asp Ser Asp Val Ser Gly Arg Ser Phe
            115                 120                 125

His Asn Gly Arg Phe Ile Gln Arg Met Arg Glu Lys Ala Ala Ser Leu
    130                 135                 140

Pro Asn Val Arg Leu Glu Glu Gly Thr Val Thr Ser Leu Leu Glu Val
145                 150                 155                 160

Lys Gly Thr Ile Lys Gly Val Gln Tyr Lys Thr Lys Asn Gly Glu Glu
                165                 170                 175

Leu Thr Ala Ser Ala Pro Leu Thr Ile Val Cys Asp Gly Cys Phe Ser
                180                 185                 190

Asn Leu Arg Arg Ser Leu Cys Asn Pro Lys Val Asp Ile Pro Ser Cys
            195                 200                 205

Phe Val Ala Leu Ile Leu Glu Asn Ser Gly Gln Lys Leu Pro Ser Ile
    210                 215                 220

Ser Asn Gly Asp Met Ala Asn Tyr Leu Lys Ser Val Val Ala Pro Gln
225                 230                 235                 240

Ile Pro Pro Val Leu Ser Glu Ala Phe Ile Ser Ala Ile Glu Lys Gly
                245                 250                 255

Lys Ile Arg Thr Met Pro Asn Arg Ser Met Pro Ala Ala Pro His Pro
                260                 265                 270

Thr Pro Gly Ala Leu Leu Leu Gly Asp Ala Phe Asn Met Arg His Pro
            275                 280                 285
```

```
Leu Thr Gly Gly Gly Met Thr Val Ala Leu Ser Asp Ile Val Val Leu
        290                 295                 300

Arg Asn Leu Leu Lys Pro Leu His Asp Leu Thr Asp Ala Ser Ala Leu
305                 310                 315                 320

Cys Glu Tyr Leu Lys Ser Phe Tyr Ser Leu Arg Lys Pro Val Ala Ser
                325                 330                 335

Thr Ile Asn Thr Leu Ala Gly Ala Leu Tyr Lys Val Phe Ser Ala Ser
                340                 345                 350

His Asp Pro Ala Arg Asn Glu Met Arg Gln Ala Cys Phe Asp Tyr Leu
                355                 360                 365

Ser Leu Gly Gly Val Phe Ser Asn Gly Pro Ile Ala Leu Leu Ser Gly
370                 375                 380

Leu Asn Pro Arg Pro Leu Ser Leu Val Ala His Phe Phe Ala Val Ala
385                 390                 395                 400

Ile Tyr Gly Val Gly Arg Leu Ile Phe Pro Leu Pro Ser Ala Lys Gly
                405                 410                 415

Met Trp Met Gly Ala Arg Met Ile Lys Val Ala Ser Gly Ile Ile Phe
                420                 425                 430

Pro Ile Ile Arg Ala Glu Gly Val Gln His Met Phe Phe Ser Lys Thr
                435                 440                 445

Leu Ser Ala Phe Ser Arg Ser Gln Thr Ser
450                 455

<210> SEQ ID NO 19
<211> LENGTH: 485
<212> TYPE: PRT
<213> ORGANISM: Ricinus communis

<400> SEQUENCE: 19

Met Glu Tyr Gln Tyr Phe Val Gly Gly Ile Ile Ala Ser Ala Leu Leu
1               5                   10                  15

Phe Val Leu Val Cys Arg Leu Ala Gly Lys Arg Gln Arg Arg Ala Leu
                20                  25                  30

Arg Asp Thr Val Asp Arg Asp Glu Ile Ser Gln Asn Ser Glu Asn Gly
            35                  40                  45

Ile Ser Gln Ser Glu Lys Asn Met Asn Thr Asp Ile Ile Val Gly
50                  55                  60

Ala Gly Val Ala Gly Ser Thr Leu Ala Tyr Thr Leu Gly Lys Asp Gly
65                  70                  75                  80

Arg Arg Val Arg Val Ile Glu Arg Asp Leu Ser Leu Gln Asp Arg Ile
                85                  90                  95

Val Gly Glu Leu Leu Gln Pro Gly Gly Tyr Leu Lys Leu Ile Glu Leu
                100                 105                 110

Gly Leu Glu Asp Cys Val Glu Glu Ile Asp Ala Leu Gln Val Phe Gly
            115                 120                 125

Tyr Ala Leu Tyr Lys Asn Gly Arg Ser Thr Lys Leu Ser Tyr Pro Leu
        130                 135                 140

Asp Ser Phe Asp Ser Asp Val Ser Gly Arg Ser Phe His Asn Gly Arg
145                 150                 155                 160

Phe Ile Gln Arg Met Arg Glu Lys Ala Ala Ser Leu Pro Asn Val Arg
                165                 170                 175

Met Glu Gly Gly Thr Val Thr Ser Leu Leu Glu Val Lys Gly Thr Ile
                180                 185                 190

Lys Gly Val Gln Tyr Lys Asn Lys Asn Gly Glu Glu Leu Ile Ala Cys
        195                 200                 205
```

Ala Pro Leu Thr Ile Val Cys Asp Gly Cys Phe Ser Asn Leu Arg Arg
    210                 215                 220

Ser Leu Cys Asn Ser Lys Val Asp Ile Pro Phe Cys Phe Val Ala Leu
225                 230                 235                 240

Ile Leu Glu Asn Cys Glu Leu Pro Tyr Pro Asn His Gly His Val Ile
                245                 250                 255

Leu Ala Asp Pro Ser Pro Ile Leu Phe Tyr Arg Ile Ser Ile Ser Glu
            260                 265                 270

Ile Arg Cys Leu Val Asp Ile Pro Ala Gly Gln Lys Leu Pro Ser Ile
        275                 280                 285

Ser Asn Gly Glu Met Ala Asn Tyr Leu Lys Ser Val Val Ala Pro Gln
    290                 295                 300

Ile Pro Pro Glu Leu Ser Asn Ala Phe Leu Ser Ala Ile Glu Lys Gly
305                 310                 315                 320

Lys Ile Arg Thr Met Pro Lys Arg Ser Met Pro Ala Ala Pro His Pro
                325                 330                 335

Thr Pro Gly Ala Leu Leu Leu Gly Asp Ala Phe Asn Met Arg His Pro
            340                 345                 350

Leu Thr Gly Gly Val Met Thr Val Ala Leu Ser Asp Ile Val Val Leu
        355                 360                 365

Arg Ser Leu Leu Arg Pro Leu His Asp Leu Thr Asp Ala Ser Ala Leu
    370                 375                 380

Cys Glu Tyr Leu Lys Ser Phe Tyr Ser Leu Arg Lys Pro Met Val Ser
385                 390                 395                 400

Thr Ile Asn Thr Leu Ala Gly Ala Leu Tyr Arg Val Phe Ser Ala Ser
                405                 410                 415

Gln Asp Pro Ala Arg Asp Glu Met Arg Gln Ala Cys Phe Asp Tyr Leu
            420                 425                 430

Ser Leu Gly Gly Val Phe Ser Asn Gly Pro Ile Ala Leu Leu Ser Gly
        435                 440                 445

Leu Asn Pro Arg Pro Leu Ser Leu Ile Val His Phe Phe Ala Val Ala
    450                 455                 460

Val Tyr Gly Val Gly Arg Leu Ile Phe Pro Leu Pro Ser Ala Lys Arg
465                 470                 475                 480

Met Trp Met Gln Glu
                485

<210> SEQ ID NO 20
<211> LENGTH: 220
<212> TYPE: PRT
<213> ORGANISM: Ricinus communis

<400> SEQUENCE: 20

Met Glu Tyr Gln Tyr Leu Met Gly Gly Gly Ile Met Thr Leu Leu Phe
1               5                   10                  15

Val Leu Ser Tyr Arg Leu Lys Arg Glu Thr Arg Ala Ser Val Glu Asn
            20                  25                  30

Ala Arg Asp Glu Val Leu Gln Asn Ser Glu Asn Gly Ile Ser Gln Ser
        35                  40                  45

Glu Lys Ala Met Asn Thr Asp Ile Lys Leu Leu Leu Glu Gln Ile Val
    50                  55                  60

Gln Lys Ile Ala Met Leu Asn Ser Ile Arg Leu Glu Glu Gly Thr Val
65                  70                  75                  80

Thr Ser Leu Leu Glu Val Lys Arg Asp Ile Lys Gly Val Gln Tyr Lys

```
                85                  90                  95

Thr Lys Asn Gly Glu Glu Leu Thr Ala Cys Ala Pro Leu Thr Ile Val
            100                 105                 110

Ser His Gly Cys Phe Ser Asn Leu Arg Leu His Val Thr Pro Ser Thr
        115                 120                 125

Ser Lys Phe Lys Ser Phe Ile Gly Leu Glu Val Asp Ile Pro Ser Ser
    130                 135                 140

Phe Ala Ala Leu Ile Leu Gly Asn Cys Glu Leu Pro Phe Pro Asn His
145                 150                 155                 160

Gly His Val Ile Leu Ala Asp Pro Ser Ser Ile Leu Phe Tyr Arg Ile
                165                 170                 175

Ser Ser Ser Glu Ile Cys Cys Leu Val Asp Val Pro Ala Gly Gln Lys
            180                 185                 190

Leu Pro Ser Ile Ser Asn Gly Glu Met Ala Asn Tyr Leu Lys Ser Val
        195                 200                 205

Val Ala His Gln Ala Phe Lys Val Gly Leu Ala Tyr
    210                 215                 220

<210> SEQ ID NO 21
<211> LENGTH: 642
<212> TYPE: PRT
<213> ORGANISM: Ricinus communis

<400> SEQUENCE: 21

Met Ser Pro Ile Ser Ile Gln Leu Pro Pro Arg Pro Gln Leu Tyr Arg
1               5                   10                  15

Ser Leu Ile Ser Ser Leu Ser Leu Ser Thr Tyr Lys Gln Pro Pro Ser
            20                  25                  30

Pro Pro Ser Phe Ser Leu Thr Ile Ala Asn Ser Pro Pro Gln Pro Gln
        35                  40                  45

Pro Gln Ala Thr Val Ser Ser Lys Thr Arg Thr Ile Thr Arg Leu Ser
    50                  55                  60

Asn Ser Ser Asn Arg Val Asn Leu Leu Gln Ala Glu Gln His Pro Gln
65                  70                  75                  80

Glu Pro Ser Ser Asp Leu Ser Tyr Ser Ser Ser Pro Pro His Cys Val
                85                  90                  95

Ser Gly Gly Tyr Asn Ile Lys Leu Met Glu Val Gly Thr Asp Asn Tyr
            100                 105                 110

Ala Val Ile Ile Ile Leu Gly Thr Phe Phe Ala Ser Leu Phe Ala Phe
        115                 120                 125

Val Phe Leu Ser Ile Leu Arg Tyr Asn Phe Lys Asn Lys Asn Lys Ala
    130                 135                 140

Lys Ile His Asp Glu Thr Thr Leu Lys Thr Gln Asn Asp Asn Val Arg
145                 150                 155                 160

Leu Pro Asp Asn Gly Ser Gly Asn Asp Val Ile Ile Val Gly Ala Gly
                165                 170                 175

Val Ala Gly Ala Ala Leu Ala Tyr Thr Leu Gly Lys Asp Gly Arg Arg
            180                 185                 190

Val His Val Ile Glu Arg Asp Leu Thr Glu Pro Asp Arg Ile Val Gly
        195                 200                 205

Glu Leu Leu Gln Pro Gly Gly Tyr Leu Lys Leu Ile Glu Leu Gly Leu
    210                 215                 220

Glu Asp Cys Val Gln Glu Ile Asp Ala Gln Arg Val Leu Gly Tyr Ala
225                 230                 235                 240
```

```
Leu Phe Lys Asp Gly Lys Asn Thr Arg Leu Ser Tyr Pro Leu Glu Lys
                245                 250                 255

Phe His Ala Asp Val Ala Gly Arg Ser Phe His Asn Gly Arg Phe Ile
            260                 265                 270

Gln Arg Met Arg Glu Lys Ala Ala Ser Leu Pro Asn Val Lys Leu Glu
        275                 280                 285

Gln Gly Thr Val Thr Ser Leu Leu Glu Glu Asn Gly Thr Ile Lys Gly
    290                 295                 300

Val Gln Tyr Lys Thr Lys Asp Gly Gln Glu Ile Arg Ala Tyr Ala Pro
305                 310                 315                 320

Leu Thr Ile Val Cys Asp Gly Cys Phe Ser Asn Leu Arg Arg Ser Leu
                325                 330                 335

Cys Asn Pro Lys Val Asp Val Pro Ser Cys Phe Val Gly Leu Val Leu
            340                 345                 350

Glu Asn Cys Gln Leu Pro Phe Ala Asn His Gly His Val Val Leu Ala
        355                 360                 365

Asp Pro Ser Pro Ile Leu Phe Tyr Pro Ile Ser Ser Thr Glu Val Arg
    370                 375                 380

Cys Leu Val Asp Val Pro Gly Gln Lys Val Pro Ser Ile Ala Asn Gly
385                 390                 395                 400

Glu Met Ala Lys Tyr Leu Lys Asn Val Val Ala Pro Gln Ile Pro Pro
                405                 410                 415

Val Leu His Asp Ala Phe Ile Ser Ala Ile Asp Lys Gly Asn Ile Arg
            420                 425                 430

Thr Met Pro Asn Arg Ser Met Pro Ala Asp Pro His Pro Thr Pro Gly
        435                 440                 445

Ala Leu Leu Met Gly Asp Ala Phe Asn Met Arg His Pro Leu Thr Gly
    450                 455                 460

Gly Gly Met Thr Val Ala Leu Ser Asp Ile Val Val Leu Arg Asp Leu
465                 470                 475                 480

Leu Lys Pro Leu Arg Asp Leu Asn Asp Ala Thr Ser Leu Thr Lys Tyr
                485                 490                 495

Leu Glu Ser Phe Tyr Thr Leu Arg Lys Pro Val Ala Ser Thr Ile Asn
            500                 505                 510

Thr Leu Ala Gly Ala Leu Tyr Lys Val Phe Ser Ala Ser Pro Asp Gln
        515                 520                 525

Ala Arg Lys Glu Met Arg Gln Ala Cys Phe Asp Tyr Leu Ser Leu Gly
    530                 535                 540

Gly Ile Phe Ser Ser Gly Pro Val Ala Leu Leu Ser Gly Leu Asn Pro
545                 550                 555                 560

Arg Pro Leu Ser Leu Val Met His Phe Phe Ala Val Ala Ile Tyr Gly
                565                 570                 575

Val Gly Arg Leu Leu Leu Pro Phe Pro Ser Pro Lys Ser Val Trp Ile
            580                 585                 590

Gly Ala Arg Leu Ile Ser Ser Ala Ser Gly Ile Ile Phe Pro Ile Ile
        595                 600                 605

Lys Ala Glu Gly Val Arg Gln Met Phe Phe Pro Ala Thr Ile Pro Ala
    610                 615                 620

Ile Tyr Arg Pro Pro Pro Val Lys Asp Thr Ser Asp Asp Glu Gln Lys
625                 630                 635                 640

Ser Arg

<210> SEQ ID NO 22
```

<211> LENGTH: 2280
<212> TYPE: DNA
<213> ORGANISM: Siraitia grosvenorii

<400> SEQUENCE: 22

```
atgtggaggt taaaggtcgg agcagaaagc gttggggaga atgatgagaa atggttgaag      60
agcataagca atcacttggg acgccaggtg tgggagttct gtccggatgc cggcacccaa     120
caacagctct tgcaagtcca caaagctcgt aaagctttcc acgatgaccg tttccaccga     180
aagcaatctt ccgatctctt tatcactatt cagtatggaa aggaagtaga aaatggtgga     240
aagacagcgg gagtgaaatt gaaagaaggg gaagaggtga ggaaagaggc agtagagagt     300
agcttagaga gggcattaag tttctactca agcatccaga caagcgatgg gaactgggct     360
tcggatcttg gggggcccat gttttactt ccgggtctgg tgattgccct ctacgttaca      420
ggcgtcttga attctgtttt atccaagcac caccggcaag agatgtgcag atatgtttac     480
aatcaccaga tgaagatggg ggggtggggt ctccacatcg agggcccaag caccatgttt     540
ggttccgcac tgaattatgt tgcactcagg ctgcttggag aagacgccaa cgccggggca     600
atgccaaaag cacgtgcttg gatcttggac cacggtggcg ccaccggaat cacttcctgg     660
ggcaaattgt ggctttctgt acttggagtc tacgaatgga gtggcaataa tcctcttcca     720
cccgaatttt ggttatttcc ttacttccta ccatttcatc caggaagaat gtggtgccat     780
tgtcgaatgg tttatctacc aatgtcatac ttatatggaa agagatttgt tgggccaatc     840
acacccatag ttctgtctct cagaaaagaa ctctacgcag ttccatatca tgaaatagac     900
tggaataaat ctcgcaatac atgtgcaaag gaggatctgt actatccaca tcccaagatg     960
caagatattc tgtggggatc tctccaccac gtgtatgagc ccttgtttac tcgttggcct    1020
gccaaacgcc tgagagaaaa ggctttgcag actgcaatgc aacatattca ctatgaagat    1080
gagaataccc gatatatatg ccttggccct gtcaacaagg tactcaatct gctttgttgt    1140
tgggttgaag atccctactc cgacgccttc aaacttcatc ttcaacgagt ccatgactat    1200
ctctggggttg ctgaagatgg catgaaaatg cagggttata atgggagcca gttgtgggac    1260
actgcttttct ccatccaagc aatcgtatcc accaaacttg tagacaacta tggcccaacc    1320
ttaagaaagg cacacgactt cgttaaaagt tctcagattc agcaggactg tcctggggat    1380
cctaatgttt ggtaccgtca cattcataaa ggtgcatggc cattttcaac tcgagatcat    1440
ggatggctca tctctgactg tacagcagag ggattaaagg ctgctttgat gttatccaaa    1500
cttccatccg aaacagttgg ggaatcatta gaacggaatc gccttttgcga tgctgtaaac    1560
gttctccttt ctttgcaaaa cgataatggt ggctttgcat catatgagtt gacaagatca    1620
taccttggt tggagttgat caaccccgca gaaacgtttg gagatattgt cattgattat    1680
ccgtatgtgg agtgcacctc agccacaatg gaagcactga cgttgtttaa gaaattacat    1740
cccggccata ggaccaaaga aattgatact gctattgtca gggcggccaa cttccttgaa    1800
aatatgcaaa ggacggatgg ctcttggtat ggatgttggg gggtttgctt cacgtatgcg    1860
gggtggtttg gcataaaggg attggtggct gcaggaagga catataataa ttgccttgcc    1920
attcgcaagg cttgcgattt tttactatct aaagagctgc ccggcggtgg atggggagag    1980
agttaccttt catgtcagaa taaggtatac acaaatcttg aaggaaacag accgcacctg    2040
gttaacacgg cctgggtttt aatggccctc atagaagctg gccaggctga gagagaccca    2100
acaccattgc atcgtgcagc aaggttgtta atcaattccc agttggagaa tggtgatttc    2160
ccccaacagg agatcatggg agtctttaat aaaaaattgca tgatcacata tgctgcatac    2220
```

```
                                                 cgaaacattt ttcccatttg ggctcttgga gagtattgcc atcgggtttt gactgaataa     2280
```

<210> SEQ ID NO 23
<211> LENGTH: 2280
<212> TYPE: DNA
<213> ORGANISM: Artificial Sequence
<220> FEATURE:
<223> OTHER INFORMATION: Codon-optimized S. grosvenorii cucurbitadienol
      synthase nucleotide sequence

<400> SEQUENCE: 23

```
atgtggagat tgaaagtagg tgctgaatcc gtaggtgaaa acgacgaaaa gtggttgaaa       60
agtataagta atcatttggg tagacaagtc tgggaatttt gtccagatgc aggtacacaa      120
caacaattgt tgcaagtaca taggctaga aaggcatttc atgatgacag attccacaga       180
aagcaatctt cagatttgtt catcaccatc caatacggca aggaagtaga aaacggtggc      240
aagactgctg gtgttaaatt gaaggaaggt gaagaagtta gaaaagaagc agttgaatcc      300
agtttggaaa gagccttgtc tttctactct tcaatccaaa cctctgatgg taattgggca      360
tcagacttgg gtggtccaat gttcttgtta cctggtttgg tcattgcctt gtacgtaact      420
ggtgttttga actctgtatt gtcaaagcat acagacaag aaatgtgtag atacgtttac       480
aaccatcaaa acgaagatgg tggttggggt ttgcacattg aaggtccatc cactatgttt      540
ggtagtgcat tgaattatgt cgccttaaga ttgttaggtg aagatgcaaa cgccggtgct      600
atgcctaagg caagagcctg gatattagac catggtggtg ctactggtat cacatcctgg      660
ggtaaattgt ggttaagtgt cttaggtgta tatgaatggt ctggtaataa cccattgcca      720
cctgaatttt ggttgttccc ttactttta ccattccatc tggtagaat gtggtgtcac        780
tgcagaatgg tttacttgcc aatgtcttac ttgtacggca agagattcgt tggtccaata      840
acacctatcg tcttgtcatt gagaaaggaa ttgtacgcag ttccttacca tgaaatcgat      900
tggaacaagt ccagaaacac ctgtgctaag gaagatttgt attcccaca ccctaaaatg       960
caagacattt tgtggggtag tttacatcac gtttacgaac cattatttac tagatggcct     1020
gctaaaagat tgagagaaaa ggcattacaa acagccatgc aacatatcca ctacgaagat     1080
gaaaacacca gatacatctg cttgggtcca gttaacaagg tcttgaactt gttgtgttgc     1140
tgggttgaag atcctattc tgacgctttc aagttgcatt tgcaaagagt acacgattac      1200
ttgtgggttg cagaagacgg tatgaaaatg caaggttaca atggttcaca attgtgggat     1260
acagcttttt ccattcaagc aatagtcagt actaagttgg tagataacta cggtccaaca     1320
ttaagaaaag ctcatgactt cgtaaagtcc agtcaaatac aacaagattg tccaggtgac     1380
cctaatgttt ggtatagaca tatccacaaa ggtgcatggc cattttctac cagagatcat     1440
ggttggttga tttcagactg tactgctgaa ggtttgaagg ctgcattgat gttgtctaag     1500
ttgccatcag aaactgttgg tgaatccttg gaaagaaata gattatgcga tgccgttaac     1560
gtcttgttga gtttgcaaaa cgacaacggt ggtttcgctt cttacgaatt gactagatca     1620
tacccatggt tggaattaat taatcctgct gaaacattcg gtgatatcgt cattgactat     1680
ccatacgtag aatgtacctc cgctactatg gaagcattga ccttgttcaa gaagttgcat     1740
cctggtcaca gaacaaagga aatcgatacc gcaattgtta gagccgctaa tttcttggaa     1800
aacatgcaaa gaacagacgg ttcttggtat ggttgttggg gtgtttgctt tacctacgct     1860
ggttggttcg gtattaaagg tttagtcgca gccggtagaa catacaataa ctgtttggcc     1920
ataagaaaag cttgcgattt cttgttatct aaggaattac aggtggtgg ttggggtgaa     1980
```

```
tcctacttga gttgtcaaaa caaggtttac actaatttgg aaggcaacag acctcattta   2040
gttaacacag cctgggtctt gatggcttta atcgaagccg gtcaagctga aagagatcca   2100
actcctttgc atagagctgc aagattgttg atcaactcac aattggaaaa cggtgatttt   2160
ccacaacaag aaatcatggg tgttttcaac aagaactgca tgataacata tgccgcttac   2220
agaaacattt ttcctatatg ggctttgggt gaatactgcc acagagtctt gaccgaataa   2280
```

<210> SEQ ID NO 24
<211> LENGTH: 759
<212> TYPE: PRT
<213> ORGANISM: Siraitia grosvenorii

<400> SEQUENCE: 24

```
Met Trp Arg Leu Lys Val Gly Ala Glu Ser Val Gly Glu Asn Asp Glu
1               5                   10                  15

Lys Trp Leu Lys Ser Ile Ser Asn His Leu Gly Arg Gln Val Trp Glu
            20                  25                  30

Phe Cys Pro Asp Ala Gly Thr Gln Gln Leu Leu Gln Val His Lys
        35                  40                  45

Ala Arg Lys Ala Phe His Asp Asp Arg Phe His Arg Lys Gln Ser Ser
    50                  55                  60

Asp Leu Phe Ile Thr Ile Gln Tyr Gly Lys Glu Val Glu Asn Gly Gly
65                  70                  75                  80

Lys Thr Ala Gly Val Lys Leu Lys Glu Gly Glu Val Arg Lys Glu
                85                  90                  95

Ala Val Glu Ser Ser Leu Glu Arg Ala Leu Ser Phe Tyr Ser Ser Ile
            100                 105                 110

Gln Thr Ser Asp Gly Asn Trp Ala Ser Asp Leu Gly Gly Pro Met Phe
        115                 120                 125

Leu Leu Pro Gly Leu Val Ile Ala Leu Tyr Val Thr Gly Val Leu Asn
130                 135                 140

Ser Val Leu Ser Lys His His Arg Gln Glu Met Cys Arg Tyr Val Tyr
145                 150                 155                 160

Asn His Gln Asn Glu Asp Gly Gly Trp Gly Leu His Ile Glu Gly Pro
                165                 170                 175

Ser Thr Met Phe Gly Ser Ala Leu Asn Tyr Val Ala Leu Arg Leu Leu
            180                 185                 190

Gly Glu Asp Ala Asn Ala Gly Ala Met Pro Lys Ala Arg Ala Trp Ile
        195                 200                 205

Leu Asp His Gly Gly Ala Thr Gly Ile Thr Ser Trp Gly Lys Leu Trp
    210                 215                 220

Leu Ser Val Leu Gly Val Tyr Glu Trp Ser Gly Asn Asn Pro Leu Pro
225                 230                 235                 240

Pro Glu Phe Trp Leu Phe Pro Tyr Phe Leu Pro Phe His Pro Gly Arg
                245                 250                 255

Met Trp Cys His Cys Arg Met Val Tyr Leu Pro Met Ser Tyr Leu Tyr
            260                 265                 270

Gly Lys Arg Phe Val Gly Pro Ile Thr Pro Ile Val Leu Ser Leu Arg
        275                 280                 285

Lys Glu Leu Tyr Ala Val Pro Tyr His Glu Ile Asp Trp Asn Lys Ser
    290                 295                 300

Arg Asn Thr Cys Ala Lys Glu Asp Leu Tyr Tyr Pro His Pro Lys Met
305                 310                 315                 320
```

-continued

Gln Asp Ile Leu Trp Gly Ser Leu His His Val Tyr Glu Pro Leu Phe
            325                 330                 335

Thr Arg Trp Pro Ala Lys Arg Leu Arg Glu Lys Ala Leu Gln Thr Ala
            340                 345                 350

Met Gln His Ile His Tyr Glu Asp Glu Asn Thr Arg Tyr Ile Cys Leu
            355                 360                 365

Gly Pro Val Asn Lys Val Leu Asn Leu Leu Cys Cys Trp Val Glu Asp
            370                 375                 380

Pro Tyr Ser Asp Ala Phe Lys Leu His Leu Gln Arg Val His Asp Tyr
385                 390                 395                 400

Leu Trp Val Ala Glu Asp Gly Met Lys Met Gln Gly Tyr Asn Gly Ser
            405                 410                 415

Gln Leu Trp Asp Thr Ala Phe Ser Ile Gln Ala Ile Val Ser Thr Lys
            420                 425                 430

Leu Val Asp Asn Tyr Gly Pro Thr Leu Arg Lys Ala His Asp Phe Val
            435                 440                 445

Lys Ser Ser Gln Ile Gln Gln Asp Cys Pro Gly Asp Pro Asn Val Trp
            450                 455                 460

Tyr Arg His Ile His Lys Gly Ala Trp Pro Phe Ser Thr Arg Asp His
465                 470                 475                 480

Gly Trp Leu Ile Ser Asp Cys Thr Ala Glu Gly Leu Lys Ala Ala Leu
            485                 490                 495

Met Leu Ser Lys Leu Pro Ser Glu Thr Val Gly Glu Ser Leu Glu Arg
            500                 505                 510

Asn Arg Leu Cys Asp Ala Val Asn Val Leu Leu Ser Leu Gln Asn Asp
            515                 520                 525

Asn Gly Gly Phe Ala Ser Tyr Glu Leu Thr Arg Ser Tyr Pro Trp Leu
            530                 535                 540

Glu Leu Ile Asn Pro Ala Glu Thr Phe Gly Asp Ile Val Ile Asp Tyr
545                 550                 555                 560

Pro Tyr Val Glu Cys Thr Ser Ala Thr Met Glu Ala Leu Thr Leu Phe
            565                 570                 575

Lys Lys Leu His Pro Gly His Arg Thr Lys Glu Ile Asp Thr Ala Ile
            580                 585                 590

Val Arg Ala Ala Asn Phe Leu Glu Asn Met Gln Arg Thr Asp Gly Ser
            595                 600                 605

Trp Tyr Gly Cys Trp Gly Val Cys Phe Thr Tyr Ala Gly Trp Phe Gly
            610                 615                 620

Ile Lys Gly Leu Val Ala Ala Gly Arg Thr Tyr Asn Asn Cys Leu Ala
625                 630                 635                 640

Ile Arg Lys Ala Cys Asp Phe Leu Leu Ser Lys Glu Leu Pro Gly Gly
            645                 650                 655

Gly Trp Gly Glu Ser Tyr Leu Ser Cys Gln Asn Lys Val Tyr Thr Asn
            660                 665                 670

Leu Glu Gly Asn Arg Pro His Leu Val Asn Thr Ala Trp Val Leu Met
            675                 680                 685

Ala Leu Ile Glu Ala Gly Gln Ala Glu Arg Asp Pro Thr Pro Leu His
            690                 695                 700

Arg Ala Ala Arg Leu Leu Ile Asn Ser Gln Leu Glu Asn Gly Asp Phe
705                 710                 715                 720

Pro Gln Gln Glu Ile Met Gly Val Phe Asn Lys Asn Cys Met Ile Thr
            725                 730                 735

Tyr Ala Ala Tyr Arg Asn Ile Phe Pro Ile Trp Ala Leu Gly Glu Tyr

```
                           740                 745                 750

Cys His Arg Val Leu Thr Glu
                755

<210> SEQ ID NO 25
<211> LENGTH: 764
<212> TYPE: PRT
<213> ORGANISM: Cucurbita pepo

<400> SEQUENCE: 25

Met Trp Arg Leu Lys Val Gly Ala Glu Ser Val Gly Glu Glu Asp Glu
1               5                   10                  15

Lys Trp Val Lys Ser Val Ser Asn His Leu Gly Arg Gln Val Trp Glu
            20                  25                  30

Phe Cys Ala Asp Ala Ala Ala Asp Thr Pro His Gln Leu Leu Gln Ile
        35                  40                  45

Gln Asn Ala Arg Asn His Phe His His Asn Arg Phe His Arg Lys Gln
    50                  55                  60

Ser Ser Asp Leu Phe Leu Ala Ile Gln Tyr Glu Lys Glu Ile Ala Lys
65                  70                  75                  80

Gly Ala Lys Gly Gly Ala Val Lys Val Lys Glu Gly Glu Glu Val Gly
                85                  90                  95

Lys Glu Ala Val Lys Ser Thr Leu Glu Arg Ala Leu Gly Phe Tyr Ser
            100                 105                 110

Ala Val Gln Thr Arg Asp Gly Asn Trp Ala Ser Asp Leu Gly Gly Pro
        115                 120                 125

Leu Phe Leu Leu Pro Gly Leu Val Ile Ala Leu His Val Thr Gly Val
130                 135                 140

Leu Asn Ser Val Leu Ser Lys His His Arg Val Glu Met Cys Arg Tyr
145                 150                 155                 160

Leu Tyr Asn His Gln Asn Glu Asp Gly Gly Trp Gly Leu His Ile Glu
                165                 170                 175

Gly Thr Ser Thr Met Phe Gly Ser Ala Leu Asn Tyr Val Ala Leu Arg
            180                 185                 190

Leu Leu Gly Glu Asp Ala Asp Gly Gly Asp Gly Ala Met Thr Lys
        195                 200                 205

Ala Arg Ala Trp Ile Leu Glu Arg Gly Gly Ala Thr Ala Ile Thr Ser
    210                 215                 220

Trp Gly Lys Leu Trp Leu Ser Val Leu Gly Val Tyr Glu Trp Ser Gly
225                 230                 235                 240

Asn Asn Pro Leu Pro Pro Glu Phe Trp Leu Leu Pro Tyr Ser Leu Pro
                245                 250                 255

Phe His Pro Gly Arg Met Trp Cys His Cys Arg Met Val Tyr Leu Pro
            260                 265                 270

Met Ser Tyr Leu Tyr Gly Lys Arg Phe Val Gly Pro Ile Thr Pro Lys
        275                 280                 285

Val Leu Ser Leu Arg Gln Glu Leu Tyr Thr Ile Pro Tyr His Glu Ile
    290                 295                 300

Asp Trp Asn Lys Ser Arg Asn Thr Cys Ala Lys Glu Asp Leu Tyr Tyr
305                 310                 315                 320

Pro His Pro Lys Met Gln Asp Ile Leu Trp Gly Ser Ile Tyr His Val
                325                 330                 335

Tyr Glu Pro Leu Phe Thr Arg Trp Pro Gly Lys Arg Leu Arg Glu Lys
            340                 345                 350
```

-continued

```
Ala Leu Gln Ala Ala Met Lys His Ile His Tyr Glu Asp Glu Asn Ser
            355                 360                 365
Arg Tyr Ile Cys Leu Gly Pro Val Asn Lys Val Leu Asn Met Leu Cys
        370                 375                 380
Cys Trp Val Glu Asp Pro Tyr Ser Asp Ala Phe Lys Leu His Leu Gln
385                 390                 395                 400
Arg Val His Asp Tyr Leu Trp Val Ala Glu Asp Gly Met Arg Met Gln
                405                 410                 415
Gly Tyr Asn Gly Ser Gln Leu Trp Asp Thr Ala Phe Ser Ile Gln Ala
            420                 425                 430
Ile Val Ala Thr Lys Leu Val Asp Ser Tyr Ala Pro Thr Leu Arg Lys
        435                 440                 445
Ala His Asp Phe Val Lys Asp Ser Gln Ile Gln Glu Asp Cys Pro Gly
    450                 455                 460
Asp Pro Asn Val Trp Phe Arg His Ile His Lys Gly Ala Trp Pro Leu
465                 470                 475                 480
Ser Thr Arg Asp His Gly Trp Leu Ile Ser Asp Cys Thr Ala Glu Gly
                485                 490                 495
Leu Lys Ala Ser Leu Met Leu Ser Lys Leu Pro Ser Thr Met Val Gly
            500                 505                 510
Glu Pro Leu Glu Lys Asn Arg Leu Cys Asp Ala Val Asn Val Leu Leu
        515                 520                 525
Ser Leu Gln Asn Asp Asn Gly Gly Phe Ala Ser Tyr Glu Leu Thr Arg
    530                 535                 540
Ser Tyr Pro Trp Leu Glu Leu Ile Asn Pro Ala Glu Thr Phe Gly Asp
545                 550                 555                 560
Ile Val Ile Asp Tyr Pro Tyr Val Glu Cys Thr Ala Ala Thr Met Glu
                565                 570                 575
Ala Leu Thr Leu Phe Lys Lys Leu His Pro Gly His Arg Thr Lys Glu
            580                 585                 590
Ile Asp Thr Ala Ile Gly Lys Ala Ala Asn Phe Leu Glu Lys Met Gln
        595                 600                 605
Arg Ala Asp Gly Ser Trp Tyr Gly Cys Trp Gly Val Cys Phe Thr Tyr
    610                 615                 620
Ala Gly Trp Phe Gly Ile Lys Gly Leu Val Ala Ala Gly Arg Thr Tyr
625                 630                 635                 640
Asn Ser Cys Leu Ala Ile Arg Lys Ala Cys Glu Phe Leu Leu Ser Lys
                645                 650                 655
Glu Leu Pro Gly Gly Gly Trp Gly Glu Ser Tyr Leu Ser Cys Gln Asn
            660                 665                 670
Lys Val Tyr Thr Asn Leu Glu Gly Asn Lys Pro His Leu Val Asn Thr
        675                 680                 685
Ala Trp Val Leu Met Ala Leu Ile Glu Ala Gly Gln Gly Glu Arg Asp
    690                 695                 700
Pro Ala Pro Leu His Arg Ala Arg Leu Leu Met Asn Ser Gln Leu
705                 710                 715                 720
Glu Asn Gly Asp Phe Val Gln Gln Glu Ile Met Gly Val Phe Asn Lys
                725                 730                 735
Asn Cys Met Ile Thr Tyr Ala Ala Tyr Arg Asn Ile Phe Pro Ile Trp
            740                 745                 750
Ala Leu Gly Glu Tyr Cys His Arg Val Leu Thr Glu
        755                 760
```

-continued

```
<210> SEQ ID NO 26
<211> LENGTH: 250
<212> TYPE: PRT
<213> ORGANISM: Artificial Sequence
<220> FEATURE:
<223> OTHER INFORMATION: Truncated S. grosvenorii cucurbitadienol
      synthase polypeptide

<400> SEQUENCE: 26
```

Leu Glu Arg Asn Arg Leu Cys Asp Ala Val Asn Val Leu Leu Ser Leu
1               5                   10                  15

Gln Asn Asp Asn Gly Gly Phe Ala Ser Tyr Glu Leu Thr Arg Ser Tyr
            20                  25                  30

Pro Trp Leu Glu Leu Ile Asn Pro Ala Glu Thr Phe Gly Asp Ile Val
        35                  40                  45

Ile Asp Tyr Pro Tyr Val Glu Cys Thr Ser Ala Thr Met Glu Ala Leu
50                  55                  60

Thr Leu Phe Lys Lys Leu His Pro Gly His Arg Thr Lys Glu Ile Asp
65                  70                  75                  80

Thr Ala Ile Val Arg Ala Ala Asn Phe Leu Glu Asn Met Gln Arg Thr
                85                  90                  95

Asp Gly Ser Trp Tyr Gly Cys Trp Gly Val Cys Phe Thr Tyr Ala Gly
            100                 105                 110

Trp Phe Gly Ile Lys Gly Leu Val Ala Ala Gly Arg Thr Tyr Asn Asn
        115                 120                 125

Cys Leu Ala Ile Arg Lys Ala Cys Asp Phe Leu Leu Ser Lys Glu Leu
130                 135                 140

Pro Gly Gly Gly Trp Gly Glu Ser Tyr Leu Ser Cys Gln Asn Lys Val
145                 150                 155                 160

Tyr Thr Asn Leu Glu Gly Asn Arg Pro His Leu Val Asn Thr Ala Trp
                165                 170                 175

Val Leu Met Ala Leu Ile Glu Ala Gly Gln Ala Glu Arg Asp Pro Thr
            180                 185                 190

Pro Leu His Arg Ala Ala Arg Leu Leu Ile Asn Ser Gln Leu Glu Asn
        195                 200                 205

Gly Asp Phe Pro Gln Gln Glu Ile Met Gly Val Phe Asn Lys Asn Cys
210                 215                 220

Met Ile Thr Tyr Ala Ala Tyr Arg Asn Ile Phe Pro Ile Trp Ala Leu
225                 230                 235                 240

Gly Glu Tyr Cys His Arg Val Leu Thr Glu
                245                 250

```
<210> SEQ ID NO 27
<211> LENGTH: 1563
<212> TYPE: DNA
<213> ORGANISM: Siraitia grosvenorii

<400> SEQUENCE: 27
```
atggaaatgt cgtcgtctgt tgcagctacg atttcaatat ggatggttgt ggtgtgcata    60
gtgggagtgg gatggagagt tgtgaactgg gtttggttga ggccgaagaa gcttgagaag   120
cggctgagag agcaaggcct cgccggaaac tcttaccggc ttctgttcgg agacttgaag   180
gagagggcgg cgatggagga gcaggccaac tccaagccca tcaacttctc ccatgatatc   240
ggaccacgtg tcttcccctc catgtacaaa accatccaga attatggtaa gaattcgtac   300
atgtggcttg gccatatcc aagagtgcac atcatggacc ctcagcaact taaaactgtt   360
tttactctag tctatgatat ccaaaagcca aatttgaacc cccttatcaa gtttcttttg   420

```
gatggaatag taactcatga aggagaaaaa tgggctaaac acagaaagat aatcaaccct      480
gcatttcatt tggaaaagtt gaaggatatg ataccagcat tctttcatag ttgtaatgag      540
atagttaacg aatgggaaag attaatctcg aaagagggtt cgtgtgagtt ggatgttatg      600
ccatatctgc aaaatttggc agctgatgcc atttctcgaa ctgcatttgg gagtagctat      660
gaagaaggaa aaatgatctt ccaacttttaa aaagaactaa ctgatttggt ggttaaagtt      720
gcatttggag tttatattcc cggatggagg tttctaccaa ctaagtcaaa caataaaatg      780
aaagaaataa atagaaaaat taaagtttg cttttgggta ttataaacaa aaggcaaaag       840
gctatggaag aaggtgaagc tggacaaagt gatttattag gcattctcat ggaatccaat      900
tcaaacgaaa ttcaaggaga aggaaacaat aaagaagatg gaatgagcat agaagatgtt      960
attgaagaat gcaaggtttt ctatattggt ggccaagaaa ccacagccag attactgatt     1020
tggaccatga ttttgttgag ttcacacacg gaatggcaag agcgagcaag aactgaggta     1080
ttaaaagtat ttggtaacaa gaagccagat tttgatggtt tgagtcgact aaaagttgta     1140
actatgattt tgaacgaggt tctcaggtta tacccaccag caagtatgct tactcgtatt     1200
attcaaaagg aaacaagagt tggaaaattg actctaccag ctggtgtgat attgatcatg     1260
ccaattattc ttatccatcg tgatcatgac ctatggggtg aagatgcaaa cgaatttaaa     1320
ccagaaagat tttctaaggg agtctctaaa gcagcaaaag ttcaacccgc tttcttccca     1380
tttggatggg gtcctcgaat atgcatgggg cagaactttg cgatgattga agcaaaaatg     1440
gcattatcat taattctaca acgcttctca tttgagcttt cttcgtcgta tgttcatgct     1500
cctaccgtcg ttttcactac tcaacctcaa catggagctc atatcgtcct gcgcaaactg     1560
tag                                                                   1563
```

<210> SEQ ID NO 28
<211> LENGTH: 1563
<212> TYPE: DNA
<213> ORGANISM: Artificial Sequence
<220> FEATURE:
<223> OTHER INFORMATION: Codon-optimized S. grosvenorii CYP1798
      nucelotide sequence

<400> SEQUENCE: 28

```
atggaaatgt cctcttctgt tgctgccacc atttctatt ggatggttgt tgtatgtatc       60
gttggtgttg gttggagagt tgttaattgg gtttggttaa gaccaaagaa gttggaaaag      120
agattgagag aacaaggttt ggctggtaac tcttacagat tgttgttcgg tgacttgaaa      180
gaaagagctg ctatggaaga caagctaac tctaagccaa tcaacttctc ccatgatatt       240
ggtccaagag ttttcccatc tatgtacaag accattcaaa actacggtaa gaactcctat      300
atgtggttgg gtccataccc aagagttcat attatggatc acaacaatt gaaaaccgtc       360 tttaccttgg tttacgacat ccaaaagcca aacttgaacc cattgatcaa gttcttgttg      420
gatggtattg tcacccatga aggtgaaaaa tgggctaaac atagaaagat tatcaaccca      480
gccttccact tggaaaagtt gaaagatatg attccagcct tcttccactc ttgcaacgaa      540
atagttaatg aatgggaaag attgatctcc aaagaaggtt cttgcgaatt ggatgttatg      600
ccatacttgc aaaatttggc tgctgatgct atttctagaa ctgcttttgg ttcctcttac      660
gaagaaggta gatgatcctt ccaattattg aaagaattga ccgacttggt tgttaaggtt      720
gctttcggtg tttacattcc aggttggaga ttttgccaa ctaagtccaa caacaagatg       780
aaggaaatca acagaaagat caagtctttg ttgttaggta tcatcaacaa gagacaaaag      840
```

-continued

```
gccatggaag aaggtgaagc tggtcaatct gatttgttgg gtattttgat ggaatccaac    900
tccaacgaaa ttcaaggtga aggtaacaac aaagaagatg gtatgtccat cgaagatgtt    960
atcgaagaat gcaaggtttt ctacatcggt ggtcaagaaa ctaccgccag attattgatt   1020
tggaccatga tcttgttgag ttcccatact gaatggcaag aaagagcaag aactgaagtc   1080
ttgaaggttt tcggtaacaa aaagccagat ttcgacggtt tgtctagatt gaaggttgtc   1140
accatgattt tgaacgaagt tttgagatta tacccaccag cttctatgtt gaccagaatc   1200
attcaaaaag aaaccagagt cggtaagttg actttgccag ctggtgttat tttgatcatg   1260
ccaatcatct tgatccacag agatcatgat tgtgggggtg aagatgctaa tgaattcaag   1320
ccagaaagat tctccaaggg tgtttctaaa gctgctaaag ttcaaccagc tttctttcca   1380
tttggttggg gtccaagaat atgtatgggt caaaatttcg ctatgatcga agctaagatg   1440
gccttgtctt tgatcttgca aagattttcc ttcgaattgt cctcctcata tgttcatgct   1500
ccaactgttg ttttcaccac tcaaccacaa catggtgctc atatcgtttt gagaaagttg   1560
taa                                                                 1563
```

<210> SEQ ID NO 29
<211> LENGTH: 520
<212> TYPE: PRT
<213> ORGANISM: Siraitia grosvenorii

<400> SEQUENCE: 29

```
Met Glu Met Ser Ser Val Ala Ala Thr Ile Ser Ile Trp Met Val
1               5                   10                  15

Val Val Cys Ile Val Gly Val Gly Trp Arg Val Asn Trp Val Trp
                20                  25                  30

Leu Arg Pro Lys Lys Leu Glu Lys Arg Leu Arg Glu Gln Gly Leu Ala
            35                  40                  45

Gly Asn Ser Tyr Arg Leu Leu Phe Gly Asp Leu Lys Glu Arg Ala Ala
        50                  55                  60

Met Glu Glu Gln Ala Asn Ser Lys Pro Ile Asn Phe Ser His Asp Ile
65                  70                  75                  80

Gly Pro Arg Val Phe Pro Ser Met Tyr Lys Thr Ile Gln Asn Tyr Gly
                85                  90                  95

Lys Asn Ser Tyr Met Trp Leu Gly Pro Tyr Pro Arg Val His Ile Met
            100                 105                 110

Asp Pro Gln Gln Leu Lys Thr Val Phe Thr Leu Val Tyr Asp Ile Gln
        115                 120                 125

Lys Pro Asn Leu Asn Pro Leu Ile Lys Phe Leu Leu Asp Gly Ile Val
    130                 135                 140

Thr His Glu Gly Glu Lys Trp Ala Lys His Arg Lys Ile Ile Asn Pro
145                 150                 155                 160

Ala Phe His Leu Glu Lys Leu Lys Asp Met Ile Pro Ala Phe His
                165                 170                 175

Ser Cys Asn Glu Ile Val Asn Glu Trp Glu Arg Leu Ile Ser Lys Glu
            180                 185                 190

Gly Ser Cys Glu Leu Asp Val Met Pro Tyr Leu Gln Asn Leu Ala Ala
        195                 200                 205

Asp Ala Ile Ser Arg Thr Ala Phe Gly Ser Ser Tyr Glu Glu Gly Lys
    210                 215                 220

Met Ile Phe Gln Leu Leu Lys Glu Leu Thr Asp Leu Val Val Lys Val
225                 230                 235                 240
```

Ala Phe Gly Val Tyr Ile Pro Gly Trp Arg Phe Leu Pro Thr Lys Ser
            245                 250                 255

Asn Asn Lys Met Lys Glu Ile Asn Arg Lys Ile Lys Ser Leu Leu Leu
        260                 265                 270

Gly Ile Ile Asn Lys Arg Gln Lys Ala Met Glu Glu Gly Ala Gly
    275                 280                 285

Gln Ser Asp Leu Leu Gly Ile Leu Met Glu Ser Asn Ser Asn Glu Ile
290                 295                 300

Gln Gly Glu Gly Asn Asn Lys Glu Asp Gly Met Ser Ile Glu Asp Val
305                 310                 315                 320

Ile Glu Glu Cys Lys Val Phe Tyr Ile Gly Gly Gln Glu Thr Thr Ala
                325                 330                 335

Arg Leu Leu Ile Trp Thr Met Ile Leu Leu Ser Ser His Thr Glu Trp
            340                 345                 350

Gln Glu Arg Ala Arg Thr Glu Val Leu Lys Val Phe Gly Asn Lys Lys
        355                 360                 365

Pro Asp Phe Asp Gly Leu Ser Arg Leu Lys Val Val Thr Met Ile Leu
    370                 375                 380

Asn Glu Val Leu Arg Leu Tyr Pro Pro Ala Ser Met Leu Thr Arg Ile
385                 390                 395                 400

Ile Gln Lys Glu Thr Arg Val Gly Lys Leu Thr Leu Pro Ala Gly Val
                405                 410                 415

Ile Leu Ile Met Pro Ile Ile Leu Ile His Arg Asp His Asp Leu Trp
            420                 425                 430

Gly Glu Asp Ala Asn Glu Phe Lys Pro Glu Arg Phe Ser Lys Gly Val
        435                 440                 445

Ser Lys Ala Ala Lys Val Gln Pro Ala Phe Phe Pro Phe Gly Trp Gly
    450                 455                 460

Pro Arg Ile Cys Met Gly Gln Asn Phe Ala Met Ile Glu Ala Lys Met
465                 470                 475                 480

Ala Leu Ser Leu Ile Leu Gln Arg Phe Ser Phe Glu Leu Ser Ser Ser
                485                 490                 495

Tyr Val His Ala Pro Thr Val Val Phe Thr Thr Gln Pro Gln His Gly
            500                 505                 510

Ala His Ile Val Leu Arg Lys Leu
        515                 520

<210> SEQ ID NO 30
<211> LENGTH: 1422
<212> TYPE: DNA
<213> ORGANISM: Artificial Sequence
<220> FEATURE:
<223> OTHER INFORMATION: Codon-optimized S. grosvenorii CYP5491
      nucleotide sequence

<400> SEQUENCE: 30
atgtggactg ttgttttggg tttggctact ttgtttgttg cctactacat tcactggatc     60
aacaagtgga gagactctaa gtttaatggt gttttgccac aggtactat gggttttgcca    120 ttgattggtg aaaccatcca attgtcaaga ccatccgatt ctttgatgt tcatccattc    180 atccaaaaaa aggtcgaaag atacggtcca atcttcaaga cttgtttggc tggtagacca    240
gttgttgttt ctgctgatgc tgaatttaac aactacatca tgttgcaaga aggtagagct    300
gttgaaatgt ggtacttgga tactttgtct aagttcttcg gttggatac cgaatggttg    360 aaggctttgg gtttaatcca taagtacatc agatccatca ccttgaatca ttttggtgct    420

```
gaagccttga gagaaagatt cttgccttt  attgaagcct cttctatgga agccttgcat    480
tcttggtcta ctcaaccatc tgttgaagtt aagaatgctc ccgctttgat ggttttcaga    540
acctctgtta acaagatgtt tggtgaagat gccaagaagt tgtctggtaa tattccaggt    600
aagttcacca agttgttggg tggtttttg tctttgcctt tgaatttccc aggtacaacc    660
taccataagt gcttgaaaga tatgaaggaa atccaaaaga agttgagaga agtcgttgat    720
gatagattgg ctaatgttgg tccagatgtc gaagattttt tgggtcaagc cttgaaggac    780
aaagaatccg aaaagttcat ctccgaagaa tttatcattc aattgttgtt ctctatctcc    840
ttcgcctcct tcgaatctat ttctactact ttgaccttga tcttgaagtt gttagacgaa    900
catccagaag tcgtcaaaga attggaagct gaacatgaag ctattagaaa ggctagagct    960
gatccagatg tcccaattac ttgggaagaa tacaagtcta tgaccttcac cttgcaagtt   1020
atcaacgaaa ctttgagatt gggttctgtt actccagctt tgttgagaaa aactgtcaag   1080
gacttacaag tcaagggtta cattattcct gaaggttgga ccattatgtt ggttactgct   1140
tcaagacata gagatccaaa ggtttacaaa gacccacata ttttcaatcc ttggagatgg   1200
aaggatttgg actccattac tattcaaaag aacttcatgc cattcggtgg tggttttgaga   1260 cattgtgctg gtgcagaata ctctaaggtt tacttgtgta cttcttgca catcttgtgc    1320 actaagtaca gatggacaaa atttgggtggt ggtagaattg ctagagccca tattttgtca   1380
ttcgaagatg gtttacatgt caagttcacc ccaaaagaat ga                      1422
```

<210> SEQ ID NO 31
<211> LENGTH: 473
<212> TYPE: PRT
<213> ORGANISM: Siraitia grosvenorii

<400> SEQUENCE: 31

```
Met Trp Thr Val Val Leu Gly Leu Ala Thr Leu Phe Val Ala Tyr Tyr
1               5                   10                  15

Ile His Trp Ile Asn Lys Trp Arg Asp Ser Lys Phe Asn Gly Val Leu
            20                  25                  30

Pro Pro Gly Thr Met Gly Leu Pro Leu Ile Gly Glu Thr Ile Gln Leu
        35                  40                  45

Ser Arg Pro Ser Asp Ser Leu Asp Val His Pro Phe Ile Gln Lys Lys
    50                  55                  60

Val Glu Arg Tyr Gly Pro Ile Phe Lys Thr Cys Leu Ala Gly Arg Pro
65                  70                  75                  80

Val Val Val Ser Ala Asp Ala Glu Phe Asn Asn Tyr Ile Met Leu Gln
                85                  90                  95

Glu Gly Arg Ala Val Glu Met Trp Tyr Leu Asp Thr Leu Ser Lys Phe
            100                 105                 110

Phe Gly Leu Asp Thr Glu Trp Leu Lys Ala Leu Gly Leu Ile His Lys
        115                 120                 125

Tyr Ile Arg Ser Ile Thr Leu Asn His Phe Gly Ala Glu Ala Leu Arg
    130                 135                 140

Glu Arg Phe Leu Pro Phe Ile Glu Ala Ser Ser Met Glu Ala Leu His
145                 150                 155                 160

Ser Trp Ser Thr Gln Pro Ser Val Glu Val Lys Asn Ala Ser Ala Leu
                165                 170                 175

Met Val Phe Arg Thr Ser Val Asn Lys Met Phe Gly Asp Ala Lys
            180                 185                 190
```

```
Lys Leu Ser Gly Asn Ile Pro Gly Lys Phe Thr Lys Leu Leu Gly Gly
            195                 200                 205

Phe Leu Ser Leu Pro Leu Asn Phe Pro Gly Thr Thr Tyr His Lys Cys
        210                 215                 220

Leu Lys Asp Met Lys Glu Ile Gln Lys Leu Arg Glu Val Val Asp
225                 230                 235                 240

Asp Arg Leu Ala Asn Val Gly Pro Asp Val Glu Asp Phe Leu Gly Gln
                245                 250                 255

Ala Leu Lys Asp Lys Glu Ser Glu Lys Phe Ile Ser Glu Phe Ile
            260                 265                 270

Ile Gln Leu Leu Phe Ser Ile Ser Phe Ala Ser Phe Glu Ser Ile Ser
        275                 280                 285

Thr Thr Leu Thr Leu Ile Leu Lys Leu Leu Asp Glu His Pro Glu Val
    290                 295                 300

Val Lys Glu Leu Glu Ala Glu His Glu Ala Ile Arg Lys Ala Arg Ala
305                 310                 315                 320

Asp Pro Asp Gly Pro Ile Thr Trp Glu Glu Tyr Lys Ser Met Thr Phe
                325                 330                 335

Thr Leu Gln Val Ile Asn Glu Thr Leu Arg Leu Gly Ser Val Thr Pro
            340                 345                 350

Ala Leu Leu Arg Lys Thr Val Lys Asp Leu Gln Val Lys Gly Tyr Ile
        355                 360                 365

Ile Pro Glu Gly Trp Thr Ile Met Leu Val Thr Ala Ser Arg His Arg
    370                 375                 380

Asp Pro Lys Val Tyr Lys Asp Pro His Ile Phe Asn Pro Trp Arg Trp
385                 390                 395                 400

Lys Asp Leu Asp Ser Ile Thr Ile Gln Lys Asn Phe Met Pro Phe Gly
                405                 410                 415

Gly Gly Leu Arg His Cys Ala Gly Ala Glu Tyr Ser Lys Val Tyr Leu
            420                 425                 430

Cys Thr Phe Leu His Ile Leu Cys Thr Lys Tyr Arg Trp Thr Lys Leu
        435                 440                 445

Gly Gly Gly Arg Ile Ala Arg Ala His Ile Leu Ser Phe Glu Asp Gly
    450                 455                 460

Leu His Val Lys Phe Thr Pro Lys Glu
465                 470

<210> SEQ ID NO 32
<211> LENGTH: 2106
<212> TYPE: DNA
<213> ORGANISM: Siraitia grosvenorii

<400> SEQUENCE: 32
atgaaggtct ctccatttga gttcatgtcg gcaataatta agggcaggat ggacccgtcc        60
aattcttcat tgagtcgac tggcgaggtt gcctcagtta ttttcgagaa ccgtgagctg       120
gttgcgatct taaccacctc gatcgccgtc atgattggct gcttcgttgt tctcatgtgg       180
cgaagagccg gcagtcggaa agttaagaac gtggagctac ctaagccgtt gattgtgcac       240
gagccggagc ccgaagttga agacggcaag aagaaggttt caatcttctt cggtacacag       300
acaggcaccg ccgaaggatt tgcaaaggct ctagctgacg aggcgaaagc acgatacgag       360
aaggccacat ttagagttgt tgatttggat gattatgcag ctgatgacga tcagtatgaa       420
gagaagttga agaacgagtc tttcgctgtc ttcttattgg caacgtatgg cgatggagag       480
cccactgata atgccgcaag attctataaa tggttcgcgg aggggaaaga gagaggggag       540
```

```
tggcttcaga accttcatta tgcggtcttt ggccttggca accgacagta cgagcatttt      600
aataagattg caaaggtggc agatgagctg cttgaggcac agggaggcaa ccgccttgtt      660
aaagttggtc ttggagatga cgatcagtgc atagaggatg acttcagtgc ctggagagaa      720
tcattgtggc ctgagttgga tatgttgctt cgagatgagg atgatgcaac aacagtgacc      780
accccttaca cagctgccgt attagaatat cgagttgtat ccatgattc tgcagatgta       840 gctgctgagg acaagagctg gatcaatgca aacggtcatg ctgtacatga tgctcagcat      900
cccttcagat ctaatgtggt tgtgaggaag gagctccata cgtccgcatc tgatcgctcc      960
tgtagtcatc tagaatttaa tatttctggg tctgcactca attatgaaac agggatcat     1020 gtcggtgttt actgtgaaaa cttaactgag actgtggacg aggcactaaa cttattgggt     1080
ttgtctcctg aaacgtattt ctccatatat actgataacg aggatggcac tccacttggt     1140
ggaagctctt taccacctcc ttttccatcc tgcaccctca gaacagcatt gactcgatat     1200
gcagatctct tgaattcacc caagaagtca gctttgcttg cattagcagc acatgcttca     1260
aatccagtag aggctgaccg attaagatat cttgcatcac ctgccgggaa ggatgaatac     1320
gcccagtctg tgattggtag ccagaaaagc cttcttgagg tcatggctga atttccttct     1380
gccaagcccc cacttggtgt cttcttcgca gctgttgcac cgcgcttgca gcctcgattc     1440
tactccatat catcatctcc aaggatggct ccatctagaa ttcatgttac ttgtgcttta     1500
gtctatgaca aaatgccaac aggacgtatt cataaaggag tgtgctcaac ttggatgaag     1560
aattctgtgc ccatggagaa aagccatgaa tgcagttggg ctccaatttt cgtgagacaa     1620
tcaaacttca agcttcctgc agagagtaaa gtgcccatta tcatggttgg tcctggaact     1680
ggattggctc ctttcagagg tttcttacag gaaagattag ctttgaagga atctggagta     1740
gaattggggc cttccatatt gttctttgga tgcagaaacc gtaggatgga ttacatatac     1800
gaggatgagc tgaacaactt tgttgagact ggtgctctct ctgagttggt tattgccttc     1860
tcacgcgaag ggccaactaa ggaatatgtg cagcataaaa tggcagagaa ggcttcggat     1920
atctggaatt tgatatcaga aggggcttac ttatatgtat gtggtgatgc aaagggcatg     1980
gctaaggatg tccaccgaac tctccatact atcatgcaag agcagggatc tcttgacagc     2040
tcaaaagctg agagcatggt gaagaatctg caaatgaatg gaaggtatct gcgtgatgtc     2100
tggtga                                                                2106
```

<210> SEQ ID NO 33
<211> LENGTH: 2106
<212> TYPE: DNA
<213> ORGANISM: Artificial Sequence
<220> FEATURE:
<223> OTHER INFORMATION: Codon-optimized S. grosvenorii CPR4497
      nucleotide sequence

<400> SEQUENCE: 33

```
atgaaggtca gtccattcga attcatgtcc gctattatca agggtagaat ggacccatct       60
aactcctcat tgaatctac tggtgaagtt gcctccgtta tctttgaaaa cagagaattg      120
gttgccatct tgaccacttc tattgctgtt atgattggtt gcttcgttgt cttgatgtgg      180
agaagagctg gttctagaaa ggttaagaat gtcgaattgc caaagccatt gattgtccat     240
gaaccagaac ctgaagttga agatggtaag aagaaggttt ccatcttctt cggtactcaa     300
actggtactc tgaaggttt tgctaaggct ttggctgata agctaaagc tagatacgaa       360 aaggctacct tcagagttgt tgatttggat gattatgctg ccgatgatga ccaatacgaa     420
```

```
gaaaaattga agaacgaatc cttcgccgtt ttcttgttgg ctacttatgg tgatggtgaa    480
cctactgata atgctgctag attttacaag tggttcgccg aaggtaaaga aagaggtgaa    540
tggttgcaaa acttgcacta tgctgttttt ggtttgggta acagacaata cgaacacttc    600
aacaagattg ctaaggttgc cgacgaatta ttggaagctc aaggtggtaa tagattggtt    660
aaggttggtt taggtgatga cgatcaatgc atcgaagatg attttctgc ttggagagaa     720 tctttgtggc cagaattgga tatgttgttg agagatgaag atgatgctac tactgttact    780
actccatata ctgctgctgt cttggaatac agagttgtct ttcatgattc tgctgatgtt    840
gctgctgaag ataagtcttg gattaacgct aatggtcatg ctgttcatga tgctcaacat    900
ccattcagat ctaacgttgt cgtcagaaaa gaattgcata cttctgcctc tgatagatcc    960
tgttctcatt tggaattcaa catttccggt tccgctttga attacgaaac tggtgatcat   1020
gttggtgtct actgtgaaaa cttgactgaa actgttgatg aagccttgaa cttgttgggt   1080
ttgtctccag aaacttactt ctctatctac accgataacg aagatggtac tccattgggt   1140
ggttcttcat tgccaccacc atttccatca tgtactttga aactgctttt gaccagatac   1200
gctgatttgt tgaactctcc aaaaaagtct gctttgttgg cttttagctgc tcatgcttct   1260 aatccagttg aagctgatag attgagatac ttggcttctc cagctggtaa agatgaatat   1320
gcccaatctg ttatcggttc ccaaaagtct tgttggaag ttatggctga attcccatct    1380
gctaaaccac cattaggtgt ttttttttgct gctgttgctc caagattgca acctagattc   1440
tactccattt catcctctcc aagaatggct ccatctagaa tccatgttac ttgtgctttg   1500
gtttacgata agatgccaac tggtagaatt cataagggtg tttgttctac ctggatgaag   1560
aattctgttc caatggaaaa gtcccatgaa tgttcttggg ctccaatttt cgttagacaa   1620
tccaatttta agttgccagc cgaatccaag gttccaatta tcatggttgg tccaggtact   1680
ggtttggctc cttttagagg tttttttacaa gaaagattgg ccttgaaaga tccggtgtt    1740 gaattgggtc catccatttt tgttttcggt tgcagaaaca aagaatgga ttacatctac     1800 gaagatgaat tgaacaactt cgttgaaacc ggtgctttgt ccgaattggt tattgctttt    1860
tctagagaag gtcctaccaa agaatacgtc aacataaga tggctgaaaa ggcttctgat    1920
atctggaact tgatttctga aggtgcttac ttgtacgttt gtggtgatgc taaaggtatg    1980
gctaaggatg ttcatagaac cttgcatacc atcatgcaag aacaaggttc tttgattct     2040 tccaaagctg aatccatggt caagaacttg caaatgaatg gtagatactt aagagatgtt    2100
tggtaa                                                               2106
```

<210> SEQ ID NO 34
<211> LENGTH: 701
<212> TYPE: PRT
<213> ORGANISM: Siraitia grosvenorii

<400> SEQUENCE: 34

Met Lys Val Ser Pro Phe Glu Phe Met Ser Ala Ile Ile Lys Gly Arg
1               5                   10                  15

Met Asp Pro Ser Asn Ser Ser Phe Glu Ser Thr Gly Glu Val Ala Ser
            20                  25                  30

Val Ile Phe Glu Asn Arg Glu Leu Val Ala Ile Leu Thr Thr Ser Ile
        35                  40                  45

Ala Val Met Ile Gly Cys Phe Val Val Leu Met Trp Arg Arg Ala Gly
    50                  55                  60

```
Ser Arg Lys Val Lys Asn Val Glu Leu Pro Lys Pro Leu Ile Val His
 65                  70                  75                  80

Glu Pro Glu Pro Glu Val Glu Asp Gly Lys Lys Val Ser Ile Phe
             85                  90                  95

Phe Gly Thr Gln Thr Gly Thr Ala Glu Gly Phe Ala Lys Ala Leu Ala
                100                 105                 110

Asp Glu Ala Lys Ala Arg Tyr Glu Lys Ala Thr Phe Arg Val Val Asp
            115                 120                 125

Leu Asp Asp Tyr Ala Ala Asp Asp Gln Tyr Glu Lys Leu Lys
        130                 135                 140

Asn Glu Ser Phe Ala Val Phe Leu Leu Ala Thr Tyr Gly Asp Gly Glu
145                 150                 155                 160

Pro Thr Asp Asn Ala Ala Arg Phe Tyr Lys Trp Phe Ala Glu Gly Lys
                165                 170                 175

Glu Arg Gly Glu Trp Leu Gln Asn Leu His Tyr Ala Val Phe Gly Leu
            180                 185                 190

Gly Asn Arg Gln Tyr Glu His Phe Asn Lys Ile Ala Lys Val Ala Asp
        195                 200                 205

Glu Leu Leu Glu Ala Gln Gly Gly Asn Arg Leu Val Lys Val Gly Leu
    210                 215                 220

Gly Asp Asp Asp Gln Cys Ile Glu Asp Phe Ser Ala Trp Arg Glu
225                 230                 235                 240

Ser Leu Trp Pro Glu Leu Asp Met Leu Leu Arg Asp Glu Asp Ala
                245                 250                 255

Thr Thr Val Thr Thr Pro Tyr Thr Ala Ala Val Leu Glu Tyr Arg Val
                260                 265                 270

Val Phe His Asp Ser Ala Asp Val Ala Ala Glu Asp Lys Ser Trp Ile
        275                 280                 285

Asn Ala Asn Gly His Ala Val His Asp Ala Gln His Pro Phe Arg Ser
    290                 295                 300

Asn Val Val Val Arg Lys Glu Leu His Thr Ser Ala Ser Asp Arg Ser
305                 310                 315                 320

Cys Ser His Leu Glu Phe Asn Ile Ser Gly Ser Ala Leu Asn Tyr Glu
                325                 330                 335

Thr Gly Asp His Val Gly Val Tyr Cys Glu Asn Leu Thr Glu Thr Val
                340                 345                 350

Asp Glu Ala Leu Asn Leu Leu Gly Leu Ser Pro Glu Thr Tyr Phe Ser
        355                 360                 365

Ile Tyr Thr Asp Asn Glu Asp Gly Thr Pro Leu Gly Gly Ser Ser Leu
    370                 375                 380

Pro Pro Pro Phe Pro Ser Cys Thr Leu Arg Thr Ala Leu Thr Arg Tyr
385                 390                 395                 400

Ala Asp Leu Leu Asn Ser Pro Lys Lys Ser Ala Leu Leu Ala Leu Ala
                405                 410                 415

Ala His Ala Ser Asn Pro Val Glu Ala Asp Arg Leu Arg Tyr Leu Ala
        420                 425                 430

Ser Pro Ala Gly Lys Asp Glu Tyr Ala Gln Ser Val Ile Gly Ser Gln
    435                 440                 445

Lys Ser Leu Leu Glu Val Met Ala Glu Phe Pro Ser Ala Lys Pro Pro
450                 455                 460

Leu Gly Val Phe Phe Ala Ala Val Ala Pro Arg Leu Gln Pro Arg Phe
465                 470                 475                 480

Tyr Ser Ile Ser Ser Ser Pro Arg Met Ala Pro Ser Arg Ile His Val
```

```
                    485                 490                 495
Thr Cys Ala Leu Val Tyr Asp Lys Met Pro Thr Gly Arg Ile His Lys
                500                 505                 510
Gly Val Cys Ser Thr Trp Met Lys Asn Ser Val Pro Met Glu Lys Ser
                515                 520                 525
His Glu Cys Ser Trp Ala Pro Ile Phe Val Arg Gln Ser Asn Phe Lys
                530                 535                 540
Leu Pro Ala Glu Ser Lys Val Pro Ile Ile Met Val Gly Pro Gly Thr
545                 550                 555                 560
Gly Leu Ala Pro Phe Arg Gly Phe Leu Gln Glu Arg Leu Ala Leu Lys
                565                 570                 575
Glu Ser Gly Val Glu Leu Gly Pro Ser Ile Leu Phe Phe Gly Cys Arg
                580                 585                 590
Asn Arg Arg Met Asp Tyr Ile Tyr Glu Asp Glu Leu Asn Asn Phe Val
                595                 600                 605
Glu Thr Gly Ala Leu Ser Glu Leu Val Ile Ala Phe Ser Arg Glu Gly
                610                 615                 620
Pro Thr Lys Glu Tyr Val Gln His Lys Met Ala Glu Lys Ala Ser Asp
625                 630                 635                 640
Ile Trp Asn Leu Ile Ser Glu Gly Ala Tyr Leu Tyr Val Cys Gly Asp
                    645                 650                 655
Ala Lys Gly Met Ala Lys Asp Val His Arg Thr Leu His Thr Ile Met
                660                 665                 670
Gln Glu Gln Gly Ser Leu Asp Ser Ser Lys Ala Glu Ser Met Val Lys
                675                 680                 685
Asn Leu Gln Met Asn Gly Arg Tyr Leu Arg Asp Val Trp
                690                 695                 700

<210> SEQ ID NO 35
<211> LENGTH: 954
<212> TYPE: DNA
<213> ORGANISM: Artificial Sequence
<220> FEATURE:
<223> OTHER INFORMATION: Codon-optimized S. grosvenorii epoxide
      hydrolase 1 nucleotide sequence

<400> SEQUENCE: 35
atggacgcga ttgaacatag aaccgtaagt gttaatggta tcaatatgca tgtggcagaa    60
aagggagagg gacctgtcgt gttgttgctt catggtttcc agaattgtg  gtacagttgg   120
agacatcaaa tattggctct ttcctcttta ggttacagag ctgtcgcacc agacttacga   180
ggctacgggg atacagatgc cccagggtca atttcatcat acacatgctt tcacatcgta   240
ggagatctcg tggctctagt tgagtctctg gtatggaca  gggttttgt  tgtagcccac   300
gattggggtg ccatgatcgc ttggtgtttg tgtctgttta gacctgaaat ggttaaagct   360
tttgtttgtc tctccgtccc attcagacag agaaacccta gatgaaacc  agttcaaagt   420
atgagagcct ttttcggcga tgattactat atttgcagat tcaaaatcc  tggggaaatc   480
gaagaggaga tggctcaagt gggtgcaagg gaagtcttaa gaggaattct aacatctcgt   540
cgtcctggac accaatcttt accaaaaggg caagctttta gagcaagacc aggagcatcc   600
actgcattgc catcttggct atctgaaaaa gatctgtcat ttttcgcttc taagtatgat   660
caaaagggct ttacaggccc actaaactac tacagagcca tggatcttaa ttgggaattg   720
actgcgtcat ggactggtgt ccaagttaaa gtacctgtca atacatcgt  gggtgacgtt   780
gacatggttt ttacgactcc tggtgtaaag gaatatgtca acggcggtgg tttcaaaaag   840
```

```
gacgttccat ttttacagga agtggtaatc atggaaggcg ttggtcattt cattaatcag    900
gaaaaacctg aggagatttc atctcatata cacgatttca taagcaaatt ctaa          954
```

<210> SEQ ID NO 36
<211> LENGTH: 317
<212> TYPE: PRT
<213> ORGANISM: Siraitia grosvenorii

<400> SEQUENCE: 36

```
Met Asp Ala Ile Glu His Arg Thr Val Ser Val Asn Gly Ile Asn Met
1               5                   10                  15

His Val Ala Glu Lys Gly Glu Gly Pro Val Val Leu Leu Leu His Gly
            20                  25                  30

Phe Pro Glu Leu Trp Tyr Ser Trp Arg His Gln Ile Leu Ala Leu Ser
        35                  40                  45

Ser Leu Gly Tyr Arg Ala Val Ala Pro Asp Leu Arg Gly Tyr Gly Asp
    50                  55                  60

Thr Asp Ala Pro Gly Ser Ile Ser Ser Tyr Thr Cys Phe His Ile Val
65                  70                  75                  80

Gly Asp Leu Val Ala Leu Val Glu Ser Leu Gly Met Asp Arg Val Phe
                85                  90                  95

Val Val Ala His Asp Trp Gly Ala Met Ile Ala Trp Cys Leu Cys Leu
            100                 105                 110

Phe Arg Pro Glu Met Val Lys Ala Phe Val Cys Leu Ser Val Pro Phe
        115                 120                 125

Arg Gln Arg Asn Pro Lys Met Lys Pro Val Gln Ser Met Arg Ala Phe
    130                 135                 140

Phe Gly Asp Asp Tyr Tyr Ile Cys Arg Phe Gln Asn Pro Gly Glu Ile
145                 150                 155                 160

Glu Glu Glu Met Ala Gln Val Gly Ala Arg Glu Val Leu Arg Gly Ile
                165                 170                 175

Leu Thr Ser Arg Arg Pro Gly Pro Pro Ile Leu Pro Lys Gly Gln Ala
            180                 185                 190

Phe Arg Ala Arg Pro Gly Ala Ser Thr Ala Leu Pro Ser Trp Leu Ser
        195                 200                 205

Glu Lys Asp Leu Ser Phe Phe Ala Ser Lys Tyr Asp Gln Lys Gly Phe
    210                 215                 220

Thr Gly Pro Leu Asn Tyr Tyr Arg Ala Met Asp Leu Asn Trp Glu Leu
225                 230                 235                 240

Thr Ala Ser Trp Thr Gly Val Gln Val Lys Val Pro Val Lys Tyr Ile
                245                 250                 255

Val Gly Asp Val Asp Met Val Phe Thr Thr Pro Gly Val Lys Glu Tyr
            260                 265                 270

Val Asn Gly Gly Gly Phe Lys Lys Asp Val Pro Phe Leu Gln Glu Val
        275                 280                 285

Val Ile Met Glu Gly Val Gly His Phe Ile Asn Gln Glu Lys Pro Glu
    290                 295                 300

Glu Ile Ser Ser His Ile His Asp Phe Ile Ser Lys Phe
305                 310                 315
```

<210> SEQ ID NO 37
<211> LENGTH: 951
<212> TYPE: DNA
<213> ORGANISM: Siraitia grosvenorii

<400> SEQUENCE: 37

```
atggacgaga ttgagcatat caccatcaac accaatggca tcaaaatgca cattgcctct        60
gtagggacgg gcccagtagt tcttcttctc catggcttcc cggagctctg gtactcatgg       120
cgccaccagc ttctgtatct ttcttccgta ggatatcgag ctattgcgcc ggacctccgc       180
ggctatggcg acacggactc gccggcgtct cctacctcct acaccgcgct ccacatcgtc       240
ggcgatttgg ttggggctct ggacgagctt gggatcgaga aggtgttcct ggtcggacat       300
gactgggggg cgatcatcgc ctggtacttt tgcttgttca ggcccgatag aatcaaggcg       360
ctggtgaatc tgagcgtcca gttcataccc agaaacccag cgattccttt catcgagggt       420
ttcagaactg cgttcggtga tgacttctat atttgcaggt ttcaggttcc aggagaggca       480
gaagaagatt ttgcctccat cgacacagct cagctgttca agacatcatt atgtaataga       540
agttctgcac ctccatgctt gcctaaagaa attggatttc gtgcgatccc acctccagag       600
aaccttcctt cttggctgac agaagaagat atcaacttttt atgctgccaa atttaagcag       660
acaggcttca ccggagcgtt gaactactat cgagcttttg acctaacttg ggagctcacg       720
gcgccatgga cggagcacac gattcaggta ccggtgaagt tcatcgtcgg ggattcggat       780
ctaacttacc attttccggg agccaaggaa tatatccata atggcggatt caaaagggac       840
gtgccgttgc tggaggaagt agttgtagta aaagatgctt gtcacttcat caaccaagaa       900
aggccacaag aaatcaatgc tcacatccat gacttcatca ataaattctg a                951
```

<210> SEQ ID NO 38
<211> LENGTH: 951
<212> TYPE: DNA
<213> ORGANISM: Artificial Sequence
<220> FEATURE:
<223> OTHER INFORMATION: Codon-optimized S. grosvenorii epoxide
hydrolase 2 nucleotide sequence

<400> SEQUENCE: 38

```
atggatgaaa tcgaacatat taccatcaat acaaatggaa tcaaaatgca tattgcgtca        60
gtcggcacag gaccagttgt tctcttgcta cacggctttc cagaattatg gtactcttgg       120
agacaccaac tactttacct gtcctccgtt gggtacagag caatagctcc agatttgaga       180
ggctatggcg atactgacag tccagctagt cctacctctt atactgctct tcatattgta       240
ggtgacctgg tcggcgcatt agacgaattg ggaatagaaa aggtcttttt agtgggtcat       300
gactggggtg ctattatcgc atggtacttt tgtttgttta gaccagatag aattaaagca       360
cttgtgaatt tgtctgtcca gtttatccca cgtaacccag caatacccttt tatagaaggt       420
ttcagaacag cttttggtga tgacttctac atttgtagat ttcaagtacc tggggaagct       480
gaagaggatt tcgcgtctat cgatactgct caattgttta aaacttcatt atgcaataga       540
agctcagccc ctccttgttt gcctaaagag attggtttta gggctatccc accaccagaa       600
aatctgccat cttggctcac agaggaagat atcaacttct acgcagccaa gtttaaacaa       660
actggttttta ctggtgccct aactattat agagcattcg acttgacatg ggaattaaca       720
gccccatgga caggagccca gatccaagtt cctgtaaagt tcatagttgg tgattcagat       780
ctcacgtacc atttccctgg tgctaaggaa tacatccaca acggagggtt aaaagagat       840
gtgccactat tagaggaagt tgttgtggta aaagatgcct gccacttcat taaccaagag       900
cgaccacaag agattaatgc tcatattcat gacttcatca ataagttcta a                951
```

<210> SEQ ID NO 39

```
<211> LENGTH: 316
<212> TYPE: PRT
<213> ORGANISM: Siraitia grosvenorii

<400> SEQUENCE: 39

Met Asp Glu Ile Glu His Ile Thr Ile Asn Thr Asn Gly Ile Lys Met
1               5                   10                  15

His Ile Ala Ser Val Gly Thr Gly Pro Val Val Leu Leu His Gly
            20                  25                  30

Phe Pro Glu Leu Trp Tyr Ser Trp Arg His Gln Leu Leu Tyr Leu Ser
            35                  40                  45

Ser Val Gly Tyr Arg Ala Ile Ala Pro Asp Leu Arg Gly Tyr Gly Asp
    50                  55                  60

Thr Asp Ser Pro Ala Ser Pro Thr Ser Tyr Thr Ala Leu His Ile Val
65                  70                  75                  80

Gly Asp Leu Val Gly Ala Leu Asp Glu Leu Gly Ile Glu Lys Val Phe
                85                  90                  95

Leu Val Gly His Asp Trp Gly Ala Ile Ile Ala Trp Tyr Phe Cys Leu
            100                 105                 110

Phe Arg Pro Asp Arg Ile Lys Ala Leu Val Asn Leu Ser Val Gln Phe
        115                 120                 125

Ile Pro Arg Asn Pro Ala Ile Pro Phe Ile Glu Gly Phe Arg Thr Ala
    130                 135                 140

Phe Gly Asp Asp Phe Tyr Ile Cys Arg Phe Gln Val Pro Gly Glu Ala
145                 150                 155                 160

Glu Glu Asp Phe Ala Ser Ile Asp Thr Ala Gln Leu Phe Lys Thr Ser
                165                 170                 175

Leu Cys Asn Arg Ser Ser Ala Pro Pro Cys Leu Pro Lys Glu Ile Gly
            180                 185                 190

Phe Arg Ala Ile Pro Pro Glu Asn Leu Pro Ser Trp Leu Thr Glu
        195                 200                 205

Glu Asp Ile Asn Phe Tyr Ala Ala Lys Phe Lys Gln Thr Gly Phe Thr
    210                 215                 220

Gly Ala Leu Asn Tyr Tyr Arg Ala Phe Asp Leu Thr Trp Glu Leu Thr
225                 230                 235                 240

Ala Pro Trp Thr Gly Ala Gln Ile Gln Val Pro Val Lys Phe Ile Val
                245                 250                 255

Gly Asp Ser Asp Leu Thr Tyr His Phe Pro Gly Ala Lys Glu Tyr Ile
            260                 265                 270

His Asn Gly Gly Phe Lys Arg Asp Val Pro Leu Leu Glu Val Val
        275                 280                 285

Val Val Lys Asp Ala Cys His Phe Ile Asn Gln Glu Arg Pro Gln Glu
    290                 295                 300

Ile Asn Ala His Ile His Asp Phe Ile Asn Lys Phe
305                 310                 315

<210> SEQ ID NO 40
<211> LENGTH: 1572
<212> TYPE: DNA
<213> ORGANISM: Siraitia grosvenorii

<400> SEQUENCE: 40
atggaactct ctctaccaa  aactgcagcc gagatcatcg ctgttgtctt gttttctac        60 gctctcatcc ggctattatc tggaagattc agctctcaac agaagagact gccacctgaa      120
gccggtggcg cctggccact gatcggccat ctccatctcc taggtgggtc ggaacctgca      180
```

| | |
|---|---|
| cataaaacct tggcgaacat ggcggacgcc tacggaccag tttttacgtt gaaactgggc | 240 |
| atgcatacag ctttggttat gagcagttgg gaaatagcga gagagtgctt tactaaaaac | 300 |
| gacagaatct ttgcctcccg ccccatagtc actgcctcaa agcttctcac ctataaccat | 360 |
| accatgtttg ggttcagcca atatggtcca ttctggcgcc atatgcgcaa aatagccacg | 420 |
| cttcaactcc tctcaaacca ccgcctcgag cagctccaac acatcagaat atcggaggtc | 480 |
| cagacttcga ttaagaaact gtacgagttg tgggtcaaca gcagaaataa tggaggcgag | 540 |
| aaagtgttgg tggagatgaa gacgtggttc ggaggcataa ccttgaacac catattcagg | 600 |
| atggtggtcg gaaagcgatt ctcgactgct ttcgaaggca gtggtggcga acggtatcgg | 660 |
| aaggcgttga gggattctct tgaatggttt ggggcattcg ttccgtcaga ttcattcccg | 720 |
| ttttttaagat ggttggattt gggaggatat gagaaggcga tgaagaagac ggcgagtgtg | 780 |
| ctggacgagg tgcttgataa atggctcaaa gagcatcagc agaggagaaa ctccggtgaa | 840 |
| ctggagacga aggagcacga cttcatgcac gtgatgctgt ctattgttaa ggatgatgaa | 900 |
| gaactatccg gctacgatgc cgatacagtc acaaaagcta catgtttgaa tttaatagtt | 960 |
| ggtggattcg acactacaca agtaactatg acatgggctc tttctttgct tctcaacaat | 1020 |
| gaagaggtat taaaaaaggc ccaacttgaa ctagacgaac aagttggaag agagaggttt | 1080 |
| gtggaagagt ccgatgttaa aaatctgtta tatctccagg ccatcgtgaa ggaaactttg | 1140 |
| cgtttgtacc cttcagcgcc aatctcgaca tttcatgagg ccatggaaga ttgcactgtt | 1200 |
| tctggctacc acatcttttc agggacgcgt ttgatggtga atcttcaaaa gcttcaaaga | 1260 |
| gatccacttg catgggagga tccatgtgac tttcgaccgg agagatttct gacaactcat | 1320 |
| aaggatttcg atcttagagg acatagtcct caattgatac catttgggag tggtcgaaga | 1380 |
| atatgccctg gcatctcgtt tgccattcaa gttttgcatc ttacgcttgc aaatctactt | 1440 |
| catgggtttg acattggaag gccatctcat gaaccaatcg atatgcagga gagtaaagga | 1500 |
| ctaacgagta ttaaaacaac tccacttgag gttgttttag ctccacgcct tgctgctcaa | 1560 |
| gtttatgagt ga | 1572 |

<210> SEQ ID NO 41
<211> LENGTH: 523
<212> TYPE: PRT
<213> ORGANISM: Siraitia grosvenorii

<400> SEQUENCE: 41

Met Glu Leu Phe Ser Thr Lys Thr Ala Ala Glu Ile Ile Ala Val Val
1               5                   10                  15

Leu Phe Phe Tyr Ala Leu Ile Arg Leu Leu Ser Gly Arg Phe Ser Ser
            20                  25                  30

Gln Gln Lys Arg Leu Pro Pro Glu Ala Gly Ala Trp Pro Leu Ile
        35                  40                  45

Gly His Leu His Leu Leu Gly Gly Ser Glu Pro Ala His Lys Thr Leu
    50                  55                  60

Ala Asn Met Ala Asp Ala Tyr Gly Pro Val Phe Thr Leu Lys Leu Gly
65                  70                  75                  80

Met His Thr Ala Leu Val Met Ser Ser Trp Glu Ile Ala Arg Glu Cys
                85                  90                  95

Phe Thr Lys Asn Asp Arg Ile Phe Ala Ser Arg Pro Ile Val Thr Ala
            100                 105                 110

Ser Lys Leu Leu Thr Tyr Asn His Thr Met Phe Gly Phe Ser Gln Tyr

```
            115                 120                 125
Gly Pro Phe Trp Arg His Met Arg Lys Ile Ala Thr Leu Gln Leu Leu
130                 135                 140

Ser Asn His Arg Leu Glu Gln Leu Gln His Ile Arg Ile Ser Glu Val
145                 150                 155                 160

Gln Thr Ser Ile Lys Lys Leu Tyr Glu Leu Trp Val Asn Ser Arg Asn
                165                 170                 175

Asn Gly Gly Glu Lys Val Leu Val Glu Met Lys Thr Trp Phe Gly Gly
            180                 185                 190

Ile Thr Leu Asn Thr Ile Phe Arg Met Val Val Gly Lys Arg Phe Ser
        195                 200                 205

Thr Ala Phe Glu Gly Ser Gly Gly Glu Arg Tyr Arg Lys Ala Leu Arg
210                 215                 220

Asp Ser Leu Glu Trp Phe Gly Ala Phe Val Pro Ser Asp Ser Phe Pro
225                 230                 235                 240

Phe Leu Arg Trp Leu Asp Leu Gly Gly Tyr Glu Lys Ala Met Lys Lys
                245                 250                 255

Thr Ala Ser Val Leu Asp Glu Val Leu Asp Lys Trp Leu Lys Glu His
            260                 265                 270

Gln Gln Arg Arg Asn Ser Gly Glu Leu Glu Thr Glu His Asp Phe
        275                 280                 285

Met His Val Met Leu Ser Ile Val Lys Asp Asp Glu Glu Leu Ser Gly
290                 295                 300

Tyr Asp Ala Asp Thr Val Thr Lys Ala Thr Cys Leu Asn Leu Ile Val
305                 310                 315                 320

Gly Gly Phe Asp Thr Thr Gln Val Thr Met Thr Trp Ala Leu Ser Leu
                325                 330                 335

Leu Leu Asn Asn Glu Glu Val Leu Lys Lys Ala Gln Leu Glu Leu Asp
            340                 345                 350

Glu Gln Val Gly Arg Glu Arg Phe Val Glu Glu Ser Asp Val Lys Asn
        355                 360                 365

Leu Leu Tyr Leu Gln Ala Ile Val Lys Glu Thr Leu Arg Leu Tyr Pro
370                 375                 380

Ser Ala Pro Ile Ser Thr Phe His Glu Ala Met Glu Asp Cys Thr Val
385                 390                 395                 400

Ser Gly Tyr His Ile Phe Ser Gly Thr Arg Leu Met Val Asn Leu Gln
                405                 410                 415

Lys Leu Gln Arg Asp Pro Leu Ala Trp Glu Asp Pro Cys Asp Phe Arg
            420                 425                 430

Pro Glu Arg Phe Leu Thr Thr His Lys Asp Phe Asp Leu Arg Gly His
        435                 440                 445

Ser Pro Gln Leu Ile Pro Phe Gly Ser Gly Arg Arg Ile Cys Pro Gly
450                 455                 460

Ile Ser Phe Ala Ile Gln Val Leu His Leu Thr Leu Ala Asn Leu Leu
465                 470                 475                 480

His Gly Phe Asp Ile Gly Arg Pro Ser His Glu Pro Ile Asp Met Gln
                485                 490                 495

Glu Ser Lys Gly Leu Thr Ser Ile Lys Thr Thr Pro Leu Glu Val Val
            500                 505                 510

Leu Ala Pro Arg Leu Ala Ala Gln Val Tyr Glu
        515                 520

<210> SEQ ID NO 42
```

<211> LENGTH: 1497
<212> TYPE: DNA
<213> ORGANISM: Siraitia grosvenorii

<400> SEQUENCE: 42

```
atgccgatcg cagaaggtgc agtctctgat ttgtttggtc gcccactctt ctttgcacta    60
tatgattggt tcttagagca tggatctgtt tataaacttg cctttggacc aaaagccttt   120
gttgttgtat cagatcccat tgtggcaaga tatattcttc gagaaaatgc atttggttat   180
gacaagggag tgcttgctga tatttttagaa ccgataatgg gtaaaggact aataccagct   240
gaccttggca cttggaagca gaggagacga gttattgctc caggattcca tgccttgtac   300
ttggaagcta tgaccaaagt atttgccaat tgttcagaac gatcaatatt gaaattggag   360
aagcttctag agaaggtgaa actacaggag aataaaacca ttgagttgga tatgaagcaa   420
gagttttcaa gtttggctct tgatatcatt ggactcggtg ttttcaacta tgattttggt   480
tctgtaacca agaatctccc ggtgattaag gctgtatatg ggactctttt tgaagcagag   540
catagatcga ctttctatat cccatattgg aaagtacctt tggcaaggtg atagtccca    600
aggcagcgta aattccatgg tgaccttaag gttattaatg agtgtcttga tggcctaata   660
cgcaacgcaa gagaaacccg agacgaaacg gatgttgaga aattgcagca aagggactac   720
ttaaatctca aggatgccag tcttttgcgt ttcttagttg atatgcgggg agctgatgtt   780
gatgatcgcc agcttaggga cgatctgatg acgatgctta ttgctggcca tgaaacaact   840
gctgctgtgc ttacatgggc tgtttttttg cttgcacaaa atccttcaaa aatgaaaaaa   900
gcgcaagcag agattgattt ggttcttggc atggggaggc caactttga atcatttaaa   960
gcattgaagt acatcagact tatcgttgca gagactcttc gtttgttttcc tcagcctcca   1020
ttgctgataa gacgagctct caaatcagat atattaccag gaggatacaa tggtgacaaa   1080
actggatatg caattcctgc agggactgac atcttcatct ctgtttacaa tctccacaga   1140
tctccctact tctgggataa tcctcaagaa tttgaaccag agagatttca gtaaagagg    1200
gcaagcgagg gaattgaagg atgggatggt ttcgacccat ctagaagccc tggagctcta   1260
tacccgaatg agattgtagc agacttttcc ttcttaccat ttggtggagg ccctagaaaa   1320
tgtgtgggag atcaatttgc tctaatggag tcaactatag cattggccat gttactgcag   1380
aagtttgatg tggagctaaa aggaagtcca gaatctgtag aactagttac tggagccaca   1440
atacatacca aaagtgggtt gtggtgcaaa ctgagaagaa gatcacaagt aaactga      1497
```

<210> SEQ ID NO 43
<211> LENGTH: 498
<212> TYPE: PRT
<213> ORGANISM: Siraitia grosvenorii

<400> SEQUENCE: 43

```
Met Pro Ile Ala Glu Gly Ala Val Ser Asp Leu Phe Gly Arg Pro Leu
1               5                   10                  15

Phe Phe Ala Leu Tyr Asp Trp Phe Leu Glu His Gly Ser Val Tyr Lys
                20                  25                  30

Leu Ala Phe Gly Pro Lys Ala Phe Val Val Ser Asp Pro Ile Val
            35                  40                  45

Ala Arg Tyr Ile Leu Arg Glu Asn Ala Phe Gly Tyr Asp Lys Gly Val
        50                  55                  60

Leu Ala Asp Ile Leu Glu Pro Ile Met Gly Lys Gly Leu Ile Pro Ala
65                  70                  75                  80
```

```
Asp Leu Gly Thr Trp Lys Gln Arg Arg Val Ile Ala Pro Gly Phe
                85                  90                  95

His Ala Leu Tyr Leu Glu Ala Met Thr Lys Val Phe Ala Asn Cys Ser
            100                 105                 110

Glu Arg Ser Ile Leu Lys Leu Glu Lys Leu Leu Gly Glu Gly Glu Leu
        115                 120                 125

Gln Glu Asn Lys Thr Ile Glu Leu Asp Met Glu Ala Glu Phe Ser Ser
    130                 135                 140

Leu Ala Leu Asp Ile Ile Gly Leu Gly Val Phe Asn Tyr Asp Phe Gly
145                 150                 155                 160

Ser Val Thr Lys Glu Ser Pro Val Ile Lys Ala Val Tyr Gly Thr Leu
                165                 170                 175

Phe Glu Ala Glu His Arg Ser Thr Phe Tyr Ile Pro Tyr Trp Lys Val
            180                 185                 190

Pro Leu Ala Arg Trp Ile Val Pro Arg Gln Arg Lys Phe His Gly Asp
        195                 200                 205

Leu Lys Val Ile Asn Glu Cys Leu Asp Gly Leu Ile Arg Asn Ala Arg
    210                 215                 220

Glu Thr Arg Asp Glu Thr Asp Val Glu Lys Leu Gln Gln Arg Asp Tyr
225                 230                 235                 240

Leu Asn Leu Lys Asp Ala Ser Leu Leu Arg Phe Leu Val Asp Met Arg
                245                 250                 255

Gly Ala Asp Val Asp Asp Arg Gln Leu Arg Asp Asp Leu Met Thr Met
            260                 265                 270

Leu Ile Ala Gly His Glu Thr Thr Ala Ala Val Leu Thr Trp Ala Val
        275                 280                 285

Phe Leu Leu Ala Gln Asn Pro Ser Lys Met Lys Lys Ala Gln Ala Glu
    290                 295                 300

Ile Asp Leu Val Leu Gly Met Gly Arg Pro Thr Phe Glu Ser Phe Lys
305                 310                 315                 320

Ala Leu Lys Tyr Ile Arg Leu Ile Val Ala Glu Thr Leu Arg Leu Phe
                325                 330                 335

Pro Gln Pro Pro Leu Leu Ile Arg Arg Ala Leu Lys Ser Asp Ile Leu
            340                 345                 350

Pro Gly Gly Tyr Asn Gly Asp Lys Thr Gly Tyr Ala Ile Pro Ala Gly
        355                 360                 365

Thr Asp Ile Phe Ile Ser Val Tyr Asn Leu His Arg Ser Pro Tyr Phe
    370                 375                 380

Trp Asp Asn Pro Gln Glu Phe Glu Pro Glu Arg Phe Gln Val Lys Arg
385                 390                 395                 400

Ala Ser Glu Gly Ile Glu Gly Trp Asp Gly Phe Asp Pro Ser Arg Ser
                405                 410                 415

Pro Gly Ala Leu Tyr Pro Asn Glu Ile Val Ala Asp Phe Ser Phe Leu
            420                 425                 430

Pro Phe Gly Gly Gly Pro Arg Lys Cys Val Gly Asp Gln Phe Ala Leu
        435                 440                 445

Met Glu Ser Thr Ile Ala Leu Ala Met Leu Leu Gln Lys Phe Asp Val
    450                 455                 460

Glu Leu Lys Gly Ser Pro Glu Ser Val Glu Leu Val Thr Gly Ala Thr
465                 470                 475                 480

Ile His Thr Lys Ser Gly Leu Trp Cys Lys Leu Arg Arg Arg Ser Gln
                485                 490                 495

Val Asn
```

<210> SEQ ID NO 44
<211> LENGTH: 1563
<212> TYPE: DNA
<213> ORGANISM: Artificial Sequence
<220> FEATURE:
<223> OTHER INFORMATION: Codon-optimized S. grosvenorii CYP1798
      nucleotide sequence

<400> SEQUENCE: 44

| | | | | | | |
|---|---|---|---|---|---|---|
| atggaaatgt | cctcaagtgt | cgcagccaca | atcagtatct | ggatggtcgt | cgtatgtatc | 60 |
| gtaggtgtag | gttggagagt | cgtaaattgg | gtttggttga | gaccaaagaa | attggaaaag | 120 |
| agattgagag | aacaaggttt | ggccggtaat | tcttacagat | tgttgttcgg | tgacttgaag | 180 |
| gaaagagctg | caatggaaga | acaagcaaat | tcaaagccta | taaacttctc | ccatgacatc | 240 |
| ggtccaagag | ttttcccttc | aatgtacaag | accatccaaa | actacggtaa | aaactcctac | 300 |
| atgtggttag | gtccataccc | tagagtccac | atcatggatc | cacaacaatt | gaagaccgtt | 360 |
| tttactttgg | tctacgacat | tcaaaagcca | aatttgaacc | ctttgattaa | attcttgtta | 420 |
| gatggtatcg | ttacacatga | aggtgaaaag | tgggctaagc | acagaaagat | tattaaccca | 480 |
| gcattccatt | tggaaaagtt | gaaggatatg | atacctgctt | tctttcactc | atgtaatgaa | 540 |
| atcgtcaacg | aatgggaaag | attgatttca | aagaaggtt | cctgcgaatt | ggatgtaatg | 600 |
| ccttatttgc | aaaatttggc | cgctgacgcc | atttcaagaa | ccgcttttgg | ttcttcatac | 660 |
| gaagaaggta | aatgatctt | ccaattgttg | aaggaattga | ctgatttggt | tgtcaaggta | 720 |
| gcttttggtg | tttatattcc | aggttggaga | ttcttgccta | caaagagtaa | caacaaaatg | 780 |
| aaggaaatta | atagaaaaat | caagtctttg | ttgttgggta | tcattaacaa | gagacaaaag | 840 |
| gcaatggaag | aaggtgaagc | cggtcaatct | gatttgttgg | gtatattaat | ggaaagtaat | 900 |
| tctaacgaaa | tccaaggtga | aggtaataac | aaggaagatg | gcatgtctat | gaagacgtc | 960 |
| atcgaagagt | gtaaggtatt | ttatataggt | ggtcaagaaa | ctacagcaag | attattgatc | 1020 |
| tggactatga | tattgttgtc | cagtcataca | gaatggcaag | aaagagccag | aaccgaagtc | 1080 |
| ttgaaggtat | ttggtaataa | gaaaccagat | ttcgacggtt | tgtcaagatt | gaaggtagtt | 1140 |
| actatgatct | tgaacgaagt | tttaagattg | tacccacctg | cttccatgtt | gacaagaatc | 1200 |
| atccaaaagg | aaacaagagt | tggtaaatta | accttgccag | caggtgttat | cttgataatg | 1260 |
| cctatcatct | tgatacatag | agatcacgac | ttgtggggtg | aagatgctaa | cgagtttaaa | 1320 |
| ccagaaagat | tcagtaaagg | tgtttctaag | gcagccaaag | tccaaccagc | ctttttccct | 1380 |
| tttggttggg | gtcctagaat | tgcatgggt | caaaacttcg | ctatgatcga | agctaagatg | 1440 |
| gcattgagtt | tgatcttgca | aagattttct | ttcgaattgt | cttcatccta | cgttcatgca | 1500 |
| ccaactgtcg | tcttcactac | acaaccacaa | cacggtgccc | acatcgtttt | gagaaagtta | 1560 |
| tga | | | | | | 1563 |

<210> SEQ ID NO 45

<400> SEQUENCE: 45

000

<210> SEQ ID NO 46
<211> LENGTH: 1602
<212> TYPE: DNA
<213> ORGANISM: Siraitia grosvenorii

<400> SEQUENCE: 46

```
atggaaccac aaccaagtgc ggaattcaac tggaatcaca gcctaagcac cgtcgctatc      60
ggtgtcattg ccattatttt cttccgtttt ctcgtcaaaa gagtcaccgg cgccggtgag     120
cgaaagggtc cgaagccgcc aaaagtagcc ggagggtggc tctaattgg ccacctccct      180
ctcctcggag gacctgaact gccccatgtc aaactgggtg gtttggctga taaatatggt     240
ccaatcttct cgatccggct gggtgtccac tccgccgtcg tgataaacag ttgggaggcg     300
gcgaaacagt tattaaccaa ccatgacgtc gccgtctctt cccgccccca aatgctcggc     360
ggaaaactcc tgggctacaa ctacgccgtg tttggtttcg acccctacgg ctcttactgg     420
cgcaacatgc gcaagataac cacgcaagag cttctatcca atagcagaat ccagctccta     480
agagacgttc gagcgtcaga agtgaaccaa ggcataaaag agctctacca gcactggaaa     540
gaaagaagag acggtcacga ccaagccttg gtggaactgc agcagtgggt cggggacttg     600
actatgaatc tgattctcgg agtcatcgcc gggaaaaggt tctttggagc tgcagcaacg     660
gtagacgagg aagaggcgcg acggagccat aaagcattga aggagttgtt acattatatg     720
gggcttttc tactgggtga tgctgttcca tatctaggat ggttggacgt cggcggccat      780
gtgaaggcga tgaagaaaac ttcaaaagaa ttggaccgta tgttaacaca gtggttggag     840
gagcacaaga aggaaggacc caagaaagat cataaagact tcatggacgt gatgctttca     900
gttctcaatg aaacatccga tgttctttca gataagaccc atggcttcga tgctgatacc     960
atcatcaaag ctacatgtat gacgatggtt ttaggaggga gtgatacgac ggcggtggtt    1020
gtgatatggg caatctcgct gctgctgaat aatcgccctg cgttgagaaa agtgcaagaa    1080
gaactggaag cccatatcgg ccgagacaga gaactggagg aatcggatct cggtaagcta    1140
gtgtatttgc aggcagtcgt gaaggagaca ttgcggctgt acggagccgg aggcctttc     1200
tttcgtgaaa ccacagagga tgtcaccatc gacggattcc atgtcgagaa agggacatgg    1260
ctgttcgtga acgtggggaa gatccacaga gatgggaagg tgtggccgga gccaacggag    1320
ttcaaaccgg agaggtttct gacgacccac aaagattttg atctgaaggg ccagcggttt    1380
gagctcatcc ctttcggggg aggaagaaga tcgtgccctg gaatgtcttt tgggctccaa    1440
atgctacagc ttatttttggg taaactgctt caggcttttg atatatcgac gccggggac     1500
gccgccgttg atatgaccgg atccattgga ctgacgaaca tgaaagccac tccattggaa    1560
gtgctcatca ccccgcgctt gcctctttcg ctttacgatt ga                       1602
```

<210> SEQ ID NO 47
<211> LENGTH: 533
<212> TYPE: PRT
<213> ORGANISM: Siraitia grosvenorii

<400> SEQUENCE: 47

```
Met Glu Pro Gln Pro Ser Ala Glu Phe Asn Trp Asn His Ser Leu Ser
1               5                   10                  15

Thr Val Ala Ile Gly Val Ile Ala Ile Ile Phe Phe Arg Phe Leu Val
            20                  25                  30

Lys Arg Val Thr Gly Ala Gly Glu Arg Lys Gly Pro Lys Pro Pro Lys
        35                  40                  45

Val Ala Gly Gly Trp Pro Leu Ile Gly His Leu Pro Leu Leu Gly Gly
    50                  55                  60

Pro Glu Leu Pro His Val Lys Leu Gly Gly Leu Ala Asp Lys Tyr Gly
65                  70                  75                  80
```

```
Pro Ile Phe Ser Ile Arg Leu Gly Val His Ser Ala Val Val Ile Asn
                85                  90                  95
Ser Trp Glu Ala Ala Lys Gln Leu Leu Thr Asn His Asp Val Ala Val
            100                 105                 110
Ser Ser Arg Pro Gln Met Leu Gly Gly Lys Leu Leu Gly Tyr Asn Tyr
        115                 120                 125
Ala Val Phe Gly Phe Gly Pro Tyr Gly Ser Tyr Trp Arg Asn Met Arg
    130                 135                 140
Lys Ile Thr Thr Gln Glu Leu Leu Ser Asn Ser Arg Ile Gln Leu Leu
145                 150                 155                 160
Arg Asp Val Arg Ala Ser Glu Val Asn Gln Gly Ile Lys Glu Leu Tyr
                165                 170                 175
Gln His Trp Lys Glu Arg Arg Asp Gly His Asp Gln Ala Leu Val Glu
            180                 185                 190
Leu Gln Gln Trp Val Gly Asp Leu Thr Met Asn Leu Ile Leu Gly Val
        195                 200                 205
Ile Ala Gly Lys Arg Phe Phe Gly Ala Ala Ala Thr Val Asp Glu Glu
    210                 215                 220
Glu Ala Arg Arg Ser His Lys Ala Leu Lys Glu Leu Leu His Tyr Met
225                 230                 235                 240
Gly Leu Phe Leu Leu Gly Asp Ala Val Pro Tyr Leu Gly Trp Leu Asp
                245                 250                 255
Val Gly Gly His Val Lys Ala Met Lys Lys Thr Ser Lys Glu Leu Asp
            260                 265                 270
Arg Met Leu Thr Gln Trp Leu Glu Glu His Lys Lys Glu Gly Pro Lys
        275                 280                 285
Lys Asp His Lys Asp Phe Met Asp Val Met Leu Ser Val Leu Asn Glu
    290                 295                 300
Thr Ser Asp Val Leu Ser Asp Lys Thr His Gly Phe Asp Ala Asp Thr
305                 310                 315                 320
Ile Ile Lys Ala Thr Cys Met Thr Met Val Leu Gly Gly Ser Asp Thr
                325                 330                 335
Thr Ala Val Val Val Ile Trp Ala Ile Ser Leu Leu Leu Asn Asn Arg
            340                 345                 350
Pro Ala Leu Arg Lys Val Gln Glu Glu Leu Glu Ala His Ile Gly Arg
        355                 360                 365
Asp Arg Glu Leu Glu Glu Ser Asp Leu Gly Lys Leu Val Tyr Leu Gln
    370                 375                 380
Ala Val Val Lys Glu Thr Leu Arg Leu Tyr Gly Ala Gly Gly Leu Phe
385                 390                 395                 400
Phe Arg Glu Thr Thr Glu Asp Val Thr Ile Asp Gly Phe His Val Glu
                405                 410                 415
Lys Gly Thr Trp Leu Phe Val Asn Val Gly Lys Ile His Arg Asp Gly
            420                 425                 430
Lys Val Trp Pro Glu Pro Thr Glu Phe Lys Pro Glu Arg Phe Leu Thr
        435                 440                 445
Thr His Lys Asp Phe Asp Leu Lys Gly Gln Arg Phe Glu Leu Ile Pro
    450                 455                 460
Phe Gly Gly Gly Arg Arg Ser Cys Pro Gly Met Ser Phe Gly Leu Gln
465                 470                 475                 480
Met Leu Gln Leu Ile Leu Gly Lys Leu Leu Gln Ala Phe Asp Ile Ser
                485                 490                 495
Thr Pro Gly Asp Ala Ala Val Asp Met Thr Gly Ser Ile Gly Leu Thr
```

Asn Met Lys Ala Thr Pro Leu Glu Val Leu Ile Thr Pro Arg Leu Pro
500                 505                 510
                515                 520                 525

Leu Ser Leu Tyr Asp
        530

<210> SEQ ID NO 48
<211> LENGTH: 1236
<212> TYPE: DNA
<213> ORGANISM: Siraitia grosvenorii

<400> SEQUENCE: 48

```
atggagactc ttcttcttca tcttcaatcg ttatttcatc caatttcctt cactggtttc      60
gttgtcctct ttagcttcct gttcctgctc cagaaatggt tactgacacg tccaaactct     120
tcatcagaag cctcaccccc ttctccacca aagcttccca tcttcggaca ccttctaaac     180
ctgggtctgc atccccacat caccctcgga gcctacgctc gccgctatgg ccctctcttc     240
ctcctccact tcggcagcaa gcccaccatc gtcgtctctt ctgccgaaat cgctcgcgat     300
atcatgaaga cccacgacct cgtcttcgcc aaccgtccta aatcaagcat cagcgaaaag     360
attctttacg gctccaaaga tttagccgca tctccttacg gcgaatactg gaggcagatg     420
aaaagcgttg gcgtgcttca tcttttgagc aacaaagggt tcaatccctt cgctctgtc      480
agagaagaag aagtcgaact gatgatccag aagatccaac agaaccccct atcagttaat     540
ttaagcgaaa tattctctgg actgacgaac gacatagttt gcagggtggc tttagggaga     600
aagtatggcg tgggagaaga cggaaagaag ttccggtctc ttctgctgga gtttggggaa     660
gtattgggaa gtttcagtac gagagacttc atcccgtggc tgggttggat tgatcgtatc     720
agtgggctgg acgccaaagc cgagagggta gccaaagagc tcgatgcttt ctttgacaga     780
gtgatcgaag atcacatcca tctaaacaag agagagaata atcccgatga gcagaaggac     840
ttggtggatg tgctgctttg tgtacagaga aagactccat cgggtttcc ccttgagatg      900
gatagcataa aagctttaat cttggacatg tttgctgcag gcacagacac gacatacacg     960
gtgttggagt gggcaatgtc ccaactgttg agacacccag aagcgatgaa gaaactgcag    1020
agggaggtca gagaaatagc aggtgagaaa gaacacgtaa gtgaggatga tttagaaaag    1080
atgcattact tgaaggcagt aatcaaagaa acgctgcggc tacacccacc aatcccactc    1140
ctcgtcccca gagaatcaac ccaagacatc aggttgaggg ggtacgatat cagaggcggc    1200
acccgggtta tgatcaatgc atgggccatc ggaaga                              1236
```

<210> SEQ ID NO 49
<211> LENGTH: 412
<212> TYPE: PRT
<213> ORGANISM: Siraitia grosvenorii

<400> SEQUENCE: 49

Met Glu Thr Leu Leu His Leu Gln Ser Leu Phe His Pro Ile Ser
1               5                   10                  15

Phe Thr Gly Phe Val Val Leu Phe Ser Phe Leu Phe Leu Leu Gln Lys
                20                  25                  30

Trp Leu Leu Thr Arg Pro Asn Ser Ser Glu Ala Ser Pro Pro Ser
            35                  40                  45

Pro Pro Lys Leu Pro Ile Phe Gly His Leu Leu Asn Leu Gly Leu His
        50                  55                  60

Pro His Ile Thr Leu Gly Ala Tyr Ala Arg Arg Tyr Gly Pro Leu Phe

```
                65                  70                  75                  80
Leu Leu His Phe Gly Ser Lys Pro Thr Ile Val Val Ser Ser Ala Glu
                85                  90                  95

Ile Ala Arg Asp Ile Met Lys Thr His Asp Leu Val Phe Ala Asn Arg
            100                 105                 110

Pro Lys Ser Ser Ile Ser Glu Lys Ile Leu Tyr Gly Ser Lys Asp Leu
        115                 120                 125

Ala Ala Ser Pro Tyr Gly Glu Tyr Trp Arg Gln Met Lys Ser Val Gly
    130                 135                 140

Val Leu His Leu Leu Ser Asn Lys Arg Val Gln Ser Phe Arg Ser Val
145                 150                 155                 160

Arg Glu Glu Val Glu Leu Met Ile Gln Lys Ile Gln Gln Asn Pro
                165                 170                 175

Leu Ser Val Asn Leu Ser Glu Ile Phe Ser Gly Leu Thr Asn Asp Ile
                180                 185                 190

Val Cys Arg Val Ala Leu Gly Arg Lys Tyr Gly Val Gly Glu Asp Gly
            195                 200                 205

Lys Lys Phe Arg Ser Leu Leu Leu Glu Phe Gly Glu Val Leu Gly Ser
        210                 215                 220

Phe Ser Thr Arg Asp Phe Ile Pro Trp Leu Gly Trp Ile Asp Arg Ile
225                 230                 235                 240

Ser Gly Leu Asp Ala Lys Ala Glu Arg Val Ala Lys Glu Leu Asp Ala
                245                 250                 255

Phe Phe Asp Arg Val Ile Glu Asp His Ile His Leu Asn Lys Arg Glu
                260                 265                 270

Asn Asn Pro Asp Glu Gln Lys Asp Leu Val Asp Val Leu Leu Cys Val
            275                 280                 285

Gln Arg Glu Asp Ser Ile Gly Phe Pro Leu Glu Met Asp Ser Ile Lys
        290                 295                 300

Ala Leu Ile Leu Asp Met Phe Ala Ala Gly Thr Asp Thr Thr Tyr Thr
305                 310                 315                 320

Val Leu Glu Trp Ala Met Ser Gln Leu Leu Arg His Pro Glu Ala Met
                325                 330                 335

Lys Lys Leu Gln Arg Glu Val Arg Glu Ile Ala Gly Glu Lys His
                340                 345                 350

Val Ser Glu Asp Leu Glu Lys Met His Tyr Leu Lys Ala Val Ile
            355                 360                 365

Lys Glu Thr Leu Arg Leu His Pro Pro Ile Pro Leu Leu Val Pro Arg
370                 375                 380

Glu Ser Thr Gln Asp Ile Arg Leu Arg Gly Tyr Asp Ile Arg Gly Gly
385                 390                 395                 400

Thr Arg Val Met Ile Asn Ala Trp Ala Ile Gly Arg
                405                 410

<210> SEQ ID NO 50
<211> LENGTH: 1614
<212> TYPE: DNA
<213> ORGANISM: Siraitia grosvenorii

<400> SEQUENCE: 50
atgtcgatga gtagtgaaat tgaaagcctc tgggttttcg cgctggcttc taaatgctct      60
gctttaacta agaaaaacat cctctggtct ttactcttct ttttcctaat ctgggttct     120 gtttccattc tccactgggc ccatccgggc ggcccggctt ggggccgcta ctggtggcgc    180
```

```
cgccgccgca gcaattccac cgccgctgct attcccggcc cgagaggcct ccccctcgtc    240
ggcagcatgg gcttgatggc cgacttggcc caccaccgga ttgccgccgt ggctgactcc    300
ttaaacgcca cccgcctcat ggccttttcg ctcggcgaca ctcgcgtgat cgtcacatgc    360
aaccccgacg tcgccaaaga gattctcaac agctccctct tcgccgaccg ccccgttaag    420
gagtccgctt actccttgat gttcaaccgc gccattgggt cgcccccta tggcctttac    480 tggcggaccc tccgccgcat cgcttcccac acctcttct gccccaagca aatcaagtcc     540
tcccagtccc agcgccgcca aatcgcttcc caaatggtcg caatgttcgc aaaccgcgat    600
gccacacaga gcctctgcgt cgcgactct ctcaagcggg cttctctcaa caacatgatg     660
ggctctgttt tcggccgagt ttacgacctc tctgactcgg ctaacaatga cgtccaagaa    720
ctccagagcc tcgtcgacga aggctacgac ttgctgggcc tcctcaactg gtccgaccat    780
ctcccatggc tcgccgactt cgactctcag aaaatccggt tcagatgctc ccgactcgtc    840
cccaaggtga accacttcgt cggccggatc atcgccgaac accgcgccaa atccgacaac    900
caagtcctag atttcgtcga cgttttgctc tctctccaag aagccgacaa actctctgac    960
tccgatatga tcgccgttct ttgggaaatg attttttcgtg ggacggacac ggtggcagtt   1020
ttaatcgagt ggatactggc caggatggta cttcacaacg atatccaaag gaaagttcaa   1080
gaggagctag ataacgtggt tgggagtaca cgcgccgtcg cggaatccga cattccgtcg   1140
ctggtgtatc taacgctgt ggttaaggaa gttctgaggt tacatccgcc gggcccactc    1200
ctgtcgtggg cccgcctagc catcactgat acaatcatcg atgggcatca cgtgccccgg   1260
gggaccaccg ctatggttaa catgtggtcg atagcgcggg acccacaggt ctggtcggac   1320
ccactcgaat ttatgcccca gaggtttgtg tccgaccccg tgacgtgga gttctcggtc    1380 atgggttcgg atctccggct ggctccgttc gggtcgggca aaggacctg ccccgggaag    1440 gccttcgcct ggacaactgt caccttctgg gtggccacgc ttttacacga cttcaaatgg   1500
tcgccgtccg atcaaaacga cgccgtcgac ttgtcggagg tcctcaagct ctcctgcgag   1560
atggccaatc ccctcaccgt taaagtacac ccaaggcgca gtttaagctt ttaa         1614
```

<210> SEQ ID NO 51
<211> LENGTH: 537
<212> TYPE: PRT
<213> ORGANISM: Siraitia grosvenorii

<400> SEQUENCE: 51

```
Met Ser Met Ser Ser Glu Ile Glu Ser Leu Trp Val Phe Ala Leu Ala
1               5                   10                  15

Ser Lys Cys Ser Ala Leu Thr Lys Glu Asn Ile Leu Trp Ser Leu Leu
            20                  25                  30

Phe Phe Phe Leu Ile Trp Val Ser Val Ser Ile Leu His Trp Ala His
        35                  40                  45

Pro Gly Gly Pro Ala Trp Gly Arg Tyr Trp Trp Arg Arg Arg Arg Ser
    50                  55                  60

Asn Ser Thr Ala Ala Ala Ile Pro Gly Pro Arg Gly Leu Pro Leu Val
65                  70                  75                  80

Gly Ser Met Gly Leu Met Ala Asp Leu Ala His His Arg Ile Ala Ala
                85                  90                  95

Val Ala Asp Ser Leu Asn Ala Thr Arg Leu Met Ala Phe Ser Leu Gly
            100                 105                 110

Asp Thr Arg Val Ile Val Thr Cys Asn Pro Asp Val Ala Lys Glu Ile
        115                 120                 125
```

```
Leu Asn Ser Ser Leu Phe Ala Asp Arg Pro Val Lys Glu Ser Ala Tyr
        130                 135                 140

Ser Leu Met Phe Asn Arg Ala Ile Gly Phe Ala Pro Tyr Gly Leu Tyr
145                 150                 155                 160

Trp Arg Thr Leu Arg Arg Ile Ala Ser His His Leu Phe Cys Pro Lys
                165                 170                 175

Gln Ile Lys Ser Ser Gln Ser Gln Arg Arg Gln Ile Ala Ser Gln Met
                180                 185                 190

Val Ala Met Phe Ala Asn Arg Asp Ala Thr Gln Ser Leu Cys Val Arg
            195                 200                 205

Asp Ser Leu Lys Arg Ala Ser Leu Asn Asn Met Met Gly Ser Val Phe
210                 215                 220

Gly Arg Val Tyr Asp Leu Ser Asp Ser Ala Asn Asn Asp Val Gln Glu
225                 230                 235                 240

Leu Gln Ser Leu Val Asp Glu Gly Tyr Asp Leu Leu Gly Leu Leu Asn
                245                 250                 255

Trp Ser Asp His Leu Pro Trp Leu Ala Asp Phe Asp Ser Gln Lys Ile
                260                 265                 270

Arg Phe Arg Cys Ser Arg Leu Val Pro Lys Val Asn His Phe Val Gly
            275                 280                 285

Arg Ile Ile Ala Glu His Arg Ala Lys Ser Asp Asn Gln Val Leu Asp
290                 295                 300

Phe Val Asp Val Leu Leu Ser Leu Gln Glu Ala Asp Lys Leu Ser Asp
305                 310                 315                 320

Ser Asp Met Ile Ala Val Leu Trp Glu Met Ile Phe Arg Gly Thr Asp
                325                 330                 335

Thr Val Ala Val Leu Ile Glu Trp Ile Leu Ala Arg Met Val Leu His
                340                 345                 350

Asn Asp Ile Gln Arg Lys Val Gln Glu Glu Leu Asp Asn Val Val Gly
            355                 360                 365

Ser Thr Arg Ala Val Ala Glu Ser Asp Ile Pro Ser Leu Val Tyr Leu
370                 375                 380

Thr Ala Val Val Lys Glu Val Leu Arg Leu His Pro Pro Gly Pro Leu
385                 390                 395                 400

Leu Ser Trp Ala Arg Leu Ala Ile Thr Asp Thr Ile Ile Asp Gly His
                405                 410                 415

His Val Pro Arg Gly Thr Thr Ala Met Val Asn Met Trp Ser Ile Ala
            420                 425                 430

Arg Asp Pro Gln Val Trp Ser Asp Pro Leu Glu Phe Met Pro Gln Arg
            435                 440                 445

Phe Val Ser Asp Pro Gly Asp Val Glu Phe Ser Val Met Gly Ser Asp
450                 455                 460

Leu Arg Leu Ala Pro Phe Gly Ser Gly Arg Arg Thr Cys Pro Gly Lys
465                 470                 475                 480

Ala Phe Ala Trp Thr Thr Val Thr Phe Trp Val Ala Thr Leu Leu His
                485                 490                 495

Asp Phe Lys Trp Ser Pro Ser Asp Gln Asn Asp Ala Val Asp Leu Ser
            500                 505                 510

Glu Val Leu Lys Leu Ser Cys Glu Met Ala Asn Pro Leu Thr Val Lys
            515                 520                 525

Val His Pro Arg Arg Ser Leu Ser Phe
530                 535
```

<210> SEQ ID NO 52
<211> LENGTH: 1506
<212> TYPE: DNA
<213> ORGANISM: Siraitia grosvenorii

<400> SEQUENCE: 52

```
atggatggtt ttcttccaac agtggcggcg agcgtgcctg tgggagtggg tgcaatattg      60
ttcacggcgt tgtgcgtcgt cgtgggaggg gttttggttt atttctatgg accttactgg     120
ggagtgagaa gggtgcctgg tccaccagct attccactgg tcggacatct tcccttgctg     180
gctaagtacg gcccagacgt tttctctgtc cttgccaccc aatatggccc tatcttcagg     240
ttccatatgg gtaggcagcc attgataatt atagcagacc ctgagctttg taaagaagct     300
ggtattaaga aattcaagga catcccaaat agaagtgtcc cttctccaat atcagcttcc     360
cctcttcatc agaagggtct tttcttcaca agggatgcaa gatggtcgac aatgcggaac     420
acgatattat cggtctatca gtcctcccat ctagcgagac taatacctac tatgcaatca     480
atcattgaaa ctgcaactca aaatctccat tcctctgtcc aggaagacat ccctttctcc     540
aatctctccc tcaaattgac caccgatgtg attggaacag cagccttcgg tgtcaacttt     600
gggctctcta atccacaggc aaccaaaact tgtgctacca acggccaaga caacaaaaat     660
gacgaagttt cagacttcat caatcaacac atctactcca caacgcagct caagatggat     720
ttatcaggtt ccttctcaat catacttgga ctgcttgtcc ctatactcca gaaccattt     780
agacaagtcc taaagagaat accattcacc atggactgga agtggaccg gacaaatcag     840
aaaattaagt gtcggcttaa tgagattgtg gagaagagaa tgaagtgtaa cgatcaaggt     900
tcaaaagact tcttatcgct cattttgaga gcaagagagt cagagacagt atcaaggaat     960
gtcttcactc cagactacat cagtgcagtt acgtatgaac acctacttgc tgggtcggct    1020
accacggcgt ttacgttgtc ttctattgta tatttagttg ctgggcatcc agaagtcgag    1080
aagaagttgc tagaagagat tgacaacttt ggtccatccg atcagatacc aacagctaat    1140
gatcttcatc agaagtttcc atatcttgat caggtgatta agaggctat gaggttctac    1200
actgtttccc ctctagtagc cagagaaaca gctaaagatg tggagattgg tggatatctt    1260
cttccaaagg ggacatgggt ttggttagca cttggagttc ttgccaagga tccaaagaac    1320
tttccagaac cagataaatt caaaccagag aggtttgatc caaatgaaga agaggagaaa    1380
caaaggcatc cttatgcttt aatccccttt ggaattggtc ctcgagcatg cattggtaaa    1440
aaattcgccc ttcaggagtt gaagctctcg ttgattcatt tgtacaggaa gtttgtattt    1500
cggcat                                                               1506
```

<210> SEQ ID NO 53
<211> LENGTH: 502
<212> TYPE: PRT
<213> ORGANISM: Siraitia grosvenorii

<400> SEQUENCE: 53

```
Met Asp Gly Phe Leu Pro Thr Val Ala Ala Ser Val Pro Val Gly Val
1               5                   10                  15

Gly Ala Ile Leu Phe Thr Ala Leu Cys Val Val Val Gly Gly Val Leu
            20                  25                  30

Val Tyr Phe Tyr Gly Pro Tyr Trp Gly Val Arg Arg Val Pro Gly Pro
        35                  40                  45

Pro Ala Ile Pro Leu Val Gly His Leu Pro Leu Leu Ala Lys Tyr Gly
    50                  55                  60
```

```
Pro Asp Val Phe Ser Val Leu Ala Thr Gln Tyr Gly Pro Ile Phe Arg
 65                  70                  75                  80

Phe His Met Gly Arg Gln Pro Leu Ile Ile Ala Asp Pro Glu Leu
                 85                  90                  95

Cys Lys Glu Ala Gly Ile Lys Lys Phe Lys Asp Ile Pro Asn Arg Ser
                100                 105                 110

Val Pro Ser Pro Ile Ser Ala Ser Pro Leu His Gln Lys Gly Leu Phe
                115                 120                 125

Phe Thr Arg Asp Ala Arg Trp Ser Thr Met Arg Asn Thr Ile Leu Ser
            130                 135                 140

Val Tyr Gln Ser Ser His Leu Ala Arg Leu Ile Pro Thr Met Gln Ser
145                 150                 155                 160

Ile Ile Glu Thr Ala Thr Gln Asn Leu His Ser Ser Val Gln Glu Asp
                165                 170                 175

Ile Pro Phe Ser Asn Leu Ser Leu Lys Leu Thr Thr Asp Val Ile Gly
                180                 185                 190

Thr Ala Ala Phe Gly Val Asn Phe Gly Leu Ser Asn Pro Gln Ala Thr
            195                 200                 205

Lys Thr Cys Ala Thr Asn Gly Gln Asp Asn Lys Asn Asp Glu Val Ser
210                 215                 220

Asp Phe Ile Asn Gln His Ile Tyr Ser Thr Thr Gln Leu Lys Met Asp
225                 230                 235                 240

Leu Ser Gly Ser Phe Ser Ile Ile Leu Gly Leu Leu Val Pro Ile Leu
                245                 250                 255

Gln Glu Pro Phe Arg Gln Val Leu Lys Arg Ile Pro Phe Thr Met Asp
                260                 265                 270

Trp Lys Val Asp Arg Thr Asn Gln Lys Leu Ser Gly Arg Leu Asn Glu
            275                 280                 285

Ile Val Glu Lys Arg Met Lys Cys Asn Asp Gln Gly Ser Lys Asp Phe
            290                 295                 300

Leu Ser Leu Ile Leu Arg Ala Arg Glu Ser Glu Thr Val Ser Arg Asn
305                 310                 315                 320

Val Phe Thr Pro Asp Tyr Ile Ser Ala Val Thr Tyr Glu His Leu Leu
                325                 330                 335

Ala Gly Ser Ala Thr Thr Ala Phe Thr Leu Ser Ser Ile Val Tyr Leu
            340                 345                 350

Val Ala Gly His Pro Glu Val Glu Lys Lys Leu Leu Glu Glu Ile Asp
            355                 360                 365

Asn Phe Gly Pro Ser Asp Gln Ile Pro Thr Ala Asn Asp Leu His Gln
            370                 375                 380

Lys Phe Pro Tyr Leu Asp Gln Val Ile Lys Glu Ala Met Arg Phe Tyr
385                 390                 395                 400

Thr Val Ser Pro Leu Val Ala Arg Glu Thr Ala Lys Asp Val Glu Ile
                405                 410                 415

Gly Gly Tyr Leu Leu Pro Lys Gly Thr Trp Val Trp Leu Ala Leu Gly
            420                 425                 430

Val Leu Ala Lys Asp Pro Lys Asn Phe Pro Glu Pro Asp Lys Phe Lys
            435                 440                 445

Pro Glu Arg Phe Asp Pro Asn Glu Glu Glu Lys Gln Arg His Pro
            450                 455                 460

Tyr Ala Leu Ile Pro Phe Gly Ile Gly Pro Arg Ala Cys Ile Gly Lys
465                 470                 475                 480
```

Lys Phe Ala Leu Gln Glu Leu Lys Leu Ser Leu Ile His Leu Tyr Arg
            485                 490                 495

Lys Phe Val Phe Arg His
            500

<210> SEQ ID NO 54
<211> LENGTH: 1566
<212> TYPE: DNA
<213> ORGANISM: Siraitia grosvenorii

<400> SEQUENCE: 54

```
atggaaatca ttttatcata tctcaacagc tccatagctg gactcttcct cttgcttctc      60
ttctcgtttt ttgttttgaa aaaggctaga acctgtaaac gcagacagcc tcctgaagca     120
gccggcggat ggccgatcat cggccacctg agactgctcg ggggttcgca acttccccat     180
gaaaccttgg gagccatggc cgacaagtat ggaccaatct tcagcatccg agttggtgtc     240
cacccatctc ttgttataag cagttgggaa gtggctaaag agtgctacac cacccctcgac    300
tcagttgtct cttctcgtcc caagagtttg ggtgaaagt tgttgggcta caacttcgcc     360
gcttttgggt tcaggcctta tgattccttt taccggagta tccgcaaaac catagcctcc     420
gaggtgctgt cgaaccgccg tctggagttg cagagacaca ttcgagtttc tgaggtgaag     480
agatcggtga aggagcttta caatctgtgg acgcagagag aggaaggctc agaccacata     540
cttattgatg cggatgaatg gattggtaat attaatttga acgtgattct gatgatggtt     600
tgtgggaagc ggtttcttgg cggttctgcc agcgatgaga aggagatgag gcggtgtctc     660
aaagtctcga gagatttctt cgatttgaca gggcagttta cggtgggaga tgccattcct     720
ttcctgcgat ggctggattt gggtggatat gcgaaggcga tgaagaaaac tgcaaaagaa     780
atggactgtc tcgttgagga atggctggaa gaacaccgcc ggaagagaga ctccggcgcc     840
accgacggtg aacgtgactt catggatgtg atgctttcga ttcttgaaga gatggacctt     900
gctggctacg acgctgacac agtcaacaaa gccacatgcc tgagcattat ttctggggga     960
atcgatacta aacgctaac tctgacatgg gcgatctcgt tattgctgaa caatcgagag    1020
gcactgcgaa gggttcaaga ggaggtggac atccatgtcg aaacaaaag cttgtggat    1080
gaatcagact tgagcaagct ggtgtatctc caagccgtcg tgaaagagac attaaggttg    1140
tacccagcag ggccgctgtc gggagctcga gagttcagtc gggactgcac ggtcggaggg    1200
tatgacgtgg ccgccggcac acggctcatc acaaaccttt ggaagataca gacggaccct    1260
cgggtgtggc cggagccact tgagttcagg ccggagaggt ttctgagcag ccaccagcag    1320
ttggatgtga agggccagaa ctttgaactg gccccatttg gttgtggaag aagagtgtgc    1380
cctggggcgg gcttgggggt tcagatgacg cagttggtgc tggcgagtct gattcattcg    1440
gtggaacttg gaactcgctc cgatgaagcg gtggacatgg ctgctaagtt tggactcaca    1500
atgtacagag ccaccccctct tcaggctctc gtcaagccac gcctccaagc cggtgcttat    1560
tcatga                                                              1566
```

<210> SEQ ID NO 55
<211> LENGTH: 521
<212> TYPE: PRT
<213> ORGANISM: Siraitia grosvenorii

<400> SEQUENCE: 55

Met Glu Ile Ile Leu Ser Tyr Leu Asn Ser Ser Ile Ala Gly Leu Phe
1               5                   10                  15

-continued

```
Leu Leu Leu Leu Phe Ser Phe Phe Val Leu Lys Lys Ala Arg Thr Cys
            20              25                  30

Lys Arg Arg Gln Pro Pro Glu Ala Ala Gly Gly Trp Pro Ile Ile Gly
        35              40                  45

His Leu Arg Leu Leu Gly Gly Ser Gln Leu Pro His Glu Thr Leu Gly
    50                  55                  60

Ala Met Ala Asp Lys Tyr Gly Pro Ile Phe Ser Ile Arg Val Gly Val
65              70                  75                  80

His Pro Ser Leu Val Ile Ser Ser Trp Glu Val Ala Lys Glu Cys Tyr
                85                  90                  95

Thr Thr Leu Asp Ser Val Val Ser Ser Arg Pro Lys Ser Leu Gly Gly
            100                 105                 110

Lys Leu Leu Gly Tyr Asn Phe Ala Ala Phe Gly Phe Arg Pro Tyr Asp
        115                 120                 125

Ser Phe Tyr Arg Ser Ile Arg Lys Thr Ile Ala Ser Glu Val Leu Ser
    130                 135                 140

Asn Arg Arg Leu Glu Leu Gln Arg His Ile Arg Val Ser Glu Val Lys
145                 150                 155                 160

Arg Ser Val Lys Glu Leu Tyr Asn Leu Trp Thr Gln Arg Glu Glu Gly
                165                 170                 175

Ser Asp His Ile Leu Ile Asp Ala Asp Glu Trp Ile Gly Asn Ile Asn
            180                 185                 190

Leu Asn Val Ile Leu Met Met Val Cys Gly Lys Arg Phe Leu Gly Gly
        195                 200                 205

Ser Ala Ser Asp Glu Lys Glu Met Arg Arg Cys Leu Lys Val Ser Arg
    210                 215                 220

Asp Phe Phe Asp Leu Thr Gly Gln Phe Thr Val Gly Asp Ala Ile Pro
225                 230                 235                 240

Phe Leu Arg Trp Leu Asp Leu Gly Gly Tyr Ala Lys Ala Met Lys Lys
                245                 250                 255

Thr Ala Lys Glu Met Asp Cys Leu Val Glu Glu Trp Leu Glu Glu His
            260                 265                 270

Arg Arg Lys Arg Asp Ser Gly Ala Thr Asp Gly Glu Arg Asp Phe Met
        275                 280                 285

Asp Val Met Leu Ser Ile Leu Glu Glu Met Asp Leu Ala Gly Tyr Asp
    290                 295                 300

Ala Asp Thr Val Asn Lys Ala Thr Cys Leu Ser Ile Ile Ser Gly Gly
305                 310                 315                 320

Ile Asp Thr Ile Thr Leu Thr Leu Thr Trp Ala Ile Ser Leu Leu Leu
                325                 330                 335

Asn Asn Arg Glu Ala Leu Arg Arg Val Gln Glu Glu Val Asp Ile His
            340                 345                 350

Val Gly Asn Lys Arg Leu Val Asp Glu Ser Asp Leu Ser Lys Leu Val
        355                 360                 365

Tyr Leu Gln Ala Val Val Lys Glu Thr Leu Arg Leu Tyr Pro Ala Gly
    370                 375                 380

Pro Leu Ser Gly Ala Arg Glu Phe Ser Arg Asp Cys Thr Val Gly Gly
385                 390                 395                 400

Tyr Asp Val Ala Ala Gly Thr Arg Leu Ile Thr Asn Leu Trp Lys Ile
                405                 410                 415

Gln Thr Asp Pro Arg Val Trp Pro Glu Pro Leu Glu Phe Arg Pro Glu
            420                 425                 430

Arg Phe Leu Ser Ser His Gln Gln Leu Asp Val Lys Gly Gln Asn Phe
```

435               440                445
Glu Leu Ala Pro Phe Gly Cys Gly Arg Arg Val Cys Pro Gly Ala Gly
            450                455                460

Leu Gly Val Gln Met Thr Gln Leu Val Leu Ala Ser Leu Ile His Ser
465                470                475                480

Val Glu Leu Gly Thr Arg Ser Asp Glu Ala Val Asp Met Ala Ala Lys
                485                490                495

Phe Gly Leu Thr Met Tyr Arg Ala Thr Pro Leu Gln Ala Leu Val Lys
            500                505                510

Pro Arg Leu Gln Ala Gly Ala Tyr Ser
            515                520

<210> SEQ ID NO 56
<211> LENGTH: 1425
<212> TYPE: DNA
<213> ORGANISM: Siraitia grosvenorii

<400> SEQUENCE: 56
atgggtgtat tgtccatttt attattcaga tattccgtca agaagaagcc attaagatgc       60
ggtcacgatc aaagaagtac cacagatagt ccacctggtt caagaggttt gccattgata      120
ggtgaaactt tgcaattcat ggctgctatt aattctttga cggtgtata cgatttcgtt      180
agaataagat gtttgagata cggtagatgc tttaagacaa gaatcttcgg tgaaacccat      240
gttttttgtct caactacaga atccgctaag ttgatcttga aggatggtgg tgaaaaattc      300
accaaaaagt acatcagatc aatcgctgaa ttggttggtg acagaagttt gttatgtgca      360
tctcatttgc aacacaagag attgagaggt tgttgactaa atttgttttc tgccacattc      420
ttggcttctt cgtaactca attcgatgaa caaatcgttg aagcttttag atcatgggaa      480
tccggtagta ccataatcgt tttgaacgaa gcattgaaga tcacttgtaa ggccatgtgc      540
aaaatggtca tgtccttaga aagagaaaac gaattggaag ctttgcaaaa ggaattgggt      600
catgtttgtg aagctatgtt ggcatttcca tgcagattcc ctggtacaag atttcacaat      660
ggttgaagg caagaagaag aatcattaaa gttgtcgaaa tggccattag agaaagaaga      720
agatctgaag ctcctagaga agatttcttg caaagattgt tgacagaaga aaaggaagaa      780
gaagacggtg tggtgttttt aagtgatgcc gaaattggtg acaacatatt gacaatgatg      840
atcgcaggtc aagataccac tgcctctgct attacctgga tggtcaagtt tttggaagaa      900
aaccaagatg tattgcaaaa cttaagagac gaacaattcg aaatcatggg taaacaagaa      960
ggttgtggtt catgcttctt gacattagaa gatttgggta tatgtcctca tggtgcaaaa     1020
gtagttaagg aatcattgag attagcctcc gtcgtaccat ggtttcctag attggtttta     1080
caagattctt tgatccaagg ttacaaaatt aaaaagggtt ggaacgtcaa catagacgta     1140
agatctttac attcagatcc atccttgtat aatgacccaa caaagtttaa ccctagtaga     1200
ttcgatgacg aagctaaacc ttactcattt ttggcattcg gtatgggtgg tagacaatgt     1260
ttgggtatga acatggcaaa ggccatgatg ttggttttct gcacagatt ggtcacctca     1320
ttcagatgga aggttataga ttccgactct tcaatcgaaa atgggctttt gttctctaag     1380
ttgaagtcag gttgccctat cgtagttacc cacatcggtt cctaa                     1425

<210> SEQ ID NO 57
<211> LENGTH: 474
<212> TYPE: PRT
<213> ORGANISM: Siraitia grosvenorii

<400> SEQUENCE: 57

```
Met Gly Val Leu Ser Ile Leu Leu Phe Arg Tyr Ser Val Lys Lys Lys
1               5                   10                  15

Pro Leu Arg Cys Gly His Asp Gln Arg Ser Thr Thr Asp Ser Pro Pro
            20                  25                  30

Gly Ser Arg Gly Leu Pro Leu Ile Gly Glu Thr Leu Gln Phe Met Ala
        35                  40                  45

Ala Ile Asn Ser Leu Asn Gly Val Tyr Asp Phe Val Arg Ile Arg Cys
    50                  55                  60

Leu Arg Tyr Gly Arg Cys Phe Lys Thr Arg Ile Phe Gly Glu Thr His
65                  70                  75                  80

Val Phe Val Ser Thr Thr Glu Ser Ala Lys Leu Ile Leu Lys Asp Gly
                85                  90                  95

Gly Glu Lys Phe Thr Lys Lys Tyr Ile Arg Ser Ile Ala Glu Leu Val
                100                 105                 110

Gly Asp Arg Ser Leu Leu Cys Ala Ser His Leu Gln His Lys Arg Leu
            115                 120                 125

Arg Gly Leu Leu Thr Asn Leu Phe Ser Ala Thr Phe Leu Ala Ser Phe
        130                 135                 140

Val Thr Gln Phe Asp Glu Gln Ile Val Glu Ala Phe Arg Ser Trp Glu
145                 150                 155                 160

Ser Gly Ser Thr Ile Ile Val Leu Asn Glu Ala Leu Lys Ile Thr Cys
                165                 170                 175

Lys Ala Met Cys Lys Met Val Met Ser Leu Glu Arg Glu Asn Glu Leu
                180                 185                 190

Glu Ala Leu Gln Lys Glu Leu Gly His Val Cys Glu Ala Met Leu Ala
            195                 200                 205

Phe Pro Cys Arg Phe Pro Gly Thr Arg Phe His Asn Gly Leu Lys Ala
        210                 215                 220

Arg Arg Arg Ile Ile Lys Val Val Glu Met Ala Ile Arg Glu Arg Arg
225                 230                 235                 240

Arg Ser Glu Ala Pro Arg Glu Asp Phe Leu Gln Arg Leu Leu Thr Glu
                245                 250                 255

Glu Lys Glu Glu Glu Asp Gly Gly Val Leu Ser Asp Ala Glu Ile
                260                 265                 270

Gly Asp Asn Ile Leu Thr Met Met Ile Ala Gly Gln Asp Thr Thr Ala
            275                 280                 285

Ser Ala Ile Thr Trp Met Val Lys Phe Leu Glu Glu Asn Gln Asp Val
        290                 295                 300

Leu Gln Asn Leu Arg Asp Glu Gln Phe Glu Ile Met Gly Lys Gln Glu
305                 310                 315                 320

Gly Cys Gly Ser Cys Phe Leu Thr Leu Glu Asp Leu Gly Asn Met Ser
                325                 330                 335

Tyr Gly Ala Lys Val Val Lys Glu Ser Leu Arg Leu Ala Ser Val Val
            340                 345                 350

Pro Trp Phe Pro Arg Leu Val Leu Gln Asp Ser Leu Ile Gln Gly Tyr
        355                 360                 365

Lys Ile Lys Lys Gly Trp Asn Val Asn Ile Asp Val Arg Ser Leu His
370                 375                 380

Ser Asp Pro Ser Leu Tyr Asn Asp Pro Thr Lys Phe Asn Pro Ser Arg
385                 390                 395                 400

Phe Asp Asp Glu Ala Lys Pro Tyr Ser Phe Leu Ala Phe Gly Met Gly
                405                 410                 415
```

```
Gly Arg Gln Cys Leu Gly Met Asn Met Ala Lys Ala Met Met Leu Val
            420                 425                 430

Phe Leu His Arg Leu Val Thr Ser Phe Arg Trp Lys Val Ile Asp Ser
            435                 440                 445

Asp Ser Ser Ile Glu Lys Trp Ala Leu Phe Ser Lys Leu Lys Ser Gly
            450                 455                 460

Cys Pro Ile Val Val Thr His Ile Gly Ser
465                 470

<210> SEQ ID NO 58
<211> LENGTH: 1509
<212> TYPE: DNA
<213> ORGANISM: Siraitia grosvenorii

<400> SEQUENCE: 58
atggatttct actggatctg tgttcttctg ctttgcttcg catggttttc cattttatcc      60
cttcactcga gaacaaacag cagcggcact tccaaacttc ctcccggacc gaaacccttg     120
ccgatcatcg gaagcctttt ggctctcggc cacgagcccc acaagtcttt ggctaatctc     180
gctaaatctc atggccctct tatgacctta agctcggcc aaatcaccac cgtcgtagtt      240
tcctccgctg ccatggctaa gcaagttctc caaacgcacg accagtttct gtccagcagg     300
accgttccag acgcaatgac ctctcacaac cacgatgctt tcgcactccc atggattccg     360
gtttcacccc tctggcgaaa ccttcgacga atatgcaaca accagttgtt tgccggcaag     420
attctcgacg ccaacgagaa tctccggcga accaaagtgg ccgagctcgt atccgatatc     480
tcgagaagtg cattgaaagg tgagatggtg gattttggaa acgtggtgtt cgtcacttcg     540
ctcaatctgc tttccaatac gattttctcg gtggatttct tcgacccaaa ttctgaaatt     600
gggaaagagt tcaggcacgc agtacgaggc ctcatggaag aagctgccaa accaaatttg     660
ggggattatt cccctctgct gaagaagata gatcttcaag gaataaagag agacagacc      720
acttacttcg atcgggtttt taatgttttg gagcacatga tcgaccagcg tcttcagcag     780
cagaagacga cgtctggttc tacctccaac aacaacaacg acttactgca ctaccttctc     840
aacctcagca acgaaaatag cgacatgaaa ttggggaaac ttgagctgaa acacttctta     900
ttggtgctat cgtcgctgg gactgaaacg agttctgcaa cactgcaatg gcaatggca      960
gaactactaa gaaacccaga aaagttagca aaagctcaag cggagaccag gcgggtgatt    1020
gggaaaggga acccaattga gaatcagac atttcgaggc tgccttatct gcaagcagtg     1080
gtgaaagaaa ctttcagatt gcacaccaca gcgccatttc tactgccgcg caaagcacta    1140
caggacgtgg aaattgcagg tttcacagtc ccaaggacg ctcaggtact ggtaaattta     1200
tgggctatga gcagagattc aagcatctgg gagaacccag agtggttcga ccagaaagg     1260
ttttggagt cggagctgga cgttagaggg agagattttg agctgatccc gttcggcggt    1320
gggcggagga tttgccccgg tctgccgttg gcgatgagaa tgttgcattt gatttggt      1380
tctctcatcc acttctttga ttggaagctt gaagatgggt gtcggccgga agacgtgaaa    1440
atggacgaaa agcttggcct cactctggag ttggcttttc ccctcacagc cttgcctgtc    1500
cttgtctaa                                                           1509

<210> SEQ ID NO 59
<211> LENGTH: 502
<212> TYPE: PRT
<213> ORGANISM: Siraitia grosvenorii
```

-continued

<400> SEQUENCE: 59

| | | | | | | | | | | | | | | |
|---|---|---|---|---|---|---|---|---|---|---|---|---|---|---|
|Met|Asp|Phe|Tyr|Trp|Ile|Cys|Val|Leu|Leu|Cys|Phe|Ala|Trp|Phe|
|1| | | |5| | | |10| | | | |15| |
|Ser|Ile|Leu|Ser|Leu|His|Ser|Arg|Thr|Asn|Ser|Ser|Gly|Thr|Ser|Lys|
| | | |20| | | | |25| | | | |30| | |
|Leu|Pro|Pro|Gly|Pro|Lys|Pro|Leu|Pro|Ile|Ile|Gly|Ser|Leu|Leu|Ala|
| | | |35| | | | |40| | | | |45| | |
|Leu|Gly|His|Glu|Pro|His|Lys|Ser|Leu|Ala|Asn|Leu|Ala|Lys|Ser|His|
| |50| | | | |55| | | | |60| | | | |
|Gly|Pro|Leu|Met|Thr|Leu|Lys|Leu|Gly|Gln|Ile|Thr|Thr|Val|Val|
|65| | | | |70| | | | |75| | | | |80|
|Ser|Ser|Ala|Ala|Met|Ala|Lys|Gln|Val|Leu|Gln|Thr|His|Asp|Gln|Phe|
| | | | |85| | | | |90| | | | |95| |
|Leu|Ser|Ser|Arg|Thr|Val|Pro|Asp|Ala|Met|Thr|Ser|His|Asn|His|Asp|
| | | |100| | | | |105| | | | |110| | |
|Ala|Phe|Ala|Leu|Pro|Trp|Ile|Pro|Val|Ser|Pro|Leu|Trp|Arg|Asn|Leu|
| | |115| | | | |120| | | | |125| | | |
|Arg|Arg|Ile|Cys|Asn|Asn|Gln|Leu|Phe|Ala|Gly|Lys|Ile|Leu|Asp|Ala|
| |130| | | | |135| | | | |140| | | | |
|Asn|Glu|Asn|Leu|Arg|Arg|Thr|Lys|Val|Ala|Glu|Leu|Val|Ser|Asp|Ile|
|145| | | | |150| | | | |155| | | | |160|
|Ser|Arg|Ser|Ala|Leu|Lys|Gly|Glu|Met|Val|Asp|Phe|Gly|Asn|Val|Val|
| | | | |165| | | | |170| | | | |175| |
|Phe|Val|Thr|Ser|Leu|Asn|Leu|Leu|Ser|Asn|Thr|Ile|Phe|Ser|Val|Asp|
| | | |180| | | | |185| | | | |190| | |
|Phe|Phe|Asp|Pro|Asn|Ser|Glu|Ile|Gly|Lys|Glu|Phe|Arg|His|Ala|Val|
| | |195| | | | |200| | | | |205| | | |
|Arg|Gly|Leu|Met|Glu|Glu|Ala|Ala|Lys|Pro|Asn|Leu|Gly|Asp|Tyr|Phe|
| |210| | | | |215| | | | |220| | | | |
|Pro|Leu|Leu|Lys|Lys|Ile|Asp|Leu|Gln|Gly|Ile|Lys|Arg|Arg|Gln|Thr|
|225| | | | |230| | | | |235| | | | |240|
|Thr|Tyr|Phe|Asp|Arg|Val|Phe|Asn|Val|Leu|Glu|His|Met|Ile|Asp|Gln|
| | | | |245| | | | |250| | | | |255| |
|Arg|Leu|Gln|Gln|Gln|Lys|Thr|Thr|Ser|Gly|Ser|Thr|Ser|Asn|Asn|Asn|
| | | |260| | | | |265| | | | |270| | |
|Asn|Asp|Leu|Leu|His|Tyr|Leu|Leu|Asn|Leu|Ser|Asn|Glu|Asn|Ser|Asp|
| | |275| | | | |280| | | | |285| | | |
|Met|Lys|Leu|Gly|Lys|Leu|Glu|Leu|Lys|His|Phe|Leu|Leu|Val|Leu|Phe|
| |290| | | | |295| | | | |300| | | | |
|Val|Ala|Gly|Thr|Glu|Thr|Ser|Ser|Ala|Thr|Leu|Gln|Trp|Ala|Met|Ala|
|305| | | | |310| | | | |315| | | | |320|
|Glu|Leu|Leu|Arg|Asn|Pro|Glu|Lys|Leu|Ala|Lys|Ala|Gln|Ala|Glu|Thr|
| | | | |325| | | | |330| | | | |335| |
|Arg|Arg|Val|Ile|Gly|Lys|Gly|Asn|Pro|Ile|Glu|Glu|Ser|Asp|Ile|Ser|
| | | |340| | | | |345| | | | |350| | |
|Arg|Leu|Pro|Tyr|Leu|Gln|Ala|Val|Val|Lys|Glu|Thr|Phe|Arg|Leu|His|
| | |355| | | | |360| | | | |365| | | |
|Thr|Pro|Ala|Pro|Phe|Leu|Leu|Pro|Arg|Lys|Ala|Leu|Gln|Asp|Val|Glu|
| |370| | | | |375| | | | |380| | | | |
|Ile|Ala|Gly|Phe|Thr|Val|Pro|Lys|Asp|Ala|Gln|Val|Leu|Val|Asn|Leu|
|385| | | | |390| | | | |395| | | | |400|
|Trp|Ala|Met|Ser|Arg|Asp|Ser|Ser|Ile|Trp|Glu|Asn|Pro|Glu|Trp|Phe|
| | | | |405| | | | |410| | | | |415| |

```
Glu Pro Glu Arg Phe Leu Glu Ser Gly Leu Asp Val Arg Gly Arg Asp
                420                 425                 430

Phe Glu Leu Ile Pro Phe Gly Gly Arg Arg Ile Cys Pro Gly Leu
            435                 440                 445

Pro Leu Ala Met Arg Met Leu His Leu Ile Leu Gly Ser Leu Ile His
    450                 455                 460

Phe Phe Asp Trp Lys Leu Glu Asp Gly Cys Arg Pro Glu Asp Val Lys
465                 470                 475                 480

Met Asp Glu Lys Leu Gly Leu Thr Leu Glu Leu Ala Phe Pro Leu Thr
                485                 490                 495

Ala Leu Pro Val Leu Val
            500

<210> SEQ ID NO 60
<211> LENGTH: 1734
<212> TYPE: DNA
<213> ORGANISM: Siraitia grosvenorii

<400> SEQUENCE: 60
atgtcctcct gcggtggtcc aactcctttg aatgttatcg gtatcttatt acaatcagaa      60
tcctccagag cctgcaactc agacgaaaac tcaagaattt tgagagattt cgtaacaaga     120
gaagttaacg ctttcttatg gttgtccttg atcactatca cagcagtttt gatcagtaaa     180
gttgtcggtt tgtttagatt gtggtctaag gcaaagcaat tgagaggtcc accttgtcca     240
tcattctacg gtcattctaa gatcatctca agacaaaatt tgactgattt gttatatgac     300
tcccacaaaa agtacggtcc agtagttaaa ttgtggttag gtcctatgca attgttagtc     360
tccgtaaagg aaccaagttt gttgaaggaa atattggtta agctgaggga taagttgcct     420
ttaacaggta gagcctttag attggctttc ggtagatctt cattatttgc atccagtttc     480
gaaaaggttc aaaacagaag acaaagattg gccgaaaagt tgaataagat cgcattccaa     540
agagccaaca tcattccaga aaaggccgta gcttgtttca tgggtagagt tcaagatttg     600
atgatagaag aatctgtcga ctgtaataag gtttctcaac atttggcttt tactttgtta     660
ggttgcacat tgtttggtga cgccttctta ggttggtcta aggctacaat ctatgaagaa     720
ttgttgatga tgatcgctaa ggacgcatcc ttttgggcta gttatagagt taccccaatc     780
tggaagcaag gttctggag ataccaaaga ttgtgtatga agttgaagtg cttgactcaa     840
gatatcgttc aacaatacag aaagcattac aagttgtttt ctcactcaca aaaccaaaac     900
ttacacaacg aaaccaagtc aactggtgtt gaagtcgctt ttgatattcc accttgtcct     960
gctgcagacg ttagaaattc ttgcttttc tacggtttga cgatcatgt taacccaaac    1020 gaagaacctt gtggtaatat tatgggtgtc atgtttcacg ttgcttgac tacaacctct    1080 ttgatcgcat caatcttgga agattggcc actaacccag aaatccaaga aaagattaat    1140
tctgaattga acttagttca aagggtccca gtcaaggatc atagaaagaa tgttgacaac    1200
atgcctttgt tattggcaac aatctatgaa tcagctagat tattgccagc aggtcctta    1260 ttgcaaagat gtccttgaa gcaagatttg gttttgaaaa caggtatcac cattccagct    1320
ggtaccttgg tcgtagttcc tattaaattg gttcaaatgg atgactcttc atggggttca    1380
gatgccaatg agtttaatcc atacagattc ttgtccatgg cttgtaatgg tattgacatg    1440
atacaaagaa ccccctttagc tggtgaaaac attggtgacc aaggtgaagg ttcatttgtc    1500
ttgaatgacc caattggtaa cgtaggtttc ttaccttttg gtttcggtgc aagagcctgc    1560
```

-continued

```
gttggtcaaa agtttataat ccaaggtgtc gctactttgt tcgcaagttt gttggcccat   1620
tacgaaatta aattgcaatc cgagagtaag aatgattcta aaccatccag taacacctct   1680
gccagtcaaa tcgtcccaaa ctcaaaaatc gtattcgtaa gaagaaactc ataa         1734
```

<210> SEQ ID NO 61
<211> LENGTH: 577
<212> TYPE: PRT
<213> ORGANISM: Siraitia grosvenorii

<400> SEQUENCE: 61

```
Met Ser Ser Cys Gly Gly Pro Thr Pro Leu Asn Val Ile Gly Ile Leu
1               5                   10                  15

Leu Gln Ser Glu Ser Ser Arg Ala Cys Asn Ser Asp Glu Asn Ser Arg
            20                  25                  30

Ile Leu Arg Asp Phe Val Thr Arg Glu Val Asn Ala Phe Leu Trp Leu
        35                  40                  45

Ser Leu Ile Thr Ile Thr Ala Val Leu Ile Ser Lys Val Val Gly Leu
    50                  55                  60

Phe Arg Leu Trp Ser Lys Ala Lys Gln Leu Arg Gly Pro Pro Cys Pro
65                  70                  75                  80

Ser Phe Tyr Gly His Ser Lys Ile Ile Ser Arg Gln Asn Leu Thr Asp
                85                  90                  95

Leu Leu Tyr Asp Ser His Lys Lys Tyr Gly Pro Val Val Lys Leu Trp
            100                 105                 110

Leu Gly Pro Met Gln Leu Leu Val Ser Val Lys Glu Pro Ser Leu Leu
        115                 120                 125

Lys Glu Ile Leu Val Lys Ala Glu Asp Lys Leu Pro Leu Thr Gly Arg
    130                 135                 140

Ala Phe Arg Leu Ala Phe Gly Arg Ser Ser Leu Phe Ala Ser Ser Phe
145                 150                 155                 160

Glu Lys Val Gln Asn Arg Arg Gln Arg Leu Ala Glu Lys Leu Asn Lys
                165                 170                 175

Ile Ala Phe Gln Arg Ala Asn Ile Ile Pro Glu Lys Ala Val Ala Cys
            180                 185                 190

Phe Met Gly Arg Val Gln Asp Leu Met Ile Glu Glu Ser Val Asp Cys
        195                 200                 205

Asn Lys Val Ser Gln His Leu Ala Phe Thr Leu Leu Gly Cys Thr Leu
    210                 215                 220

Phe Gly Asp Ala Phe Leu Gly Trp Ser Lys Ala Thr Ile Tyr Glu Glu
225                 230                 235                 240

Leu Leu Met Met Ile Ala Lys Asp Ala Ser Phe Trp Ala Ser Tyr Arg
                245                 250                 255

Val Thr Pro Ile Trp Lys Gln Gly Phe Trp Arg Tyr Gln Arg Leu Cys
            260                 265                 270

Met Lys Leu Lys Cys Leu Thr Gln Asp Ile Val Gln Gln Tyr Arg Lys
        275                 280                 285

His Tyr Lys Leu Phe Ser His Ser Gln Asn Gln Asn Leu His Asn Glu
    290                 295                 300

Thr Lys Ser Thr Gly Val Glu Val Ala Phe Asp Ile Pro Pro Cys Pro
305                 310                 315                 320

Ala Ala Asp Val Arg Asn Ser Cys Phe Phe Tyr Gly Leu Asn Asp His
                325                 330                 335

Val Asn Pro Asn Glu Glu Pro Cys Gly Asn Ile Met Gly Val Met Phe
            340                 345                 350
```

His Gly Cys Leu Thr Thr Thr Ser Leu Ile Ala Ser Ile Leu Glu Arg
            355                 360                 365

Leu Ala Thr Asn Pro Glu Ile Gln Glu Lys Ile Asn Ser Glu Leu Asn
    370                 375                 380

Leu Val Gln Lys Gly Pro Val Lys Asp His Arg Lys Asn Val Asp Asn
385                 390                 395                 400

Met Pro Leu Leu Leu Ala Thr Ile Tyr Glu Ser Ala Arg Leu Leu Pro
                405                 410                 415

Ala Gly Pro Leu Leu Gln Arg Cys Pro Leu Lys Gln Asp Leu Val Leu
            420                 425                 430

Lys Thr Gly Ile Thr Ile Pro Ala Gly Thr Leu Val Val Val Pro Ile
            435                 440                 445

Lys Leu Val Gln Met Asp Asp Ser Ser Trp Gly Ser Asp Ala Asn Glu
    450                 455                 460

Phe Asn Pro Tyr Arg Phe Leu Ser Met Ala Cys Asn Gly Ile Asp Met
465                 470                 475                 480

Ile Gln Arg Thr Pro Leu Ala Gly Glu Asn Ile Gly Asp Gln Gly Glu
                485                 490                 495

Gly Ser Phe Val Leu Asn Asp Pro Ile Gly Asn Val Gly Phe Leu Pro
            500                 505                 510

Phe Gly Phe Gly Ala Arg Ala Cys Val Gly Gln Lys Phe Ile Ile Gln
            515                 520                 525

Gly Val Ala Thr Leu Phe Ala Ser Leu Leu Ala His Tyr Glu Ile Lys
            530                 535                 540

Leu Gln Ser Glu Ser Lys Asn Asp Ser Lys Pro Ser Ser Asn Thr Ser
545                 550                 555                 560

Ala Ser Gln Ile Val Pro Asn Ser Lys Ile Val Phe Val Arg Arg Asn
                565                 570                 575

Ser

<210> SEQ ID NO 62
<211> LENGTH: 1422
<212> TYPE: DNA
<213> ORGANISM: Siraitia grosvenorii

<400> SEQUENCE: 62

```
atgtggactg tcgtgctcgg tttggcgacg ctgtttgtcg cctactacat ccattggatt      60
aacaaatgga gagattccaa gttcaacgga gttctgccgc gggcaccat gggtttgccg      120 ctcatcggag agacgattca actgagtcga cccagtgact ccctcgacgt tcacccttc     180 atccagaaaa aagttgaaag atacgggccg atcttcaaaa catgtctggc cggaaggccg     240
gtggtggtgt cggcggacgc agagttcaac aactacataa tgctgcagga aggaagagca     300
gtggaaatgt ggtatttgga tacgctctcc aaattttcg gcctcgacac cgagtggctc     360
aaagctctgg gcctcatcca caagtacatc agaagcatta ctctcaatca cttcggcgcc     420
gaggccctgc gggagagatt tcttcctttt attgaagcat cctccatgga agcccttcac     480
tcctggtcta ctcaacctag cgtcgaagtc aaaaatgcct ccgctctcat ggttttagg     540 acctcggtga taagatgtt cggtgaggat gcgaagaagc tatcgggaaa tatccctggg     600
aagttcacga agcttctagg aggatttctc agtttaccac tgaattttcc cggcaccacc     660
taccacaaat gcttgaagga tatgaaggaa atccagaaga agctaagaga ggttgtagac     720
gatagattgg ctaatgtggg ccctgatgtg gaagatttct tggggcaagc ccttaaagat     780
```

```
aaggaatcag agaagttcat tcagaggag ttcatcatcc aactgttgtt ttctatcagt      840
tttgctagct ttgagtccat ctccaccact cttactttga ttctcaagct ccttgatgaa      900
cacccagaag tagtgaaaga gttggaagct gaacacgagg cgattcgaaa agctagagca      960
gatccagatg gaccaattac ttgggaagaa tacaaatcca tgacttttac attacaagtc     1020
atcaatgaaa ccctaaggtt ggggagtgtc acacctgcct tgttgaggaa acagttaaa      1080 gatcttcaag taaaaggata cataatcccg gaaggatgga caataatgct tgtcaccgct     1140
tcacgtcaca gagacccaaa agtctataag gaccctcata tcttcaatcc atggcgttgg     1200
aaggacttgg actcaattac catccaaaag aacttcatgc cttttggggg aggcttaagg     1260
cattgtgctg gtgctgagta ctctaaagtc tacttgtgca ccttcttgca catcctctgt     1320
accaaatacc gatggaccaa acttggggga ggaaggattg caagagctca tatattgagt     1380
tttgaagatg ggttacatgt gaagttcaca cccaaggaat ga                        1422

<210> SEQ ID NO 63

<400> SEQUENCE: 63

000

<210> SEQ ID NO 64
<211> LENGTH: 1374
<212> TYPE: DNA
<213> ORGANISM: Siraitia grosvenorii

<400> SEQUENCE: 64
atgaagatga agatggaatc catgcgcacc tccctggata tctccgacca tgacatactt       60
ccaagggttt atcctcatgt tcacctatgg atcaacaaat atgggaaaaa cttcattcag      120
tggaatggca acgtagctca gttgattgtt tcggatcctg cacgatcaa ggagatactc       180 caaaaccgag aacaagctgt tcccaaaata gatctcagcg gagatgcacg gaggatattc      240
gggaatgggc tttcgacttc tgacggtgaa aaatgggcta aggctcgaag aatcgctgat      300 tacgcttttcc acgggatct cctaagaaat atggggccaa ccatggtttc ctgtgctgag      360
gcaatggtgg aaaagtggaa gcatcatcaa ggcaaagagc ttgatttgtt cgaagagttt      420
aaggtgctca cttcagatat cattgcacat acagcctttg gaagcagtta tttggaaggg      480
aaagttattt tcagactct aagtaagctg agcatgatat tatttaagaa tcagttcaaa      540
cgaaggattc ctgttatcag caagttcttc agatcaaagg atgcgaggga gggagaggag      600
ctggaaagaa ggttgaaaaa ttccataatt tcaataatgg aaaagagaga agagaaggtg      660
ataagtggtg aagcagataa ctatggtaat gatttcttg gattactttt gaaggcaaag      720
aatgagcctg accagaggca gaggattttct gttgatgatg tagtggatga atgcaaaaca      780
gtttacttcg ctgggcaaga aactacaagt gttttgcttg cttggaccgc ctttctttta      840
gcaactcatg agcattggca agaagaagca agaaaggaag tgctgaatat gttttggcaac      900 aagaatccaa cttagaagg catcacaaaa ttaagaatta tgagcatgat catcaaggaa      960
tctctaagat tatatcctcc agccccgccc atgtcaagga aggttaaaaa ggaagtcaga     1020
ttggggaagc tggttctccc ccccaacatt caagtaagca tctcaactat tgcagttcat     1080
catgatactg caatatgggg tgaagatgcc catgtattca accagaaag atttttctgaa     1140 ggaacagcta agatatccc atcagctgca tacatcccat ttggctttgg tcctcgaaac     1200
tgcatcggca atatcttggc catcaacgaa actaagattg cactgtcgat gattctacaa     1260
```

```
cgattttctt tcaccatctc cccggcctac gtccacgcac ctttccagtt cctcactatc    1320
tgcccccaac acggggttca ggtaaagctt cagtccctat taagtgaaag gtga           1374
```

<210> SEQ ID NO 65
<211> LENGTH: 457
<212> TYPE: PRT
<213> ORGANISM: Siraitia grosvenorii

<400> SEQUENCE: 65

```
Met Lys Met Lys Met Glu Ser Met Arg Thr Ser Leu Asp Ile Ser Asp
1               5                   10                  15

His Asp Ile Leu Pro Arg Val Tyr Pro His Val His Leu Trp Ile Asn
            20                  25                  30

Lys Tyr Gly Lys Asn Phe Ile Gln Trp Asn Gly Asn Val Ala Gln Leu
        35                  40                  45

Ile Val Ser Asp Pro Asp Thr Ile Lys Glu Ile Leu Gln Asn Arg Glu
    50                  55                  60

Gln Ala Val Pro Lys Ile Asp Leu Ser Gly Asp Ala Arg Arg Ile Phe
65                  70                  75                  80

Gly Asn Gly Leu Ser Thr Ser Asp Gly Glu Lys Trp Ala Lys Ala Arg
                85                  90                  95

Arg Ile Ala Asp Tyr Ala Phe His Gly Asp Leu Leu Arg Asn Met Gly
            100                 105                 110

Pro Thr Met Val Ser Cys Ala Glu Ala Met Val Glu Lys Trp Lys His
        115                 120                 125

His Gln Gly Lys Glu Leu Asp Leu Phe Glu Glu Phe Lys Val Leu Thr
    130                 135                 140

Ser Asp Ile Ile Ala His Thr Ala Phe Gly Ser Ser Tyr Leu Glu Gly
145                 150                 155                 160

Lys Val Ile Phe Gln Thr Leu Ser Lys Leu Ser Met Ile Leu Phe Lys
                165                 170                 175

Asn Gln Phe Lys Arg Arg Ile Pro Val Ile Ser Lys Phe Phe Arg Ser
            180                 185                 190

Lys Asp Ala Arg Glu Gly Glu Glu Leu Glu Arg Arg Leu Lys Asn Ser
        195                 200                 205

Ile Ile Ser Ile Met Glu Lys Arg Glu Lys Val Ile Ser Gly Glu
    210                 215                 220

Ala Asp Asn Tyr Gly Asn Asp Phe Leu Gly Leu Leu Leu Lys Ala Lys
225                 230                 235                 240

Asn Glu Pro Asp Gln Arg Gln Arg Ile Ser Val Asp Asp Val Val Asp
                245                 250                 255

Glu Cys Lys Thr Val Tyr Phe Ala Gly Gln Glu Thr Thr Ser Val Leu
            260                 265                 270

Leu Ala Trp Thr Ala Phe Leu Leu Ala Thr His Glu His Trp Gln Glu
        275                 280                 285

Glu Ala Arg Lys Glu Val Leu Asn Met Phe Gly Asn Lys Asn Pro Thr
    290                 295                 300

Leu Glu Gly Ile Thr Lys Leu Lys Ile Met Ser Met Ile Ile Lys Glu
305                 310                 315                 320

Ser Leu Arg Leu Tyr Pro Pro Ala Pro Met Ser Arg Lys Val Lys
                325                 330                 335

Lys Glu Val Arg Leu Gly Lys Leu Val Leu Pro Pro Asn Ile Gln Val
            340                 345                 350

Ser Ile Ser Thr Ile Ala Val His His Asp Thr Ala Ile Trp Gly Glu
```

```
                355                 360                 365
Asp Ala His Val Phe Lys Pro Glu Arg Phe Ser Glu Gly Thr Ala Lys
        370                 375                 380

Asp Ile Pro Ser Ala Ala Tyr Ile Pro Phe Gly Phe Gly Pro Arg Asn
385                 390                 395                 400

Cys Ile Gly Asn Ile Leu Ala Ile Asn Glu Thr Lys Ile Ala Leu Ser
                405                 410                 415

Met Ile Leu Gln Arg Phe Ser Phe Thr Ile Ser Pro Ala Tyr Val His
        420                 425                 430

Ala Pro Phe Gln Phe Leu Thr Ile Cys Pro Gln His Gly Val Gln Val
        435                 440                 445

Lys Leu Gln Ser Leu Leu Ser Glu Arg
        450                 455

<210> SEQ ID NO 66
<211> LENGTH: 1590
<212> TYPE: DNA
<213> ORGANISM: Siraitia grosvenorii

<400> SEQUENCE: 66
atggaagctg aatttggtgc cggtgctact atggtattat ccgttgtcgc aatcgtcttc      60
tttttcacat ttttacactt gtttgaatct ttcttttttga agccagatag attgagatct    120
aagttgagaa agcaaggtat tggtggtcca tctccttcat ttttgttggg taatttgtca     180
gaaattaaat ccatcagagc tttgtcttca caagctaaga acgcagaaga tgcctctgct     240
ggtggtggtg gtggttccgc cagtatagct catggttgga cttcaaattt gtttcctcac    300
ttagaacaat ggagaaacag atatggtcca attttcgtat actccagtgg tacaatccaa    360
atcttgtgta tcacagaaat ggaaaccgtt aaggaaatct ctttgtcaac ctccttgagt    420
ttaggtaaac ctgctcattt gtctaaggat agaggtccat gttaggtttt gggtatctta    480
gcctcttcag gtcctatttg ggttcaccaa agaaagatca tcgctccaca attgtatttg    540
gataaagtaa agggtatgac ctcattgatg gttgaaagtg caattctat gttaagatcc    600 tgggaaacta agttgaaaaa tcatggtggt caagccgaaa ttaacgtcga tggtgacttg    660
agagcattaa gtgccgatat catttctaag gcttgctttg gttcaaacta ttccgaaggt    720
gaagaaattt tcttgaagtt gagagcattg caagttgtca tgagtaaggg ttctattggt    780
atacctggtt ttagatacat accaactaaa aataacagag aaatgtggaa gttggaaaag    840
gaaatcgaat caatgatctt gaaggttgcc aacgaaagaa cacaacattc cagtcacgaa    900
caagatttgt tgcaaatgat tttggaaggt gcaagtcttt gggtgaaga caataagagt    960 atgaacatat caagagacaa gtttattgtt gacaattgta agaacatcta tttcgctggt   1020
catgaaacta cagctataac cgcatcttgg tgcttgatgt tgttagctgc acaccctgat    1080
tggcaagcaa gagccagatc tgaagtttta caatgttgcg atgacagacc aatcgatgca    1140
gacacagtca aaaatatgaa gaccttgact atggtaattc aagaaacttt gagattgtac    1200
ccacctgctg tattcgttac aagacaagca ttagaagata tcagattcaa aaacatcaca    1260
ataccaaagg gtatgaactt tcatatacca atccctatgt tgcaacaaga cttccactta    1320
tggggtcctg atgcttgttc atttgaccca caaagattct ccaatggtgt cttaggtgca    1380
tgcaaaaacc cacaagccta tgccttttt ggtgttggtc aagagtctg tgccggtcaa     1440 catttcgcta tgatcgaatt gaaagtcatc gtatcattgg ttttgtccag attcgaattt    1500
tctttgtcac cttcctacaa gcattcacca gccttcagat tagttgtcga accagaaaac    1560
```

```
ggtgtcatat tgcatgtcag aaagttgtga                                           1590
```

<210> SEQ ID NO 67
<211> LENGTH: 529
<212> TYPE: PRT
<213> ORGANISM: Siraitia grosvenorii

<400> SEQUENCE: 67

| | | | | | | | | | | | | | | |
|---|---|---|---|---|---|---|---|---|---|---|---|---|---|---|
| Met | Glu | Ala | Glu | Phe | Gly | Ala | Gly | Ala | Thr | Met | Val | Leu | Ser | Val | Val |
| 1 | | | | 5 | | | | | 10 | | | | | 15 | |
| Ala | Ile | Val | Phe | Phe | Thr | Phe | Leu | His | Leu | Phe | Glu | Ser | Phe | Phe | |
| | | | 20 | | | | | 25 | | | | | 30 | | |
| Leu | Lys | Pro | Asp | Arg | Leu | Arg | Ser | Lys | Leu | Arg | Lys | Gln | Gly | Ile | Gly |
| | | | 35 | | | | 40 | | | | | 45 | | | |
| Gly | Pro | Ser | Pro | Ser | Phe | Leu | Leu | Gly | Asn | Leu | Ser | Glu | Ile | Lys | Ser |
| | 50 | | | | | 55 | | | | | 60 | | | | |
| Ile | Arg | Ala | Leu | Ser | Ser | Gln | Ala | Lys | Asn | Ala | Glu | Asp | Ala | Ser | Ala |
| 65 | | | | | 70 | | | | | 75 | | | | | 80 |
| Gly | Gly | Gly | Gly | Ser | Ala | Ser | Ile | Ala | His | Gly | Trp | Thr | Ser | Asn | |
| | | | | 85 | | | | | 90 | | | | | 95 | |
| Leu | Phe | Pro | His | Leu | Glu | Gln | Trp | Arg | Asn | Arg | Tyr | Gly | Pro | Ile | Phe |
| | | | 100 | | | | | 105 | | | | | 110 | | |
| Val | Tyr | Ser | Ser | Gly | Thr | Ile | Gln | Ile | Leu | Cys | Ile | Thr | Glu | Met | Glu |
| | | | 115 | | | | | 120 | | | | | 125 | | |
| Thr | Val | Lys | Glu | Ile | Ser | Leu | Ser | Thr | Ser | Leu | Ser | Leu | Gly | Lys | Pro |
| | 130 | | | | | 135 | | | | | 140 | | | | |
| Ala | His | Leu | Ser | Lys | Asp | Arg | Gly | Pro | Leu | Leu | Gly | Leu | Gly | Ile | Leu |
| 145 | | | | | 150 | | | | | 155 | | | | | 160 |
| Ala | Ser | Ser | Gly | Pro | Ile | Trp | Val | His | Gln | Arg | Lys | Ile | Ile | Ala | Pro |
| | | | | 165 | | | | | 170 | | | | | 175 | |
| Gln | Leu | Tyr | Leu | Asp | Lys | Val | Lys | Gly | Met | Thr | Ser | Leu | Met | Val | Glu |
| | | | 180 | | | | | 185 | | | | | 190 | | |
| Ser | Ala | Asn | Ser | Met | Leu | Arg | Ser | Trp | Glu | Thr | Lys | Val | Glu | Asn | His |
| | | 195 | | | | | 200 | | | | | 205 | | | |
| Gly | Gly | Gln | Ala | Glu | Ile | Asn | Val | Asp | Gly | Asp | Leu | Arg | Ala | Leu | Ser |
| | 210 | | | | | 215 | | | | | 220 | | | | |
| Ala | Asp | Ile | Ile | Ser | Lys | Ala | Cys | Phe | Gly | Ser | Asn | Tyr | Ser | Glu | Gly |
| 225 | | | | | 230 | | | | | 235 | | | | | 240 |
| Glu | Glu | Ile | Phe | Leu | Lys | Leu | Arg | Ala | Leu | Gln | Val | Val | Met | Ser | Lys |
| | | | | 245 | | | | | 250 | | | | | 255 | |
| Gly | Ser | Ile | Gly | Ile | Pro | Gly | Phe | Arg | Tyr | Ile | Pro | Thr | Lys | Asn | Asn |
| | | | 260 | | | | | 265 | | | | | 270 | | |
| Arg | Glu | Met | Trp | Lys | Leu | Glu | Lys | Glu | Ile | Glu | Ser | Met | Ile | Leu | Lys |
| | | 275 | | | | | 280 | | | | | 285 | | | |
| Val | Ala | Asn | Glu | Arg | Thr | Gln | His | Ser | Ser | His | Glu | Gln | Asp | Leu | Leu |
| | 290 | | | | | 295 | | | | | 300 | | | | |
| Gln | Met | Ile | Leu | Glu | Gly | Ala | Lys | Ser | Leu | Gly | Glu | Asp | Asn | Lys | Ser |
| 305 | | | | | 310 | | | | | 315 | | | | | 320 |
| Met | Asn | Ile | Ser | Arg | Asp | Lys | Phe | Ile | Val | Asp | Asn | Cys | Lys | Asn | Ile |
| | | | | 325 | | | | | 330 | | | | | 335 | |
| Tyr | Phe | Ala | Gly | His | Glu | Thr | Thr | Ala | Ile | Thr | Ala | Ser | Trp | Cys | Leu |
| | | | 340 | | | | | 345 | | | | | 350 | | |
| Met | Leu | Leu | Ala | Ala | His | Pro | Asp | Trp | Gln | Ala | Arg | Ala | Arg | Ser | Glu |
| | | 355 | | | | | 360 | | | | | 365 | | | |

```
Val Leu Gln Cys Cys Asp Asp Arg Pro Ile Asp Ala Asp Thr Val Lys
        370                 375                 380

Asn Met Lys Thr Leu Thr Met Val Ile Gln Glu Thr Leu Arg Leu Tyr
385                 390                 395                 400

Pro Pro Ala Val Phe Val Thr Arg Gln Ala Leu Glu Asp Ile Arg Phe
                405                 410                 415

Lys Asn Ile Thr Ile Pro Lys Gly Met Asn Phe His Ile Pro Ile Pro
                420                 425                 430

Met Leu Gln Gln Asp Phe His Leu Trp Gly Pro Asp Ala Cys Ser Phe
            435                 440                 445

Asp Pro Gln Arg Phe Ser Asn Gly Val Leu Gly Ala Cys Lys Asn Pro
        450                 455                 460

Gln Ala Tyr Met Pro Phe Gly Val Gly Pro Arg Val Cys Ala Gly Gln
465                 470                 475                 480

His Phe Ala Met Ile Glu Leu Lys Val Ile Val Ser Leu Val Leu Ser
                485                 490                 495

Arg Phe Glu Phe Ser Leu Ser Pro Ser Tyr Lys His Ser Pro Ala Phe
                500                 505                 510

Arg Leu Val Val Glu Pro Glu Asn Gly Val Ile Leu His Val Arg Lys
            515                 520                 525

Leu

<210> SEQ ID NO 68
<211> LENGTH: 1554
<212> TYPE: DNA
<213> ORGANISM: Siraitia grosvenorii

<400> SEQUENCE: 68
atggaagtgg atatcaatat cttcaccgtc ttttccttcg tattatgcac agtcttcctc      60
ttctttctat ccttcttgat cctcctcctc ctccgaacgc tcgccggaaa atccataacg     120
agctccgagt acacgccagt gtacggcacc gtctacggtc aggctttcta tttcaacaac     180
ctgtacgatc atctaacgga ggtggccaag agacatcgaa ccttccggct gcttgcgccg     240
gcatacagcg agatatacac gaccgatccg agaaacatcg agcatatgtt gaagacgaaa     300
ttcgataagt attcgaaagg aagcaaggat caagaaatcg ttggggatct gtttggagag     360
gggatatttg cagtcgatgg agataagtgg aagcagcaga ggaagctggc tagctatgaa     420
ttctcgacga ggattcttag ggattttagc tgctcggttt cagacgaag tgctgctaaa      480 cttgttggag ttgtttcgga ttttccagc atgggtcggg tttttgatat ccaggatttg       540
ctaatgcggt gcgctttgga ctccattttc aaagtggggt cgggggttga tttgaattgc     600
ttggaggaat caagcaaaga agggagcgat ttcatgaaag ccttcgatga ttctagcgct     660 cagattttt ggcgctatat cgatcccttc tggaaattga agagattgct taacatcggt      720
tccgaagctt cgtttaggaa caacataaaa accatagatg cttttgtgca ccagttgatc     780
agagacaaga gaaaattgct tcagcaaccg aatcacaaga atgacaaaga ggacatactt     840
tggaggtttc tgatggaaag tgagaaggat ccaacaagaa tgaatgatca atatctaagg     900
gatatagtcc tcaatttcat gttggctggc aaagattcaa gtgaggaac tctgtcctgg     960 ttcttctaca tgctatgcaa gaacccttta atacaggaaa agttgcaga agaagtgagg    1020 caaattgttg cgtttgaagg ggaagaagtt gacatcaatt tgttcataca aaacttaact    1080
gattcagctc ttgacaaaat gcattatctt catgcagcat tgaccgagac tctgaggcta    1140
```

```
tatcctgcag tcccttgga tggaaggact gcagaaatag atgacattct tcctgatggc    1200
tataaactaa gaaaagggga tggagtatac tacatggcct attccatggg caggatgtcc    1260 tcccttggg gagaagatgc tgaagatttt aaacccgaaa gatggcttga agtggaact     1320 tttcaacccg aatcacctt caaattcatc gcttttcatg cgggtcctcg aatgtgtttg    1380
ggaaaagagt ttgcttatcg acaaatgaag atagtatctg ctgctttgct tcaatttttt    1440
cgattcaaag tagctgatac aacgaggaat gtgacttata ggatcatgct tacccttcac    1500
attgatggag gtctccctct tcttgcaatt ccgagaatta gaaaatttac ctaa          1554
```

<210> SEQ ID NO 69
<211> LENGTH: 517
<212> TYPE: PRT
<213> ORGANISM: Siraitia grosvenorii

<400> SEQUENCE: 69

```
Met Glu Val Asp Ile Asn Ile Phe Thr Val Phe Ser Phe Val Leu Cys
1               5                   10                  15

Thr Val Phe Leu Phe Phe Leu Ser Phe Leu Ile Leu Leu Leu Leu Arg
            20                  25                  30

Thr Leu Ala Gly Lys Ser Ile Thr Ser Ser Glu Tyr Thr Pro Val Tyr
        35                  40                  45

Gly Thr Val Tyr Gly Gln Ala Phe Tyr Phe Asn Asn Leu Tyr Asp His
    50                  55                  60

Leu Thr Glu Val Ala Lys Arg His Arg Thr Phe Arg Leu Leu Ala Pro
65                  70                  75                  80

Ala Tyr Ser Glu Ile Tyr Thr Thr Asp Pro Arg Asn Ile Glu His Met
                85                  90                  95

Leu Lys Thr Lys Phe Asp Lys Tyr Ser Lys Gly Ser Lys Asp Gln Glu
            100                 105                 110

Ile Val Gly Asp Leu Phe Gly Glu Gly Ile Phe Ala Val Asp Gly Asp
        115                 120                 125

Lys Trp Lys Gln Gln Arg Lys Leu Ala Ser Tyr Glu Phe Ser Thr Arg
    130                 135                 140

Ile Leu Arg Asp Phe Ser Cys Ser Val Phe Arg Arg Ser Ala Ala Lys
145                 150                 155                 160

Leu Val Gly Val Val Ser Glu Phe Ser Ser Met Gly Arg Val Phe Asp
                165                 170                 175

Ile Gln Asp Leu Leu Met Arg Cys Ala Leu Asp Ser Ile Phe Lys Val
            180                 185                 190

Gly Phe Gly Val Asp Leu Asn Cys Leu Glu Glu Ser Ser Lys Glu Gly
        195                 200                 205

Ser Asp Phe Met Lys Ala Phe Asp Asp Ser Ser Ala Gln Ile Phe Trp
    210                 215                 220

Arg Tyr Ile Asp Pro Phe Trp Lys Leu Lys Arg Leu Leu Asn Ile Gly
225                 230                 235                 240

Ser Glu Ala Ser Phe Arg Asn Asn Ile Lys Thr Ile Asp Ala Phe Val
                245                 250                 255

His Gln Leu Ile Arg Asp Lys Arg Lys Leu Leu Gln Gln Pro Asn His
            260                 265                 270

Lys Asn Asp Lys Glu Asp Ile Leu Trp Arg Phe Leu Met Glu Ser Glu
        275                 280                 285

Lys Asp Pro Thr Arg Met Asn Asp Gln Tyr Leu Arg Asp Ile Val Leu
    290                 295                 300
```

```
Asn Phe Met Leu Ala Gly Lys Asp Ser Ser Gly Gly Thr Leu Ser Trp
305                 310                 315                 320

Phe Phe Tyr Met Leu Cys Lys Asn Pro Leu Ile Gln Glu Lys Val Ala
                325                 330                 335

Glu Glu Val Arg Gln Ile Val Ala Phe Glu Gly Glu Val Asp Ile
            340                 345                 350

Asn Leu Phe Ile Gln Asn Leu Thr Asp Ser Ala Leu Asp Lys Met His
                355                 360                 365

Tyr Leu His Ala Ala Leu Thr Glu Thr Leu Arg Leu Tyr Pro Ala Val
            370                 375                 380

Pro Leu Asp Gly Arg Thr Ala Glu Ile Asp Asp Ile Leu Pro Asp Gly
385                 390                 395                 400

Tyr Lys Leu Arg Lys Gly Asp Gly Val Tyr Tyr Met Ala Tyr Ser Met
                405                 410                 415

Gly Arg Met Ser Ser Leu Trp Gly Glu Asp Ala Glu Asp Phe Lys Pro
            420                 425                 430

Glu Arg Trp Leu Glu Ser Gly Thr Phe Gln Pro Glu Ser Pro Phe Lys
                435                 440                 445

Phe Ile Ala Phe His Ala Gly Pro Arg Met Cys Leu Gly Lys Glu Phe
450                 455                 460

Ala Tyr Arg Gln Met Lys Ile Val Ser Ala Ala Leu Leu Gln Phe Phe
465                 470                 475                 480

Arg Phe Lys Val Ala Asp Thr Thr Arg Asn Val Thr Tyr Arg Ile Met
                485                 490                 495

Leu Thr Leu His Ile Asp Gly Gly Leu Pro Leu Leu Ala Ile Pro Arg
            500                 505                 510

Ile Arg Lys Phe Thr
        515
```

<210> SEQ ID NO 70
<211> LENGTH: 1686
<212> TYPE: DNA
<213> ORGANISM: Siraitia grosvenorii

<400> SEQUENCE: 70

```
ttggatagtg gagttaaaag agtgaaacgg ctagttgaag agaaacggcg agcagaattg      60
tctgcccgga ttgcctctgg agaattcaca gtcgaaaaag ctggttttcc atctgtattg     120
aggagtggct tatcaaagat gggtgttccc agtgagattc tggacatatt atttggtttc     180
gttgatgctc aagaagaata cccaagatt cccgaagcaa aggatcagt aaatgcaatt      240
cgtagtgagg ccttcttcat acctctctat gagctttatc tcacatatgg tggaatattt     300
aggttgactt tgggccaaa gtcattcttg atagtttctg atccttccat tgctaaacat     360
atactgaagg ataatccgag gaattattct aagggtatct tagctgaaat tctagagttt     420
gtcatgggga agggacttat accagctgac gagaagatat ggcgtgtacg aaggcgggct     480
atagtcccat ctttgcatct gaagtatgta ggtgctatga ttaatctttt tggagaagct     540
gcagataggc tttgcaagaa gctagatgct gcagcatctg atggggttga tgtggaaatg     600
gagtccctgt tctcccgttt gactttagat atcattggca aggcagtttt taactatgac     660
tttgattcac ttacaaatga cactggcata gttgaggctg tttacactgt gctaagagaa     720
gcagaggatc gcagtgttgc accaattcca gtatgggaaa ttccaatttg aaggatatt     780
tcaccacggc aaaaaaaggt ctctaaagcc ctcaaattga tcaacgacac cctcgatcaa     840
ctaattgcta tatgcaagag gatggttgat gaggaggagc tgcagtttca tgaggaatac     900
```

```
atgaatgagc aagatccaag catccttcat ttccttttgg catcaggaga tgatgtttca      960
agcaagcagc ttcgtgatga cttgatgact atgcttatag ctgggcatga aacatctgct     1020
gcagttttaa catggacctt ttatcttctt tccaaggagc cgaggatcat gtccaagctc     1080
caggaggagg ttgattcagt ccttggggat cggtttccaa ctattgaaga tatgaagaac     1140
ctcaaatatg ccacacgaat aattaacgaa tccttgaggc tttacccaca gccaccagtt     1200
ttaatacgtc gatctcttga caatgatatg ctcgggaagt accccattaa aaagggtgag     1260
gacatattca tttctgtttg gaacttgcat cgcagtccaa aactctggga tgatgcggat     1320
aaatttaatc ctgaaaggtg gcctctggat ggacccaatc caaatgagac aaatcaaaat     1380
ttcagatatt tacctttggg tggcggacca cggaaatgtg tgggagacat gtttgcttcg     1440
tacgagactg ttgtagcact tgcaatgctt gttcggcgat ttgacttcca aatggcactt     1500
ggagcacctc ctgtaaaaat gacaactgga gctacaattc acacaacaga tggattgaaa     1560
atgacagtta cacgaagaat gagacctcca atcatacccca cattagagat gcctgcagtg     1620
gtcgttgact cgtctgtcgt ggactcgtcc gtcgccattt tgaaagaaga aacacaaatt     1680
ggttag                                                                1686
```

<210> SEQ ID NO 71
<211> LENGTH: 515
<212> TYPE: PRT
<213> ORGANISM: Siraitia grosvenorii

<400> SEQUENCE: 71

```
Met Gly Val Pro Ser Glu Ile Leu Asp Ile Leu Phe Gly Phe Val Asp
1               5                   10                  15

Ala Gln Glu Glu Tyr Pro Lys Ile Pro Glu Ala Lys Gly Ser Val Asn
            20                  25                  30

Ala Ile Arg Ser Glu Ala Phe Phe Ile Pro Leu Tyr Glu Leu Tyr Leu
        35                  40                  45

Thr Tyr Gly Gly Ile Phe Arg Leu Thr Phe Gly Pro Lys Ser Phe Leu
    50                  55                  60

Ile Val Ser Asp Pro Ser Ile Ala Lys His Ile Leu Lys Asp Asn Pro
65                  70                  75                  80

Arg Asn Tyr Ser Lys Gly Ile Leu Ala Glu Ile Leu Glu Phe Val Met
                85                  90                  95

Gly Lys Gly Leu Ile Pro Ala Asp Glu Lys Ile Trp Arg Val Arg Arg
            100                 105                 110

Arg Ala Ile Val Pro Ser Leu His Leu Lys Tyr Val Gly Ala Met Ile
        115                 120                 125

Asn Leu Phe Gly Glu Ala Ala Asp Arg Leu Cys Lys Lys Leu Asp Ala
    130                 135                 140

Ala Ala Ser Asp Gly Val Asp Val Glu Met Glu Ser Leu Phe Ser Arg
145                 150                 155                 160

Leu Thr Leu Asp Ile Ile Gly Lys Ala Val Phe Asn Tyr Asp Phe Asp
                165                 170                 175

Ser Leu Thr Asn Asp Thr Gly Ile Val Glu Ala Val Tyr Thr Val Leu
            180                 185                 190

Arg Glu Ala Glu Asp Arg Ser Val Ala Pro Ile Pro Val Trp Glu Ile
        195                 200                 205

Pro Ile Trp Lys Asp Ile Ser Pro Arg Gln Lys Lys Val Ser Lys Ala
    210                 215                 220
```

Leu Lys Leu Ile Asn Asp Thr Leu Asp Gln Leu Ile Ala Ile Cys Lys
225                 230                 235                 240

Arg Met Val Asp Glu Glu Leu Gln Phe His Glu Glu Tyr Met Asn
            245                 250                 255

Glu Gln Asp Pro Ser Ile Leu His Phe Leu Ala Ser Gly Asp Asp
            260                 265                 270

Val Ser Ser Lys Gln Leu Arg Asp Asp Leu Met Thr Met Leu Ile Ala
        275                 280                 285

Gly His Glu Thr Ser Ala Ala Val Leu Thr Trp Thr Phe Tyr Leu Leu
        290                 295                 300

Ser Lys Glu Pro Arg Ile Met Ser Lys Leu Gln Glu Glu Val Asp Ser
305                 310                 315                 320

Val Leu Gly Asp Arg Phe Pro Thr Ile Glu Asp Met Lys Asn Leu Lys
            325                 330                 335

Tyr Ala Thr Arg Ile Ile Asn Glu Ser Leu Arg Leu Tyr Pro Gln Pro
            340                 345                 350

Pro Val Leu Ile Arg Arg Ser Leu Asp Asn Asp Met Leu Gly Lys Tyr
        355                 360                 365

Pro Ile Lys Lys Gly Glu Asp Ile Phe Ile Ser Val Trp Asn Leu His
370                 375                 380

Arg Ser Pro Lys Leu Trp Asp Ala Asp Lys Phe Asn Pro Glu Arg
385                 390                 395                 400

Trp Pro Leu Asp Gly Pro Asn Pro Asn Glu Thr Asn Gln Asn Phe Arg
            405                 410                 415

Tyr Leu Pro Phe Gly Gly Gly Pro Arg Lys Cys Val Gly Asp Met Phe
        420                 425                 430

Ala Ser Tyr Glu Thr Val Val Ala Leu Ala Met Leu Val Arg Arg Phe
        435                 440                 445

Asp Phe Gln Met Ala Leu Gly Ala Pro Pro Val Lys Met Thr Thr Gly
        450                 455                 460

Ala Thr Ile His Thr Thr Asp Gly Leu Lys Met Thr Val Thr Arg Arg
465                 470                 475                 480

Met Arg Pro Pro Ile Ile Pro Thr Leu Glu Met Pro Ala Val Val Val
            485                 490                 495

Asp Ser Ser Val Val Asp Ser Ser Val Ala Ile Leu Lys Glu Glu Thr
            500                 505                 510

Gln Ile Gly
    515

<210> SEQ ID NO 72
<211> LENGTH: 1299
<212> TYPE: DNA
<213> ORGANISM: Siraitia grosvenorii

<400> SEQUENCE: 72
cagttcctct cctggtcctc ccagtttggc aagaggttca tcttctggaa tgggatcgag      60
cccagaatgt gcctcaccga gaccgatttg atcaaagagc ttctctctaa gtacagcgcc     120
gtctccggta agtcatggct tcagcaacag ggctccaagc acttcatcgg ccgcggtctc     180
ttaatggcca acggccaaaa ctggtaccac cagcgtcaca tcgtcgcgcc ggccttcatg     240
ggagacagac tcaagagtta cgccgggtac atggtggaat gcacaaagga gatgcttcag     300
tcaattgaaa acgaggtcaa ctcggggcga tccgagttcg aaatcggtga gtatatgacc     360
agactcaccg ccgatataat atcacgaacc gagttcgaaa gcagctacga aagggaaag     420

```
caaatttttcc atttgctcac cgttttacag catctctgcg ctcaggcgag ccgccacctc    480
tgccttcctg gaagccggtt ttttccgagt aaatacaaca gagagataaa ggcattgaag    540
acgaaggtgg aggggttgtt aatggagata atacagagca gaagagactg tgtggaggtg    600
gggaggagca gttcgtatgg aaatgatctg ttgggaatgt tgctgaatga gatgcagaag    660
aagaaagatg ggaatgggtt gagcttgaat ttgcagatta aatggatga atgcaagacc    720 ttcttcttcg ccggccatga aaccactgct cttttgctca cttggactgt aatgttattg    780
gccagcaacc cttcttggca acacaaggtt cgagccgaag ttatggccgt ctgcaatgga    840
ggaactctct ctcttgaaca tctctccaag ctctctctgt tgagtatggt gataaatgaa    900
tcgttgaggc tatacccgcc agcaagtatt cttccaagaa tggcatttga agatataaag    960
ctgggagatc ttgagatccc aaaagggctg tcgatatgga tcccagtgct tgcaattcac   1020
cacagtgaag agctatgggg caaagatgca aatgagttca acccagaaag atttgcaaat   1080
tcaaaagcct tcacttcggg gagattcatt ccctttgctt ctggcccttcg caactgcgtt   1140 ggccaatcat ttgctctcat ggaaaccaag atcattttgg ctatgctcat ctccaagttt   1200
tccttcacca tctctgacaa ttatcgccat gcaccccgtgg tcgtcctcac tataaaaccc   1260 aaatacgag tccaagtttg cttgaagcct ttcaattaa                            1299
```

<210> SEQ ID NO 73
<211> LENGTH: 410
<212> TYPE: PRT
<213> ORGANISM: Siraitia grosvenorii

<400> SEQUENCE: 73

```
Met Cys Leu Thr Glu Thr Asp Leu Ile Lys Glu Leu Leu Ser Lys Tyr
1               5                   10                  15

Ser Ala Val Ser Gly Lys Ser Trp Leu Gln Gln Gly Ser Lys His
            20                  25                  30

Phe Ile Gly Arg Gly Leu Leu Met Ala Asn Gly Gln Asn Trp Tyr His
        35                  40                  45

Gln Arg His Ile Val Ala Pro Ala Phe Met Gly Asp Arg Leu Lys Ser
    50                  55                  60

Tyr Ala Gly Tyr Met Val Glu Cys Thr Lys Glu Met Leu Gln Ser Ile
65                  70                  75                  80

Glu Asn Glu Val Asn Ser Gly Arg Ser Glu Phe Glu Ile Gly Glu Tyr
                85                  90                  95

Met Thr Arg Leu Thr Ala Asp Ile Ile Ser Arg Thr Glu Phe Glu Ser
            100                 105                 110

Ser Tyr Glu Lys Gly Lys Gln Ile Phe His Leu Leu Thr Val Leu Gln
        115                 120                 125

His Leu Cys Ala Gln Ala Ser Arg His Leu Cys Leu Pro Gly Ser Arg
    130                 135                 140

Phe Phe Pro Ser Lys Tyr Asn Arg Glu Ile Lys Ala Leu Lys Thr Lys
145                 150                 155                 160

Val Glu Gly Leu Leu Met Glu Ile Ile Gln Ser Arg Arg Asp Cys Val
                165                 170                 175

Glu Val Gly Arg Ser Ser Ser Tyr Gly Asn Asp Leu Leu Gly Met Leu
            180                 185                 190

Leu Asn Glu Met Gln Lys Lys Lys Asp Gly Asn Gly Leu Ser Leu Asn
        195                 200                 205

Leu Gln Ile Ile Met Asp Glu Cys Lys Thr Phe Phe Phe Ala Gly His
    210                 215                 220
```

```
Glu Thr Thr Ala Leu Leu Leu Thr Trp Thr Val Met Leu Leu Ala Ser
225                 230                 235                 240

Asn Pro Ser Trp Gln His Lys Val Arg Ala Glu Val Met Ala Val Cys
                245                 250                 255

Asn Gly Gly Thr Leu Ser Leu Glu His Leu Ser Lys Leu Ser Leu Leu
            260                 265                 270

Ser Met Val Ile Asn Glu Ser Leu Arg Leu Tyr Pro Pro Ala Ser Ile
            275                 280                 285

Leu Pro Arg Met Ala Phe Glu Asp Ile Lys Leu Gly Asp Leu Glu Ile
            290                 295                 300

Pro Lys Gly Leu Ser Ile Trp Ile Pro Val Leu Ala Ile His His Ser
305                 310                 315                 320

Glu Glu Leu Trp Gly Lys Asp Ala Asn Glu Phe Asn Pro Glu Arg Phe
                325                 330                 335

Ala Asn Ser Lys Ala Phe Thr Ser Gly Arg Phe Ile Pro Phe Ala Ser
            340                 345                 350

Gly Pro Arg Asn Cys Val Gly Gln Ser Phe Ala Leu Met Glu Thr Lys
            355                 360                 365

Ile Ile Leu Ala Met Leu Ile Ser Lys Phe Ser Phe Thr Ile Ser Asp
370                 375                 380

Asn Tyr Arg His Ala Pro Val Val Leu Thr Ile Lys Pro Lys Tyr
385                 390                 395                 400

Gly Val Gln Val Cys Leu Lys Pro Phe Asn
                405                 410

<210> SEQ ID NO 74
<211> LENGTH: 1506
<212> TYPE: DNA
<213> ORGANISM: Siraitia grosvenorii

<400> SEQUENCE: 74
atggaagaca ccttcctact ctatccttcc ctctctcttc tctttcttct ttttgctttc      60
aagctcatcc gtcgatccgg aggagttcgc aggaacttac cgccgagtcc gccctctctt     120
ccggttatcg gccacctcca tctcttgaaa aagccactcc accggacttt ccagaaactt     180
tccgccaaat atggtcctgt tatgtccctc cgcctcgggt ctcgcctcgc agtcattgta     240
tcgtcgtcgt cggcggtgga cgagtgtttc actaaaaacg acgtcgtgct cgccaaccgt     300
cctcgtttgc taattggcaa acacctcggc tacaactaca ctaccatggt tgggctccc      360 tacggcgacc actggcgtag cctccgccgc atcggtgccc tcgaaatctt ctcttcatct     420
cgcctcaaca aattcgccga catccgaagg gatgaagtag agggattgct cgcaaactc      480 tcacgcaatt cgctccatca attctcgaaa gtggaagttc aatcggcctt gtcggagctg     540
acgttcaaca tctcgatgag aatggcggca gggaaacggt attacggaga tgacgtgacg     600
gacgaggaag aggcgagaaa gttcagagag ttaattaaac agatagtggc gctgggcgga     660
gtatcaaatc cagggatt cgtcccgatt ctgaattgga ttccgaacgg tttcgagagg     720
aagttgatcg agtgtgggaa gaagacggat gcgttcttgc aggggctgat cgaggaccac     780
cggagaaaga aggaagaggg taggaacacg atgatcgatc acctgctctc tctgcaagaa     840
tcggagcctg ctcactacgg agaccaaata atcaaggat ttatactggt gttactgacg     900
gcggggaccg atacatcggc cgtgacaatg gagtgggcgc tatctcatct cctgaacaat     960
cctgaagtgc taaagaaggc aagagatgag gtcgacactg aaattggaca agaacgactt    1020
```

```
gtcgaagaat cagacgtagt atctaagtta ccctatcttc aagggatcat ctccgagact    1080
ctccggctga atcccgccgc tccgatgttg ttgccccatt acgcctcgga cgactgcacg    1140
atatgtggat acgacgtgcc acgtgacaca atcgtaatgg tcaatgcatg gccatacat    1200 agggatccaa acgaatggga ggagcccacg tgtttcagac cagaacgata tgaaaagtcg    1260
tcgtcggaag cggaggtaca caagtcggtg agtttcgggg tgggaaggcg agcttgtcct    1320
gggtctggca tggcgcagag ggtgatgggc ttgactttgg cggcactggt tcagtgcttc    1380
gagtgggaga gagttggaga agaagaagtg gacatgaacg aaggctcagg tgccacaatg    1440
cccaagatgg tgccattgga ggccatgtgc agagctcgtc ccatcgtcca caaccttctt    1500
tactga                                                               1506
```

<210> SEQ ID NO 75
<211> LENGTH: 501
<212> TYPE: PRT
<213> ORGANISM: Siraitia grosvenorii

<400> SEQUENCE: 75

```
Met Glu Asp Thr Phe Leu Leu Tyr Pro Ser Leu Ser Leu Phe Leu
1               5                   10                  15

Leu Phe Ala Phe Lys Leu Ile Arg Arg Ser Gly Gly Val Arg Asn
                20                  25                  30

Leu Pro Pro Ser Pro Pro Ser Leu Pro Val Ile Gly His Leu His Leu
                35                  40                      45

Leu Lys Lys Pro Leu His Arg Thr Phe Gln Lys Leu Ser Ala Lys Tyr
    50                      55                  60

Gly Pro Val Met Ser Leu Arg Leu Gly Ser Arg Leu Ala Val Ile Val
65                  70                      75                  80

Ser Ser Ser Ser Ala Val Asp Glu Cys Phe Thr Lys Asn Asp Val Val
                    85                  90                  95

Leu Ala Asn Arg Pro Arg Leu Leu Ile Gly Lys His Leu Gly Tyr Asn
                100                 105                 110

Tyr Thr Thr Met Val Gly Ala Pro Tyr Gly Asp His Trp Arg Ser Leu
                115                 120                 125

Arg Arg Ile Gly Ala Leu Glu Ile Phe Ser Ser Ser Arg Leu Asn Lys
        130                 135                 140

Phe Ala Asp Ile Arg Arg Asp Glu Val Glu Gly Leu Leu Arg Lys Leu
145                 150                 155                 160

Ser Arg Asn Ser Leu His Gln Phe Ser Lys Val Glu Val Gln Ser Ala
                165                 170                 175

Leu Ser Glu Leu Thr Phe Asn Ile Ser Met Arg Met Ala Ala Gly Lys
                180                 185                 190

Arg Tyr Tyr Gly Asp Asp Val Thr Asp Glu Glu Ala Arg Lys Phe
        195                 200                 205

Arg Glu Leu Ile Lys Gln Ile Val Ala Leu Gly Val Ser Asn Pro
    210                 215                 220

Gly Asp Phe Val Pro Ile Leu Asn Trp Ile Pro Asn Gly Phe Glu Arg
225                 230                 235                 240

Lys Leu Ile Glu Cys Gly Lys Lys Thr Asp Ala Phe Leu Gln Gly Leu
                245                 250                 255

Ile Glu Asp His Arg Arg Lys Glu Glu Gly Arg Asn Thr Met Ile
            260                 265                 270

Asp His Leu Leu Ser Leu Gln Glu Ser Glu Pro Ala His Tyr Gly Asp
        275                 280                 285
```

```
Gln Ile Ile Lys Gly Phe Ile Leu Val Leu Thr Ala Gly Thr Asp
            290                 295                 300
Thr Ser Ala Val Thr Met Glu Trp Ala Leu Ser His Leu Leu Asn Asn
305                 310                 315                 320
Pro Glu Val Leu Lys Lys Ala Arg Asp Glu Val Asp Thr Glu Ile Gly
                325                 330                 335
Gln Glu Arg Leu Val Glu Glu Ser Asp Val Val Ser Lys Leu Pro Tyr
                340                 345                 350
Leu Gln Gly Ile Ile Ser Glu Thr Leu Arg Leu Asn Pro Ala Ala Pro
            355                 360                 365
Met Leu Leu Pro His Tyr Ala Ser Asp Asp Cys Thr Ile Cys Gly Tyr
370                 375                 380
Asp Val Pro Arg Asp Thr Ile Val Met Val Asn Ala Trp Ala Ile His
385                 390                 395                 400
Arg Asp Pro Asn Glu Trp Glu Pro Thr Cys Phe Arg Pro Glu Arg
                405                 410                 415
Tyr Glu Lys Ser Ser Ser Glu Ala Glu Val His Lys Ser Val Ser Phe
                420                 425                 430
Gly Val Gly Arg Arg Ala Cys Pro Gly Ser Gly Met Ala Gln Arg Val
            435                 440                 445
Met Gly Leu Thr Leu Ala Ala Leu Val Gln Cys Phe Glu Trp Glu Arg
450                 455                 460
Val Gly Glu Glu Val Asp Met Asn Glu Gly Ser Gly Ala Thr Met
465                 470                 475                 480
Pro Lys Met Val Pro Leu Glu Ala Met Cys Arg Ala Arg Pro Ile Val
                485                 490                 495
His Asn Leu Leu Tyr
            500

<210> SEQ ID NO 76
<211> LENGTH: 496
<212> TYPE: PRT
<213> ORGANISM: Arabidopsis thaliana

<400> SEQUENCE: 76

Met Ala Thr Glu Lys Thr His Gln Phe His Pro Ser Leu His Phe Val
1               5                   10                  15
Leu Phe Pro Phe Met Ala Gln Gly His Met Ile Pro Met Ile Asp Ile
                20                  25                  30
Ala Arg Leu Leu Ala Gln Arg Gly Val Thr Ile Thr Ile Val Thr Thr
            35                  40                  45
Pro His Asn Ala Ala Arg Phe Lys Asn Val Leu Asn Arg Ala Ile Glu
        50                  55                  60
Ser Gly Leu Ala Ile Asn Ile Leu His Val Lys Phe Pro Tyr Gln Glu
65                  70                  75                  80
Phe Gly Leu Pro Glu Gly Lys Glu Asn Ile Asp Ser Leu Asp Ser Thr
                85                  90                  95
Glu Leu Met Val Pro Phe Phe Lys Ala Val Asn Leu Leu Glu Asp Pro
                100                 105                 110
Val Met Lys Leu Met Glu Glu Met Lys Pro Arg Pro Ser Cys Leu Ile
                115                 120                 125
Ser Asp Trp Cys Leu Pro Tyr Thr Ser Ile Ile Ala Lys Asn Phe Asn
        130                 135                 140
Ile Pro Lys Ile Val Phe His Gly Met Gly Cys Phe Asn Leu Leu Cys
```

```
            145                 150                 155                 160
Met His Val Leu Arg Arg Asn Leu Glu Ile Leu Glu Asn Val Lys Ser
                165                 170                 175

Asp Glu Glu Tyr Phe Leu Val Pro Ser Phe Pro Asp Arg Val Glu Phe
            180                 185                 190

Thr Lys Leu Gln Leu Pro Val Lys Ala Asn Ala Ser Gly Asp Trp Lys
        195                 200                 205

Glu Ile Met Asp Glu Met Val Lys Ala Glu Tyr Thr Ser Tyr Gly Val
    210                 215                 220

Ile Val Asn Thr Phe Gln Glu Leu Glu Pro Pro Tyr Val Lys Asp Tyr
225                 230                 235                 240

Lys Glu Ala Met Asp Gly Lys Val Trp Ser Ile Gly Pro Val Ser Leu
                245                 250                 255

Cys Asn Lys Ala Gly Ala Asp Lys Ala Glu Arg Gly Ser Lys Ala Ala
            260                 265                 270

Ile Asp Gln Asp Glu Cys Leu Gln Trp Leu Asp Ser Lys Glu Glu Gly
        275                 280                 285

Ser Val Leu Tyr Val Cys Leu Gly Ser Ile Cys Asn Leu Pro Leu Ser
    290                 295                 300

Gln Leu Lys Glu Leu Gly Leu Gly Leu Glu Glu Ser Arg Arg Ser Phe
305                 310                 315                 320

Ile Trp Val Ile Arg Gly Ser Glu Lys Tyr Lys Glu Leu Phe Glu Trp
                325                 330                 335

Met Leu Glu Ser Gly Phe Glu Glu Arg Ile Lys Glu Arg Gly Leu Leu
            340                 345                 350

Ile Lys Gly Trp Ala Pro Gln Val Leu Ile Leu Ser His Pro Ser Val
        355                 360                 365

Gly Gly Phe Leu Thr His Cys Gly Trp Asn Ser Thr Leu Glu Gly Ile
    370                 375                 380

Thr Ser Gly Ile Pro Leu Ile Thr Trp Pro Leu Phe Gly Asp Gln Phe
385                 390                 395                 400

Cys Asn Gln Lys Leu Val Val Gln Val Leu Lys Ala Gly Val Ser Ala
                405                 410                 415

Gly Val Glu Glu Val Met Lys Trp Gly Glu Glu Asp Lys Ile Gly Val
            420                 425                 430

Leu Val Asp Lys Glu Gly Val Lys Lys Ala Val Glu Glu Leu Met Gly
        435                 440                 445

Asp Ser Asp Asp Ala Lys Glu Arg Arg Arg Val Lys Glu Leu Gly
    450                 455                 460

Glu Leu Ala His Lys Ala Val Glu Lys Gly Gly Ser Ser His Ser Asn
465                 470                 475                 480

Ile Thr Leu Leu Leu Gln Asp Ile Met Gln Leu Ala Gln Phe Lys Asn
                485                 490                 495

<210> SEQ ID NO 77
<211> LENGTH: 495
<212> TYPE: PRT
<213> ORGANISM: Arabidopsis thaliana

<400> SEQUENCE: 77

Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
            20                  25                  30
```

-continued

Leu Leu Ala Gln Arg Gly Val Ile Thr Ile Val Thr Pro His
         35                  40              45

Asn Ala Ala Arg Phe Lys Asn Val Leu Asn Arg Ala Ile Glu Ser Gly
 50                  55                  60

Leu Pro Ile Asn Leu Val Gln Val Lys Phe Pro Tyr Leu Glu Ala Gly
 65                  70                  75                  80

Leu Gln Glu Gly Gln Glu Asn Ile Asp Ser Leu Asp Thr Met Glu Arg
                 85                  90                  95

Met Ile Pro Phe Phe Lys Ala Val Asn Phe Leu Glu Glu Pro Val Gln
                100                 105                 110

Lys Leu Ile Glu Glu Met Asn Pro Arg Pro Ser Cys Leu Ile Ser Asp
         115                 120                 125

Phe Cys Leu Pro Tyr Thr Ser Lys Ile Ala Lys Lys Phe Asn Ile Pro
 130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
                180                 185                 190

Thr Gln Val Pro Val Glu Thr Tyr Val Pro Ala Gly Asp Trp Lys Asp
         195                 200                 205

Ile Phe Asp Gly Met Val Glu Ala Asn Glu Thr Ser Tyr Gly Val Ile
 210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
                260                 265                 270

Asp Gln Asp Glu Cys Leu Lys Trp Leu Asp Ser Lys Lys His Gly Ser
         275                 280                 285

Val Leu Tyr Val Cys Leu Gly Ser Ile Cys Asn Leu Pro Leu Ser Gln
 290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
                340                 345                 350

Lys Gly Trp Ser Pro Gln Met Leu Ile Leu Ser His Pro Ser Val Gly
         355                 360                 365

Gly Phe Leu Thr His Cys Gly Trp Asn Ser Thr Leu Glu Gly Ile Thr
 370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Lys Ile Gly Val Leu
                420                 425                 430

Val Asp Lys Glu Gly Val Lys Lys Ala Val Glu Glu Leu Met Gly Glu
         435                 440                 445

Ser Asp Asp Ala Lys Glu Arg Arg Arg Arg Ala Lys Glu Leu Gly Asp

```
              450                 455                 460
Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495

<210> SEQ ID NO 78
<211> LENGTH: 495
<212> TYPE: PRT
<213> ORGANISM: Arabidopsis thaliana

<400> SEQUENCE: 78

Met Ala Phe Glu Lys Asn Asn Glu Pro Phe Pro Leu His Phe Val Leu
1               5                   10                  15

Phe Pro Phe Met Ala Gln Gly His Met Ile Pro Met Val Asp Ile Ala
                20                  25                  30

Arg Leu Leu Ala Gln Arg Gly Val Leu Ile Thr Ile Val Thr Thr Pro
            35                  40                  45

His Asn Ala Ala Arg Phe Lys Asn Val Leu Asn Arg Ala Ile Glu Ser
        50                  55                  60

Gly Leu Pro Ile Asn Leu Val Gln Val Lys Phe Pro Tyr Gln Glu Ala
65                  70                  75                  80

Gly Leu Gln Glu Gly Gln Glu Asn Met Asp Leu Leu Thr Thr Met Glu
                85                  90                  95

Gln Ile Thr Ser Phe Phe Lys Ala Val Asn Leu Leu Lys Glu Pro Val
            100                 105                 110

Gln Asn Leu Ile Glu Glu Met Ser Pro Arg Pro Ser Cys Leu Ile Ser
        115                 120                 125

Asp Met Cys Leu Ser Tyr Thr Ser Glu Ile Ala Lys Lys Phe Lys Ile
130                 135                 140

Pro Lys Ile Leu Phe His Gly Met Gly Cys Phe Cys Leu Leu Cys Val
145                 150                 155                 160

Asn Val Leu Arg Lys Asn Arg Glu Ile Leu Asp Asn Leu Lys Ser Asp
                165                 170                 175

Lys Glu Tyr Phe Ile Val Pro Tyr Phe Pro Asp Arg Val Glu Phe Thr
            180                 185                 190

Arg Pro Gln Val Pro Val Glu Thr Tyr Val Pro Ala Gly Trp Lys Glu
        195                 200                 205

Ile Leu Glu Asp Met Val Glu Ala Asp Lys Thr Ser Tyr Gly Val Ile
210                 215                 220

Val Asn Ser Phe Gln Glu Leu Glu Pro Ala Tyr Ala Lys Asp Phe Lys
225                 230                 235                 240

Glu Ala Arg Ser Gly Lys Ala Trp Thr Ile Gly Pro Val Ser Leu Cys
                245                 250                 255

Asn Lys Val Gly Val Asp Lys Ala Glu Arg Gly Asn Lys Ser Asp Ile
            260                 265                 270

Asp Gln Asp Glu Cys Leu Glu Trp Leu Asp Ser Lys Glu Pro Gly Ser
        275                 280                 285

Val Leu Tyr Val Cys Leu Gly Ser Ile Cys Asn Leu Pro Leu Ser Gln
290                 295                 300

Leu Leu Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335
```

```
Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Met Leu Thr Trp Pro Leu Phe Ala Asp Gln Phe Cys
385                 390                 395                 400

Asn Glu Lys Leu Val Val Gln Ile Leu Lys Val Gly Val Ser Ala Glu
                405                 410                 415

Val Lys Glu Val Met Lys Trp Gly Glu Glu Lys Ile Gly Val Leu
            420                 425                 430

Val Asp Lys Glu Gly Val Lys Lys Ala Val Glu Glu Leu Met Gly Glu
            435                 440                 445

Ser Asp Asp Ala Lys Glu Arg Arg Arg Ala Lys Glu Leu Gly Glu
            450                 455                 460

Ser Ala His Lys Ala Val Glu Glu Gly Ser Ser His Ser Asn Ile
465                 470                 475                 480

Thr Phe Leu Leu Gln Asp Ile Met Gln Leu Ala Gln Ser Asn Asn
                485                 490                 495

<210> SEQ ID NO 79
<211> LENGTH: 495
<212> TYPE: PRT
<213> ORGANISM: Arabidopsis thaliana

<400> SEQUENCE: 79

Met Ser Pro Lys Met Val Ala Pro Pro Thr Asn Leu His Phe Val Leu
1               5                   10                  15

Phe Pro Leu Met Ala Gln Gly His Leu Val Pro Met Val Asp Ile Ala
                20                  25                  30

Arg Ile Leu Ala Gln Arg Gly Ala Thr Val Thr Ile Ile Thr Thr Pro
            35                  40                  45

Tyr His Ala Asn Arg Val Arg Pro Val Ile Ser Arg Ala Ile Ala Thr
        50                  55                  60

Asn Leu Lys Ile Gln Leu Leu Glu Leu Gln Leu Arg Ser Thr Glu Ala
65              70                  75                  80

Gly Leu Pro Glu Gly Cys Glu Ser Phe Asp Gln Leu Pro Ser Phe Glu
                85                  90                  95

Tyr Trp Lys Asn Ile Ser Thr Ala Ile Asp Leu Leu Gln Gln Pro Ala
            100                 105                 110

Glu Asp Leu Leu Arg Glu Leu Ser Pro Pro Asp Cys Ile Ile Ser
        115                 120                 125

Asp Phe Leu Phe Pro Trp Thr Thr Asp Val Ala Arg Arg Leu Asn Ile
            130                 135                 140

Pro Arg Leu Val Phe Asn Gly Pro Gly Cys Phe Tyr Leu Leu Cys Ile
145                 150                 155                 160

His Val Ala Ile Thr Ser Asn Ile Leu Gly Glu Asn Glu Pro Val Ser
                165                 170                 175

Ser Asn Thr Glu Arg Val Val Leu Pro Gly Leu Pro Asp Arg Ile Glu
            180                 185                 190

Val Thr Lys Leu Gln Ile Val Gly Ser Ser Arg Pro Ala Asn Val Asp
        195                 200                 205

Glu Met Gly Ser Trp Leu Arg Ala Val Glu Ala Glu Lys Ala Ser Phe
210                 215                 220
```

```
Gly Ile Val Val Asn Thr Phe Glu Glu Leu Glu Pro Glu Tyr Val Glu
225                 230                 235                 240

Glu Tyr Lys Thr Val Lys Asp Lys Lys Met Trp Cys Ile Gly Pro Val
            245                 250                 255

Ser Leu Cys Asn Lys Thr Gly Pro Asp Leu Ala Glu Arg Gly Asn Lys
        260                 265                 270

Ala Ala Ile Thr Glu His Asn Cys Leu Lys Trp Leu Asp Glu Arg Lys
    275                 280                 285

Leu Gly Ser Val Leu Tyr Val Cys Leu Gly Ser Leu Ala Arg Ile Ser
290                 295                 300

Ala Ala Gln Ala Ile Glu Leu Gly Leu Gly Leu Glu Ser Ile Asn Arg
305                 310                 315                 320

Pro Phe Ile Trp Cys Val Arg Asn Glu Thr Asp Glu Leu Lys Thr Trp
                325                 330                 335

Phe Leu Asp Gly Phe Glu Glu Arg Val Arg Asp Arg Gly Leu Ile Val
            340                 345                 350

His Gly Trp Ala Pro Gln Val Leu Ile Leu Ser His Pro Thr Ile Gly
        355                 360                 365

Gly Phe Leu Thr His Cys Gly Trp Asn Ser Thr Ile Glu Ser Ile Thr
370                 375                 380

Ala Gly Val Pro Met Ile Thr Trp Pro Phe Phe Ala Asp Gln Phe Leu
385                 390                 395                 400

Asn Glu Ala Phe Ile Val Glu Val Leu Lys Ile Gly Val Arg Ile Gly
                405                 410                 415

Val Glu Arg Ala Cys Leu Phe Gly Glu Asp Lys Val Gly Val Leu
            420                 425                 430

Val Lys Lys Glu Asp Val Lys Lys Ala Val Glu Cys Leu Met Asp Glu
            435                 440                 445

Asp Glu Asp Gly Asp Gln Arg Arg Lys Arg Val Ile Glu Leu Ala Lys
        450                 455                 460

Met Ala Lys Ile Ala Met Ala Glu Gly Gly Ser Ser Tyr Glu Asn Val
465                 470                 475                 480

Ser Ser Leu Ile Arg Asp Val Thr Glu Thr Val Arg Ala Pro His
                485                 490                 495

<210> SEQ ID NO 80
<211> LENGTH: 481
<212> TYPE: PRT
<213> ORGANISM: Arabidopsis thaliana

<400> SEQUENCE: 80

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
                20                  25                  30

Leu Leu His His Lys Gly Leu Gln Ile Thr Phe Val Asn Thr Asp Phe
            35                  40                  45

Ile His Asn Gln Phe Leu Glu Ser Gly Pro His Cys Leu Asp Gly
        50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
```

```
                        100                 105                 110
Pro Pro Thr Cys Ile Ile Ser Asp Gly Phe Leu Ser Val Phe Thr Ile
            115                 120                 125
Asp Ala Ala Lys Lys Leu Gly Ile Pro Val Met Met Tyr Trp Thr Leu
            130                 135                 140
Ala Ala Cys Gly Phe Met Gly Phe Tyr His Ile His Ser Leu Ile Glu
145                 150                 155                 160
Lys Gly Phe Ala Pro Leu Lys Asp Ala Ser Tyr Leu Thr Asn Gly Tyr
                165                 170                 175
Leu Asp Thr Val Ile Asp Trp Val Pro Gly Met Glu Gly Ile Arg Leu
            180                 185                 190
Lys Asp Phe Pro Leu Asp Trp Ser Thr Asp Leu Asn Asp Lys Val Leu
            195                 200                 205
Met Phe Thr Thr Glu Ala Pro Gln Arg Ser His Lys Val Ser His His
210                 215                 220
Ile Phe His Thr Phe Asp Glu Leu Glu Pro Ser Ile Ile Lys Thr Leu
225                 230                 235                 240
Ser Leu Arg Tyr Asn His Ile Tyr Thr Ile Gly Pro Leu Gln Leu Leu
                245                 250                 255
Leu Asp Gln Ile Pro Glu Glu Lys Lys Gln Thr Gly Ile Thr Ser Leu
                260                 265                 270
His Gly Tyr Ser Leu Val Lys Glu Glu Pro Glu Cys Phe Gln Trp Leu
            275                 280                 285
Gln Ser Lys Glu Pro Asn Ser Val Val Tyr Val Asn Phe Gly Ser Thr
            290                 295                 300
Thr Val Met Ser Leu Glu Asp Met Thr Glu Phe Gly Trp Gly Leu Ala
305                 310                 315                 320
Asn Ser Asn His Tyr Phe Leu Trp Ile Ile Arg Ser Asn Leu Val Ile
                325                 330                 335
Gly Glu Asn Ala Val Leu Pro Pro Glu Leu Glu Glu His Ile Lys Lys
            340                 345                 350
Arg Gly Phe Ile Ala Ser Trp Cys Ser Gln Glu Lys Val Leu Lys His
            355                 360                 365
Pro Ser Val Gly Gly Phe Leu Thr His Cys Gly Trp Gly Ser Thr Ile
            370                 375                 380
Glu Ser Leu Ser Ala Gly Val Pro Met Ile Cys Trp Pro Tyr Ser Trp
385                 390                 395                 400
Asp Gln Leu Thr Asn Cys Arg Tyr Ile Cys Lys Glu Trp Glu Val Gly
                405                 410                 415
Leu Glu Met Gly Thr Lys Val Lys Arg Asp Glu Val Lys Arg Leu Val
            420                 425                 430
Gln Glu Leu Met Gly Glu Gly His Lys Met Arg Asn Lys Ala Lys
            435                 440                 445
Asp Trp Lys Glu Lys Ala Arg Ile Ala Ile Ala Pro Asn Gly Ser Ser
            450                 455                 460
Ser Leu Asn Ile Asp Lys Met Val Lys Glu Ile Thr Val Leu Ala Arg
465                 470                 475                 480

Asn

<210> SEQ ID NO 81
<211> LENGTH: 1410
<212> TYPE: DNA
<213> ORGANISM: Siraitia grosvenorii
```

<400> SEQUENCE: 81

```
atggagcaag ctcatgatct tcttcacgtc ctcctttttc cgtatccggc gaagggccac        60
atcaagccct tcctctgcct cgccgagctc ctctgcaacg ccggtctcaa cgtcaccttc       120
ctcaacaccg actacaacca ccgccgcctc cacaatctcc atctcctcgc cgcctgcttt       180
ccctctcttc atttcgagtc catttccgac ggcctccagc ccgatcagcc tcgagatata       240
ctggaccccca gtttttatat atccatctgt caagtcacta accccctttt ccgggagctc      300
ctcctttcct acaaacgaac ttccagtgtc cagaccggcc gcccgccaat aacttgcgtt       360
attacagatg tgattttttcg ttttccgatc gacgtagctg aagaactgga tattcctgtg     420
tttagtttct gtactttcag tgcccgtttc atgtttcttt acttctggat tcccaagctc       480
attgaagatg ccagcttcc atacccaaac ggcaatatca accagaaact ctacggtgtt       540
gctcctgagg cggaaggcct tttaagatgt aaagatttgc cgggacattg ggctttcgca       600
gacgaactaa aagatgatca acttaacttt gtgaccagaa caacggcgtc acttcgatcc       660
tccggtctca ttctcaacac attcgacgac ctcgaagctc catttctggg gcgtctctcc       720
accatcttta agaaaatcta cgccgttgga cccatccacg ctctgttgaa ctcccaccac       780
tgtggtcttt ggaagaagaa tcacagttgc ctggcgtggc tcgactcccg ggcggcgaga       840
tccgtcgtgt tcgtcagctt cgggagcttg gtgaagataa caagtaggca gctgatggag       900
ttttggcatg gcttgctcaa cagtggaacg tcgttcctct tcgtgttgag atctgacgta       960
gttgagggcg atggtgaaaa acaagtcgtc aaagaaattt acgagacgaa ggcagagggg     1020
aaatggttgg ttgtgggggtg ggctccgcaa gagaaggtgt tagcccatga agctgttggt      1080
ggatttctga cccattcggg ctggaactcc attttagaga gcattgctgc tggggttcct       1140
atgatctcct gccccaaaat tggagaccag tccagtaact gtacgtggat cagtaaagta     1200
tggaaaattg gctcgaaat ggaggaccaa tacgaccggg ccacggtcga ggcaatggtt       1260
aggtctataa tgaaacatga aggagaaaaa attcaaaaga caattgcaga gttagcaaaa     1320
cgagccaagt ataaagttag taaagatggg acatcgtatc gaaatttaga aattttaatt      1380
gaggatatta aaaaaattaa accaaattaa                                        1410
```

<210> SEQ ID NO 82
<211> LENGTH: 1410
<212> TYPE: DNA
<213> ORGANISM: Artificial Sequence
<220> FEATURE:
<223> OTHER INFORMATION: Codon-optimized S. grosvenorii UGT430 nucleotide sequence

<400> SEQUENCE: 82

```
atggaacaag cccacgattt gctgcatgtt ttactttttc catatccagc taagggcat        60
attaagccct ttttgtgtct tgcggaactt ttatgcaacg caggtcttaa tgttacgttt       120
ttgaataccg attataatca cagaagatta cacaatctgc acctattagc ggcttgtttt       180
cctagtttgc attttgaaag tatcagtgat ggtttgcagc cagatcaacc tagagatatc       240
ttggacccaa gttttacat ctctatttgc caagttacca agccattatt cagagaattg       300
ttattatcct ataaaaggac atcctcagta caaaccggca ggccgccaat aacttgtgtt       360
ataacagatg ttatatttcg ttttccaatc gatgtagccg aggaattaga tatccctgtt      420
ttttcttttct gtactttag cgcgcgtttt atgtttcttt acttctggat cccaaagctt      480
atcgaggatg ggcaattgcc ttacccaaac ggtaacataa tcagaaaact gtatggtgtt      540
```

-continued

```
gcacctgaag cagaaggatt attaaggtgt aaggatttac cgggacactg ggctttcgct    600
gatgagttaa aagacgatca gttgaacttt gttgatcaaa ctaccgccag tttgagatca    660
tctggtttga tcttaaacac tttcgacgat ttggaagctc cattcctggg acgtttgtca    720
acaatattta agaagatcta cgctgttggg ccaatacatg cgttgctaaa cagtcaccat    780
tgcggtttat ggaaagaaga ccacagctgt ttggcctggt tagatagtag agcggcacgt    840
tctgtcgtgt tcgtcagttt cggttctttg gttaagatca cttctaggca attgatggaa    900
ttctggcatg gattgttgaa tagcgggaca agcttttttgt ttgtcttgag aagtgatgtt    960
gtagaaggtg atggggaaaa gcaagttgtc aaagaaatct acgaaacgaa agcagagggt    1020
aaatggttag ttgttggttg ggctccacaa gaaaaagtat tggcacatga agccgttgga    1080
ggtttcttaa ctcattccgg ttggaactca atcttagagt ctatagccgc aggtgtacct    1140
atgataagtt gcccaaaaat aggagaccaa tcttctaatt gtacctggat tagtaaagtt    1200
tggaagattg gtttagaaat ggaagaccag tatgacagag caactgtgga agctatggtg    1260
agatcaatta tgaaacacga aggtgagaag atacaaaaga ctattgcgga acttgcaaaa    1320
agagcaaaat ataaagtttc caaggacggc acttcatata gaaatctgga aattttgatc    1380
gaagatatca gaagatcaa gccgaattag                                      1410
```

<210> SEQ ID NO 83
<211> LENGTH: 469
<212> TYPE: PRT
<213> ORGANISM: Siraitia grosvenorii

<400> SEQUENCE: 83

```
Met Glu Gln Ala His Asp Leu Leu His Val Leu Leu Phe Pro Tyr Pro
1               5                   10                  15

Ala Lys Gly His Ile Lys Pro Phe Leu Cys Leu Ala Glu Leu Leu Cys
            20                  25                  30

Asn Ala Gly Leu Asn Val Thr Phe Leu Asn Thr Asp Tyr Asn His Arg
        35                  40                  45

Arg Leu His Asn Leu His Leu Leu Ala Ala Cys Phe Pro Ser Leu His
    50                  55                  60

Phe Glu Ser Ile Ser Asp Gly Leu Gln Pro Asp Gln Pro Arg Asp Ile
65                  70                  75                  80

Leu Asp Pro Lys Phe Tyr Ile Ser Ile Cys Gln Val Thr Lys Pro Leu
                85                  90                  95

Phe Arg Glu Leu Leu Leu Ser Tyr Lys Arg Thr Ser Ser Val Gln Thr
            100                 105                 110

Gly Arg Pro Pro Ile Thr Cys Val Ile Thr Asp Val Ile Phe Arg Phe
        115                 120                 125

Pro Ile Asp Val Ala Glu Glu Leu Asp Ile Pro Val Phe Ser Phe Cys
    130                 135                 140

Thr Phe Ser Ala Arg Phe Met Phe Leu Tyr Phe Trp Ile Pro Lys Leu
145                 150                 155                 160

Ile Glu Asp Gly Gln Leu Pro Tyr Pro Asn Gly Asn Ile Asn Gln Lys
                165                 170                 175

Leu Tyr Gly Val Ala Pro Glu Ala Glu Gly Leu Leu Arg Cys Lys Asp
            180                 185                 190

Leu Pro Gly His Trp Ala Phe Ala Asp Glu Leu Lys Asp Asp Gln Leu
        195                 200                 205

Asn Phe Val Asp Gln Thr Thr Ala Ser Leu Arg Ser Ser Gly Leu Ile
    210                 215                 220
```

Leu Asn Thr Phe Asp Asp Leu Glu Ala Pro Phe Leu Gly Arg Leu Ser
225                 230                 235                 240

Thr Ile Phe Lys Lys Ile Tyr Ala Val Gly Pro Ile His Ala Leu Leu
            245                 250                 255

Asn Ser His His Cys Gly Leu Trp Lys Glu Asp His Ser Cys Leu Ala
        260                 265                 270

Trp Leu Asp Ser Arg Ala Ala Arg Ser Val Val Phe Val Ser Phe Gly
    275                 280                 285

Ser Leu Val Lys Ile Thr Ser Arg Gln Leu Met Glu Phe Trp His Gly
290                 295                 300

Leu Leu Asn Ser Gly Thr Ser Phe Leu Phe Val Leu Arg Ser Asp Val
305                 310                 315                 320

Val Glu Gly Asp Gly Glu Lys Gln Val Lys Glu Ile Tyr Glu Thr
                325                 330                 335

Lys Ala Glu Gly Lys Trp Leu Val Val Gly Trp Ala Pro Gln Glu Lys
                340                 345                 350

Val Leu Ala His Glu Ala Val Gly Gly Phe Leu Thr His Ser Gly Trp
                355                 360                 365

Asn Ser Ile Leu Glu Ser Ile Ala Ala Gly Val Pro Met Ile Ser Cys
370                 375                 380

Pro Lys Ile Gly Asp Gln Ser Ser Asn Cys Thr Trp Ile Ser Lys Val
385                 390                 395                 400

Trp Lys Ile Gly Leu Glu Met Glu Asp Gln Tyr Asp Arg Ala Thr Val
                405                 410                 415

Glu Ala Met Val Arg Ser Ile Met Lys His Gly Glu Lys Ile Gln
                420                 425                 430

Lys Thr Ile Ala Glu Leu Ala Lys Arg Ala Lys Tyr Lys Val Ser Lys
            435                 440                 445

Asp Gly Thr Ser Tyr Arg Asn Leu Glu Ile Leu Ile Glu Asp Ile Lys
        450                 455                 460

Lys Ile Lys Pro Asn
465

<210> SEQ ID NO 84
<211> LENGTH: 1425
<212> TYPE: DNA
<213> ORGANISM: Siraitia grosvenorii

<400> SEQUENCE: 84
atggtgcaac ctcgggtact gctgtttcct ttcccggcac tgggccacgt gaagcccttc      60
ttatcactgg cggagctgct ttccgacgcc ggcatagacg tcgtcttcct cagcaccgag     120
tataaccacc gtcggatctc caacactgaa gccctagcct cccgcttccc gacgcttcat     180
ttcgaaacta taccggatgg cctgccgcct aatgagtcgc gcgctcttgc cgacggccca     240
ctgtatttct ccatgcgtga gggaactaaa ccgagattcc ggcaactgat tcaatctctt     300
aacgacggtc gttggcccat cacctgcatt atcactgaca tcatgttatc ttctccgatt     360
gaagtagcgg aagaatttgg gattccagta attgccttct gccctgcag tgctcgctac     420 ttatcgattc acttttttat accgaagctc gttgaggaag tcaaattcc atacgcagat     480 gacgatccga ttggagagat ccaggggggtg cccttgttcg aaggtctttt gcgacggaat     540
catttgcctg gttcttggtc tgataaatct gcagatatat ctttctcgca tggcttgatt     600
aatcagaccc ttgcagctgg tcgagcctcg gctcttatac tcaacacctt cgacgagctc     660

| | |
|---|---|
| gaagctccat ttctgaccca tctctcttcc attttcaaca aaatctacac cattggaccc | 720 |
| ctccatgctc tgtccaaatc aaggctcggc gactcctcct cctccgcttc tgccctctcc | 780 |
| ggattctgga aagaggatag agcctgcatg tcctggctcg actgtcagcc gccgagatct | 840 |
| gtggttttcg tcagtttcgg gagtacgatg aagatgaaag ccgatgaatt gagagagttc | 900 |
| tggtatgggt tggtgagcag cgggaaaccg ttcctctgcg tgttgagatc cgacgttgtt | 960 |
| tccggcggag aagcggcgga attgatcgaa cagatggcgg aggaggaggg agctggaggg | 1020 |
| aagctgggaa tggtagtgga gtgggcagcg caagagaagg tcctgagcca ccctgccgtc | 1080 |
| ggtgggtttt tgacgcactg cgggtggaac tcaacggtgg aaagcattgc cgcgggagtt | 1140 |
| ccgatgatgt gctggccgat ctcggcgac caacccagca acgccacttg gatcgacaga | 1200 |
| gtgtggaaaa ttgggggttga aaggaacaat cgtgaatggg acaggttgac ggtggagaag | 1260 |
| atggtgagag cattgatgga aggccaaaag agagtggaga ttcagagatc aatggagaag | 1320 |
| ctttcaaagt tggcaaatga gaaggttgtc aggggtgggt tgtcttttga taacttggaa | 1380 |
| gttctcgttg aagacatcaa aaaattgaaa ccatataaat tttaa | 1425 |

<210> SEQ ID NO 85
<211> LENGTH: 1425
<212> TYPE: DNA
<213> ORGANISM: Artificial Sequence
<220> FEATURE:
<223> OTHER INFORMATION: Codon-optimized S. grosvenorii UGT1697
      nucleotide sequence

<400> SEQUENCE: 85

| | |
|---|---|
| atggttcaac ctagggtctt attgtttccc ttccctgctt tgggacatgt caaacccttt | 60 |
| ctgtcactgg cagaattact ttccgatgct gggatagacg ttgtatttct tagtacagaa | 120 |
| tacaatcata ggaggattag taacacggag gctctggcct caagatttcc aaccttgcat | 180 |
| tttgaaacaa taccagatgg tcttccacct aacgagagca gggctttggc agacggccct | 240 |
| ttgtacttta gcatgcgtga ggggacaaaa cccagattca gacagctgat acagagcctg | 300 |
| aacgatggca gatggcctat cacgtgtatc attaccgata tcatgttgag tagccccatc | 360 |
| gaagtagctg aggagtttgg aattccagta attgcctttt gtccctgctc cgctagatac | 420 |
| ttgtctattc atttttttcat acccaagttg gttgaagagg tcagatccc ttatgcagat | 480 |
| gatgatccaa tcggtgaaat tcaaggtgtg ccacttttcg aagggcttct gaggagaaat | 540 |
| catttgccag gcagctggag tgataagtct gcagacatct catttttccca tggttttgatc | 600 |
| aaccaaacat tagcagccgg tagagcttct gcattaatct tgaatacgtt tgatgagttg | 660 |
| gaagctccat ttctgactca tcttttctagt attttttaata agatttatac aattggtcct | 720 |
| ttgcatgcct tatctaagtc aaggttagga gactcctcat ctagtgctag tgcacttagt | 780 |
| ggattctgga aggaagatag ggcttgtatg tcttggttgg attgtcaacc tcctagatct | 840 |
| gttgttttcg tctcttttgg cagtactatg aaaatgaagg cggacgaact aagagaattt | 900 |
| tggtatggat tagtatcttc aggaaaacca ttttttatgcg ttttaagatc cgatgtagtc | 960 |
| tcaggcggag aagctgcgga gttaattgaa caaatggcag aagaggaagg tgccggggt | 1020 |
| aagttgggca tggttgttga tgggcagct caggagaagg tacttagcca tccagcggtt | 1080 |
| ggtggatttt tgacgcattg cgggtggaat agcactgtgg aaagtatagc agcagggtc | 1140 |
| ccgatgatgt gttggccaat cttgggagat caaccatcca acgcgacctg gatcgataga | 1200 |
| gtttggaaaa tcggtgtaga aagaaataat agagaatggg atagattaac tgttgaaaaa | 1260 |

-continued

```
atggttagag ccttgatgga aggacagaaa agagttgaaa ttcagcgttc aatggaaaag    1320
ctatcaaagt tggccaatga aaaagtagtt aggggggtc tttcatttga taatcttgaa     1380
gttcttgtcg aagatattaa aaagttaaag ccgtacaagt tttaa                    1425
```

<210> SEQ ID NO 86
<211> LENGTH: 474
<212> TYPE: PRT
<213> ORGANISM: Siraitia grosvenorii

<400> SEQUENCE: 86

```
Met Val Gln Pro Arg Val Leu Leu Phe Pro Phe Pro Ala Leu Gly His
1               5                   10                  15

Val Lys Pro Phe Leu Ser Leu Ala Glu Leu Leu Ser Asp Ala Gly Ile
            20                  25                  30

Asp Val Val Phe Leu Ser Thr Glu Tyr Asn His Arg Ile Ser Asn
        35                  40                  45

Thr Glu Ala Leu Ala Ser Arg Phe Pro Thr Leu His Phe Glu Thr Ile
    50                  55                  60

Pro Asp Gly Leu Pro Pro Asn Glu Ser Arg Ala Leu Ala Asp Gly Pro
65                  70                  75                  80

Leu Tyr Phe Ser Met Arg Glu Gly Thr Lys Pro Arg Phe Arg Gln Leu
                85                  90                  95

Ile Gln Ser Leu Asn Asp Gly Arg Trp Pro Ile Thr Cys Ile Ile Thr
            100                 105                 110

Asp Ile Met Leu Ser Ser Pro Ile Glu Val Ala Glu Glu Phe Gly Ile
        115                 120                 125

Pro Val Ile Ala Phe Cys Pro Cys Ser Ala Arg Tyr Leu Ser Ile His
    130                 135                 140

Phe Phe Ile Pro Lys Leu Val Glu Glu Gly Gln Ile Pro Tyr Ala Asp
145                 150                 155                 160

Asp Asp Pro Ile Gly Glu Ile Gln Gly Val Pro Leu Phe Glu Gly Leu
                165                 170                 175

Leu Arg Arg Asn His Leu Pro Gly Ser Trp Ser Asp Lys Ser Ala Asp
            180                 185                 190

Ile Ser Phe Ser His Gly Leu Ile Asn Gln Thr Leu Ala Ala Gly Arg
        195                 200                 205

Ala Ser Ala Leu Ile Leu Asn Thr Phe Asp Glu Leu Glu Ala Pro Phe
    210                 215                 220

Leu Thr His Leu Ser Ser Ile Phe Asn Lys Ile Tyr Thr Ile Gly Pro
225                 230                 235                 240

Leu His Ala Leu Ser Lys Ser Arg Leu Gly Asp Ser Ser Ser Ala
                245                 250                 255

Ser Ala Leu Ser Gly Phe Trp Lys Glu Asp Arg Ala Cys Met Ser Trp
            260                 265                 270

Leu Asp Cys Gln Pro Pro Arg Ser Val Val Phe Val Ser Phe Gly Ser
        275                 280                 285

Thr Met Lys Met Lys Ala Asp Glu Leu Arg Glu Phe Trp Tyr Gly Leu
    290                 295                 300

Val Ser Ser Gly Lys Pro Phe Leu Cys Val Leu Arg Ser Asp Val Val
305                 310                 315                 320

Ser Gly Gly Glu Ala Ala Glu Leu Ile Glu Gln Met Ala Glu Glu
                325                 330                 335

Gly Ala Gly Gly Lys Leu Gly Met Val Val Glu Trp Ala Ala Gln Glu
            340                 345                 350
```

```
Lys Val Leu Ser His Pro Ala Val Gly Gly Phe Leu Thr His Cys Gly
            355                 360                 365

Trp Asn Ser Thr Val Glu Ser Ile Ala Ala Gly Val Pro Met Met Cys
        370                 375                 380

Trp Pro Ile Leu Gly Asp Gln Pro Ser Asn Ala Thr Trp Ile Asp Arg
385                 390                 395                 400

Val Trp Lys Ile Gly Val Glu Arg Asn Asn Arg Glu Trp Asp Arg Leu
                405                 410                 415

Thr Val Glu Lys Met Val Arg Ala Leu Met Glu Gly Gln Lys Arg Val
            420                 425                 430

Glu Ile Gln Arg Ser Met Glu Lys Leu Ser Lys Leu Ala Asn Glu Lys
            435                 440                 445

Val Val Arg Gly Gly Leu Ser Phe Asp Asn Leu Glu Val Leu Val Glu
            450                 455                 460

Asp Ile Lys Lys Leu Lys Pro Tyr Lys Phe
465                 470
```

<210> SEQ ID NO 87
<211> LENGTH: 1491
<212> TYPE: DNA
<213> ORGANISM: Siraitia grosvenorii

<400> SEQUENCE: 87

```
atggcttctc ctcgccacac tcctcacttt ctgctcttcc ctttcatggc tcaaggccac     60
atgatcccca tgattgacct tgccaggctt ctggctcagc gaggagttat catcactatt    120
atcaccacgc cccacaatgc tgctcgctac cactctgttc ttgctcgcgc catcgattct    180
gggttacaca tccatgtcct ccaactgcag tttccatgta aggaaggtgg gctgccagaa    240
gggtgcgaga atgtggactt gctaccttca cttgcttcca tacccagatt ctacagagca    300
gcaagtgatc tcctttacga accatctgaa aaactgtttg aggaactcat cccccggccg    360
acctgcataa tctccgatat gtgcctgccc tggaccatgc gaattgctct gaaatatcac    420
gtcccaaggc tcgttttcta cagtttgagc tgcttctttc ttctctgtat gcggagttta    480
aaaaacaatc tagcgcttat aagctccaag tctgattctg agttcgtaac tttctctgac    540
ttgcctgatc cagtcgagtt tctcaagtcg agctaccta aatccaccga tgaagacttg    600
gtgaagttta gttatgaaat gggggaggcc gatcggcagt catacggcgt tattttaaat    660
ctatttgagg atgggaacc aaagtatctt gcagaatatg aaaaggaaag agaatcgccg    720
gaaagagtct ggtgcgtcgg cccagtttcg ctttgcaacg acaacaaact cgacaaagct    780
gaaagaggca caaagcctc atcgacgaa tacaaatgca tcaggtggct cgacgggcag    840
cagccatctt cggtggttta cgtctcttta ggaagcttgt gcaatctggt gacgcgcag    900
atcatagagc tgggtttggg tttggaggca tcaagaaaac ccttcatttg ggtcataaga    960
agaggaaaca taacagagga gttacagaaa tggcttgtgg agtacgattt cgaggagaaa   1020
attaaaggga gagggctggt gattcttggc tgggctcccc aagttctgat actgtcacac   1080
cctgcaatcg gatgcttttt gacgcactgc ggttggaact caagcatcga agggatatcg   1140
gccggcgtgc aatggtcac ctggccgctt tttgcggatc aagtcttcaa cgagaagcta   1200
attgtacaaa tactcagaat cggcgtaagt gtaggcacgg aaactactat gaactgggga   1260
gaggaagagg agaaggggt ggttgtgaag agagagaaag tgagggaagc catagaaata   1320
gtgatggatg gagatgagag agaagagagg agagagagat gcaaagagct tgctgaaacg   1380
```

```
gcgaagagag ctatagaaga aggggggctcg tctcaccgga acctcacgat gttgattgaa    1440
gatataattc atggaggagg tttgagttat gagaaaggaa gttgtcgctg a              1491
```

<210> SEQ ID NO 88
<211> LENGTH: 1491
<212> TYPE: DNA
<213> ORGANISM: Artificial Sequence
<220> FEATURE:
<223> OTHER INFORMATION: Codon-optimized S. grosvenorii UGT1576
      nucleotide sequence

<400> SEQUENCE: 88

```
atggcgtcac ctagacatac tcctcatttc ttgttatttc catttatggc tcaaggacat      60
atgataccta tgattgatct ggctaggcta ctagcacaaa gaggtgttat tatcactatt     120
attactactc cacataatgc agctcgttat catagtgttt tagctcgtgc cattgactct     180
ggtttacata tccacgtttt acaactacaa ttcccttgca agaaggcgg actaccggaa      240 ggttgtgaga acgtagactt acttccatcc ttagcgagca ttccaagatt ttacagagct     300
gcctctgatc tactatatga acctagcgaa aaacttttcg aagagttgat accgagacca     360
acttgtatca tttctgatat gtgtttacca tggactatga aattgccctt aaagtatcat     420
gtgcccagac ttgttttcta ctctttgtct tgcttttttc tgctgtgcat gagaagctta     480
aagaacaatt tagcattaat ttctagcaag tcagattccg agttcgtaac tttctctgat     540
ttacccgatc cagttgaatt tttgaagtct gagcttccta agtccacaga cgaagacttg     600
gttaaatttt catatgaaat gggtgaggca gacagacaat catatggcgt tatactaaac     660
ttgtttgaag aaatggagcc caaatatttg gcagagtatg aaaaagaaag agaaagtccc     720
gaaagagttt ggtgtgttgg tccagtatct ttgtgcaacg ataacaaatt agataaagca     780
gagaggggta acaaagcatc aattgacgaa tataagtgta ttagatggtt agatgggcaa     840
caacctagca gtgttgttta tgttagtctt ggatcattat gcaacttggt tactgctcaa     900
attattgaat tggggttggg gttggaagct tctaaaaagc cattcatttg ggttattagg     960 agggcaaca taacagaaga actacaaaaa tggctggttg aatatgactt tgaggagaag    1020
attaagggac gtggattagt catattaggg tgggcgcccc aagtacttat tctatctcat    1080
ccagctattg gttgcttctt aactcattgc ggttggaatt cctctatcga aggtatttcc    1140
gccggtgttc ctatggttac ctggcctcta tttgcagatc aggttttcaa cgaaaaatta    1200
atagttcaaa tcttgagaat cggagttagc gttggtacag aaacaaccat gaactggggt    1260
gaggaagaag aaaaggtgt ggtggtcaaa agggagaaag tgagagaggc gatagagatc    1320
gtaatggatg gcgacgaaag agaagaaaga agagaaaggt gtaaagaact agcagaaact    1380
gccaaacgtg ctatcgagga aggtggtagc agtcatagaa atttgaccat gctaattgaa    1440
gatattatcc acgtggtgg cttatcttac gagaaagggt cctgcaggta g              1491
```

<210> SEQ ID NO 89
<211> LENGTH: 496
<212> TYPE: PRT
<213> ORGANISM: Siraitia grosvenorii

<400> SEQUENCE: 89

```
Met Ala Ser Pro Arg His Thr Pro His Phe Leu Phe Pro Phe Met
1               5                   10                  15

Ala Gln Gly His Met Ile Pro Met Ile Asp Leu Ala Arg Leu Leu Ala
                20                  25                  30
```

```
Gln Arg Gly Val Ile Ile Thr Ile Thr Thr Pro His Asn Ala Ala
            35                  40                  45

Arg Tyr His Ser Val Leu Ala Arg Ala Ile Asp Ser Gly Leu His Ile
 50                  55                  60

His Val Leu Gln Leu Gln Phe Pro Cys Lys Glu Gly Leu Pro Glu
 65                  70                  75                  80

Gly Cys Glu Asn Val Asp Leu Leu Pro Ser Leu Ala Ser Ile Pro Arg
                 85                  90                  95

Phe Tyr Arg Ala Ala Ser Asp Leu Leu Tyr Glu Pro Ser Glu Lys Leu
                100                 105                 110

Phe Glu Glu Leu Ile Pro Arg Pro Thr Cys Ile Ile Ser Asp Met Cys
            115                 120                 125

Leu Pro Trp Thr Met Arg Ile Ala Leu Lys Tyr His Val Pro Arg Leu
            130                 135                 140

Val Phe Tyr Ser Leu Ser Cys Phe Phe Leu Leu Cys Met Arg Ser Leu
145                 150                 155                 160

Lys Asn Asn Leu Ala Leu Ile Ser Ser Lys Ser Asp Ser Glu Phe Val
                165                 170                 175

Thr Phe Ser Asp Leu Pro Asp Pro Val Glu Phe Leu Lys Ser Glu Leu
            180                 185                 190

Pro Lys Ser Thr Asp Glu Asp Leu Val Lys Phe Ser Tyr Glu Met Gly
            195                 200                 205

Glu Ala Asp Arg Gln Ser Tyr Gly Val Ile Leu Asn Leu Phe Glu Glu
            210                 215                 220

Met Glu Pro Lys Tyr Leu Ala Glu Tyr Glu Lys Glu Arg Glu Ser Pro
225                 230                 235                 240

Glu Arg Val Trp Cys Val Gly Pro Val Ser Leu Cys Asn Asp Asn Lys
                245                 250                 255

Leu Asp Lys Ala Glu Arg Gly Asn Lys Ala Ser Ile Asp Glu Tyr Lys
            260                 265                 270

Cys Ile Arg Trp Leu Asp Gly Gln Gln Pro Ser Ser Val Val Tyr Val
            275                 280                 285

Ser Leu Gly Ser Leu Cys Asn Leu Val Thr Ala Gln Ile Ile Glu Leu
290                 295                 300

Gly Leu Gly Leu Glu Ala Ser Lys Lys Pro Phe Ile Trp Val Ile Arg
305                 310                 315                 320

Arg Gly Asn Ile Thr Glu Glu Leu Gln Lys Trp Leu Val Glu Tyr Asp
                325                 330                 335

Phe Glu Glu Lys Ile Lys Gly Arg Gly Leu Val Ile Leu Gly Trp Ala
            340                 345                 350

Pro Gln Val Leu Ile Leu Ser His Pro Ala Ile Gly Cys Phe Leu Thr
            355                 360                 365

His Cys Gly Trp Asn Ser Ser Ile Glu Gly Ile Ser Ala Gly Val Pro
            370                 375                 380

Met Val Thr Trp Pro Leu Phe Ala Asp Gln Val Phe Asn Glu Lys Leu
385                 390                 395                 400

Ile Val Gln Ile Leu Arg Ile Gly Val Ser Val Gly Thr Glu Thr Thr
                405                 410                 415

Met Asn Trp Gly Glu Glu Glu Lys Gly Val Val Lys Arg Glu
            420                 425                 430

Lys Val Arg Glu Ala Ile Glu Ile Val Met Asp Gly Asp Glu Arg Glu
            435                 440                 445

Glu Arg Arg Glu Arg Cys Lys Glu Leu Ala Glu Thr Ala Lys Arg Ala
```

```
             450               455               460
Ile Glu Glu Gly Gly Ser Ser His Arg Asn Leu Thr Met Leu Ile Glu
465                 470               475                 480

Asp Ile Ile His Gly Gly Gly Leu Ser Tyr Glu Lys Gly Ser Cys Arg
                485               490               495
```

<210> SEQ ID NO 90
<211> LENGTH: 1380
<212> TYPE: DNA
<213> ORGANISM: Siraitia grosvenorii

<400> SEQUENCE: 90

```
atggatgccc agcgaggtca caccaccacc attttgatgc ttccatgggt cggctacggc    60
catctcttgc ctttcctcga gctggccaaa agcctctcca ggaggaaatt attccacatc   120
tacttctgtt caacgtctgt tagcctcgac gccattaaac aaagcttcc tccttctatc    180 tcttctgatg attccatcca acttgtggaa cttcgtctcc cttcttctcc tgagttacct   240
cctcatcttc acacaaccaa cggccttccc tctcacctca tgcccgctct ccaccaagcc   300
ttcgtcatgg ccgcccaaca ctttcaggtc attttacaaa cacttgcccc gcatctcctc   360
atttatgaca ttctccaacc ttgggctcct caagtggctt catccctcaa cattccagcc   420
atcaacttca gtactaccgg agcttcaatg cttctcgaa cgcttcaccc tactcactac    480
ccaagttcta aattcccaat ctcagagttt gttcttcaca atcactggag agccatgtac   540
accaccgccg atggggctct tacagaagaa ggccacaaaa ttgaagaaac acttgcgaat   600
tgcttgcata cttcttgcgg ggtagttttg gtcaatagtt tcagagagct tgagacgaaa   660
tatatcgatt atctctctgt tctcttgaac aagaaagttg ttccggtcgg tcctttggtt   720
tacgaaccga atcaagaagg ggaagatgaa ggttattcaa gcatcaaaaa ttggcttgac   780
aaaaaggaac cgtcctcaac cgtcttcgtt tcatttggaa ccgaatactt cccgtcaaag   840
gaagaaatgg aagagatagc gtatgggtta gagctgagcg aggttaattt catctgggtc   900
cttagatttc ctcaaggaga cagcaccagc accattgaag acgccttgcc gaaggggttt   960
ctggagagag cggagagag ggcgatggtg gtgaagggtt gggctcctca ggcgaagata    1020
ctgaagcatt ggagcacagg ggggcttgtg agtcactgtg atggaactc gatgatggag    1080 ggcatgatgt ttggcgtacc cataatagcg gtcccgatgc atctggacca gcccttaac    1140 gccggactct tggaagaagc tggcgtcggc gtggaagcca agcgaggttc ggacggcaaa   1200
attcaaagag aagaagttgc aaagtcgatc aaagaagtgg tgattgagaa aaccagggaa   1260
gacgtgagga agaaagcaag agaaatgggt gagatttga ggagtaaagg agatgagaaa    1320
attgatgagt tggtggctga aatttctctt ttgcgcaaaa aggctccatg ttcaattaa    1380
```

<210> SEQ ID NO 91
<211> LENGTH: 1377
<212> TYPE: DNA
<213> ORGANISM: Siraitia grosvenorii

<400> SEQUENCE: 91

```
atggatgccc agcgaggtca caccacaacc attttgatgt ttccatggct cggctatggc    60
catctttcgg ctttcctaga gttggccaaa agcctctcaa ggaggaactt ccatatctac   120
ttctgttcaa cctctgttaa cctcgacgcc attaaaccaa agcttccttc ttcttcctct   180
tctgattcca tccaacttgt ggaactttgt cttccatctt ctcctgatca gctccctcct   240
catcttcaca caaccaacgc cctcccccct cacctcatgc ccactctcca ccaagccttc   300
```

```
tccatggctg cccaacactt tgctgccatt ttacacacac ttgctccgca tctcctcatt    360
tacgactctt tccaaccttg ggctcctcaa ctagcttcat ccctcaacat tccagccatc    420
aacttcaata ctacgggagc ttcagtcctg acccgaatgc ttcacgctac tcactaccca    480
agttctaaat tcccaatttc agagtttgtt ctccacgatt attggaaagc catgtacagc    540
gccgccggtg gggctgttac aaaaaaagac cacaaaattg agaaacact tgcgaattgc     600 ttgcatgctt cttgtagtgt aattctaatc aatagtttca gagagctcga ggagaaatat    660
atggattatc tctccgttct cttgaacaag aaagttgttc cggttggtcc tttggtttac    720
gaaccgaatc aagacgggga agatgaaggt tattcaagca tcaaaaattg gcttgacaaa    780
aaggaaccgt cctccaccgt cttcgtttca tttggaagcg aatacttccc gtcaaaggaa    840
gaaatggaag agatagccca tgggttagag gcgagcgagg ttcatttcat ctgggtcgtt    900
aggtttcctc aaggagacaa caccagcgcc attgaagatg ccttgccgaa ggggtttctg    960
gagagggtgg gagagagagg gatggtggtg aagggttggg ctcctcaggc gaagatactg    1020
aagcattgga gcacaggggg attcgtgagc cactgtggat ggaactcggt gatggaaagc    1080
atgatgtttg gcgttcccat aatagggtt ccgatgcatc tggaccagcc ctttaacgcc     1140
ggactcgcgg aagaagctgg cgtcggcgtg aagccaagc gagattcgga cggcaaaatt     1200
caaagagaag aagttgcaaa gtcgatcaaa gaagtggtga ttgagaaaac cagggaagac    1260
gtgaggaaga agcaagaga atgggtgag attttgagga gtaaaggaga tgagaaaatt      1320
gatgagttgg tggctgaaat ttctcttttg cgcaaaaagg ctccatgttc aatttaa       1377
```

<210> SEQ ID NO 92
<211> LENGTH: 1377
<212> TYPE: DNA
<213> ORGANISM: Artificial Sequence
<220> FEATURE:
<223> OTHER INFORMATION: Codon-optimized S. grosvenorii UGT98 nucleotide sequence

<400> SEQUENCE: 92

```
atggatgccc agcgaggtca caccacaacc attttgatgt ttccatggct cggctatggc    60
catctttcgg ctttcctaga gttggccaaa agcctctcaa ggaggaactt ccatatctac    120
ttctgttcaa cctctgttaa cctcgacgcc attaaaccaa agcttccttc ttcttcctct    180
tctgattcca tccaacttgt ggaactttgt cttccatctt ctcctgatca gctccctcct    240
catcttcaca caaccaacgc cctcccccct cacctcatgc ccactctcca ccaagccttc    300
tccatggctg cccaacactt tgctgccatt ttacacacac ttgctccgca tctcctcatt    360
tacgactctt tccaaccttg ggctcctcaa ctagcttcat ccctcaacat tccagccatc    420
aacttcaata ctacgggagc ttcagtcctg acccgaatgc ttcacgctac tcactaccca    480
agttctaaat tcccaatttc agagtttgtt ctccacgatt attggaaagc catgtacagc    540
gccgccggtg gggctgttac aaaaaaagac cacaaaattg agaaacact tgcgaattgc     600 ttgcatgctt cttgtagtgt aattctaatc aatagtttca gagagctcga ggagaaatat    660
atggattatc tctccgttct cttgaacaag aaagttgttc cggttggtcc tttggtttac    720
gaaccgaatc aagacgggga agatgaaggt tattcaagca tcaaaaattg gcttgacaaa    780
aaggaaccgt cctccaccgt cttcgtttca tttggaagcg aatacttccc gtcaaaggaa    840
gaaatggaag agatagccca tgggttagag gcgagcgagg ttcatttcat ctgggtcgtt    900
aggtttcctc aaggagacaa caccagcgcc attgaagatg ccttgccgaa ggggtttctg    960
```

-continued

```
gagagggtgg gagagagagg gatggtggtg aagggttggg ctcctcaggc gaagatactg    1020
aagcattgga gcacaggggg attcgtgagc cactgtggat ggaactcggt gatggaaagc    1080
atgatgtttg gcgttcccat aatagggggtt ccgatgcatc tggaccagcc ctttaacgcc    1140
ggactcgcgg aagaagctgg cgtcggcgtg aagccaagc gagattcgga cggcaaaatt    1200
caaagagaag aagttgcaaa gtcgatcaaa gaagtggtga ttgagaaaac cagggaagac    1260
gtgaggaaga aagcaagaga aatgggtgag attttgagga gtaaaggaga tgagaaaatt    1320
gatgagttgg tggctgaaat ttctcttttg cgcaaaaagg ctccatgttc aatttaa      1377
```

<210> SEQ ID NO 93
<211> LENGTH: 458
<212> TYPE: PRT
<213> ORGANISM: Siraitia grosvenorii

<400> SEQUENCE: 93

```
Met Asp Ala Gln Arg Gly His Thr Thr Thr Ile Leu Met Phe Pro Trp
1               5                   10                  15

Leu Gly Tyr Gly His Leu Ser Ala Phe Leu Glu Leu Ala Lys Ser Leu
            20                  25                  30

Ser Arg Arg Asn Phe His Ile Tyr Phe Cys Ser Thr Ser Val Asn Leu
        35                  40                  45

Asp Ala Ile Lys Pro Lys Leu Pro Ser Ser Ser Ser Asp Ser Ile
    50                  55                  60

Gln Leu Val Glu Leu Cys Leu Pro Ser Ser Pro Asp Gln Leu Pro Pro
65                  70                  75                  80

His Leu His Thr Thr Asn Ala Leu Pro Pro His Leu Met Pro Thr Leu
                85                  90                  95

His Gln Ala Phe Ser Met Ala Ala Gln His Phe Ala Ala Ile Leu His
            100                 105                 110

Thr Leu Ala Pro His Leu Leu Ile Tyr Asp Ser Phe Gln Pro Trp Ala
        115                 120                 125

Pro Gln Leu Ala Ser Ser Leu Asn Ile Pro Ala Ile Asn Phe Asn Thr
    130                 135                 140

Thr Gly Ala Ser Val Leu Thr Arg Met Leu His Ala Thr His Tyr Pro
145                 150                 155                 160

Ser Ser Lys Phe Pro Ile Ser Glu Phe Val Leu His Asp Tyr Trp Lys
                165                 170                 175

Ala Met Tyr Ser Ala Ala Gly Gly Ala Val Thr Lys Lys Asp His Lys
            180                 185                 190

Ile Gly Glu Thr Leu Ala Asn Cys Leu His Ala Ser Cys Ser Val Ile
        195                 200                 205

Leu Ile Asn Ser Phe Arg Glu Leu Glu Glu Lys Tyr Met Asp Tyr Leu
    210                 215                 220

Ser Val Leu Leu Asn Lys Lys Val Val Pro Val Gly Pro Leu Val Tyr
225                 230                 235                 240

Glu Pro Asn Gln Asp Gly Glu Asp Glu Gly Tyr Ser Ser Ile Lys Asn
                245                 250                 255

Trp Leu Asp Lys Lys Glu Pro Ser Ser Thr Val Phe Val Ser Phe Gly
            260                 265                 270

Ser Glu Tyr Phe Pro Ser Lys Glu Glu Met Glu Glu Ile Ala His Gly
        275                 280                 285

Leu Glu Ala Ser Glu Val His Phe Ile Trp Val Val Arg Phe Pro Gln
    290                 295                 300
```

Gly Asp Asn Thr Ser Ala Ile Glu Asp Ala Leu Pro Lys Gly Phe Leu
305                 310                 315                 320

Glu Arg Val Gly Glu Arg Gly Met Val Val Lys Gly Trp Ala Pro Gln
            325                 330                 335

Ala Lys Ile Leu Lys His Trp Ser Thr Gly Gly Phe Val Ser His Cys
        340                 345                 350

Gly Trp Asn Ser Val Met Glu Ser Met Met Phe Gly Val Pro Ile Ile
    355                 360                 365

Gly Val Pro Met His Leu Asp Gln Pro Phe Asn Ala Gly Leu Ala Glu
370                 375                 380

Glu Ala Gly Val Gly Val Glu Ala Lys Arg Asp Ser Asp Gly Lys Ile
385                 390                 395                 400

Gln Arg Glu Glu Val Ala Lys Ser Ile Lys Glu Val Val Ile Glu Lys
            405                 410                 415

Thr Arg Glu Asp Val Arg Lys Lys Ala Arg Glu Met Gly Glu Ile Leu
        420                 425                 430

Arg Ser Lys Gly Asp Glu Lys Ile Asp Glu Leu Val Ala Glu Ile Ser
    435                 440                 445

Leu Leu Arg Lys Lys Ala Pro Cys Ser Ile
    450                 455

<210> SEQ ID NO 94
<211> LENGTH: 1380
<212> TYPE: DNA
<213> ORGANISM: Siraitia grosvenorii

<400> SEQUENCE: 94
atggatgccc agcgaggtca caccaccacc attttgatgc ttccatgggt cggctacggc     60
catctcttgc ctttcctcga gctggccaaa agcctctcca ggaggaaatt attccacatc    120
tacttctgtt caacgtctgt tagcctcgac gccattaaac aaagcttcc tccttctatc     180
tcttctgatg attccatcca acttgtggaa cttcgtctcc cttcttctcc tgagttacct    240
cctcatcttc acacaaccaa cggccttccc tctcacctca tgcccgctct ccaccaagcc    300
ttcgtcatgg ccgcccaaca ctttcaggtc atttttacaaa cacttgcccc gcatctcctc    360
atttatgaca ttctccaacc ttgggctcct caagtggctt catccctcaa cattccagcc    420
atcaacttca gtactaccgg agcttcaatg ctttctcgaa cgcttcaccc tactcactac    480
ccaagttcta aattcccaat ctcagagttt gttcttcaca atcactggag agccatgtac    540
accaccgccg atgggctct acagaagaa ggccacaaaa ttgaagaaac acttgcgaat    600
tgcttgcata cttcttgcgg ggtagttttg gtcaatagtt tcagagagct gagacgaaa    660
tatatcgatt atctctctgt tctccttgaac aagaaagttg ttccggtcgg tcctttggtt    720
tacgaaccga atcaagaagg ggaagatgaa ggttattcaa gcatcaaaaa ttggcttgac    780
aaaaaggaac cgtcctcaac cgtcttcgtt tcatttggaa ccgaatactt cccgtcaaag    840
gaagaaatgg aagagatagc gtatgggtta gagctgagcg aggttaattt catctgggtc    900
cttagatttc tcaaggaga cagcaccagc accattgaag acgccttgcc gaagggtttt    960
ctggagagag cggagagag ggcgatggtg gtgaagggtt gggctcctca ggcgaagata   1020
ctgaagcatt ggagcacagg ggggcttgtg agtcactgtg atggaactc gatgatggag   1080
ggcatgatgt ttggcgtacc cataatagcg gtcccgatgc atctggacca gcccttttaac   1140
gccggactct tggaagaagc tggcgtcggc gtggaagcca agcgaggttc ggacggcaaa   1200

-continued

```
attcaaagag aagaagttgc aaagtcgatc aaagaagtgg tgattgagaa aaccagggaa    1260
gacgtgagga agaaagcaag agaaatgggt gagattttga ggagtaaagg agatgagaaa    1320
attgatgagt tggtggctga aatttctctt ttgcgcaaaa aggctccatg ttcaatttaa    1380
```

<210> SEQ ID NO 95
<211> LENGTH: 459
<212> TYPE: PRT
<213> ORGANISM: Siraitia grosvenorii

<400> SEQUENCE: 95

```
Met Asp Ala Gln Arg Gly His Thr Thr Thr Ile Leu Met Leu Pro Trp
1               5                   10                  15

Val Gly Tyr Gly His Leu Leu Pro Phe Leu Glu Leu Ala Lys Ser Leu
            20                  25                  30

Ser Arg Arg Lys Leu Phe His Ile Tyr Phe Cys Ser Thr Ser Val Ser
        35                  40                  45

Leu Asp Ala Ile Lys Pro Lys Leu Pro Pro Ser Ile Ser Ser Asp Asp
    50                  55                  60

Ser Ile Gln Leu Val Glu Leu Arg Leu Pro Ser Ser Pro Glu Leu Pro
65                  70                  75                  80

Pro His Leu His Thr Thr Asn Gly Leu Pro Ser His Leu Met Pro Ala
                85                  90                  95

Leu His Gln Ala Phe Val Met Ala Ala Gln His Phe Gln Val Ile Leu
            100                 105                 110

Gln Thr Leu Ala Pro His Leu Leu Ile Tyr Asp Ile Leu Gln Pro Trp
        115                 120                 125

Ala Pro Gln Val Ala Ser Ser Leu Asn Ile Pro Ala Ile Asn Phe Ser
    130                 135                 140

Thr Thr Gly Ala Ser Met Leu Ser Arg Thr Leu His Pro Thr His Tyr
145                 150                 155                 160

Pro Ser Ser Lys Phe Pro Ile Ser Glu Phe Val Leu His Asn His Trp
                165                 170                 175

Arg Ala Met Tyr Thr Thr Ala Asp Gly Ala Leu Thr Glu Glu Gly His
            180                 185                 190

Lys Ile Glu Glu Thr Leu Ala Asn Cys Leu His Thr Ser Cys Gly Val
        195                 200                 205

Val Leu Val Asn Ser Phe Arg Glu Leu Glu Thr Lys Tyr Ile Asp Tyr
    210                 215                 220

Leu Ser Val Leu Leu Asn Lys Lys Val Val Pro Val Gly Pro Leu Val
225                 230                 235                 240

Tyr Glu Pro Asn Gln Glu Gly Glu Asp Glu Gly Tyr Ser Ser Ile Lys
                245                 250                 255

Asn Trp Leu Asp Lys Lys Glu Pro Ser Ser Thr Val Phe Val Ser Phe
            260                 265                 270

Gly Thr Glu Tyr Phe Pro Ser Lys Glu Glu Met Glu Glu Ile Ala Tyr
        275                 280                 285

Gly Leu Glu Leu Ser Glu Val Asn Phe Ile Trp Val Leu Arg Phe Pro
    290                 295                 300

Gln Gly Asp Ser Thr Ser Thr Ile Glu Asp Ala Leu Pro Lys Gly Phe
305                 310                 315                 320

Leu Glu Arg Ala Gly Glu Arg Ala Met Val Val Lys Gly Trp Ala Pro
                325                 330                 335

Gln Ala Lys Ile Leu Lys His Trp Ser Thr Gly Gly Leu Val Ser His
            340                 345                 350
```

```
Cys Gly Trp Asn Ser Met Met Glu Gly Met Met Phe Gly Val Pro Ile
        355                 360                 365
Ile Ala Val Pro Met His Leu Asp Gln Pro Phe Asn Ala Gly Leu Leu
    370                 375                 380
Glu Glu Ala Gly Val Gly Val Glu Ala Lys Arg Gly Ser Asp Gly Lys
385                 390                 395                 400
Ile Gln Arg Glu Glu Val Ala Lys Ser Ile Lys Glu Val Val Ile Glu
                405                 410                 415
Lys Thr Arg Glu Asp Val Arg Lys Lys Ala Arg Glu Met Gly Glu Ile
            420                 425                 430
Leu Arg Ser Lys Gly Asp Glu Lys Ile Asp Glu Leu Val Ala Glu Ile
        435                 440                 445
Ser Leu Leu Arg Lys Lys Ala Pro Cys Ser Ile
    450                 455
```

<210> SEQ ID NO 96
<211> LENGTH: 1359
<212> TYPE: DNA
<213> ORGANISM: Siraitia grosvenorii

<400> SEQUENCE: 96

```
atggatgcaa aagaagaaag cttgaaagtt tttatgcttc catggttggc ccatggtcat      60
atatcgccct acctagagct agccaagagg cttgcaaaga gaaatttcct tgtttatttc     120
tgctccacgc ctgtaaattt ggaagccatt aaaccaaagc tttccaaaag ctactctgat     180
tcgatccaac taatggaggt tcctctcgaa tcgacgccgg agcttcctcc tcactatcat     240
acagccaaag gccttccgcc gcatttaatg cccaaactca tgaatgcctt aaaatggtt      300
gctcccaatc tcgaatcgat cctaaaaacc ctaaacccag atctgctcat cgtcgacatt     360
ctccttccat ggatgcttcc actcgcttca tcgctcaaaa ttccgatggt tttcttcact     420
attttcggtg ccatggccat ctcctttatg atttataatc gaaccgtctc gaacgagctt     480
ccatttccag aatttgaact tcacgagtgc tggaaatcga agtgccccta tttgttcaag     540
gaccaagcgg aaagtcaatc gttcttagaa tacttggatc aatcttcagg cgtaattttg     600
atcaaaactt ccagagagat tgaggctaag tatgtagact ttctcacttc gtcgtttacg     660
aagaaggttt gaccaccgg tcccctggtt cagcaaccct tcttccggcg agacgagaag      720
cagtactccg atatcatcga tggctagac aagaaggagc cgttatcgac ggtgctcgtt      780
tcgtttggga gcgagtatta tctgtcaaag gaagagatgg aagaaatcgc ctacgggctg     840
gagagcgcca gcgaggtgaa tttcatctgg attgttaggt ttccgatggg acaggaaacg     900
gaggtcgagg cggcgctgcc ggagggttc atccagaggg caggagagag agggaaagtg      960
gtcgagggct gggctccgca gcgaaaata ttggcgcatc cgagcaccgg cggccatgtg     1020
agccacaacg ggtggagctc gattgtggag tgcttgatgt ccggtgtacc ggtgatcggc    1080
gcgccgatgc aacttgacgg gccaatcgtc gcaaggctgg tggaggagat cggcgtgggt    1140
ttggaaatca agagagatga ggaagggaga atcacgaggg gcgaagttgc cgatgcaatc    1200
aagacggtgg cggtgggcaa aaccggggaa gatttttagaa ggaaagcaaa aaaaatcagc   1260
agcattttga agatgaaaga tgaagaagag gttgacactt tggcaatgga attagtgagg   1320
ttatgccaaa tgaaaagagg gcaggagtct caggactaa                           1359
```

<210> SEQ ID NO 97
<211> LENGTH: 1359

<212> TYPE: DNA
<213> ORGANISM: Artificial Sequence
<220> FEATURE:
<223> OTHER INFORMATION: Codon-optimized S. grosvenorii UGT11789
      nucleotide sequence

<400> SEQUENCE: 97

```
atggacgcca aagaagaatc cttgaaggtt tttatgttgc catggttggc tcatggtcat      60
atttctccat atttggaatt ggctaagaga ttggccaaga gaaagttctt ggtttacttc     120
tgttctaccc cagttaactt ggaagctatt aagccaaagt tgtccaagtc ctactccgat     180
tctattcaat gatggaagt cccattggaa tccactccag aattgccacc acattatcat      240
actgctaaag gtttgccacc tcatttgatg ccaaaattga tgaacgcttt caagatggtt     300
gctccaaact tggaatcaat cttgaaaacc ttgaacccag acttgttgat cgttgatatt     360
ttgttgcctt ggatgttgcc tttggcctcc tctttgaaaa ttcctatggt tttcttcacc     420
atcttcggtg ctatggctat ttctttcatg atctacaaca gaaccgtttc caacgaattg     480
ccatttccag aatttgaatt gcacgaatgc tggaagtcta agtgtccata cttgtttaag     540
gatcaagccg aatcccaatc cttcttggaa tatttggatc aatcctccgg tgtcattttg     600
atcaagacct ctagagaaat gaagccaag tacgttgatt tcttgacctc ttcattcacc      660
aagaaggttg ttactactgg tccattggtt caacaaccat catctggtga agatgaaaag     720
caatactccg atatcattga tggttggac aagaagaaac cattgtccac tgttttggtt      780
tctttcggtt ccgaatatta cttgtctaaa gaagaaatgg aagaaatcgc ctacggtttg     840
gaatctgctt ctgaagttaa tttcatctgg atcgtcagat cccaatggg tcaagaaact      900 gaagttgaag ctgctttgcc agaaggtttt attcaaagag ctggtgaaag aggtaaagtt     960
gttgaaggtt gggctccaca agctaagatt ttggctcatc catctactgg tggtcacgtt    1020
tctcataatg ttggtcatc tatcgttgaa tgcttgatgt ctggtgttcc agttattggt     1080
gctccaatgc aattggatgg tccaatagtt gctagattgg tcgaagaaat tggtgttggt    1140
ttggaaatca agagagatga agaaggtaga atcaccagag gtgaagttgc tgatgctatt    1200
aagactgttg ctgttggtaa aaccggtgaa gattttagaa gaaaggccaa gaagatctcc    1260
tccattttaa agatgaagga cgaagaagaa gttgacacct tggctatgga attggttaga    1320
ttgtgtcaaa tgaagagagg tcaagaatcc caagactga                           1359
```

<210> SEQ ID NO 98
<211> LENGTH: 1359
<212> TYPE: DNA
<213> ORGANISM: Artificial Sequence
<220> FEATURE:
<223> OTHER INFORMATION: Codon-optimized S. grosvenorii UGT11789
      nucleotide sequence

<400> SEQUENCE: 98

```
atggatgcta aggaagaatc tttgaaagtc tttatgctgc cttggttggc tcacggtcat      60
atttccccgt atttggaatt ggcaaaaaga ctggccaaga gaaaattctt agtgtatttc     120
tgttcaactc cagtgaattt ggaagccatc aaaccaaaat tgtctaagtc atattctgac     180
tctatacaac tgatggaagt tcctttggaa agtacaccgg aactgccacc ccattatcat     240
acagctaaag gttacccccc acacttgatg cccaagctaa tgaatgcatt taagatggtc     300
gcaccaaatc tggaaagtat acttaagacg ctaaaccctg attttattaat tgtagatatc     360 cttctaccat ggatgttgcc cttagcttca tctttaaaaa ttccgatggt tttttttcact    420
```

```
atctttggag ccatggcaat ttcctttatg atttacaata gaacagtctc aaatgagtta      480
cctttcccag agtttgaatt acatgaatgc tggaaatcta aatgtccata tttgttcaaa      540
gaccaagcag aatcccaatc tttcttagaa tacttagatc agagttccgg agttatcttg      600
atcaagacat ctagggaaat tgaagcaaag tatgtggact ttttgacctc cagtttttact     660 aagaaagtcg taacaacggg tcctctagtc caacaaccta gttcaggaga ggatgagaaa      720
caatatagcg atataatcga atggttagat aaaaaagagc cattgagtac cgttctagtg      780
tcctttggtt cagaatatta tttgtctaaa gaagagatgg aagagattgc ctacggctta      840
gaatcagctt ccgaagtaaa ctttatatgg attgtcagat ttcccatggg acaagaaacc      900
gaggtcgaag cagctttgcc cgaaggtttt attcaacgtg ccggcgaaag aggaaaagta      960
gtggaaggtt gggctccaca agccaaaatt ctagctcacc cgtccactgg tggtcatgtc      1020
tctcataacg gatggagttc aattgttgaa tgtttgatga gtggtgttcc agtgatagga      1080
gctcctatgc agctggacgg tccaatagtc gccaggttag tcgaagaaat tggtgttggt      1140
ttagaaataa agagagacga agaaggtaga attactagag tgaagtagc agatgcaatt       1200 aaaactgttg ctgtcggcaa gactggagag gattttcgta gaaaagccaa aaaatatca       1260 tctatactaa aaatgaaaga cgaagaggag gttgatacgc tggcgatgga actagttaga      1320
ttgtgtcaga tgaagcgtgg tcaggaaagt caagactaa                             1359
```

<210> SEQ ID NO 99
<211> LENGTH: 452
<212> TYPE: PRT
<213> ORGANISM: Siraitia grosvenorii

<400> SEQUENCE: 99

```
Met Asp Ala Lys Glu Glu Ser Leu Lys Val Phe Met Leu Pro Trp Leu
1               5                   10                  15

Ala His Gly His Ile Ser Pro Tyr Leu Glu Leu Ala Lys Arg Leu Ala
            20                  25                  30

Lys Arg Lys Phe Leu Val Tyr Phe Cys Ser Thr Pro Val Asn Leu Glu
        35                  40                  45

Ala Ile Lys Pro Lys Leu Ser Lys Ser Tyr Ser Asp Ser Ile Gln Leu
    50                  55                  60

Met Glu Val Pro Leu Glu Ser Thr Pro Glu Leu Pro Pro His Tyr His
65                  70                  75                  80

Thr Ala Lys Gly Leu Pro Pro His Leu Met Pro Lys Leu Met Asn Ala
                85                  90                  95

Phe Lys Met Val Ala Pro Asn Leu Glu Ser Ile Leu Lys Thr Leu Asn
            100                 105                 110

Pro Asp Leu Leu Ile Val Asp Ile Leu Leu Pro Trp Met Leu Pro Leu
        115                 120                 125

Ala Ser Ser Leu Lys Ile Pro Met Val Phe Phe Thr Ile Phe Gly Ala
    130                 135                 140

Met Ala Ile Ser Phe Met Ile Tyr Asn Arg Thr Val Ser Asn Glu Leu
145                 150                 155                 160

Pro Phe Pro Glu Phe Glu Leu His Glu Cys Trp Lys Ser Lys Cys Pro
                165                 170                 175

Tyr Leu Phe Lys Asp Gln Ala Glu Ser Gln Ser Phe Leu Glu Tyr Leu
            180                 185                 190

Asp Gln Ser Ser Gly Val Ile Leu Ile Lys Thr Ser Arg Glu Ile Glu
        195                 200                 205
```

```
Ala Lys Tyr Val Asp Phe Leu Thr Ser Ser Phe Thr Lys Lys Val Val
    210                 215                 220

Thr Thr Gly Pro Leu Val Gln Gln Pro Ser Ser Gly Glu Asp Glu Lys
225                 230                 235                 240

Gln Tyr Ser Asp Ile Ile Glu Trp Leu Asp Lys Lys Glu Pro Leu Ser
                245                 250                 255

Thr Val Leu Val Ser Phe Gly Ser Glu Tyr Tyr Leu Ser Lys Glu Glu
                260                 265                 270

Met Glu Glu Ile Ala Tyr Gly Leu Leu Ser Ala Ser Glu Val Asn Phe
            275                 280                 285

Ile Trp Ile Val Arg Phe Pro Met Gly Gln Glu Thr Glu Val Glu Ala
290                 295                 300

Ala Leu Pro Glu Gly Phe Ile Gln Arg Ala Gly Glu Arg Gly Lys Val
305                 310                 315                 320

Val Glu Gly Trp Ala Pro Gln Ala Lys Ile Leu Ala His Pro Ser Thr
                325                 330                 335

Gly Gly His Val Ser His Asn Gly Trp Ser Ser Ile Val Glu Cys Leu
                340                 345                 350

Met Ser Gly Val Pro Val Ile Gly Ala Pro Met Gln Leu Asp Gly Pro
            355                 360                 365

Ile Val Ala Arg Leu Val Glu Glu Ile Gly Val Gly Leu Glu Ile Lys
370                 375                 380

Arg Asp Glu Glu Gly Arg Ile Thr Arg Gly Glu Val Ala Asp Ala Ile
385                 390                 395                 400

Lys Thr Val Ala Val Gly Lys Thr Gly Glu Asp Phe Arg Arg Lys Ala
                405                 410                 415

Lys Lys Ile Ser Ser Ile Leu Lys Met Lys Asp Glu Glu Val Asp
                420                 425                 430

Thr Leu Ala Met Glu Leu Val Arg Leu Cys Gln Met Lys Arg Gly Gln
            435                 440                 445

Glu Ser Gln Asp
    450

<210> SEQ ID NO 100
<211> LENGTH: 1434
<212> TYPE: DNA
<213> ORGANISM: Siraitia grosvenorii

<400> SEQUENCE: 100
atgcttccat ggctggctca cggccatgtc tcccctttct tcgagctcgc caagttgctc      60
gccgctagaa acttccacat attcttctgc tccaccgccg taaacctccg ctccgtcgaa     120
ccaaaactct ctcagaagct ctcctcccac gtggagctgg tggagctcaa cctaccgccc     180
tcgccggagc tccctccgca ccgccacacc accgccggcc ttccaccgca cctcatgttc     240
tcgctcaagc gagctttcga catggccgct cccgccttcg ccgccatcct ccgcgacctg     300
aacccggact tgctcatcta cgacttcctg cagccgtggg cggcggcgga ggctctgtcg     360
gcggatattc cggccgtgat gttcaaaagc acgggtgcgc tcatggcggc catggtcgcg     420
tacgagctga cgtttccgaa ctctgatttt ttctcgcttt tccctgagat tgtctctcc      480 gagtgcgaga ttaaacagct gaagaacttg tttcaatgtt ctgtgaatga tgcgaaagac     540
aagcaaagga ttaagggatg ttatgagaga tcttgcggca tgattttggt gaaatctttc     600
agagaaatcg aaggcaaata tattgatttt ctctctactc tgctgggcaa gaaggttgtt     660
ccagttggtc cacttgttca acaaacagaa gacgacgtcg tatcaggaag ttttgacgaa     720
```

| | |
|---|---|
| tggctaaatg gaaaagatag atcgtcttcc atactcgtgt ctttcggaag cgagttctac | 780 |
| ctgtccagag aagacatgga agagatcgcg catggcttag agctgagcca ggtgaacttc | 840 |
| atatgggtcg tcaggtttcc ggcgggagga gagagaaaca cgacaaaggt ggaagaagaa | 900 |
| ctgccaaaag ggtttctaga gagagttaga gagagaggga tggtggtgga gggctgggcg | 960 |
| ccgcaggctc agatcttgaa acatccaagc gtcggcggat tcctcagcca ctgcgggtgg | 1020 |
| agctccgtcg tggagagcat gaaattcggc gttccgatca tcgccatgcc gatgcacctc | 1080 |
| gaccagccgc tgaattcccg gctggtcgag cggctcggcg tcggcgtagt ggtggagaga | 1140 |
| gacggccgcc tccggggaga ggtggagaga gttgtcagag aggtggtggt ggagaaaagt | 1200 |
| ggagagagag tgaggaagaa ggtggaggag tttgcagaga tcatgaagaa gaaaaaagac | 1260 |
| aatgaagaga tggacgtagt cgtggaagag ttggtgacgc tctgcaggaa gaagaagaag | 1320 |
| gaggaggatt tacagagtaa ttattggtgc agaaccgcca ttgatgacca ttgttctgaa | 1380 |
| gtcgtgaaga ttgaagatgc tgcagcagcc gacgaggagc tctctttgcaa ataa | 1434 |

<210> SEQ ID NO 101
<211> LENGTH: 477
<212> TYPE: PRT
<213> ORGANISM: Siraitia grosvenorii

<400> SEQUENCE: 101

```
Met Leu Pro Trp Leu Ala His Gly His Val Ser Pro Phe Phe Glu Leu
1               5                   10                  15

Ala Lys Leu Leu Ala Ala Arg Asn Phe His Ile Phe Phe Cys Ser Thr
            20                  25                  30

Ala Val Asn Leu Arg Ser Val Glu Pro Lys Leu Ser Gln Lys Leu Ser
        35                  40                  45

Ser His Val Glu Leu Val Glu Leu Asn Leu Pro Pro Ser Pro Glu Leu
    50                  55                  60

Pro Pro His Arg His Thr Thr Ala Gly Leu Pro Pro His Leu Met Phe
65                  70                  75                  80

Ser Leu Lys Arg Ala Phe Asp Met Ala Ala Pro Ala Phe Ala Ala Ile
                85                  90                  95

Leu Arg Asp Leu Asn Pro Asp Leu Leu Ile Tyr Asp Phe Leu Gln Pro
            100                 105                 110

Trp Ala Ala Glu Ala Leu Ser Ala Asp Ile Pro Ala Val Met Phe
        115                 120                 125

Lys Ser Thr Gly Ala Leu Met Ala Ala Met Val Ala Tyr Glu Leu Thr
    130                 135                 140

Phe Pro Asn Ser Asp Phe Phe Ser Leu Phe Pro Glu Ile Arg Leu Ser
145                 150                 155                 160

Glu Cys Glu Ile Lys Gln Leu Lys Asn Leu Phe Gln Cys Ser Val Asn
                165                 170                 175

Asp Ala Lys Asp Lys Gln Arg Ile Lys Gly Cys Tyr Glu Arg Ser Cys
            180                 185                 190

Gly Met Ile Leu Val Lys Ser Phe Arg Glu Ile Glu Gly Lys Tyr Ile
        195                 200                 205

Asp Phe Leu Ser Thr Leu Leu Gly Lys Lys Val Pro Val Gly Pro
    210                 215                 220

Leu Val Gln Gln Thr Glu Asp Asp Val Val Ser Gly Ser Phe Asp Glu
225                 230                 235                 240

Trp Leu Asn Gly Lys Asp Arg Ser Ser Ser Ile Leu Val Ser Phe Gly
```

```
                      245                 250                 255
         Ser Glu Phe Tyr Leu Ser Arg Glu Asp Met Glu Glu Ile Ala His Gly
                         260                 265                 270

Leu Glu Leu Ser Gln Val Asn Phe Ile Trp Val Val Arg Phe Pro Ala
                         275                 280                 285

Gly Gly Glu Arg Asn Thr Thr Lys Val Glu Glu Leu Pro Lys Gly
                         290                 295                 300

Phe Leu Glu Arg Val Arg Glu Arg Gly Met Val Val Glu Gly Trp Ala
         305                 310                 315                 320

Pro Gln Ala Gln Ile Leu Lys His Pro Ser Val Gly Gly Phe Leu Ser
                         325                 330                 335

His Cys Gly Trp Ser Ser Val Val Glu Ser Met Lys Phe Gly Val Pro
                         340                 345                 350

Ile Ile Ala Met Pro Met His Leu Asp Gln Pro Leu Asn Ser Arg Leu
                         355                 360                 365

Val Glu Arg Leu Gly Val Gly Val Val Glu Arg Asp Gly Arg Leu
                         370                 375                 380

Arg Gly Glu Val Glu Arg Val Val Arg Glu Val Val Glu Lys Ser
         385                 390                 395                 400

Gly Glu Arg Val Arg Lys Lys Val Glu Glu Phe Ala Glu Ile Met Lys
                         405                 410                 415

Lys Lys Lys Asp Asn Glu Glu Met Asp Val Val Glu Leu Val
                         420                 425                 430

Thr Leu Cys Arg Lys Lys Lys Glu Glu Asp Leu Gln Ser Asn Tyr
                         435                 440                 445

Trp Cys Arg Thr Ala Ile Asp Asp His Cys Ser Glu Val Val Lys Ile
                         450                 455                 460

Glu Asp Ala Ala Ala Ala Asp Glu Glu Pro Leu Cys Lys
         465                 470                 475

<210> SEQ ID NO 102
         <211> LENGTH: 1383
         <212> TYPE: DNA
         <213> ORGANISM: Siraitia grosvenorii

<400> SEQUENCE: 102
atggctgtca cttacagcct gcacatagca atgtacccct tggtttgctt tcggccacttg     60 actccatttc tccaagtctc caacaagctt gccaaggaag ccacaaaaat ctccttcttc    120
atcccaacga aaacgctaac caaattgcag cctttcaatc tctttccaga tctcattacc    180
tttgtcccca tcactgttcc tcatgttgat ggtctccctc ttggagctga gactactgct    240
gatgtttctc acccttcaca gctcagtctc atcatgactg ctatggattg cacccaaccc    300
gaaatcgagt gtcttcttcg agacataaaa cctgatgcca tcttcttcga tttcgcgcac    360
tgggtgccaa aattggcatg tggattgggc attaagtcga ttgattacag tgtctgttct    420
gcagtatcaa ttggttatgt tttgccccta ttaaggaaag tttgtggaca agatttatta    480
actgaagatg attttatgca gccatctcct ggctacccga gttccaccat caatcttcaa    540
gctcatgagg ctcgatattt tgcatctctg agccgctgga ggtttggcag tgatgtccct    600
ttctttagtc gccatcttac tgcacttaat gaatgcaatg ctttagcatt caggtcatgt    660
agggagattg aagggccttt tatagactat ccagaaagtg aattaaaaaa gcctgtgttg    720
cttttccgga gcagtggatct acaaccgcca ccacaactg tagaagaaag atgggcaaaa    780
tggctatcag ggttcaacac cgactcggtc gtatattgtg catttggaag tgagtgtacc    840
```

```
ttagcaaaag accaattcca agaactgctg ttgggttttg agctttcaaa tatgccattc    900
tttgctgcac ttaaaccacc ttttggtgtt gactcggttg aagcagcctt gcctgaaggt    960
tttgaacaga gagttcaggg aagaggggtg gtctatgggg gatgggtcca acagcagctc   1020
attttggagc acccatcaat tggatgcttt gttacacatt gtggatcagg ctccttatca   1080
gaggcgttag tgaagaagtg tcaattagtg ttgttacctc gtatcggtga ccactttttc   1140
cgagcaagaa tgttgagcaa ttatttgaaa gttggtgtgg aggtagagaa aggagaagga   1200
gatggatctt ttacaaagga aagtgtgtgg aaggcagtga agacagtgat ggatgaagag   1260
aatgaaactg ggaaagagtt cagagcgaac cgtgccaaga taagagagct attgctcgac   1320
gaagatctcg aggagtctta tatcaacaat ttcatccaca gcctgcatac tttgaatgca   1380
tga                                                                1383
```

<210> SEQ ID NO 103
<211> LENGTH: 460
<212> TYPE: PRT
<213> ORGANISM: Siraitia grosvenorii

<400> SEQUENCE: 103

```
Met Ala Val Thr Tyr Ser Leu His Ile Ala Met Tyr Pro Trp Phe Ala
1               5                   10                  15

Phe Gly His Leu Thr Pro Phe Leu Gln Val Ser Asn Lys Leu Ala Lys
            20                  25                  30

Glu Gly His Lys Ile Ser Phe Phe Ile Pro Thr Lys Thr Leu Thr Lys
        35                  40                  45

Leu Gln Pro Phe Asn Leu Phe Pro Asp Leu Ile Thr Phe Val Pro Ile
    50                  55                  60

Thr Val Pro His Val Asp Gly Leu Pro Leu Gly Ala Glu Thr Thr Ala
65                  70                  75                  80

Asp Val Ser His Pro Ser Gln Leu Ser Leu Ile Met Thr Ala Met Asp
                85                  90                  95

Cys Thr Gln Pro Glu Ile Glu Cys Leu Leu Arg Asp Ile Lys Pro Asp
            100                 105                 110

Ala Ile Phe Phe Asp Phe Ala His Trp Val Pro Lys Leu Ala Cys Gly
        115                 120                 125

Leu Gly Ile Lys Ser Ile Asp Tyr Ser Val Cys Ser Ala Val Ser Ile
    130                 135                 140

Gly Tyr Val Leu Pro Leu Leu Arg Lys Val Cys Gly Gln Asp Leu Leu
145                 150                 155                 160

Thr Glu Asp Asp Phe Met Gln Pro Ser Pro Gly Tyr Pro Ser Ser Thr
                165                 170                 175

Ile Asn Leu Gln Ala His Glu Ala Arg Tyr Phe Ala Ser Leu Ser Arg
            180                 185                 190

Trp Arg Phe Gly Ser Asp Val Pro Phe Phe Ser Arg His Leu Thr Ala
        195                 200                 205

Leu Asn Glu Cys Asn Ala Leu Ala Phe Arg Ser Cys Arg Glu Ile Glu
    210                 215                 220

Gly Pro Phe Ile Asp Tyr Pro Glu Ser Glu Leu Lys Lys Pro Val Leu
225                 230                 235                 240

Leu Ser Gly Ala Val Asp Leu Gln Pro Pro Thr Thr Val Glu Glu
                245                 250                 255

Arg Trp Ala Lys Trp Leu Ser Gly Phe Asn Thr Asp Ser Val Val Tyr
            260                 265                 270
```

```
Cys Ala Phe Gly Ser Glu Cys Thr Leu Ala Lys Asp Gln Phe Gln Glu
            275                 280                 285

Leu Leu Leu Gly Phe Glu Leu Ser Asn Met Pro Phe Phe Ala Ala Leu
        290                 295                 300

Lys Pro Pro Phe Gly Val Asp Ser Val Glu Ala Ala Leu Pro Glu Gly
305                 310                 315                 320

Phe Glu Gln Arg Val Gln Gly Arg Gly Val Val Tyr Gly Gly Trp Val
                325                 330                 335

Gln Gln Gln Leu Ile Leu Glu His Pro Ser Ile Gly Cys Phe Val Thr
            340                 345                 350

His Cys Gly Ser Gly Ser Leu Ser Glu Ala Leu Val Lys Lys Cys Gln
            355                 360                 365

Leu Val Leu Leu Pro Arg Ile Gly Asp His Phe Phe Arg Ala Arg Met
        370                 375                 380

Leu Ser Asn Tyr Leu Lys Val Gly Val Glu Val Glu Lys Gly Glu Gly
385                 390                 395                 400

Asp Gly Ser Phe Thr Lys Glu Ser Val Trp Lys Ala Val Lys Thr Val
                405                 410                 415

Met Asp Glu Glu Asn Glu Thr Gly Lys Glu Phe Arg Ala Asn Arg Ala
            420                 425                 430

Lys Ile Arg Glu Leu Leu Leu Asp Glu Asp Leu Glu Glu Ser Tyr Ile
        435                 440                 445

Asn Asn Phe Ile His Ser Leu His Thr Leu Asn Ala
450                 455                 460

<210> SEQ ID NO 104
<211> LENGTH: 1347
<212> TYPE: DNA
<213> ORGANISM: Siraitia grosvenorii

<400> SEQUENCE: 104
atggaagcta agaactgcaa aaaggttctg atgttcccat ggctggcgca tggtcacata      60
tcaccatttg tagagctggc caagaagctc acagacaaca acttcgccgt ttttctatgt     120
tcttcccctg caaatcttca aaacgtcaag ccaaaactcc cccatcacta ctctgattcc     180
attgaactcg tggagctcaa ccttccatcg tcgccggagc ttccccctca tatgcacacc     240
accaatggcc tcccttttgca tttagttccc accctcgttg acgccttgga catggccgct     300
ccgcacttct ccgccatttt acaggaactg aatccagatt ttctcatatt cgacatcttc     360
caaccctggg cggctgaaat cgcttcctcc ttcggcgttc ctgctatttt gttgcttatc     420
gttggatctg ctataaccgc tttaggggtt catttgtcc ggagctccgg tacggaattc     480
ccctttcccg agcttactaa atcattcaag aaggaggacg accgaaaacc tccaggagat     540
tccggcaacg atagaggaaa acggctattc aaatgtctgc tggacctgga acattcttca     600
gagactattt tggtgaacag ttttacagag atagagggca aatatatgga ctatctctcg     660
gtcttactga agaagaagat ccttccgatt ggtcctttgg ttcagaaaat ggctccgat      720 gacgatgaat cgggaatcct ccggtggctt gacaagaaga aaccgaattc aactgtgtac     780
gtttcgttcg ggagtgagta ctatttgagc aagaagaca tagcagagct tgcgcatggt      840
ctggaaatca gcggcgtcaa tttcatctgg attgttcggt ttccaaaggg agagaaaatc     900
gccattgaag aggcattacc agatgaattt cttgaaagag tcggagagag aggcgtcgtc     960
gttgatggat gggcgccgca gatgaaaata ttagggcatt cgagcgtcgg cgggtttctg    1020
```

```
tctcactgcg atggaactc tgtgctggag agtctggtgc tcggcgtgcc gatcatatcc    1080
ctgccgatac acctcgaaca gccgtggaac gccttggtag cggagcacgt cggcgtttgt    1140
gtgagggcga agagagacga cggaggaaat cttcaaagag agttggtggc ggaggccatt    1200
aaagaagtgg tggttgagga aacaggagcg gaactgagaa gcaaagcaag agtaattagt    1260
gaaatcttga aaataaaga agctgaaaca atacaagatt tggtggctga gcttcaccgg    1320
ctttctgacg caagaagagc ttgttga                                       1347
```

<210> SEQ ID NO 105
<211> LENGTH: 448
<212> TYPE: PRT
<213> ORGANISM: Siraitia grosvenorii

<400> SEQUENCE: 105

```
Met Glu Ala Lys Asn Cys Lys Lys Val Leu Met Phe Pro Trp Leu Ala
1               5                   10                  15

His Gly His Ile Ser Pro Phe Val Glu Leu Ala Lys Lys Leu Thr Asp
            20                  25                  30

Asn Asn Phe Ala Val Phe Leu Cys Ser Ser Pro Ala Asn Leu Gln Asn
        35                  40                  45

Val Lys Pro Lys Leu Pro His His Tyr Ser Asp Ser Ile Glu Leu Val
    50                  55                  60

Glu Leu Asn Leu Pro Ser Ser Pro Glu Leu Pro Pro His Met His Thr
65                  70                  75                  80

Thr Asn Gly Leu Pro Leu His Leu Val Pro Thr Leu Val Asp Ala Leu
                85                  90                  95

Asp Met Ala Ala Pro His Phe Ser Ala Ile Leu Gln Glu Leu Asn Pro
            100                 105                 110

Asp Phe Leu Ile Phe Asp Ile Phe Gln Pro Trp Ala Ala Glu Ile Ala
        115                 120                 125

Ser Ser Phe Gly Val Pro Ala Ile Leu Leu Ile Val Gly Ser Ala
    130                 135                 140

Ile Thr Ala Leu Gly Val His Phe Val Arg Ser Ser Gly Thr Glu Phe
145                 150                 155                 160

Pro Phe Pro Glu Leu Thr Lys Ser Phe Lys Lys Glu Asp Asp Arg Lys
                165                 170                 175

Pro Pro Gly Asp Ser Gly Asn Asp Arg Gly Lys Arg Leu Phe Lys Cys
            180                 185                 190

Leu Leu Asp Leu Glu His Ser Ser Glu Thr Ile Leu Val Asn Ser Phe
        195                 200                 205

Thr Glu Ile Glu Gly Lys Tyr Met Asp Tyr Leu Ser Val Leu Leu Lys
    210                 215                 220

Lys Lys Ile Leu Pro Ile Gly Pro Leu Val Gln Lys Ile Gly Ser Asp
225                 230                 235                 240

Asp Asp Glu Ser Gly Ile Leu Arg Trp Leu Asp Lys Lys Pro Asn
                245                 250                 255

Ser Thr Val Tyr Val Ser Phe Gly Ser Glu Tyr Tyr Leu Ser Lys Glu
            260                 265                 270

Asp Ile Ala Glu Leu Ala His Gly Leu Glu Ile Ser Gly Val Asn Phe
        275                 280                 285

Ile Trp Ile Val Arg Phe Pro Lys Gly Glu Lys Ile Ala Ile Glu Glu
    290                 295                 300

Ala Leu Pro Asp Glu Phe Leu Glu Arg Val Gly Glu Arg Gly Val Val
305                 310                 315                 320
```

```
Val Asp Gly Trp Ala Pro Gln Met Lys Ile Leu Gly His Ser Ser Val
                325                 330                 335

Gly Gly Phe Leu Ser His Cys Gly Trp Asn Ser Val Leu Glu Ser Leu
            340                 345                 350

Val Leu Gly Val Pro Ile Ile Ser Leu Pro Ile His Leu Glu Gln Pro
        355                 360                 365

Trp Asn Ala Leu Val Ala Glu His Val Gly Val Cys Val Arg Ala Lys
370                 375                 380

Arg Asp Asp Gly Gly Asn Leu Gln Arg Glu Leu Val Ala Glu Ala Ile
385                 390                 395                 400

Lys Glu Val Val Val Glu Glu Thr Gly Ala Glu Leu Arg Ser Lys Ala
                405                 410                 415

Arg Val Ile Ser Glu Ile Leu Lys Asn Lys Glu Ala Glu Thr Ile Gln
                420                 425                 430

Asp Leu Val Ala Glu Leu His Arg Leu Ser Asp Ala Arg Arg Ala Cys
            435                 440                 445

<210> SEQ ID NO 106
<211> LENGTH: 1389
<212> TYPE: DNA
<213> ORGANISM: Siraitia grosvenorii

<400> SEQUENCE: 106
atggaaaaaa atcttcacat agtgatgctt ccatggtcgg cgttcggcca tctcatacca      60
ttttttcacc tctccatagc cttagccaaa gccaaagttt atatctcctt cgtctcccact    120 ccaagaaata ttcagagact yccccaaatc ccgccggact tagcttcttt catagatttg    180
gtggccattc ccttgccgag actcgacgac gatctgttgc tagaatctgc agaggccact    240
tctgatattc cgatcgacaa gattcagtat ttgaagcgag ccgtcgacct cctccgccac    300
cccttcaaga gtttgtcgc cgaacaatcg ccggactggg tcgtcgttga ttttcatgct    360
tattgggccg gcgagatcta ccaggagttt caagttcccg tcgcctactt ctgtatttc    420 tcggccatct gtttgcttta tcttggacct ccagacgtgt attcgaagga tcctcagatc    480
atggcacgaa tatctcccgt taccatgacg gtgccgccgg agtgggtcgg ttttccgtcc    540
gccgtagcct acaacttgca tgaggcgacg gtcatgtact ctgctctcta tgaaacaaat    600
gggtctggaa taagcgactg cgagaggatt cgccggctcg tcctttcctg tcaagccgtg    660
gccattcgaa gctgcgagga gattgaaggc gaataccttta ggttatgtaa gaaactgatt    720
ccaccgcagg ggattgccgt cggcttgctt ccgccggaaa agccaccaaa atcagatcac    780
gagctcatca aatggcttga cgagcaaaag ctccgattcg tcgtgtacgt gacattcggc    840
agcgaatgca acctgacgaa ggaccaagtt cacgagatag cccacgggct ggaactgtcg    900
gagctgccat ttttatgggc actgaggaaa cccagctggg cagctgagga agacgatggg    960
ctgccgtctg ggtttcgtga gaaacgtcc gggagagggg tggtgagcat ggagtgggtg   1020
ccgcagttgg agattctggc gcaccaggcc atcggcgtct ctttagttca gggggctgg   1080 ggctctatta tcgagtcgct acaagctggg cactgtctgg ttgtgctgcc gtttatcatc   1140
gaccagccgc tgaactcaaa gcttttggtg gagaaaggga tggcgcttga atcagaagg   1200 aacggttctg atggatggtt tagtagagaa gacatcgccg gaactttgag agaagctatg   1260
cggtcgtctg aggaaggcgg gcagctgagg agccgtgcaa agaggcggc ggccatcgtt   1320 ggagatgaga agctgcagtg ggaacaatac ttcggcgcgt cgtacagtt tctgagggac   1380
``` aagtcttga                                                                                1389

<210> SEQ ID NO 107
<211> LENGTH: 462
<212> TYPE: PRT
<213> ORGANISM: Siraitia grosvenorii
<220> FEATURE:
<221> NAME/KEY: misc_feature
<222> LOCATION: (47)..(47)
<223> OTHER INFORMATION: Xaa can be any naturally occurring amino acid

<400> SEQUENCE: 107

Met Glu Lys Asn Leu His Ile Val Met Leu Pro Trp Ser Ala Phe Gly
1               5                   10                  15

His Leu Ile Pro Phe Phe His Leu Ser Ile Ala Leu Ala Lys Ala Lys
            20                  25                  30

Val Tyr Ile Ser Phe Val Ser Thr Pro Arg Asn Ile Gln Arg Xaa Pro
        35                  40                  45

Gln Ile Pro Pro Asp Leu Ala Ser Phe Ile Asp Leu Val Ala Ile Pro
    50                  55                  60

Leu Pro Arg Leu Asp Asp Leu Leu Leu Glu Ser Ala Glu Ala Thr
65                  70                  75                  80

Ser Asp Ile Pro Ile Asp Lys Ile Gln Tyr Leu Lys Arg Ala Val Asp
                85                  90                  95

Leu Leu Arg His Pro Phe Lys Lys Phe Val Ala Glu Gln Ser Pro Asp
            100                 105                 110

Trp Val Val Asp Phe His Ala Tyr Trp Ala Gly Glu Ile Tyr Gln
        115                 120                 125

Glu Phe Gln Val Pro Val Ala Tyr Phe Cys Ile Phe Ser Ala Ile Cys
    130                 135                 140

Leu Leu Tyr Leu Gly Pro Pro Asp Val Tyr Ser Lys Asp Pro Gln Ile
145                 150                 155                 160

Met Ala Arg Ile Ser Pro Val Thr Met Thr Val Pro Pro Glu Trp Val
                165                 170                 175

Gly Phe Pro Ser Ala Val Ala Tyr Asn Leu His Glu Ala Thr Val Met
            180                 185                 190

Tyr Ser Ala Leu Tyr Glu Thr Asn Gly Ser Gly Ile Ser Asp Cys Glu
        195                 200                 205

Arg Ile Arg Arg Leu Val Leu Ser Cys Gln Ala Val Ala Ile Arg Ser
    210                 215                 220

Cys Glu Glu Ile Glu Gly Glu Tyr Leu Arg Leu Cys Lys Lys Leu Ile
225                 230                 235                 240

Pro Pro Gln Gly Ile Ala Val Gly Leu Leu Pro Glu Lys Pro Pro
                245                 250                 255

Lys Ser Asp His Glu Leu Ile Lys Trp Leu Asp Glu Gln Lys Leu Arg
            260                 265                 270

Phe Val Val Tyr Val Thr Phe Gly Ser Glu Cys Asn Leu Thr Lys Asp
        275                 280                 285

Gln Val His Glu Ile Ala His Gly Leu Glu Leu Ser Glu Leu Pro Phe
    290                 295                 300

Leu Trp Ala Leu Arg Lys Pro Ser Trp Ala Ala Glu Glu Asp Asp Gly
305                 310                 315                 320

Leu Pro Ser Gly Phe Arg Glu Arg Thr Ser Arg Gly Val Val Ser
                325                 330                 335

Met Glu Trp Val Pro Gln Leu Glu Ile Leu Ala His Gln Ala Ile Gly
            340                 345                 350

```
Val Ser Leu Val His Gly Gly Trp Gly Ser Ile Ile Glu Ser Leu Gln
        355                 360                 365

Ala Gly His Cys Leu Val Val Leu Pro Phe Ile Ile Asp Gln Pro Leu
    370                 375                 380

Asn Ser Lys Leu Leu Val Glu Lys Gly Met Ala Leu Glu Ile Arg Arg
385                 390                 395                 400

Asn Gly Ser Asp Gly Trp Phe Ser Arg Glu Asp Ile Ala Gly Thr Leu
                405                 410                 415

Arg Glu Ala Met Arg Ser Ser Glu Glu Gly Gly Gln Leu Arg Ser Arg
                420                 425                 430

Ala Lys Glu Ala Ala Ala Ile Val Gly Asp Glu Lys Leu Gln Trp Glu
                435                 440                 445

Gln Tyr Phe Gly Ala Phe Val Gln Phe Leu Arg Asp Lys Ser
    450                 455                 460

<210> SEQ ID NO 108
<211> LENGTH: 1395
<212> TYPE: DNA
<213> ORGANISM: Siraitia grosvenorii

<400> SEQUENCE: 108
atgtccgagg agaaaggcag agggcacagc tcgtcgacgg agagacacac tgctgccgcc      60
atgaacgccg agaacgaag caccaaaatc ttgatgctcc catggctggc tcacggccac     120
atatctccat acttcgagct cgccaagagg ctcaccaaga aaaactgcca cgtttacttg     180
tgttcttcgc ctgtaaatct ccaaggcatc aagccgaaac tctctgaaaa ttactcttcc     240
tccattgaac ttgtggagct tcatcttcca tctctccccg accttcctcc ccatatgcac     300
acgaccaaag catccctct acatctacaa tccaccctca tcaaagcctt cgacatggcc     360
gcccctgatt tttccgacct gttgcagaaa ctcgagccgg atctcgtcat tccgatctc     420
ttccagccat gggcagttca attagcgtcg tctcggaaca ttcccgtcgt caatttcgtt     480
gtcaccggag tcgctgttct tagtcgtttg gctcacgtgt tttgcaactc cgttaaggaa     540
ttcccttttcc cggaactcga tctaaccgac cattggatct ccaagagccg ccgcaaaacg     600
tccgacgaat taggtcgcga gtgcgcgatg cgatttttca actgcatgaa acaatcttca     660
aacatcactc tagccaacac tttccccgag ttcgaagaaa aatacatcga ttatctctct     720
tcctcgttta agaaaaagat tcttccggtt gctcctctag ttcctgaaat cgacgcagac     780
gacgagaaat cggaaattat cgagtggctt gacaagaaga aaccgaaatc gactgtttac     840
gtttcgtttg ggagtgagta ttatctgacg aaagaagaca gggaagagct cgcccatggc     900
ttagaaaaga gcggcgtgaa tttcatctgg gttattaggt ttccaaaggg cgagaagatc     960
accattgaag aggctttacc agaaggattt ctcgagagag taggggacag gggagtgatt    1020
atcgacgggt gggcgccgca gttgaaaata ttgaggcatt caagcgtggg cgggttcgtg    1080
tgccactgcg ggtggaactc tgtggtggag agcgtggtgt tggggtgcc gatcatagcc    1140
ttgccgatgc agctcgatca gccatggcat gcgaaggtgg cggaggacgg cggcgtctgt    1200
gcggaggcga agagagacgt tgaagggagc gttcagagag aagaggtggc gaaggccatt    1260
aaagaggtgg tgtttgagaa gaaggggggg gttctgagtg aaaagcaag agagatcagc    1320
gaggccttga aaagaggga aggggaaatc atagaggaat tggttgctga gtttcaccag    1380
ctctgtgaag cttga                                                    1395
```

<210> SEQ ID NO 109
<211> LENGTH: 464
<212> TYPE: PRT
<213> ORGANISM: Siraitia grosvenorii

<400> SEQUENCE: 109

Met Ser Glu Glu Lys Gly Arg Gly His Ser Ser Thr Glu Arg His
1               5                   10                  15

Thr Ala Ala Met Asn Ala Glu Lys Arg Ser Thr Lys Ile Leu Met
            20                  25                  30

Leu Pro Trp Leu Ala His Gly His Ile Ser Pro Tyr Phe Glu Leu Ala
        35                  40                  45

Lys Arg Leu Thr Lys Lys Asn Cys His Val Tyr Leu Cys Ser Ser Pro
    50                  55                  60

Val Asn Leu Gln Gly Ile Lys Pro Lys Leu Ser Glu Asn Tyr Ser Ser
65                  70                  75                  80

Ser Ile Glu Leu Val Glu Leu His Leu Pro Ser Leu Pro Asp Leu Pro
                85                  90                  95

Pro His Met His Thr Thr Lys Gly Ile Pro Leu His Leu Gln Ser Thr
            100                 105                 110

Leu Ile Lys Ala Phe Asp Met Ala Ala Pro Asp Phe Ser Asp Leu Leu
        115                 120                 125

Gln Lys Leu Glu Pro Asp Leu Val Ile Ser Asp Leu Phe Gln Pro Trp
    130                 135                 140

Ala Val Gln Leu Ala Ser Ser Arg Asn Ile Pro Val Val Asn Phe Val
145                 150                 155                 160

Val Thr Gly Val Ala Val Leu Ser Arg Leu Ala His Val Phe Cys Asn
                165                 170                 175

Ser Val Lys Glu Phe Pro Phe Pro Glu Leu Asp Leu Thr Asp His Trp
            180                 185                 190

Ile Ser Lys Ser Arg Arg Lys Thr Ser Asp Glu Leu Gly Arg Glu Cys
        195                 200                 205

Ala Met Arg Phe Phe Asn Cys Met Lys Gln Ser Ser Asn Ile Thr Leu
    210                 215                 220

Ala Asn Thr Phe Pro Glu Phe Glu Glu Lys Tyr Ile Asp Tyr Leu Ser
225                 230                 235                 240

Ser Ser Phe Lys Lys Lys Ile Leu Pro Val Ala Pro Leu Val Pro Glu
                245                 250                 255

Ile Asp Ala Asp Asp Glu Lys Ser Glu Ile Ile Glu Trp Leu Asp Lys
            260                 265                 270

Lys Lys Pro Lys Ser Thr Val Tyr Val Ser Phe Gly Ser Glu Tyr Tyr
        275                 280                 285

Leu Thr Lys Glu Asp Arg Glu Glu Leu Ala His Gly Leu Glu Lys Ser
    290                 295                 300

Gly Val Asn Phe Ile Trp Val Ile Arg Phe Pro Lys Gly Glu Lys Ile
305                 310                 315                 320

Thr Ile Glu Glu Ala Leu Pro Glu Gly Phe Leu Glu Arg Val Gly Asp
                325                 330                 335

Arg Gly Val Ile Ile Asp Gly Trp Ala Pro Gln Leu Lys Ile Leu Arg
            340                 345                 350

His Ser Ser Val Gly Gly Phe Val Cys His Cys Gly Trp Asn Ser Val
        355                 360                 365

Val Glu Ser Val Val Phe Gly Val Pro Ile Ile Ala Leu Pro Met Gln
    370                 375                 380

Leu Asp Gln Pro Trp His Ala Lys Val Ala Glu Asp Gly Gly Val Cys
385                 390                 395                 400

Ala Glu Ala Lys Arg Asp Val Glu Gly Ser Val Gln Arg Glu Val
            405                 410                 415

Ala Lys Ala Ile Lys Glu Val Val Phe Glu Lys Lys Gly Gly Val Leu
            420                 425                 430

Ser Gly Lys Ala Arg Glu Ile Ser Glu Ala Leu Arg Lys Arg Glu Gly
            435                 440                 445

Glu Ile Ile Glu Glu Leu Val Ala Glu Phe His Gln Leu Cys Glu Ala
        450                 455                 460

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114
<211> LENGTH: 1347
<212> TYPE: DNA
<213> ORGANISM: Saccharomyces cerevisiae

<400> SEQUENCE: 114
atgctttcgc ttaaaacgtt actgtgtacg ttgttgactg tgtcatcagt actcgctacc      60
ccagtccctg caagagaccc ttcttccatt caatttgttc atgaggagaa caagaaaaga     120
tactacgatt atgaccacgg ttccctcgga gaaccaatcc gtggtgtcaa cattggtggt     180
tggttacttc ttgaaccata cattactcca tctttgttcg aggcttttcc gtacaaatgat    240 gacaacgacg aaggaattcc tgtcgacgaa tatcacttct gtcaatattt aggtaaggat     300
ttggctaaaa gccgtttaca gagccattgg tctactttct accaagaaca agatttcgct     360
aatattgctt cccaaggttt caaccttgtc agaattccta tcggttactg ggctttccaa     420
actttggacg atgatcctta tgttagcggc tacaggaat cttacctaga ccaagccatc      480
ggttgggcta gaaacaacag cttgaaagtt tgggttgatt tgcatggtgc cgctggttcg     540
cagaacgggt ttgataactc tggttttgaga gattcataca gttttttgga agacagcaat    600
ttggccgtta ctacaaatgt cttgaactac atattgaaaa aatactctgc ggaggaatac    660
ttggacactg ttattggtat cgaattgatt aatgagccat gggtcctgt tctagacatg     720 gataaaatga gaatgactaa cttggcaccta gcttacgaat acttgagaaa caacatcaag    780
agtgaccaag ttatcatcat ccatgacgct ttccaaccat acaattattg ggatgacttc    840

-continued

```
atgactgaaa acgatggcta ctggggtgtc actatcgacc atcatcacta ccaagtcttt    900
gcttctgatc aattggaaag atccattgat gaacatatta agtagcttg tgaatggggt     960
accggagttt tgaatgaatc ccactggact gtttgtggtg agtttgctgc cgctttgact   1020
gattgtacaa aatggttgaa tagtgttggc ttcggcgcta gatacgacgg ttcttgggtc   1080
aatggtgacc aaacatcttc ttacattggc tcttgtgcta caacgatga tatagcttac    1140
tggtctgacg aaagaaagga aaacacaaga cgttatgtgg aggcacaact agatgccttt   1200
gaaatgagag ggggttggat tatctggtgt tacaagacag aatctagttt ggaatgggat   1260
gctcaaagat tgatgttcaa tggtttattc cctcaaccat tgactgacag aaagtatcca   1320
aaccaatgtg gcacaatttc taactaa                                       1347
```

<210> SEQ ID NO 115
<211> LENGTH: 448
<212> TYPE: PRT
<213> ORGANISM: Saccharomyces cerevisiae

<400> SEQUENCE: 115

```
Met Leu Ser Leu Lys Thr Leu Cys Thr Leu Leu Thr Val Ser Ser
1               5                   10                  15

Val Leu Ala Thr Pro Val Pro Ala Arg Asp Pro Ser Ser Ile Gln Phe
            20                  25                  30

Val His Glu Glu Asn Lys Lys Arg Tyr Tyr Asp Tyr Asp His Gly Ser
        35                  40                  45

Leu Gly Glu Pro Ile Arg Gly Val Asn Ile Gly Gly Trp Leu Leu Leu
    50                  55                  60

Glu Pro Tyr Ile Thr Pro Ser Leu Phe Glu Ala Phe Arg Thr Asn Asp
65                  70                  75                  80

Asp Asn Asp Glu Gly Ile Pro Val Asp Glu Tyr His Phe Cys Gln Tyr
                85                  90                  95

Leu Gly Lys Asp Leu Ala Lys Ser Arg Leu Gln Ser His Trp Ser Thr
            100                 105                 110

Phe Tyr Gln Glu Gln Asp Phe Ala Asn Ile Ala Ser Gln Gly Phe Asn
        115                 120                 125

Leu Val Arg Ile Pro Ile Gly Tyr Trp Ala Phe Gln Thr Leu Asp Asp
    130                 135                 140

Asp Pro Tyr Val Ser Gly Leu Gln Glu Ser Tyr Leu Asp Gln Ala Ile
145                 150                 155                 160

Gly Trp Ala Arg Asn Asn Ser Leu Lys Val Trp Val Asp Leu His Gly
                165                 170                 175

Ala Ala Gly Ser Gln Asn Gly Phe Asp Asn Ser Gly Leu Arg Asp Ser
            180                 185                 190

Tyr Lys Phe Leu Glu Asp Ser Asn Leu Ala Val Thr Thr Asn Val Leu
        195                 200                 205

Asn Tyr Ile Leu Lys Lys Tyr Ser Ala Glu Glu Tyr Leu Asp Thr Val
    210                 215                 220

Ile Gly Ile Glu Leu Ile Asn Glu Pro Leu Gly Pro Val Leu Asp Met
225                 230                 235                 240

Asp Lys Met Lys Asn Asp Tyr Leu Ala Pro Ala Tyr Glu Tyr Leu Arg
                245                 250                 255

Asn Asn Ile Lys Ser Asp Gln Val Ile Ile His Asp Ala Phe Gln
            260                 265                 270

Pro Tyr Asn Tyr Trp Asp Asp Phe Met Thr Glu Asn Asp Gly Tyr Trp
        275                 280                 285
```

```
Gly Val Thr Ile Asp His His Tyr Gln Val Phe Ala Ser Asp Gln
    290                 295                 300

Leu Glu Arg Ser Ile Asp Glu His Ile Lys Val Ala Cys Glu Trp Gly
305                 310                 315                 320

Thr Gly Val Leu Asn Glu Ser His Trp Thr Val Cys Gly Glu Phe Ala
                325                 330                 335

Ala Ala Leu Thr Asp Cys Thr Lys Trp Leu Asn Ser Val Gly Phe Gly
                340                 345                 350

Ala Arg Tyr Asp Gly Ser Trp Val Asn Gly Asp Gln Thr Ser Ser Tyr
            355                 360                 365

Ile Gly Ser Cys Ala Asn Asn Asp Asp Ile Ala Tyr Trp Ser Asp Glu
    370                 375                 380

Arg Lys Glu Asn Thr Arg Arg Tyr Val Glu Ala Gln Leu Asp Ala Phe
385                 390                 395                 400

Glu Met Arg Gly Gly Trp Ile Ile Trp Cys Tyr Lys Thr Glu Ser Ser
                405                 410                 415

Leu Glu Trp Asp Ala Gln Arg Leu Met Phe Asn Gly Leu Phe Pro Gln
            420                 425                 430

Pro Leu Thr Asp Arg Lys Tyr Pro Asn Gln Cys Gly Thr Ile Ser Asn
            435                 440                 445

<210> SEQ ID NO 116
<211> LENGTH: 1689
<212> TYPE: DNA
<213> ORGANISM: Saccharomyces cerevisiae

<400> SEQUENCE: 116
atgcctttga agtcgttttt ttttttcagca tttctagttt tatgcctgtc taaattcacg      60
caaggcgttg gcaccacaga aaggaagaa tcgttatcgc ctttggaact aaatatttta     120
caaaacaaat tcgcctccta ctatgcaaac gacactatca ccgtgaaagg tattactatt     180
ggcggctggc tagtaacaga accttatatc acgccatcat tatatcgtaa tgctacgtca     240
ctggcaaaac agcaaaactc ttccagcaat atctccattg tcgacgaatt tactctttgt     300
aaaaccttag gatataacac ctctctaact ttattggata tcacttcaa aacttggatt      360 acagaggatg attttgaaca aatcaaaacc aacggtttca atttagttag gatccccatc     420
ggatattggg cgtggaaaca aaatactgat aaaaacttgt acatcgataa cataactttc     480
aatgatccat acgtaagtga tggattacaa ctgaaatatt taaataatgc tctcgaatgg     540
gcgcaaaagt acgaactaaa tgtatggtta gatctacatg gtgctcctgg atcccagaat     600
ggattcgata ttccggtgaa agaatactc tatggcgatt taggctggtt aaggttgaat      660
aatactaaag aactgactct ggctatttgg agagatatgt ccagacatt tttaaataaa      720 ggtgacaaaa gtcctgtggt gggtattcaa atcgtcaacg aaccgcttgg tggcaaaatc     780
gatgtttcag acataacgga gatgtattac gaagcatttg acttgctcaa gaaaaatcag     840
aattcgagtg acaacactac gtttgttatt catgacggtt ttcaaggaat cggtcactgg     900
aacttggagc taaacccaac ctaccagaat gtatcgcatc attatttcaa tttgactggt     960
gcaaattaca gctctcaaga tatattggtc gaccatcatc attatgaagt gttactgat     1020 gcgcaattgg ccgaaactca gtttgcacgt attgaaaaca ttatcaatta tggggactct    1080
atccacaaag aactttctt tcacccagca gtagtcggag aatggtcagg cgctattact      1140
gattgtgcaa cctggctaaa tggtgttggg gtgggtgcac gttacgatgg atcatactac    1200
```

-continued

```
aatacaacgt tgtttaccac caacgacaag ccagttggaa catgtatatc ccaaaatagc    1260
ttagctgatt ggacgcaaga ttaccgtgac cgtgtgagac aattcattga ggcacagcta    1320
gccacttatt cgtcaaaaac aacgggatgg atttttttgga attggaagac cgaagacgcc   1380
gtagaatggg attatttgaa gctaaaagaa gctaacctttt tcccttcccc tttcgacaac    1440
tacacgtact tcaaagcaga tggatctatc gaagaaaaat tctcatcctc tttatcagca    1500
caggcatttc caagaacaac gtcatcggtt ttgtcctcca ctacgacttc caggaagagt   1560
aagaatgctg caatttctaa taaactaaca acttcgcagc tattaccaat caaaaatatg    1620
agtttgacct ggaaagcgag cgtatgcgca ctcgctatca ccattgccgc tctttgcgct    1680
tctctttaa                                                             1689
```

<210> SEQ ID NO 117
<211> LENGTH: 562
<212> TYPE: PRT
<213> ORGANISM: Saccharomyces cerevisiae

<400> SEQUENCE: 117

```
Met Pro Leu Lys Ser Phe Phe Ser Ala Phe Leu Val Leu Cys Leu
1               5                   10                  15

Ser Lys Phe Thr Gln Gly Val Gly Thr Thr Glu Lys Glu Glu Ser Leu
            20                  25                  30

Ser Pro Leu Glu Leu Asn Ile Leu Gln Asn Lys Phe Ala Ser Tyr Tyr
        35                  40                  45

Ala Asn Asp Thr Ile Thr Val Lys Gly Ile Thr Ile Gly Gly Trp Leu
    50                  55                  60

Val Thr Glu Pro Tyr Ile Thr Pro Ser Leu Tyr Arg Asn Ala Thr Ser
65                  70                  75                  80

Leu Ala Lys Gln Gln Asn Ser Ser Ser Asn Ile Ser Ile Val Asp Glu
                85                  90                  95

Phe Thr Leu Cys Lys Thr Leu Gly Tyr Asn Thr Ser Leu Thr Leu Leu
            100                 105                 110

Asp Asn His Phe Lys Thr Trp Ile Thr Glu Asp Asp Phe Glu Gln Ile
        115                 120                 125

Lys Thr Asn Gly Phe Asn Leu Val Arg Ile Pro Ile Gly Tyr Trp Ala
    130                 135                 140

Trp Lys Gln Asn Thr Asp Lys Asn Leu Tyr Ile Asp Asn Ile Thr Phe
145                 150                 155                 160

Asn Asp Pro Tyr Val Ser Asp Gly Leu Gln Leu Lys Tyr Leu Asn Asn
                165                 170                 175

Ala Leu Glu Trp Ala Gln Lys Tyr Glu Leu Asn Val Trp Leu Asp Leu
            180                 185                 190

His Gly Ala Pro Gly Ser Gln Asn Gly Phe Asp Asn Ser Gly Glu Arg
        195                 200                 205

Ile Leu Tyr Gly Asp Leu Gly Trp Leu Arg Leu Asn Asn Thr Lys Glu
    210                 215                 220

Leu Thr Leu Ala Ile Trp Arg Asp Met Phe Gln Thr Phe Leu Asn Lys
225                 230                 235                 240

Gly Asp Lys Ser Pro Val Val Gly Ile Gln Ile Val Asn Glu Pro Leu
                245                 250                 255

Gly Gly Lys Ile Asp Val Ser Asp Ile Thr Glu Met Tyr Tyr Glu Ala
            260                 265                 270

Phe Asp Leu Leu Lys Lys Asn Gln Asn Ser Ser Asp Asn Thr Thr Phe
        275                 280                 285
```

Val Ile His Asp Gly Phe Gln Gly Ile Gly His Trp Asn Leu Glu Leu
            290                 295                 300

Asn Pro Thr Tyr Gln Asn Val Ser His His Tyr Phe Asn Leu Thr Gly
305                 310                 315                 320

Ala Asn Tyr Ser Ser Gln Asp Ile Leu Val Asp His His Tyr Glu
            325                 330                 335

Val Phe Thr Asp Ala Gln Leu Ala Glu Thr Gln Phe Ala Arg Ile Glu
            340                 345                 350

Asn Ile Ile Asn Tyr Gly Asp Ser Ile His Lys Glu Leu Ser Phe His
            355                 360                 365

Pro Ala Val Val Gly Glu Trp Ser Gly Ala Ile Thr Asp Cys Ala Thr
370                 375                 380

Trp Leu Asn Gly Val Gly Val Gly Ala Arg Tyr Asp Gly Ser Tyr Tyr
385                 390                 395                 400

Asn Thr Thr Leu Phe Thr Thr Asn Asp Lys Pro Val Gly Thr Cys Ile
            405                 410                 415

Ser Gln Asn Ser Leu Ala Asp Trp Thr Gln Asp Tyr Arg Asp Arg Val
            420                 425                 430

Arg Gln Phe Ile Glu Ala Gln Leu Ala Thr Tyr Ser Ser Lys Thr Thr
            435                 440                 445

Gly Trp Ile Phe Trp Asn Trp Lys Thr Glu Asp Ala Val Glu Trp Asp
450                 455                 460

Tyr Leu Lys Leu Lys Glu Ala Asn Leu Phe Pro Ser Pro Phe Asp Asn
465                 470                 475                 480

Tyr Thr Tyr Phe Lys Ala Asp Gly Ser Ile Glu Glu Lys Phe Ser Ser
            485                 490                 495

Ser Leu Ser Ala Gln Ala Phe Pro Arg Thr Thr Ser Ser Val Leu Ser
            500                 505                 510

Ser Thr Thr Thr Ser Arg Lys Ser Lys Asn Ala Ala Ile Ser Asn Lys
            515                 520                 525

Leu Thr Thr Ser Gln Leu Leu Pro Ile Lys Asn Met Ser Leu Thr Trp
530                 535                 540

Lys Ala Ser Val Cys Ala Leu Ala Ile Thr Ile Ala Ala Leu Cys Ala
545                 550                 555                 560

Ser Leu

<210> SEQ ID NO 118
<211> LENGTH: 731
<212> TYPE: PRT
<213> ORGANISM: Saccharomyces cerevisiae

<400> SEQUENCE: 118

Met Thr Glu Phe Tyr Ser Asp Thr Ile Gly Leu Pro Lys Thr Asp Pro
1               5                   10                  15

Arg Leu Trp Arg Leu Arg Thr Asp Glu Leu Gly Arg Glu Ser Trp Glu
            20                  25                  30

Tyr Leu Thr Pro Gln Gln Ala Ala Asn Asp Pro Pro Ser Thr Phe Thr
        35                  40                  45

Gln Trp Leu Leu Gln Asp Pro Lys Phe Pro Gln Pro His Pro Glu Arg
    50                  55                  60

Asn Lys His Ser Pro Asp Phe Ser Ala Phe Asp Ala Cys His Asn Gly
65                  70                  75                  80

Ala Ser Phe Phe Lys Leu Leu Gln Glu Pro Asp Ser Gly Ile Phe Pro
                85                  90                  95

```
Cys Gln Tyr Lys Gly Pro Met Phe Met Thr Ile Gly Tyr Val Ala Val
            100                 105                 110

Asn Tyr Ile Ala Gly Ile Glu Ile Pro Glu His Glu Arg Ile Glu Leu
            115                 120                 125

Ile Arg Tyr Ile Val Asn Thr Ala His Pro Val Asp Gly Gly Trp Gly
130                 135                 140

Leu His Ser Val Asp Lys Ser Thr Val Phe Gly Thr Val Leu Asn Tyr
145                 150                 155                 160

Val Ile Leu Arg Leu Leu Gly Leu Pro Lys Asp His Pro Val Cys Ala
                165                 170                 175

Lys Ala Arg Ser Thr Leu Leu Arg Leu Gly Ala Ile Gly Ser Pro
            180                 185                 190

His Trp Gly Lys Ile Trp Leu Ser Ala Leu Asn Leu Tyr Lys Trp Glu
            195                 200                 205

Gly Val Asn Pro Ala Pro Pro Glu Thr Trp Leu Leu Pro Tyr Ser Leu
            210                 215                 220

Pro Met His Pro Gly Arg Trp Trp Val His Thr Arg Gly Val Tyr Ile
225                 230                 235                 240

Pro Val Ser Tyr Leu Ser Leu Val Lys Phe Ser Cys Pro Met Thr Pro
                245                 250                 255

Leu Leu Glu Glu Leu Arg Asn Glu Ile Tyr Thr Lys Pro Phe Asp Lys
            260                 265                 270

Ile Asn Phe Ser Lys Asn Arg Asn Thr Val Cys Gly Val Asp Leu Tyr
                275                 280                 285

Tyr Pro His Ser Thr Thr Leu Asn Ile Ala Asn Ser Leu Val Val Phe
            290                 295                 300

Tyr Glu Lys Tyr Leu Arg Asn Arg Phe Ile Tyr Ser Leu Ser Lys Lys
305                 310                 315                 320

Lys Val Tyr Asp Leu Ile Lys Thr Glu Leu Gln Asn Thr Asp Ser Leu
                325                 330                 335

Cys Ile Ala Pro Val Asn Gln Ala Phe Cys Ala Leu Val Thr Leu Ile
            340                 345                 350

Glu Glu Gly Val Asp Ser Glu Ala Phe Gln Arg Leu Gln Tyr Arg Phe
            355                 360                 365

Lys Asp Ala Leu Phe His Gly Pro Gln Gly Met Thr Ile Met Gly Thr
370                 375                 380

Asn Gly Val Gln Thr Trp Asp Cys Ala Phe Ala Ile Gln Tyr Phe Phe
385                 390                 395                 400

Val Ala Gly Leu Ala Glu Arg Pro Glu Phe Tyr Asn Thr Ile Val Ser
                405                 410                 415

Ala Tyr Lys Phe Leu Cys His Ala Gln Phe Asp Thr Glu Cys Val Pro
            420                 425                 430

Gly Ser Tyr Arg Asp Lys Arg Lys Gly Ala Trp Gly Phe Ser Thr Lys
            435                 440                 445

Thr Gln Gly Tyr Thr Val Ala Asp Cys Thr Ala Glu Ala Ile Lys Ala
            450                 455                 460

Ile Ile Met Val Lys Asn Ser Pro Val Phe Ser Glu Val His His Met
465                 470                 475                 480

Ile Ser Ser Glu Arg Leu Phe Glu Gly Ile Asp Val Leu Leu Asn Leu
                485                 490                 495

Gln Asn Ile Gly Ser Phe Glu Tyr Gly Ser Phe Ala Tyr Glu Lys
            500                 505                 510
```

Ile Lys Ala Pro Leu Ala Met Glu Thr Leu Asn Pro Ala Glu Val Phe
            515                 520                 525

Gly Asn Ile Met Val Glu Tyr Pro Tyr Val Glu Cys Thr Asp Ser Ser
530                 535                 540

Val Leu Gly Leu Thr Tyr Phe His Lys Tyr Phe Asp Tyr Arg Lys Glu
545                 550                 555                 560

Glu Ile Arg Thr Arg Ile Arg Ile Ala Ile Glu Phe Ile Lys Lys Ser
                565                 570                 575

Gln Leu Pro Asp Gly Ser Trp Tyr Gly Ser Trp Gly Ile Cys Phe Thr
            580                 585                 590

Tyr Ala Gly Met Phe Ala Leu Glu Ala Leu His Thr Val Gly Glu Thr
        595                 600                 605

Tyr Glu Asn Ser Ser Thr Val Arg Lys Gly Cys Asp Phe Leu Val Ser
    610                 615                 620

Lys Gln Met Lys Asp Gly Gly Trp Gly Glu Ser Met Lys Ser Ser Glu
625                 630                 635                 640

Leu His Ser Tyr Val Asp Ser Glu Lys Ser Leu Val Val Gln Thr Ala
                645                 650                 655

Trp Ala Leu Ile Ala Leu Leu Phe Ala Glu Tyr Pro Asn Lys Glu Val
            660                 665                 670

Ile Asp Arg Gly Ile Asp Leu Leu Lys Asn Arg Gln Glu Glu Ser Gly
        675                 680                 685

Glu Trp Lys Phe Glu Ser Val Glu Gly Val Phe Asn His Ser Cys Ala
    690                 695                 700

Ile Glu Tyr Pro Ser Tyr Arg Phe Leu Phe Pro Ile Lys Ala Leu Gly
705                 710                 715                 720

Met Tyr Ser Arg Ala Tyr Glu Thr His Thr Leu
                725                 730

<210> SEQ ID NO 119
<211> LENGTH: 444
<212> TYPE: PRT
<213> ORGANISM: Saccharomyces cerevisiae

<400> SEQUENCE: 119

Met Gly Lys Leu Leu Gln Leu Ala Leu His Pro Val Glu Met Lys Ala
1               5                   10                  15

Ala Leu Lys Leu Lys Phe Cys Arg Thr Pro Leu Phe Ser Ile Tyr Asp
            20                  25                  30

Gln Ser Thr Ser Pro Tyr Leu Leu His Cys Phe Glu Leu Leu Asn Leu
        35                  40                  45

Thr Ser Arg Ser Phe Ala Ala Val Ile Arg Glu Leu His Pro Glu Leu
    50                  55                  60

Arg Asn Cys Val Thr Leu Phe Tyr Leu Ile Leu Arg Ala Leu Asp Thr
65                  70                  75                  80

Ile Glu Asp Asp Met Ser Ile Glu His Asp Leu Lys Ile Asp Leu Leu
                85                  90                  95

Arg His Phe His Glu Lys Leu Leu Leu Thr Lys Trp Ser Phe Asp Gly
            100                 105                 110

Asn Ala Pro Asp Val Lys Asp Arg Ala Val Leu Thr Asp Phe Glu Ser
        115                 120                 125

Ile Leu Ile Glu Phe His Lys Leu Lys Pro Glu Tyr Gln Glu Val Ile
    130                 135                 140

Lys Glu Ile Thr Glu Lys Met Gly Asn Gly Met Ala Asp Tyr Ile Leu
145                 150                 155                 160

```
Asp Glu Asn Tyr Asn Leu Asn Gly Leu Gln Thr Val His Asp Tyr Asp
                165                 170                 175

Val Tyr Cys His Tyr Val Ala Gly Leu Val Gly Asp Gly Leu Thr Arg
            180                 185                 190

Leu Ile Val Ile Ala Lys Phe Ala Asn Glu Ser Leu Tyr Ser Asn Glu
        195                 200                 205

Gln Leu Tyr Glu Ser Met Gly Leu Phe Leu Gln Lys Thr Asn Ile Ile
    210                 215                 220

Arg Asp Tyr Asn Glu Asp Leu Val Asp Gly Arg Ser Phe Trp Pro Lys
225                 230                 235                 240

Glu Ile Trp Ser Gln Tyr Ala Pro Gln Leu Lys Asp Phe Met Lys Pro
                245                 250                 255

Glu Asn Glu Gln Leu Gly Leu Asp Cys Ile Asn His Leu Val Leu Asn
            260                 265                 270

Ala Leu Ser His Val Ile Asp Val Leu Thr Tyr Leu Ala Gly Ile His
        275                 280                 285

Glu Gln Ser Thr Phe Gln Phe Cys Ala Ile Pro Gln Val Met Ala Ile
    290                 295                 300

Ala Thr Leu Ala Leu Val Phe Asn Asn Arg Glu Val Leu His Gly Asn
305                 310                 315                 320

Val Lys Ile Arg Lys Gly Thr Thr Cys Tyr Leu Ile Leu Lys Ser Arg
                325                 330                 335

Thr Leu Arg Gly Cys Val Glu Ile Phe Asp Tyr Tyr Leu Arg Asp Ile
            340                 345                 350

Lys Ser Lys Leu Ala Val Gln Asp Pro Asn Phe Leu Lys Leu Asn Ile
        355                 360                 365

Gln Ile Ser Lys Ile Glu Gln Phe Met Glu Glu Met Tyr Gln Asp Lys
    370                 375                 380

Leu Pro Pro Asn Val Lys Pro Asn Glu Thr Pro Ile Phe Leu Lys Val
385                 390                 395                 400

Lys Glu Arg Ser Arg Tyr Asp Asp Glu Leu Val Pro Thr Gln Gln Glu
                405                 410                 415

Glu Glu Tyr Lys Phe Asn Met Val Leu Ser Ile Ile Leu Ser Val Leu
            420                 425                 430

Leu Gly Phe Tyr Tyr Ile Tyr Thr Leu His Arg Ala
        435                 440

<210> SEQ ID NO 120
<211> LENGTH: 675
<212> TYPE: DNA
<213> ORGANISM: Saccharomyces cerevisiae

<400> SEQUENCE: 120
atgtctgtta ttaatttcac aggtagttct ggtccattgg tgaaagtttg cggcttgcag      60
agcacagagg ccgcagaatg tgctctagat tccgatgctg acttgctggg tattatatgt     120
gtgcccaata gaaagagaac aattgacccg gttattgcaa ggaaaatttc aagtcttgta     180
aaagcatata aaaatagttc aggcactccg aaatacttgg ttggcgtgtt tcgtaatcaa     240
cctaaggagg atgttttggc tctggtcaat gattacggca ttgatatcgt ccaactgcat     300
ggagatgagt cgtggcaaga ataccaagag ttcctcggtt tgccagttat taaaagactc     360
gtatttccaa aagactgcaa catactactc agtgcagctt cacagaaacc tcattcgttt     420
attcccttgt ttgattcaga agcaggtggg acaggtgaac ttttggattg gaactcgatt     480
```

-continued

```
tctgactggg ttggaaggca agagagcccc gaaagcttac attttatgtt agctggtgga    540
ctgacgccag aaaatgttgg tgatgcgctt agattaaatg cgttattggt gttgatgta    600 agcggaggtg tggagacaaa tggtgtaaaa gactctaaca aaatagcaaa tttcgtcaaa    660
aatgctaaga aatag                                                     675
```

<210> SEQ ID NO 121
<211> LENGTH: 224
<212> TYPE: PRT
<213> ORGANISM: Saccharomyces cerevisiae

<400> SEQUENCE: 121

```
Met Ser Val Ile Asn Phe Thr Gly Ser Ser Gly Pro Leu Val Lys Val
1               5                   10                  15

Cys Gly Leu Gln Ser Thr Glu Ala Ala Glu Cys Ala Leu Asp Ser Asp
            20                  25                  30

Ala Asp Leu Leu Gly Ile Ile Cys Val Pro Asn Arg Lys Arg Thr Ile
        35                  40                  45

Asp Pro Val Ile Ala Arg Lys Ile Ser Ser Leu Val Lys Ala Tyr Lys
    50                  55                  60

Asn Ser Ser Gly Thr Pro Lys Tyr Leu Val Gly Val Phe Arg Asn Gln
65                  70                  75                  80

Pro Lys Glu Asp Val Leu Ala Leu Val Asn Asp Tyr Gly Ile Asp Ile
                85                  90                  95

Val Gln Leu His Gly Asp Glu Ser Trp Gln Glu Tyr Gln Glu Phe Leu
            100                 105                 110

Gly Leu Pro Val Ile Lys Arg Leu Val Phe Pro Lys Asp Cys Asn Ile
        115                 120                 125

Leu Leu Ser Ala Ala Ser Gln Lys Pro His Ser Phe Ile Pro Leu Phe
    130                 135                 140

Asp Ser Glu Ala Gly Gly Thr Gly Glu Leu Leu Asp Trp Asn Ser Ile
145                 150                 155                 160

Ser Asp Trp Val Gly Arg Gln Glu Ser Pro Glu Ser Leu His Phe Met
                165                 170                 175

Leu Ala Gly Gly Leu Thr Pro Glu Asn Val Gly Asp Ala Leu Arg Leu
            180                 185                 190

Asn Gly Val Ile Gly Val Asp Val Ser Gly Gly Val Glu Thr Asn Gly
        195                 200                 205

Val Lys Asp Ser Asn Lys Ile Ala Asn Phe Val Lys Asn Ala Lys Lys
    210                 215                 220
```

<210> SEQ ID NO 122
<211> LENGTH: 1584
<212> TYPE: DNA
<213> ORGANISM: Saccharomyces cerevisiae

<400> SEQUENCE: 122

```
atggcagctg accaattggt gaaaactgaa gtcaccaaga agtcttttac tgctcctgta    60
caaaaggctt ctacaccagt tttaaccaat aaaacagtca tttctggatc gaaagtcaaa    120
agtttatcat ctgcgcaatc gagctcatca ggaccttcat catctagtga ggaagatgat    180
tcccgcgata ttgaaagctt ggataagaaa atacgtcctt agaagaatt agaagcatta    240 ttaagtagtg aaatacaaa acaattgaag aacaaagagg tcgctgcctt ggttattcac    300
ggtaagttac ctttgtacgc tttggagaaa aaattaggtg atactacgag agcggttgcg    360
gtacgtagga aggctctttc aattttggca gaagctcctg tattagcatc tgatcgttta    420
```

```
ccatataaaa attatgacta cgaccgcgta tttggcgctt gttgtgaaaa tgttataggt    480
tacatgcctt tgcccgttgg tgttataggc cccttggtta tcgatggtac atcttatcat    540
ataccaatgg caactacaga gggttgtttg gtagcttctg ccatgcgtgg ctgtaaggca    600
atcaatgctg gcggtggtgc aacaactgtt ttaactaagg atggtatgac aagaggccca    660
gtagtccgtt tcccaacttt gaaaagatct ggtgcctgta agatatggtt agactcagaa    720
gagggacaaa acgcaattaa aaaagctttt aactctacat caagatttgc acgtctgcaa    780
catattcaaa cttgtctagc aggagattta ctcttcatga gatttagaac aactactggt    840
gacgcaatgg gtatgaatat gatttctaaa ggtgtcgaat actcattaaa gcaaatggta    900
gaagagtatg gctgggaaga tatggaggtt gtctccgttt ctggtaacta ctgtaccgac    960
aaaaaaccag ctgccatcaa ctggatcgaa ggtcgtggta agagtgtcgt cgcagaagct   1020
actattcctg gtgatgttgt cagaaaagtg ttaaaaagtg atgtttccgc attggttgag   1080
ttgaacattg ctaagaattt ggttggatct gcaatggctg gtctgttgg tggatttaac   1140 gcacatgcag ctaatttagt gacagctgtt ttcttggcat taggacaaga tcctgcacaa   1200
aatgttgaaa gttccaactg tataacattg atgaaagaag tggacggtga tttgagaatt   1260
tccgtatcca tgccatccat cgaagtaggt accatcggtg gtggtactgt tctagaacca   1320
caaggtgcca tgttggactt attaggtgta agaggcccgc atgctaccgc tcctggtacc   1380
aacgcacgtc aattagcaag aatagttgcc tgtgccgtct tggcaggtga attatcctta   1440
tgtgctgccc tagcagccgg ccatttggtt caaagtcata tgacccacaa caggaaacct   1500
gctgaaccaa caaaacctaa caatttggac gccactgata taaatcgttt gaaagatggg   1560
tccgtcacct gcattaaatc ctaa                                          1584
```

<210> SEQ ID NO 123
<211> LENGTH: 527
<212> TYPE: PRT
<213> ORGANISM: Saccharomyces cerevisiae

<400> SEQUENCE: 123

```
Met Ala Ala Asp Gln Leu Val Lys Thr Glu Val Thr Lys Lys Ser Phe
1               5                   10                  15

Thr Ala Pro Val Gln Lys Ala Ser Thr Pro Val Leu Thr Asn Lys Thr
            20                  25                  30

Val Ile Ser Gly Ser Lys Val Lys Ser Leu Ser Ser Ala Gln Ser Ser
        35                  40                  45

Ser Ser Gly Pro Ser Ser Ser Ser Glu Glu Asp Asp Ser Arg Asp Ile
    50                  55                  60

Glu Ser Leu Asp Lys Lys Ile Arg Pro Leu Glu Glu Leu Glu Ala Leu
65                  70                  75                  80

Leu Ser Ser Gly Asn Thr Lys Gln Leu Lys Asn Lys Glu Val Ala Ala
                85                  90                  95

Leu Val Ile His Gly Lys Leu Pro Leu Tyr Ala Leu Glu Lys Lys Leu
            100                 105                 110

Gly Asp Thr Thr Arg Ala Val Ala Val Arg Arg Lys Ala Leu Ser Ile
        115                 120                 125

Leu Ala Glu Ala Pro Val Leu Ala Ser Asp Arg Leu Pro Tyr Lys Asn
    130                 135                 140

Tyr Asp Tyr Asp Arg Val Phe Gly Ala Cys Cys Glu Asn Val Ile Gly
145                 150                 155                 160
```

```
Tyr Met Pro Leu Pro Val Gly Val Ile Gly Pro Leu Val Ile Asp Gly
            165                 170                 175

Thr Ser Tyr His Ile Pro Met Ala Thr Thr Glu Gly Cys Leu Val Ala
            180                 185                 190

Ser Ala Met Arg Gly Cys Lys Ala Ile Asn Ala Gly Gly Gly Ala Thr
            195                 200                 205

Thr Val Leu Thr Lys Asp Gly Met Thr Arg Gly Pro Val Val Arg Phe
            210                 215                 220

Pro Thr Leu Lys Arg Ser Gly Ala Cys Lys Ile Trp Leu Asp Ser Glu
225                 230                 235                 240

Glu Gly Gln Asn Ala Ile Lys Lys Ala Phe Asn Ser Thr Ser Arg Phe
                    245                 250                 255

Ala Arg Leu Gln His Ile Gln Thr Cys Leu Ala Gly Asp Leu Leu Phe
                    260                 265                 270

Met Arg Phe Arg Thr Thr Thr Gly Asp Ala Met Gly Met Asn Met Ile
            275                 280                 285

Ser Lys Gly Val Glu Tyr Ser Leu Lys Gln Met Val Glu Glu Tyr Gly
            290                 295                 300

Trp Glu Asp Met Glu Val Val Ser Val Ser Gly Asn Tyr Cys Thr Asp
305                 310                 315                 320

Lys Lys Pro Ala Ala Ile Asn Trp Ile Glu Gly Arg Gly Lys Ser Val
                    325                 330                 335

Val Ala Glu Ala Thr Ile Pro Gly Asp Val Val Arg Lys Val Leu Lys
                    340                 345                 350

Ser Asp Val Ser Ala Leu Val Glu Leu Asn Ile Ala Lys Asn Leu Val
            355                 360                 365

Gly Ser Ala Met Ala Gly Ser Val Gly Gly Phe Asn Ala His Ala Ala
            370                 375                 380

Asn Leu Val Thr Ala Val Phe Leu Ala Leu Gly Gln Asp Pro Ala Gln
385                 390                 395                 400

Asn Val Glu Ser Ser Asn Cys Ile Thr Leu Met Lys Glu Val Asp Gly
                    405                 410                 415

Asp Leu Arg Ile Ser Val Ser Met Pro Ser Ile Glu Val Gly Thr Ile
                    420                 425                 430

Gly Gly Gly Thr Val Leu Glu Pro Gln Gly Ala Met Leu Asp Leu Leu
            435                 440                 445

Gly Val Arg Gly Pro His Ala Thr Ala Pro Gly Thr Asn Ala Arg Gln
            450                 455                 460

Leu Ala Arg Ile Val Ala Cys Ala Val Leu Ala Gly Glu Leu Ser Leu
465                 470                 475                 480

Cys Ala Ala Leu Ala Ala Gly His Leu Val Gln Ser His Met Thr His
                    485                 490                 495

Asn Arg Lys Pro Ala Glu Pro Thr Lys Pro Asn Asn Leu Asp Ala Thr
                    500                 505                 510

Asp Ile Asn Arg Leu Lys Asp Gly Ser Val Thr Cys Ile Lys Ser
            515                 520                 525
```